US009409910B2

(12) United States Patent
Hung et al.

(10) Patent No.: US 9,409,910 B2
(45) Date of Patent: Aug. 9, 2016

(54) AZEPINO[4,5-B]INDOLES AND METHODS OF USE

(71) Applicant: Medivation Technologies, Inc., San Francisco, CA (US)

(72) Inventors: David T. Hung, Redwood City, CA (US); Andrew Asher Protter, Palo Alto, CA (US); Rajendra Parasmal Jain, Pune (IN); Sarvajit Chakravarty, Mountain View, CA (US)

(73) Assignee: Medivation Technologies, Inc., San Francisco, CA (US)

( * ) Notice: Subject to any disclaimer, the term of this patent is extended or adjusted under 35 U.S.C. 154(b) by 446 days.

(21) Appl. No.: 13/791,648

(22) Filed: Mar. 8, 2013

(65) Prior Publication Data

US 2014/0088087 A1 Mar. 27, 2014

Related U.S. Application Data

(63) Continuation of application No. 12/610,152, filed on Oct. 30, 2009, now Pat. No. 8,569,287.

(60) Provisional application No. 61/110,527, filed on Oct. 31, 2008, provisional application No. 61/173,965, filed on Apr. 29, 2009, provisional application No. 61/245,257, filed on Sep. 23, 2009.

(51) Int. Cl.
*C07D 487/04* (2006.01)
*A61K 31/55* (2006.01)
*C07D 471/04* (2006.01)

(52) U.S. Cl.
CPC .............. *C07D 487/04* (2013.01); *A61K 31/55* (2013.01); *C07D 471/04* (2013.01)

(58) Field of Classification Search
None
See application file for complete search history.

(56) References Cited

U.S. PATENT DOCUMENTS

| | | | |
|---|---|---|---|
| 3,419,569 A | 12/1968 | Renner et al. | |
| 3,525,750 A | 8/1970 | Renner | |
| 3,529,062 A | 9/1970 | Renner | |
| 4,754,038 A | 6/1988 | Abou-Gharbia | |
| 6,187,785 B1 | 2/2001 | Zefirov et al. | |
| 6,828,314 B2 | 12/2004 | Frank et al. | |
| 7,071,206 B2 | 7/2006 | Zefirov et al. | |
| 8,338,408 B2 | 12/2012 | Hung et al. | |
| 8,338,447 B2 | 12/2012 | Hung et al. | |
| 8,362,277 B2 | 1/2013 | McKnight et al. | |
| 8,541,437 B2 | 9/2013 | Ivashchenko et al. | |
| 8,546,381 B2 | 10/2013 | Hung et al. | |
| 8,569,287 B2 | 10/2013 | Hung et al. | |
| 8,604,074 B2 | 12/2013 | McKnight et al. | |
| 8,735,440 B2 | 5/2014 | McKnight et al. | |
| 8,741,919 B2 | 6/2014 | Jain et al. | |
| 8,791,132 B2 | 7/2014 | Protter et al. | |
| 8,815,843 B2 | 8/2014 | Protter et al. | |
| 8,859,561 B2 | 10/2014 | Jain et al. | |
| 8,877,797 B2 | 11/2014 | McKnight et al. | |
| 8,906,925 B2 | 12/2014 | Hung et al. | |
| 8,907,097 B2 | 12/2014 | Hung et al. | |
| 8,927,571 B2 | 1/2015 | Jain et al. | |
| 8,999,977 B2 | 4/2015 | Hung et al. | |
| 8,999,978 B2 | 4/2015 | Hung et al. | |
| 9,006,234 B2 | 4/2015 | Jain et al. | |
| 9,006,263 B2 | 4/2015 | Protter et al. | |
| 9,034,865 B2 | 5/2015 | Chakravarty et al. | |
| 9,034,869 B2 | 5/2015 | Hung et al. | |
| 9,034,880 B2 | 5/2015 | Hung et al. | |
| 9,035,056 B2 | 5/2015 | Chakravarty et al. | |
| 9,040,519 B2 | 5/2015 | Chakravarty et al. | |
| 9,045,482 B2 | 6/2015 | Jain et al. | |
| 9,051,314 B2 | 6/2015 | Hung et al. | |
| 9,079,904 B2 | 7/2015 | Jain et al. | |
| 9,085,580 B2 | 7/2015 | Jain et al. | |
| 9,096,591 B2 | 8/2015 | Hung et al. | |
| 9,115,137 B2 | 8/2015 | Hung et al. | |
| 9,181,240 B2 | 11/2015 | Hung et al. | |
| 9,187,471 B2 | 11/2015 | Chakravarty et al. | |
| 9,193,728 B2 | 11/2015 | Chakravarty et al. | |
| 9,199,985 B2 | 12/2015 | Protter et al. | |
| 9,199,996 B2 | 12/2015 | Jain et al. | |
| 2001/0020028 A1 | 9/2001 | Zefirov et al. | |
| 2002/0077318 A1 | 6/2002 | Frank et al. | |
| 2002/0115682 A1 | 8/2002 | Zefirov et al. | |
| 2003/0225058 A1 | 12/2003 | Frank et al. | |
| 2004/0044022 A1 | 3/2004 | Zefirov et al. | |
| 2006/0140866 A1 | 6/2006 | Zefirov et al. | |
| 2007/0015746 A1 | 1/2007 | Martin et al. | |
| 2007/0117834 A1 | 5/2007 | Hung | |
| 2007/0117835 A1 | 5/2007 | Hung | |
| 2007/0179174 A1 | 8/2007 | Bachurin et al. | |
| 2007/0225316 A1 | 9/2007 | Bachurin et al. | |
| 2008/0234310 A1 | 9/2008 | Bachurin et al. | |
| 2010/0022580 A1 | 1/2010 | Hung et al. | |
| 2010/0029706 A1 | 2/2010 | Miller et al. | |
| 2010/0087471 A1 | 4/2010 | Schrimpf et al. | |
| 2010/0099700 A1 | 4/2010 | Hung | |
| 2010/0120792 A1 | 5/2010 | Ivashchenko et al. | |

(Continued)

FOREIGN PATENT DOCUMENTS

| | | |
|---|---|---|
| CH | 445 512 A | 10/1967 |
| EP | 0 466 548 A1 | 1/1992 |

(Continued)

OTHER PUBLICATIONS

Levin. Current Drug Targets CNS and Neurological Disorders, 2002, 1(4), 423-31, Medline abstract.*

(Continued)

*Primary Examiner* — Noble Jarrell
(74) *Attorney, Agent, or Firm* — Morrison & Foerster LLP

(57) ABSTRACT

This disclosure relates to new azepino[4,5-b]indole compounds that may be used to modulate a histamine receptor in an individual. Novel compounds are described, including new 1,2,3,4,5,6-tetrahydroazepino[4,5-b]indoles. Pharmaceutical compositions are also provided.

16 Claims, No Drawings

(56) References Cited

U.S. PATENT DOCUMENTS

| | | |
|---|---|---|
| 2010/0152108 A1 | 6/2010 | Hung et al. |
| 2010/0152225 A1 | 6/2010 | Hung |
| 2010/0178277 A1 | 7/2010 | Hung et al. |
| 2010/0249105 A1 | 9/2010 | Schrimpf et al. |
| 2010/0286188 A1 | 11/2010 | Bachurin et al. |
| 2011/0046368 A1 | 2/2011 | Ivashchenko et al. |
| 2011/0112132 A1 | 5/2011 | Bachurin et al. |
| 2011/0237582 A1 | 9/2011 | Jain et al. |
| 2011/0269777 A1 | 11/2011 | Bachurin et al. |
| 2012/0022096 A1 | 1/2012 | McKnight et al. |
| 2012/0101121 A1 | 4/2012 | Bachurin et al. |
| 2012/0136008 A1 | 5/2012 | Jain et al. |
| 2013/0040977 A1 | 2/2013 | McKnight et al. |
| 2013/0079352 A1 | 3/2013 | Hung et al. |
| 2013/0123277 A1 | 5/2013 | Jain et al. |
| 2013/0131054 A1 | 5/2013 | Hung et al. |
| 2013/0131077 A1 | 5/2013 | Hung et al. |
| 2013/0137705 A1 | 5/2013 | Jain et al. |
| 2013/0172320 A1 | 7/2013 | Chakravarty et al. |
| 2013/0184303 A1 | 7/2013 | Jain et al. |
| 2013/0184304 A1 | 7/2013 | Jain et al. |
| 2013/0184306 A1 | 7/2013 | Hung et al. |
| 2013/0190293 A1 | 7/2013 | Chakravarty et al. |
| 2013/0190294 A1 | 7/2013 | Protter et al. |
| 2013/0190295 A1* | 7/2013 | Hung ............... A61K 31/55 514/215 |
| 2013/0190304 A1 | 7/2013 | Hung et al. |
| 2013/0190308 A1 | 7/2013 | Jain et al. |
| 2013/0190323 A1 | 7/2013 | Hung et al. |
| 2013/0190328 A1 | 7/2013 | Jain et al. |
| 2013/0190344 A1 | 7/2013 | Jain et al. |
| 2013/0190347 A1 | 7/2013 | Hung et al. |
| 2013/0190348 A1 | 7/2013 | Hung et al. |
| 2013/0190359 A1 | 7/2013 | Jain et al. |
| 2013/0210803 A1 | 8/2013 | Chakravarty et al. |
| 2013/0217703 A1 | 8/2013 | Ivachtchenko et al. |
| 2013/0225558 A1 | 8/2013 | Chakravarty et al. |
| 2014/0024643 A1 | 1/2014 | Hung et al. |
| 2014/0155384 A1 | 6/2014 | Protter et al. |
| 2014/0213577 A1* | 7/2014 | Hung ............... A61K 31/55 514/215 |
| 2014/0228353 A1 | 8/2014 | Protter et al. |
| 2014/0296209 A1 | 10/2014 | Protter et al. |
| 2014/0303144 A1 | 10/2014 | Protter et al. |
| 2015/0005322 A1 | 1/2015 | Jain et al. |
| 2015/0051218 A1 | 2/2015 | Hung et al. |
| 2015/0182509 A1 | 7/2015 | Hung et al. |
| 2015/0258075 A1 | 9/2015 | Chakravarty et al. |
| 2015/0266884 A1 | 9/2015 | Protter et al. |
| 2015/0315188 A1 | 11/2015 | Protter et al. |
| 2015/0335656 A1 | 11/2015 | Miyoshi et al. |

FOREIGN PATENT DOCUMENTS

| | | |
|---|---|---|
| EP | 2 145 887 A2 | 1/2010 |
| EP | 2 236 511 A2 | 10/2010 |
| FR | 1 524 830 A | 5/1968 |
| GB | 1062840 A | 3/1967 |
| JP | 63-163347 A | 7/1988 |
| WO | WO-97/15225 A1 | 5/1997 |
| WO | WO-97/44040 A1 | 11/1997 |
| WO | WO-01/05793 A1 | 1/2001 |
| WO | WO-01/13905 A2 | 3/2001 |
| WO | WO-01/13905 A3 | 3/2001 |
| WO | WO-02/24700 A2 | 3/2002 |
| WO | WO-02/24700 A3 | 3/2002 |
| WO | WO-02/24701 A2 | 3/2002 |
| WO | WO-02/24701 A3 | 3/2002 |
| WO | WO-2005/005951 A2 | 6/2005 |
| WO | WO-2005/005951 A3 | 6/2005 |
| WO | WO-2006/101434 A1 | 9/2006 |
| WO | WO-2007/016353 A2 | 2/2007 |
| WO | WO-2007/016353 A3 | 2/2007 |
| WO | WO-2007/041697 A2 | 4/2007 |
| WO | WO-2007/041697 A3 | 4/2007 |
| WO | WO-2007/087425 A1 | 8/2007 |
| WO | WO-2008/024029 A1 | 2/2008 |
| WO | WO-2008/036400 A2 | 3/2008 |
| WO | WO-2008/036400 A3 | 3/2008 |
| WO | WO-2008/036410 A2 | 3/2008 |
| WO | WO-2008/036410 A3 | 3/2008 |
| WO | WO-2008/051599 A2 | 5/2008 |
| WO | WO-2008/051599 A3 | 5/2008 |
| WO | WO-2008/060190 A2 | 5/2008 |
| WO | WO-2008/060190 A3 | 5/2008 |
| WO | WO-2008/069963 A1 | 6/2008 |
| WO | WO-2008/073231 A1 | 6/2008 |
| WO | WO-2008/115098 A2 | 9/2008 |
| WO | WO-2008/115098 A3 | 9/2008 |
| WO | WO-2008/123796 A2 | 10/2008 |
| WO | WO-2008/123796 A3 | 10/2008 |
| WO | WO-2008/123800 A2 | 10/2008 |
| WO | WO-2008/123800 A3 | 10/2008 |
| WO | WO-2008/147551 A1 | 12/2008 |
| WO | WO-2009/005771 A1 | 1/2009 |
| WO | WO-2009/017836 A1 | 2/2009 |
| WO | WO-2009/039420 A1 | 3/2009 |
| WO | WO-2009/039420 A9 | 3/2009 |
| WO | WO-2009/055828 A1 | 4/2009 |
| WO | WO-2009/082268 A2 | 7/2009 |
| WO | WO-2009/082268 A3 | 7/2009 |
| WO | WO-2009/094668 A1 | 7/2009 |
| WO | WO-2009/094668 A8 | 7/2009 |
| WO | WO-2009/094668 C1 | 7/2009 |
| WO | WO-2009/111540 A1 | 9/2009 |
| WO | WO-2009/120717 A2 | 10/2009 |
| WO | WO-2009/120717 A3 | 10/2009 |
| WO | WO-2009/120720 A1 | 10/2009 |
| WO | WO-2009/135091 A1 | 11/2009 |
| WO | WO-2010/036998 A2 | 4/2010 |
| WO | WO-2010/036998 A3 | 4/2010 |
| WO | WO-2010/051501 A1 | 5/2010 |
| WO | WO-2010/051503 A1 | 5/2010 |
| WO | WO 2010/081115 A1 | 7/2010 |
| WO | WO-2010/127177 A1 | 11/2010 |
| WO | WO-2011/008312 A2 | 1/2011 |
| WO | WO-2011/008312 A3 | 1/2011 |
| WO | WO-2011/014695 A1 | 2/2011 |
| WO | WO-2011/019417 A1 | 2/2011 |
| WO | WO-2011/038161 A1 | 3/2011 |
| WO | WO-2011/038162 A1 | 3/2011 |
| WO | WO-2011/038163 A1 | 3/2011 |
| WO | WO-2011/038164 A1 | 3/2011 |
| WO | WO-2011/103430 A1 | 8/2011 |
| WO | WO-2011/103433 A1 | 8/2011 |
| WO | WO-2011/103448 A1 | 8/2011 |
| WO | WO-2011/103460 A1 | 8/2011 |
| WO | WO-2011/103485 A1 | 8/2011 |
| WO | WO-2011/103487 A1 | 8/2011 |
| WO | WO-2012/006419 A2 | 1/2012 |
| WO | WO-2012/006419 A3 | 1/2012 |
| WO | WO-2012/112961 A1 | 8/2012 |
| WO | WO-2012/112962 A1 | 8/2012 |
| WO | WO-2012/112963 A1 | 8/2012 |
| WO | WO-2012/112964 A2 | 8/2012 |
| WO | WO-2012/112964 A3 | 8/2012 |
| WO | WO-2012/112965 A1 | 8/2012 |
| WO | WO-2012/112966 A1 | 8/2012 |
| WO | WO-2012/154261 A1 | 11/2012 |
| WO | WO-2014/031125 A1 | 2/2014 |
| WO | WO-2014/031165 A1 | 2/2014 |
| WO | WO-2014/031167 A1 | 2/2014 |
| WO | WO-2014/031170 A1 | 2/2014 |

OTHER PUBLICATIONS

Abou-Gharbia, M. (Jan. 1, 1989). "Biological Activity of Substituted γ-Carbolines," *Drugs of the Future* 14(5):453-459.

Adham, N. et al. (Jun. 23, 1998). "Functional Characterization of the Recombinant Human 5-Hydroxytryptamine$_{7(a)}$ Receptor Isoform Coupled to Adenylate Cyclase Stimulation," *The Journal of Pharmacology and Experimental Therapeutics*. 287(2):508-514.

(56) References Cited

OTHER PUBLICATIONS

Barbero, A. et al. (Jul. 8, 1992). "Ring-Formation from Allyl- and Vinylstannanes Initiated by Treatment with Butyl-Lithium," *Tetrahedron Letters* 33(39):5841-5842.
Bartolini, L. et al. (1996). "Aniracetam Restores Object Recognition Impaired by Age, Scopolamine, and Nucleus Basalis Lesions," *Pharmacology Biochemistry Behavior* 53(2):277-283.
Berge, S.M. et al. (Jan. 1977). "Pharmaceutical Salts," *J. Pharm. Sci.* 66(1):1-19.
Boess, F.G. et al. (1997). "Analysis of the Ligand Binding Site of the 5-$HT_3$ Receptor Using Site Directed Mutagenesis: Importance of Glutamate 106," *Neuropharmacology* 36(4/5):637-647.
Bonhaus, D.W. et al. (1995). "The Pharmacology and Distribution of Human 5-Hydroxytryptamine$_{2B}$ (5-$HT_{2B}$) Receptor Gene Products: Comparison with 5-$HT_{2A}$ and 5-$HT_{2C}$ Receptors," *British Journal of Pharmacology* 115:622-628.
Brown, C.M. et al. (1990). "$\alpha_2$-Adrenoceptor Subtypes and Imidazoline-Like Binding Sites in the Rat Brain," *Br. J. Pharmacol.* 99:803-809.
Bubber, P. et al. (May 2005, e-pub. Apr. 25, 2005). "Mitochondrial Abnormalities in Alzheimer Brain: Mechanistic Implications," *Ann Neurol.* 57(5):695-703.
CAPLUS, Accession No. 1968:486857, abstract, STN Entry Date May 12, 1984, 2 pages.
CAPLUS, Accession No. 1972:469985, abstract, STN Entry Date May 12, 1984, 1 page.
De Backer, M.D. et al. (Dec. 30, 1993). "Genomic Cloning, Heterologous Expression and Pharmacological Characterization of a Human Histamine H1 Receptor," *Biochemical and Biophysical Research Communications* 197(3):1601-1608.
Dezi, C. (2007). "Modeling of 5-$HT_{2A}$ and 5-$HT_{2C}$ Receptors and of Their Complexes with Actual and Potential Antipsychotic Drugs," PhD Thesis, Pompeu Fabra University, Barcelona, pp. 1-239.
Extended European Search Report mailed on Apr. 23, 2012, for EP Application No. EP 09 82 4200.1, filed on Oct. 30, 2009, 5 pages.
Extended European Search Report mailed on Jul. 10, 2012, for EP Application No. EP 09 82 4199.5, filed on Oct. 30, 2009, 11 pages.
Ennaceur, A. et al. (1988). "A New One-Trial Test for Neurobiological Studies of Memory in Rats. 1: Behavioral Data," *Behav. Brain. Res.* 31:47-59.
Final Office Action mailed on Dec. 2, 2011, for U.S. Appl. No. 12/360,061, filed Jan. 26, 2009, 13 pages.
Galstyan, L.S. et al. (Jan. 1, 1976). "Indole Derivatives," *Armenian Chemical Journal* 3:255-258. (English Translation with Certification.).
Galstyan, L. S. et al. (Jan. 1, 1974). "Indole Derivatives," *Armenian Chemical Journal* 4:331-336. (English Translation with Certification.).
García-Sáinz, J.A. et al. (Jul. 31, 1992). "Species Heterogeneity of Hepatic $\alpha_1$-Adrenoceptors: $\alpha_{1A}$-, $\alpha_{1B}$- and $\alpha_{1C}$-Subtypes," *Biochemical and Biophysical Research Communications* 186(2):760-767.
Gilliland, S.L. et al. (2000, e-pub. Feb. 29, 2000). "Characterization of Dopaminergic Compounds at $hD_{2short}$, $hD_{4.2}$ and $hD_{4.7}$ Receptors in Agonist-Stimulated [$^{35}$S]GTP$\gamma$S Binding Assays," *Naunyn-Schmiedeberg's Archives of Pharmacology* 361:498-504.
Grandy, D.K. et al. (Dec. 1989). "Cloning of the cDNA and Gene for a Human $D_2$ Dopamine Receptor," *Proc. Natl. Acad. Sci. USA* 86:9762-9766.
Grossman, C.J. et al. (1993). "Development of a Radioligand Binding Assay for 5-$HT_4$ Receptors in Guinea-Pig and Rat Brain," *Br. J. Pharmacol.* 109:618-624.
Hardy, J. (1996). "New Insights Into the Genetics of Alzheimer's Disease," *Annals of Medicine* 28:255-258.
Hardy, J. (1997). "Amyloid, the Presenilins and Alzheimer's Disease," *Trends Neurosci.* 20(4):154-159.
Hayes, G. et al. (1992). "Structural Subtypes of the Dopamine D2 Receptor are Functionally Distinct: Expression of the Cloned $D2_A$ and $D2_B$ Subtypes in a Heterologous Cell Line," *Mol. Endocrinol.* 6(6):920-926.

Hoyer, D. et al. (1985). "Characterization of the 5-$HT_{1B}$ Recognition Site in Rat Brain: Binding Studies with (-)[$^{125}$I] Iodocyanopindolol," *European Journal of Pharmacology* 118:1-12.
International Search Report mailed on Mar. 3, 2010, for PCT Patent Application No. PCT/US09/062872, filed on Oct. 30, 2009, 1 page.
Jentsch, J.D. et al. (Aug. 15, 1997). "Enduring Cognitive Deficits and Cortical Dopamine Dysfunction in Monkeys After Long-Term Administration of Phencyclidine," *Science* 277:953-955.
Jerman, J.C. et al. (2001). "Pharmacological Characterisation of Human 5-$HT_2$ Receptor Subtypes," *European Journal of Pharmacology* 414:23-30.
Kenny, B.A. et al. (1995). "Characterization of an $\alpha_{1D}$-Adrenoceptor Mediating the Contractile Response of Rat Aorta to Noradrenaline," *British Journal of Pharmacology* 115:981-986.
Ko-Chetkov, N.K. et al. (1961). "Derivatives of Indole. VII. Synthesis of Some Derivatives of 1,2,3,4,4a,9b-Hexahydro-$\gamma$-Carboline," *Zhurnal Obshchei Khimii*, Chemical Abstracts CAPLUS Abstract No. 1961:124840, 6 pages.
Kohen, R. et al. (1996). "Cloning, Characterization, and Chromosomal Localization of a Human 5-$HT_6$ Serotonin Receptor," *J. Neurochem.* 66(1):47-56.
Kroeze, W.K. et al. (2003). "HI-Histamine Receptor Affinity Predicts Short-Term Weight Gain for Typical and Atypical Antipsychotic Drugs," *Neuropsychopharmacology* 28:519-526.
Kucherova, N.F. et al. (1961). "Derivatives of Indole. VIII. 5-Acyl-1,2,3,4,4a,9b-Hexahydro-$\gamma$-Carbolines," *Zhurnal Obshchei Khimii*, Chemical Abstracts CAPLUS Abstract No. 1961:124841, 8 pages.
Levin, E.D. et al. (Aug. 2002). "Nicotinic Treatment for Cognitive Dysfunction," *Current Drug Targets CNS and Neurological Disorders* 1(4):423-431.
Lohr, J.B. et al. (Aug. 28, 1995). "Motor Asymmetry, a Neurobiologic Abnormality in the Major Psychoses," *Psychiatry Research* 57(3):279-282.
Martin, G.R. (1994). "Receptors for 5-Hydroxytryptamine: Current Perspectives on Classification and Nomenclature," *Neuropharmacology* 33(3/4):261-273.
May, J.A. et al. (2003). "Evaluation of the Ocular Hypotensive Response of Serotonin 5-$HT_{1A}$ and 5-$HT_2$ Receptor Ligands in Conscious Ocular Hypertenisve Cynomolgus Monkeys," *The Journal of Pharmacology and Experimental Therapeutics* 306(1):301-309.
Michel, A.D. et al. (1989). "Identification of a Single $\alpha_1$-Adrenoceptor Corresponding to the $\alpha_{1A}$-Subtype in Rat Submaxillary Gland," *Br. J. Pharmacol.* 98:883-889.
Miller, K et al. (1992). "Membrane-Bound and Solubilized Brain 5$HT_3$ Receptors: Improved Radioligand Binding Assays Using Bovine Area Postrema or Rat Cortex and the Radioligands $^3$H-GR65630, $^3$H-BRL43694, and $^3$H-LY278584," *Synapse* 11:58-66.
Miller, T.R. et al. (1999). "Analysis of Apparent Noncompetitive Responses to Competitive $H_1$-Histamine Receptor Antagonists in Fluorescent Imaging Plate Reader-Based Calcium Assays," *Journal of Biomolecular Screening* 4(5):249-258.
Monsma, F.J. Jr. et al. (1993). "Cloning and Expression of a Novel Serotonin Receptor with High Affinity for Tricyclic Psychotropic Drugs," *Molecular Pharmacology* 43:320-327.
Non-Final Office Action mailed on Jun. 14, 2011, for U.S. Appl. No. 12/360,061, filed Jan. 26, 2009, 22 pages.
Non-Final Office Action mailed on Feb. 14, 2014, for U.S. Appl. No. 13/498,099, filed Jan. 14, 2013, 20 pages.
Non-Final Office Action mailed on Jul. 31, 2014, for U.S. Appl. No. 13/734,873, filed Jan. 4, 2013, 16 pages.
Pani, L et al. (2007, e-pub. Apr. 6, 2007). "Antipsychotic Efficacy: Relationship to Optimal $D_2$-Receptor Occupancy," *European Psychiatry* 22:276-275.
Pazos, A. et al. (1985). "Mesulergine, A Selective Serotonin-2 Ligand in the Rat Cortex, Does Not Label these Receptors in Porcine and Human Cortex: Evidence for Species Differences in Brain Serotonin-2 Receptors," *European Journal of Pharmacology* 106:531-538.
Pazourkova et al. (2003). "Antioxidant Activity of Pyridoindoles and N-(Alkoxyphenyl)-2-2-(2-oxo-1-aza-1-cycloalkyl) Acetamides in Biological, Enzymic, and Chemical Systems," *Ceska a Slovenska Farmacie*, 52(4): 171-175. (Translation of summary only).

(56) References Cited

OTHER PUBLICATIONS

Piercey, M.F. et al. (1988). "Dramatic Limbic and Cortical Effects Mediated by High Affinity PCP Receptors," *Life Sciences* 43(4):379-385.

Prichep, L.S. et al. (1994). "Quantitative EEG Correlates of Cognitive Deterioration in the Elderly," *Neurobiology of Aging* 15(1):85-90.

Reddy, P.H. et al. (2005, e-pub. Apr. 19, 2005). "Are Mitochondria Critical in the Pathogenesis of Alzheimer's Disease?" *Brain Res Rev.* 49(3):618-632.

Rees, S. et al. (Oct. 11, 1994). "Cloning and Characterisation of the Human 5-HT$_{5A}$ Serotonin Receptor," *FEBS Letters* 355:242-246.

Reisberg, B. et al. (Sep. 1982). "The Global Deterioration Scale for Assessment of Primary Degenerative Dementia," *Am. J. Psychiatry* 139(9):1136-1139.

Rodriguez-Spong, B. et al. (2004). "General Principles of Pharmaceutical Solid Polymorphism: a Supramolecular Perspective," *Advanced Drug Delivery Reviews*, 56:241-274.

Roth, B.L. et al. (1994). "Binding of Typical and Atypical Antipsychotic Agents to 5-Hydroxytryptamine-6 and 5-Hydroxytryptamine-7 Receptors," *J. Pharmacol. Exp. Ther.* 268(3):1403-1410.

Ruat, M. et al. (Mar. 1990). "Reversible and Irreversible Labeling and Autoradiographic Localization of the Cerebral Histamine H$_2$ Receptor Using [$^{125}$I]Iodinated Probes," *Proc. Natl. Acad. Sci. USA* 87(5):1658-1662.

Saucier, C. et al. (1997). "Identification of an Endogenous 5-Hydroxytryptamine$_{2A}$ Receptor in NIH-3T3 Cells: Agonist-Induced Down-Regulation Involves Decreases in Receptor RNA and Number," *Journal of Neurochemistry* 68(5):1998-2011.

Scali, C. et al. (1994). "Nerve Growth Factor Increases Extracellular Acetylcholine Levels in the Parietal Cortex and Hippocampus of Aged Rats and Restores Object Recognition," *Neuroscience Letters* 170:117-120.

Senogles, S.E. et al. (Mar. 15, 1990). "Specificity of Receptor-G Protein Interactions. Discrimination of G$_i$ Subtypes by the D$_2$ Dopamine Receptor in a Reconstituted System," *Journal of Biological Chemistry* 265(8):4507-4514.

Shen, Y. et al. (Aug. 25, 1993). "Molecular Cloning and Expression of a 5-Hydroxytryptamine$_7$ Serotonin Receptor Subtype," *The Journal of Biological Chemistry* 268(24):18200-18204.

Swerdlow, R.H. et al. (2002). "Mitochondria in Alzheimer's Disease," *International Review of Neurobiology* 53:341-385.

Tanzi, R.E. et al. (1996). "The Gene Defects Responsible for Familial Alzheimer's Disease," *Neurobiology of Disease* 3:159-168.

Trofimov, F.A. et al. (1967). "Pyridylethylation of γ-Carbolines," *Khimiko-Farmatsevticheskii Zhurnal*, Chemical Abstracts CAPLUS Abstract No. 1961:500029, 4 pages.

Uhlén, S. et al. (1994). "The Novel *Alpha*-2 Adrenergic RadioLigand [$^3$H]-MK912 is *Alpha*-2C Selective Among Human *Alpha*-2A, *Alpha*-2B and *Alpha*-2C Adrenoceptors," *Journal of Pharmacology and Experimental Therapeutics* 271(3):1558-1565.

Uhlén, S. et al. (1998). "[$^3$H]RS79948-197 Binding to Human, Rat, Guinea Pig and Pig α$_{2A}$-, α$_{2B}$- and α$_{2C}$-Adrenoceptors. Comparison with MK912, RX821002, Rauwolscine and Yohimbine," *European Journal of Pharmacology* 343:93-101.

Wang, X. et al. (2007, e-pub. Sep. 21, 2007). "Insights Into Amyloid-β-Induced Mitochondrial Dysfunction in Alzheimer Disease," *Free Radical Biology & Medicine* 43:1569-1573.

Wolf, W.A. et al. (1997). "The Serotonin 5-HT$_{2C}$ Receptor Is a Prominent Serotonin Receptor in Basal Ganglia: Evidence from Functional Studies on Serotonin-Mediated Phosphoinositide Hydrolysis," *Journal of Neurochemistry* 69(4):1449-1458.

Written Opinion mailed on Mar. 3, 2010, for PCT Patent Application No. PCT/US09/62872, filed on Oct. 30, 2009, 5 pages.

Yanai, K. et al. (1994). "Binding Characteristics of a Histamine H$_3$-Receptor Antagonist, [$^3$H]S-Methylthioperamide: Comparison with [$^3$H](R)α-Methylhistamine Binding to Rat Tissues," *Jpn. J. Pharmacol.* 65:107-112.

Yu, J-Q. et al. (2002). "Diverse Pathways for the Palladium(II)-Mediated Oxidation of Olefins by *tert*-Butylhydroperoxide," *Organic Letters* 4(16):2727-2730.

Zhu, Y. et al. (2001). "Cloning, Expression, and Pharmacological Characterization of a Novel Human Histamine Receptor," *Molecular Pharmacology* 59(3):434-441.

U.S. Appl. No. 14/423,027, filed Feb. 20, 2015, by Protter et al.
U.S. Appl. No. 14/631,615, filed Feb. 25, 2015, by Hung et al.
U.S. Appl. No. 14/641,232, filed Mar. 6, 2015, by Protter et al.
U.S. Appl. No. 14/666,101, filed Mar. 23, 2015, by Chakravarty et al.
U.S. Appl. No. 14/701,244, filed Apr. 30, 2015, by Chakravarty et al.
Jain et al., U.S. Appl. No. 14/738,465, filed Jun. 12, 2015.
Chakravarty et al., U.S. Appl. No. 14/882,303, filed Oct. 13, 2015.
International Preliminary Report on Patentability received for PCT Patent Application No. PCT/US2009/062872, mailed on May 12, 2011, 7 pages.

\* cited by examiner

AZEPINO[4,5-B]INDOLES AND METHODS OF USE

CROSS-REFERENCE TO RELATED APPLICATIONS

This application is a continuation of U.S. Non-provisional patent application Ser. No. 12/610,152, filed on Oct. 30, 2009, which claims priority to U.S. Provisional Patent Application No. 61/110,527 filed Oct. 31, 2008, U.S. Provisional Patent Application No. 61/173,965 filed Apr. 29, 2009 and U.S. Provisional Patent Application No. 61/245,257 filed Sep. 23, 2009, the disclosures of each of which are hereby incorporated herein by reference in their entireties.

STATEMENT OF RIGHTS TO INVENTIONS MADE UNDER FEDERALLY SPONSORED RESEARCH

Not applicable.

BACKGROUND OF THE INVENTION

Neurotransmitters such as histamine, serotonin, dopamine and norepinephrine mediate a large number of processes in the central nervous system (CNS) as well as outside the CNS. Abnormal neurotransmitter levels are associated with a wide variety of diseases and conditions including, but not limited to, Alzheimer's disease, Parkinson's Disease, autism, ADD, ADHD, Guillain-Barré syndrome, mild cognitive impairment, schizophrenia (such as cognitive impairment associated with schizophrenia (CIAS), positive symptoms, disorganized symptoms, and negative symptoms of schizophrenia), anxiety, multiple sclerosis, stroke, traumatic brain injury, spinal cord injury, diabetic neuropathy, fibromyalgia, bipolar disorders, psychosis, depression, attention-deficit disorder (ADD), attention-deficit hyperactivity disorder (ADHD) and a variety of allergic diseases. Compounds that modulate these neurotransmitters may be useful therapeutics.

Histamine receptors belong to the superfamily of G protein-coupled seven transmembrane proteins. G protein-coupled receptors constitute one of the major signal transduction systems in eukaryotic cells. Coding sequences for these receptors, in those regions believed to contribute to the agonist-antagonist binding site, are strongly conserved across mammalian species. Histamine receptors are found in most peripheral tissue and within the central nervous system. Compounds capable of modulating a histamine receptor may find use in therapy, e.g., histamine antagonists may find use as antihistamines.

Dimebon is a known anti-histamine drug that has also been characterized as a neuroprotective agent useful to treat, inter alia, neurodegenerative diseases. Dimebon has been shown to inhibit the death of brain cells (neurons) in preclinical models of Alzheimer's disease and Huntington's disease, making it a novel potential treatment for these and other neurodegenerative diseases. In addition, dimebon has been shown to improve the mitochondrial function of cells in the setting of cellular stress with very high potency. For example, dimebon treatment improved mitochondrial function and increased the number of surviving cells after treatment with the cell toxin ionomycin in a dose dependent fashion. Dimebon has also been shown to promote neurite outgrowth and neurogenesis, processes important in the formation of new and/or enhanced neuronal cell connections, and evidence of dimebon's potential for use in additional diseases or conditions. See, e.g., U.S. Pat. Nos. 6,187,785 and 7,071,206 and PCT Patent Application Nos. PCT/US2004/041081, PCT/US2007/020483, PCT/US2006/039077, PCT/US2008/077090, PCT/US2007/020516, PCT/US2007/022645, PCT/US2007/002117, PCT/US2008/006667, PCT/US2007/024626, PCT/US2008/009357, PCT/US2007/024623, PCT/US2008/008121, and PCT/US2009/032065. Hydrogenated pyrido[4,3-b]indoles and uses thereof have been disclosed in PCT Patent Application Nos. PCT/US2008/081390, PCT/US2009/032065 and PCT/US2009/038142. Hydrogenated pyrido[3,4-b]indoles and uses thereof have been described in PCT/US2009/038138. All references disclosed herein and throughout, such as publications, patents, patent applications and published patent applications, are incorporated herein by reference in their entireties.

Although dimebon holds great promise as a drug for the treatment of neurodegenerative diseases and/or diseases in which neurite outgrowth and/or neurogenesis may be implicated in therapy, there remains a need for new and alternative therapies for the treatment of such diseases or conditions. In addition, there remains a need for new and alternative antihistamine drugs, preferably ones in which side-effects such as drowsiness are reduced or eliminated. Compounds that exhibit enhanced and/or more desirable properties than dimebon (e.g., superior safety and efficacy) may find particular use in the treatment of at least those indications for which dimebon is believed to be advantageous. Further, compounds that exhibit a different therapeutic profile than dimebon as determined, e.g. by in vitro and/or in vivo assays, may find use in additional diseases and conditions.

BRIEF SUMMARY OF THE INVENTION

Azepino[4,5-b]indole compounds of the general Formula (I) are described as new histamine receptor modulators. Other compounds are also detailed herein. Compositions comprising the compounds are provided, as are kits comprising the compound as well as methods of using and making the compounds. Compounds of the invention may also find use in treating neurodegenerative diseases. Compounds of the invention may also find use in treating diseases and/or conditions in which modulation of aminergic G protein-coupled receptors and/or neurite outgrowth may be implicated in therapy. Compounds disclosed herein may find use in the methods disclosed herein, including use in treating, preventing, delaying the onset and/or delaying the development of a cognitive disorder, psychotic disorder, neurotransmitter-mediated disorder and/or a neuronal disorder in an individual in need thereof, such as humans.

The invention embraces compounds of the formula (I):

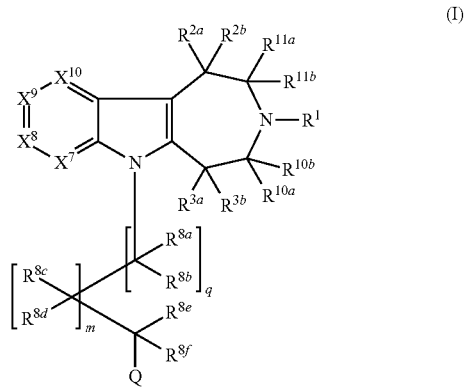

where:

$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy;

each $R^{2a}$, $R^{2b}$, $R^{3a}$ and $R^{3b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^2$ or $R^3$ to form a cycloalkyl moiety or a carbonyl moiety;

each $R^{10a}$, $R^{10b}$, $R^{11a}$ and $R^{11b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^{10}$ or $R^{11}$ to form a cycloalkyl moiety or a carbonyl moiety;

each $X^7$, $X^8$, $X^9$ and $X^{10}$ is independently N or $CR^4$;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each of m and q is independently 0 or 1;

each $R^{8a}$, $R^{8b}$, $R^{8c}$, $R^{8d}$, $R^{8e}$ and $R^{8f}$ is independently H, hydroxyl, alkoxy, halo, $C_1$-$C_8$ perhaloalkyl, carboxy, carbonylalkoxy, substituted or unsubstituted aryl, substituted or unsubstituted heteroaryl, substituted or unsubstituted $C_1$-$C_8$ alkyl, substituted or unsubstituted $C_3$-$C_8$ cycloalkyl, substituted or unsubstituted $C_2$-$C_8$ alkenyl, or is taken together with a geminal $R^8$ to form a moiety of the formula —OCH$_2$CH$_2$O—, is taken together with the carbon to which it is attached and a geminal $R^8$ to form a cycloalkyl moiety or a carbonyl moiety, is taken together with a geminal $R^8$ to form a methylene or a substituted methylene, is taken together with a vicinal $R^8$ and the carbon atoms to which they are attached to form a substituted or unsubstituted $C_3$-$C_8$ cycloalkyl, substituted or unsubstituted $C_3$-$C_8$ cycloalkenyl or substituted or unsubstituted heterocyclyl moiety or is taken together with a vicinal $R^8$ to form a bond, provided when an $R^8$ is taken together with a vicinal $R^8$ to form a bond, the geminal $R^8$ is other than hydroxyl;

Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted amino, alkoxy, aminoacyl, acyloxy, carbonylalkoxy, aminocarbonylalkoxy, acylamino, carboxy, cyano or alkynyl;

provided that the compound is other than a compound in Table 1;

or a salt or solvate thereof.

In one variation, the compounds of the invention, pharmaceutical compositions thereof, isolated forms thereof and methods of using and administering the compounds detailed herein, encompass any of the compounds of Formula (I), including those listed in Table 1 or a salt thereof.

TABLE 1

| Compound No. | Compound Structure |
|---|---|
| 1x | 1-Propanone, 3-(diethylamino)-1-[1,4,5,6-tetrahydro-6-(phenylmethyl)azepino[4,5-b]indol-3(2H)-yl]- |
| 2x | Azepino[4,5-b]indol-4(1H)-one, 2,3,5,6-tetrahydro-3,5,6-tris(phenylmethyl)- |
| 3x | Azepino[4,5-b]indol-4(1H)-one, 2,3,5,6-tetrahydro-3,6-bis(phenylmethyl)- |
| 4x | Azepino[4,5-b]indol-4(1H)-one, 2,3,5,6-tetrahydro-5-(2-oxo-2-phenylethyl)-3,6-bis(phenylmethyl)- |
| 5x | Azepino[4,5-b]indol-4(1H)-one, 2,3,5,6-tetrahydro-5-(2-oxo-2-phenylethyl)-6-(phenylmethyl)- |
| 6x | Azepino[4,5-b]indol-4(1H)-one, 2,3,5,6-tetrahydro-5,5-diphenyl-3,6-bis(phenylmethyl)- |
| 7x | Azepino[4,5-b]indol-4(1H)-one, 2,3,5,6-tetrahydro-5,5-diphenyl-6-(phenylmethyl)- |
| 8x | Azepino[4,5-b]indol-4(1H)-one, 2,3,5,6-tetrahydro-5,6-bis(phenylmethyl)- |
| 9x | Azepino[4,5-b]indol-4(1H)-one, 2,3,5,6-tetrahydro-5-phenyl-3,6-bis(phenylmethyl)- |
| 10x | Azepino[4,5-b]indol-4(1H)-one, 2,3,5,6-tetrahydro-5-phenyl-6-(phenylmethyl)- |
| 11x | Azepino[4,5-b]indol-4(1H)-one, 2,3,5,6-tetrahydro-6-(phenylmethyl)- |
| 12x | Azepino[4,5-b]indol-5(2H)-one, 1,3,4,6-tetrahydro-3-methyl-6-(phenylmethyl)- |
| 13x | Azepino[4,5-b]indol-5-ol, 1,2,3,4,5,6-hexahydro-6-(m-methoxybenzyl)-3-methyl- |
| 14x | Azepino[4,5-b]indol-5-ol, 1,2,3,4,5,6-hexahydro-8-methoxy-6-(m-methoxybenzyl)-3-methyl- |
| 15x | Azepino[4,5-b]indol-5-ol, 6-benzyl-1,2,3,4,5,6-hexahydro-3-methyl- |
| 16x | Azepino[4,5-b]indol-5-ol, 6-benzyl-1,2,3,4,5,6-hexahydro-3-methyl-, acetate (ester) |
| 17x | Azepino[4,5-b]indol-5-ol, 6-benzyl-3-ethyl-1,2,3,4,5,6-hexahydro- |
| 18x | Azepino[4,5-b]indol-5-ol, 6-benzyl-3-ethyl-1,2,3,4,5,6-hexahydro-8-methoxy- |
| 19x | Azepino[4,5-b]indol-5-ol, 6-benzyl-9-chloro-1,2,3,4,5,6-hexahydro-3-methyl- |
| 20x | Azepino[4,5-b]indole, 1,2,3,4,5,6-hexahydro-3,5,6-tris(phenylmethyl)- |

TABLE 1-continued

| Compound No. | Compound Structure |
|---|---|
| 21x | Azepino[4,5-b]indole, 1,2,3,4,5,6-hexahydro-3,6-bis(phenylmethyl)- |
| 22x | Azepino[4,5-b]indole, 1,2,3,4,5,6-hexahydro-3-methyl-6-(2-pyridylmethyl)- |
| 23x | Azepino[4,5-b]indole, 1,2,3,4,5,6-hexahydro-3-methyl-6-(alpha-methylbenzyl)- |
| 24x | Azepino[4,5-b]indole, 1,2,3,4,5,6-hexahydro-3-methyl-6-[3-(4-methyl-1-piperazinyl)propyl]- |
| 25x | Azepino[4,5-b]indole, 1,2,3,4,5,6-hexahydro-5,5-diphenyl-3,6-bis(phenylmethyl)- |
| 26x | Azepino[4,5-b]indole, 1,2,3,4,5,6-hexahydro-5,5-diphenyl-6-(phenylmethyl)- |
| 27x | Azepino[4,5-b]indole, 1,2,3,4,5,6-hexahydro-5,6-bis(phenylmethyl)- |
| 28x | Azepino[4,5-b]indole, 1,2,3,4,5,6-hexahydro-5-phenyl-3,6-bis(phenylmethyl)- |
| 29x | Azepino[4,5-b]indole, 1,2,3,4,5,6-hexahydro-5-phenyl-6-(phenylmethyl)- |
| 30x | Azepino[4,5-b]indole, 1,2,3,4,5,6-hexahydro-6-(phenylmethyl)- |
| 31x | Azepino[4,5-b]indole, 1,2,3,4,5,6-hexahydro-6-[(3-methoxyphenyl)methyl]-3-methyl- |
| 32x | Azepino[4,5-b]indole, 10-chloro-1,2,3,4,5,6-hexahydro-3-methyl-6-(phenylmethyl)- |
| 33x | Azepino[4,5-b]indole, 10-chloro-3-ethyl-1,2,3,4,5,6-hexahydro-6-(phenylmethyl)- |
| 34x | Azepino[4,5-b]indole, 3-(1H-benzimidazol-2-ylmethyl)-1,2,3,4,5,6-hexahydro-5-phenyl-6-(phenylmethyl)- |
| 35x | Azepino[4,5-b]indole, 3-(3-chloro-1-oxopropyl)-1,2,3,4,5,6-hexahydro-6-(phenylmethyl)- (9CI) |
| 36x | Azepino[4,5-b]indole, 3-(chloroacetyl)-1,2,3,4,5,6-hexahydro-5-phenyl-6-(phenylmethyl)- |
| 37x | Azepino[4,5-b]indole, 3-ethyl-1,2,3,4,5,6-hexahydro-10-methyl-6-(phenylmethyl)- |
| 38x | Azepino[4,5-b]indole, 3-ethyl-1,2,3,4,5,6-hexahydro-8-methoxy-6-(phenylmethyl)- |
| 39x | Azepino[4,5-b]indole, 3-ethyl-1,2,3,4,5,6-hexahydro-8-methyl-6-(phenylmethyl)- |
| 40x | Azepino[4,5-b]indole, 3-ethyl-1,2,3,4,5,6-hexahydro-9-methyl-6-(phenylmethyl) |
| 41x | Azepino[4,5-b]indole, 6-(1H-benzimidazol-2-ylmethyl)-10-bromo-1,2,3,4,5,6-hexahydro- |
| 42x | Azepino[4,5-b]indole, 6-[(2-chlorophenyl)methyl]-1,2,3,4,5,6-hexahydro-3-methyl- |
| 43x | Azepino[4,5-b]indole, 6-[(4-chlorophenyl)methyl]-3-ethyl-1,2,3,4,5,6-hexahydro- |
| 44x | Azepino[4,5-b]indole, 6-benzyl-1,2,3,4,5,6-hexahydro-3-methyl- |
| 45x | Azepino[4,5-b]indole, 6-benzyl-3-ethyl-1,2,3,4,5,6-hexahydro- |
| 46x | Azepino[4,5-b]indole, 8,9-dichloro-1,2,3,4,5,6-hexahydro-6-(3-phenylpropyl)- |
| 47x | Azepino[4,5-b]indole, 8-chloro-1,2,3,4,5,6-hexahydro-3-methyl-6-(phenylmethyl)- |
| 48x | Azepino[4,5-b]indole, 8-chloro-3-ethyl-1,2,3,4,5,6-hexahydro-6-(phenylmethyl)- |
| 49x | Azepino[4,5-b]indole, 9,10-dichloro-1,2,3,4,5,6-hexahydro-6-(3-phenylpropyl)- |
| 50x | Azepino[4,5-b]indole, 9-chloro-1,2,3,4,5,6-hexahydro-3-methyl-6-(phenylmethyl)- |
| 51x | Azepino[4,5-b]indole, 9-chloro-3-ethyl-1,2,3,4,5,6-hexahydro-6-(phenylmethyl)- |
| 52x | Azepino[4,5-b]indole-3(2H)-carboxylic acid, 1,4,5,6-tetrahydro-6-[2-(phenylamino)ethyl]-, 1,1-dimethylethyl ester |
| 53x | Azepino[4,5-b]indole-3(2H)-carboxylic acid, 1,4,5,6-tetrahydro-6-[2-[(3-methylphenyl)amino]-2-oxoethyl]-, 1,1-dimethylethyl ester |
| 54x | Azepino[4,5-b]indole-3(2H)-carboxylic acid, 1,4,5,6-tetrahydro-6-[2-[(4-methoxyphenyl)amino]-2-oxoethyl]-, 1,1-dimethylethyl ester |
| 55x | Azepino[4,5-b]indole-3(2H)-carboxylic acid, 1,4,5,6-tetrahydro-6-[2-[[(phenylamino)carbonyl]amino]ethyl]-, 1,1-dimethylethyl ester |
| 56x | Azepino[4,5-b]indole-3(2H)-carboxylic acid,1,4,5,6-tetrahydro-6-[2-oxo-2-(phenylamino)ethyl]-, 1,1-dimethylethyl ester |
| 57x | Azepino[4,5-b]indole-3(2H)-carboxylic acid, 1,4,5,6-tetrahydro-6-[2-oxo-2-[(2,4,6-trimethylphenyl)amino]ethyl]-, 1,1-dimethylethyl ester |
| 58x | Azepino[4,5-b]indole-3(2H)-carboxylic acid, 1,4,5,6-tetrahydro-6-[3-[(4-methoxyphenyl)amino]-3-oxopropyl]-, 1,1-dimethylethyl ester |
| 59x | Azepino[4,5-b]indole-3(2H)-carboxylic acid, 10-bromo-1,4,5,6-tetrahydro-6-[2-[(4-methyl-2-thiazolyl)amino]-2-oxoethyl]-, 1,1-dimethylethyl ester |
| 60x | Azepino[4,5-b]indole-3(2H)-carboxylic acid, 6-(1H-benzimidazol-2-ylmethyl)-10-bromo-1,4,5,6-tetrahydro-, 1,1-dimethylethyl ester |
| 61x | Azepino[4,5-b]indole-3(2H)-carboxylic acid, 6-(2-amino-2-oxoethyl)-1,4,5,6-tetrahydro-, 1,1-dimethylethyl ester |
| 62x | Azepino[4,5-b]indole-3(2H)-carboxylic acid, 6-(2-aminoethyl)-1,4,5,6-tetrahydro-, 1,1-dimethylethyl ester |
| 65x | Azepino[4,5-b]indole-3(2H)-carboxylic acid, 6-[2-(benzoylamino)ethyl]-1,4,5,6-tetrahydro-, 1,1-dimethylethyl ester |
| 66x | Azepino[4,5-b]indole-3(2H)-carboxylic acid, 6-[2-(dimethylamino)-2-oxoethyl]-1,4,5,6-tetrahydro-, 1,1-dimethylethyl ester |
| 67x | Azepino[4,5-b]indole-3(2H)-carboxylic acid, 6-[2-[(2,3-dimethylphenyl)amino]-2-oxoethyl]-1,4,5,6-tetrahydro-, 1,1-dimethylethyl ester |
| 68x | Azepino[4,5-b]indole-3(2H)-carboxylic acid, 6-[2-[(2-fluoro-4-methylphenyl)amino]-2-oxoethyl]-1,4,5,6-tetrahydro-, 1,1-dimethylethyl ester |
| 69x | Azepino[4,5-b]indole-3(2H)-carboxylic acid, 7-bromo-1,4,5,6-tetrahydro-6-[2-[(4-methyl-2-thiazolyl)amino]-2-oxoethyl]-, 1,1-dimethylethyl ester |
| 70x | Azepino[4,5-b]indole-3(2H)-carboxylic acid, 8,9-dichloro-1,4,5,6-tetrahydro-6-(3-phenylpropyl)-, 1,1-dimethylethyl ester |
| 71x | Azepino[4,5-b]indole-3(2H)-carboxylic acid, 8,9-dichloro-1,4,5,6-tetrahydro-6-[2-[(4-methoxyphenyl)amino]-2-oxoethyl]-, 1,1-dimethylethyl ester |
| 72x | Azepino[4,5-b]indole-3(2H)-carboxylic acid, 8,9-dichloro-1,4,5,6-tetrahydro-6-[2-oxo-2-(phenylamino)ethyl]-, 1,1-dimethylethyl ester |
| 73x | Azepino[4,5-b]indole-3(2H)-carboxylic acid, 8,9-dichloro-6-[2-[(2,3-dimethylphenyl)amino]-2-oxoethyl]-1,4,5,6-tetrahydro-, 1,1-dimethylethyl ester |

TABLE 1-continued

| Compound No. | Compound Structure |
|---|---|
| 74x | Azepino[4,5-b]indole-3(2H)-carboxylic acid, 9,10-dichloro-1,4,5,6-tetrahydro-6-(3-phenylpropyl)-, 1,1-dimethylethyl ester |
| 75x | Azepino[4,5-b]indole-3(2H)-carboxylic acid, 9,10-dichloro-1,4,5,6-tetrahydro-6-[2-[(4-methoxyphenyl)amino]-2-oxoethyl]-, 1,1-dimethylethyl ester |
| 76x | Azepino[4,5-b]indole-3(2H)-carboxylic acid, 9,10-dichloro-1,4,5,6-tetrahydro-6-[2-oxo-2-(phenylamino)ethyl]-,1,1-dimethylethyl ester |
| 77x | Azepino[4,5-b]indole-3(2H)-carboxylic acid, 9,10-dichloro-6-[2-[(2,3-dimethylphenyl)amino]-2-oxoethyl]-1,4,5,6-tetrahydro-, 1,1-dimethylethyl ester |
| 78x | Azepino[4,5-b]indole-3,6-dicarboxylic acid, 5-[3,3-dimethoxy-2-(methoxycarbonyl)propyl]-1,2,4,5-tetrahydro-, 3,6-bis(1,1-dimethylethyl) ester |
| 80x | Azepino[4,5-b]indole-6(1H)-acetamide, 2,3,4,5-tetrahydro- |
| 81x | Azepino[4,5-b]indole-6(1H)-acetamide, 2,3,4,5-tetrahydro-N,N-dimethyl- |
| 82x | Azepino[4,5-b]indole-6(1H)-acetamide, 2,3,4,5-tetrahydro-N-2-pyridinyl- |
| 83x | Azepino[4,5-b]indole-6(1H)-acetamide, 2,3,4,5-tetrahydro-N-3-pyridinyl- |
| 84x | Azepino[4,5-b]indole-6(1H)-acetamide, 2,3,4,5-tetrahydro-N-phenyl- |
| 85x | Azepino[4,5-b]indole-6(1H)-acetamide, 10-bromo-2,3,4,5-tetrahydro-N-(4-methyl-2-thiazolyl)- |
| 86x | Azepino[4,5-b]indole-6(1H)-acetamide, 2,3,4,5-tetrahydro-N-(2,4,6-trimethylphenyl)- |
| 87x | Azepino[4,5-b]indole-6(1H)-acetamide, 2,3,4,5-tetrahydro-N-(3-methoxyphenyl)- |
| 88x | Azepino[4,5-b]indole-6(1H)-acetamide, 2,3,4,5-tetrahydro-N-(3-methylphenyl)- |
| 89x | Azepino[4,5-b]indole-6(1H)-acetamide, 2,3,4,5-tetrahydro-N-(3-nitrophenyl)- |
| 90x | Azepino[4,5-b]indole-6(1H)-acetamide, 2,3,4,5-tetrahydro-N-(4-methoxyphenyl)- |
| 91x | Azepino[4,5-b]indole-6(1H)-acetamide,2,3,4,5-tetrahydro-N-(4-methyl-2-thiazolyl)- |
| 92x | Azepino[4,5-b]indole-6(1H)-acetamide, 2,3,4,5-tetrahydro-N-(5,6,7,8-tetrahydro-1-naphthalenyl)- |
| 93x | Azepino[4,5-b]indole-6(1H)-acetamide, 2,3,4,5-tetrahydro-N-[2-methyl-3-(trifluoromethyl)phenyl]- |
| 94x | Azepino[4,5-b]indole-6(1H)-acetamide, 7,10-dichloro-2,3,4,5-tetrahydro-N-(4-methyl-2-thiazolyl)- |
| 95x | Azepino[4,5-b]indole-6(1H)-acetamide, 7,10-dichloro-2,3,4,5-tetrahydro-N-(4-phenyl-2-thiazolyl)- |
| 96x | Azepino[4,5-b]indole-6(1H)-acetamide, 7,10-dichloro-2,3,4,5-tetrahydro-N-(5,6,7,8-tetrahydro-1-naphthalenyl)- |
| 97x | Azepino[4,5-b]indole-6(1H)-acetamide, 7,10-dichloro-2,3,4,5-tetrahydro-N-(5-methyl-2-thiazolyl)- |
| 98x | Azepino[4,5-b]indole-6(1H)-acetamide, 7,10-dichloro-2,3,4,5-tetrahydro-N-[3-(1-methylethyl)phenyl]- |
| 99x | Azepino[4,5-b]indole-6(1H)-acetamide, 7,10-dichloro-N-(2,3-dimethylphenyl)-2,3,4,5-tetrahydro- |
| 100x | Azepino[4,5-b]indole-6(1H)-acetamide, 7,10-dichloro-N-(3-ethylphenyl)-2,3,4,5-tetrahydro- |
| 101x | Azepino[4,5-b]indole-6(1H)-acetamide, 7,10-dichloro-N-[3-(1,1-dimethylethyl)phenyl]-2,3,4,5-tetrahydro- |
| 102x | Azepino[4,5-b]indole-6(1H)-acetamide, 7,10-dichloro-N-[4-(1,1-dimethylethyl)-2-thiazolyl]-2,3,4,5-tetrahydro- |
| 103x | Azepino[4,5-b]indole-6(1H)-acetamide, 7,8-dichloro-2,3,4,5-tetrahydro-N-(4-methyl-2-thiazolyl)- |
| 104x | Azepino[4,5-b]indole-6(1H)-acetamide, 7,8-dichloro-2,3,4,5-tetrahydro-N-(4-phenyl-2-thiazolyl)- |
| 105x | Azepino[4,5-b]indole-6(1H)-acetamide, 7,8-dichloro-2,3,4,5-tetrahydro-N-(5,6,7,8-tetrahydro-1-naphthalenyl)- |
| 106x | Azepino[4,5-b]indole-6(1H)-acetamide, 7,8-dichloro-2,3,4,5-tetrahydro-N-(5-methyl-2-thiazolyl)- |
| 107x | Azepino[4,5-b]indole-6(1H)-acetamide, 7,8-dichloro-2,3,4,5-tetrahydro-N-[3-(1-methylethyl)phenyl]- |
| 108x | Azepino[4,5-b]indole-6(1H)-acetamide, 7,8-dichloro-N-(2,3-dimethylphenyl)-2,3,4,5-tetrahydro- |
| 109x | Azepino[4,5-b]indole-6(1H)-acetamide, 7,8-dichloro-N-(3-ethylphenyl)-2,3,4,5-tetrahydro- |
| 110x | Azepino[4,5-b]indole-6(1H)-acetamide, 7,8-dichloro-N-[3-(1,1-dimethylethyl)phenyl]-2,3,4,5-tetrahydro- |
| 111x | Azepino[4,5-b]indole-6(1H)-acetamide, 7,8-dichloro-N-[4-(1,1-dimethylethyl)-2-thiazolyl]-2,3,4,5-tetrahydro- |
| 112x | Azepino[4,5-b]indole-6(1H)-acetamide, 7,9-dichloro-2,3,4,5-tetrahydro-N-(4-methyl-2-thiazolyl)- |
| 113x | Azepino[4,5-b]indole-6(1H)-acetamide, 7,9-dichloro-2,3,4,5-tetrahydro-N-(4-phenyl-2-thiazolyl)- |
| 114x | Azepino[4,5-b]indole-6(1H)-acetamide, 7,9-dichloro-2,3,4,5-tetrahydro-N-(5,6,7,8-tetrahydro-1-naphthalenyl)- |
| 115x | Azepino[4,5-b]indole-6(1H)-acetamide, 7,9-dichloro-2,3,4,5-tetrahydro-N-(5-methyl-2-thiazolyl)- |
| 116x | Azepino[4,5-b]indole-6(1H)-acetamide, 7,9-dichloro-2,3,4,5-tetrahydro-N-[3-(1-methylethyl)phenyl]- |
| 117x | Azepino[4,5-b]indole-6(1H)-acetamide, 7,9-dichloro-N-(2,3-dimethylphenyl)-2,3,4,5-tetrahydro- |

TABLE 1-continued

| Compound No. | Compound Structure |
|---|---|
| 118x | Azepino[4,5-b]indole-6(1H)-acetamide, 7,9-dichloro-N-(3-ethylphenyl)-2,3,4,5-tetrahydro- |
| 119x | Azepino[4,5-b]indole-6(1H)-acetamide, 7,9-dichloro-N-[3-(1,1-dimethylethyl)phenyl]-2,3,4,5-tetrahydro- |
| 120x | Azepino[4,5-b]indole-6(1H)-acetamide, 7,9-dichloro-N-[4-(1,1-dimethylethyl)-2-thiazolyl]-2,3,4,5-tetrahydro- |
| 121x | Azepino[4,5-b]indole-6(1H)-acetamide, 7-bromo-2,3,4,5-tetrahydro-N-(4-methoxyphenyl)- |
| 122x | Azepino[4,5-b]indole-6(1H)-acetamide, 7-bromo-2,3,4,5-tetrahydro-N-(4-methyl-2-thiazolyl)- |
| 123x | Azepino[4,5-b]indole-6(1H)-acetamide, 8,10-dichloro-2,3,4,5-tetrahydro-N-(4-methyl-2-thiazolyl)- |
| 124x | Azepino[4,5-b]indole-6(1H)-acetamide,8,10-dichloro-2,3,4,5-tetrahydro-N-(4-phenyl-2-thiazolyl)- |
| 125x | Azepino[4,5-b]indole-6(1H)-acetamide, 8,10-dichloro-2,3,4,5-tetrahydro-N-(5,6,7,8-tetrahydro-1-naphthalenyl)- |
| 126x | Azepino[4,5-b]indole-6(1H)-acetamide, 8,10-dichloro-2,3,4,5-tetrahydro-N-(5-methyl-2-thiazolyl)- |
| 127x | Azepino[4,5-b]indole-6(1H)-acetamide, 8,10-dichloro-2,3,4,5-tetrahydro-N-[3-(1-methylethyl)phenyl]- |
| 128x | Azepino[4,5-b]indole-6(1H)-acetamide, 8,10-dichloro-N-(2,3-dimethylphenyl)-2,3,4,5-tetrahydro- |
| 129x | Azepino[4,5-b]indole-6(1H)-acetamide,8,10-dichloro-N-(3-ethylphenyl)-2,3,4,5-tetrahydro- |
| 130x | Azepino[4,5-b]indole-6(1H)-acetamide, 8,10-dichloro-N-[3-(1,1-dimethylethyl)phenyl]-2,3,4,5-tetrahydro- |
| 131x | Azepino[4,5-b]indole-6(1H)-acetamide, 8,10-dichloro-N-[4-(1,1-dimethylethyl)-2-thiazolyl]-2,3,4,5-tetrahydro- |
| 132x | Azepino[4,5-b]indole-6(1H)-acetamide, 8,9-dichloro-2,3,4,5-tetrahydro-N-(4-methoxyphenyl)- |
| 133x | Azepino[4,5-b]indole-6(1H)-acetamide, 8,9-dichloro-2,3,4,5-tetrahydro-N-(4-methyl-2-thiazolyl)- |
| 134x | Azepino[4,5-b]indole-6(1H)-acetamide, 8,9-dichloro-2,3,4,5-tetrahydro-N-(4-phenyl-2-thiazolyl)- |
| 135x | Azepino[4,5-b]indole-6(1H)-acetamide, 8,9-dichloro-2,3,4,5-tetrahydro-N-(5,6,7,8-tetrahydro-1-naphthalenyl)- |
| 136x | Azepino[4,5-b]indole-6(1H)-acetamide, 8,9-dichloro-2,3,4,5-tetrahydro-N-(5-methyl-2-thiazolyl)- |
| 137x | Azepino[4,5-b]indole-6(1H)-acetamide, 8,9-dichloro-2,3,4,5-tetrahydro-N-[3-(1-methylethyl)phenyl]- |
| 138x | Azepino[4,5-b]indole-6(1H)-acetamide, 8,9-dichloro-2,3,4,5-tetrahydro-N-phenyl- |
| 139x | Azepino[4,5-b]indole-6(1H)-acetamide, 8,9-dichloro-N-(2,3-dimethylphenyl)-2,3,4,5-tetrahydro- |
| 140x | Azepino[4,5-b]indole-6(1H)-acetamide, 8,9-dichloro-N-(3-ethylphenyl)-2,3,4,5-tetrahydro- |
| 141x | Azepino[4,5-b]indole-6(1H)-acetamide, 8,9-dichloro-N-[3-(1,1-dimethylethyl)phenyl]-2,3,4,5-tetrahydro- |
| 142x | Azepino[4,5-b]indole-6(1H)-acetamide, 8,9-dichloro-N-[4-(1,1-dimethylethyl)-2-thiazolyl]-2,3,4,5-tetrahydro- |
| 143x | Azepino[4,5-b]indole-6(1H)-acetamide, 8-bromo-2,3,4,5-tetrahydro-N-(4-methyl-2-thiazolyl)- |
| 144x | Azepino[4,5-b]indole-6(1H)-acetamide, 9,10-dichloro-2,3,4,5-tetrahydro-N-(4-methoxyphenyl)- |
| 145x | Azepino[4,5-b]indole-6(1H)-acetamide, 9,10-dichloro-2,3,4,5-tetrahydro-N-(4-methyl-2-thiazolyl)- |
| 146x | Azepino[4,5-b]indole-6(1H)-acetamide, 9,10-dichloro-2,3,4,5-tetrahydro-N-(4-phenyl-2-thiazolyl)- |
| 147x | Azepino[4,5-b]indole-6(1H)-acetamide, 9,10-dichloro-2,3,4,5-tetrahydro-N-(5,6,7,8-tetrahydro-1-naphthalenyl)- |
| 148x | Azepino[4,5-b]indole-6(1H)-acetamide, 9,10-dichloro-2,3,4,5-tetrahydro-N-(5-methyl-2-thiazolyl)- |
| 149x | Azepino[4,5-b]indole-6(1H)-acetamide, 9,10-dichloro-2,3,4,5-tetrahydro-N-[3-(1-methylethyl)phenyl]- |
| 150x | Azepino[4,5-b]indole-6(1H)-acetamide, 9,10-dichloro-2,3,4,5-tetrahydro-N-phenyl- |
| 151x | Azepino[4,5-b]indole-6(1H)-acetamide, 9,10-dichloro-N-(2,3-dimethylphenyl)-2,3,4,5-tetrahydro- |
| 152x | Azepino[4,5-b]indole-6(1H)-acetamide,9,10-dichloro-N-(3-ethylphenyl)-2,3,4,5-tetrahydro- |
| 153x | Azepino[4,5-b]indole-6(1H)-acetamide, 9,10-dichloro-N-[3-(1,1-dimethylethyl)phenyl]-2,3,4,5-tetrahydro- |
| 154x | Azepino[4,5-b]indole-6(1H)-acetamide, 9,10-dichloro-N-[4-(1,1-dimethylethyl)-2-thiazolyl]-2,3,4,5-tetrahydro- |
| 155x | Azepino[4,5-b]indole-6(1H)-acetamide, 9-bromo-2,3,4,5-tetrahydro-N-(4-methyl-2-thiazolyl)- |
| 156x | Azepino[4,5-b]indole-6(1H)-acetamide, N-(1,3-dihydro-4-isobenzofuranyl)-2,3,4,5-tetrahydro- |
| 157x | Azepino[4,5-b]indole-6(1H)-acetamide, N-(2,3-dimethylphenyl)-2,3,4,5-tetrahydro- |

TABLE 1-continued

| Compound No. | Compound Structure |
|---|---|
| 158x | Azepino[4,5-b]indole-6(1H)-acetamide, N-(2,4-dimethoxyphenyl)-2,3,4,5-tetrahydro- |
| 159x | Azepino[4,5-b]indole-6(1H)-acetamide, N-(2-fluoro-4-methylphenyl)-2,3,4,5-tetrahydro- |
| 160x | Azepino[4,5-b]indole-6(1H)-acetamide, N-(3,5-dimethoxyphenyl)-2,3,4,5-tetrahydro- |
| 161x | Azepino[4,5-b]indole-6(1H)-acetamide, N-(3-chloro-2-methylphenyl)-2,3,4,5-tetrahydro- |
| 162x | Azepino[4,5-b]indole-6(1H)-acetamide, N-(3-chloro-4-fluorophenyl)-2,3,4,5-tetrahydro- |
| 163x | Azepino[4,5-b]indole-6(1H)-acetamide, N-(4-cyanophenyl)-2,3,4,5-tetrahydro- |
| 164x | Azepino[4,5-b]indole-6(1H)-acetamide, N-(4-fluorophenyl)-2,3,4,5-tetrahydro- |
| 165x | Azepino[4,5-b]indole-6(1H)-acetamide, N-2-benzothiazolyl-7,10-dichloro-2,3,4,5-tetrahydro- |
| 166x | Azepino[4,5-b]indole-6(1H)-acetamide, N-2-benzothiazolyl-7,8-dichloro-2,3,4,5-tetrahydro- |
| 167x | Azepino[4,5-b]indole-6(1H)-acetamide, N-2-benzothiazolyl-7,9-dichloro-2,3,4,5-tetrahydro- |
| 168x | Azepino [4,5-b]indole-6(1H)-acetamide, N-2-benzothiazolyl-8,10-dichloro-2,3,4,5-tetrahydro- |
| 169x | Azepino[4,5-b]indole-6(1H)-acetamide, N-2-benzothiazolyl-8,9-dichloro-2,3,4,5-tetrahydro- |
| 170x | Azepino[4,5-b]indole-6(1H)-acetamide, N-2-benzothiazolyl-9,10-dichloro-2,3,4,5-tetrahydro- |
| 171x | Azepino[4,5-b]indole-6(1H)-acetic acid, 10-bromo-2,3,4,5-tetrahydro-, 2-methylpropyl ester |
| 172x | Azepino[4,5-b]indole-6(1H)-acetic acid, 9,10-dichloro-2,3,4,5-tetrahydro-, ethyl ester |
| 173x | Azepino[4,5-b]indole-6(1H)-ethanamine, 2,3,4,5-tetrahydro- |
| 174x | Azepino[4,5-b]indole-6(1H)-ethanamine, 2,3,4,5-tetrahydro-N-phenyl- |
| 176x | Azepino[4,5-b]indole-6(1H)-propanamide, 2,3,4,5-tetrahydro-N-(4-methoxyphenyl)- |
| 177x | Azepino[4,5-b]indole-6(1H)-propanamine, 2,3,4,5-tetrahydro-N,N,3,9-tetramethyl- |
| 178x | Azepino[4,5-b]indole-6(1H)-propanamine, 2,3,4,5-tetrahydro-N,N,3-trimethyl- |
| 179x | Azepino[4,5-b]indole-6(1H)-propanoic acid, 3-benzoyl-2,3,4,5-tetrahydro-, ethyl ester |
| 180x | Azepino[4,5-b]indole-6-acetic acid, 10-bromo-3-[(1,1-dimethylethoxy)carbonyl]-1,2,4,5-tetrahydro-, ethyl ester |
| 181x | Azepino[4,5-b]indole-6-acetic acid, 10-bromo-3-[(1,1-dimethylethoxy)carbonyl]-1,2,4,5-tetrahydro-, 2-methylpropyl ester |
| 182x | Azepino[4,5-b]indole-6-acetic acid, 3-[(1,1-dimethylethoxy)carbonyl]-1,2,4,5-tetrahydro-, ethyl ester |
| 183x | Azepino[4,5-b]indole-6-acetic acid, 3-[(1,1-dimethylethoxy)carbonyl]-1,2,4,5-tetrahydro-7-nitro-, ethyl ester |
| 184x | Azepino[4,5-b]indole-6-acetic acid, 7,10-dichloro-3-[(1,1-dimethylethoxy)carbonyl]-1,2,4,5-tetrahydro-, ethyl ester |
| 185x | Azepino[4,5-b]indole-6-acetic acid, 7,8-dichloro-3-[(1,1-dimethylethoxy)carbonyl]-1,2,4,5-tetrahydro-, ethyl ester |
| 186x | Azepino[4,5-b]indole-6-acetic acid, 7,9-dichloro-3-[(1,1-dimethylethoxy)carbonyl]-1,2,4,5-tetrahydro-, ethyl ester |
| 187x | Azepino[4,5-b]indole-6-acetic acid, 8,10-dichloro-3-[(1,1-dimethylethoxy)carbonyl]-1,2,4,5-tetrahydro-, ethyl ester |
| 188x | Azepino[4,5-b]indole-6-acetic acid, 8,9-dichloro-3-[(1,1-dimethylethoxy)carbonyl]-1,2,4,5-tetrahydro-, ethyl ester |
| 189x | Azepino[4,5-b]indole-6-acetic acid, 9,10-dichloro-3-[(1,1-dimethylethoxy)carbonyl]-1,2,4,5-tetrahydro-, ethyl ester |
| 190x | Azepino[4,5-b]indole-9-carboxylic acid, 1,2,3,4,5,6-hexahydro-3-methyl-6-(phenylmethyl)-, ethyl ester |
| 191x | Benzamide, N-[2-(2,3,4,5-tetrahydroazepino[4,5-b]indol-6(1H)-yl)ethyl]- |
| 192x | Ethanone, 2-(diethylamino)-1-[1,4,5,6-tetrahydro-5-phenyl-6-(phenylmethyl)azepino[4,5-b]indol-3(2H)-yl]- |
| 193x | Ethanone, 2-[1,2,3,4,5,6-hexahydro-3,6-bis(phenylmethyl)azepino[4,5-b]indol-5-yl]-1-phenyl- |
| 194x | Ethanone, 2-[1,2,3,4,5,6-hexahydro-6-(phenylmethyl)azepino[4,5-b]indol-5-yl]-1-phenyl- |

The invention also embraces compounds of the formula (I) wherein each of m and q is 0 (Formula (Ia)). In another variation, the compound is of the formula (I) wherein each of m and q is 1 (Formula (Ib)). In another variation, the compound is of the formula (I) wherein m=1 and q=0 (Formula (Ic)). In one embodiment, the compound is of the formula (I) wherein m=1, q=0 and $R^{8c}$ and $R^{8e}$ are taken together to form a bond (Formula (C)).

In another variation, the compound is of the formula (I), (Ia), (Ib), (Ic) or (C) or any variation thereof detailed herein where Q is a substituted or unsubstituted cycloalkyl, substituted or unsubstituted cycloalkenyl, or substituted or a unsubstituted heterocyclyl, or a salt or solvate thereof. In one variation, the compound is of the formula (I), (Ia), (Ib), (Ic) or (C) or any variation thereof detailed herein, where Q is a carbocycle, such as a 5, 6 or 7 membered carbocycle. In one variation, the compound is of the formula (I), (Ia), (Ib), (Ic) or (C) or any variation thereof detailed herein, where Q is a heterocycle, such as a 5, 6 or 7 membered carbocycle.

In another variation, the compound is of the formula (I), (Ia), (Ib), (Ic) or (C) or any variation thereof detailed herein where Q is substituted or unsubstituted aryl or a substituted or unsubstituted heteroaryl, or a salt or solvate thereof. In another variation, the compound is of the formula (I), (Ia), (Ib), (Ic) or (C) or any variation thereof detailed herein where Q is substituted or unsubstituted heteroaryl, such as a 5, 6 or 7 membered heteroaryl. In one variation, the compound is of the formula (I), (Ia), (Ib), (Ic) or (C) or any variation thereof detailed herein where Q is a substituted or unsubstituted aryl, such as a 5, 6 or 7 membered aryl, or a salt or solvate thereof.

The invention also includes all salts of compounds referred to herein, such as pharmaceutically acceptable salts. The invention also includes any or all of the stereochemical forms, including any enantiomeric or diastereomeric forms, of the compounds described. Unless stereochemistry is explicitly indicated in a chemical structure or name, the structure or name is intended to embrace all possible stereoisomers, including geometric isomers, of a compound depicted. Unless olefin geometry is explicitly indicated, substituted olefinic bonds may be present as cis or trans or (Z) or (E) isomeric forms, or as mixtures thereof. In addition, where a specific stereochemical form is depicted, it is understood that other stereochemical forms are also embraced by the invention. For example, where only a Z form of a compound is specifically listed, it is understood that the E form of the compound is also embraced. All forms of the compounds are also embraced by the invention, such as crystalline or non-crystalline forms of the compounds. Compositions comprising a compound of the invention are also intended, such as a composition of substantially pure compound, including a specific stereochemical form thereof. Compositions comprising a mixture of compounds of the invention in any ratio are also embraced by the invention, including mixtures of two or more stereochemical forms of a compound of the invention in any ratio, such that racemic, non-racemic, enantioenriched and scalemic mixtures of a compound are embraced.

The invention is also directed to pharmaceutical compositions comprising a compound of the invention and a pharmaceutically acceptable carrier or excipient. Kits comprising a compound of the invention and instructions for use are also embraced by this invention. Compounds as detailed herein or a pharmaceutically acceptable salt thereof are also provided for the manufacture of a medicament for the treatment of a cognitive disorder, psychotic disorder, neurotransmitter-mediated disorder or a neuronal disorder.

The invention also includes all salts of compounds referred to herein, such as pharmaceutically acceptable salts. The invention also includes any or all of the stereochemical forms, including any enantiomeric or diastereomeric forms, and any tautomers or other forms of the compounds described. Unless stereochemistry is explicitly indicated in a chemical structure or name, the structure or name is intended to embrace all possible stereoisomers of a compound depicted. In addition, where a specific stereochemical form is depicted, it is understood that other stereochemical forms are also embraced by the invention. All forms of the compounds are also embraced by the invention, such as crystalline or non-crystalline forms of the compounds. Compositions comprising a compound of the invention are also intended, such as a composition of substantially pure compound, including a specific stereochemical form thereof. Compositions comprising a mixture of compounds of the invention in any ratio are also embraced by the invention, including mixtures of two or more stereochemical forms of a compound of the invention in any ratio, such that racemic, non-racemic, enantioenriched and scalemic mixtures of a compound are embraced.

In one aspect, compounds of the invention are used to treat, prevent, delay the onset and/or delay the development of any one or more of the following: cognitive disorders, psychotic disorders, neurotransmitter-mediated disorders and/or neuronal disorders in individuals in need thereof, such as humans. In one variation, compounds of the invention are used to treat, prevent, delay the onset and/or delay the development of diseases or conditions for which the modulation of an aminergic G protein-coupled receptor is believed to be or is beneficial. In one variation, compounds of the invention are used to treat, prevent, delay the onset and/or delay the development of any one or more of diseases or conditions for which neurite outgrowth and/or neurogenesis and/or neurotrophic effects are believed to be or are beneficial. In another variation, compounds of the invention are used to treat, prevent, delay the onset and/or delay the development of diseases or conditions for which the modulation of an aminergic G protein-coupled receptor and neurite outgrowth and/or neurogenesis and/or neurotrophic effects are believed to be or are beneficial. In one variation, the disease or condition is a cognitive disorder, psychotic disorder, neurotransmitter-mediated disorder and/or a neuronal disorder.

In another aspect, compounds of the invention are used to improve cognitive function and/or reduce psychotic effects in an individual, comprising administering to an individual in need thereof an amount of a compound described herein or a pharmaceutically acceptable salt thereof effective to improve cognitive function and/or reduce psychotic effects.

In a further aspect, compounds of the invention are used to stimulate neurite outgrowth and/or promote neurogenesis and/or enhance neurotrophic effects in an individual comprising administering to an individual in need thereof an amount of a compound described herein or a pharmaceutically acceptable salt thereof effective to stimulate neurite outgrowth and/or to promote neurogenesis and/or to enhance neurotrophic effects. Synapse loss is associated with a variety of neurodegenerative diseases and conditions including Alzheimer's disease, schizophrenia, Huntington's disease, Parkinson's disease, amyotrophic lateral sclerosis, stroke, head trauma and spinal cord injury. Compounds of the invention that stimulate neurite outgrowth may have a benefit in these settings.

In another aspect, compounds described herein are used to modulate an aminergic G protein-coupled receptor comprising administering to an individual in need thereof an amount of a compound described herein or a pharmaceutically acceptable salt thereof effective to modulate an aminergic G protein-coupled receptor. In one variation, a compound of the invention modulates at least one of the following receptors: adrenergic receptor (e.g., $\alpha_{1D}$, $\alpha_{2A}$ and/or $\alpha_{2B}$), serotonin receptor (e.g., 5-$HT_{2A}$, 5-$HT_{2C}$, 5-$HT_6$ and/or 5-$HT_7$), dopamine receptor (e.g., $D_{2L}$) and histamine receptor (e.g., $H_1$, $H_2$ and/or $H_3$). In another variation, at least two of the following receptors are modulated: adrenergic receptor (e.g., $\alpha_{1D}$, $\alpha_{2A}$ and/or $\alpha_{2B}$), serotonin receptor (e.g., 5-$HT_{2A}$, 5-$HT_{2C}$, 5-$HT_6$ and/or 5-$HT_7$), dopamine receptor (e.g., $D_{2L}$) and histamine receptor (e.g., $H_1$, $H_2$ and/or $H_3$). In another variation, at least three of the following receptors are modulated: adrenergic receptor (e.g., $\alpha_{1D}$, $\alpha_{2A}$ and/or $\alpha_{2B}$), serotonin receptor (e.g., 5-$HT_{2A}$, 5-$HT_{2C}$, 5-$HT_6$ and/or 5-$HT_7$), dopamine receptor (e.g., $D_{2L}$) and histamine receptor (e.g., $H_1$, $H_2$ and/or $H_3$). In another variation, each of the following receptors is modulated: adrenergic receptor (e.g., $\alpha_{1D}$, $\alpha_{2A}$ and/or $\alpha_{2B}$), serotonin receptor (e.g., 5-$HT_{2A}$, 5-$HT_{2C}$, 5-$HT_6$ and/or 5-$HT_7$), dopamine receptor (e.g., $D_{2L}$) and histamine receptor (e.g., $H_1$, $H_2$ and/or $H_3$). In another variation, at least one of the following receptors is modulated: a1D, a2A, a2B, 5-HT2A, 5-HT2C, 5-HT6, 5-HT7, $D_2$, H1, H2 and H3. In another variation, at least one of the following receptors is modulated: $\alpha_{1D}$, $\alpha_{2A}$, $\alpha_{2B}$, 5-$HT_{2A}$, 5-$HT_{2C}$, 5-$HT_6$, 5-$HT_7$, $D_{2L}$, $H_1$, $H_2$ and $H_3$. In another variation, at least two or three or four or five or six or seven or eight or nine or ten or eleven of the following receptors are modulated: a1D, a2A, a2B, 5-HT2A, 5-HT2C, 5-HT6, 5-HT7, $D_2$, H1, H2 and H3. In another variation, at least two or three or four or five or six or seven or eight or nine or ten or eleven of the following receptors are modulated: $\alpha_{1D}$, $\alpha_{2A}$, $\alpha_{2B}$, 5-$HT_{2A}$, 5-$HT_{2C}$, 5-$HT_6$, 5-$HT_7$, $D_{2L}$, $H_1$, $H_2$ and $H_3$. In still another variation, at least dopamine receptor $D_{2L}$ is modulated. In another particular variation, at least dopamine receptor $D_2$ and serotonin receptor 5-HT2A are modulated. In a particular variation, at least dopamine receptor $D_{2L}$ is modulated. In another particular variation, at least dopamine receptor $D_{2L}$ and serotonin receptor 5-$HT_{2A}$ are modulated. In a further particular variation, at least adrenergic receptors $\alpha_{1D}$, $\alpha_{2A}$, $\alpha_{2B}$ and serotonin receptor 5-$HT_6$ are modulated. In another particular variation, at least adrenergic receptors $\alpha_{1D}$, $\alpha_{2A}$, $\alpha_{2B}$, serotonin receptor 5-$HT_6$ and one or more of serotonin receptor 5-$HT_7$, 5-$HT_{2A}$, 5-$HT_{2C}$ and histamine receptor $H_1$ and $H_2$ are modulated. In a further particular variation, histamine receptor $H_1$ is modulated. In another variation, compounds of the invention exhibit any receptor modulation activity detailed herein and further stimulate neurite outgrowth and/or neurogenesis and/or enhance neurotrophic effects. In one variation, compounds detailed herein inhibit binding of a ligand to histamine receptor $H_1$ and/or $H_2$ by less than about 80% as determined by a suitable assay known in the art such as the assays described herein. In another variation, binding of a ligand to histamine receptor $H_1$ and/or $H_2$ is inhibited by less than about any of 75%, 70%, 65%, 60%, 55%, or 50% as determined by a suitable assay known in the art such as the assays described herein. In a further variation, compounds detailed herein: (a) inhibit binding of a ligand to histamine receptor $H_1$ and/or $H_2$ by less than about 80% (which can in different variations be less than about any of 75%, 70%, 65%, 60%, 55%, or 50%) as determined by a suitable assay known in the art such as the assays described herein and (b) inhibit binding of a ligand to dopamine receptor $D_{2L}$ by greater than about any of 80%, 85%, 90%, 95%, 100% or between about 85% and about 95% or between about 90% and about 100%, as determined in a suitable assay known in the art such as the assays described herein. In a further variation, compounds detailed herein: (a) inhibit binding of a ligand to histamine receptor H1 and/or H2 by less than about 80% (which can in different variations be less than about any of 75%, 70%, 65%, 60%, 55%, or 50%) as determined by a suitable assay known in the art such as the assays described herein and (b) inhibit binding of a ligand to a dopamine receptor $D_2$ by greater than about any of 80%, 85%, 90%, 95%, 100% or between about 85% and about 95% or between about 90% and about 100%, as determined in a suitable assay known in the art such as the assays described herein.

The invention is also directed to pharmaceutical compositions comprising a compound of the invention and a pharmaceutically acceptable carrier or excipient. Kits comprising a compound of the invention and instructions for use are also embraced by this invention.

Compounds of the formula (I) are provided:

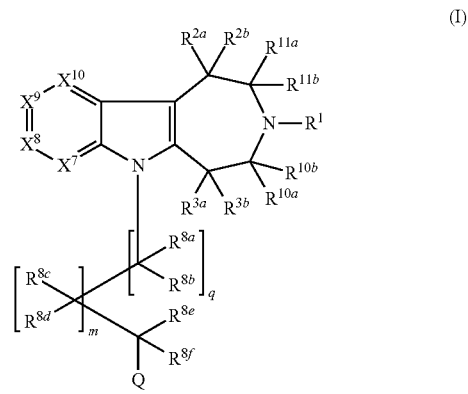

where:

$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy;

each $R^{2a}$, $R^{2b}$, $R^{3a}$ and $R^{3b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^2$ or $R^3$ to form a cycloalkyl moiety or a carbonyl moiety;

each $R^{10a}$, $R^{10b}$, $R^{11a}$ and $R^{11b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^{10}$ or $R^{11}$ to form a cycloalkyl moiety or a carbonyl moiety;

each $X^7$, $X^8$, $X^9$ and $X^{10}$ is independently N or $CR^4$;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each m and q is independently 0 or 1;

each $R^{8a}$, $R^{8b}$, $R^{8c}$, $R^{8d}$, $R^{8e}$ and $R^{8f}$ is independently H, hydroxyl, alkoxy, halo, $C_1$-$C_8$ perhaloalkyl, carboxy, carbonylalkoxy, substituted or unsubstituted aryl, substituted or unsubstituted heteroaryl, substituted or unsubstituted $C_1$-$C_8$ alkyl, substituted or unsubstituted $C_3$-$C_6$ cycloalkyl, substituted or unsubstituted $C_2$-$C_8$ alkenyl, or is taken together with a geminal $R^8$ to form a moiety of the formula —OCH$_2$CH$_2$O—, is taken together with the carbon to which it is attached and a geminal $R^8$ to form a cycloalkyl moiety or a carbonyl moiety, is taken together with a geminal $R^8$ to form a methylene or a substituted methylene, is taken together with a vicinal $R^8$ and the carbon atoms to which they are attached to form a substituted or unsubstituted $C_3$-$C_8$ cycloalkyl, substituted or unsubstituted $C_3$-$C_8$ cycloalkenyl or substituted or unsubstituted heterocyclyl moiety or is taken together with a vicinal $R^8$ to form a bond, provided when an $R^8$ is taken together with a vicinal $R^8$ to form a bond, the geminal $R^8$ is other than hydroxyl;

Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted amino, alkoxy, aminoacyl, acyloxy, carbonylalkoxy, aminocarbonylalkoxy, acylamino, carboxy, cyano or alkynyl;

or a salt or solvate thereof. In one aspect, compounds are of the formula (I) where, if applicable, any one or more of the following apply: $X^7$, $X^8$, $X^9$ and $X^{10}$ are $CR^4$; at least one of $X^7$, $X^8$, $X^9$ and $X^{10}$ is N; at least two of $X^7$, $X^8$, $X^9$ and $X^{10}$ are N; two of $X^7$, $X^8$, $X^9$ and $X^{10}$ are N and two of $X^7$, $X^8$, $X^9$ and $X^{10}$ are $CR^4$; one of $X^7$, $X^8$, $X^9$ and $X^{10}$ is N and three of $X^7$, $X^8$, $X^9$ and $X^{10}$ are $CR^4$; if present, each $R^4$ is independently H, halo, substituted or unsubstituted $C_1$-$C_8$ alkyl, $C_1$-$C_8$ perhaloalkyl, substituted or unsubstituted heterocyclyl or a substituted or unsubstituted aryl; if present, each $R^4$ is independently H or a substituted or unsubstituted $C_1$-$C_8$ alkyl; if present, each $R^4$ is H; if present, each $R^4$ is independently H, halo, unsubstituted $C_1$-$C_4$ alkyl, $C_1$-$C_4$ perhaloalkyl or a substituted or unsubstituted aryl; if present, each $R^4$ is independently H, halo, methyl, trifluoromethyl or cyclopropyl; $X^7$, $X^8$, $X^9$ and $X^{10}$ are taken together to provide an aromatic moiety selected from the group consisting of:

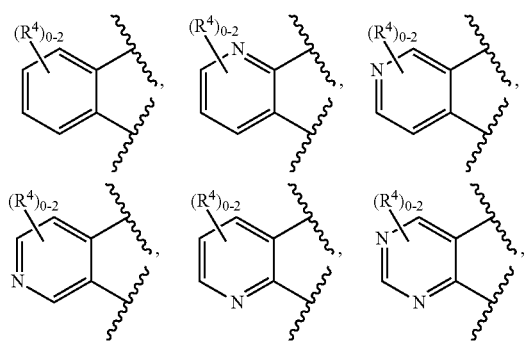

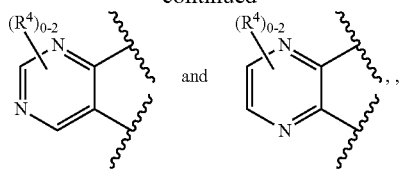

wherein each $R^4$ is independently hydroxyl, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, substituted or unsubstituted heterocyclyl, substituted or unsubstituted aralkyl, thioalkyl, substituted or unsubstituted amino, alkylsulfonylamino or acyl; $X^7$, $X^8$, $X^9$ and $X^{10}$ are taken together provide an aromatic moiety selected from the group consisting of:

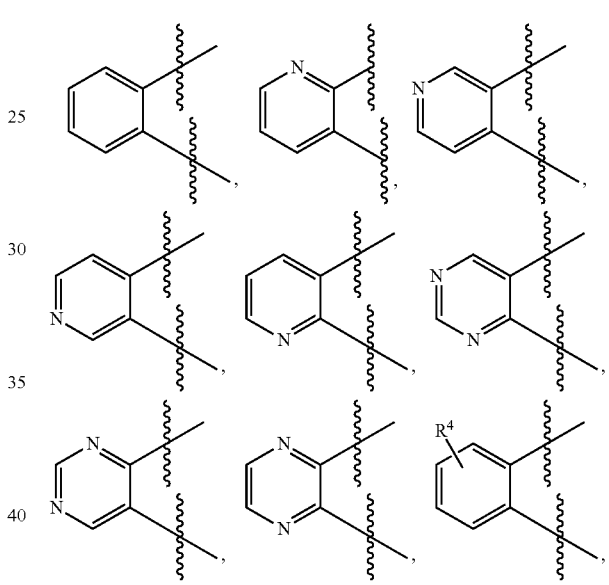

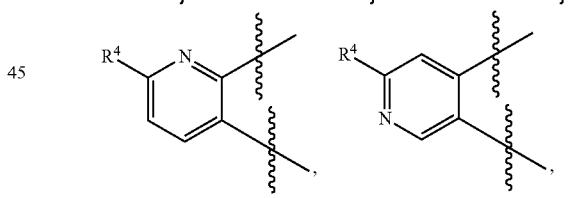

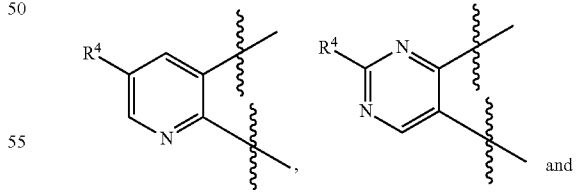

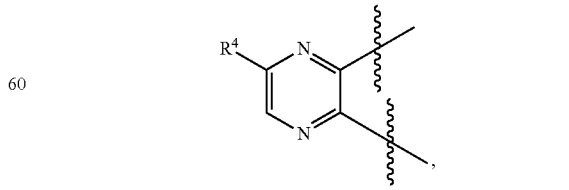

wherein $R^4$ is hydroxyl, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, substituted or unsubstituted heterocyclyl, substituted or unsubstituted aralkyl, thioalkyl, substituted or unsubstituted amino, alkylsulfonylamino or acyl; if present, each $R^4$ is independently halo, unsubstituted $C_1$-$C_4$ alkyl or $C_1$-$C_4$ perhaloalkyl; $R^1$ is H, substituted or unsubstituted $C_1$-$C_8$ alkyl, acyl, acyloxy, carbonylalkoxy, substituted or unsubstituted heterocyclyl, substituted or unsubstituted aryl, substituted or unsubstituted heteroaryl, substituted or unsubstituted aralkyl; $R^1$ is a substituted or unsubstituted $C_1$-$C_8$ alkyl, acyl, acyloxy, carbonylalkoxy, substituted or unsubstituted heterocyclyl or substituted or unsubstituted aryl; $R^1$ is methyl, ethyl, cyclopropyl, propylate, trifluoromethyl, isopropyl, tert-butyl, sec-butyl, 2-methylbutyl, propanal, 1-methyl-2-hydroxyethyl, 2-hydroxyethanal, 2-hydroxyethyl, 2-hydroxypropyl, 2-hydroxy-2-methylpropyl, cyclobutyl, cyclopentyl, cyclohexyl, substituted phenyl, piperidin-4-yl, hydroxycyclopent-3-yl, hydroxycyclopent-2-yl, hydroxycycloprop-2-yl, 1-hydroxy-1-methylcycloprop-2-yl, or 1-hydroxy-1,2,2-trimethyl-cycloprop-3-yl; each $R^{2a}$ and $R^{2b}$ is independently H, substituted or unsubstituted $C_1$-$C_8$ alkyl, halo, cyano, nitro or $R^{2a}$ and $R^{2b}$ are taken together to form a carbonyl moiety; and each $R^{3a}$ and $R^{3b}$ is independently H, substituted or unsubstituted $C_1$-$C_8$ alkyl, halo, cyano or nitro; each $R^{2a}$ and $R^{2b}$ is independently H, unsubstituted $C_1$-$C_8$ alkyl, halo or $R^{2a}$ and $R^{2b}$ are taken together to form a carbonyl moiety; each $R^{3a}$ and $R^{3b}$ is independently H, unsubstituted $C_1$-$C_8$ alkyl, halo or $R^{3a}$ and $R^{3b}$ are taken together to form a carbonyl moiety; each $R^{2a}$ and $R^{2b}$ is independently H, methyl, halo or $R^{2a}$ and $R^{2b}$ are taken together to form a carbonyl moiety; each $R^{3a}$ and $R^{3b}$ is independently H, methyl, halo or $R^{3a}$ and $R^{3b}$ are taken together to form a carbonyl moiety; each of $R^{2a}$, $R^{2b}$, $R^{3a}$ and $R^{3b}$ is H; n at least one of $R^{2a}$, $R^{2b}$, $R^{3a}$ and $R^{3b}$ is a substituted or unsubstituted $C_1$-$C_8$ alkyl, halo, cyano, nitro or is taken together with the carbon to which it is attached and a geminal $R^2$ or $R^3$ to form a carbonyl moiety; at least two of $R^{2a}$, $R^{2b}$, $R^{3a}$ and $R^{3b}$ is a substituted or unsubstituted $C_1$-$C_8$ alkyl, halo, cyano, nitro or is taken together with the carbon to which it is attached and a geminal $R^2$ or $R^3$ to form a carbonyl moiety; at least one of $R^{2a}$, $R^{2b}$, $R^{3a}$ and $R^{3b}$ is fluoro, methyl or is taken together with the carbon to which it is attached and a geminal $R^2$ or $R^3$ to form a carbonyl moiety; either $R^{2a}$ and $R^{2b}$ or $R^{3a}$ and $R^{3b}$ are each methyl, fluoro or are taken together with the carbon to which it is attached and a geminal $R^2$ or $R^3$ to form a carbonyl moiety; each $R^{10a}$, $R^{10b}$, $R^{11a}$ and $R^{11b}$ is independently H, halo, an unsubstituted $C_1$-$C_8$ alkyl, hydroxyl or $R^{11a}$ and $R^{11b}$ are taken together with the carbon to which they are attached to form a carbonyl or $R^{11a}$ and $R^{11b}$ are taken together with the carbon to which they are attached to form a carbonyl; each $R^{10a}$, $R^{10b}$, $R^{11a}$ and $R^{11b}$ is independently H, halo, an unsubstituted $C_1$-$C_4$ alkyl, hydroxyl or $R^{11a}$ and $R^{11b}$ are taken together with the carbon to which they are attached to form a carbonyl or $R^{11a}$ and $R^{11b}$ are taken together with the carbon to which they are attached to form a carbonyl; each $R^{10a}$, $R^{10b}$, $R^{11a}$ and $R^{11b}$ is independently H, bromo, methyl, hydroxyl or $R^{10a}$ and $R^{10b}$ are taken together with the carbon to which they are attached to form a carbonyl or $R^{11a}$ and $R^{11b}$ are taken together with the carbon to which they are attached to form a carbonyl; at least one of $R^{10}$, $R^{10b}$, $R^{11a}$ and $R^{11b}$ is an unsubstituted $C_1$-$C_8$ alkyl, hydroxyl, halo or $R^{10a}$ and $R^{10b}$ are taken together with the carbon to which they are attached to form a carbonyl or $R^{11a}$ and $R^{11b}$ are taken together with the carbon to which they are attached to form a carbonyl; at least one of $R^{10}$, $R^{10b}$, $R^{11a}$ and $R^{11b}$ is methyl, bromo, hydroxyl or $R^{10a}$ and $R^{10b}$ are taken together with the carbon to which they are attached to form a carbonyl or $R^{11a}$ and $R^{11b}$ are taken together with the carbon to which they are attached to form a carbonyl; both $R^{10a}$ and $R^{10b}$ are methyl or both $R^{11a}$ and $R^{11b}$ are methyl; $R^{10a}$ and $R^{10b}$ are taken together with the carbon to which they are attached to form a carbonyl or $R^{11a}$ and $R^{11b}$ are taken together with the carbon to which they are attached to form a carbonyl; $R^{10a}$ is H and $R^{10b}$ is methyl or bromo; the carbon bearing $R^{10a}$ and $R^{10b}$ is in the R configuration or the S configuration; $R^{11a}$ is H and $R^{11b}$ is methyl; the carbon bearing $R^{11a}$ and $R^{11b}$ is in the R configuration or the S configuration; $R^1$, $R^{2a}$, $R^{2b}$, $R^{3a}$, $R^{3b}$, $R^{10a}$, $R^{11a}$ and $R^{11b}$ are taken together to form a ring selected from the group consisting of:

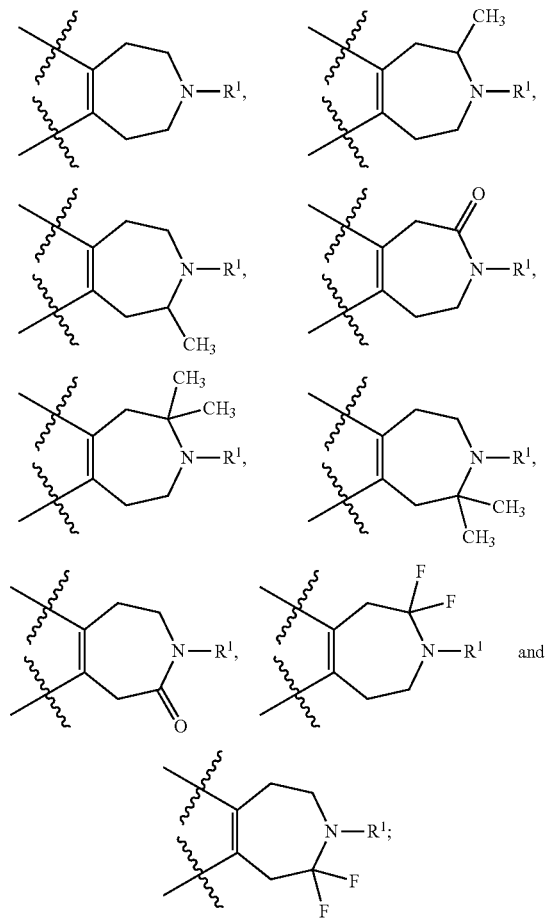

each $R^{8a}$, $R^{8b}$, $R^{8c}$, $R^{8d}$, $R^{8e}$ and $R^{8f}$ is independently H, hydroxyl, unsubstituted $C_1$-$C_4$ alkyl or is taken together with the carbon to which it is attached and a geminal $R_8$ to form a cycloalkyl moiety; each $R^{8a}$, $R^{8b}$, $R^{8c}$, $R^{8d}$, $R^{8e}$ and $R^{8f}$ is independently H, hydroxyl, methyl or is taken together with the carbon to which it is attached and a geminal $R_8$ to form a cyclopropyl moiety; at least one of $R^{8a}$, $R^{8b}$, $R^{8c}$, $R^{8d}$, $R^{8e}$ and $R^{8f}$ is taken together with a geminal $R^8$ to form a methylene or a substituted methylene; at least one of $R^{8a}$, $R^{8b}$, $R^{8c}$, $R^{8d}$, $R^{8e}$ and $R^{8f}$ is taken together with a vicinal $R^8$ to form a bond; q is 0 and m is 1; q and m are both 0; q, m, $R^{8a}$, $R^{8b}$, $R^{8c}$, $R^{8d}$, $R^{8e}$ and $R^{8f}$ are taken together to form a moiety selected from the group consisting of:

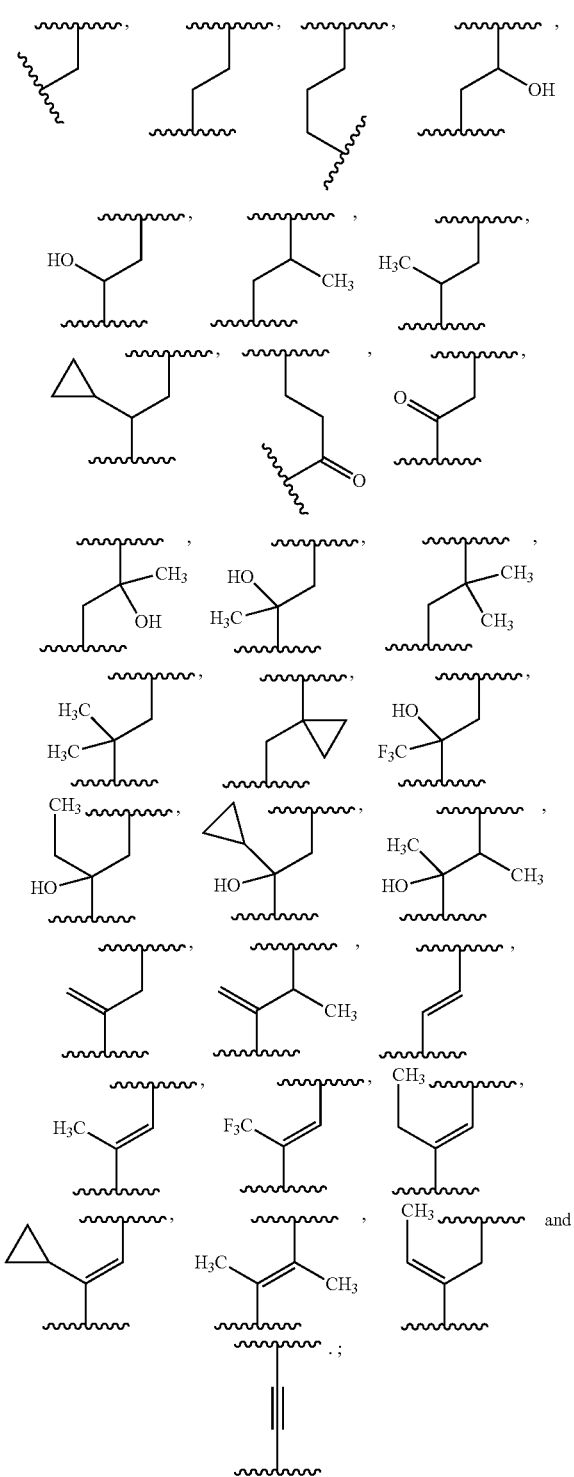

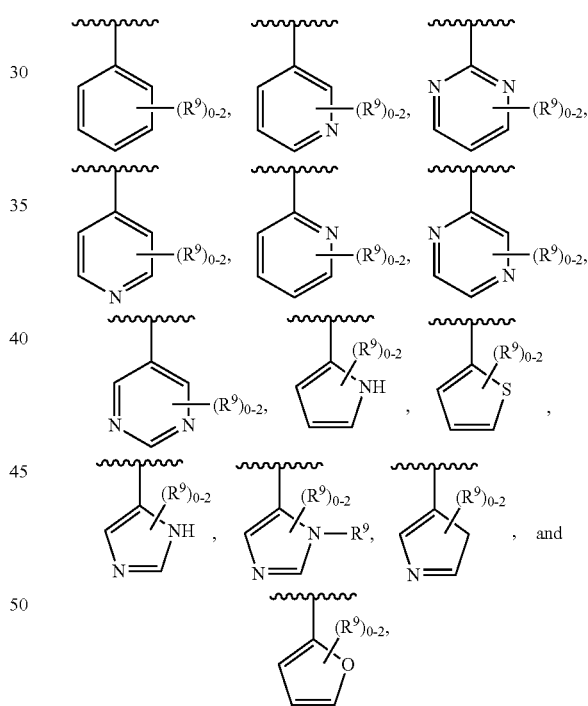

$R^1$ is a substituted or unsubstituted $C_1$-$C_8$ alkyl, acyl, acyloxy, carbonylalkoxy, substituted or unsubstituted heterocyclyl or substituted or unsubstituted aryl; each $R^{2a}$ and $R^{2b}$ is independently H, methyl, fluoro or $R^{2a}$ and $R^{2b}$ are taken together to form a carbonyl moiety; each $R^{3a}$ and $R^{3b}$ is independently H or fluoro; each $R^{10a}$ and $R^{10b}$ is independently H, fluoro or methyl or $R^{10a}$ and $R^{10b}$ are taken together to form a carbonyl; each $R^{11a}$ and $R^{11b}$ is independently H, fluoro or methyl or $R^{10a}$ and $R^{10b}$ are taken together to form a carbonyl; Q is a substituted or unsubstituted aryl; Q is a substituted or unsubstituted pyridyl, phenyl, pyrimidinyl, pyrazinyl, imidazolyl, furanyl, pyrrolyl or thiophenyl group; Q is a substituted or unsubstituted phenyl or pyridyl group; Q is a phenyl or pyridyl group substituted with at least one methyl group; Q is a pyridyl, phenyl, pyrimidinyl, pyrazinyl, imidazolyl, furanyl, pyrrolyl or thiophenyl group substituted with at least one substituted or unsubstituted $C_1$-$C_8$ alkyl, halo or perhaloalkyl moiety; Q is a substituted or unsubstituted cycloalkyl or a substituted or unsubstituted heterocyclyl; Q is a substituted or unsubstituted pyridyl, phenyl, pyrazinyl, piperazinyl, pyrrolidinyl or thiomorpholinyl group; Q is a pyridyl, phenyl, pyrazinyl, piperazinyl, pyrrolidinyl or thiomorpholinyl group substituted with at least one methyl or halo group; Q is an unsubstituted cycloalkyl or an unsubstituted heterocyclyl; Q is a substituted or unsubstituted cyclohexyl, morpholinyl, piperazinyl, thiomorpholinyl, cyclopentyl or pyrrolidinyl moiety; Q is a substituted cyclohexyl, morpholinyl, piperazinyl, thiomorpholinyl, cyclopentyl or pyrrolidinyl moiety substituted with at least one carbonyl, hydroxymethyl, methyl or hydroxyl group; Q is selected from the group consisting of:

wherein each $R^9$ is independently a halo, cyano, nitro, perhaloalkyl, perhaloalkoxy, substituted or unsubstituted $C_1$-$C_8$ alkyl, substituted or unsubstituted $C_2$-$C_8$ alkenyl, substituted or unsubstituted $C_2$-$C_8$ alkynyl, acyl, acyloxy, carbonylalkoxy, thioalkyl, substituted or unsubstituted heterocyclyl, alkoxy, substituted or unsubstituted amino, acylamino, sulfonylamino, sulfonyl, aminoacyl or aminocarbonylamino; Q is substituted with no more than one $R^9$ group; Q is substituted with only one $R^9$ group; Q is selected from the group consisting of:

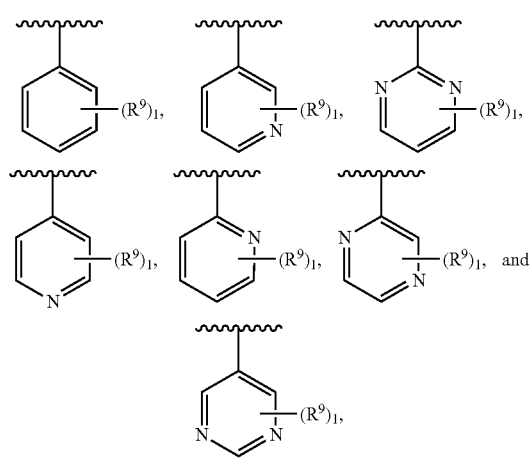

and wherein R⁹ is connected to Q ortho or para to the position at which Q is connected to the carbon bearing $R^{8e}$ and $R^{8f}$; Q is

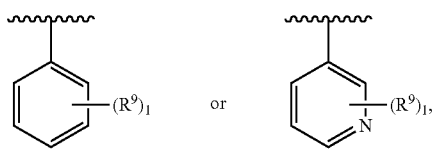

and
$R^9$ is connected to Q para to the position at which Q is connected to the carbon bearing $R^{8e}$ and $R^{8f}$;
Q is substituted with two $R^9$ groups; Q is selected from the group consisting of:

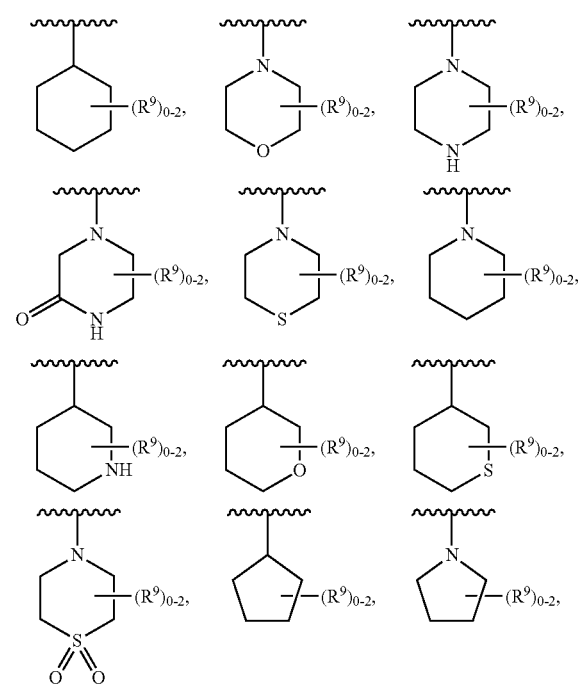

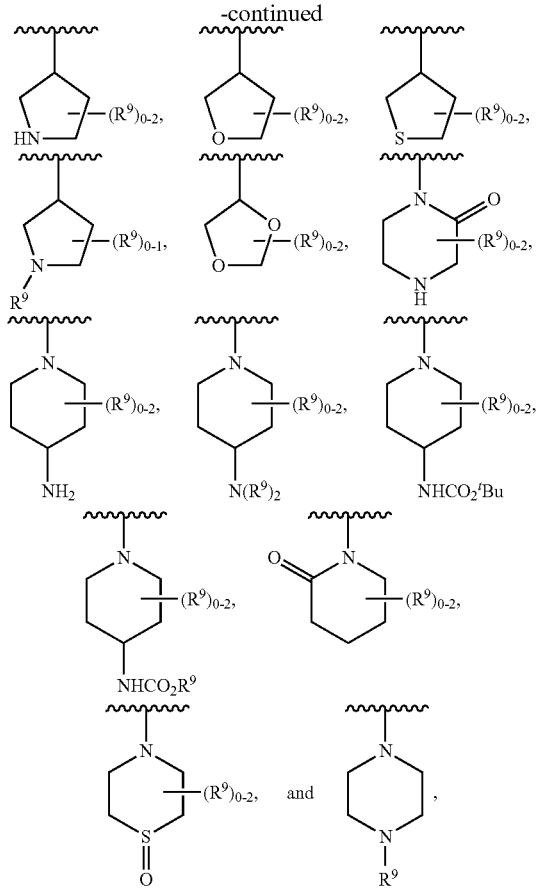

wherein each $R^9$ is independently a halo, cyano, nitro, perhaloalkyl, perhaloalkoxy, substituted or unsubstituted $C_1$-$C_8$ alkyl, substituted or unsubstituted $C_2$-$C_8$ alkenyl, substituted or unsubstituted $C_2$-$C_8$ alkynyl, acyl, acyloxy, carbonylalkoxy, thioalkyl, alkoxy, substituted or unsubstituted amino, acylamino, sulfonylamino, sulfonyl, aminoacyl or aminocarbonylamino; Q is substituted with no more than one $R^9$ group; Q is substituted with only one $R^9$ group; Q is substituted with two $R^9$ groups; each $R^9$ is independently a substituted or unsubstituted $C_1$-$C_4$ alkyl, halo, trifluoromethyl or hydroxyl; each $R^9$ is independently methyl, —CH₂OH, isopropyl, halo, trifluoromethyl or hydroxyl; Q is selected from the group consisting of:

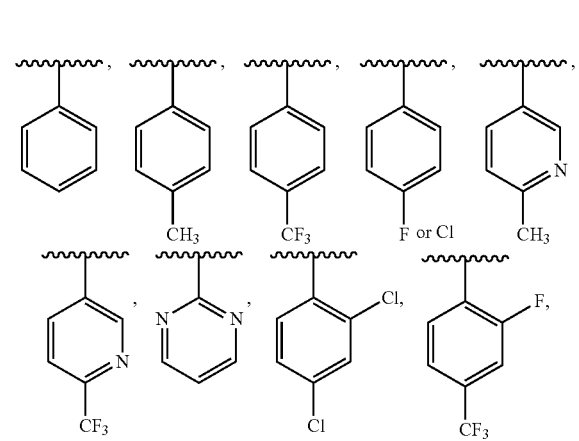

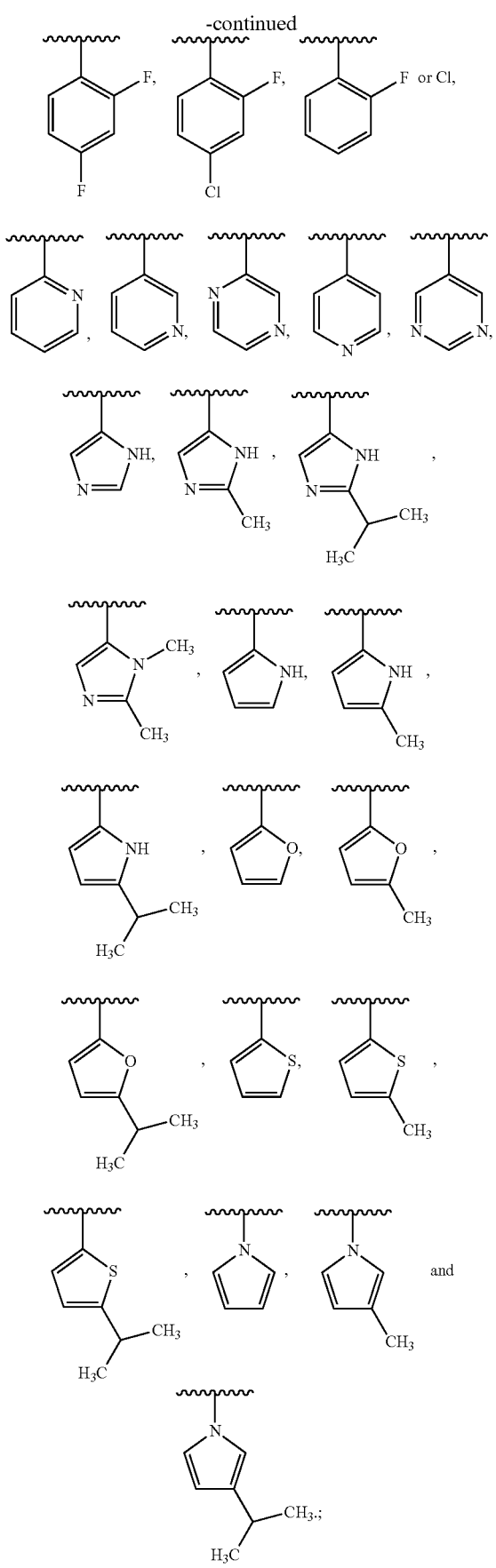
Q is selected from the group consisting of:
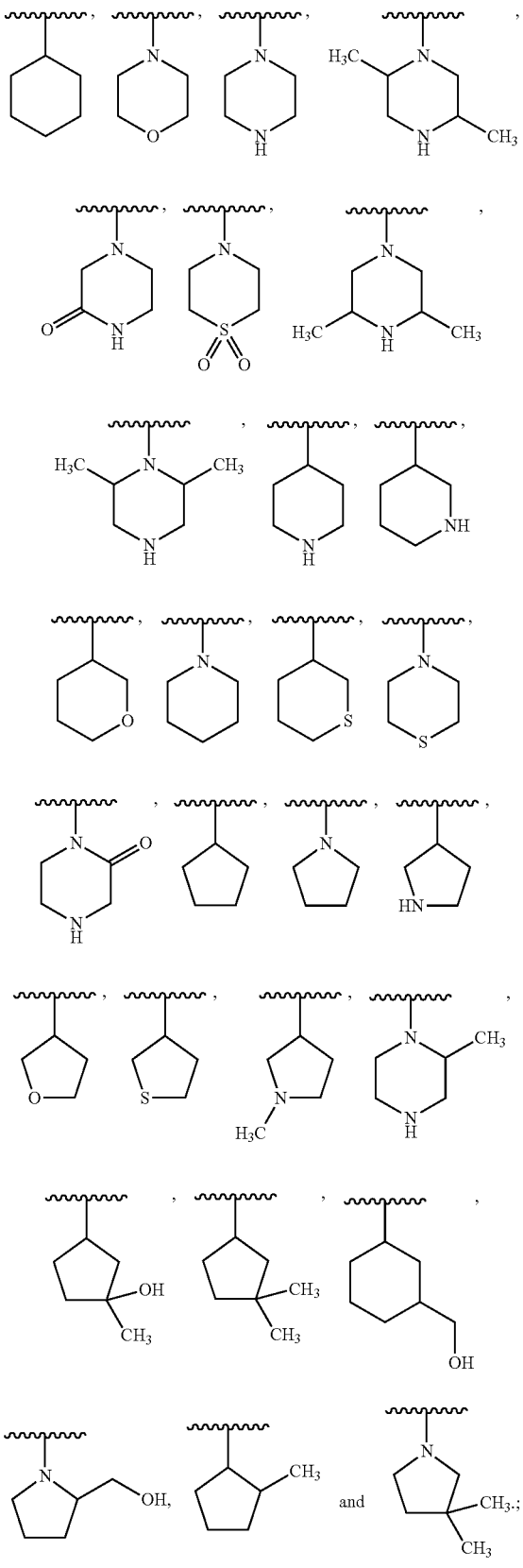

Q is selected from the group consisting of:

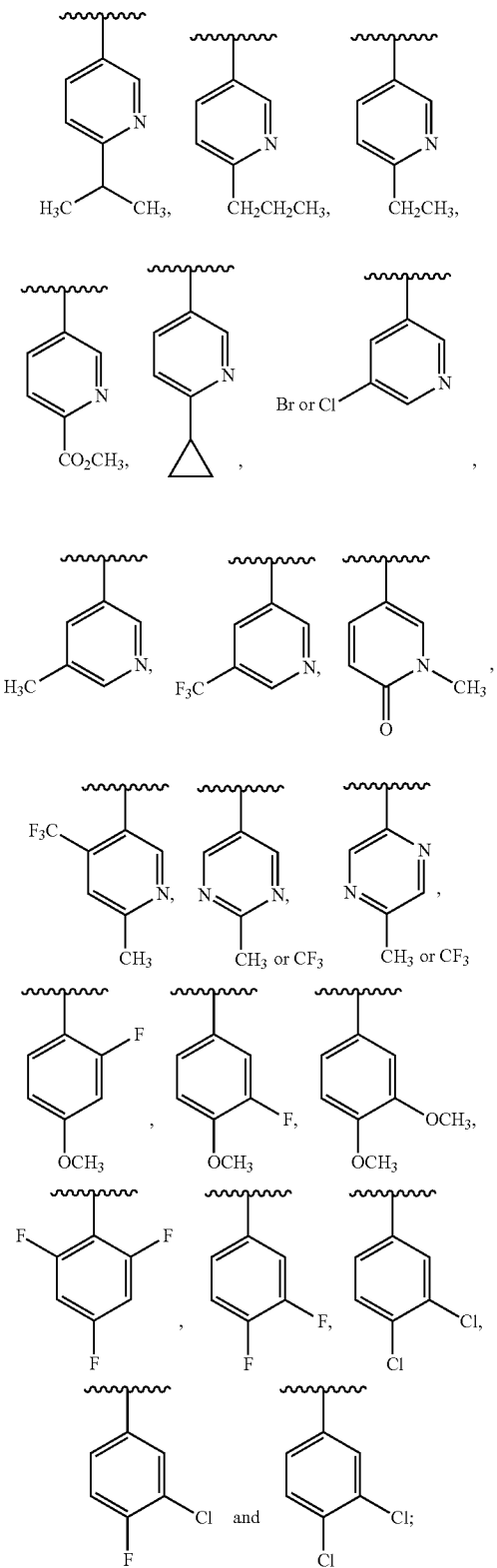

Q is substituted or unsubstituted amino, alkoxy, aminoacyl, acyloxy, carbonylalkoxy, aminocarbonylalkoxy or acylamino; Q is selected from the group consisting of:

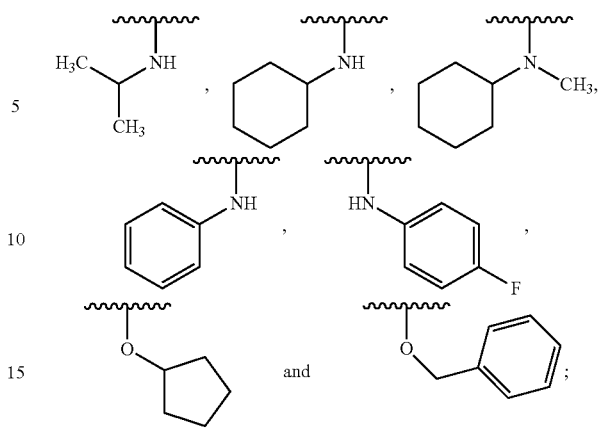

$R^1$ is an unsubstituted alkyl; $R^{2a}$, $R^{2b}$, $R^{3a}$, $R^{3b}$, $R^{10a}$, $R^{10b}$, $R^{11a}$ and $R^{11b}$ are each H; each $X^7$, $X^8$, $X^9$ and $X^{10}$ is independently N or CH; each $R^{8a}$, $R^{8b}$, $R^{8c}$, $R^{8d}$, $R^{8e}$ and $R^{8f}$ is independently H, $C_1$-$C_4$ alkyl or hydroxyl; Q is a substituted or unsubstituted aryl; $R^1$ is an unsubstituted alkyl; $R^{2a}$, $R^{2b}$, $R^{3a}$, $R^{3b}$, $R^{10a}$, $R^{10b}$, $R^{11a}$ and $R^{11b}$ are each H; each $X^7$, $X^8$, $X^9$ and $X^{10}$ is independently N or CH; each $R^{8a}$, $R^{8b}$, $R^{8c}$, $R^{8d}$, $R^{8e}$ and $R^{8f}$ is independently H or $C_1$-$C_4$ alkyl or is taken together with a geminal $R^8$ to form a methylene or a substituted methylene; Q is a substituted or unsubstituted aryl; at least one of $R^{8a}$, $R^{8b}$, $R^{8c}$, $R^{8d}$, $R^{8e}$ and $R^{8f}$ is taken together with a geminal $R^8$ to form a methylene or a substituted methylene; $R^{2a}$, $R^{2b}$, $R^{3a}$, $R^{3b}$, $R^{10a}$, $R^{10b}$, $R^{11a}$ and $R^{11b}$ are each H; each $X^7$, $X^8$, $X^9$ and $X^{10}$ is independently N or CH; each $R^{8a}$, $R^{8b}$, $R^{8c}$, $R^{8d}$, $R^{8e}$ and $R^{8f}$ is independently H or $C_1$-$C_4$ alkyl or is taken together with a vicinal $R^8$ to form a bond; Q is a substituted or unsubstituted aryl; at least one of $R^{8a}$, $R^{8b}$, $R^{8c}$, $R^{8d}$, $R^{8e}$ and $R^{8f}$ is taken together with a vicinal $R^8$ to form a bond; Q is a substituted or unsubstituted phenyl or pyridyl group; Q is a phenyl or pyridyl group substituted with at least one methyl group; $R^1$ is a substituted or unsubstituted $C_1$-$C_8$ alkyl, acyl, acyloxy, carbonylalkoxy, substituted or unsubstituted heterocyclyl, substituted or unsubstituted aryl; each $R^{2a}$ and $R^{2b}$ is independently H, unsubstituted $C_1$-$C_8$ alkyl or halo; each $R^{3a}$ and $R^{3b}$ is independently H or halo; each $X^7$, $X^8$, $X^9$ and $X^{10}$ is $CR^4$; each $R^{10a}$, $R^{10b}$, $R^{11a}$ and $R^{11b}$ is independently H or methyl; Q is a substituted or unsubstituted aryl; Q is a substituted or unsubstituted pyridyl, phenyl, pyrimidinyl, pyrazinyl, imidazolyl, furanyl, pyrrolyl or thiophenyl group; Q is a pyridyl, phenyl, pyrimidinyl, pyrazinyl, imidazolyl, furanyl, pyrrolyl or thiophenyl group substituted with at least one substituted or unsubstituted $C_1$-$C_8$ alkyl, halo or perhaloalkyl moiety; $R^4$ is H, halo, pyridyl, methyl or trifluoromethyl; $R^1$ is propylate, methyl, ethyl, cyclopropyl, trifluoromethyl, isopropyl, tert-butyl, sec-butyl, 2-methylbutyl, propanal, 1-methyl-2-hydroxyethyl, 2-hydroxyethanal, 2-hydroxyethyl, 2-hydroxypropyl, 2-hydroxy-2-methylpropyl, cyclobutyl, cyclopentyl, cyclohexyl, substituted phenyl, piperidin-4-yl, hydroxycyclopent-3-yl, hydroxycyclopent-2-yl, hydroxycycloprop-2-yl, 1-hydroxy-1-methylcycloprop-2-yl, or 1-hydroxy-1,2,2-trimethyl-cycloprop-3-yl; each $R^{2a}$, $R^{2b}$, $R^{3a}$ and $R^{3b}$ is independently H or halo; each $R^{10a}$, $R^{10b}$, $R^{11a}$, $R^{11b}$ is independently H or methyl; each $R^4$ is independently H, halo, $C_1$-$C_8$ perhaloalkyl, substituted or an unsubstituted $C_1$-$C_8$ alkyl; each $R^{8a}$, $R^{8b}$, $R^{8c}$, $R^{8d}$, $R^{8e}$ and $R^{8f}$ is H; Q is a substituted or unsubstituted cyclohexyl, morpholinyl, piperazinyl, thiomorpholinyl, cyclopentyl or pyrrolidinyl moiety;

$R^1$ is a methyl; at least one of $X^7$, $X^8$, $X^9$ and $X^{10}$ is $CR^4$ and each $R^4$ is independently H, halo, methyl or trifluoromethyl; Q is substituted with at least one carbonyl, hydroxymethyl, methyl or hydroxyl group; each $R^{2a}$ and $R^{2b}$ is independently H, a substituted or unsubstituted $C_1$-$C_8$ alkyl or $R^{2a}$ and $R^{2b}$ are taken together to form a carbonyl moiety; each $R^{3a}$ and $R^{3b}$ is independently H, a substituted or unsubstituted $C_1$-$C_8$ alkyl or $R^{3a}$ and $R^{3b}$ are taken together to form a carbonyl moiety; each $R^4$ is independently H, halo or substituted or unsubstituted $C_1$-$C_8$ alkyl; each $R^{8a}$, $R^{8b}$, $R^{8c}$, $R^{8d}$, $R^{8e}$ and $R^{8f}$ is H; each $R^{10a}$ and $R^{10b}$ is independently H, halo, a substituted or unsubstituted $C_1$-$C_8$ alkyl or $R^{10a}$ and $R^{10b}$ are taken together to form a carbonyl (=O); each $R^{11a}$ and $R^{11b}$ is independently H, halo, a substituted or unsubstituted $C_1$-$C_8$ alkyl or $R^{11a}$ and $R^{11b}$ are taken together to form a carbonyl (=O); Q is a substituted or unsubstituted pyridyl, phenyl, pyrazinyl, piperazinyl, pyrrolidinyl or thiomorpholinyl group; Q is a pyridyl, phenyl, pyrazinyl, piperazinyl, pyrrolidinyl or thiomorpholinyl group substituted with at least one methyl or halo group; at least one of $X^7$, $X^8$, $X^9$ and $X^{10}$ is $CR^4$ and each $R^4$ is independently H, halo or methyl.

Method of modulating a histamine receptor in an individual are provided, comprising administering to an individual in need thereof a compound as detailed herein.

A pharmaceutical composition comprising a compound as detailed herein and a pharmaceutically acceptable carrier are also provided.

Kits are also described, such as kits comprising a compound as detailed herein and instructions for use.

Methods of treating a cognitive disorder or a disorder characterized by causing at least one symptom associated with impaired cognition are also provided, comprising administering to an individual in need thereof a low dose of a compound as detailed herein, or a pharmaceutically acceptable salt thereof. A method of treating (i) a psychotic disorder, (ii) a psychotic disorder in an individual who is also in need of improved cognition or (iii) a disorder characterized by causing at least one psychotic symptom and at least one symptom associated with impaired cognition is also provided comprising administering to an individual in need thereof a high dose of a compound as detailed herein, or a pharmaceutically acceptable salt thereof. Use of a low dose of a compound as detailed herein, or a pharmaceutically acceptable salt thereof, in the manufacture of a medicament for the treatment of a cognitive disorder or a disorder characterized by causing at least one symptom associated with impaired cognition is also provided. Use of a high dose of a compound as detailed herein, or a pharmaceutically acceptable salt thereof in the manufacture of a medicament for the treatment of a (i) psychotic disorder, (ii) a psychotic disorder in an individual who is also in need of improved cognition or (iii) a disorder characterized by causing at least one psychotic symptom and at least one symptom associated with impaired cognition is also provided. In one instance, a kit comprising a low dose of a compound and instructions for achieving a procognitive effect in the treatment of a cognitive disorder or a disorder characterized by causing at least one symptom associated with impaired cognition is provided. In another, a kit comprising a high dose of a compound as detailed herein or a pharmaceutically acceptable salt thereof, and instructions for achieving (i) a procognitive effect in the treatment of a cognitive disorder or a disorder characterized by causing at least one symptom associated with impaired cognition and (ii) an antipsychotic effect in the treatment of a psychotic disorder; a psychotic disorder in an individual who is also in need of improved cognition or a disorder characterized by causing at least one psychotic symptom and at least one symptom associated with impaired cognition is provided.

DETAILED DESCRIPTION OF THE INVENTION

Definitions

For use herein, unless clearly indicated otherwise, use of the terms "a", "an" and the like refers to one or more.

Reference to "about" a value or parameter herein includes (and describes) embodiments that are directed to that value or parameter per se. For example, description referring to "about X" includes description of "X".

Unless clearly indicated otherwise, "an individual" as used herein intends a mammal, including but not limited to a human.

As used herein, the term "aminergic G protein-coupled receptors" refers to a family of transmembrane proteins involved in cellular communication. Aminergic G protein coupled receptors are activated by biogenic amines and represent a subclass of the superfamily of G protein coupled receptors, which are structurally characterized by seven transmembrane helices. Aminergic G protein-coupled receptors include but are not limited to adrenergic receptors, serotonin receptors, dopamine receptors, histamine receptors and imidazoline receptors.

As used herein, the term "adrenergic receptor modulator" intends and encompasses a compound that binds to or inhibits binding of a ligand to an adrenergic receptor or reduces or eliminates or increases or enhances or mimics an activity of an adrenergic receptor. As such, an "adrenergic receptor modulator" encompasses both an adrenergic receptor antagonist and an adrenergic receptor agonist. In some aspects, the adrenergic receptor modulator binds to or inhibits binding to a ligand to an $\alpha_1$-adrenergic receptor (e.g., $\alpha_{1A}$, $\alpha_{1B}$ and/or $\alpha_{1D}$) and/or a $\alpha_2$-adrenergic receptor (e.g., $\alpha_{2A}$, $\alpha_{2B}$ and/or $\alpha_{2C}$) and/or reduces or eliminates or increases or enhances or mimics an activity of a $\alpha_1$-adrenergic receptor (e.g., $\alpha_{1A}$, $\alpha_{1B}$ and/or $\alpha_{1D}$) and/or a $\alpha_2$-adrenergic receptor (e.g., $\alpha_{2A}$, $\alpha_{2B}$ and/or $\alpha_{2C}$) in a reversible or irreversible manner. In some aspects, the adrenergic receptor modulator inhibits binding of a ligand by at least about or about any one of 10%, 20%, 30%, 40%, 50%, 60%, 70%, 80%, 90%, 95% or 100% as determined in the assays described herein. In some aspects, the adrenergic receptor modulator reduces an activity of an adrenergic receptor by at least or about any of 10%, 20%, 30%, 40%, 50%, 60%, 70%, 80%, 90%, 95% or 100% as compared to the corresponding activity in the same subject prior to treatment with the adrenergic receptor modulator or compared to the corresponding activity in other subjects not receiving the adrenergic receptor modulator. In some aspects, the adrenergic receptor modulator enhances an activity of an adrenergic receptor by at least about or about any of 10%, 20%, 30%, 40%, 50%, 60%, 70%, 80%, 90%, 95% or 100 or 200% or 300% or 400% or 500% or more as compared to the corresponding activity in the same subject prior to treatment with the adrenergic receptor modulator or compared to the corresponding activity in other subjects not receiving the adrenergic receptor modulator. In some aspects, the adrenergic receptor modulator is capable of binding to the active site of an adrenergic receptor (e.g., a binding site for a ligand). In some embodiments, the adrenergic receptor modulator is capable of binding to an allosteric site of an adrenergic receptor.

As used herein, the term "dopamine receptor modulator" intends and encompasses a compound that binds to or inhibits binding of a ligand to a dopamine receptor or reduces or eliminates or increases or enhances or mimics an activity of a dopamine receptor. As such, a "dopamine receptor modulator" encompasses both a dopamine receptor antagonist and a dopamine receptor agonist. In some aspects, the dopamine receptor modulator binds to or inhibits binding of a ligand to a dopamine-1 ($D_1$) and/or a dopamine-2 ($D_2$) receptor or reduces or eliminates or increases or enhances or mimics an activity of a dopamine-1 ($D_1$) and/or a dopamine-2 ($D_2$) receptor in a reversible or irreversible manner. Dopamine $D_2$ receptors are divided into two categories, $D_{2L}$ and $D_{2S}$, which are formed from a single gene by differential splicing. $D_{2L}$ receptors have a longer intracellular domain than $D_{2S}$. In some embodiments, the dopamine receptor modulator inhibits binding of a ligand by at least about or about any one of 10%, 20%, 30%, 40%, 50%, 60%, 70%, 80%, 90%, 95% or 100% as determined in the assays described herein. In some embodiments, the dopamine receptor modulator reduces an activity of a dopamine receptor by at least about or about any of 10%, 20%, 30%, 40%, 50%, 60%, 70%, 80%, 90%, 95% or 100% as compared to the corresponding activity in the same subject prior to treatment with the dopamine receptor modulator or compared to the corresponding activity in other subjects not receiving the dopamine receptor modulator. In some embodiments, the dopamine receptor modulator enhances an activity of a dopamine receptor by at least about or about any of 10%, 20%, 30%, 40%, 50%, 60%, 70%, 80%, 90%, 95% or 100 or 200% or 300% or 400% or 500% or more as compared to the corresponding activity in the same subject prior to treatment with the dopamine receptor modulator or compared to the corresponding activity in other subjects not receiving the dopamine receptor modulator. In some embodiments, the dopamine receptor modulator is capable of binding to the active site of a dopamine receptor (e.g., a binding site for a ligand). In some embodiments, the dopamine receptor modulator is capable of binding to an allosteric site of a dopamine receptor.

As used herein, the term "serotonin receptor modulator" intends and encompasses a compound that binds to or inhibits binding of a ligand to a serotonin receptor or reduces or eliminates or increases or enhances or mimics an activity of a serotonin receptor. As such, a "serotonin receptor modulator" encompasses both a serotonin receptor antagonist and a serotonin receptor agonist. In some embodiments, the serotonin receptor modulator binds to or inhibits binding of a ligand to a $5\text{-}HT_{1A}$ and/or a $5\text{-}HT_{1B}$ and/or a $5\text{-}HT_{2A}$ and/or a $5\text{-}HT_{2B}$ and/or a $5\text{-}HT_{2C}$ and/or a $5\text{-}HT_3$ and/or a $5\text{-}HT_4$ and/or a $5\text{-}HT_6$ and/or a $5\text{-}HT_7$ receptor or reduces or eliminates or increases or enhances or mimics an activity of a $5\text{-}HT_{1A}$ and/or a $5\text{-}HT_{1B}$ and/or a $5\text{-}HT_{2A}$ and/or a $5\text{-}HT_{2B}$ and/or a $5\text{-}HT_{2C}$ and/or a $5\text{-}HT_3$ and/or a $5\text{-}HT_4$ and/or a $5\text{-}HT_6$ and/or a $5\text{-}HT_7$ receptor in a reversible or irreversible manner. In some embodiments, the serotonin receptor modulator inhibits binding of a ligand by at least about or about any one of 10%, 20%, 30%, 40%, 50%, 60%, 70%, 80%, 90%, 95% or 100% as determined in the assays described herein. In some embodiments, the serotonin receptor modulator reduces an activity of a serotonin receptor by at least about or about any of 10%, 20%, 30%, 40%, 50%, 60%, 70%, 80%, 90%, 95% or 100% as compared to the corresponding activity in the same subject prior to treatment with the serotonin receptor modulator or compared to the corresponding activity in other subjects not receiving the serotonin receptor modulator. In some embodiments, the serotonin receptor modulator enhances an activity of a serotonin receptor by at least about or about any of 10%, 20%, 30%, 40%, 50%, 60%, 70%, 80%, 90%, 95% or 100 or 200% or 300% or 400% or 500% or more as compared to the corresponding activity in the same subject prior to treatment with the serotonin receptor modulator or compared to the corresponding activity in other subjects not receiving the serotonin receptor modulator. In some embodiments, the serotonin receptor modulator is capable of binding to the active site of a serotonin receptor (e.g., a binding site for a ligand). In some embodiments, the serotonin receptor modulator is capable of binding to an allosteric site of a serotonin receptor.

As used herein, the term "histamine receptor modulator" intends and encompasses a compound that binds to or inhibits binding of a ligand to a histamine receptor or reduces or eliminates or increases or enhances or mimics an activity of a histamine receptor. As such, a "histamine receptor modulator" encompasses both a histamine receptor antagonist and a histamine receptor agonist. In some embodiments, the histamine receptor modulator binds to or inhibits binding of a ligand to a histamine $H_1$ and/or $H_2$ and/or $H_3$ receptor or reduces or eliminates or increases or enhances or mimics an activity of a histamine $H_1$ and/or $H_2$ and/or $H_3$ receptor in a reversible or irreversible manner. In some embodiments, the histamine receptor modulator inhibits binding of a ligand by at least about or about any one of 10%, 20%, 30%, 40%, 50%, 60%, 70%, 80%, 90%, 95% or 100% as determined in the assays described herein. In some embodiments, the histamine receptor modulator reduces an activity of a histamine receptor by at least about or about any of 10%, 20%, 30%, 40%, 50%, 60%, 70%, 80%, 90%, 95% or 100% as compared to the corresponding activity in the same subject prior to treatment with the histamine receptor modulator or compared to the corresponding activity in other subjects not receiving the histamine receptor modulator. In some embodiments, the histamine receptor modulator enhances an activity of a histamine receptor by at least about or about any of 10%, 20%, 30%, 40%, 50%, 60%, 70%, 80%, 90%, 95% or 100 or 200% or 300% or 400% or 500% or more as compared to the corresponding activity in the same subject prior to treatment with the histamine receptor modulator or compared to the corresponding activity in other subjects not receiving the histamine receptor modulator. In some embodiments, the histamine receptor modulator is capable of binding to the active site of a histamine receptor (e.g., a binding site for a ligand). In some embodiments, the histamine receptor modulator is capable of binding to an allosteric site of a histamine receptor.

Unless clearly indicated otherwise, "an individual" as used herein intends a mammal, including but not limited to a human, bovine, primate, equine, canine, feline, porcine, and ovine animals. Thus, the invention finds use in both human medicine and in the veterinary context, including use in agricultural animals and domestic pets. The individual may be a human who has been diagnosed with or is suspected of having a cognitive disorder, a psychotic disorder, a neurotransmitter-mediated disorder and/or a neuronal disorder. The individual may be a human who exhibits one or more symptoms associated with a cognitive disorder, a psychotic disorder, a neurotransmitter-mediated disorder and/or a neuronal disorder. The individual may be a human who has a mutated or abnormal gene associated with a cognitive disorder, a psychotic disorder, a neurotransmitter-mediated disorder and/or a neuronal disorder. The individual may be a human who is genetically or otherwise predisposed to developing a cognitive disorder, a psychotic disorder, a neurotransmitter-mediated disorder and/or a neuronal disorder.

As used herein, "treatment" or "treating" is an approach for obtaining a beneficial or desired result, such as a clinical result. For purposes of this invention, beneficial or desired clinical results include, but are not limited to, alleviation of a symptom and/or diminishment of the extent of a symptom and/or preventing a worsening of a symptom associated with a disease or condition. In one variation, beneficial or desired clinical results include, but are not limited to, alleviation of a symptom and/or diminishment of the extent of a symptom and/or preventing a worsening of a symptom associated with a cognitive disorder, a psychotic disorder, a neurotransmitter-mediated disorder and/or a neuronal disorder. Preferably, treatment of a disease or condition with a compound of the invention or a pharmaceutically acceptable salt thereof is accompanied by no or fewer side effects than are associated with currently available therapies for the disease or condition and/or improves the quality of life of the individual.

As used herein, "delaying" development of a disease or condition means to defer, hinder, slow, retard, stabilize and/or postpone development of the disease or condition. This delay can be of varying lengths of time, depending on the history of the disease and/or individual being treated. As is evident to one skilled in the art, a sufficient or significant delay can, in effect, encompass prevention, in that the individual does not develop the disease or condition. For example, a method that "delays" development of Alzheimer's disease is a method that reduces probability of disease development in a given time frame and/or reduces extent of the disease in a given time frame, when compared to not using the method. Such comparisons are typically based on clinical studies, using a statistically significant number of subjects. For example, Alzheimer's disease development can be detected using standard clinical techniques, such as routine neurological examination, patient interview, neuroimaging, detecting alterations of levels of specific proteins in the serum or cerebrospinal fluid (e.g., amyloid peptides and Tau), computerized tomography (CT) or magnetic resonance imaging (MRI). Similar techniques are known in the art for other diseases and conditions. Development may also refer to disease progression that may be initially undetectable and includes occurrence, recurrence and onset.

As used herein, an "at risk" individual is an individual who is at risk of developing a cognitive disorder, a psychotic disorder, a neurotransmitter-mediated disorder and/or a neuronal disorder that can be treated with a compound of the invention. An individual "at risk" may or may not have a detectable disease or condition, and may or may not have displayed detectable disease prior to the treatment methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s). These risk factors include, but are not limited to, age, sex, race, diet, history of previous disease, presence of precursor disease, genetic (i.e., hereditary) considerations, and environmental exposure. For example, individuals at risk for Alzheimer's disease include, e.g., those having relatives who have experienced this disease and those whose risk is determined by analysis of genetic or biochemical markers. Genetic markers of risk for Alzheimer's disease include mutations in the APP gene, particularly mutations at position 717 and positions 670 and 671 referred to as the Hardy and Swedish mutations, respectively (Hardy, *Trends Neurosci.*, 20:154-9, 1997). Other markers of risk are mutations in the presenilin genes (e.g., PS1 or PS2), ApoE4 alleles, family history of Alzheimer's disease, hypercholesterolemia and/or atherosclerosis. Other such factors are known in the art for other diseases and conditions.

As used herein, the term "pro-cognitive" includes but is not limited to an improvement of one or more mental processes such as memory, attention, perception and/or thinking, which may be assessed by methods known in the art.

As used herein, the term "neurotrophic" effects includes but is not limited to effects that enhance neuron function such as growth, survival and/or neurotransmitter synthesis.

As used herein, the term "cognitive disorders" refers to and intends diseases and conditions that are believed to involve or be associated with or do involve or are associated with progressive loss of structure and/or function of neurons, including death of neurons, and where a central feature of the disorder may be the impairment of cognition (e.g., memory, attention, perception and/or thinking). These disorders include pathogen-induced cognitive dysfunction, e.g. HIV associated cognitive dysfunction and Lyme disease associated cognitive dysfunction. Examples of cognitive disorders include Alzheimer's Disease, Huntington's Disease, Parkinson's Disease, schizophrenia, amyotrophic lateral sclerosis (ALS), autism, ADD, ADHD, mild cognitive impairment (MCI), stroke, traumatic brain injury (TBI) and age-associated memory impairment (AAMI).

As used herein, the term "psychotic disorders" refers to and intends mental diseases or conditions that are believed to cause or do cause abnormal thinking and perceptions. Psychotic disorders are characterized by a loss of reality which may be accompanied by delusions, hallucinations (perceptions in a conscious and awake state in the absence of external stimuli which have qualities of real perception, in that they are vivid, substantial, and located in external objective space), personality changes and/or disorganized thinking. Other common symptoms include unusual or bizarre behavior, as well as difficulty with social interaction and impairment in carrying out the activities of daily living. Exemplary psychotic disorders are schizophrenia, bipolar disorders, psychosis, anxiety and depression.

As used herein, the term "neurotransmitter-mediated disorders" refers to and intends diseases or conditions that are believed to involve or be associated with or do involve or are associated with abnormal levels of neurotransmitters such as histamine, serotonin, dopamine, norepinephrine or impaired function of aminergic G protein-coupled receptors. Exemplary neurotransmitter-mediated disorders include spinal cord injury, diabetic neuropathy, allergic diseases and diseases involving geroprotective activity such as age-associated hair loss (alopecia), age-associated weight loss and age-associated vision disturbances (cataracts). Abnormal neurotransmitter levels are associated with a wide variety of diseases and conditions including, but not limited, to Alzheimer's disease, Parkinson's Disease, autism, ADD, ADHD, Guillain-Barré syndrome, mild cognitive impairment, schizophrenia, anxiety, multiple sclerosis, stroke, traumatic brain injury, spinal cord injury, diabetic neuropathy, fibromyalgia, bipolar disorders, psychosis, depression and a variety of allergic diseases.

As used herein, the term "neuronal disorders" refers to and intends diseases or conditions that are believed to involve, or be associated with, or do involve or are associated with neuronal cell death and/or impaired neuronal function or decreased neuronal function. Exemplary neuronal indications include neurodegenerative diseases and disorders such as Alzheimer's disease, Huntington's disease, amyotrophic lateral sclerosis (ALS), Parkinson's disease, canine cognitive dysfunction syndrome (CCDS), Lewy body disease, Menkes disease, Wilson disease, Creutzfeldt-Jakob disease, Fahr disease, an acute or chronic disorder involving cerebral circulation, such as ischemic or hemorrhagic stroke or other cerebral hemorrhagic insult, age-associated memory impairment (AAMI), mild cognitive impairment (MCI), injury-related mild cognitive impairment (MCI), post-concussion syndrome, post-traumatic stress disorder, adjuvant chemotherapy, traumatic brain injury (TBI), neuronal death mediated ocular disorder, macular degeneration, age-related macular degeneration, autism, including autism spectrum disorder, Asperger syndrome, and Rett syndrome, an avulsion injury, a spinal cord injury, myasthenia gravis, Guillain-Barré syndrome, multiple sclerosis, diabetic neuropathy, fibromyalgia, neuropathy associated with spinal cord injury, schizophrenia, bipolar disorder, psychosis, anxiety or depression.

As used herein, the term "neuron" represents a cell of ectodermal embryonic origin derived from any part of the nervous system of an animal. Neurons express well-characterized neuron-specific markers, including neurofilament proteins, NeuN (Neuronal Nuclei marker), MAP2, and class III tubulin. Included as neurons are, for example, hippocampal, cortical, midbrain dopaminergic, spinal motor, sensory, sympathetic, septal cholinergic, and cerebellar neurons.

As used herein, the term "neurite outgrowth" or "neurite activation" refers to the extension of existing neuronal processes (e.g., axons and dendrites) and the growth or sprouting of new neuronal processes (e.g., axons and dendrites). Neurite outgrowth or neurite activation may alter neural connectivity, resulting in the establishment of new synapses or the remodeling of existing synapses.

As used herein, the term "neurogenesis" refers to the generation of new nerve cells from undifferentiated neuronal progenitor cells, also known as multipotential neuronal stem cells. Neurogenesis actively produces new neurons, astrocytes, glia, Schwann cells, oligodendrocytes and/or other neural lineages. Much neurogenesis occurs early in human development, though it continues later in life, particularly in certain localized regions of the adult brain.

As used herein, the term "neural connectivity" refers to the number, type, and quality of connections ("synapses") between neurons in an organism. Synapses form between neurons, between neurons and muscles (a "neuromuscular junction"), and between neurons and other biological structures, including internal organs, endocrine glands, and the like. Synapses are specialized structures by which neurons transmit chemical or electrical signals to each other and to non-neuronal cells, muscles, tissues, and organs. Compounds that affect neural connectivity may do so by establishing new synapses (e.g., by neurite outgrowth or neurite activation) or by altering or remodeling existing synapses. Synaptic remodeling refers to changes in the quality, intensity or type of signal transmitted at particular synapses.

As used herein, the term "neuropathy" refers to a disorder characterized by altered function and/or structure of motor, sensory, and autonomic neurons of the nervous system, initiated or caused by a primary lesion or other dysfunction of the nervous system. Patterns of peripheral neuropathy include polyneuropathy, mononeuropathy, mononeuritis multiplex and autonomic neuropathy. The most common form is (symmetrical) peripheral polyneuropathy, which mainly affects the feet and legs. A radiculopathy involves spinal nerve roots, but if peripheral nerves are also involved the term radiculoneuropathy is used. The form of neuropathy may be further broken down by cause, or the size of predominant fiber involvement, e.g. large fiber or small fiber peripheral neuropathy. Central neuropathic pain can occur in spinal cord injury, multiple sclerosis, and some strokes, as well as fibromyalgia. Neuropathy may be associated with varying combinations of weakness, autonomic changes and sensory changes. Loss of muscle bulk or fasciculations, a particular fine twitching of muscle may also be seen. Sensory symptoms encompass loss of sensation and "positive" phenomena including pain. Neuropathies are associated with a variety of disorders, including diabetes (e.g., diabetic neuropathy), fibromyalgia, multiple sclerosis, and herpes zoster infection, as well as with spinal cord injury and other types of nerve damage.

As used herein, the term "Alzheimer's disease" refers to a degenerative brain disorder characterized clinically by progressive memory deficits, confusion, behavioral problems, inability to care for oneself, gradual physical deterioration and, ultimately, death. Histologically, the disease is characterized by neuritic plaques, found primarily in the association cortex, limbic system and basal ganglia. The major constituent of these plaques is amyloid beta peptide (Aβ), which is the cleavage product of beta amyloid precursor protein (βAPP or APP). APP is a type I transmembrane glycoprotein that contains a large ectopic N-terminal domain, a transmembrane domain and a small cytoplasmic C-terminal tail. Alternative splicing of the transcript of the single APP gene on chromosome 21 results in several isoforms that differ in the number of amino acids. A13 appears to have a central role in the neuropathology of Alzheimer's disease. Familial forms of the disease have been linked to mutations in APP and the presenilin genes (Tanzi et al., 1996, *Neurobiol. Dis.*, 3:159-168; Hardy, 1996, *Ann. Med.*, 28:255-258). Diseased-linked mutations in these genes result in increased production of the 42-amino acid form of Aβ, the predominant form found in amyloid plaques. Mitochondrial dysfunction has also been reported to be an important component of Alzheimer's disease (Bubber et al., Mitochondrial abnormalities in Alzheimer brain: Mechanistic Implications, *Ann Neurol.*, 2005, 57(5), 695-703; Wang et al., Insights into amyloid-β-induced mitochondrial dysfunction in Alzheimer disease, *Free Radical Biology & Medicine*, 2007, 43, 1569-1573; Swerdlow et al., Mitochondria in Alzheimer's disease, *Int. Rev. Neurobiol.*, 2002, 53, 341-385; and Reddy et al., Are mitochondria critical in the pathogenesis of Alzheimer's disease?, *Brain Res Rev.* 2005, 49(3), 618-32). It has been proposed that mitochondrial dysfunction has a causal relationship with neuronal function (including neurotransmitter synthesis and secretion) and viability. Compounds which stabilize mitochondria may therefore have a beneficial impact on Alzheimer's patients.

As used herein, the term "Huntington's disease" refers to a fatal neurological disorder characterized clinically by symptoms such as involuntary movements, cognition impairment or loss of cognitive function and a wide spectrum of behavioral disorders. Common motor symptoms associated with Huntington's disease include chorea (involuntary writhing and spasming), clumsiness, and progressive loss of the abilities to walk, speak (e.g., exhibiting slurred speech) and swallow. Other symptoms of Huntington's disease can include cognitive symptoms such as loss of intellectual speed, attention and short-term memory and/or behavioral symptoms that can span the range of changes in personality, depression, irritability, emotional outbursts and apathy. Clinical symptoms typically appear in the fourth or fifth decade of life. Huntington's disease is a devastating and often protracted illness, with death usually occurring approximately 10-20 years after the onset of symptoms. Huntington's disease is inherited through a mutated or abnormal gene encoding an abnormal protein called the mutant huntingtin protein; the mutated huntingtin protein produces neuronal degeneration in many different regions of the brain. The degeneration focuses on neurons located in the basal ganglia, structures deep within the brain that control many important functions including coordinating movement, and on neurons on the outer surface of the brain or cortex, which controls thought, perception and memory.

"Amyotrophic lateral sclerosis" or "ALS" is used herein to denote a progressive neurodegenerative disease that affects upper motor neurons (motor neurons in the brain) and/or lower motor neurons (motor neurons in the spinal cord) and results in motor neuron death. As used herein, the term "ALS" includes all of the classifications of ALS known in the art, including, but not limited to classical ALS (typically affecting both lower and upper motor neurons), Primary Lateral Sclerosis (PLS, typically affecting only the upper motor neurons), Progressive Bulbar Palsy (PBP or Bulbar Onset, a version of ALS that typically begins with difficulties swallowing, chewing and speaking), Progressive Muscular Atrophy (PMA, typically affecting only the lower motor neurons) and familial ALS (a genetic version of ALS).

The term "Parkinson's disease" as used herein refers to any medical condition wherein an individual experiences one or more symptoms associated with Parkinson's disease, such as without limitation one or more of the following symptoms: rest tremor, cogwheel rigidity, bradykinesia, postural reflex impairment, symptoms having good response to 1-dopa treatment, the absence of prominent oculomotor palsy, cerebellar or pyramidal signs, amyotrophy, dyspraxia and/or dysphasia. In a specific embodiment, the present invention is utilized for the treatment of a dopaminergic dysfunction-related disorder. In a specific embodiment, the individual with Parkinson's disease has a mutation or polymorphism in a synuclein, parkin or NURR1 nucleic acid that is associated with Parkinson's disease. In one embodiment, the individual with Parkinson's disease has defective or decreased expression of a nucleic acid or a mutation in a nucleic acid that regulates the development and/or survival of dopaminergic neurons.

As used herein, the term "canine cognitive dysfunction syndrome," or "CCDS" refers to an age-related deterioration of mental function typified by multiple cognitive impairments that affect an afflicted canine's ability to function normally. The decline in cognitive ability that is associated with CCDS cannot be completely attributed to a general medical condition such as neoplasia, infection, sensory impairment, or organ failure. Diagnosis of CCDS in canines, such as dogs, is generally a diagnosis of exclusion, based on thorough behavior and medical histories and the presence of clinical symptoms of CCDS that are unrelated to other disease processes. Owner observation of age-related changes in behavior is a practical means used to detect the possible onset of CCDS in aging domestic dogs. A number of laboratory cognitive tasks may be used to help diagnose CCDS, while blood counts, chemistry panels and urinalysis can be used to rule out other underlying diseases that could mimic the clinical symptoms of CCDS. Symptoms of CCDS include memory loss, which in domestic dogs may be manifested by disorientation and/or confusion, decreased or altered interaction with family members and/or greeting behavior, changes in sleep-wake cycle, decreased activity level, and loss of house training or frequent, inappropriate elimination. A canine suffering from CCDS may exhibit one or more of the following clinical or behavioral symptoms: decreased appetite, decreased awareness of surroundings, decreased ability to recognize familiar places, people or other animals, decreased hearing, decreased ability to climb up and down stairs, decreased tolerance to being alone, development of compulsive behavior or repetitive behaviors or habits, circling, tremors or shaking, disorientation, decreased activity level, abnormal sleep wake cycles, loss of house training, decreased or altered responsiveness to family members, and decreased or altered greeting behavior. CCDS can dramatically affect the health and well-being of an afflicted canine. Moreover, the companionship offered by a pet with CCDS can become less rewarding as the severity of the disease increases and its symptoms become more severe.

As used herein, the term "age-associated memory impairment" or "AAMI" refers to a condition that may be identified as GDS stage 2 on the global deterioration scale (GDS) (Reisberg, et al. (1982) Am. J. Psychiatry 139: 1136-1139) which differentiates the aging process and progressive degenerative dementia in seven major stages. The first stage of the GDS is one in which individuals at any age have neither subjective complaints of cognitive impairment nor objective evidence of impairment. These GDS stage 1 individuals are considered normal. The second stage of the GDS applies to those generally elderly persons who complain of memory and cognitive functioning difficulties such as not recalling names as well as they could five or ten years previously or not recalling where they have placed things as well as they could five or ten years previously. These subjective complaints appear to be very common in otherwise normal elderly individuals. AAMI refers to persons in GDS stage 2, who may differ neurophysiologically from elderly persons who are normal and free of subjective complaints, i.e., GDS stage 1. For example, AAMI subjects have been found to have more electrophysiologic slowing on a computer analyzed EEG than GDS stage 1 elderly persons (Prichep, John, Ferris, Reisberg, et al. (1994) Neurobiol. Aging 15: 85-90).

As used herein, the term "mild cognitive impairment" or "MCI" refers to a type of cognitive disorder characterized by a more pronounced deterioration in cognitive functions than is typical for normal age-related decline. As a result, elderly or aged patients with MCI have greater than normal difficulty performing complex daily tasks and learning, but without the inability to perform normal social, everyday, and/or professional functions typical of patients with Alzheimer's disease, or other similar neurodegenerative disorders eventually resulting in dementia. MCI is characterized by subtle, clinically manifest deficits in cognition, memory, and functioning, amongst other impairments, which are not of sufficient magnitude to fulfill criteria for diagnosis of Alzheimer's disease or other dementia. MCI also encompasses injury-related MCI, defined herein as cognitive impairment resulting from certain types of injury, such as nerve injury (i.e., battlefield injuries, including post-concussion syndrome, and the like), neurotoxic treatment (i.e., adjuvant chemotherapy resulting in "chemo brain" and the like), and tissue damage resulting from physical injury or other neurodegeneration, which is separate and distinct from mild cognitive impairment resulting from stroke, ischemia, hemorrhagic insult, blunt force trauma, and the like.

As used herein, the term "traumatic brain injury" or "TBI" refers to a brain injury caused by a sudden trauma, such as a blow or jolt or a penetrating head injury, which disrupts the function or damages the brain. Symptoms of TBI can range from mild, moderate to severe and can significantly affect many cognitive (deficits of language and communication, information processing, memory, and perceptual skills), physical (ambulation, balance, coordination, fine motor skills, strength, and endurance), and psychological skills.

"Neuronal death mediated ocular disease" intends an ocular disease in which death of the neuron is implicated in whole or in part. The disease may involve death of photoreceptors. The disease may involve retinal cell death. The disease may involve ocular nerve death by apoptosis. Particular neuronal death mediated ocular diseases include but are not limited to macular degeneration, glaucoma, retinitis pigmentosa, congenital stationary night blindness (Oguchi disease), childhood onset severe retinal dystrophy, Leber congenital amaurosis, Bardet-Biedle syndrome, Usher syndrome, blindness from an optic neuropathy, Leber's hereditary optic neuropathy, color blindness and Hansen-Larson-Berg syndrome.

As used herein, the term "macular degeneration" includes all forms and classifications of macular degeneration known in the art, including, but not limited to diseases that are characterized by a progressive loss of central vision associated with abnormalities of Bruch's membrane, the choroid, the neural retina and/or the retinal pigment epithelium. The term thus encompasses disorders such as age-related macular degeneration (ARMD) as well as rarer, earlier-onset dystrophies that in some cases can be detected in the first decade of life. Other maculopathies include North Carolina macular dystrophy, Sorsby's fundus dystrophy, Stargardt's disease, pattern dystrophy, Best disease, and Malattia Leventinese.

As used herein, the term "autism" refers to a brain development disorder that impairs social interaction and communication and causes restricted and repetitive behavior, typically appearing during infancy or early childhood. The cognitive and behavioral defects are thought to result in part from altered neural connectivity. Autism encompasses related disorders sometimes referred to as "autism spectrum disorder," as well as Asperger syndrome and Rett syndrome.

As used herein, the term "nerve injury" or "nerve damage" refers to physical damage to nerves, such as avulsion injury (i.e., where a nerve or nerves have been torn or ripped) or spinal cord injury (i.e., damage to white matter or myelinated fiber tracts that carry sensation and motor signals to and from the brain). Spinal cord injury can occur from many causes, including physical trauma (i.e., car accidents, sports injuries, and the like), tumors impinging on the spinal column, developmental disorders, such as spina bifida, and the like.

As used herein, the term "myasthenia gravis" or "MG" refers to a non-cognitive neuromuscular disorder caused by immune-mediated loss of acetylcholine receptors at neuromuscular junctions of skeletal muscle. Clinically, MG typically appears first as occasional muscle weakness in approximately two-thirds of patients, most commonly in the extraocular muscles. These initial symptoms eventually worsen, producing drooping eyelids (ptosis) and/or double vision (diplopia), often causing the patient to seek medical attention. Eventually, many patients develop general muscular weakness that may fluctuate weekly, daily, or even more frequently. Generalized MG often affects muscles that control facial expression, chewing, talking, swallowing, and breathing; before recent advances in treatment, respiratory failure was the most common cause of death.

As used herein, the term "Guillain-Barré syndrome" refers to a non-cognitive disorder in which the body's immune system attacks part of the peripheral nervous system. The first symptoms of this disorder include varying degrees of weakness or tingling sensations in the legs. In many instances the weakness and abnormal sensations spread to the arms and upper body. These symptoms can increase in intensity until certain muscles cannot be used at all and, when severe, the patient is almost totally paralyzed. In these cases the disorder is life threatening—potentially interfering with breathing and, at times, with blood pressure or heart rate—and is considered a medical emergency. Most patients, however, recover from even the most severe cases of Guillain-Barré syndrome, although some continue to have a certain degree of weakness.

As used herein, the term "multiple sclerosis" or "MS" refers to an autoimmune condition in which the immune system attacks the central nervous system (CNS), leading to demyelination of neurons. It may cause numerous symptoms, many of which are non-cognitive, and often progresses to physical disability. MS affects the areas of the brain and spinal cord known as the white matter. White matter cells carry signals between the grey matter areas, where the processing is done, and the rest of the body. More specifically, MS destroys oligodendrocytes which are the cells responsible for creating and maintaining a fatty layer, known as the myelin sheath, which helps the neurons carry electrical signals. MS results in a thinning or complete loss of myelin and, less frequently, the cutting (transection) of the neuron's extensions or axons. When the myelin is lost, the neurons can no longer effectively conduct their electrical signals. Almost any neurological symptom can accompany the disease. MS takes several forms, with new symptoms occurring either in discrete attacks (relapsing forms) or slowly accumulating over time (progressive forms). Most people are first diagnosed with relapsing-remitting MS but develop secondary-progressive MS (SPMS) after a number of years. Between attacks, symptoms may go away completely, but permanent neurological problems often persist, especially as the disease advances.

As used herein, the term "schizophrenia" refers to a chronic, mental disorder characterized by one or more positive symptoms (e.g., delusions and hallucinations) and/or negative symptoms (e.g., blunted emotions and lack of interest) and/or disorganized symptoms (e.g., disorganized thinking and speech or disorganized perception and behavior). Schizophrenia as used herein includes all forms and classifications of schizophrenia known in the art, including, but not limited to catatonic type, hebephrenic type, disorganized type, paranoid type, residual type or undifferentiated type schizophrenia and deficit syndrome and/or those described in American Psychiatric Association: *Diagnostic and Statistical Manual of Mental Disorders*, Fourth Edition, Washington D.C., 2000 or in International Statistical Classification of Diseases and Related Health Problems, or otherwise known to those of skill in the art.

"Cognitive impairment associated with schizophrenia" or "CIAS" includes neuropsychological deficits in attention, working memory, verbal learning, and problem solving. These deficits are believed to be linked to impairment in functional status (e.g., social behavior, work performance, and activities of daily living).

As used herein "geroprotective activity" or "geroprotector" means a biological activity that slows down ageing and/or prolongs life and/or increases or improves the quality of life via a decrease in the amount and/or the level of intensity of pathologies or conditions that are not life-threatening but are associated with the aging process and which are typical for elderly people. Pathologies or conditions that are not life-threatening but are associated with the aging process include such pathologies or conditions as loss of sight (cataract), deterioration of the dermatohairy integument (alopecia), and an age-associated decrease in weight due to the death of muscular and/or fatty cells.

As used herein, attention-deficit hyperactivity disorder (ADHD) is the most common child neuropsychiatric condition present in school-aged children, affecting about 5-8% of this population. ADHD refers to a chronic disorder that initially manifests in childhood and is characterized by hyperactivity, impulsivity, and/or inattention. ADHD is characterized by persistent patterns of inattention and/or impulsivity-hyperactivity that are much more extreme than is observed in individuals at the same developmental level or stage. There is considerable evidence, from family and twin studies, that ADHD has a significant genetic component. This disorder is thought to be due to an interaction of environmental and genetic factors. ADHD includes all known types of ADHD.

For example, *Diagnostic & Statistical Manual for Mental Disorders* (DSM-IV) identifies three subtypes of ADHD: (1) ADHD, Combined Type which is characterized by both inattention and hyperactivity-impulsivity symptoms; 2. ADHD, Predominantly Inattentive Type which is characterized by inattention but not hyperactivity-impulsivity symptoms; and 3. ADHD, Predominantly Hyperactive-Impulsive Type which is characterized by Hyperactivity-impulsivity but not inattention symptoms.

As used herein, attention-deficit disorder (ADD) refers to a disorder in processing neural stimuli that is characterized by distractibility and impulsivity that can result in inability to control behavior and can impair an individual's social, academic, or occupational function and development. ADD may be diagnosed by known methods, which may include observing behavior and diagnostic interview techniques.

As used herein "allergic disease" refers to a disorder of the immune system which is characterized by excessive activation of mast cells and basophils and production of IgE immunoglobulins, resulting in an extreme inflammatory response. It represents a form of hypersensitivity to an environmental substance known as allergen and is an acquired disease. Common allergic reactions include eczema, hives, hay fever, asthma, food allergies, and reactions to the venom of stinging insects such as wasps and bees. Allergic reactions are accompanied by an excessive release of histamines, and can thus be treated with antihistaminic agents.

As used herein, by "combination therapy" is meant a therapy that includes two or more different compounds. Thus, in one aspect, a combination therapy comprising a compound detailed herein and another compound is provided. In some variations, the combination therapy optionally includes one or more pharmaceutically acceptable carriers or excipients, non-pharmaceutically active compounds, and/or inert substances. In various embodiments, treatment with a combination therapy may result in an additive or even synergistic (e.g., greater than additive) result compared to administration of a single compound of the invention alone. In some embodiments, a lower amount of each compound is used as part of a combination therapy compared to the amount generally used for individual therapy. Preferably, the same or greater therapeutic benefit is achieved using a combination therapy than by using any of the individual compounds alone. In some embodiments, the same or greater therapeutic benefit is achieved using a smaller amount (e.g., a lower dose or a less frequent dosing schedule) of a compound in a combination therapy than the amount generally used for individual compound or therapy. Preferably, the use of a small amount of compound results in a reduction in the number, severity, frequency, and/or duration of one or more side-effects associated with the compound.

As used herein, the term "effective amount" intends such amount of a compound of the invention which in combination with its parameters of efficacy and toxicity, as well as based on the knowledge of the practicing specialist should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any of the co-administered compounds may optionally be lowered due to the combined action (e.g., additive or synergistic effects) of the compounds.

As used herein, "unit dosage form" refers to physically discrete units, suitable as unit dosages, each unit containing a predetermined quantity of active ingredient calculated to produce the desired therapeutic effect in association with the required pharmaceutical carrier. Unit dosage forms may contain a single or a combination therapy.

As used herein, the term "controlled release" refers to a drug-containing formulation or fraction thereof in which release of the drug is not immediate, i.e., with a "controlled release" formulation, administration does not result in immediate release of the drug into an absorption pool. The term encompasses depot formulations designed to gradually release the drug compound over an extended period of time. Controlled release formulations can include a wide variety of drug delivery systems, generally involving mixing the drug compound with carriers, polymers or other compounds having the desired release characteristics (e.g., pH-dependent or non-pH-dependent solubility, different degrees of water solubility, and the like) and formulating the mixture according to the desired route of delivery (e.g., coated capsules, implantable reservoirs, injectable solutions containing biodegradable capsules, and the like).

As used herein, by "pharmaceutically acceptable" or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

"Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Further examples of pharmaceutically acceptable salts include those listed in Berge et al., Pharmaceutical Salts, *J. Pharm. Sci.* 1977 January; 66(1):1-19. Pharmaceutically acceptable salts can be prepared in situ in the manufacturing process, or by separately reacting a purified compound of the invention in its free acid or base form with a suitable organic or inorganic base or acid, respectively, and isolating the salt thus formed during subsequent purification. It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The term "excipient" as used herein means an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

"Alkyl" refers to and includes saturated linear, branched, or cyclic univalent hydrocarbon structures and combinations thereof. Particular alkyl groups are those having 1 to 20 carbon atoms (a "$C_1$-$C_{20}$ alkyl"). More particular alkyl groups are those having 1 to 8 carbon atoms (a "$C_1$-$C_8$ alkyl"). When an alkyl residue having a specific number of carbons is named, all geometric isomers having that number of carbons are intended to be encompassed and described; thus, for example, "butyl" is meant to include n-butyl, sec-butyl, iso-butyl, tert-butyl and cyclobutyl; "propyl" includes n-propyl, iso-propyl and cyclopropyl. This term is exemplified by groups such as methyl, t-butyl, n-heptyl, octyl, cyclohexylmethyl, cyclopropyl and the like. Cycloalkyl is a subset of alkyl and can consist of one ring, such as cyclohexyl, or multiple rings, such as adamantyl. A cycloalkyl comprising more than one ring may be fused, spiro or bridged, or combinations thereof. A preferred cycloalkyl is a saturated cyclic hydrocarbon having from 3 to 13 annular carbon atoms. A more preferred cycloalkyl is a saturated cyclic hydrocarbon having from 3 to 8 annular carbon atoms (a "$C_3$-$C_8$ cycloalkyl"). Examples of cycloalkyl groups include adamantyl, decahydronaphthalenyl, cyclopropyl, cyclobutyl, cyclopentyl, cyclohexyl and the like.

"Alkylene" refers to the same residues as alkyl, but having bivalency. Examples of alkylene include methylene (—$CH_2$—), ethylene (—$CH_2CH_2$—), propylene (—$CH_2CH_2CH_2$—), butylene (—$CH_2CH_2CH_2CH_2$—) and the like.

"Alkenyl" refers to an unsaturated hydrocarbon group having at least one site of olefinic unsaturation (i.e., having at least one moiety of the formula C=C) and preferably having from 2 to 10 carbon atoms and more preferably 2 to 8 carbon atoms. Examples of alkenyl include but are not limited to —$CH_2$—CH=CH—$CH_3$ and —$CH_2$—$CH_2$-cyclohexenyl, where the ethyl group of the latter example can be attached to the cyclohexenyl moiety at any available position on the ring. Cycloalkenyl is a subset of alkenyl and can consist of one ring, such as cyclohexyl, or multiple rings, such as norbornenyl. A more preferred cycloalkenyl is an unsaturated cyclic hydrocarbon having from 3 to 8 annular carbon atoms (a "$C_3$-$C_8$ cycloalkenyl"). Examples of cycloalkenyl groups include cyclopropenyl, cyclobutenyl, cyclopentenyl, cyclohexenyl and the like.

"Alkynyl" refers to an unsaturated hydrocarbon group having at least one site of acetylenic unsaturation (i.e., having at least one moiety of the formula C≡C) and preferably having from 2 to 10 carbon atoms and more preferably 3 to 8 carbon atoms.

"Substituted alkyl" refers to an alkyl group having from 1 to 5 substituents including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted alkenyl" refers to alkenyl group having from 1 to 5 substituents s including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted alkynyl" refers to alkynyl groups having from 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted heterocyclyl, substituted or unsubstituted aralkyl, aminosulfonyl, sulfonylamino, sulfonyl, oxo, carbonylalkylenealkoxy and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups H—C(O)O—, alkyl-C(O)O—, substituted alkyl-C(O)O—, alkenyl-C(O)O—, substituted alkenyl-C(O)O—, alkynyl-C(O)O—, substituted alkynyl-C(O)O—, cycloalkyl-C(O)O—, substituted cycloalkyl- C(O)O—, aryl-C(O)O—, substituted aryl-C(O)O—, heteroaryl-C(O)O—, substituted heteroaryl-C(O)O—, heterocyclic-C(O)O—, and substituted heterocyclic-C(O)O—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Heterocycle", "heterocyclic", or "heterocyclyl" refers to a saturated or an unsaturated non-aromatic group having a single ring or multiple condensed rings, and having from 1 to 10 annular carbon atoms and from 1 to 4 annular heteroatoms, such as nitrogen, sulfur or oxygen. A heterocycle comprising more than one ring may be fused, spiro or bridged, or any combination thereof. In fused ring systems, one or more of the rings can be aryl or heteroaryl. A heterocycle having more than one ring where at least one ring is aromatic may be connected to the parent structure at either a non-aromatic ring position or at an aromatic ring position. In one variation, a heterocycle having more than one ring where at least one ring is aromatic is connected to the parent structure at a non-aromatic ring position.

"Substituted heterocyclic" or "substituted heterocyclyl" refers to a heterocycle group which is substituted with from 1 to 3 substituents including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted aralkyl, aminosulfonyl, sulfonylamino, sulfonyl, oxo, carbonylalkylenealkoxy and the like. In one variation, a substituted heterocycle is a heterocycle substituted with an additional ring, wherein the additional ring may be aromatic or non-aromatic.

"Aryl" or "Ar" refers to an unsaturated aromatic carbocyclic group having a single ring (e.g., phenyl) or multiple condensed rings (e.g., naphthyl or anthryl) which condensed rings may or may not be aromatic. In one variation, the aryl group contains from 6 to 14 annular carbon atoms. An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position.

"Heteroaryl" or "HetAr" refers to an unsaturated aromatic heterocyclic group having from 1 to 10 annular carbon atoms and at least one annular heteroatom, including but not limited to heteroatoms such as nitrogen, oxygen and sulfur. A heteroaryl group may have a single ring (e.g., pyridyl, furyl) or multiple condensed rings (e.g., indolizinyl, benzothienyl) which condensed rings may or may not be aromatic. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position.

"Substituted aryl" refers to an aryl group having 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted aralkyl, aminosulfonyl, sulfonylamino, sulfonyl, oxo, carbonylalkylenealkoxy and the like.

"Substituted heteroaryl" refers to a heteroaryl group having 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Aralkyl" refers to a residue in which an aryl moiety is attached to an alkyl residue and wherein the aralkyl group may be attached to the parent structure at either the aryl or the alkyl residue. Preferably, an aralkyl is connected to the parent structure via the alkyl moiety. In one variation, an aralkyl is a fused ring system where at least one cycloalkyl moiety is fused with at least one aryl moiety. A "substituted aralkyl" refers to a residue in which an aryl moiety is attached to a substituted alkyl residue and wherein the aralkyl group may be attached to the parent structure at either the aryl or the alkyl residue. When an aralkyl is connected to the parent structure via the alkyl moiety, it may also be referred to as an "alkaryl". More particular alkaryl groups are those having 1 to 3 carbon atoms in the alkyl moiety (a "$C_1$-$C_3$ alkaryl").

"Alkoxy" refers to the group alkyl-O—, which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like. Similarly, alkenyloxy refers to the group "alkenyl-O—" and alkynyloxy refers to the group "alkynyl-O—". "Substituted alkoxy" refers to the group substituted alkyl-O.

"Unsubstituted amino" refers to the group —$NH_2$.

"Substituted amino" refers to the group —$NR_aR_b$, where either (a) each $R_a$ and $R_b$ group is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, provided that both $R_a$ and $R_b$ groups are not H; or (b) $R_a$ and $R_b$ are joined together with the nitrogen atom to form a heterocyclic or substituted heterocyclic ring.

"Acylamino" refers to the group —$C(O)NR_aR_b$ where $R_a$ and $R_b$ are independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic, substituted heterocyclic or $R_a$ and $R_b$ groups can be joined together with the nitrogen atom to form a heterocyclic or substituted heterocyclic ring.

"Aminocarbonylalkoxy" refers to the group —$NR_aC(O)OR_b$ where each $R_a$ and $R_b$ group is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic and substituted heterocyclyl.

"Aminoacyl" refers to the group —$NR_aC(O)R_b$ where each $R_a$ and $R_b$ group is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic or substituted heterocyclic. Preferably, $R_a$ is H or alkyl.

"Aminosulfonyl" refers to the groups —NRSO$_2$-alkyl, —NRSO$_2$ substituted alkyl, —NRSO$_2$-alkenyl, —NRSO$_2$-substituted alkenyl, —NRSO$_2$-alkynyl, —NRSO$_2$-substituted alkynyl, —NRSO$_2$-cycloalkyl, —NRSO$_2$-substituted cycloalkyl, —NRSO$_2$-aryl, —NRSO$_2$-substituted aryl, —NRSO$_2$-heteroaryl, —NRSO$_2$-substituted heteroaryl, —NRSO$_2$-heterocyclic, and —NRSO$_2$-substituted heterocyclic, where R is H or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Sulfonylamino" refers to the groups —SO$_2$NH$_2$, —SO$_2$NR-alkyl, —SO$_2$NR-substituted alkyl, —SO$_2$NR-alkenyl, —SO$_2$NR-substituted alkenyl, —SO$_2$NR-alkynyl, —SO$_2$NR-substituted alkynyl, —SO$_2$NR-aryl, —SO$_2$NR-substituted aryl, —SO$_2$NR-heteroaryl, —SO$_2$NR-substituted heteroaryl, —SO$_2$NR-heterocyclic, and —SO$_2$NR-substituted heterocyclic, where R is H or alkyl, or —SO$_2$NR$_2$, where the two R groups are taken together and with the nitrogen atom to which they are attached to form a heterocyclic or substituted heterocyclic ring.

"Sulfonyl" refers to the groups —SO$_2$-alkyl, —SO$_2$-substituted alkyl, —SO$_2$-alkenyl, —SO$_2$-substituted alkenyl, —SO$_2$-alkynyl, —SO$_2$-substituted alkynyl, —SO$_2$-aryl, —SO$_2$-substituted aryl, —SO$_2$-heteroaryl, —SO$_2$-substituted heteroaryl, —SO$_2$-heterocyclic, and —SO$_2$-substituted heterocyclic.

"Carbonylalkylenealkoxy" refers to the group —C(=O)—(CH$_2$)$_n$—OR where R is a substituted or unsubstituted alkyl and n is an integer from 1 to 100, more preferably n is an integer from 1 to 10 or 1 to 5.

"Halo" or "halogen" refers to elements of the Group 17 series having atomic number 9 to 85. Preferred halo groups include the radicals of fluorine, chlorine, bromine and iodine. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halogen; thus 4-chloro-3-fluorophenyl is within the scope of dihaloaryl. An alkyl group in which each H is replaced with a halo group is referred to as a "perhaloalkyl." A preferred perhaloalkyl group is trifluoromethyl (—CF$_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—OCF$_3$).

"Carbonyl" refers to the group C=O.
"Cyano" refers to the group —CN.
"Oxo" refers to the moiety =O.
"Nitro" refers to the group —NO$_2$.
"Thioalkyl" refers to the groups —S-alkyl.
"Alkylsulfonylamino" refers to the groups —R$^1$SO$_2$NR$_a$R$_b$ where R$_a$ and R$_b$ are independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, or the R$_a$ and R$_b$ groups can be joined together with the nitrogen atom to form a heterocyclic or substituted heterocyclic ring and R$^1$ is an alkyl group.

"Carbonylalkoxy" refers to as used herein refers to the groups —C(O)O-alkyl, —C(O)O-substituted alkyl, —C(O)O-aryl, —C(O)O-substituted aryl, —C(O)O-alkenyl, —C(O)O-substituted alkenyl, —C(O)O-alkynyl, —C(O)O-substituted alkynyl, —C(O)O-heteroaryl, —C(O)O-substituted heteroaryl, —C(O)O-heterocyclic or —C(O)O-substituted heterocyclic.

"Geminal" refers to the relationship between two moieties that are attached to the same atom. For example, in the residue —CH$_2$—CHR$^1$R$^2$, R$^1$ and R$^2$ are geminal and R$^1$ may be referred to as a geminal R group to R$^2$.

"Vicinal" refers to the relationship between two moieties that are attached to adjacent atoms. For example, in the residue —CHR$^1$—CH$_2$R$^2$, R$^1$ and R$^2$ are vicinal and R$^1$ may be referred to as a vicinal R group to R$^2$.

A composition of "substantially pure" compound means that the composition contains no more than 15% or preferably no more than 10% or more preferably no more than 5% or even more preferably no more than 3% and most preferably no more than 1% impurity, which impurity may be the compound in a different stereochemical form. For instance, a composition of substantially pure S compound means that the composition contains no more than 15% or no more than 10% or no more than 5% or no more than 3% or no more than 1% of the R form of the compound.

Compounds of the Invention

Compounds according to the invention are detailed herein, including in the Brief Summary of the Invention and the appended claims. The invention includes the use of all of the compounds described herein, including any and all stereoisomers, including geometric isomers (cis/trans) or E/Z isomers, salts and solvates of the compounds described herein, as histamine receptor modulators, as well as methods of making such compounds.

The invention embraces compounds of the formula (I):

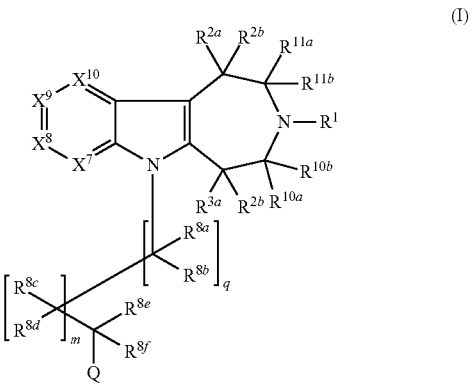

where:

R$^1$ is H, hydroxyl, nitro, cyano, halo, substituted or unsubstituted C$_1$-C$_8$ alkyl, substituted or unsubstituted C$_2$-C$_8$ alkenyl, substituted or unsubstituted C$_2$-C$_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, C$_1$-C$_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy;

each R$^{2a}$, R$^{2b}$, R$^{3a}$ and R$^{3b}$ is independently H, hydroxyl, nitro, cyano, halo, substituted or unsubstituted C$_1$-C$_8$ alkyl, substituted or unsubstituted C$_2$-C$_8$ alkenyl, substituted or unsubstituted C$_2$-C$_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^2$ or $R^3$ to form a cycloalkyl moiety or a carbonyl moiety;

each $R^{10a}$, $R^{10b}$, $R^{11a}$ and $R^{11b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^{10}$ or $R^{11}$ to form a cycloalkyl moiety or a carbonyl moiety;

each $X^7$, $X^8$, $X^9$ and $X^{10}$ is independently N or $CR^4$;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each m and q is independently 0 or 1;

each $R^{8a}$, $R^{8b}$, $R^{8c}$, $R^{8d}$, $R^{8e}$ and $R^{8f}$ is independently H, hydroxyl, alkoxy, halo, $C_1$-$C_8$ perhaloalkyl, carboxy, carbonylalkoxy, substituted or unsubstituted aryl, substituted or unsubstituted heteroaryl, substituted or unsubstituted $C_1$-$C_8$ alkyl, substituted or unsubstituted $C_3$-$C_6$ cycloalkyl, substituted or unsubstituted $C_2$-$C_8$ alkenyl, or is taken together with a geminal $R^8$ to form a moiety of the formula —OCH$_2$CH$_2$O—, is taken together with the carbon to which it is attached and a geminal $R^8$ to form a cycloalkyl moiety or a carbonyl moiety, is taken together with a geminal $R^8$ to form a methylene or a substituted methylene, is taken together with a vicinal $R^8$ and the carbon atoms to which they are attached to form a substituted or unsubstituted $C_3$-$C_8$ cycloalkyl, substituted or unsubstituted $C_3$-$C_8$ cycloalkenyl or substituted or unsubstituted heterocyclyl moiety or is taken together with a vicinal $R^8$ to form a bond, provided when an $R^8$ is taken together with a vicinal $R^8$ to form a bond, the geminal $R^8$ is other than hydroxyl;

Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted amino, alkoxy, aminoacyl, acyloxy, carbonylalkoxy, aminocarbonylalkoxy, acylamino, carboxy, cyano or alkynyl;

provided that the compound is other than a compound in Table 1;

or a salt or solvate thereof.

Compounds of the general formula (I) are described as new histamine receptor modulators. Compounds of the invention may also find use in treating neurodegenerative diseases.

In one variation, the compounds of the invention, pharmaceutical compositions thereof, isolated forms thereof and methods of using and administering the compounds detailed herein, encompass any of the compounds of Formula (I), including those listed in Table 1 or a salt thereof.

In one variation, the compound of the formula (I) is provided, where each $X^7$, $X^8$, $X^9$, $X^{10}$, $R^1$, $R^{10a}$, $R^{10b}$, $R^{11a}$, $R^{11b}$, q and m are as defined for formula (I); each $R^2$ independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^2$ or $R^3$ to form a carbonyl moiety; each $R^{8a}$, $R^{8b}$, $R^{8c}$, $R^{8d}$, $R^{8e}$ and $R^{8f}$ is independently H, hydroxyl, $C_1$-$C_8$ alkyl, $C_1$-$C_8$ perhaloalkyl, carboxy, carbonylalkoxy, is taken together with the carbon to which it is attached and a geminal $R^8$ to form a cycloalkyl moiety or a carbonyl moiety, is taken together with a geminal $R^8$ to form a methylene or a substituted methylene, is taken together with a vicinal $R^8$ and the carbon atoms to which they are attached to form a substituted or unsubstituted $C_3$-$C_8$ cycloalkyl, substituted or unsubstituted $C_3$-$C_8$ cycloalkenyl or substituted or unsubstituted heterocyclyl moiety or is taken together with a vicinal $R^8$ to form a bond, provided: (i) at most one pair of vicinal $R^8$ groups are taken together to form a bond; and (ii) when an $R^8$ is taken together with a vicinal $R^8$ to form a bond, the geminal $R^8$ is other than hydroxyl; Q is a substituted or unsubstituted aryl, substituted or unsubstituted heteroaryl, substituted or unsubstituted cycloalkyl, substituted or unsubstituted cycloalkenyl or substituted or a unsubstituted heterocyclyl, unsubstituted amino, substituted amino, alkoxy, aminoacyl, acyloxy, carbonylalkoxy, aminocarbonylalkoxy or acylamino; provided that the compound is other than a compound in Table 1; or a salt or solvate thereof. In one such variation, the compounds, pharmaceutical compositions thereof, isolated forms thereof and methods of using and administering the compounds detailed herein, encompass any of the compounds of Formula (I), including those listed in Table 1 or a salt thereof.

In another variation, the compound of the invention is of the formula (I), where each $R^{2a}$, $R^{2b}$, $R^{3a}$, $R^{3b}$, $R^{10a}$, $R^{10b}$, $R^{11a}$ and $R^{11b}$ is independently H, substituted or unsubstituted $C_1$-$C_8$ alkyl, halo, hydroxyl, alkoxy, cyano, nitro or is taken together with the carbon to which it is attached to and a geminal R group to form a carbonyl moiety or a cycloalkyl moiety. In yet another variation, the compound is of the formula (I), where each $R^{2a}$, $R^{2b}$, $R^{3a}$ and $R^{3b}$ is independently H, substituted or unsubstituted $C_1$-$C_8$ alkyl, halo, hydroxyl, alkoxy, cyano, nitro or is taken together with the carbon to which it is attached to and a geminal R group to form a carbonyl moiety and each $R^{10a}$, $R^{10b}$, $R^{11a}$ and $R^{11b}$ is independently H, substituted or unsubstituted $C_1$-$C_8$ alkyl or is taken together with the carbon to which it is attached to and a geminal R group to form a carbonyl moiety or a cycloalkyl moiety (e.g. cyclopropyl). In another variation, the compound is of the formula (I), where Q is a substituted or unsubstituted aryl, substituted or unsubstituted heteroaryl, substituted or unsubstituted $C_3$-$C_8$ cycloalkyl, substituted or unsubstituted $C_3$-$C_8$ cycloalkenyl or substituted or a unsubstituted heterocyclyl, substituted or unsubstituted amino, alkoxy, aminoacyl, acyloxy, carbonylalkoxy, aminocarbonylalkoxy or acylamino.

The invention also embraces compounds of the formula (A):

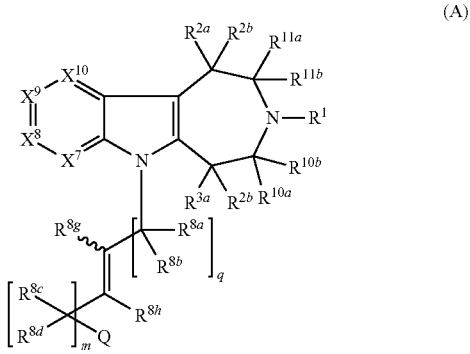

(A)

or a salt or solvate thereof,
wherein:

$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy;

each $R^{2a}$, $R^{2b}$, $R^{3a}$ and $R^{3b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^2$ or $R^3$ to form a cycloalkyl moiety or a carbonyl moiety;

each $R^{10a}$, $R^{10b}$, $R^{11a}$ and $R^{11b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^{10}$ or $R^{11}$ to form a cycloalkyl moiety or a carbonyl moiety;

each $X^7$, $X^8$, $X^9$ and $X^{10}$ is independently N or $CR^4$;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each m and q is independently 0 or 1;

each $R^{8a}$, $R^{8b}$, $R^{8c}$ and $R^{8d}$ is independently H, hydroxyl, alkoxy, halo, substituted or unsubstituted aryl, substituted or unsubstituted heteroaryl, substituted or unsubstituted $C_1$-$C_8$ alkyl, substituted or unsubstituted $C_3$-$C_8$ cycloalkyl, substituted or unsubstituted $C_2$-$C_8$ alkenyl, $C_1$-$C_8$ perhaloalkyl, carboxy, carbonylalkoxy, or is taken together with a geminal $R^{8(a-d)}$ to form a moiety of the formula —OCH$_2$CH$_2$O—, or is taken together with the carbon to which it is attached and a geminal $R^8$ to form a cycloalkyl moiety or a carbonyl moiety;

each $R^{8g}$ and $R^{8h}$ is independently H, halo, alkoxy, substituted or unsubstituted aryl, substituted or unsubstituted heteroaryl, substituted or unsubstituted $C_1$-$C_8$ alkyl, substituted or unsubstituted $C_2$-$C_8$ alkenyl, substituted or unsubstituted $C_3$-$C_8$ cycloalkyl, $C_1$-$C_8$ perhaloalkyl, carboxy, or carbonylalkoxy and the ⌇ bond indicates the presence of either an E or Z double bond configuration, or $R^{8g}$ and $R^{8h}$ are taken together to form a bond; and Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted amino, alkoxy, aminoacyl, acyloxy, carbonylalkoxy, aminocarbonylalkoxy, acylamino, carboxy, cyano or alkynyl.

In one variation, the compound of the formula (A) is provided, where each $X^7$, $X^8$, $X^9$, $X^{10}$, $R^1$, $R^{10a}$, $R^{10b}$, $R^{11a}$, $R^{11b}$, q and m are as defined for formula (A); each $R^{2a}$, $R^{2b}$, $R^{3a}$ and $R^{3b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^2$ or $R^3$ to form a carbonyl moiety; each $R^{8a}$, $R^{8b}$, $R^{8c}$ and $R^{8d}$ is independently H, hydroxyl, $C_1$-$C_8$ alkyl, $C_1$-$C_8$ perhaloalkyl, carboxy, carbonylalkoxy, is taken together with the carbon to which it is attached and a geminal $R^8$ to form a cycloalkyl moiety or a carbonyl moiety, is taken together with a geminal $R^8$ to form a methylene or a substituted methylene; $R^{8g}$ is H, $C_1$-$C_8$ alkyl, $C_3$-$C_8$ cycloalkyl, $C_1$-$C_8$ perhaloalkyl or is taken together with $R^{8h}$ and the carbon atoms to which they are attached to form a substituted or unsubstituted $C_3$-$C_8$ cycloalkyl, substituted or unsubstituted $C_3$-$C_8$ cycloalkenyl or substituted or unsubstituted heterocyclyl moiety and the ⌇ bond indicates the presence of either an E or Z double bond configuration; $R^{8h}$ is H, $C_1$-$C_8$ alkyl, $C_3$-$C_8$ cycloalkyl, $C_1$-$C_8$ perhaloalkyl or is taken together with $R^{8g}$ and the carbon atoms to which they are attached to form a substituted or unsubstituted $C_3$-$C_8$ cycloalkyl, substituted or unsubstituted $C_3$-$C_8$ cycloalkenyl or substituted or unsubstituted heterocyclyl moiety; and Q is a substituted or unsubstituted aryl, substituted or unsubstituted heteroaryl, substituted or unsubstituted cycloalkyl, substituted or unsubstituted cycloalkenyl or substituted or a unsubstituted heterocyclyl, unsubstituted amino, substituted amino, alkoxy, aminoacyl, acyloxy, carbonylalkoxy, aminocarbonylalkoxy or acylamino.

The invention further embraces compounds of the formula (A-1):

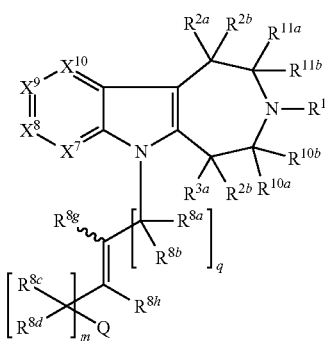

(A-1)

or a salt or solvate thereof,
wherein:

$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy;

each $R^{2a}$, $R^{2b}$, $R^{3a}$ and $R^{3b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^2$ or $R^3$ to form a cycloalkyl moiety or a carbonyl moiety;

each $R^{10a}$, $R^{10b}$, $R^{11a}$ and $R^{11b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^{10}$ or $R^{11}$ to form a cycloalkyl moiety or a carbonyl moiety;

each $X^7$, $X^8$, $X^9$ and $X^{10}$ is independently N or $CR^4$;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each m and q is independently 0 or 1;

each $R^{8a}$, $R^{8b}$, $R^{8c}$ and $R^{8d}$ is independently H, hydroxyl, alkoxy, halo, $C_1$-$C_8$ perhaloalkyl, carboxy, carbonylalkoxy, substituted or unsubstituted aryl, substituted or unsubstituted heteroaryl, substituted or unsubstituted $C_1$-$C_8$ alkyl, substituted or unsubstituted $C_3$-$C_6$ cycloalkyl, substituted or unsubstituted $C_2$-$C_8$ alkenyl, or is taken together with a geminal $R^8$ to form a moiety of the formula —$OCH_2CH_2O$—, is taken together with the carbon to which it is attached and a geminal $R^8$ to form a cycloalkyl moiety or a carbonyl moiety, is taken together with a geminal $R^8$ to form a methylene or a substituted methylene;

$R^{8g}$ is H, substituted or unsubstituted aryl, substituted or unsubstituted heteroaryl, $C_1$-$C_8$ alkyl, $C_3$-$C_8$ cycloalkyl, $C_1$-$C_8$ perhaloalkyl or is taken together with $R^{8h}$ and the carbon atoms to which they are attached to form a substituted or unsubstituted $C_3$-$C_8$ cycloalkyl, substituted or unsubstituted $C_3$-$C_8$ cycloalkenyl or substituted or unsubstituted heterocyclyl moiety and the ⁓ bond indicates the presence of either an E or Z double bond configuration;

$R^{8h}$ is H, halo, substituted or unsubstituted aryl, substituted or unsubstituted heteroaryl, substituted or unsubstituted $C_1$-$C_8$ alkyl, substituted or unsubstituted $C_2$-$C_8$ alkenyl, $C_3$-$C_8$ cycloalkyl, $C_1$-$C_8$ perhaloalkyl or is taken together with $R^{8g}$ and the carbon atoms to which they are attached to form a substituted or unsubstituted $C_3$-$C_8$ cycloalkenyl or substituted or unsubstituted heterocyclyl moiety; and Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted amino, alkoxy, aminoacyl, acyloxy, carbonylalkoxy, aminocarbonylalkoxy, acylamino, carboxy, cyano or alkynyl.

In one variation, the compound of the formula (A-1) is provided, where each $X^7$, $X^8$, $X^9$, $X^{10}$, $R^1$, $R^{10a}$, $R^{10b}$, $R^{11a}$, $R^{11b}$, q and m are as defined for formula (A-1); each $R^{2a}$, $R^{2b}$, $R^{3a}$ and $R^{3b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^2$ or $R^3$ to form a carbonyl moiety; each $R^{8a}$, $R^{8b}$, $R^{8c}$ and $R^{8d}$ is independently H, hydroxyl, $C_1$-$C_8$ alkyl, $C_1$-$C_8$ perhaloalkyl, carboxy, carbonylalkoxy, is taken together with the carbon to which it is attached and a geminal $R^8$ to form a cycloalkyl moiety or a carbonyl moiety, is taken together with a geminal $R^8$ to form a methylene or a substituted methylene; $R^{8g}$ is H, substituted or unsubstituted aryl, substituted or unsubstituted heteroaryl, $C_1$-$C_8$ alkyl, $C_3$-$C_8$ cycloalkyl, $C_1$-$C_8$ perhaloalkyl or is taken together with $R^{8h}$ and the carbon atoms to which they are attached to form a substituted or unsubstituted $C_3$-$C_8$ cycloalkenyl or substituted or unsubstituted heterocyclyl moiety and the ⌇ bond indicates the presence of either an E or Z double bond configuration; $R^{8h}$ is H, halo, substituted or unsubstituted aryl, substituted or unsubstituted heteroaryl, unsubstituted $C_1$-$C_8$ alkyl, $C_1$-$C_8$ alkyl substituted with a carbonylalkoxy, carboxyl or acylamino moiety, $C_2$-$C_8$ alkenyl, $C_3$-$C_8$ cycloalkyl, $C_1$-$C_8$ perhaloalkyl or is taken together with $R^{8g}$ and the carbon atoms to which they are attached to form a substituted or unsubstituted $C_3$-$C_8$ cycloalkyl, substituted or unsubstituted $C_3$-$C_8$ cycloalkenyl or substituted or unsubstituted heterocyclyl moiety; and Q is a substituted or unsubstituted aryl, substituted or unsubstituted heteroaryl, substituted or unsubstituted cycloalkyl, substituted or unsubstituted cycloalkenyl or substituted or a unsubstituted heterocyclyl, unsubstituted amino, substituted amino, alkoxy, aminoacyl, acyloxy, carbonylalkoxy, aminocarbonylalkoxy or acylamino.

The substituent groups $R^1$, $R^{2a}$, $R^{2b}$, $R^{3a}$, $R^{3b}$, $R^{8a}$, $R^{8b}$, $R^{8c}$, $R^{8d}$, $R^{8g}$, $R^{8h}$, $R^{10a}$, $R^{10b}$, $R^{11a}$, $R^{11b}$, m, q, Q, $X^7$, $X^8$, $X^9$, and $X^{10}$ described herein as suitable for compounds of formula (A) are also suitable for compounds of formulae (A-1). Variations of formula (A) detailed throughout, where applicable, apply to formula (A-1) the same as if each and every variation were specifically and individually listed for formula (A-1).

The invention also embraces compounds of the formula (B):

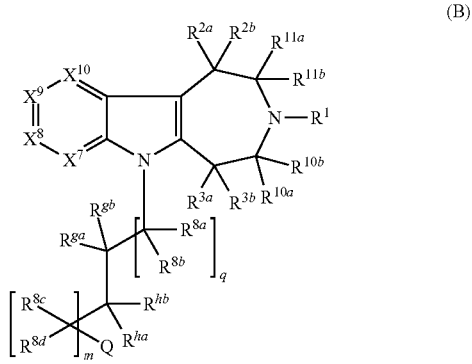

(B)

or a salt or solvate thereof;
wherein:
$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy;

each $R^{2a}$, $R^{2b}$, $R^{3a}$ and $R^{3b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^2$ or $R^3$ to form a cycloalkyl moiety or a carbonyl moiety;

$R^{10a}$, $R^{10b}$, $R^{11a}$ and $R^{11b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^{10}$ or $R^{11}$ to form a cycloalkyl moiety or a carbonyl moiety;

each $X^7$, $X^8$, $X^9$ and $X^{10}$ is independently N or $CR^4$;
each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each m and q is independently 0 or 1;
each $R^{8a}$, $R^{8b}$, $R^{8c}$ and $R^{8d}$ is independently H, hydroxyl, alkoxy, halo, substituted or unsubstituted aryl, substituted or unsubstituted heteroaryl, substituted or unsubstituted $C_1$-$C_8$ alkyl, substituted or unsubstituted $C_3$-$C_8$ cycloalkyl, substituted or unsubstituted $C_2$-$C_8$ alkenyl, $C_1$-$C_8$ perhaloalkyl, carboxy, carbonylalkoxy, or is taken together with a geminal $R^8$ to form a moiety of the formula —OCH$_2$CH$_2$O—, or is taken together with the carbon to which it is attached and a geminal $R^8$ to form a cycloalkyl moiety or a carbonyl moiety;

each $R^{ga}$ and $R^{ha}$ is independently H, hydroxyl, alkoxy, halo, substituted or unsubstituted aryl, substituted or unsubstituted heteroaryl, substituted or unsubstituted $C_1$-$C_8$ alkyl, substituted or unsubstituted $C_3$-$C_8$ cycloalkyl, substituted or unsubstituted $C_2$-$C_8$ alkenyl, $C_1$-$C_8$ perhaloalkyl, carboxy, or carbonylalkoxy; or $R^{ga}$ and $R^{ha}$ may be taken together to represent a bond;

$R^{gb}$ and $R^{hb}$ are taken together with the carbon atoms to which they are attached to form a substituted or unsubstituted $C_3$-$C_8$ cycloalkyl, substituted or unsubstituted $C_3$-$C_8$ cycloalkenyl or substituted or unsubstituted heterocyclyl moiety; and Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted amino, alkoxy, aminoacyl, acyloxy, carbonylalkoxy, aminocarbonylalkoxy, acylamino, carboxy, cyano or alkynyl.

In one variation, the compound of the formula (B) is provided, where each $X^7$, $X^8$, $X^9$, $X^{10}$, $R^1$, $R^{10a}$, $R^{10b}$, $R^{11a}$, $R^{11b}$, q and m are as defined for formula (B); each $R^{2a}$, $R^{2b}$, $R^{3a}$ and $R^{3b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^2$ or $R^3$ to form a carbonyl moiety; each $R^{8a}$, $R^{8b}$, $R^{8c}$ and $R^{8d}$ is independently H, hydroxyl, $C_1$-$C_8$ alkyl, $C_1$-$C_8$ perhaloalkyl, carboxy, carbonylalkoxy, is taken together with the carbon to which it is attached and a geminal $R^8$ to form a cycloalkyl moiety or a carbonyl moiety, is taken together with a geminal $R^8$ to form a methylene or a substituted methylene; each of $R^{ga}$ and $R^{ha}$ is independently H, hydroxyl, or $C_1$-$C_8$ alkyl; or $R^{ga}$ and $R^{ha}$ may be taken together to represent a bond; $R^{gb}$ and $R^{hb}$ are taken together with the carbon atoms to which they are attached to form a substituted or unsubstituted $C_3$-$C_8$ cycloalkyl, substituted or unsubstituted $C_3$-$C_8$ cycloalkenyl or substituted or unsubstituted heterocyclyl moiety; and Q is a substituted or unsubstituted aryl, substituted or unsubstituted heteroaryl, substituted or unsubstituted cycloalkyl, substituted or unsubstituted cycloalkenyl or substituted or a unsubstituted heterocyclyl, unsubstituted amino, substituted amino, alkoxy, aminoacyl, acyloxy, carbonylalkoxy, aminocarbonylalkoxy or acylamino.

The invention also embraces compounds of the formula (Ia):

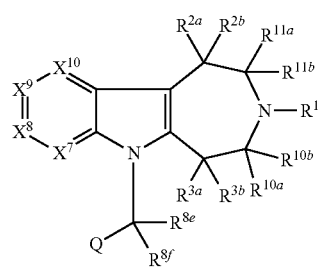

(Ia)

where:

$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy;

each $R^{2a}$, $R^{2b}$, $R^{3a}$ and $R^{3b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^2$ or $R^3$ to form a cycloalkyl moiety or a carbonyl moiety;

each $R^{10a}$, $R^{10b}$, $R^{11a}$ and $R^{11b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^{10}$ or $R^{11}$ to form a cycloalkyl moiety or a carbonyl moiety;

each $X^7$, $X^8$, $X^9$ and $X^{10}$ is independently N or $CR^4$;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8e}$ and $R^{8f}$ is independently H, hydroxyl, alkoxy, halo, substituted or unsubstituted aryl, substituted or unsubstituted heteroaryl, substituted or unsubstituted $C_1$-$C_8$ alkyl, substituted or unsubstituted $C_3$-$C_8$ cycloalkyl, substituted or unsubstituted $C_2$-$C_8$ alkenyl, $C_1$-$C_8$ perhaloalkyl, carboxy, carbonylalkoxy, or $R^{8e}$ and $R^{8f}$ are taken together to form a moiety of the formula —OCH$_2$CH$_2$O—, a methylene or a substituted methylene, or $R^{8e}$ and $R^{8f}$ are taken together with the carbon to which they are attached to form a cycloalkyl moiety or a carbonyl moiety;

Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted amino, alkoxy, aminoacyl, acyloxy, carbonylalkoxy, aminocarbonylalkoxy, acylamino, carboxy, cyano or alkynyl;

or a salt or solvate thereof.

In one variation, the compound of the formula (Ia) is provided, where each $X^7$, $X^8$, $X^9$, $X^{10}$, $R^1$, $R^{10a}$, $R^{10b}$, $R^{11a}$, $R^{11b}$, q and m are as defined for formula (Ia); each $R^{2a}$, $R^{2b}$, $R^{3a}$ and $R^{3b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^2$ or $R^3$ to form a carbonyl moiety; each $R^{8e}$ and $R^{8f}$ is independently H, hydroxyl, $C_1$-$C_8$ alkyl, $C_1$-$C_8$ perhaloalkyl, carboxy, carbonylalkoxy, is taken together with the carbon to which it is attached and a geminal $R^8$ to form a cycloalkyl moiety or a carbonyl moiety or is taken together with a geminal $R^8$ to form a methylene or a substituted methylene; and Q is a substituted or unsubstituted aryl, substituted or unsubstituted heteroaryl, substituted or unsubstituted cycloalkyl, substituted or unsubstituted cycloalkenyl or substituted or a unsubstituted heterocyclyl, unsubstituted amino, substituted amino, alkoxy, aminoacyl, acyloxy, carbonylalkoxy, aminocarbonylalkoxy or acylamino; or a salt or solvate thereof.

In one variation, the compound of the invention is of the formula (Ia), where each $R^{2a}$, $R^{2b}$, $R^{3a}$, $R^{3b}$, $R^{10a}$, $R^{10b}$, $R^{11a}$ and $R^{11b}$ is independently H, substituted or unsubstituted $C_1$-$C_8$ alkyl, halo, hydroxyl, alkoxy, cyano, nitro or is taken together with the carbon to which it is attached to and a geminal R group to form a carbonyl moiety or a cycloalkyl moiety. In another variation, the compound is of the formula (I), where each $R^{2a}$, $R^{2b}$, $R^{3a}$ and $R^{3b}$ is independently H, substituted or unsubstituted $C_1$-$C_8$ alkyl, halo, hydroxyl, alkoxy, cyano, nitro or is taken together with the carbon to which it is attached to and a geminal R group to form a carbonyl moiety and each $R^{10a}$, $R^{10b}$, $R^{11a}$ and $R^{11b}$ is independently H, substituted or unsubstituted $C_1$-$C_8$ alkyl or is taken together with the carbon to which it is attached to and a geminal R group to form a carbonyl moiety or a cycloalkyl moiety (e.g. cyclopropyl). In another variation, the compound is of the formula (Ia), where Q is a substituted or unsubstituted aryl, substituted or unsubstituted heteroaryl, substituted or unsubstituted $C_3$-$C_8$ cycloalkyl, substituted or unsubstituted $C_3$-$C_8$ cycloalkenyl or substituted or a unsubstituted heterocyclyl, substituted or unsubstituted amino, alkoxy, aminoacyl, acyloxy, carbonylalkoxy, aminocarbonylalkoxy or acylamino.

The invention also embraces compounds of the formula (Ib):

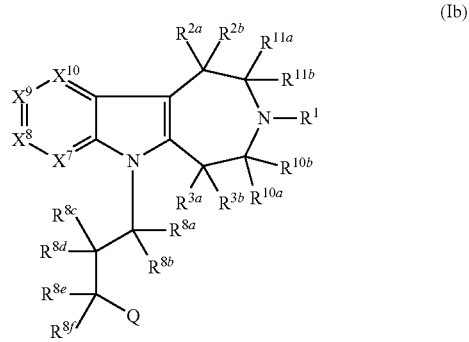

where:

$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy;

each $R^{2a}$, $R^{2b}$, $R^{3a}$ and $R^{3b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^2$ or $R^3$ to form a cycloalkyl moiety or a carbonyl moiety;

each $R^{10a}$, $R^{10b}$, $R^{11a}$ and $R^{11b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^{10}$ or $R^{11}$ to form a cycloalkyl moiety or a carbonyl moiety;

each $X^7$, $X^8$, $X^9$ and $X^{10}$ is independently N or $CR^4$;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$ and $R^{8f}$ is independently H, hydroxyl, $C_1$-$C_8$ perhaloalkyl, carboxy, carbonylalkoxy, alkoxy, halo, substituted or unsubstituted aryl, substituted or unsubstituted heteroaryl, substituted or unsubstituted $C_1$-$C_8$ alkyl, substituted or unsubstituted $C_3$-$C_6$ cycloalkyl, substituted or unsubstituted $C_2$-$C_8$ alkenyl, or is taken together with a geminal $R^8$ to form a moiety of the formula —OCH$_2$CH$_2$O—, is taken together with the carbon to which it is attached and a geminal $R^8$ to form a cycloalkyl moiety or a carbonyl moiety, is taken together with a geminal $R^8$ to form a methylene or a substituted methylene, is taken together with a vicinal $R^8$ and the carbon atoms to which they are attached to form a substituted or unsubstituted $C_3$-$C_8$ cycloalkyl, substituted or unsubstituted $C_3$-$C_8$ cycloalkenyl or substituted or unsubstituted heterocyclyl moiety or is taken together with a vicinal $R^8$ to form a bond, provided when an $R^8$ is taken together with a vicinal $R^8$ to form a bond, the geminal $R^8$ is other than hydroxyl;

Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted amino, alkoxy, aminoacyl, acyloxy, carbonylalkoxy, aminocarbonylalkoxy, acylamino, carboxy, cyano or alkynyl;

or a salt or solvate thereof.

In one variation, the compound of the formula (Ib) is provided, where each $X^7$, $X^8$, $X^9$, $X^{10}$, $R^1$, $R^{10a}$, $R^{10b}$, $R^{11a}$, $R^{11b}$, q and m are as defined for formula (Ib); each $R^{2a}$, $R^{2b}$, $R^{3a}$ and $R^{3b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^2$ or $R^3$ to form a carbonyl moiety; each $R^{8a}$, $R^{8b}$, $R^{8c}$, $R^{8d}$, $R^{8e}$ and $R^{8f}$ is independently H, hydroxyl, $C_1$-$C_8$ alkyl, $C_1$-$C_8$ perhaloalkyl, carboxy, carbonylalkoxy, is taken together with the carbon to which it is attached and a geminal $R^8$ to form a cycloalkyl moiety or a carbonyl moiety, is taken together with a geminal $R^8$ to form a methylene or a substituted methylene, is taken together with a vicinal $R^8$ and the carbon atoms to which they are attached to form a substituted or unsubstituted $C_3$-$C_8$ cycloalkyl, substituted or unsubstituted $C_3$-$C_8$ cycloalkenyl or substituted or unsubstituted heterocyclyl moiety or is taken together with a vicinal $R^8$ to form a bond, provided: (i) at most one pair of vicinal $R^8$ groups are taken together to form a bond; and (ii) when an $R^8$ is taken together with a vicinal $R^8$ to form a bond, the geminal $R^8$ is other than hydroxyl; and Q is a substituted or unsubstituted aryl, substituted or unsubstituted heteroaryl, substituted or unsubstituted cycloalkyl, substituted or unsubstituted cycloalkenyl or substituted or a unsubstituted heterocyclyl, unsubstituted amino, substituted amino, alkoxy, aminoacyl, acyloxy, carbonylalkoxy, aminocarbonylalkoxy or acylamino; or a salt or solvate thereof.

In one variation, the compound of the invention is of the formula (Ib), where each $R^{2a}$, $R^{2b}$, $R^{3a}$, $R^{3b}$, $R^{10a}$, $R^{10b}$, $R^{11a}$ and $R^{11b}$ is independently H, substituted or unsubstituted $C_1$-$C_8$ alkyl, halo, hydroxyl, alkoxy, cyano, nitro or is taken together with the carbon to which it is attached to and a geminal R group to form a carbonyl moiety or a cycloalkyl moiety. In another variation, the compound is of the formula (I), where each $R^{2a}$, $R^{2b}$, $R^{3a}$ and $R^{3b}$ is independently H, substituted or unsubstituted $C_1$-$C_8$ alkyl, halo, hydroxyl, alkoxy, cyano, nitro or is taken together with the carbon to which it is attached to and a geminal R group to form a carbonyl moiety and each $R^{10a}$, $R^{10b}$, $R^{11a}$ and $R^{11b}$ is independently H, substituted or unsubstituted $C_1$-$C_8$ alkyl or is taken together with the carbon to which it is attached to and a geminal R group to form a carbonyl moiety or a cycloalkyl moiety (e.g. cyclopropyl). In another variation, the compound is of the formula (Ib), where Q is a substituted or unsubstituted aryl, substituted or unsubstituted heteroaryl, substituted or unsubstituted $C_3$-$C_8$ cycloalkyl, substituted or unsubstituted $C_3$-$C_8$ cycloalkenyl or substituted or a unsubstituted heterocyclyl, substituted or unsubstituted amino, alkoxy, aminoacyl, acyloxy, carbonylalkoxy, aminocarbonylalkoxy or acylamino.

The invention also embraces compound of the formula (Ic):

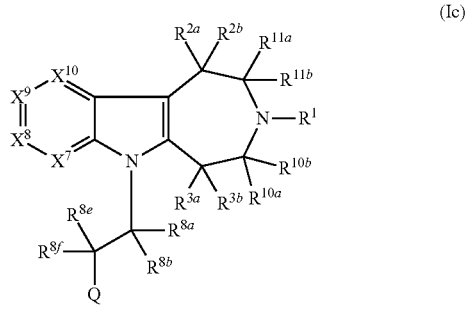

(Ic)

where:

$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy;

each $R^{2a}$, $R^{2b}$, $R^{3a}$ and $R^{3b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^2$ or $R^3$ to form a cycloalkyl moiety or a carbonyl moiety;

each $R^{10a}$, $R^{10b}$, $R^{11a}$ and $R^{11b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^{10}$ or $R^{11}$ to form a cycloalkyl moiety or a carbonyl moiety;

each $X^7$, $X^8$, $X^9$ and $X^{10}$ is independently N or $CR^4$;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8c}$, $R^{8d}$, $R^{8e}$ and $R^{8f}$ is independently H, hydroxyl, $C_1$-$C_8$ perhaloalkyl, carboxy, carbonylalkoxy, alkoxy, halo, substituted or unsubstituted aryl, substituted or unsubstituted heteroaryl, substituted or unsubstituted $C_1$-$C_8$ alkyl, substituted or unsubstituted $C_3$-$C_6$ cycloalkyl, substituted or unsubstituted $C_2$-$C_8$ alkenyl, or is taken together with a geminal $R^8$ to form a moiety of the formula —$OCH_2CH_2O$—, is taken together with the carbon to which it is attached and a geminal $R^8$ to form a cycloalkyl moiety or a carbonyl moiety, is taken together with a geminal $R^8$ to form a methylene or a substituted methylene, is taken together with a vicinal $R^8$ and the carbon atoms to which they are attached to form a substituted or unsubstituted $C_3$-$C_8$ cycloalkyl, substituted or unsubstituted $C_3$-$C_8$ cycloalkenyl or substituted or unsubstituted heterocyclyl moiety or is taken together with a vicinal $R^8$ to form a bond, provided when an $R^8$ is taken together with a vicinal $R^8$ to form a bond, the geminal $R^8$ is other than hydroxyl;

Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted amino, alkoxy, aminoacyl, acyloxy, carbonylalkoxy, aminocarbonylalkoxy, acylamino, carboxy, cyano or alkynyl;

or a salt or solvate thereof.

In one variation, the compound of the formula (Ic) is provided, where each $X^7, X^8, X^9, X^{10}, R^1, R^{10a}, R^{10b}, R^{11a}, R^{11b}$, and m are as defined for formula (Ic); each $R^{2a}, R^{2b}, R^{3a}$ and $R^{3b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^2$ or $R^3$ to form a carbonyl moiety; each $R^{8c}, R^{8d}, R^{8e}$ and $R^{8f}$ is independently H, hydroxyl, $C_1$-$C_8$ alkyl, $C_1$-$C_8$ perhaloalkyl, carboxy, carbonylalkoxy, is taken together with the carbon to which it is attached and a geminal $R^8$ to form a cycloalkyl moiety or a carbonyl moiety, is taken together with a geminal $R^8$ to form a methylene or a substituted methylene, is taken together with a vicinal $R^8$ and the carbon atoms to which they are attached to form a substituted or unsubstituted $C_3$-$C_8$ cycloalkyl, substituted or unsubstituted $C_3$-$C_8$ cycloalkenyl or substituted or unsubstituted heterocyclyl moiety or is taken together with a vicinal $R^8$ to form a bond, provided: (i) at most one pair of vicinal $R^8$ groups are taken together to form a bond; and (ii) when an $R^8$ is taken together with a vicinal $R^8$ to form a bond, the geminal $R^8$ is other than hydroxyl; and Q is a substituted or unsubstituted aryl, substituted or unsubstituted heteroaryl, substituted or unsubstituted cycloalkyl, substituted or unsubstituted cycloalkenyl or substituted or a unsubstituted heterocyclyl, unsubstituted amino, substituted amino, alkoxy, aminoacyl, acyloxy, carbonylalkoxy, aminocarbonylalkoxy or acylamino; or a salt or solvate thereof.

In one variation, the compound of the invention is of the formula (Ic), where each $R^{2a}, R^{2b}, R^{3a}, R^{3b}, R^{10a}, R^{10b}, R^{11a}$ and $R^{11b}$ is independently H, substituted or unsubstituted $C_1$-$C_8$ alkyl, halo, hydroxyl, alkoxy, cyano, nitro or is taken together with the carbon to which it is attached to and a geminal R group to form a carbonyl moiety or a cycloalkyl moiety. In another variation, the compound is of the formula (I), where each $R^{2a}, R^{2b}, R^{3a}$ and $R^{3b}$ is independently H, substituted or unsubstituted $C_1$-$C_8$ alkyl, halo, hydroxyl, alkoxy, cyano, nitro or is taken together with the carbon to which it is attached to and a geminal R group to form a carbonyl moiety and each $R^{10a}, R^{10b}, R^{11a}$ and $R^{11b}$ is independently H, substituted or unsubstituted $C_1$-$C_8$ alkyl or is taken together with the carbon to which it is attached to and a geminal R group to form a carbonyl moiety or a cycloalkyl moiety (e.g. cyclopropyl). In another variation, the compound is of the formula (Ic), where Q is a substituted or unsubstituted aryl, substituted or unsubstituted heteroaryl, substituted or unsubstituted $C_3$-$C_8$ cycloalkyl, substituted or unsubstituted $C_3$-$C_8$ cycloalkenyl or substituted or a unsubstituted heterocyclyl, substituted or unsubstituted amino, alkoxy, aminoacyl, acyloxy, carbonylalkoxy, aminocarbonylalkoxy or acylamino. In another variation, the compound is of the formula (Ic), provided that when $R^{8c}$ and $R^{8d}$ are hydrogen and $R^{8e}$ and $R^{8f}$ are taken together with the carbon to which they are attached to form a carbonyl moiety, then Q is other than —NHR where R is selected from substituted or unsubstituted aryl and substituted or unsubstituted heteroaryl.

In one embodiment, the compound is of the formula (Ic) where $R^{8c}$ and $R^{8e}$ are taken together to form a bond, each $R^{8d}$ and $R^{8f}$ is independently H, $C_1$-$C_8$ alkyl, $C_1$-$C_8$ perhaloalkyl, carboxy, carbonylalkoxy, or $R^{8d}$ and $R^{8f}$ are taken together with the carbon atoms to which they are attached to form a substituted or unsubstituted $C_3$-$C_8$ cycloalkenyl or substituted or unsubstituted heterocyclyl moiety. In one embodiment, the compound is of the formula (C) and the ⁓ bond indicates the presence of either an E or Z double bond configuration:

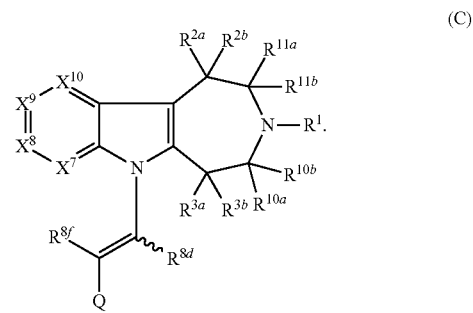

(C)

In one variation, the compound is of the formula (C), wherein:

$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy;

each $R^{2a}, R^{2b}, R^{3a}, R^{3b}, R^{10a}, R^{10b}, R^{11a}$ and $R^{11b}$ is independently H, substituted or unsubstituted $C_1$-$C_8$ alkyl, halo, hydroxyl, alkoxy, cyano, nitro or is taken together with the carbon to which it is attached to and a geminal R group to form a carbonyl moiety or a cycloalkyl moiety;

each $X^7, X^8, X^9$ and $X^{10}$ is independently N or $CR^4$;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

$R^{8d}$ is H, $C_1$-$C_8$ perhaloalkyl, alkoxy, halo, substituted or unsubstituted aryl, substituted or unsubstituted heteroaryl, substituted or unsubstituted $C_1$-$C_8$ alkyl, substituted or unsubstituted $C_3$-$C_6$ cycloalkyl, substituted or unsubstituted $C_2$-$C_8$ alkenyl, or is taken together with $R^{8f}$ and the carbon atoms to which they are attached to form a substituted or unsubstituted $C_3$-$C_8$ cycloalkyl, substituted or unsubstituted $C_3$-$C_8$ cycloalkenyl or substituted or unsubstituted heterocyclyl moiety and the ~~~ bond indicates the presence of either an E or Z double bond configuration;

$R^{8f}$ is H, $C_1$-$C_8$ perhaloalkyl, alkoxy, halo, substituted or unsubstituted aryl, substituted or unsubstituted heteroaryl, substituted or unsubstituted $C_1$-$C_8$ alkyl, substituted or unsubstituted $C_3$-$C_6$ cycloalkyl, substituted or unsubstituted $C_2$-$C_8$ alkenyl, or is taken together with $R^{8d}$ and the carbon atoms to which they are attached to form a substituted or unsubstituted $C_3$-$C_8$ cycloalkenyl or substituted or unsubstituted heterocyclyl moiety;

Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted amino, alkoxy, aminoacyl, acyloxy, carbonylalkoxy, aminocarbonylalkoxy, acylamino, carboxy, cyano or alkynyl;

or a salt or solvate thereof.

In one variation, the compound of the formula (C) is provided, where each $X^7$, $X^8$, $X^9$, $X^{10}$, $R^1$, $R^{2a}$, $R^{2b}$, $R^{3a}$, $R^{3b}$, $R^{10a}$, $R^{10b}$, $R^{11a}$, $R^{11b}$, q and m are as defined for formula (C); $R^{8d}$ is H, $C_1$-$C_8$ alkyl, $C_3$-$C_8$ cycloalkyl, $C_1$-$C_8$ perhaloalkyl or is taken together with $R^{8f}$ and the carbon atoms to which they are attached to form a substituted or unsubstituted $C_3$-$C_8$ cycloalkyl, substituted or unsubstituted $C_3$-$C_8$ cycloalkenyl or substituted or unsubstituted heterocyclyl moiety and the ~~~ bond indicates the presence of either an E or Z double bond configuration; $R^{8f}$ is H, $C_1$-$C_8$ alkyl, $C_3$-$C_8$ cycloalkyl, $C_1$-$C_8$ perhaloalkyl or is taken together with $R^{8d}$ and the carbon atoms to which they are attached to form a substituted or unsubstituted $C_3$-$C_8$ cycloalkyl, substituted or unsubstituted $C_3$-$C_8$ cycloalkenyl or substituted or unsubstituted heterocyclyl moiety; and Q is a substituted or unsubstituted aryl, substituted or unsubstituted heteroaryl, substituted or unsubstituted cycloalkyl, substituted or unsubstituted cycloalkenyl or substituted or a unsubstituted heterocyclyl, unsubstituted amino, substituted amino, alkoxy, aminoacyl, acyloxy, carbonylalkoxy, aminocarbonylalkoxy or acylamino; or a salt or solvate thereof.

In one variation, the compound is of the formula (C), wherein at least one of the $X^7$, $X^8$, $X^9$ and $X^{10}$ is $CR^4$, where each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl. In another variation, each $X^7$, $X^8$, $X^9$ and $X^{10}$ is $CR^4$. In another variation, one of $X^7$, $X^8$, $X^9$ and $X^{10}$ is $CR^4$ and the others are CH. In another variation, two of $X^7$, $X^8$, $X^9$ and $X^{10}$ are $CR^4$ and the others are CH. In one variation, at least one of $X^7$, $X^8$, $X^9$ and $X^{10}$ is $CR^4$ where $R^4$ is halo, $C_1$-$C_8$ perhaloalkyl or substituted or unsubstituted $C_1$-$C_8$ alkyl. In another variation, each $X^7$, $X^8$ and $X^{10}$ is CH and $X^9$ is $CR^4$ where $R^4$ is halo, $C_1$-$C_8$ perhaloalkyl or substituted or unsubstituted $C_1$-$C_8$ alkyl. In another variation, each $X^7$, $X^8$ and $X^{10}$ is CH and $X^9$ is $CR^4$ where $R^4$ is halo, e.g. chloro or fluoro. In another variation, each $X^7$, $X^8$ and $X^{10}$ is CH and $X^9$ is $CR^4$ where $R^4$ is unsubstituted $C_1$-$C_8$ alkyl, e.g. methyl. In another variation, each $X^7$, $X^8$ and $X^{10}$ is CH and $X^9$ is $CR^4$ where $R^4$ is unsubstituted $C_1$-$C_8$ perhaloalkyl, e.g. $CF_3$. In one variation, the compound is of the formula (C), where Q is substituted or unsubstituted aryl, substituted or unsubstituted heteroaryl, substituted or unsubstituted cycloalkyl, substituted or unsubstituted cycloalkenyl or substituted or a unsubstituted heterocyclyl. In another variation, Q is substituted or unsubstituted heteroaryl, e.g. substituted or unsubstituted pyridyl. In another variation, Q is substituted or unsubstituted aryl, e.g. substituted or unsubstituted phenyl. In another variation, Q is phenyl substituted with one or more of the substituents selected from halo, $C_1$-$C_8$ alkyl, $C_1$-$C_8$ perhaloalkyl and alkoxy, e.g. 4-fluorophenyl, 4-chlorophenyl, 4-methoxyphenyl, 4-(trifluoromethyl)phenyl, 3,4-difluorophenyl, 3-chloro-4-fluorophenyl, 4-methoxyl-2-fluorophenyl, 4-methoxyl-3-fluorophenyl and 3-methoxy-4-fluorophenyl. In one variation, the compound is of the formula (C), where each $R^1$, $R^{2a}$, $R^{2b}$, $R^{3a}$, $R^{3b}$, $R^{10a}$, $R^{10b}$, $R^{11a}$ and $R^{11b}$ is independently H, substituted or unsubstituted $C_1$-$C_8$ alkyl. In another variation, $R^1$ is substituted or unsubstituted $C_1$-$C_8$ alkyl, e.g. methyl. In another variation, each $R^{2a}$, $R^{2b}$, $R^{3a}$, $R^{3b}$, $R^{10a}$, $R^{10b}$, $R^{11a}$ and $R^{11b}$ is H. In another variation, $R^1$ is substituted or unsubstituted $C_1$-$C_8$ alkyl, e.g. methyl, and each $R^{2a}$, $R^{2b}$, $R^{3a}$, $R^{3b}$, $R^{10a}$, $R^{10b}$, $R^{11a}$ and $R^{11b}$ is H. In one variation, the compound is of the formula (C), where each $R^{8d}$ and $R^{8f}$ is independently H, $C_1$-$C_8$ perhaloalkyl or substituted or unsubstituted $C_1$-$C_8$ alkyl. In another variation, each $R^{8d}$ and $R^{8f}$ is independently H or unsubstituted $C_1$-$C_8$ alkyl, e.g. methyl, ethyl and cyclopropyl. In another variation, the compound is of the formula (C) where each $X^7$, $X^8$ and $X^{10}$ is CH and $X^9$ is $CR^4$ where $R^4$ is halo, $C_1$-$C_8$ perhaloalkyl or substituted or unsubstituted $C_1$-$C_8$ alkyl (e.g. methyl), $R^1$ is substituted or unsubstituted $C_1$-$C_8$ alkyl (e.g. methyl), each $R^{2a}$, $R^{2b}$, $R^{3a}$, $R^{3b}$, $R^{10a}$, $R^{10b}$, $R^{11a}$ and $R^{11b}$ is H, each $R^{8d}$ and $R^{8f}$ is independently H or unsubstituted $C_1$-$C_8$ alkyl, and Q is substituted or unsubstituted aryl, e.g. substituted or unsubstituted phenyl.

In one variation, compounds of the formula (X-1) are provided:

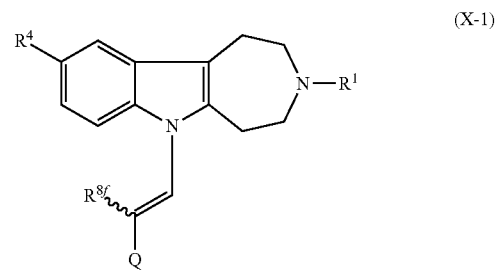

(X-1)

or a salt or solvate thereof, where $R^1$, $R^4$, $R^{8f}$ and Q are defined as for formula (C) and, where applicable, any variation thereof detailed herein. That is, variations of formula (C) detailed throughout, where applicable, apply to formula (X-1) the same as if each and every variation were specifically and individually listed for formula (X-1).

In one variation, compounds of the formula (X-1) are provided, or a salt or solvate thereof, where $R^1$ is a substituted or unsubstituted $C_1$-$C_8$ alkyl; $R^4$ is H, halo, trifluoromethyl, a $C_1$-$C_8$ unsubstituted alkyl or a substituted amino; $R^{8f}$ is substituted or unsubstituted $C_1$-$C_8$ alkyl, substituted or unsubstituted aryl, halo and alkoxy; Q is substituted aryl or a substituted or unsubstituted heteroaryl and the ~~~ bond indicates the presence of either an E or Z double bond configuration. In one variation of formula (X-1), $R^1$ is an unsubstituted $C_{1-8}$ alkyl or a $C_1$-$C_8$ alkyl substituted with a halo or hydroxyl group. In one such variation, R¹ is methyl, 2-haloethyl (e.g., 2-fluoroethyl), 2,2,2-trifluoroethyl, or a hydroxyl-substituted pentyl group. In a particular variation of formula (X-1), R¹ is —CH₃, —CH₂CH₂F, —CH₂CF₃, or —CH₂CH₂C(CH₃)₂OH. In another variation of formula (X-1), R⁴ is H, halo, methyl, trifluoromethyl, or a substituted amino of the formula —N(H)(C₁-C₈unsubstituted alkyl). When R⁴ is a halo (e.g., fluoro or chloro), in one aspect R⁴ is chloro. In one variation of formula (X-1), R⁴ is H, methyl or chloro. In one variation of formula (X-1), R⁴ is methyl or chloro. When R⁴ is a substituted amino of the formula —N(H)(C₁-C₈unsubstituted alkyl), in one aspect C₁-C₈unsubstituted alkyl is a linear C₁-C₈unsubstituted alkyl such as methyl or ethyl. In a particular variation of formula (X-1), R⁴ is —N(H)(CH₃). It is understood that any R¹ for formula (X-1) may be combined with any R⁴ of formula (X-1) the same as if each and every combination where specifically and individually listed. For example, compounds of the formula (X-1) are provided where R¹ is —CH₃, —CH₂CH₂F, —CH₂CF₃, or —CH₂CH₂C(CH₃)₂OH and R⁴ is H, chloro, fluoro, methyl, trifluoromethyl, or —N(H)(CH₃) Likewise, compounds of the formula (X-1) are provided where R¹ is methyl and R⁴ is H, halo, methyl or a substituted amino of the formula —N(H)(C₁-C₈unsubstituted alkyl). In one such aspect, compounds of the formula (X-1) are provided where R¹ is methyl and R⁴ is H, halo or methyl. In one such aspect, compounds of the formula (X-1) are provided where R¹ is methyl and R⁴ is halo (e.g., fluoro or chloro), trifluoromethyl, or methyl. In one variation of formula (X-1), R⁸ᶠ is an unsubstituted C₁₋₈ alkyl or a C₁-C₈ alkyl substituted with a halo, hydroxyl, carboxyl or acylamino group. In one such variation, R⁸ᶠ is methyl, ethyl, isopropyl, t-butyl, cyclopropyl, cyclobutyl, cyclohexyl, halo (e.g., fluoro), a carboxyl-substituted methyl group or an amido-substituted methyl group. In a particular variation, R⁸ᶠ is methyl. When Q of formula (X-1) is a substituted aryl, in one aspect Q is a substituted phenyl. In one aspect, Q is a mono-substituted phenyl. In a particular aspect, Q of formula (X-1) is a halo-substituted phenyl, alkoxy-substituted phenyl or an acylamino-substituted phenyl. Thus, compounds of the formula (X-1) are provided where Q in one variation is a phenyl mono-substituted with a fluoro, C₁-C₈ alkoxy (e.g., methoxy), an acylamino moiety of the formula —C(O)NH(C₁-C₈unsubstituted alkyl) or an acylamino moiety of the formula —C(O)N(C₁-C₈ unsubstituted alkyl)₂, such as 2-fluoro-phenyl, 4-fluoro-phenyl, 4-methoxy-phenyl, 4-(C(O)NH(CH₃) and 4-(C(O)N(CH₃)₂)-phenyl. In one aspect, Q is a di-substituted phenyl. In one aspect, Q of formula (X-1) is a di-halo substituted phenyl group such as 3,4-difluoro-phenyl. In a particular aspect, Q of formula (C-1) is a phenyl group substituted with one halo group and one C₁-C₈ alkoxy group (e.g., methoxy). Thus, compounds of the formula (X-1) are provided where Q in one variation is a phenyl substituted with a fluoro and a C₁-C₈ alkoxy group, such as 3-fluoro-4-methoxy-phenyl. When Q of formula (X-1) is a substituted or unsubstituted heteroaryl, in one variation the substituted or unsubstituted heteroaryl is a pyridyl or pyrimidyl moiety. Thus, in one aspect of formula (X-1), Q is an unsubstituted pyridyl or pyrimidyl, such as 3-pyridyl, 4-pyridyl and 4-pyrimidyl. In another aspect of formula (X-1), Q is a substituted pyridyl, such as 6-methyl-3-pyridyl. It is understood that any Q for formula (X-1) may be combined with any R¹ and/or R⁴ of formula (X-1) the same as if each and every combination where specifically and individually listed. For example, compounds of the formula (X-1) are provided where R¹ is —CH₃, —CH₂CH₂F, —CH₂CF₃, or —CH₂CH₂C(CH₃)₂OH; R⁴ is H, chloro, fluoro, methyl, trifluoromethyl, or —N(H)(CH₃) and Q is 4-pyridyl, 3-pyridyl, 6-methyl-3-pyridyl, 6-pyrimidyl, 4-fluoro-phenyl, 4-methoxy-phenyl, 3-fluoro-4-methoxy-phenyl or 4-dimethylcarbamoyl-phenyl. Likewise, compounds of the formula (X-1) are provided where R¹ is methyl; R⁴ is H, halo or methyl and Q is an unsubstituted pyridyl. In any variation of formula (X-1), in one aspect, the ⁓ bond indicates the presence of an E double bond configuration. In any variation of formula (X-1), in one aspect, the ⁓ bond indicates the presence of a Z double bond configuration.

In specific variations, compounds of the formula (X-1) have the formula:

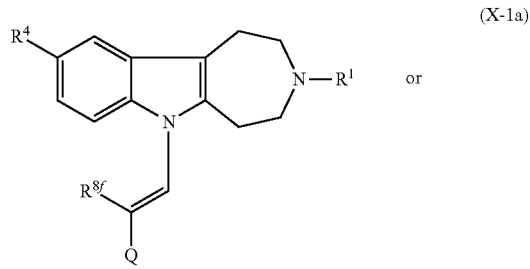

(X-1a)

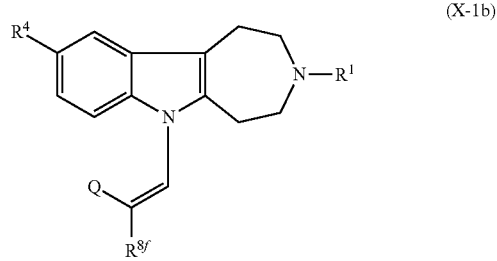

(X-1b)

or a salt or solvate thereof; wherein R¹, R⁴, R⁸ᶠ and Q are defined as for formula (X-1) and, where applicable, any variation thereof detailed herein. That is, variations of formula (X-1) detailed throughout, where applicable, apply to formulae (X-1a) and (X-1b) the same as if each and every variation were specifically and individually listed for formulae (X-1a) and (X-1b). In one particular aspect of formula (X-1a), R¹ is —CH₃, —CH₂CH₂F, —CH₂CF₃, or —CH₂CH₂C(CH₃)₂OH; R⁴ is H, chloro, fluoro, methyl, trifluoromethyl, or —N(H)(CH₃) R⁸ᶠ is an unsubstituted C₁₋₈ alkyl or a C₁-C₈ alkyl substituted with a halo, hydroxyl, carboxyl or acylamino group. In one such variation, R¹ is methyl, ethyl, isopropyl, t-butyl, cyclopropyl, cyclobutyl, cyclohexyl, halo (e.g., fluoro), a carboxyl-substituted methyl group or a amido-substituted methyl group and Q is 4-pyridyl, 3-pyridyl, 6-methyl-3-pyridyl, 6-pyrimidyl, 4-fluoro-phenyl, 4-methoxy-phenyl, 3-fluoro-4-methoxy-phenyl or 4-dimethylcarbamoyl-phenyl. In another aspect of formula (X-1a), R¹ is methyl, R⁴ is H, chloro or methyl, R⁸ᶠ is methyl. and Q is a substituted or unsubstituted pyridyl. In one particular aspect of formula (X-1b), R¹ is methyl, R⁴ is methyl, R⁸ᶠ is methyl. and Q is a substituted or unsubstituted pyridyl. Pharmaceutically acceptable salts of compounds of the formula (X-1), (X-1a) and (X-1b) are also provided.

In one variation, compounds of the formula (X-2) are provided:

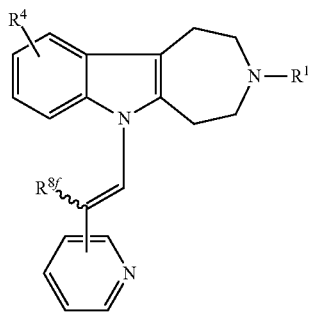

(X-2)

or a salt or solvate thereof, where $R^1$ is a substituted or unsubstituted $C_1$-$C_8$ alkyl; $R^4$ is H, halo or a $C_1$-$C_8$ unsubstituted alkyl, $R^{8f}$ is substituted or unsubstituted $C_{1-8}$ alkyl, substituted or unsubstituted aryl, halo and alkoxy and the ⁓ bond indicates the presence of either an E or Z double bond configuration and where $R^4$ and the pyridyl moiety may be connected to the parent structure at any available position. In one variation of formula (X-2), $R^1$ is an unsubstituted $C_{1-8}$ alkyl or a $C_1$-$C_8$ alkyl substituted with a halo or hydroxyl group. In one such variation, $R^1$ is methyl, 2-haloethyl (e.g., 2-fluoroethyl), 2,2,2-trifluoroethyl, or a hydroxyl-substituted pentyl group. In a particular variation of formula (X-2), $R^1$ is —$CH_3$, —$CH_2CH_2F$, —$CH_2CF_3$, or —$CH_2CH_2C(CH_3)_2$OH. In another variation of formula (X-2), $R^4$ is H, halo, trifluoromethyl, or methyl. When $R^4$ is a halo (e.g., fluoro or chloro), in one aspect $R^4$ is chloro. In one variation of formula (X-2), $R^4$ is H, methyl or chloro. In one variation of formula (X-2), $R^4$ is methyl or chloro. In one variation of formula (X-1), $R^{8f}$ is an unsubstituted $C_{1-8}$ alkyl or a $C_1$-$C_8$ alkyl substituted with a halo, hydroxyl, carboxyl or acylamino group. In one such variation, $R^1$ is methyl, ethyl, isopropyl, t-butyl, cyclopropyl, cyclobutyl, cyclohexyl, halo (e.g., fluoro), a carboxyl-substituted methyl group or an amido-substituted methyl group. In a particular variation, $R^{8f}$ is methyl. It is understood that any $R^1$ for formula (X-2) may be combined with any $R^4$ of formula (X-2) the same as if each and every combination were specifically and individually listed. For example, compounds of the formula (X-2) are provided where $R^1$ is —$CH_3$, —$CH_2CH_2F$, —$CH_2CF_3$, or —$CH_2CH_2C(CH_3)_2$OH and $R^4$ is H, chloro, fluoro, trifluoromethyl, or methyl. Likewise, compounds of the formula (X-2) are provided where $R^1$ is methyl and $R^4$ is H, halo or methyl. In one such aspect, compounds of the formula (X-2) are provided where $R^1$ is methyl and $R^4$ is halo (e.g., fluoro or chloro), trifluoromethyl, or methyl. In any variation of formula (X-2), in one aspect, the ⁓ bond indicates the presence of an E double bond configuration. In any variation of formula (X-2), in one aspect, the ⁓ bond indicates the presence of a Z double bond configuration.

In specific variations, compounds of the formula (X-2) have the formula:

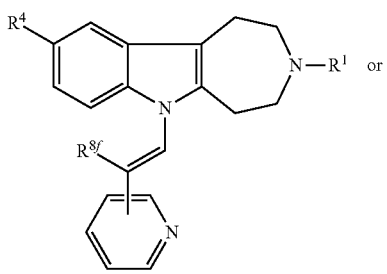

(X-2a)

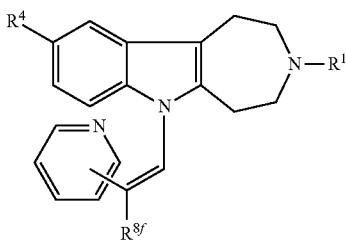

(X-2b)

or a salt or solvate thereof; wherein $R^1$, $R^4$ and $R^{8f}$ are defined as for formula (X-2). That is, variations of formula (X-2) detailed throughout, where applicable, apply to formulae (X-2a) and (X-2b) the same as if each and every variation were specifically and individually listed for formulae (X-2a) and (X-2b). Pharmaceutically acceptable salts of compounds of the formula (X-2), (X-2a) and (X-2b) are also provided.

Compounds of the formula (X-3) and (X-4) are also provided:

(X-3)

(X-4)

or a salt or solvate thereof, wherein $R^1$ is $CH_3$, —$CH_2CH_2$—$C(CH_3)_2(OH)$, —$CH_2CF_3$, or —$CH_2CH_2F$; $R^{4a}$ is H or F; $R^{4c}$ is H, $CH_3$, Cl, F, $CF_3$, or —$NHCH_3$; $R^{9b}$ is H or F; $R^9$ is F, $OCH_3$, —$CONH(CH_3)$ or —$CON(CH_3)_2$ and $R^{8f}$ is an unsubstituted $C_{1-8}$ alkyl or a $C_1$-$C_8$ alkyl substituted with a halo, hydroxyl, carboxyl or acylamino group. In one embodiment of formula (X-3) and (X-4), $R^1$ is $CH_3$; $R^{4a}$ is H; $R^{4c}$ is $CH_3$, Cl, F or —$NHCH_3$; $R^{9b}$ is H or F; $R^9$ is F, $OCH_3$, —$CONH(CH_3)$ or —$CON(CH_3)_2$; and $R^{8f}$ is methyl, ethyl, isopropyl, t-butyl, cyclopropyl, cyclobutyl, cyclohexyl, halo (e.g., fluoro), a carboxyl-substituted methyl group or a amido-substituted methyl group. In a further embodiment, $R^1$ is $CH_3$; $R^{4a}$ is H; $R^{4c}$ is $CH_3$, Cl, F or —$NHCH_3$; $R^{9b}$ is H; $R^{9c}$ is F, $OCH_3$; and $R^{8f}$ is methyl Compounds of the formula (X-5) and (X-6) are also embraced,

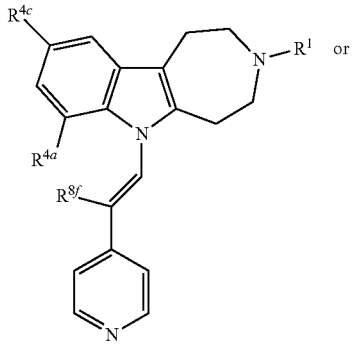

(X-5)

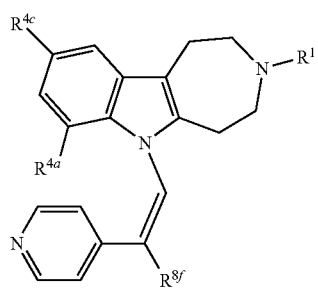

(X-6)

or a salt or solvate thereof, wherein $R^1$ is $CH_3$, —$CH_2CH_2$—$C(CH_3)_2(OH)$, —$CH_2CF_3$, or —$CH_2CH_2F$; $R^{4a}$ is H or F; $R^{4c}$ is H, $CH_3$, Cl, F, $CF_3$, or —$NHCH_3$; and $R^{8f}$ is methyl, ethyl, isopropyl, t-butyl, cyclopropyl, cyclobutyl, cyclohexyl, halo (e.g., fluoro), a carboxyl-substituted methyl group or a amido-substituted methyl group. In one embodiment of formula (X-5) and (X-6) $R^1$ is $CH_3$; $R^{4a}$ is H; $R^{4c}$ is $CH_3$, Cl, F or —$NHCH_3$; and $R^{8f}$ is $CH_3$. In yet another variation, $R^1$ is $CH_3$; $R^{4a}$ is H; $R^{4c}$ is $CH_3$, Cl or F; and $R^{8f}$ is $CH_3$.

In one variation, compounds of the formula (X-7) or (X-8) are provided

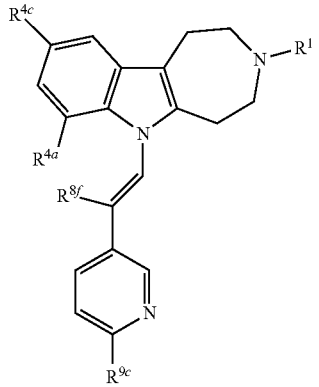

(X-7)

or

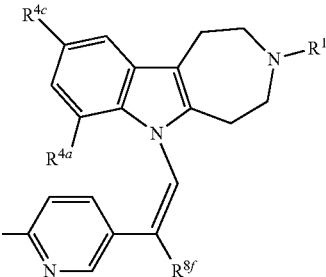

(X-8)

or a salt or solvate thereof, wherein $R^1$ is $CH_3$, —$CH_2CH_2$—$C(CH_3)_2(OH)$, —$CH_2CF_3$, or —$CH_2CH_2F$; $R^{4a}$ is H or F; $R^{4c}$ is H, $CH_3$, Cl, F, $CF_3$, or —$NHCH_3$; $R^{9c}$ is H, F, $CH_3$, $CF_3$, $OCH_3$, —$CONH(CH_3)$ or —$CON(CH_3)_2$; and $R^{8f}$ is methyl, ethyl, isopropyl, t-butyl, cyclopropyl, cyclobutyl, cyclohexyl, halo (e.g., fluoro), a carboxyl-substituted methyl group or a amido-substituted methyl group. In one variation of formula (X-7) and (X-8) $R^1$ is $CH_3$; $R^{4a}$ is H; $R^{4c}$ is $CH_3$, Cl, F, $CF_3$, or —$NHCH_3$; and $R^{9c}$ is H, F, $CF_3$, or $CH_3$; and $R^{8f}$ is methyl. In a particular variation, $R^1$ is $CH_3$; $R^{4a}$ is H; $R^{4c}$ is $CH_3$, $CF_3$, Cl or F; and $R^{9c}$ is H, $CF_3$, or $CH_3$.

In another variation, compounds of the formula (X-9) and (X-10) are provided:

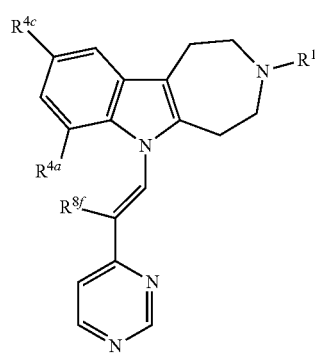

(X-9)

or

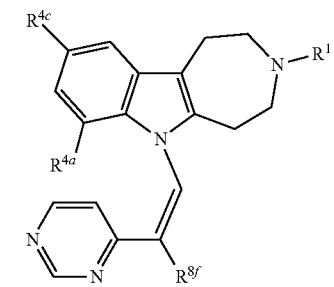

(X-10)

or a salt or solvate thereof, wherein $R^1$ is $CH_3$, —$CH_2CH_2$—$C(CH_3)_2(OH)$, —$CH_2CF_3$, or —$CH_2CH_2F$; $R^{4a}$ is H or F; and $R^{4c}$ is H, $CH_3$, Cl, F, —$CF_3$, or —$NHCH_3$. $R^{8f}$ is methyl, ethyl, isopropyl, t-butyl, cyclopropyl, cyclobutyl, cyclohexyl, halo (e.g., fluoro), a carboxyl-substituted methyl group or a amido-substituted methyl group In one embodiment of formula (X-9) and (X-10), $R^1$ is $CH_3$; $R^{4a}$ is H; and $R^{4c}$ is $CH_3$, Cl, F, $CF_3$, or —$NHCH_3$. In one embodiment $R^1$ is $CH_3$; $R^{4a}$ is H; $R^{4c}$ is $CH_3$, $CF_3$, Cl or F; and $R^{8f}$ is methyl.

In one variation, compounds of the formula (C-1) are provided:

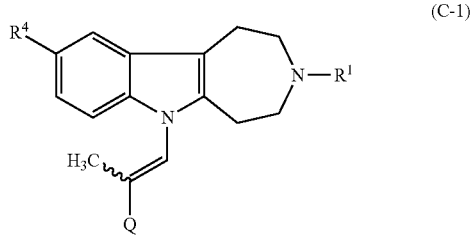

(C-1)

or a salt or solvate thereof, where $R^1$, $R^4$ and Q are defined as for formula (C) and, where applicable, any variation thereof detailed herein. That is, variations of formula (C) detailed throughout, where applicable, apply to formula (C-1) the same as if each and every variation were specifically and individually listed for formula (C-1).

In one variation, compounds of the formula (C-1) are provided, or a salt or solvate thereof, where $R^1$ is a substituted or unsubstituted $C_1$-$C_8$ alkyl; $R^4$ is H, halo, trifluoromethyl, a $C_1$-$C_8$ unsubstituted alkyl or a substituted amino; Q is substituted aryl or a substituted or unsubstituted heteroaryl and the ⁓ bond indicates the presence of either an E or Z double bond configuration. In one variation of formula (C-1), $R^1$ is an unsubstituted $C_{1-8}$ alkyl or a $C_1$-$C_8$ alkyl substituted with a halo or hydroxyl group. In one such variation, $R^1$ is methyl, 2-haloethyl (e.g., 2-fluoroethyl), 2,2,2-trifluoroethyl, or a hydroxyl-substituted pentyl group. In a particular variation of formula (C-1), $R^1$ is —$CH_3$, —$CH_2CH_2F$, —$CH_2CF_3$, or —$CH_2CH_2C(CH_3)_2OH$. In another variation of formula (C-1), $R^4$ is H, halo, methyl, trifluoromethyl, or a substituted amino of the formula —$N(H)(C_1$-$C_8$unsubstituted alkyl). When $R^4$ is a halo (e.g., fluoro or chloro), in one aspect $R^4$ is chloro. In one variation of formula (C-1), $R^4$ is H, methyl or chloro. In one variation of formula (C-1), $R^4$ is methyl or chloro. When $R^4$ is a substituted amino of the formula —$N(H)$ ($C_1$-$C_8$unsubstituted alkyl), in one aspect $C_1$-$C_8$unsubstituted alkyl is a linear $C_1$-$C_8$unsubstituted alkyl such as methyl or ethyl. In a particular variation of formula (C-1), $R^4$ is —$N(H)$ ($CH_3$). It is understood that any $R^1$ for formula (C-1) may be combined with any $R^4$ of formula (C-1) the same as if each and every combination where specifically and individually listed. For example, compounds of the formula (C-1) are provided where $R^1$ is —$CH_3$, —$CH_2CH_2F$, —$CH_2CF_3$, or —$CH_2CH_2C(CH_3)_2OH$ and $R^4$ is H, chloro, fluoro, methyl, trifluoromethyl, or —$N(H)(CH_3)$. Likewise, compounds of the formula (C-1) are provided where $R^1$ is methyl and $R^4$ is H, halo, methyl or a substituted amino of the formula —$N(H)$ ($C_1$-$C_8$unsubstituted alkyl). In one such aspect, compounds of the formula (C-1) are provided where $R^1$ is methyl and $R^4$ is H, halo, trifluoromethyl, or methyl. In one such aspect, compounds of the formula (C-1) are provided where $R^1$ is methyl and $R^4$ is halo (e.g., fluoro or chloro) or methyl. When Q of formula (C-1) is a substituted aryl, in one aspect Q is a substituted phenyl. In one aspect, Q is a mono-substituted phenyl. In a particular aspect, Q of formula (C-1) is a halo-substituted phenyl, alkoxy-substituted phenyl or a acylamino-substituted phenyl. Thus, compounds of the formula (C-1) are provided where Q in one variation is a phenyl mono-substituted with a fluoro, $C_1$-$C_8$ alkoxy (e.g., methoxy), an acylamino moiety of the formula —$C(O)NH(C_1$-$C_8$ unsubstituted alkyl) or an acylamino moiety of the formula —$C(O)N(C_1$-$C_8$ unsubstituted alkyl)$_2$, such as 2-fluoro-phenyl, 4-fluoro-phenyl, 4-methoxy-phenyl, 4-($C(O)NH(CH_3)$ and 4-($C(O)N(CH_3)_2$)-phenyl. In one aspect, Q is a di-substituted phenyl. In one aspect, Q of formula (C-1) is a di-halo substituted phenyl group such as 3,4-difluoro-phenyl. In a particular aspect, Q of formula (C-1) is a phenyl group substituted with one halo group and one $C_1$-$C_8$ alkoxy group (e.g., methoxy). Thus, compounds of the formula (C-1) are provided where Q in one variation is a phenyl substituted with a fluoro and a $C_1$-$C_8$ alkoxy group, such as 3-fluoro-4-methoxy-phenyl. When Q of formula (C-1) is a substituted or unsubstituted heteroaryl, in one variation the substituted or unsubstituted heteroaryl is a pyridyl or pyrimidyl moiety. Thus, in one aspect of formula (C-1), Q is an unsubstituted pyridyl or pyrimidyl, such as 3-pyridyl, 4-pyridyl and 4-pyrimidyl. In another aspect of formula (C-1), Q is a substituted pyridyl, such as 6-methyl-3-pyridyl. It is understood that any Q for formula (C-1) may be combined with any $R^1$ and/or $R^4$ of formula (C-1) the same as if each and every combination where specifically and individually listed. For example, compounds of the formula (C-1) are provided where $R^1$ is —$CH_3$, —$CH_2CH_2F$, —$CH_2CF_3$, or —$CH_2CH_2C(CH_3)_2OH$; $R^4$ is H, chloro, fluoro, trifluoromethyl, methyl or —$N(H)(CH_3)$ and Q is 4-pyridyl, 3-pyridyl, 6-methyl-3-pyridyl, 6-trifluoromethyl-3-pyridyl, 6-pyrimidyl, 4-fluoro-phenyl, 4-methoxy-phenyl, 3-fluoro-4-methoxy-phenyl or 4-dimethylcarbamoyl-phenyl. Likewise, compounds of the formula (C-1) are provided where $R^1$ is methyl; $R^4$ is H, halo or methyl and Q is an unsubstituted pyridyl. In any variation of formula (C-1), in one aspect, the ⁓ bond indicates the presence of an E double bond configuration. In any variation of formula (C-1), in one aspect, the ⁓ bond indicates the presence of a Z double bond configuration.

In specific variations, compounds of the formula (C-1) have the formula:

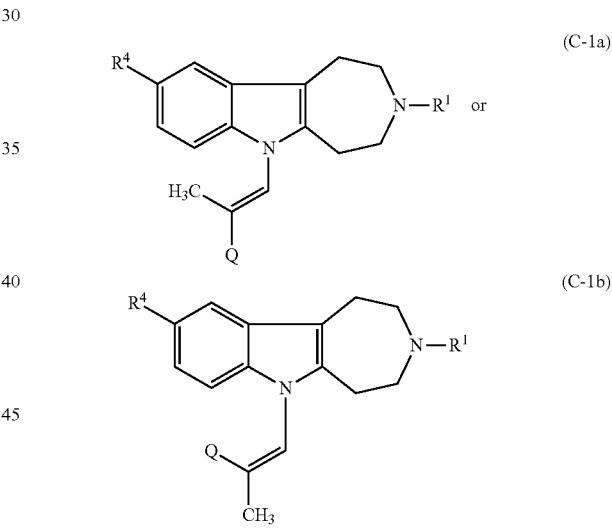

or a salt or solvate thereof; wherein $R^1$, $R^4$ and Q are defined as for formula (C-1) and, where applicable, any variation thereof detailed herein. That is, variations of formula (C-1) detailed throughout, where applicable, apply to formulae (C-1a) and (C-1b) the same as if each and every variation were specifically and individually listed for formulae (C-1a) and (C-1b). In one particular aspect of formula (C-1a), $R^1$ is —$CH_3$, —$CH_2CH_2F$, —$CH_2CF_3$, or —$CH_2CH_2C(CH_3)_2$ OH; $R^4$ is H, chloro, fluoro, methyl trifluoromethyl, or —$N(H)(CH_3)$ and Q is 4-pyridyl, 3-pyridyl, 6-methyl-3-pyridyl, 6-trifluoromethyl-3-pyridyl, 6-pyrimidyl, 4-fluoro-phenyl, 4-methoxy-phenyl, 3-fluoro-4-methoxy-phenyl or 4-dimethylcarbamoyl-phenyl. In another aspect of formula (C-1a), $R^1$ is methyl, $R^4$ is H, chloro or methyl and Q is a substituted or unsubstituted pyridyl. In one particular aspect of formula (C-1b), $R^1$ is methyl, $R^4$ is methyl and Q is a substituted or unsubstituted pyridyl. Pharmaceutically acceptable salts of compounds of the formula (C-1), (C-1a) and (C-1b) are also provided.

In one variation, compounds of the formula (C-2) are provided:

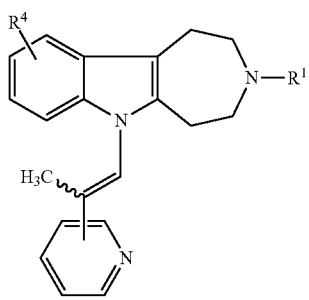

(C-2)

or a salt or solvate thereof, where $R^1$ is a substituted or unsubstituted $C_1$-$C_8$ alkyl; $R^4$ is H, halo or a $C_1$-$C_8$ unsubstituted alkyl and the ⁓ bond indicates the presence of either an E or Z double bond configuration and where $R^4$ and the pyridyl moiety may be connected to the parent structure at any available position. In one variation of formula (C-2), $R^1$ is an unsubstituted $C_{1-8}$ alkyl or a $C_1$-$C_8$ alkyl substituted with a halo or hydroxyl group. In one such variation, $R^1$ is methyl, 2-haloethyl (e.g., 2-fluoroethyl), 2,2,2-trifluoroethyl, or a hydroxyl-substituted pentyl group. In a particular variation of formula (C-2), $R^1$ is —$CH_3$, —$CH_2CH_2F$, —$CH_2CF_3$, or —$CH_2CH_2C(CH_3)_2OH$. In another variation of formula (C-2), $R^4$ is H, halo, trifluoromethyl, or methyl. When $R^4$ is a halo (e.g., fluoro or chloro), in one aspect $R^4$ is chloro. In one variation of formula (C-2), $R^4$ is H, methyl or chloro. In one variation of formula (C-2), $R^4$ is methyl or chloro. It is understood that any $R^1$ for formula (C-2) may be combined with any $R^4$ of formula (C-2) the same as if each and every combination were specifically and individually listed. For example, compounds of the formula (C-2) are provided where $R^1$ is —$CH_3$, —$CH_2CH_2F$, —$CH_2CF_3$, or —$CH_2CH_2C(CH_3)_2OH$ and $R^4$ is H, chloro, fluoro, trifluoromethyl, or methyl. Likewise, compounds of the formula (C-2) are provided where $R^1$ is methyl and $R^4$ is H, halo or methyl. In one such aspect, compounds of the formula (C-2) are provided where $R^1$ is methyl and $R^4$ is halo (e.g., fluoro or chloro) or methyl. In any variation of formula (C-2), in one aspect, the ⁓ bond indicates the presence of an E double bond configuration. In any variation of formula (C-2), in one aspect, the ⁓ bond indicates the presence of a Z double bond configuration.

In specific variations, compounds of the formula (C-2) have the formula:

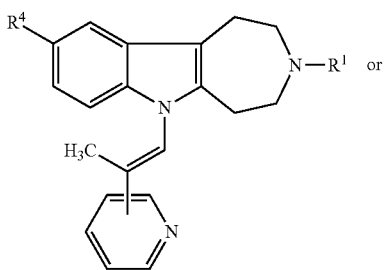

(C-2a)

or

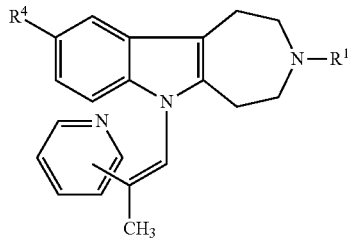

(C-2b)

or a salt or solvate thereof; wherein $R^1$ and $R^4$ are defined as for formula (C-2). That is, variations of formula (C-2) detailed throughout, where applicable, apply to formulae (C-2a) and (C-2b) the same as if each and every variation were specifically and individually listed for formulae (C-2a) and (C-2b). Pharmaceutically acceptable salts of compounds of the formula (C-2), (C-2a) and (C-2b) are also provided.

Compounds of the formula (C-3a) and (C-3b) are also provided:

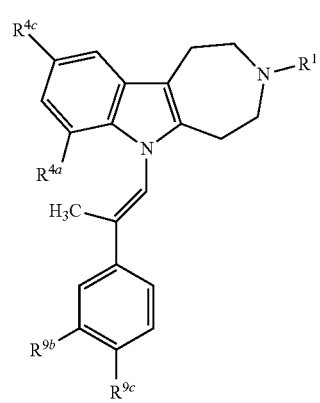

(C-3a)

or

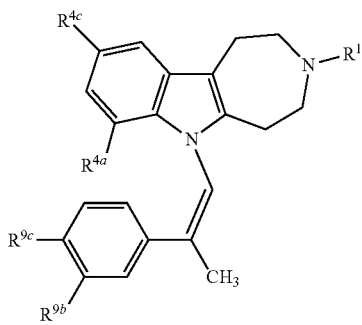

(C-3b)

or a salt or solvate thereof, wherein $R^1$ is $CH_3$, —$CH_2CH_2$—$C(CH_3)_2(OH)$, —$CH_2CF_3$, or —$CH_2CH_2F$; $R^{4a}$ is H or F; $R^{4c}$ is H, $CH_3$, $CF_3$, Cl, F or —$NHCH_3$; $R^{9b}$ is H or F; and $R^{9c}$ is F, $OCH_3$, —$CONH(CH_3)$ or —$CON(CH_3)_2$. In one embodiment of formula (C-3a) and (C-3b), $R^1$ is $CH_3$; $R^{4a}$ is H; $R^{4c}$ is $CH_3$, Cl, F, $CF_3$, or —$NHCH_3$; $R^{9b}$ is H or F; and $R^{9c}$ is F, $OCH_3$, —$CONH(CH_3)$ or —$CON(CH_3)_2$. In a further embodiment, $R^1$ is $CH_3$; $R^{4a}$ is H; $R^{4c}$ is $CH_3$, Cl, F or —$NHCH_3$; $R^{9b}$ is H; and $R^{9c}$ is F, $OCH_3$.

Compounds of the formula (C-4a) and (C-4b) are also embraced,

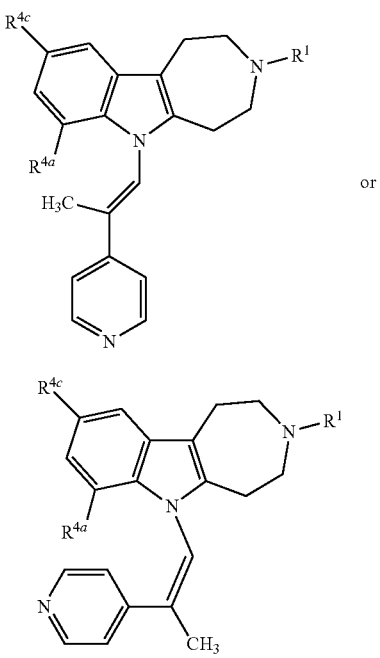

(C-4a)

(C-4b)

or a salt or solvate thereof, wherein $R^1$ is $CH_3$, —$CH_2CH_2$—$C(CH_3)_2(OH)$ or —$CH_2CH_2F$; $R^{4a}$ is H or F; and $R^{4c}$ is H, $CH_3$, Cl, F or —$NHCH_3$. In one embodiment of formula (C-4a) and (C-4b), $R^1$ is $CH_3$; $R^{4a}$ is H and $R^{4c}$ is $CH_3$, Cl, F, $CF_3$, or —$NHCH_3$. In yet another variation, $R^1$ is $CH_3$; $R^{4a}$ is H; $R^{4c}$ is $CH_3$, $CF_3$, Cl or F.

In one variation, compounds of the formula (C-5a) or (C-5b) are provided

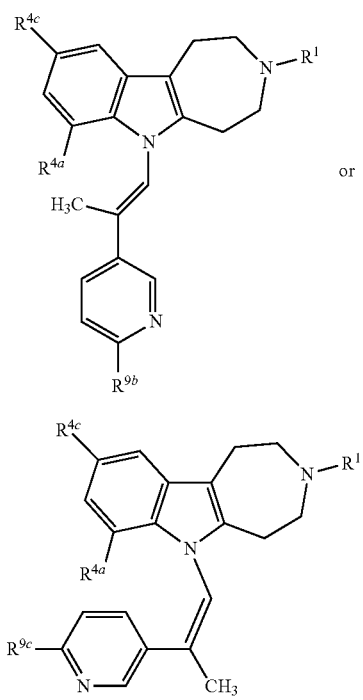

(C-5a)

(C-5b)

or a salt or solvate thereof, wherein $R^1$ is $CH_3$, —$CH_2CH_2$—$C(CH_3)_2(OH)$, —$CH_2CF_3$, or —$CH_2CH_2F$; $R^{4a}$ is H or F; $R^{4c}$ is H, $CH_3$, Cl, F, $CF_3$, or —$NHCH_3$; and $R^{9c}$ is H, F, $CH_3$, $CF_3$, $OCH_3$, —$CONH(CH_3)$ or —$CON(CH_3)_2$. In one variation of formula (C-5a) and (C-5b) $R^1$ is $CH_3$; $R^{4a}$ is H; $R^{4c}$ is $CH_3$, Cl, F, $CF_3$, or —$NHCH_3$; and $R^{9c}$ is H, F, $CF_3$, or $CH_3$. In a particular variation, $R^1$ is $CH_3$; $R^{4a}$ is H; $R^{4c}$ is $CH_3$, Cl or F; and $R^{9c}$ is H, $CF_3$, or $CH_3$.

In another variation, compounds of the formula (C-6a) and (C-6b) are provided:

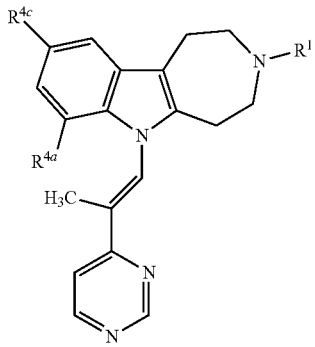

(C-6a)

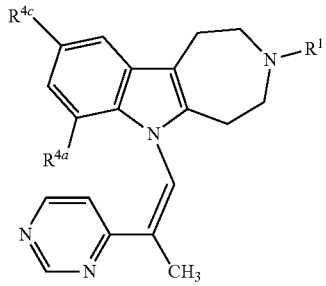

(C-6b)

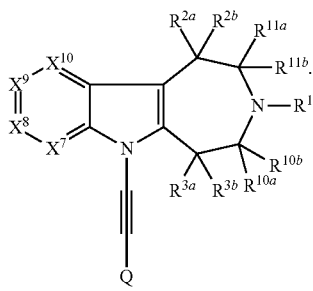

or a salt or solvate thereof, wherein $R^1$ is $CH_3$, —$CH_2CH_2$—$C(CH_3)_2(OH)$, —$CH_2CF_3$, or —$CH_2CH_2F$; $R^{4a}$ is H or F; and $R^{4c}$ is H, $CH_3$, $CF_3$, Cl, F or —$NHCH_3$. In one embodiment of formula (C-6a) and (C-6b), $R^1$ is $CH_3$; $R^{4a}$ is H; and $R^{4c}$ is $CH_3$, Cl, F, $CF_3$, or —$NHCH_3$. In one embodiment $R^1$ is $CH_3$; $R^{4a}$ is H; and $R^{4c}$ is $CH_3$, $CF_3$, Cl or F.

In one embodiment, the compound is of the formula (Ic) where $R^{8c}$ and $R^{8e}$ are taken together to form a bond and $R^{8d}$ and $R^{8f}$ are taken together to form a bond. In one embodiment, the compound is of the formula (D):

(D)

In one variation, the compound is of the formula (D), wherein:

$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy;

each $R^{2a}$, $R^{2b}$, $R^{3a}$, $R^{3b}$, $R^{10a}$, $R^{10b}$, $R^{11a}$ and $R^{11b}$ is independently H, substituted or unsubstituted $C_1$-$C_8$ alkyl, halo, hydroxyl, alkoxy, cyano, nitro or is taken together with the carbon to which it is attached to and a geminal R group to form a carbonyl moiety or a cycloalkyl moiety;

each $X^7$, $X^8$, $X^9$ and $X^{10}$ is independently N or $CR^4$;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted amino, alkoxy, aminoacyl, acyloxy, carbonylalkoxy, aminocarbonylalkoxy, acylamino, carboxy, cyano or alkynyl;

or a salt or solvate thereof.

In one variation, compounds of the formula (D-1) are provided:

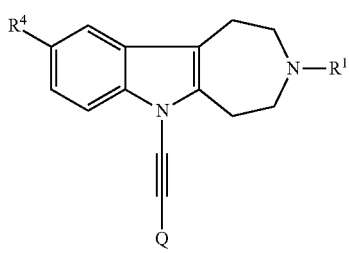

(D-1)

or a salt or solvate thereof; where $R^1$, $R^4$ and Q are as defined for formula (D). In one variation, Q of formula (D-1) is a substituted or unsubstituted aryl, such as phenyl. In one variation, $R^4$ of formula (D-1) is halo, such as chloro. In one aspect, Q of formula (D-1) is a mono-substituted phenyl, such as a mono-halo substituted phenyl, for example 4-fluoro-phenyl. In another aspect, Q of formula (D-1) is a di-substituted phenyl, such as a 3,4-di-substituted phenyl, for example 3-fluoro-4-methoxyphenyl. In another variation Q of formula (D-1) is a di-substituted phenyl and $R^1$ is an unsubstituted $C_1$-$C_8$ alkyl such as methyl. In another variation Q of formula (D-1) is a substituted phenyl and $R^4$ is halo, such as chloro. In another variation Q of formula (D-1) is a di-substituted phenyl, $R^4$ is halo such as chloro and $R^1$ is an unsubstituted $C_1$-$C_8$ alkyl such as methyl.

The invention also embraces compound of the formula (Id):

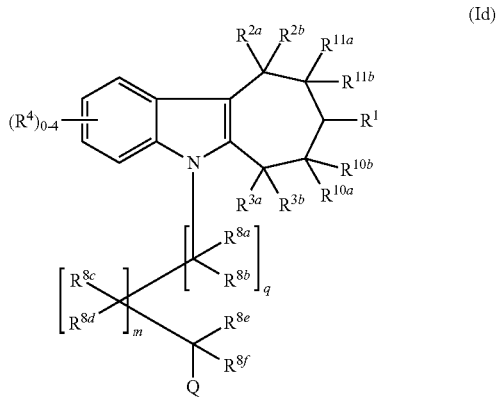

(Id)

where:

$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy;

each $R^{2a}$, $R^{2b}$, $R^{3a}$ and $R^{3b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^2$ or $R^3$ to form a cycloalkyl moiety or a carbonyl moiety;

each $R^{10a}$, $R^{10b}$, $R^{11a}$ and $R^{11b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^{10}$ or $R^{11}$ to form a cycloalkyl moiety or a carbonyl moiety;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each m and q is independently 0 or 1;

each $R^{8a}$, $R^{8b}$, $R^{8c}$, $R^{8d}$, $R^{8e}$ and $R^{8f}$ is independently H, hydroxyl, $C_1$-$C_8$ perhaloalkyl, carboxy, carbonylalkoxy, alkoxy, halo, substituted or unsubstituted aryl, substituted or unsubstituted heteroaryl, substituted or unsubstituted $C_1$-$C_8$ alkyl, substituted or unsubstituted $C_3$-$C_6$ cycloalkyl, substituted or unsubstituted $C_2$-$C_8$ alkenyl, or is taken together with a geminal $R^8$ to form a moiety of the formula —OCH$_2$CH$_2$O—, is taken together with the carbon to which it is attached and a geminal $R^8$ to form a cycloalkyl moiety or a carbonyl moiety, is taken together with a geminal $R^8$ to form a methylene or a substituted methylene, is taken together with a vicinal $R^8$ and the carbon atoms to which they are attached to form a substituted or unsubstituted $C_3$-$C_8$ cycloalkyl, substituted or unsubstituted $C_3$-$C_8$ cycloalkenyl or substituted or unsubstituted heterocyclyl moiety or is taken together with a vicinal $R^8$ to form a bond, provided: (i) at most one pair of vicinal $R^8$ groups are taken together to form a bond; and (ii) when an $R^8$ is taken together with a vicinal $R^8$ to form a bond, the geminal $R^8$ is other than hydroxyl;

Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted amino, alkoxy, aminoacyl, acyloxy, carbonylalkoxy, aminocarbonylalkoxy, acylamino, carboxy, cyano or alkynyl;

or a salt or solvate thereof.

In one variation, the compound of the formula (Id) is provided, where each $R^1$, $R^4$, $R^{10a}$, $R^{10b}$, $R^{11a}$, $R^{11b}$, q and m are as defined for formula (Id); each $R^{2a}$, $R^{2b}$, $R^{3a}$ and $R^{3b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal $R^2$ or $R^3$ to form a carbonyl moiety; each $R^{8a}$, $R^{8b}$, $R^{8c}$, $R^{8d}$, $R^{8e}$ and $R^{8f}$ is independently H, hydroxyl, $C_1$-$C_8$ alkyl, $C_1$-$C_8$ perhaloalkyl, carboxy, carbonylalkoxy, is taken together with the carbon to which it is attached and a geminal $R^8$ to form a cycloalkyl moiety or a carbonyl moiety, is taken together with a geminal $R^8$ to form a methylene or a substituted methylene, is taken together with a vicinal $R^8$ and the carbon atoms to which they are attached to form a substituted or unsubstituted $C_3$-$C_8$ cycloalkyl, substituted or unsubstituted $C_3$-$C_8$ cycloalkenyl or substituted or unsubstituted heterocyclyl moiety or is taken together with a vicinal $R^8$ to form a bond, provided: (i) at most one pair of vicinal $R^8$ groups are taken together to form a bond; and (ii) when an $R^8$ is taken together with a vicinal $R^8$ to form a bond, the geminal $R^8$ is other than hydroxyl; and Q is a substituted or unsubstituted aryl, substituted or unsubstituted heteroaryl, substituted or unsubstituted cycloalkyl, substituted or unsubstituted cycloalkenyl or substituted or a unsubstituted heterocyclyl, unsubstituted amino, substituted amino, alkoxy, aminoacyl, acyloxy, carbonylalkoxy, aminocarbonylalkoxy or acylamino; or a salt or solvate thereof.

In one variation, the compound of the invention is of the formula (Id), where each $R^{2a}$, $R^{2b}$, $R^{3a}$, $R^{3b}$, $R^{10a}$, $R^{10b}$, $R^{11a}$ and $R^{11b}$ is independently H, substituted or unsubstituted $C_1$-$C_8$ alkyl, halo, hydroxyl, alkoxy, cyano, nitro or is taken together with the carbon to which it is attached to and a geminal R group to form a carbonyl moiety or a cycloalkyl moiety. In another variation, the compound is of the formula (I), where each $R^{2a}$, $R^{2b}$, $R^{3a}$ and $R^{3b}$ is independently H, substituted or unsubstituted $C_1$-$C_8$ alkyl, halo, hydroxyl, alkoxy, cyano, nitro or is taken together with the carbon to which it is attached to and a geminal R group to form a carbonyl moiety and each $R^{10a}$, $R^{10b}$, $R^{11a}$ and $R^{11b}$ is independently H, substituted or unsubstituted $C_1$-$C_8$ alkyl or is taken together with the carbon to which it is attached to and a geminal R group to form a carbonyl moiety or a cycloalkyl moiety (e.g. cyclopropyl). In another variation, the compound is of the formula (Id), where Q is a substituted or unsubstituted aryl, substituted or unsubstituted heteroaryl, substituted or unsubstituted $C_3$-$C_8$ cycloalkyl, substituted or unsubstituted $C_3$-$C_8$ cycloalkenyl or substituted or a unsubstituted heterocyclyl, substituted or unsubstituted amino, alkoxy, aminoacyl, acyloxy, carbonylalkoxy, aminocarbonylalkoxy or acylamino.

In another variation, the compound is of the formula (I), (Ia), (Ib), (Ic), (C) or (Id) or any variation thereof detailed herein where Q is a substituted or unsubstituted cycloalkyl, substituted or unsubstituted cycloalkenyl, or substituted or a unsubstituted heterocyclyl, or a salt or solvate thereof. In one variation, the compound is of the formula (I), (Ia), (Ib), (Ic), (C) or (Id) or any variation thereof detailed herein, where Q is a carbocycle, such as a 5, 6 or 7 membered carbocycle. In one variation, the compound is of the formula (I), (Ia), (Ib), (Ic), (C) or (Id) or any variation thereof detailed herein, where Q is a heterocycle, such as a 5, 6 or 7 membered carbocycle.

In another variation, the compound is of the formula (I), (Ia), (Ib), (Ic), (C) or (Id) or any variation thereof detailed herein where Q is substituted or unsubstituted aryl or a substituted or unsubstituted heteroaryl, or a salt or solvate thereof. In another variation, the compound is of the formula (I), (Ia), (Ib), (Ic), (C) or (Id) or any variation thereof detailed herein where Q is substituted or unsubstituted heteroaryl, such as a 5, 6 or 7 membered heteroaryl, or a salt or solvate thereof. In one variation, the compound is of the formula (I), (Ia), (Ib), (Ic), (C) or (Id) or any variation thereof detailed herein where Q is a substituted or unsubstituted aryl, such as a 5, 6 or 7 membered aryl, or a salt or solvate thereof.

In one variation, a compound of the invention is of the formula (I), (Ia), (Ib), (Ic), (C) or (Id) or any variation thereof detailed herein where: $R^1$ is a substituted or unsubstituted $C_1$-$C_8$ alkyl, acyl, acyloxy, carbonylalkoxy, substituted or unsubstituted heterocyclyl or substituted or unsubstituted aryl; each $R^{2a}$ and $R^{2b}$ is independently H, methyl, fluoro or $R^{2a}$ and $R^{2b}$ are taken together to form a carbonyl moiety; each $R^{3a}$ and $R^{3b}$ is independently H or fluoro; each $R^{10a}$ and $R^{10b}$ is independently H, halo, hydroxyl or methyl or $R^{10a}$ and $R^{10b}$ are taken together to form a carbonyl, and each $R^{11a}$ and $R^{11b}$ is independently H or methyl or $R^{11a}$ and $R^{11b}$ are taken together to form a carbonyl. This variation is referred to as formula "Ie". All variations referring to formula (I), where applicable, may apply equally to any of formula (Ia)-(Ie) the same as if each and every variation were specifically and individually listed.

In another variation, a compound of the invention is of the formula (I) or (Ie) where $X^7$, $X^8$, $X^9$ and $X^{10}$ are taken together to provide an aromatic moiety selected from the following structures:

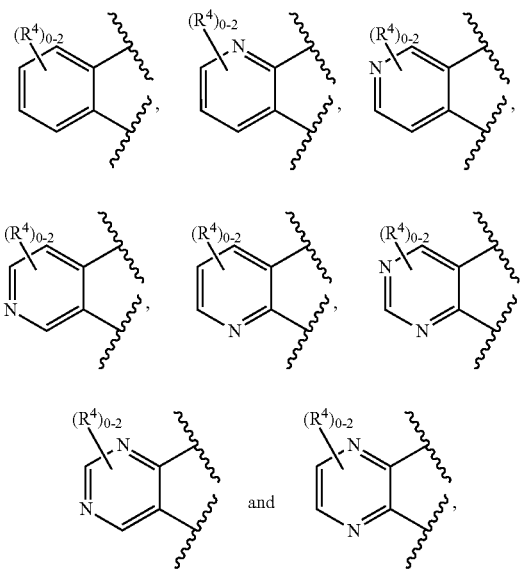

where each $R^4$ is as defined for formula (I) or (Ie); or in a particular variation, where each $R^4$ is independently hydroxyl, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, substituted or unsubstituted heterocyclyl, substituted or unsubstituted aralkyl, thioalkyl, substituted or unsubstituted amino, alkylsulfonylamino or acyl; or in still a further variation, where $R^4$ is independently halo, unsubstituted $C_1$-$C_4$ alkyl or $C_1$-$C_4$ perhaloalkyl. In another variation, each $R^4$ is independently halo or an unsubstituted $C_1$-$C_8$ alkyl. In one embodiment, the foregoing rings are substituted with an $(R^4)_1$ substituent, such that that aromatic moiety is substituted is a single $R^4$ group, which in one variation is halo or unsubstituted $C_1$-$C_8$ alkyl. In a particular variation, $R^4$ is other than H. In one such variation, the foregoing rings have $(R^4)_0$ substituents, such that that aromatic moiety is unsubstituted and contains no $R^4$ groups.

In another variation, compounds of any of the foregoing formulae are provided, where, if applicable, $X^7$, $X^8$, $X^9$ and $X^{10}$ are taken together to provide an aromatic moiety selected from the following structures:

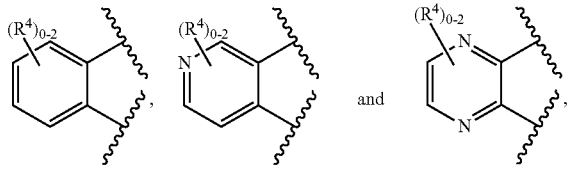

where each $R^4$ is as defined for the formulae; or in a particular variation, where each $R^4$ is independently alkyl, perhaloalkyl or halo or in an even more particular variation, where each $R^4$ is independently methyl, trifluoromethyl, chloro or fluoro. In one embodiment, the foregoing rings are substituted with an $(R^4)_1$ substituent, such that that aromatic moiety is substituted is a single $R^4$ group, which in one variation is halo or unsubstituted $C_1$-$C_8$ alkyl. In a particular variation, $R^4$ is other than H. In one such variation, the foregoing rings have $(R^4)_0$ substituents, such that that aromatic moiety is unsubstituted and contains no $R^4$ groups.

In a further variation, compounds of any of the foregoing formulae are provided, where, if applicable, $X^7$, $X^8$, $X^9$ and $X^{10}$ are taken together to provide a structure of the following formulae, where $R^4$ may be as defined in any variation hereinabove:

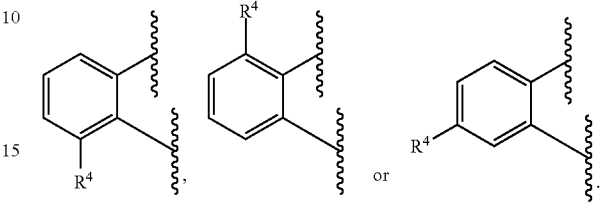

In one such variation, $R^4$ is halo or an unsubstituted $C_1$-$C_8$ alkyl.

In a particular embodiment, the compound is of the formula (I), (Ia), (Ib), (Ic) or (C) or any variation thereof detailed herein where $X^7$, $X^8$, $X^9$ and $X^{10}$ are $CR^4$. In another embodiment, the compound is of the formula (I), (Ia), (Ib), (Ic) or (C) or any variation thereof detailed herein where at least one of $X^7$, $X^8$, $X^9$ and $X^{10}$ is N. Another variation provides a compound of the formula (I), (Ia), (Ib), (Ic) or (C) or any variation thereof detailed herein where at least two of $X^7$, $X^8$, $X^9$ and $X^{10}$ are N. A further variation provides a compound of the formula (I), (Ia), (Ib), (Ic) or (C) or any variation thereof detailed herein where 2 of $X^7$, $X^8$, $X^9$ and $X^{10}$ are N and 2 of $X^7$, $X^8$, $X^9$ and $X^{10}$ are $CR^4$. A compound of the formula (I), (Ia), (Ib), (Ic) or (C) or any variation thereof detailed herein where 1 of $X^7$, $X^8$, $X^9$ and $X^{10}$ is N and 3 of $X^7$, $X^8$, $X^9$ and $X^{10}$ are $CR^4$ is also embraced by this invention.

In still a further variation, a compound of the invention is of the formula (I), (Ia), (Ib), (Ic) or (C) or any variation thereof detailed herein where $X^7$, $X^8$, $X^9$ and $X^{10}$ are taken together to provide an aromatic moiety selected from the following structures:

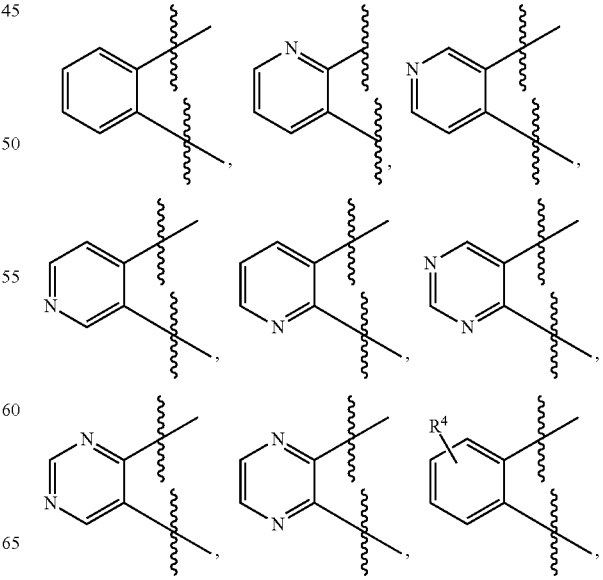

-continued

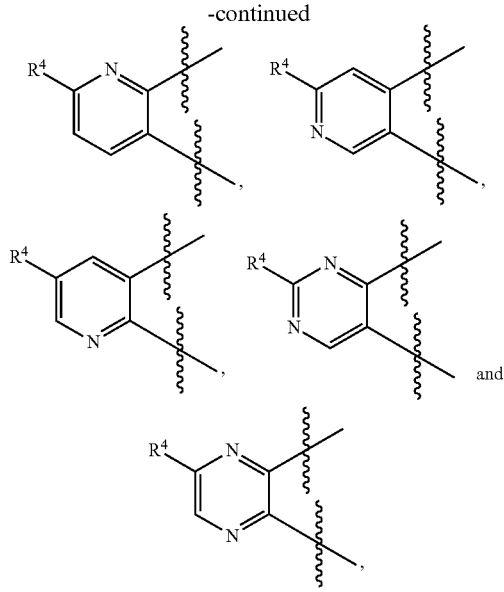

wherein $R^4$ is as defined in formula (I); or in a particular variation, where $R^4$ is hydroxyl, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, substituted or unsubstituted heterocyclyl, substituted or unsubstituted aralkyl, thioalkyl, substituted or unsubstituted amino, alkylsulfonylamino or acyl; or in still a further variation, where each $R^4$ is independently halo, unsubstituted $C_1$-$C_4$ alkyl or $C_1$-$C_4$ perhaloalkyl. In another variation, $R^4$ is halo or unsubstituted $C_1$-$C_8$ alkyl. In yet another variation, compounds of any of the foregoing formulae are provided, where, if applicable, $X^7$, $X^8$, $X^9$ and $X^{10}$ are taken together to provide a structure of the formula:

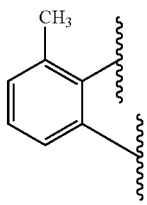

In a particular variation, a compound of the invention is of the formula (I), (Ia), (Ib), (Ic) or (C) or any variation thereof detailed herein where $X^7$, $X^8$, $X^9$ and $X^{10}$ are taken together to provide

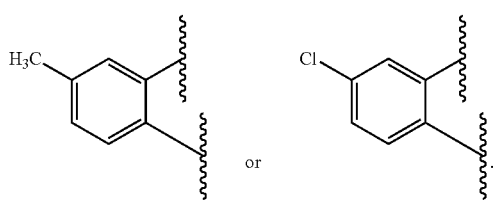

In still a further variation, compounds of any of the foregoing formulae are provided, where, if applicable, $X^7$, $X^8$, $X^9$ and $X^{10}$ are taken together provide an aromatic moiety selected from the following structures:

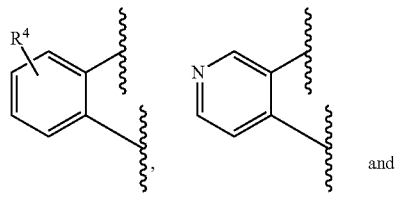
and

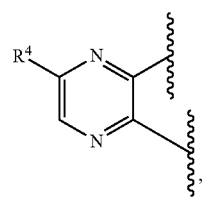

wherein $R^4$ is as defined in the formulae or in any particular variation herein, such as when each $R^4$ is independently alkyl or halo or in an even more particular variation, where each $R^4$ is independently methyl, chloro, iodo or fluoro.

In yet another variation, compounds of any of the foregoing formulae are provided, where, if applicable, $X^7$, $X^8$, $X^9$ and $X^{10}$ are taken together provide an aromatic moiety selected from the following structures:

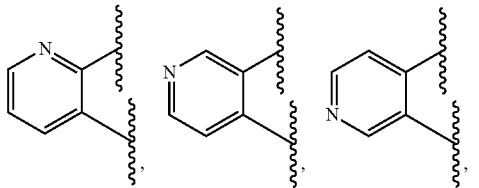

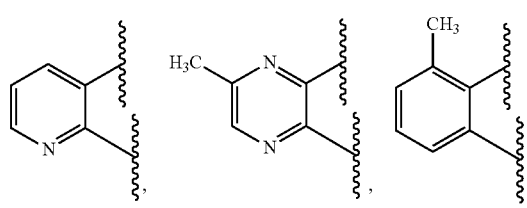

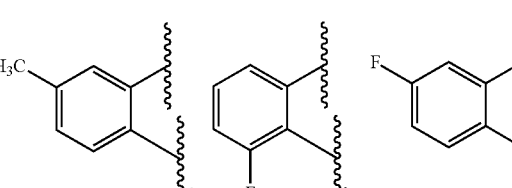

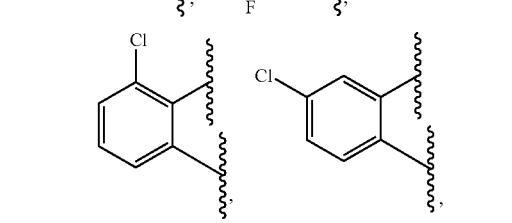

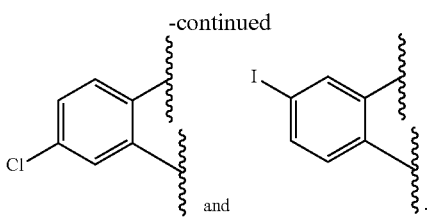

In another embodiment, a compound of the invention is of the formula (I), (Ia), (Ib), (Ic) or (C) or any variation thereof detailed herein, wherein $X^7$-$X^{10}$ are as defined in formula (I), (Ia), (Ib), (Ic) or (C) or any variation thereof detailed herein or as detailed in any variation herein, where $R^1$ is H, substituted or unsubstituted $C_1$-$C_8$ alkyl, acyl, acyloxy, carbonylalkoxy, substituted or unsubstituted heterocyclyl, substituted or unsubstituted aryl, substituted or unsubstituted heteroaryl, substituted or unsubstituted aralkyl. In a further embodiment, a compound of the invention is of the formula (I), (Ia), (Ib), (Ic) or (C) or any variation thereof detailed herein, wherein $X^7$-$X^{10}$ are as defined in formula (I) or as detailed in any variation herein, where $R^1$ is a substituted or unsubstituted $C_1$-$C_8$ alkyl, acyl, acyloxy, carbonylalkoxy, substituted or unsubstituted heterocyclyl or substituted or unsubstituted aryl. In a particular variation, a compound of the invention is of the formula (I), (Ia), (Ib), (Ic) or (C) or any variation thereof detailed herein, wherein $X^7$-$X^{10}$ are as defined in formula (I), (Ia), (Ib), (Ic) or (C) or any variation thereof detailed herein, where $R^1$ is methyl, ethyl, cyclopropyl, propylate, trifluoromethyl, isopropyl, tert-butyl, sec-butyl, 2-methylbutyl, propanal, 1-methyl-2-hydroxyethyl, 2-hydroxyethanal, 2-hydroxyethyl, 2-hydroxypropyl, 2-hydroxy-2-methylpropyl, cyclobutyl, cyclopentyl, cyclohexyl, substituted phenyl, piperidin-4-yl, hydroxycyclopent-3-yl, hydroxycyclopent-2-yl, hydroxycycloprop-2-yl, 1-hydroxy-1-methylcycloprop-2-yl, or 1-hydroxy-1,2,2-trimethyl-cycloprop-3-yl.

In another variation, the compound of the invention is of the formula (I), (Ia), (Ib), (Ic) or (C) or any variation thereof detailed herein, where $X^7$-$X^{10}$ and $R^1$ are as defined in formula (I), (Ia), (Ib), (Ic) or (C) or any variation thereof detailed herein, where $R^{2a}$ and $R^{2b}$ are independently H, substituted or unsubstituted $C_1$-$C_8$ alkyl, halo, cyano, nitro or $R^{2a}$ and $R^{2b}$ are taken together to form a carbonyl moiety and each $R^{3a}$ and $R^{3b}$ is independently H, substituted or unsubstituted $C_1$-$C_8$ alkyl, halo, cyano or nitro. In another variation, the compound of the invention is of the formula (I), (Ia), (Ib), (Ic) or (C) or any variation thereof detailed herein, where $X^7$-$X^{10}$ and $R^1$ are as defined in formula (I), (Ia), (Ib), (Ic) or (C) or any variation thereof detailed herein, where each $R^{2a}$ and $R^{2b}$ is independently H, unsubstituted $C_1$-$C_8$ alkyl, halo or $R^{2a}$ and $R^{2b}$ are taken together to form a carbonyl moiety and each $R^{3a}$ and $R^{3b}$ is independently H, unsubstituted $C_1$-$C_8$ alkyl, halo or $R^{3a}$ and $R^{3b}$ are taken together to form a carbonyl moiety. The invention also embraces compounds of the invention according to formula (I), where $X^7$-$X^{10}$ and $R^1$ are as defined in formula (I), (Ia), (Ib), (Ic) or (C) or any variation thereof detailed herein, where each $R^{2a}$ and $R^{2b}$ is independently H, methyl, halo or $R^{2a}$ and $R^{2b}$ are taken together to form a carbonyl moiety and each $R^{3a}$ and $R^{3b}$ is independently H, methyl, halo or $R^{3a}$ and $R^{3b}$ are taken together to form a carbonyl moiety. The invention further embraces compounds of the invention according to formula (I), (Ia), (Ib), (Ic) or (C) or any variation thereof detailed herein, where $X^7$-$X^{10}$ and $R^1$ are as defined in formula (I), (Ia), (Ib), (Ic) or (C) or any variation thereof detailed herein, where each of $R^{2a}$, $R^{2b}$, $R^{3a}$ and $R^{3b}$ is H. In one variation, a compound of the invention is of the formula (I), (Ia), (Ib), (Ic) or (C) or any variation thereof detailed herein where $X^7$-$X^{10}$ and $R^1$ are as defined in formula (I), (Ia), (Ib), (Ic) or (C) or any variation thereof detailed herein, where at least one of $R^{2a}$, $R^{2b}$, $R^{3a}$ and $R^{3b}$ is a substituted or unsubstituted $C_1$-$C_8$ alkyl, halo, cyano, nitro or is taken together with the carbon to which it is attached and a geminal $R^2$ or $R^3$ to form a carbonyl moiety. In another variation, a compound of the invention is of the formula (I), (Ia), (Ib), (Ic) or (C) or any variation thereof detailed herein where $X^7$-$X^{10}$ and $R^1$ are as defined in formula (I), (Ia), (Ib), (Ic) or (C) or any variation thereof detailed herein, where at least two of $R^{2a}$, $R^{2b}$, $R^{3a}$ and $R^{3b}$ is a substituted or unsubstituted $C_1$-$C_8$ alkyl, halo, cyano, nitro or is taken together with the carbon to which it is attached and a geminal $R^2$ or $R^3$ to form a carbonyl moiety. In yet another variation, a compound of the invention is of the formula (I), (Ia), (Ib), (Ic) or (C) or any variation thereof detailed herein where $X^7$-$X^{10}$ and $R^1$ are as defined in formula (I), (Ia), (Ib), (Ic) or (C) or any variation thereof detailed herein, where at least one of $R^{2a}$, $R^{2b}$, $R^{3a}$ and $R^{3b}$ is fluoro or methyl or is taken together with the carbon to which it is attached and a geminal $R^2$ or $R^3$ to form a carbonyl moiety. In still another variation, a compound of the invention is of the formula (I), (Ia), (Ib), (Ic) or (C) or any variation thereof detailed herein where $X^7$-$X^{10}$ and $R^1$ are as defined in formula (I), (Ia), (Ib), (Ic) or (C) or any variation thereof detailed herein, where either $R^{2a}$ and $R^{2b}$ or $R^{3a}$ and $R^{3b}$ are each methyl or fluoro (e.g., both $R^{2a}$ and $R^{2b}$ are methyl or one is fluoro and one is methyl) or are taken together to form a carbonyl moiety. In one variation, $R^{2a}$ and $R^{2b}$ are taken together to form a carbonyl moiety. In another variation, at least one of $R^{2a}$ and $R^{2b}$ is hydroxyl or alkoxy. In a particular variation, each $R^{2a}$ and $R^{2b}$ is independently H, substituted or unsubstituted $C_1$-$C_8$ alkyl, halo, cyano, nitro or $R^{2a}$ and $R^{2b}$ are taken together to form a carbonyl. In another variation, when $X^1$ is N, each $R^{2a}$ and $R^{2b}$ is independently H, substituted or unsubstituted $C_1$-$C_8$ alkyl, halo, cyano, nitro or $R^{2a}$ and $R^{2b}$ are taken together to form a carbonyl.

The invention also embraces compounds according to formula (I), (Ia), (Ib), (Ic) or (C) or any variation thereof detailed herein, where $X^7$-$X^{10}$, $R^1$, $R^{2a}$, $R^{2b}$, $R^{3a}$ and $R^{3b}$ are as defined in formula (I), (Ia), (Ib), (Ic) or (C) or any variation thereof detailed herein, where each $R^{10a}$ and $R^{10b}$ is independently H, halo, an unsubstituted $C_1$-$C_8$ alkyl, hydroxyl or $R^{10a}$ and $R^{10b}$ are taken together to form a cycloalkyl or a carbonyl. Also embraced are compounds according to formula (I), (Ia), (Ib), (Ic) or (C) or any variation thereof detailed herein, where $X^7$-$X^{10}$, $R^1$, $R^{2a}$, $R^{2b}$, $R^{3a}$ and $R^{3b}$ are as defined in formula (I), (Ia), (Ib), (Ic) or (C) or any variation thereof detailed herein or as detailed in any variation herein, where each $R^{10a}$ and $R^{10b}$ is independently H, halo, an unsubstituted $C_1$-$C_4$ alkyl, hydroxyl or $R^{10a}$ and $R^{10b}$ are taken together to form a cycloalkyl or a carbonyl. In another variation, a compound of the invention is of the formula (I), (Ia), (Ib), (Ic) or (C) or any variation thereof detailed herein, where $X^7$-$X^{10}$, $R^1$, $R^{2a}$, $R^{2b}$, $R^{3a}$ and $R^{3b}$ are as defined in formula (I), (Ia), (Ib), (Ic) or (C) or any variation thereof detailed herein, where each $R^{10a}$ and $R^{10b}$ is independently H, bromo, methyl, hydroxyl or $R^{10a}$ and $R^{10b}$ are taken together to form a cyclopropyl or a carbonyl. In yet another variation, a compound of the invention is of the formula (I), (Ia), (Ib), (Ic) or (C) or any variation thereof detailed herein, where $X^7$-$X^{10}$, $R^1$, $R^{2a}$, $R^{2b}$, $R^{3a}$ and $R^{3b}$ are as defined in formula (I), (Ia), (Ib), (Ic) or (C) or any variation thereof detailed herein, where at least one of $R^{10a}$ and $R^{10b}$ is an unsubstituted $C_1$-$C_8$ alkyl, hydroxyl, halo or $R^{10a}$ and $R^{10b}$ are taken together to form a cycloalkyl or a carbonyl. In still a further variation, a compound of the invention is of the formula (I), (Ia), (Ib), (Ic) or (C) or any variation thereof detailed herein, where $X^7$-$X^{10}$, $R^1$, $R^{2a}$, $R^{2b}$, $R^{3a}$ and $R^{3b}$ are as defined in formula (I), (Ia), (Ib), (Ic) or (C) or any variation thereof detailed herein, where at least one of $R^{10a}$ and $R^{10b}$ is methyl, bromo, hydroxyl or $R^{10a}$ and $R^{10b}$ are taken together to form a cyclopropyl or a carbonyl. In another variation, a compound of the invention is of the formula (I), (Ia), (Ib), (Ic) or (C) or any variation thereof detailed herein, where $X^7$-$X^{10}$, $R^1$, $R^{2a}$, $R^{2b}$, $R^{3a}$ and $R^{3b}$ are as defined in formula (I), (Ia), (Ib), (Ic) or (C) or any variation thereof detailed herein, where both $R^{10a}$ and $R^{10b}$ are methyl. In another variation, a compound of the invention is of the formula (I), (Ia), (Ib), (Ic) or (C) or any variation thereof detailed herein, where $X^7$-$X^{10}$, $R^1$, $R^{2a}$, $R^{2b}$, $R^{3a}$ and $R^{3b}$ are as defined in formula (I), (Ia), (Ib), (Ic) or (C) or any variation thereof detailed herein, where $R^{10a}$ and $R^{10b}$ are taken together to form a carbonyl. In another variation, a compound of the invention is of the formula (I), (Ia), (Ib), (Ic) or (C) or any variation thereof detailed herein, where $X^7$-$X^{10}$, $R^1$, $R^{2a}$, $R^{2b}$, $R^{3a}$ and $R^{3b}$ are as defined in formula (I), (Ia), (Ib), (Ic) or (C) or any variation thereof detailed herein, where $R^{10a}$ is H and $R^{10b}$ is methyl. In another variation, a compound of the invention is of the formula (I), (Ia), (Ib), (Ic) or (C) or any variation thereof detailed herein, where $X^7$-$X^{10}$, $R^1$, $R^{2a}$, $R^{2b}$, $R^{3a}$ and $R^{3b}$ are as defined in formula (I), (Ia), (Ib), (Ic) or (C) or any variation thereof detailed herein, where $R^{10a}$ is H and $R^{10b}$ is bromo. When the carbon of formula (I), (Ia), (Ib), (Ic) or (C) or any variation thereof detailed herein bearing $R^{10a}$ and $R^{10b}$ is optically active, it may be in the S or R configuration and compositions comprising substantially pure R or S compound or mixtures thereof in any amount are embraced by this invention.

The invention also embraces compounds according to formula (I), (Ia), (Ib), (Ic) or (C) or any variation thereof detailed herein, where $X^7$-$X^{10}$, $R^1$, $R^{2a}$, $R^{2b}$, $R^{3a}$ and $R^{3b}$ are as defined in formula (I), (Ia), (Ib), (Ic) or (C) or any variation thereof detailed herein, where each $R^{11a}$ and $R^{11b}$ is independently H, halo, an unsubstituted $C_1$-$C_8$ alkyl, hydroxyl or $R^{11a}$ and $R^{11b}$ are taken together to form a cycloalkyl or a carbonyl. Also embraced are compounds according to formula (I), (Ia), (Ib), (Ic) or (C) or any variation thereof detailed herein, where $X^7$-$X^{10}$, $R^1$, $R^{2a}$, $R^{2b}$, $R^{3a}$ and $R^{3b}$ are as defined in formula (I), (Ia), (Ib), (Ic) or (C) or any variation thereof detailed herein or as detailed in any variation herein, where each $R^{11a}$ and $R^{11b}$ is independently H, halo, an unsubstituted $C_1$-$C_4$ alkyl, hydroxyl or $R^{11a}$ and $R^{11b}$ are taken together to form a cycloalkyl or a carbonyl. In another variation, a compound of the invention is of the formula (I), (Ia), (Ib), (Ic) or (C) or any variation thereof detailed herein, where $X^7$-$X^{10}$, $R^1$, $R^{2a}$, $R^{2b}$, $R^{3a}$ and $R^{3b}$ are as defined in formula (I), (Ia), (Ib), (Ic) or (C) or any variation thereof detailed herein, where each $R^{11a}$ and $R^{11b}$ is independently H, bromo, methyl, hydroxyl or $R^{11a}$ and $R^{11b}$ are taken together to form a cyclopropyl or a carbonyl. In yet another variation, a compound of the invention is of the formula (I), (Ia), (Ib), (Ic) or (C) or any variation thereof detailed herein, where $X^7$-$X^{10}$, $R^1$, $R^{2a}$, $R^{2b}$, $R^{3a}$ and $R^{3b}$ are as defined in formula (I), (Ia), (Ib), (Ic) or (C) or any variation thereof detailed herein, where at least one of $R^{11a}$ and $R^{11b}$ is an unsubstituted $C_1$-$C_8$ alkyl, hydroxyl, halo or $R^{11a}$ and $R^{11b}$ are taken together to form a cycloalkyl or a carbonyl. In still a further variation, a compound of the invention is of the formula (I), (Ia), (Ib), (Ic) or (C) or any variation thereof detailed herein, where $X^7$-$X^{10}$, $R^1$, $R^{2a}$, $R^{2b}$, $R^{3a}$ and $R^{3b}$ are as defined in formula (I), (Ia), (Ib), (Ic) or (C) or any variation thereof detailed herein, where at least one of $R^{11a}$ and $R^{11b}$ is methyl, bromo, hydroxyl or $R^{11a}$ and $R^{11b}$ are taken together to form a cyclopropyl or a carbonyl. In another variation, a compound of the invention is of the formula (I), (Ia), (Ib), (Ic) or (C) or any variation thereof detailed herein, where $X^7$-$X^{10}$, $R^1$, $R^{2a}$, $R^{2b}$, $R^{3a}$ and $R^{3b}$ are as defined in formula (I), (Ia), (Ib), (Ic) or (C) or any variation thereof detailed herein, where both $R^{11a}$ and $R^{11b}$ are methyl. In another variation, a compound of the invention is of the formula (I), (Ia), (Ib), (Ic) or (C) or any variation thereof detailed herein, where $X^7$-$X^{10}$, $R^1$, $R^{2a}$, $R^{2b}$, $R^{3a}$ and $R^{3b}$ are as defined in formula (I), (Ia), (Ib), (Ic) or (C) or any variation thereof detailed herein, where $R^{11a}$ and $R^{11b}$ are taken together to form a carbonyl. In another variation, a compound of the invention is of the formula (I), (Ia), (Ib), (Ic) or (C) or any variation thereof detailed herein, where $X^7$-$X^{10}$, $R^1$, $R^{2a}$, $R^{2b}$, $R^{3a}$ and $R^{3b}$ are as defined in formula (I), (Ia), (Ib), (Ic) or (C) or any variation thereof detailed herein, where $R^{11a}$ is H and $R^{11b}$ is methyl. In another variation, a compound of the invention is of the formula (I), (Ia), (Ib), (Ic) or (C) or any variation thereof detailed herein, where $X^7$-$X^{10}$, $R^1$, $R^{2a}$, $R^{2b}$, $R^{3a}$ and $R^{3b}$ are as defined in formula (I), (Ia), (Ib), (Ic) or (C) or any variation thereof detailed herein, where $R^{11a}$ is H and $R^{11b}$ is bromo. When the carbon of formula (I), (Ia), (Ib), (Ic) or (C) or any variation thereof detailed herein bearing $R^{11a}$ and $R^{11b}$ is optically active, it may be in the S or R configuration and compositions comprising substantially pure R or S compound or mixtures thereof in any amount are embraced by this invention.

In a particular variation, a compound of the invention is of the formula (I), (Ia), (Ib), (Ic) or (C) or any variation thereof detailed herein where $R^1$, $R^{2a}$, $R^{2b}$, $R^{3a}$, $R^{3b}$, $R^{10a}$, $R^{10a}$, $R^{10b}$, $R^{11a}$ and $R^{11b}$ are taken together to form a ring selected from the structures:

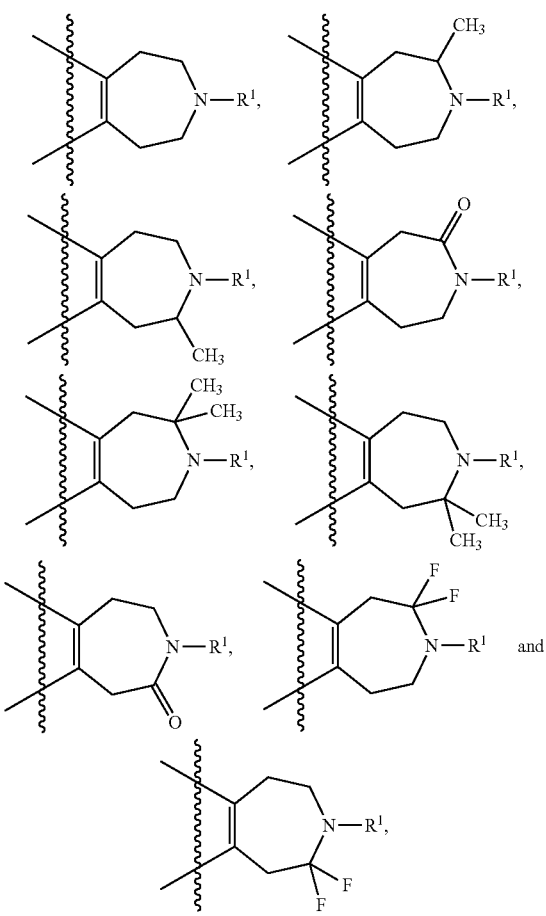

where R¹ in the structures above is as defined for formula (I), (Ia), (Ib), (Ic) or (C) or any particular variation detailed herein.
Compounds of the formulae (II-1), (II-2), (II-3), (II-4), (II-5), (II-6), (II-7) and (II-8) are also embraced by this invention:
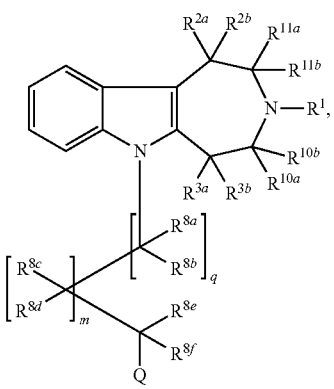
(II-1)
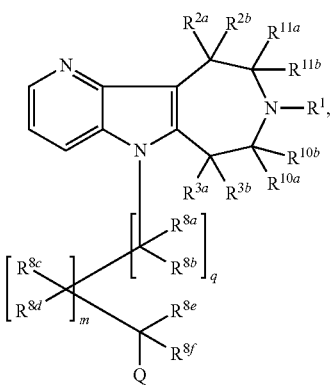
(II-2)
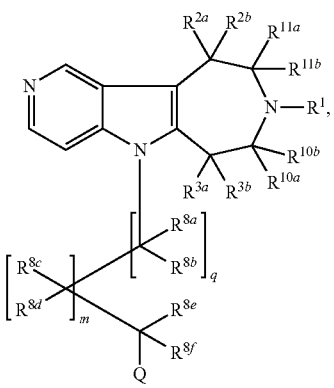
(II-3)
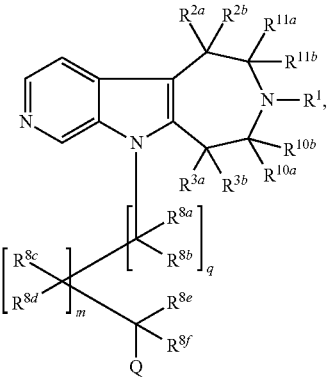
(II-4)
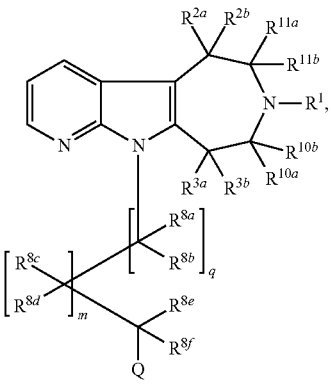
(II-5)
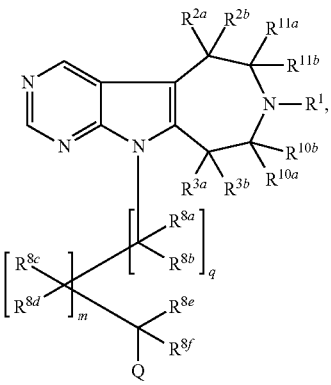
(II-6)
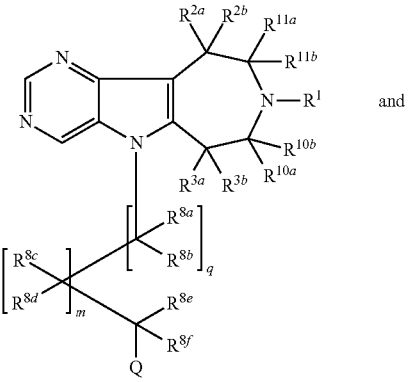
(II-7)
and

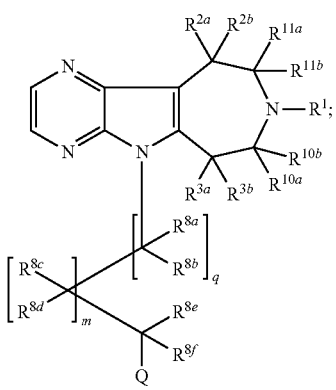
(II-8)
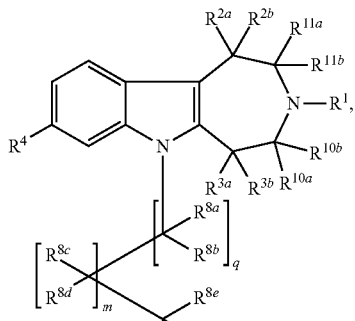
(III-3)
where in each of (II-1), (II-2), (II-3), (II-4), (II-5), (II-6), (II-7) and (II-8), $R^1$, $R^{2a}$, $R^{2b}$, $R^{3a}$, $R^{3b}$, $R^{10a}$, $R^{10b}$, $R^{11a}$, $R^{11b}$, $R^{8a}$-$R^{8f}$, m, q and Q are as described for formula (I), (Ia), (Ib), (Ic) or (C) or any applicable variation thereof.
Compounds of the formulae (III-1), (III-2), (III-3), (III-4), (III-5), (III-6), (III-7), (III-8), (III-9), (III-10), (III-11), (III-12), (III-13), (III-14) and (III-15) are further embraced this invention:
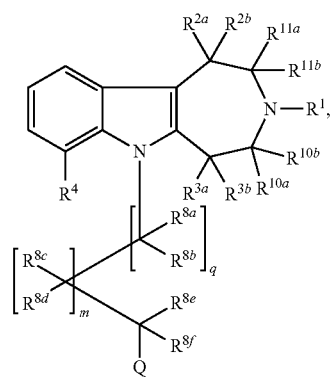
(III-4)
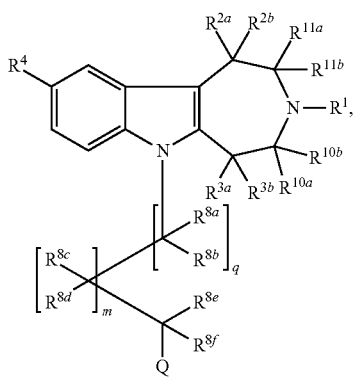
(III-1)
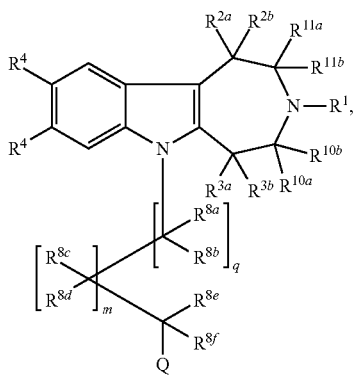
(III-5)
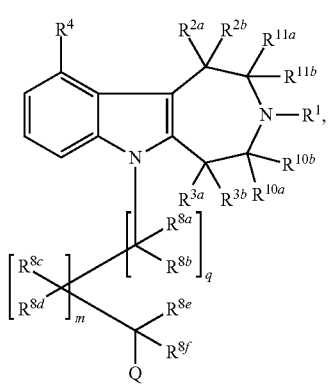
(III-2)
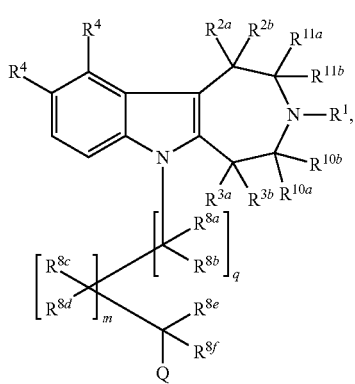
(III-6)

-continued
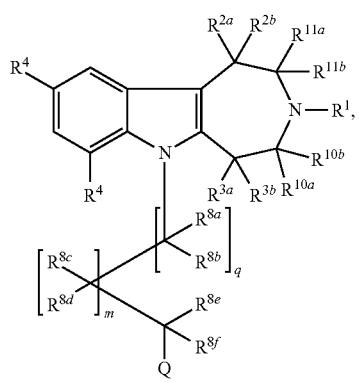
(III-7)
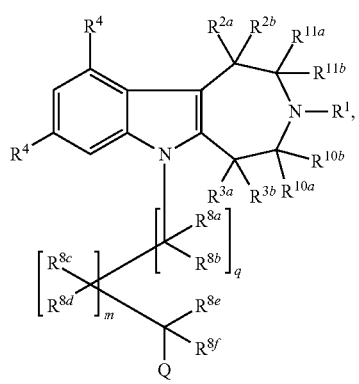
(III-8)
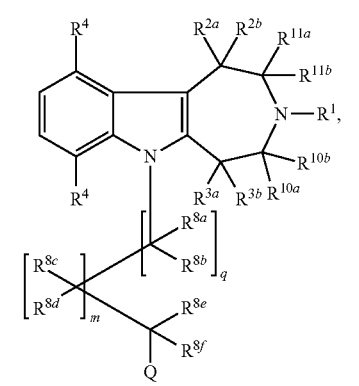
(III-9)
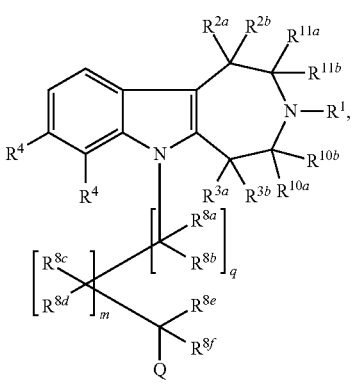
(III-10)
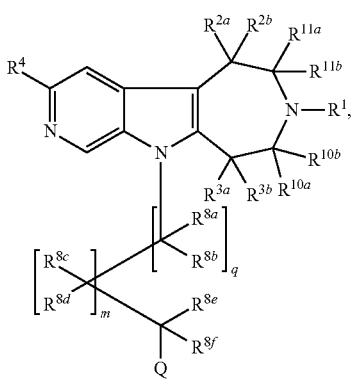
(III-11)
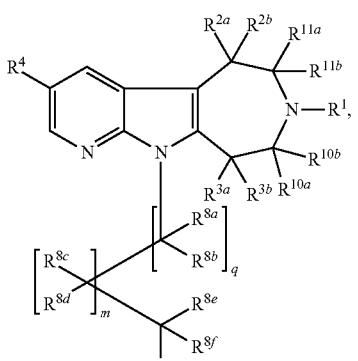
(III-12)
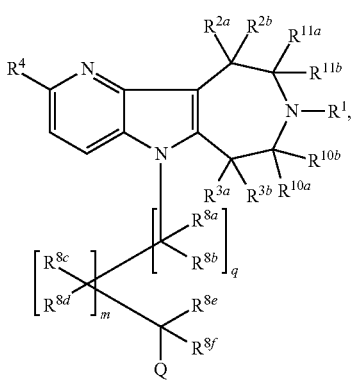
(III-13)
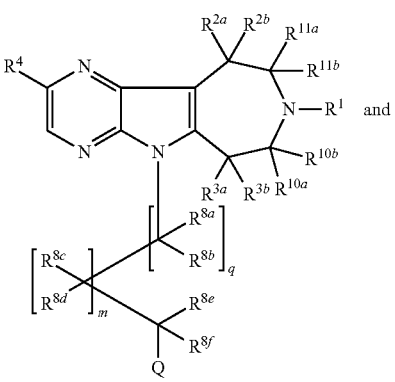
(III-14)
and (III-15)
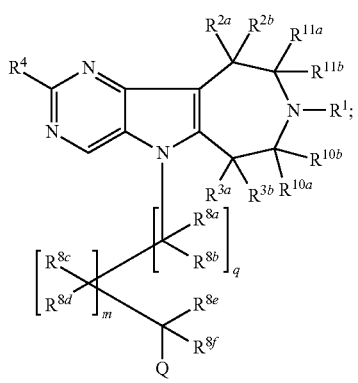
where in each of formulae (III-1), (III-2), (III-3), (III-4), (III-5), (III-6), (III-7), (III-8), (III-9), (III-10), (III-11), (III-12), (III-13), (III-14) and (III-15), $R^1$, $R^4$, $R^{2a}$, $R^{2b}$, $R^{3a}$, $R^{3b}$, $R^{10a}$, $R^{10b}$, $R^{11a}$, $R^{11b}$, $R^{8a}$-$R^{8f}$, m, q and Q are as described for formula (I), (Ia), (Ib), (Ic) or (C) or any applicable variation thereof.
Compounds of the formulae (IV-1), (IV-2), (IV-3), (IV-4), (IV-5), (IV-6), (IV-7), (IV-8) and (IV-9) are further embraced by this invention:
(IV-1)
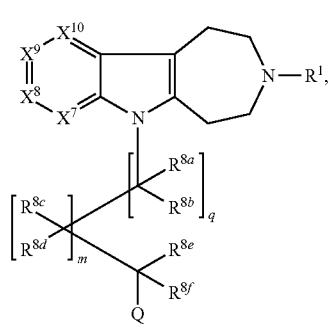
(IV-2)
(IV-3)
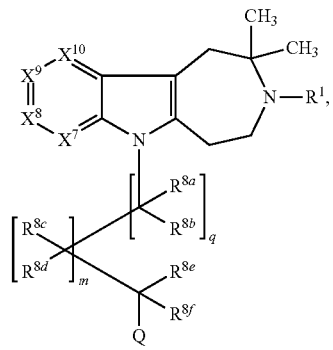
(IV-4)
(IV-5)
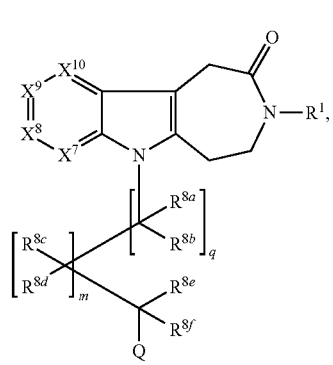
(IV-6)
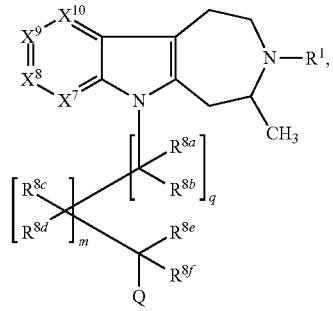

-continued

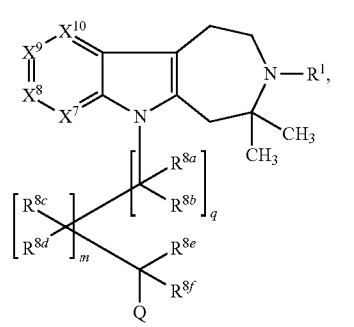

(IV-7)

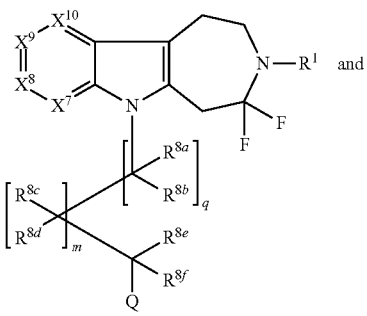

(IV-8) and

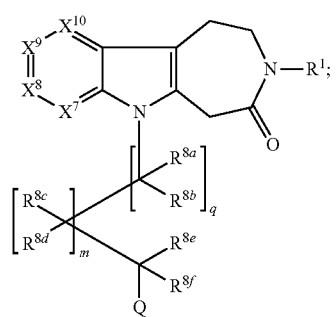

(IV-9)

where in each of formulae (IV-1), (IV-2), (IV-3), (IV-4), (IV-5), (IV-6), (IV-7), (IV-8) and (IV-9), $R^1$, $R^4$, $R^{2a}$, $R^{2b}$, $R^{3a}$, $R^{3b}$, $R^{10a}$, $R^{10b}$, $R^{11a}$, $R^{11b}$, $R^{8a}$-$R^{8f}$, m, q and Q are as described for formula (I), (Ia), (Ib), (Ic) or (C) or any applicable variation thereof.

The invention also embraces compounds of the formulae (V-1), (V-2), (V-3), (V-4), (V-5), (V-6), (V-7), (V-8), (V-9), (V-10), (V-11), (V-12), (V-13), (V-14), (V-15), (V-16), (V-17), (V-18), (V-19), (V-20), (V-21), (V-22), (V-23), (V-24), (V-25), (V-26) and (V-27) are also embraced by this invention:

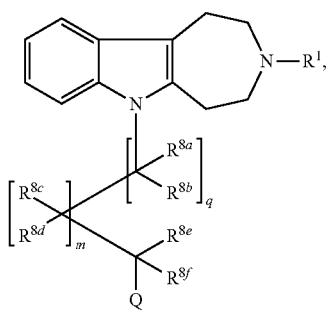

(V-1)

-continued

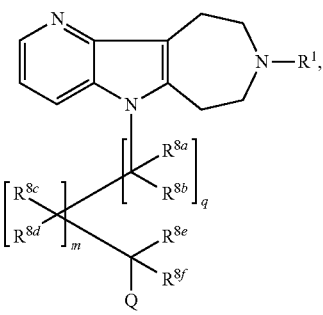

(V-2)

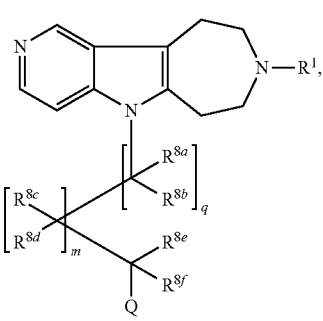

(V-3)

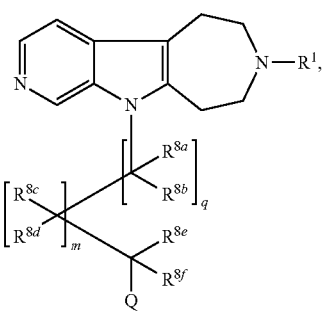

(V-4)

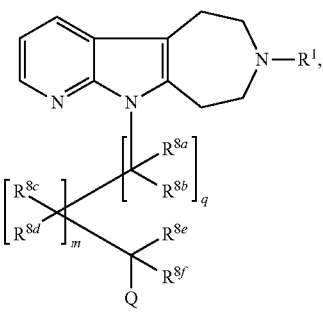

(V-5)

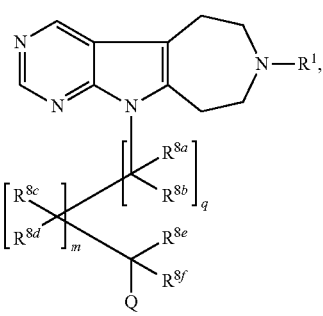

(V-6)

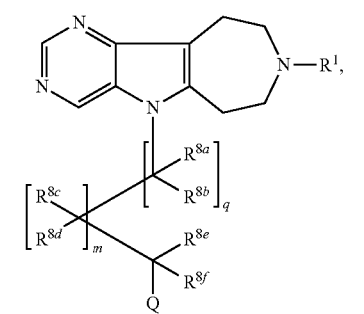
(V-7)
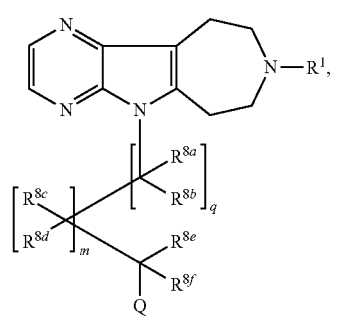
(V-8)
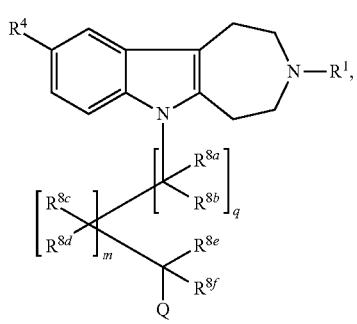
(V-9)
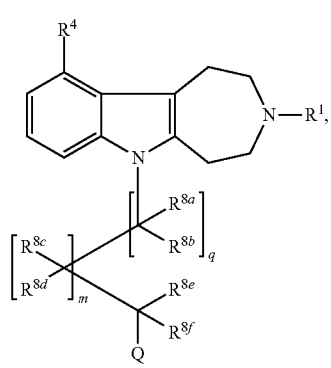
(V-10)
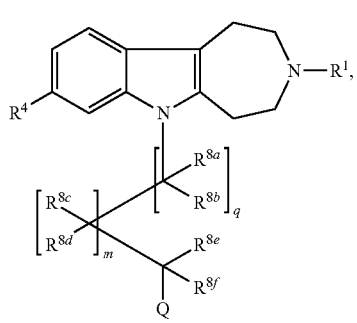
(V-11)
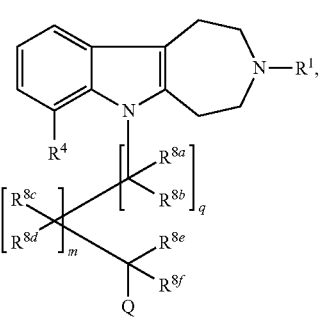
(V-12)
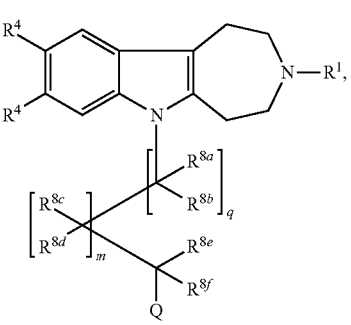
(V-13)
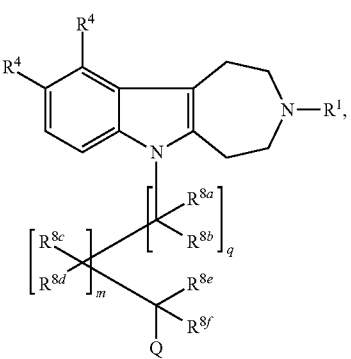
(V-14)
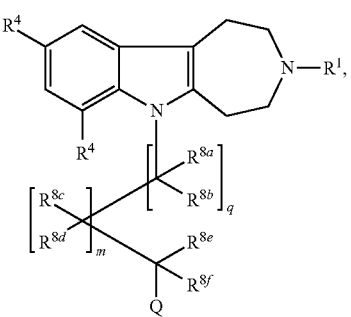
(V-15)

(V-16)
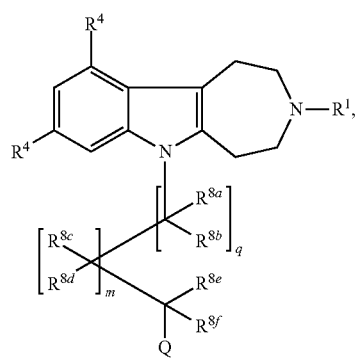
(V-17)
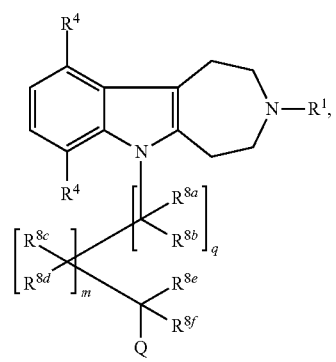
(V-18)
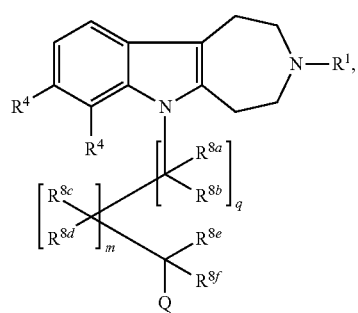
(V-19)
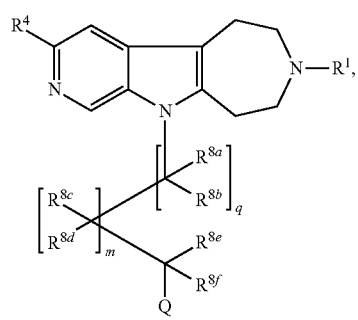
(V-20)
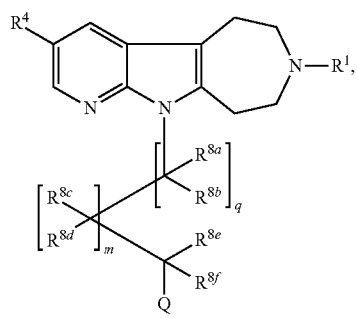
(V-21)
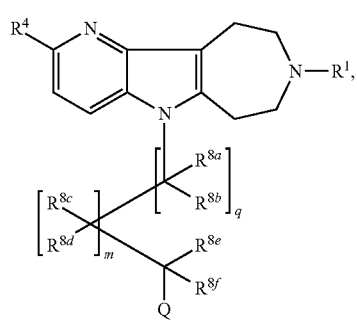
(V-22)
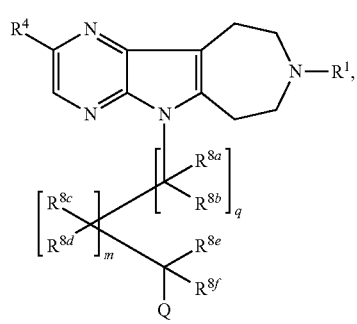
(V-23)
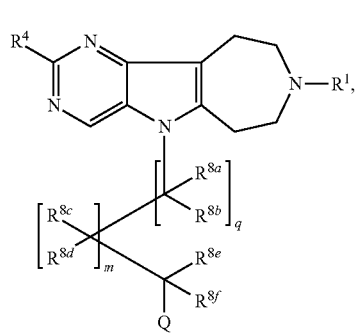
(V-24)
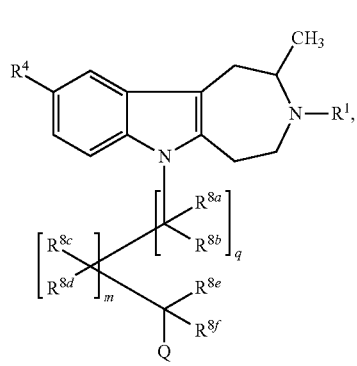

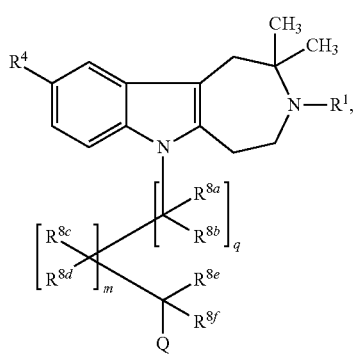

(V-25)

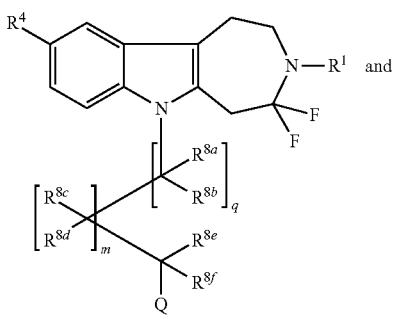

(V-26)

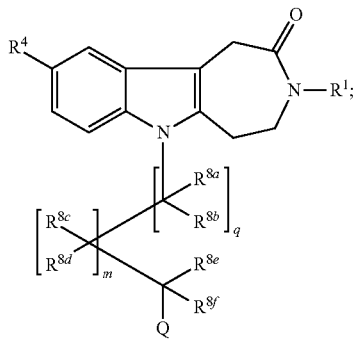

(V-27)

where in each of formulae (V-1), (V-2), (V-3), (V-4), (V-5), (V-6), (V-7), (V-8), (V-9), (V-10), (V-11), (V-12), (V-13), (V-14), (V-15), (V-16), (V-17), (V-18), (V-19), (V-20), (V-21), (V-22), (V-23), (V-24), (V-25), (V-26) and (V-27), $R^1$, $R^4$, $R^{2a}$, $R^{2b}$, $R^{3a}$, $R^{3b}$, $R^{10a}$, $R^{10b}$, $R^{11a}$, $R^{11b}$, $R^{8a}$-$R^{8f}$, m, q and Q are as described for formula (I), (Ia), (Ib), (Ic) or (C) or any applicable variation thereof.

The invention embraces a compound according to formula (I), (Ia), (Ib) or (Ic) or any variation thereof detailed herein, or a compound according to any one of the formulae (II-1)-(II-8), (III-1)-(III-15), (IV-1)-(IV-9) or (V-1)-(V-27), where each $R^{8a}$, $R^{8b}$, $R^{8c}$, $R^{8d}$, $R^{8e}$ and $R^{8f}$ is independently H, hydroxyl, $C_1$-$C_8$ alkyl, $C_1$-$C_8$ perhaloalkyl, carboxy, carbonylalkoxy, is taken together with the carbon to which it is attached and a geminal $R^8$ to form a cycloalkyl moiety or a carbonyl moiety, is taken together with a geminal $R^8$ to form a methylene or a substituted methylene, is taken together with a vicinal $R^8$ and the carbon atoms to which they are attached to form a substituted or unsubstituted $C_3$-$C_8$ cycloalkyl, substituted or unsubstituted $C_3$-$C_8$ cycloalkenyl or substituted or unsubstituted heterocyclyl moiety or is taken together with a vicinal $R^8$ to form a bond, provided: (i) at most one pair of vicinal $R^8$ groups are taken together to form a bond; and (ii) when an $R^8$ is taken together with a vicinal $R^8$ to form a bond, the geminal $R^8$ is other than hydroxyl. In one variation, a compound of the invention is of the formula (I), (Ia), (Ib) or (Ic) or any variation thereof detailed herein, or is of any one of the formulae (II-1)-(II-8), (III-1)-(III-15), (IV-1)-(IV-9) or (V-1)-(V-27), where each $R^{8a}$, $R^{8b}$, $R^{8c}$, $R^{8d}$, $R^{8e}$ and $R^{8f}$ is independently H, hydroxyl, unsubstituted $C_1$-$C_4$ alkyl or is taken together with the carbon to which it is attached and a geminal $R^8$ to form a cycloalkyl moiety. In one variation, a compound of the invention is of the formula (I), (Ia), (Ib) or (Ic) or any variation thereof detailed herein, or is of any one of the formulae (II-1)-(II-8), (III-1)-(III-15), (IV-1)-(IV-9) or (V-1)-(V-27), where at least one of $R^{8a}$, $R^{8b}$, $R^{8c}$, $R^{8d}$, $R^{8e}$ and $R^{8f}$ is taken together with the carbon to which it is attached and a geminal $R^8$ to form a carbonyl moiety. In another variation, a compound of the invention is of the formula (I), (Ia), (Ib) or (Ic) or any variation thereof detailed herein, or is of any one of the formulae (II-1)-(II-8), (III-1)-(III-15), (IV-1)-(IV-9) or (V-1)-(V-27), where each $R^{8a}$, $R^{8b}$, $R^{8c}$, $R^{8d}$, $R^{8e}$ and $R^{8f}$ is independently H, hydroxyl, methyl or is taken together with the carbon to which it is attached and a geminal $R^8$ to form a cyclopropyl moiety. In one variation, a compound of the invention is of the formula (I), (Ia), (Ib) or (Ic) or any variation thereof detailed herein, or is of any one of the formulae (II-1)-(II-8), (III-1)-(III-15), (IV-1)-(IV-9) or (V-1)-(V-27), where at least one of $R^{8a}$, $R^{8b}$, $R^{8c}$, $R^{8d}$, $R^{8e}$ and $R^{8f}$ is taken together with a geminal $R^8$ to form a methylene ($CH_2$=) or a substituted methylene such as $CH_3CH$= or the like. In another variation, a compound of the invention is of the formula (I), (Ia), (Ib) or (Ic) or any variation thereof detailed herein, or is of any one of the formulae (II-1)-(II-8), (III-1)-(III-15), (IV-1)-(IV-9) or (V-1)-(V-27), where at least one of $R^{8a}$, $R^{8b}$, $R^{8c}$, $R^{8d}$, $R^{8e}$ and $R^{8f}$ is taken together with a vicinal $R^8$ to form a bond, where the resultant double bond is in E- or Z-configuration. In one variation, a compound of the invention is of the formula (I), (Ia), (Ib) or (Ic) or any variation thereof detailed herein, or is of any one of the formulae (II-1)-(II-8), (III-1)-(III-15), (IV-1)-(IV-9) or (V-1)-(V-27), where at least one of $R^{8a}$, $R^{8b}$, $R^{8c}$, $R^{8d}$, $R^{8e}$ and $R^{8f}$ is taken together with a vicinal $R^8$ and the carbons to which they are attached to form a substituted or unsubstituted $C_3$-$C_8$ cycloalkyl, substituted or unsubstituted $C_3$-$C_8$ cycloalkenyl or substituted or unsubstituted heterocyclyl moiety. In one variation, a compound of the invention is of the formula (I), (Ia), (Ib) or (Ic) or any variation thereof detailed herein, or is of any one of the formulae (II-1)-(II-8), (III-1)-(III-15), (IV-1)-(IV-9) or (V-1)-(V-27), where at least one of $R^{8a}$, $R^{8b}$, $R^{8c}$, $R^{8d}$, $R^{8e}$ and $R^{8f}$ is taken together with a vicinal $R^8$ and the carbons to which they are attached to form a $C_3$-$C_8$ cycloalkyl. In one variation, a compound of the invention is of the formula (I), (Ia), (Ib) or (Ic) or any variation thereof detailed herein, or is of any one of the formulae (II-1)-(II-8), (III-1)-(III-15), (IV-1)-(IV-9) or (V-1)-(V-27), where $R^{8c}$, $R^{8d}$ and the carbon to which they are attached are taken together with two other $R^8$ groups that are geminal to each other and the carbon to which they are attached to form a $C_3$-$C_8$ cycloalkenyl. In yet another variation, a compound of the invention is of the formula (I), (Id) or (Ie) or any variation thereof detailed herein, or is any one of the formulae (II-1)-(II-8), (III-1)-(II-15), (IV-1)-(IV-9) or (V-1)-(V-27), where wherein q is 0 and m is 1. The invention also embraces a compound of the invention according to formula (I), (Id) or (Ie) or any variation thereof detailed herein, or a compound according to any one of the formulae (II-1)-(II-8), (III-1)-(III-15), (IV-1)-(IV-9) or (V-1)-(V-27), where q and m are both 0.

In certain embodiments, compounds of formulae detailed herein are provided where $R^1$ is selected from the following moieties:

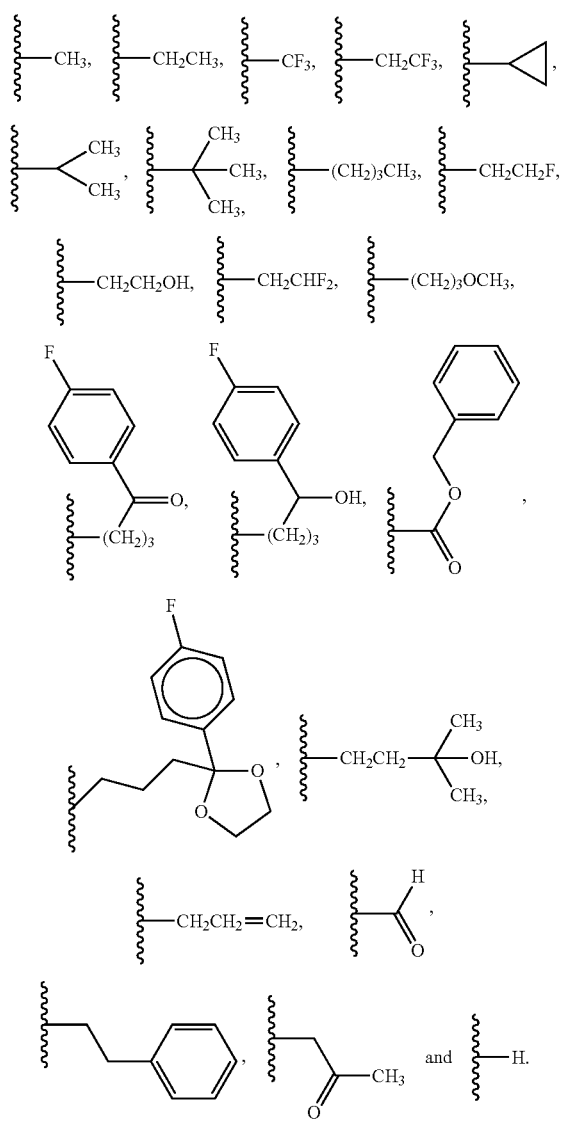

The invention further embraces a compound according to formula (I), (Ia), (Ib) or (Ic) or any variation thereof detailed herein, or a compound according to any one of the formulae (II-1)-(II-8), (III-1)-(III-15), (IV-1)-(IV-9) or (V-1)-(V-27), where q, m, $R^{8a}$, $R^{8b}$, $R^{8c}$, $R^{8d}$, $R^{8e}$ and $R^{8f}$ are taken together to form a moiety selected from the group consisting of the structures:

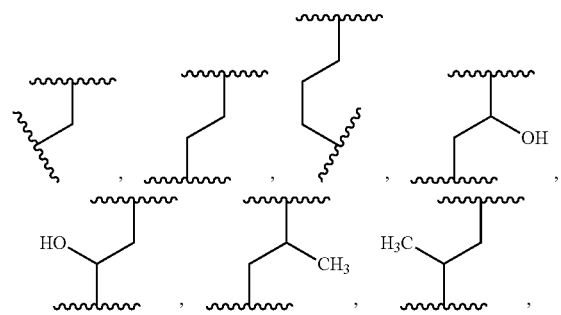

The invention further embraces a compound according to formula (A) or (A-1) or any variation thereof detailed herein, where q, m, $R^{8a}$, $R^{8b}$, $R^{8c}$, $R^{8d}$, $R^{8g}$ and $R^{8h}$ are taken together with the carbons to which they are attached to form a moiety selected from the group consisting of the structures:

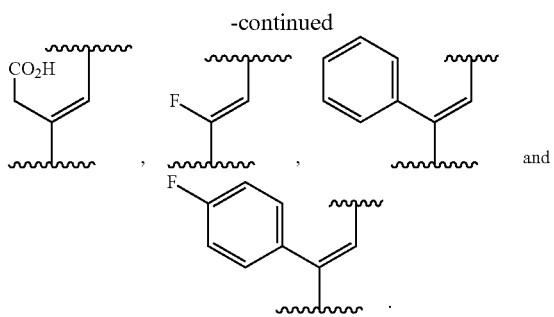

The invention further embraces a compound according to formula (I), (Ia), (Ib) or (Ic) or any variation thereof detailed herein, or a compound according to any one of the formulae (II-1)-(II-8), (III-1)-(III-15), (IV-1)-(IV-9) or (V-1)-(V-27), where $R^{8c}$, $R^{8d}$ and the carbon to which they are attached are taken together with $R^{8e}$, $R^{8f}$ and the carbon to which they are attached or $R^{8a}$, $R^{8b}$ and the carbon to which they are attached to form a moiety selected from the group consisting of the structures, each of which may be optionally substituted, where each $R^8$ is independently H, hydroxyl, $C_1$-$C_8$ alkyl, $C_1$-$C_8$ perhaloalkyl, carboxy or carbonylalkoxy:

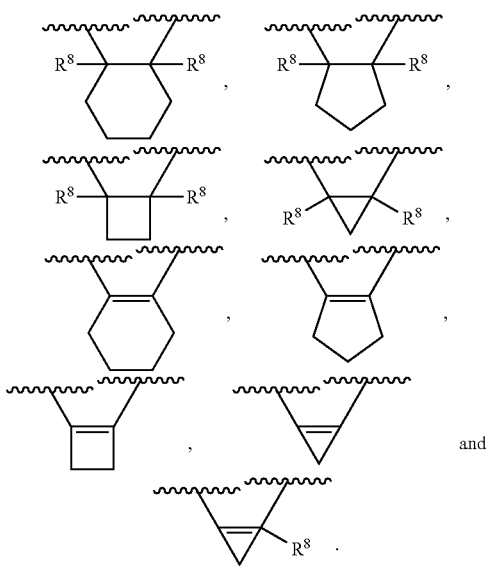

In another variation, a compound of the invention is of the formula (I), (Ia), (Ib), (Ic) or (C) or any variation thereof detailed herein, or a compound according to any one of the formulae (III-1)-(III-15), (IV-1)-(IV-9) or (V-1)-(V-27), where each $R^4$ is independently H, halo, substituted or unsubstituted $C_1$-$C_8$ alkyl, $C_1$-$C_8$ perhaloalkyl, substituted or unsubstituted heterocyclyl or a substituted or unsubstituted aryl. In yet another variation, a compound of the invention is of the formula (I), (Ia), (Ib), (Ic) or (C) or any variation thereof detailed herein, or a compound according to any one of the formulae (III-1)-(III-15), (IV-1)-(IV-9) or (V-1)-(V-27), where each $R^4$ is independently H or a substituted or unsubstituted $C_1$-$C_8$ alkyl. In still another variation, a compound of the invention is of the formula (I), (Ia), (Ib), (Ic) or (C) or any variation thereof detailed herein, or a compound according to any one of the formulae (III-1)-(III-15), (IV-1)-(IV-9) or (V-1)-(V-27), where each $R^4$ is H. The invention also embraces compounds of the formula (I), (Ia), (Ib), (Ic) or (C) or any variation thereof detailed herein, or a compound according to any one of the formulae (III-1)-(III-15), (IV-1)-(IV-9) or (V-1)-(V-27), where each $R^4$ is independently H, halo, unsubstituted $C_1$-$C_4$ alkyl, $C_1$-$C_4$ perhaloalkyl or a substituted or unsubstituted aryl. The invention further embraces compounds of the formula (I), (Ia), (Ib), (Ic) or (C) or any variation thereof detailed herein, or a compound according to any one of the formulae (III-1)-(III-15), (IV-1)-(IV-9) or (V-1)-(V-27) where each $R^4$ is independently H, halo, methyl, trifluoromethyl or cyclopropyl.

The invention also embraces compounds of the formula (I), (Ia), (Ib), (Ic) or (C) or any variation thereof detailed herein, or a compound according to any one of the formulae (II-1)-(II-8), (III-1)-(III-15), (IV-1)-(IV-9) or (V-1)-(V-27) where Q is a substituted or unsubstituted aryl, substituted or unsubstituted heteroaryl, which may be but is not limited to a substituted or unsubstituted pyridyl, phenyl, pyrimidinyl, pyrazinyl, imidazolyl, furanyl, pyrrolyl or thiophenyl group. In one variation, a compound of the invention is of the formula (I), (Ia), (Ib), (Ic) or (C) or any variation thereof detailed herein, or a compound according to any one of the formulae (II-1)-(II-8), (III-1)-(III-15), (IV-1)-(IV-9) or (V-1)-(V-27) where Q is a substituted or unsubstituted phenyl or pyridyl group. In a particular variation, Q is a phenyl or pyridyl group substituted with at least one methyl group. In another variation, a compound of the invention is of the formula (I), (Ia), (Ib), (Ic) or (C) or any variation thereof detailed herein, or a compound according to any one of the formulae (II-1)-(II-8), (III-1)-(III-15), (IV-1)-(IV-9) or (V-1)-(V-27) where Q is a pyridyl, phenyl, pyrimidinyl, pyrazinyl, imidazolyl, furanyl, pyrrolyl or thiophenyl group substituted with at least one substituted or unsubstituted $C_1$-$C_8$ alkyl, halo or perhaloalkyl moiety. In still another variation, a compound of the invention is of the formula (I), (Ia), (Ib), (Ic) or (C) or any variation thereof detailed herein, or a compound according to any one of the formulae (II-1)-(II-8), (III-1)-(III-15), (IV-1)-(IV-9) or (V-1)-(V-27) where Q is a substituted or unsubstituted cycloalkyl or a substituted or unsubstituted heterocyclyl. In yet another variation, a compound of the invention is of the formula (I), (Ia), (Ib), (Ic) or (C) or any variation thereof detailed herein, or a compound according to any one of the formulae (II-1)-(II-8), (III-1)-(III-15), (IV-1)-(IV-9) or (V-1)-(V-27) where Q is a substituted or unsubstituted pyridyl, phenyl, pyrazinyl, piperazinyl, pyrrolidinyl or thiomorpholinyl group. In a particular variation, Q is a pyridyl, phenyl, pyrazinyl, piperazinyl, pyrrolidinyl or thiomorpholinyl group substituted with at least one methyl or halo group. In one variation, a compound of the invention is of the formula (I), (Ia), (Ib), (Ic) or (C) or any variation thereof detailed herein, or a compound according to any one of the formulae (II-1)-(II-8), (III-1)-(III-15), (IV-1)-(IV-9) or (V-1)-(V-27) where Q is an unsubstituted cycloalkyl or an unsubstituted heterocyclyl. In another variation, a compound of the invention is of the formula (I), (Ia), (Ib), (Ic) or (C) or any variation thereof detailed herein, or a compound according to any one of the formulae (II-1)-(II-8), (III-1)-(III-15), (IV-1)-(IV-9) or (V-1)-(V-27) where Q is a substituted or unsubstituted cyclohexyl, morpholinyl, piperazinyl, thiomorpholinyl, cyclopentyl or pyrrolidinyl moiety. In yet another variation, a compound of the invention is of the formula (I), (Ia), (Ib), (Ic) or (C) or any variation thereof detailed herein or (Ie) or any variation of the foregoing detailed herein, or a compound according to any one of the formulae (II-1)-(II-8), (III-1)-(III-15), (IV-1)-(IV-9) or (V-1)-(V-27) where Q is a substituted cyclohexyl, morpholinyl, piperazinyl, thiomorpholinyl, cyclopentyl or pyrrolidinyl moiety substituted with at least one carbonyl, hydroxymethyl, methyl or hydroxyl group.

In another variation, the compound is of the formula (I), (Id), (II-1)-(II-8), (III-1)-(III-15), (IV-1)-(IV-9) or (V-1)-(V-27) wherein each m and q is 0. In another variation, the compound is of the formula (I), (Id), (II-1)-(II-8), (III-1)-(III-15), (IV-1)-(IV-9) or (V-1)-(V-27) wherein each m and q is 1. In another variation, the compound is of the formula (I), (Id), (II-1)-(II-8), (III-1)-(III-15), (IV-1)-(IV-9) or (V-1)-(V-27) wherein m=1 and q=0.

In another variation, the compound is of the formula (I), (Id), (II-1)-(II-8), (III-1)-(III-15), (IV-1)-(IV-9) or (V-1)-(V-27) or any applicable variation thereof, Q is a substituted or unsubstituted cycloalkyl, substituted or unsubstituted cycloalkenyl, or substituted or an unsubstituted heterocyclyl, or a salt or solvate thereof. In one variation, the compound is of the formula (I), (Id), (II-1)-(II-8), (III-1)-(III-15), (IV-1)-(IV-9) or (V-1)-(V-27) or any applicable variation thereof, Q is a carbocycle, such as a 5, 6 or 7 membered carbocycle. In one variation, the compound is of the formula (I), (Id), (II-1)-(II-8), (III-1)-(III-15), (IV-1)-(IV-9) or (V-1)-(V-27) or any applicable variation thereof, Q is a heterocycle, such as a 5, 6 or 7 membered carbocycle.

In another variation, the compound is of the formula (I), (Id), (II-1)-(II-8), (III-1)-(III-15), (IV-1)-(IV-9) or (V-1)-(V-27) or any applicable variation thereof, Q is substituted or unsubstituted aryl or a substituted or unsubstituted heteroaryl, or a salt or solvate thereof. In another variation, the compound is of the formula (I), (Id), (II-1)-(II-8), (III-1)-(III-15), (IV-1)-(IV-9) or (V-1)-(V-27) or any applicable variation thereof, Q is substituted or unsubstituted heteroaryl, such as a 5, 6 or 7 membered heteroaryl, or a salt or solvate thereof. In one variation, the compound is of the formula (I), (Id), (II-1)-(II-8), (III-1)-(III-15), (IV-1)-(IV-9) or (V-1)-(V-27) or any applicable variation thereof, Q is a substituted or unsubstituted aryl, such as a 5, 6 or 7 membered aryl, or a salt or solvate thereof.

Q groups may be attached to the parent structure at any available position on the Q moiety. Thus, although specific attachment points for certain Q moieties are depicted herein, it is understood that such Q moieties, may also be connected to the parent structure at any available position. For example, if a 2-fluoro-phenyl is depicted herein, it is understood that other mono-fluoro-phenyls are intended, e.g., 3-fluoro-phenyl and 4-fluoro-phenyl. It is also understood that any formula detailed herein, where applicable, may in one variation have a Q moiety as detailed herein.

In still another variation, a compound of the invention is of the formulae or any variation of the foregoing detailed herein, where Q is a moiety selected from the structures:

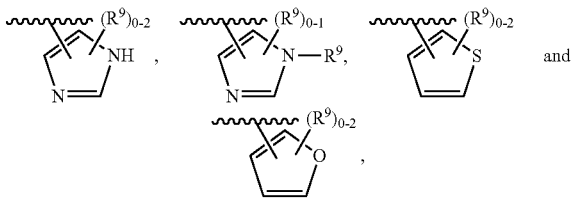

wherein each $R^9$ is independently a halo, cyano, nitro, perhaloalkyl, perhaloalkoxy, substituted or unsubstituted $C_1$-$C_8$ alkyl, substituted or unsubstituted $C_2$-$C_8$ alkenyl, substituted or unsubstituted $C_2$-$C_8$ alkynyl, acyl, acyloxy, carbonylalkoxy, thioalkyl, substituted or unsubstituted heterocyclyl, alkoxy, substituted or unsubstituted amino, acylamino, sulfonylamino, sulfonyl, carbonyl, aminoacyl or aminocarbonylamino. In one variation, Q is substituted with no more than one $R^9$ group. In another variation, Q is substituted with only one $R^9$ group. In one variation, Q is substituted with two $R^9$ groups. In a further variation, Q is selected from the aromatic structures detailed where the residue has the moiety $(R^9)_0$ such that Q either contains no $R^9$ functionality or a moiety of the formula N—$R^9$.

In still another variation, a compound of the invention is of the formula (I), (Ia), (Ib), (Ic) or (C) or any variation thereof detailed herein, or a compound according to any one of the formulae (II-1)-(II-8), (III-1)-(III-15), (IV-1)-(IV-9) or (V-1)-(V-27) where Q is a moiety selected from the structures:

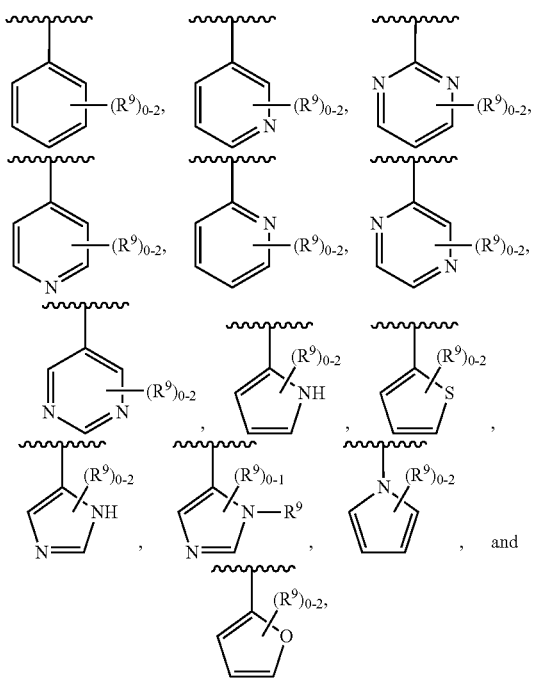

wherein each $R^9$ is independently a halo, cyano, nitro, perhaloalkyl, perhaloalkoxy, substituted or unsubstituted $C_1$-$C_8$ alkyl, substituted or unsubstituted $C_2$-$C_8$ alkenyl, substituted or unsubstituted $C_2$-$C_8$ alkynyl, acyl, acyloxy, carbonylalkoxy, thioalkyl, substituted or unsubstituted heterocyclyl, alkoxy, substituted or unsubstituted amino, acylamino, sulfonylamino, sulfonyl, carbonyl, aminoacyl or aminocarbonylamino. In one variation, Q is substituted with no more than one $R^9$ group. In another variation, Q is substituted with only one $R^9$ group. In one variation, Q is substituted with two $R^9$ groups. In a further variation, Q is selected from the aromatic structures detailed where the residue has the moiety $(R^9)_{0-2}$ such that Q either contains no $R^9$ functionality or a moiety of the formula N—$R^9$.

In another variation, a compound of the invention is of the formula (I), (Ia), (Ib), (Ic) or (C) or any variation thereof detailed herein, or a compound according to any one of the formulae (II-1)-(II-8), (III-1)-(III-15), (IV-1)-(IV-9) or (V-1)-(V-27) where Q is a moiety selected from the structures:

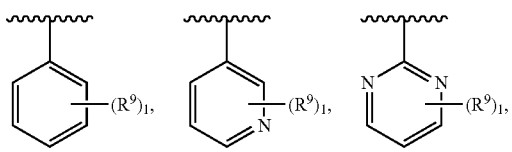

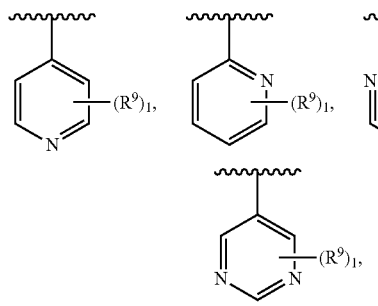

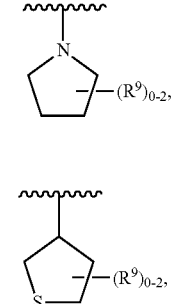

and wherein $R^9$ is connected to Q ortho or para to the position at which Q is connected to the carbon bearing $R^{8e}$ and $R^{8f}$. In a particular variation, Q is a structure of the formula:

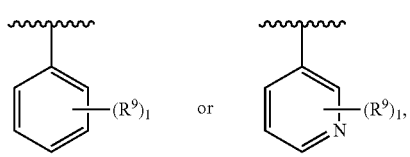

and $R^9$ is connected to Q para to the position at which Q is connected to the carbon bearing $R^{8e}$ and $R^{8f}$. In another particular variation, Q is a structure of the formula

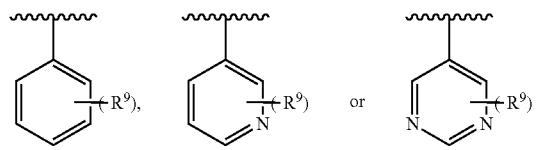

where each $R^9$ is independently alkyl, perhaloalkyl or halo.

In another variation, a compound of the invention is of the formula (I), (Ia), (Ib), (Ic) or (C) or any variation thereof detailed herein, or a compound according to any one of the formulae (II-1)-(II-8), (III-1)-(III-15), (IV-1)-(IV-9) or (V-1)-(V-27) where Q is a moiety selected from the structures:

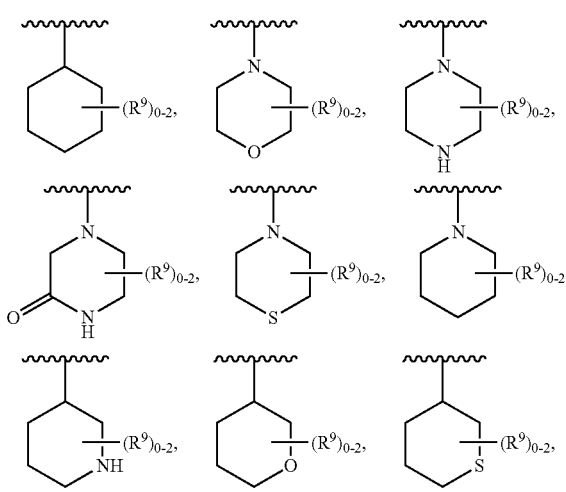

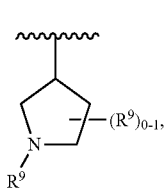

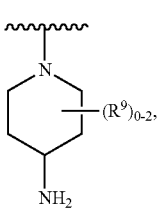

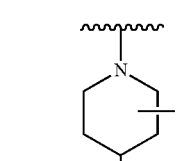

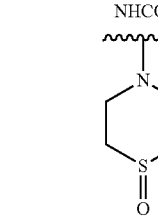

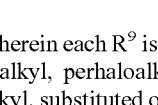

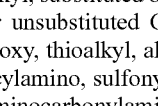

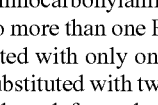

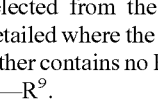

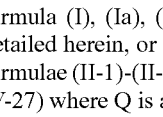

wherein each $R^9$ is independently a halo, cyano, nitro, perhaloalkyl, perhaloalkoxy, substituted or unsubstituted $C_1$-$C_8$ alkyl, substituted or unsubstituted $C_2$-$C_8$ alkenyl, substituted or unsubstituted $C_2$-$C_8$ alkynyl, acyl, acyloxy, carbonylalkoxy, thioalkyl, alkoxy, substituted or unsubstituted amino, acylamino, sulfonylamino, sulfonyl, carbonyl, aminoacyl or aminocarbonylamino. In one variation, Q is substituted with no more than one $R^9$ group. In another variation, Q is substituted with only one $R^9$ group. In yet another variation, Q is substituted with two $R^9$ groups. In a particular variation, Q is selected from the carbocyclic and heterocyclic structures detailed where the residue has the moiety $(R^9)_{0-2}$ such that Q either contains no $R^9$ functionality or a moiety of the formula N—$R^9$.

In another variation, a compound of the invention is of the formula (I), (Ia), (Ib), (Ic) or (C) or any variation thereof detailed herein, or a compound according to any one of the formulae (II-1)-(II-8), (III-1)-(III-15), (IV-1)-(IV-9) or (V-1)-(V-27) where Q is a moiety selected from the structures:

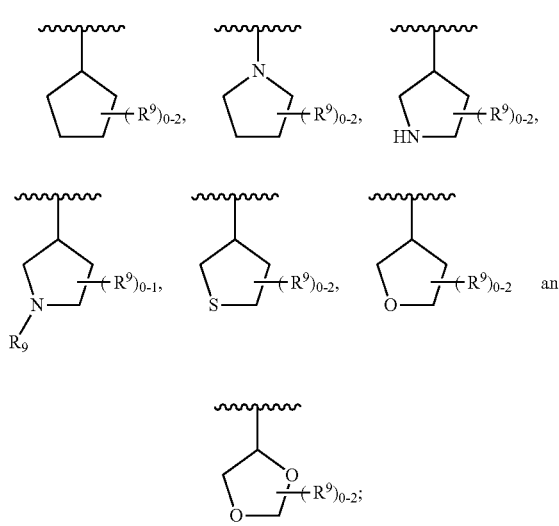

wherein each $R^9$ is independently a halo, cyano, nitro, perhaloalkyl, perhaloalkoxy, substituted or unsubstituted $C_1$-$C_8$ alkyl, substituted or unsubstituted $C_2$-$C_8$ alkenyl, substituted or unsubstituted $C_2$-$C_8$ alkynyl, acyl, acyloxy, carbonylalkoxy, thioalkyl, alkoxy, substituted or unsubstituted amino, acylamino, sulfonylamino, sulfonyl, carbonyl, aminoacyl or aminocarbonylamino. In one variation, Q is substituted with no more than one $R^9$ group. In another variation, Q is substituted with only one $R^9$ group. In yet another variation, Q is substituted with two $R^9$ groups. In a particular variation, Q is selected from the carbocyclic and heterocyclic structures detailed where the residue has the moiety $(R^9)_{0-2}$ such that Q either contains no $R^9$ functionality or a moiety of the formula N—$R^9$.

In any structure or variation detailed herein containing an $R^9$ group, in one variation, each $R^9$ is independently a substituted or unsubstituted $C_1$-$C_4$ alkyl, halo, trifluoromethyl or hydroxyl. In another variation, each $R^9$ is independently methyl, —$CH_2OH$, isopropyl, halo, trifluoromethyl or hydroxyl.

In one variation, a compound of the invention is of the formula (I), (Ia), (Ib), (Ic) or (C) or any variation thereof detailed herein, or a compound according to any one of the formulae (II-1)-(II-8), (III-1)-(III-15), (IV-1)-(IV-9) or (V-1)-(V-27) where Q is a moiety selected from the structures:

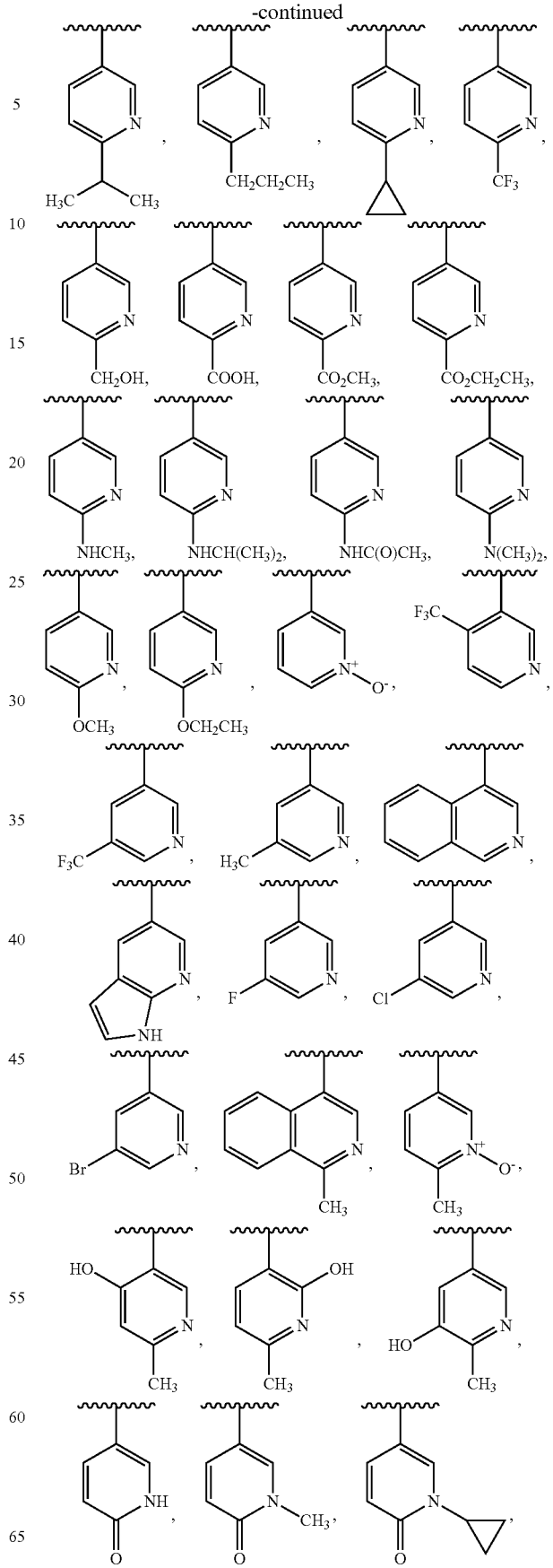

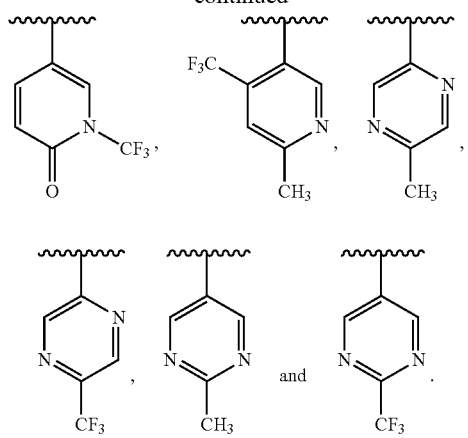

In another variation, a compound of the invention is of the formula (I), (Ia), (Ib), (Ic) or (C) or any variation thereof detailed herein, or a compound according to any one of the formulae (II-1)-(II-8), (III-1)-(III-15), (IV-1)-(IV-9) or (V-1)-(V-27) where Q is a moiety selected from the structures:

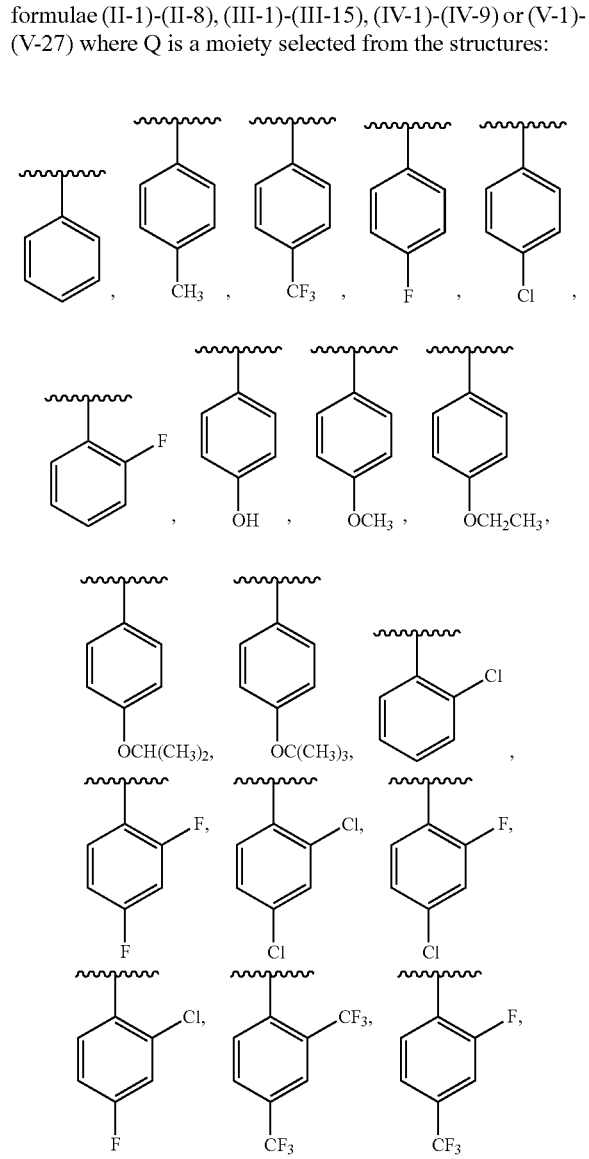

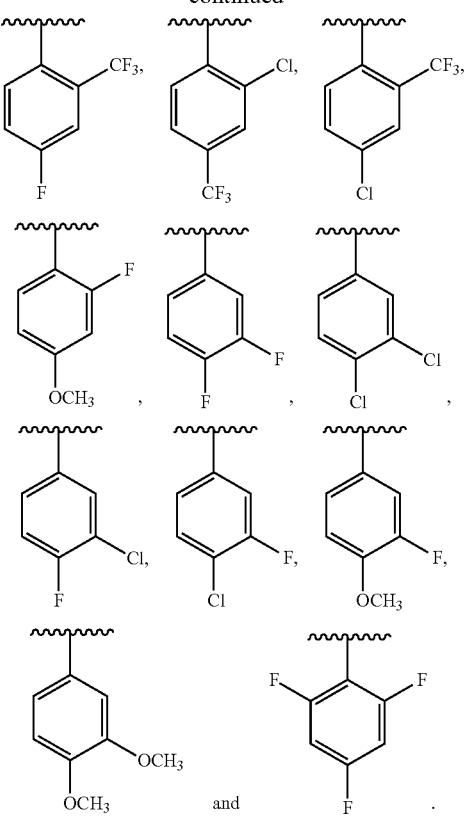

In yet another variation, a compound of the invention is of the formula (I), (Ia), (Ib), (Ic) or (C) or any variation thereof detailed herein, or a compound according to any one of the formulae (II-1)-(II-8), (III-1)-(III-15), (IV-1)-(IV-9) or (V-1)-(V-27) where Q is a moiety selected from the structures:

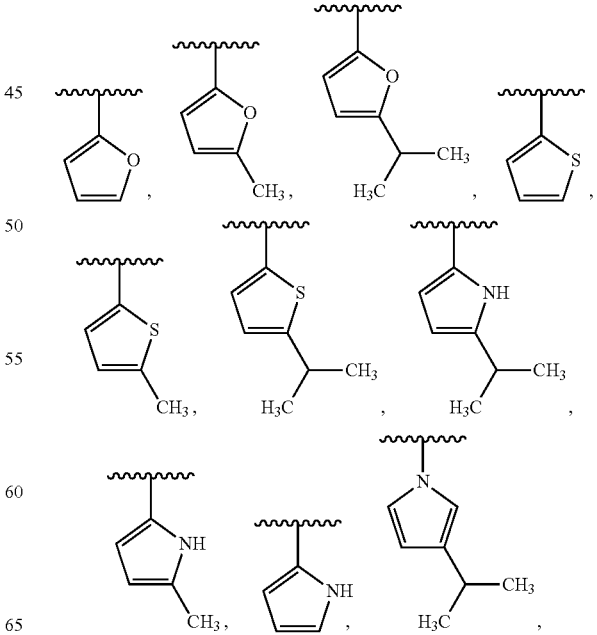

-continued

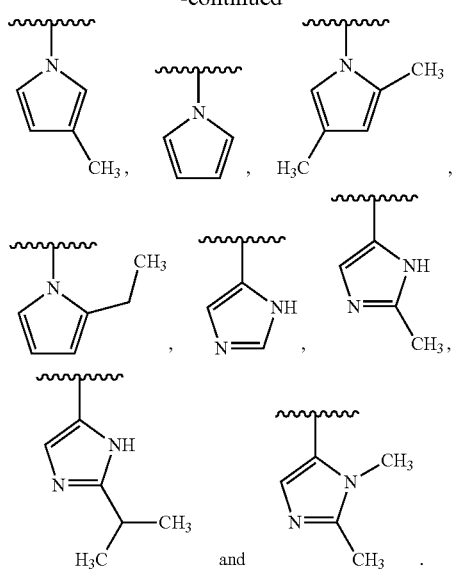

In one variation, a compound of the invention is of the formula (I), (Ia), (Ib), (Ic) or (C) or any variation thereof detailed herein, or a compound according to any one of the formula (I), (Id), (II-1)-(II-8), (III-1)-(III-15), (IV-1)-(IV-9) or (V-1)-(V-27) where Q is a moiety selected from the structures:

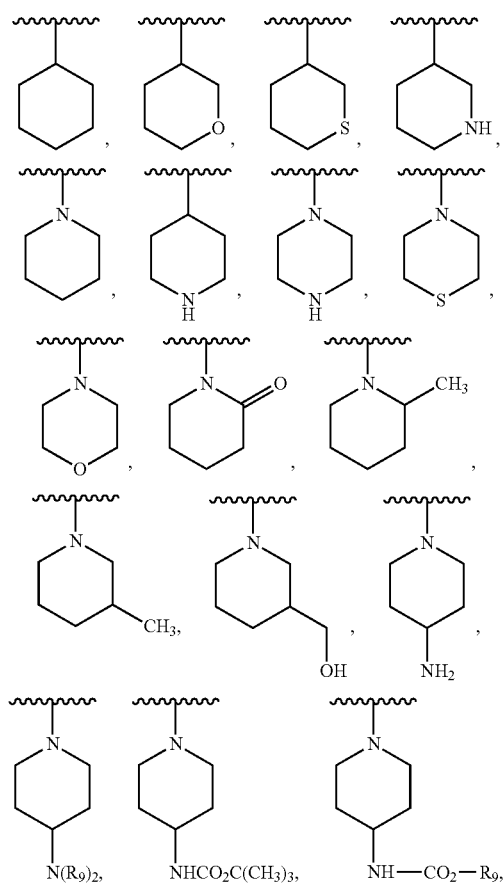

-continued

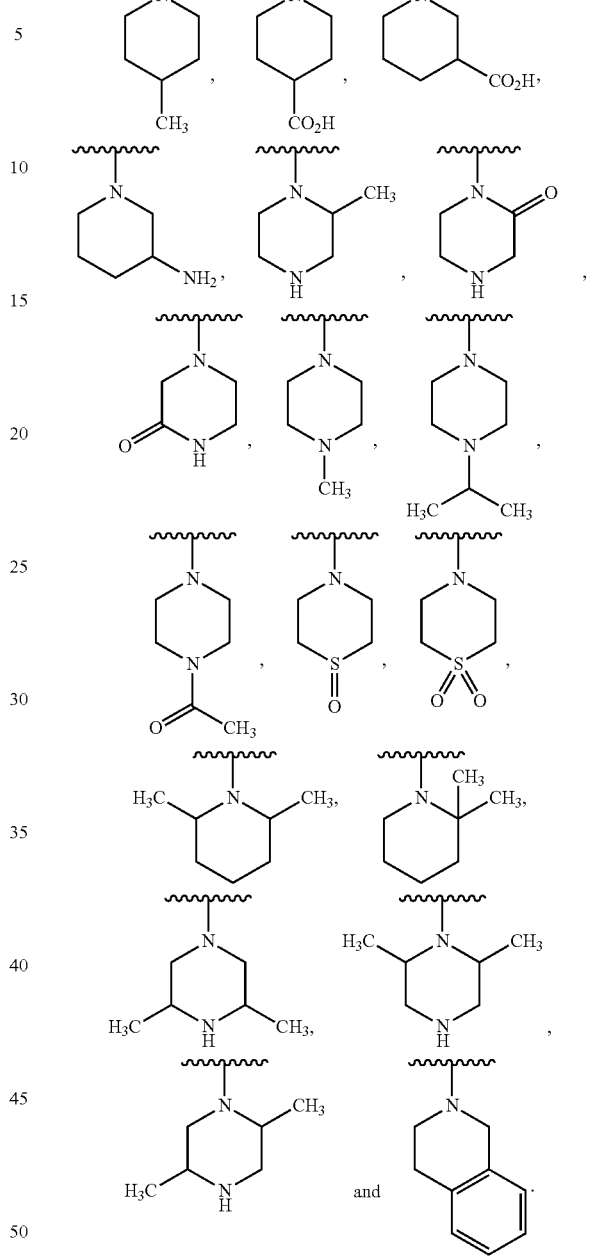

In another variation, a compound of the invention is of the formula (I), (Ia), (Ib), (Ic) or (C) or any variation thereof detailed herein, or a compound according to any one of the formula (I), (Id), (II-1)-(II-8), (III-1)-(III-15), (IV-1)-(IV-9) or (V-1)-(V-27) where Q is a moiety selected from the structures:

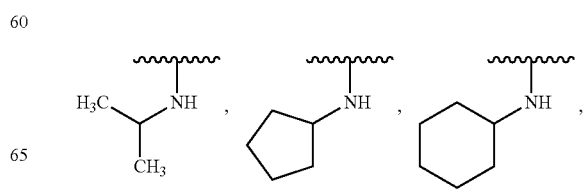

-continued

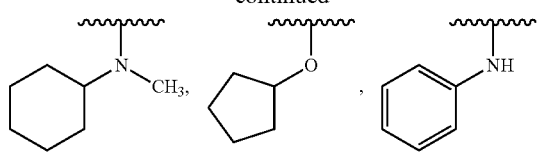

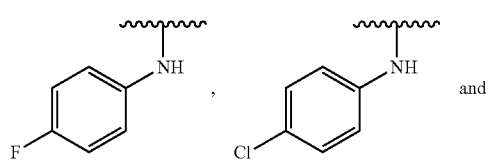

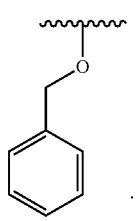

In yet another variation, a compound of the invention is of the formula (I), (Ia), (Ib), (Ic) or (C) or any variation thereof detailed herein, or a compound according to any one of the formula (I), (Id), (II-1)-(II-8), (III-1)-(III-15), (IV-1)-(IV-9) or (V-1)-(V-27) where Q is a moiety selected from the structures:

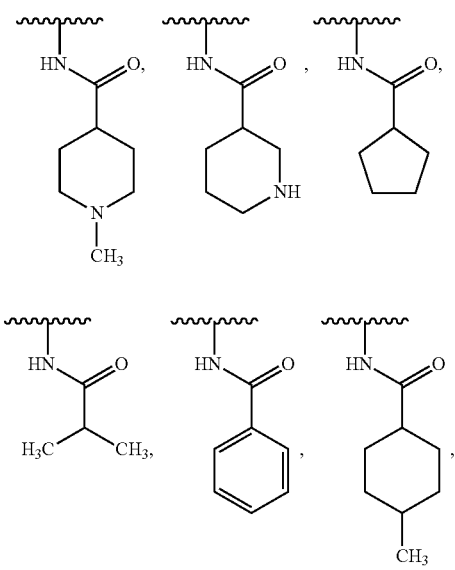

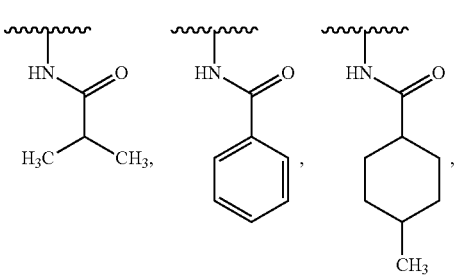

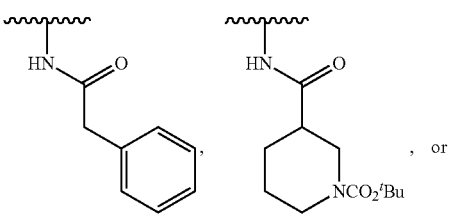

-continued

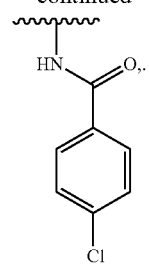

In yet another variation, a compound of the invention is of the formula (I), (Ia), (Ib), (Ic) or (C) or any variation thereof detailed herein, or a compound according to any one of the formula (I), (Id), (II-1)-(II-8), (III-1)-(III-15), (IV-1)-(IV-9) or (V-1)-(V-27) where Q is a moiety selected from the structures:

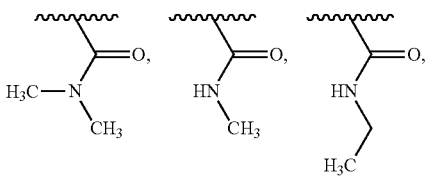

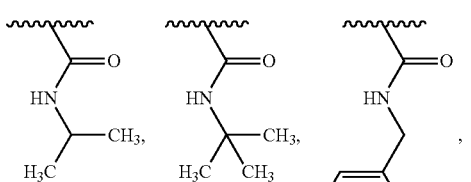

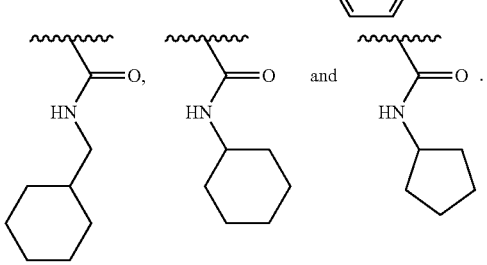

In yet another variation, a compound of the invention is of the formula (I), (Ia), (Ib), (Ic) or (C) or any variation thereof detailed herein, or a compound according to any one of the formula (I), (Id), (II-1)-(II-8), (III-1)-(III-15), (IV-1)-(IV-9) or (V-1)-(V-27) where Q is a moiety selected from the structures:

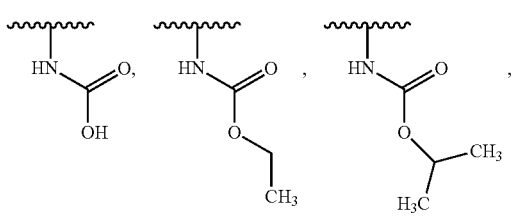

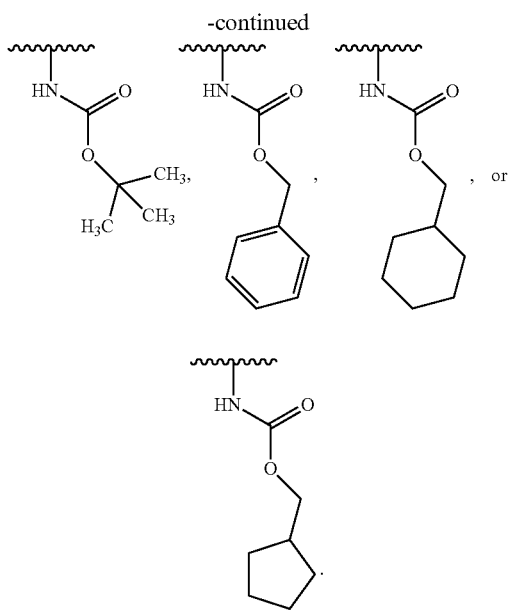

In a further variation, a compound of the invention is of the formula (I), (Ia), (Ib) or (Ic) or any variation thereof detailed herein where $R^1$ is an unsubstituted alkyl, $R^{2a}$, $R^{2b}$, $R^{3a}$, $R^{3b}$, $R^{10a}$, $R^{10b}$, $R^{11a}$ and $R^{11b}$ are each H, each $X^7$, $X^8$, $X^9$ and $X^{10}$ is independently N or CH, each $R^{8a}$, $R^{8b}$, $R^{8c}$, $R^{8d}$, $R^{8e}$ and $R^{8f}$ is independently H or hydroxyl, and Q is a substituted or unsubstituted aryl, substituted or unsubstituted heteroaryl, including but not limited to a substituted or unsubstituted phenyl or pyridyl group. Where Q is a substituted phenyl or pyridyl group, in one variation it is substituted with at least one methyl group.

In one variation, compounds of the formulae detailed herein are provided, such as compounds of the formulae (I), (Ia), (Ib), (Ic) or (C) or any variation thereof detailed herein, where $R^1$ is selected from the following moieties:

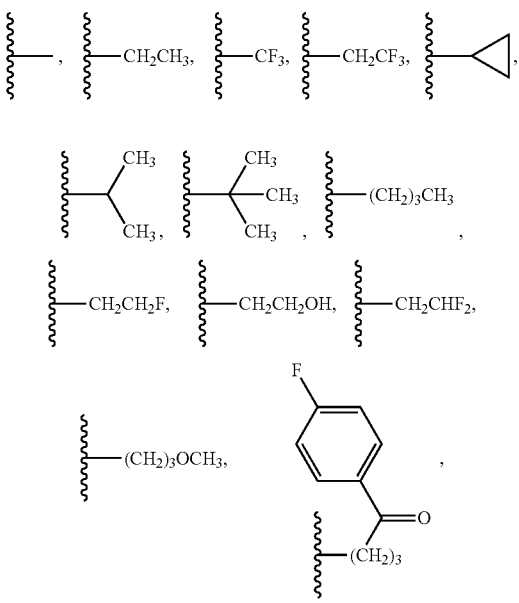

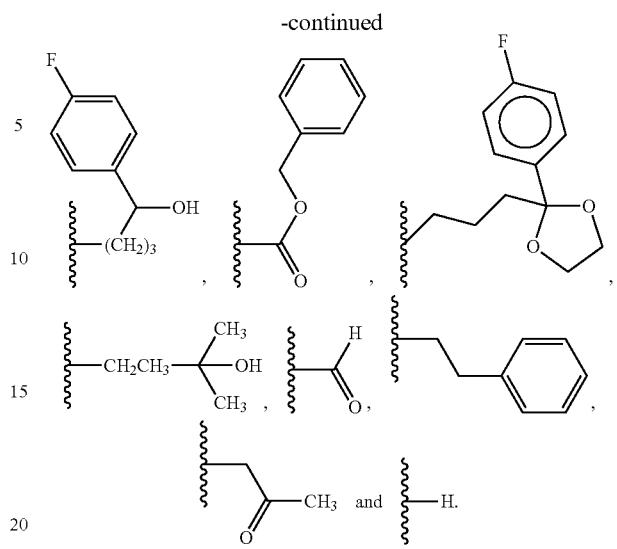

In yet a further variation, a compound of the invention is of the formula (I), (Ia), (Ib), (Ic) or (C) or any variation thereof detailed herein where $R^1$ is a substituted or unsubstituted $C_1$-$C_8$ alkyl, acyl, acyloxy, carbonylalkoxy, substituted or unsubstituted heterocyclyl, substituted or unsubstituted aryl; each $R^{2a}$ and $R^{2b}$ is independently H, unsubstituted $C_1$-$C_8$ alkyl or halo; each $R^{3a}$ and $R^{3b}$ is independently H or halo; each $X^7$, $X^8$, $X^9$ and $X^{10}$ is $CR^4$, where $R^4$ is as defined in formula (I), (Ia), (Ib), (Ic) or (C) or any variation thereof detailed herein or in a particular variation, $R^4$ is H, halo, pyridyl, methyl or trifluoromethyl; each $R^{10a}$, $R^{10b}$, $R^{11a}$ and $R^{11b}$ is independently H, unsubstituted $C_1$-$C_8$ alkyl, and Q is a substituted or unsubstituted aryl, substituted or unsubstituted heteroaryl, including but not limited to a substituted or unsubstituted pyridyl, phenyl, pyrimidinyl, pyrazinyl, imidazolyl, furanyl, pyrrolyl or thiophenyl group. In a particular variation, Q is a pyridyl, phenyl, pyrimidinyl, pyrazinyl, imidazolyl, furanyl, pyrrolyl or thiophenyl group substituted with at least one substituted or unsubstituted $C_1$-$C_8$ alkyl, halo or perhaloalkyl moiety. In one variation, a compound of the variation detailed herein is provided wherein $R^1$ is propylate, methyl, ethyl, cyclopropyl, trifluoromethyl, isopropyl, tert-butyl, sec-butyl, 2-methylbutyl, propanal, 1-methyl-2-hydroxyethyl, 2-hydroxyethanal, 2-hydroxyethyl, 2-hydroxypropyl, 2-hydroxy-2-methylpropyl, cyclobutyl, cyclopentyl, cyclohexyl, substituted phenyl, piperidin-4-yl, hydroxycyclopent-3-yl, hydroxycyclopent-2-yl, hydroxycycloprop-2-yl, 1-hydroxy-1-methylcycloprop-2-yl, or 1-hydroxy-1,2,2-trimethyl-cycloprop-3-yl.

In still a further variation, a compound of the invention is of the formula (I), (Ia), (Ib) or (Ic) or any variation thereof detailed herein where $R^1$ is a substituted or unsubstituted $C_1$-$C_8$ alkyl; each $R^{2a}$, $R^{2b}$, $R^{3a}$ and $R^{3b}$ is independently H or halo; each $R^4$ is independently H, halo, $C_1$-$C_8$ perhaloalkyl, substituted or a unsubstituted $C_1$-$C_8$ alkyl; each $R^{8a}$, $R^{8b}$, $R^{8c}$, $R^{8d}$, $R^{8e}$ and $R^{8f}$ is H; and Q is a substituted or unsubstituted cyclohexyl, morpholinyl, piperazinyl, thiomorpholinyl, cyclopentyl or pyrrolidinyl moiety. The invention also embraces a compound of the formula (I), (Ia), (Ib), (Ic) or (C) or any variation thereof detailed herein where $R^1$ is a methyl; at least one of $X^7$, $X^8$, $X^9$ and $X^{10}$ is $CR^4$, and each $R^4$ is independently H, halo, methyl or trifluoromethyl. The invention embraces compounds where Q in any variation detailed is substituted with at least one carbonyl, hydroxymethyl, methyl or hydroxyl group.

In a particular variation, the compound is of the formula (I), (Ia), (Ib) or (Ic) or any variation thereof detailed herein where $R^1$ is a substituted or unsubstituted $C_1$-$C_8$ alkyl; each $R^{2a}$, $R^{2b}$, $R^{3a}$ and $R^{3b}$ is H; each $R^4$ is independently H, halo or substituted or unsubstituted $C_1$-$C_8$ alkyl; each $R^{8a}$, $R^{8b}$, $R^{8c}$, $R^{8d}$, $R^{8e}$ and $R^{8f}$ is H; each $R^{10a}$, $R^{10b}$, $R^{11a}$ and $R^{11b}$ is independently H, unsubstituted $C_1$-$C_8$ alkyl, fluoro or $R^{10a}$ and $R^{10b}$ are taken together to form a carbonyl or $R^{11a}$ and $R^{11b}$ are taken together to form a carbonyl. In one aspect of this variation, Q may be a substituted or unsubstituted pyridyl, phenyl, pyrazinyl, piperazinyl, pyrrolidinyl or thiomorpholinyl group. In another aspect of this variation, Q is a pyridyl, phenyl, pyrazinyl, piperazinyl, pyrrolidinyl or thiomorpholinyl group substituted with at least one methyl or halo group. In another aspect of this variation, Q is a substituted amino, alkoxy or substituted alkoxy. In yet another aspect of this variation, $X^7$, $X^8$, $X^9$ and $X^{10}$ are $CR^4$ and each $R^4$ is independently H, halo or methyl.

Examples of compounds according to the invention are depicted in Table 2. The compounds depicted may be present as salts even if salts are not depicted and it is understood that the invention embraces all salts and solvates of the compounds depicted here, as well as the non-salt and non-solvate form of the compound, as is well understood by the skilled artisan.

TABLE 2

Representative Compounds According to the Invention.

| No. | Structure |
|---|---|
| 1 | 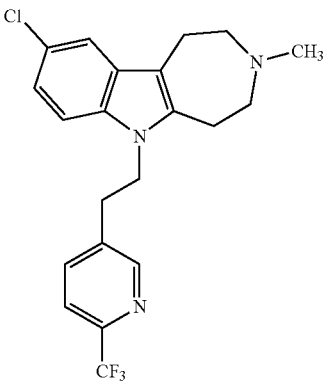 |
| 2 | 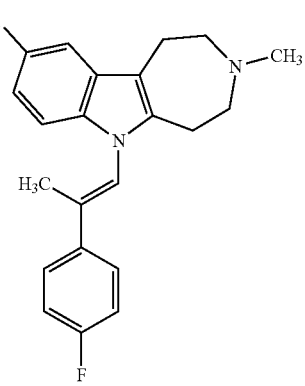 |
| 3 | 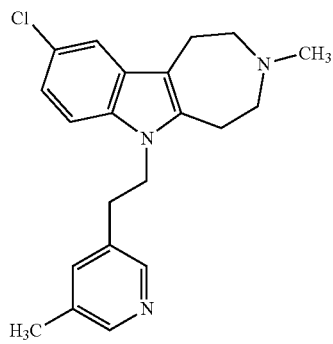 |
| 4 | 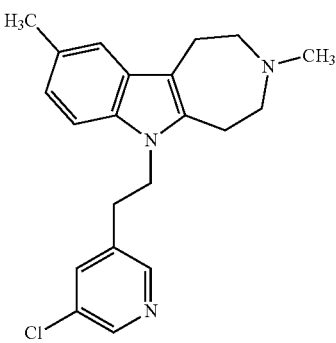 |
| 5 | 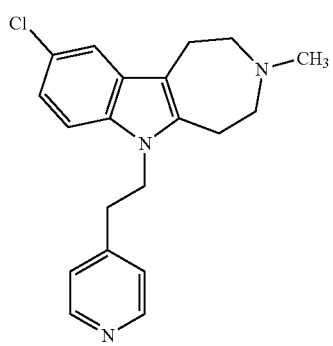 |
| 6 | 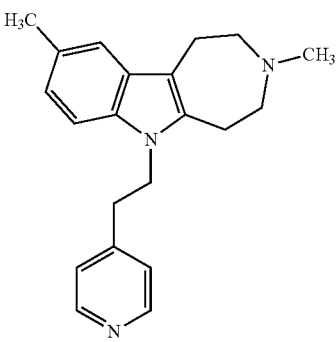 |

TABLE 2-continued

Representative Compounds According to the Invention.

| No. | Structure |
|---|---|
| 7 | (structure) |
| 8 | (structure) |
| 9 | (structure) |
| 10 | (structure) |
| 11 | (structure) |
| 12 | (structure) |
| 13 | (structure) |
| 14 | (structure) |

TABLE 2-continued
Representative Compounds According to the Invention.
| No. | Structure |
|---|---|
| 15 | 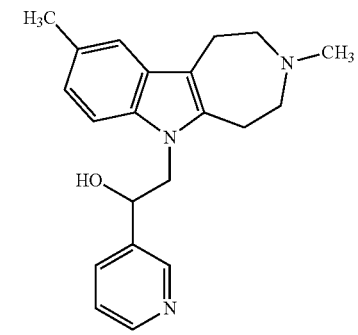 |
| 16 | 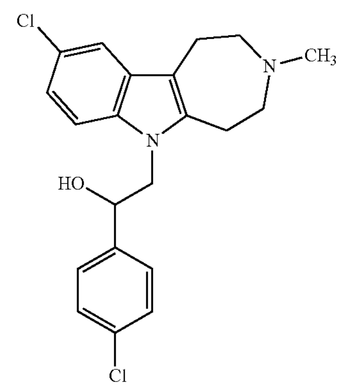 |
| 17 | 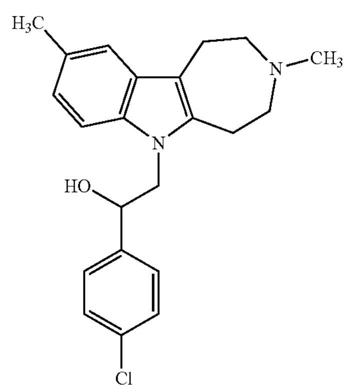 |
| 18 | 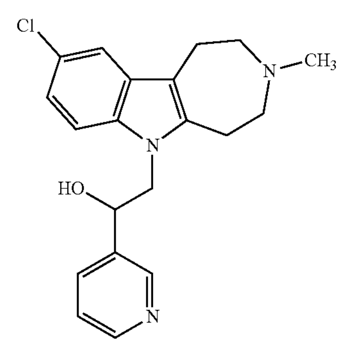 |
| 19 | 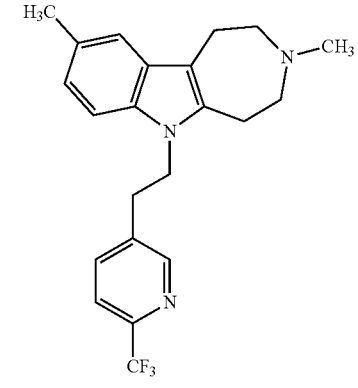 |
| 20 | |
| 21 | |
| 22 | |

TABLE 2-continued

Representative Compounds According to the Invention.

| No. | Structure |
|-----|-----------|
| 23 | (3-methyl-indole fused azepine N-CH3; N-CH2-CH(OH)- linked to 6-methylpyridin-3-yl) |
| 24 | (3-chloro-indole fused azepine N-CH3; N-CH2-CH(OH)-phenyl) |
| 25 | (3-methyl-indole fused azepine N-CH3; N-CH2-CH(OH)-phenyl) |
| 26 | (3-chloro-indole fused azepine N-CH3; N-CH2-CH(OH)-(4-methylphenyl)) |
| 27 | (3-methyl-indole fused azepine N-CH3; N-CH2-CH(OH)-(4-methylphenyl)) |
| 28 | (3-methyl-indole fused azepine N-CH3; N-CH2CH2-(4-chlorophenyl)) |
| 29 | (3-chloro-indole fused azepine N-CH3; N-CH2CH2-(2-chlorophenyl)) |
| 30 | (3-chloro-indole fused azepine N-CH3; N-CH2CH2-(4-chlorophenyl)) |

TABLE 2-continued
Representative Compounds According to the Invention.
| No. | Structure |
|---|---|
| 31 | 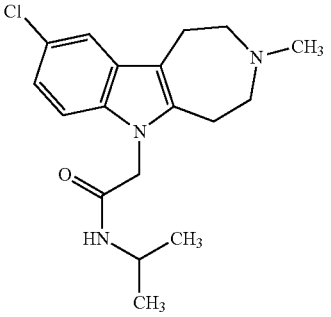 |
| 32 | 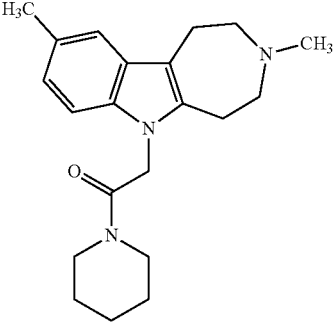 |
| 33 | 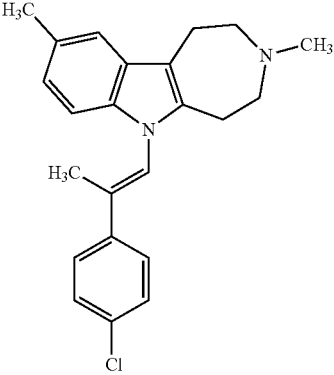 |
| 34 | 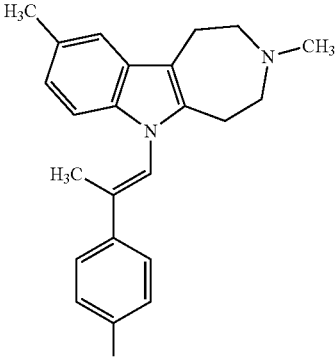 |
| 35 | 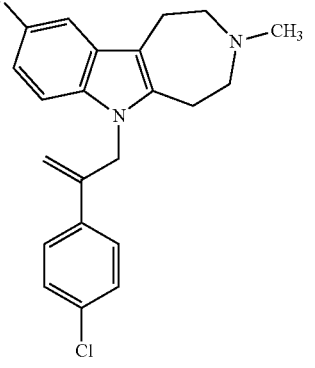 |
| 36 | 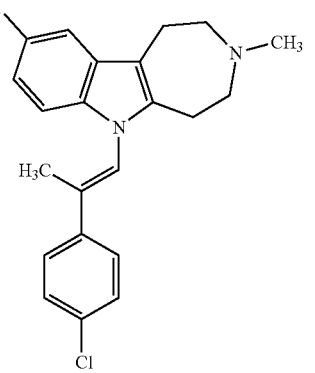 |
| 37 | 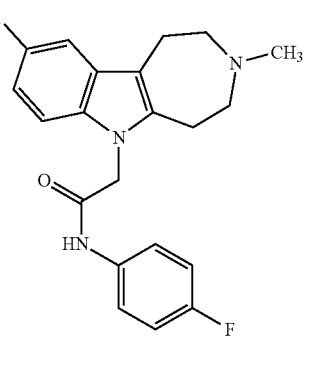 |
| 38 | 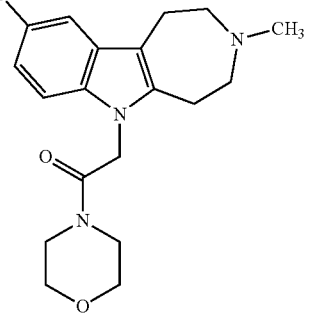 |

TABLE 2-continued

Representative Compounds According to the Invention.

| No. | Structure |
|---|---|
| 39 | 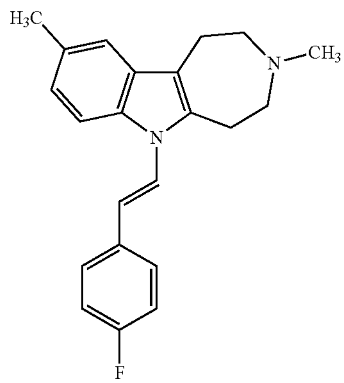 |
| 40 | 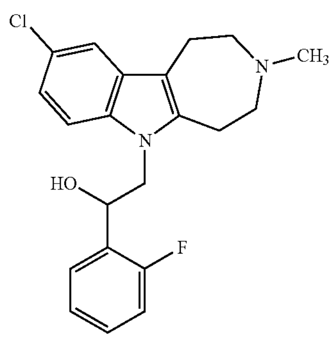 |
| 41 | 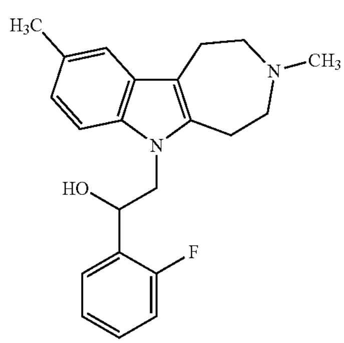 |
| 42 | 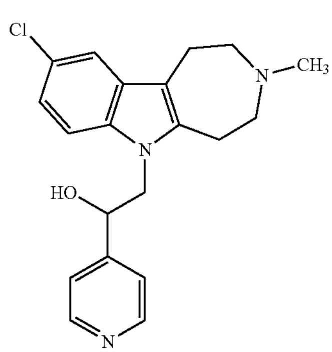 |
| 43 | |
| 44 | |
| 45 | |
| 46 | |

TABLE 2-continued

Representative Compounds According to the Invention.

| No. | Structure |
|---|---|
| 47 | (Cl-substituted tetracyclic indole-azepine with N-CH3, N-CH2-CH(OH)-phenyl-OCH3) |
| 48 | (H3C-substituted tetracyclic indole-azepine with N-CH3, N-CH2-CH(OH)-phenyl-OCH3) |
| 49 | (Cl-substituted tetracyclic indole-azepine with N-CH3, N-CH2-CH(OH)-phenyl with F and OCH3) |
| 50 | (H3C-substituted tetracyclic indole-azepine with N-CH3, N-CH2-CH(OH)-phenyl with F and OCH3) |
| 51 | (Cl-substituted tetracyclic indole-azepine with N-CH3, N-CH2-CH(OH)-phenyl-F) |
| 52 | (H3C-substituted tetracyclic indole-azepine with N-CH3, N-CH2-CH(OH)-phenyl-F) |
| 53 | (Cl-substituted tetracyclic indole-azepine with N-CH3, N-CH2-C(O)-pyrrolidine) |
| 54 | (H3C-substituted tetracyclic indole-azepine with N-CH3, N-CH2-C(O)-NH-CH(CH3)2) |

TABLE 2-continued
Representative Compounds According to the Invention.
| No. | Structure |
|---|---|
| 55 | 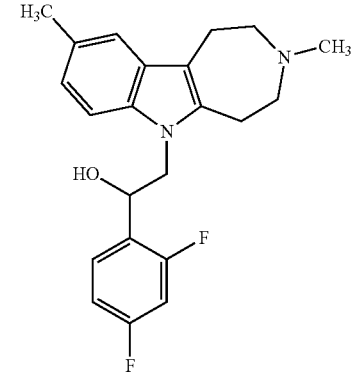 |
| 56 | 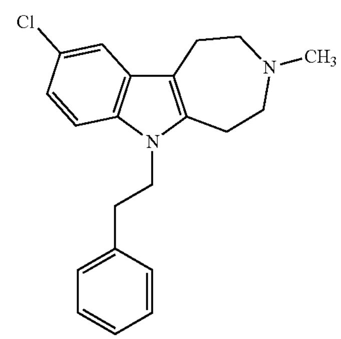 |
| 57 | 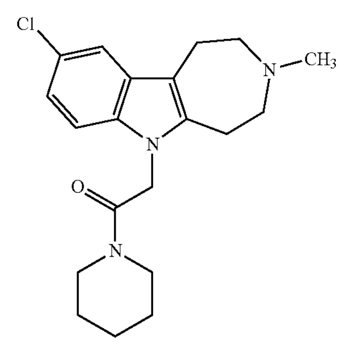 |
| 58 | 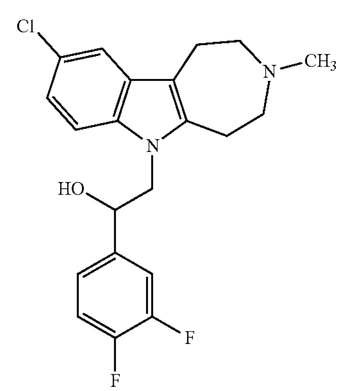 |
| 59 | 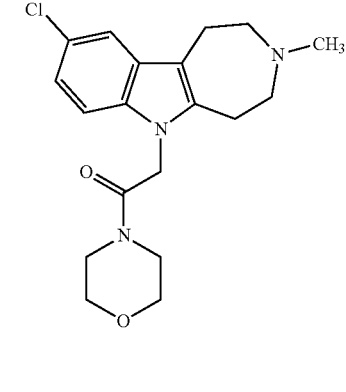 |
| 60 | |
| 61 | |
| 62 | |

TABLE 2-continued
Representative Compounds According to the Invention.
| No. | Structure |
|---|---|
| 63 | 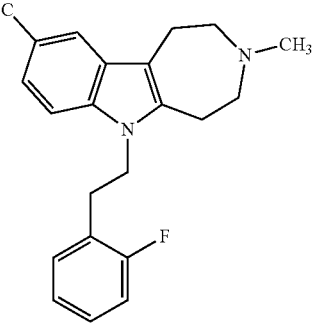 |
| 64 | 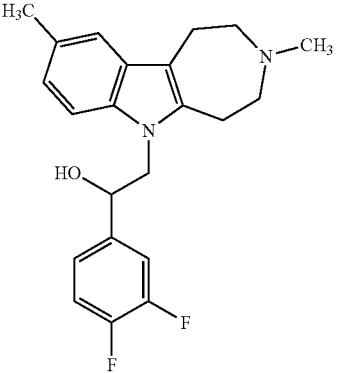 |
| 65 | 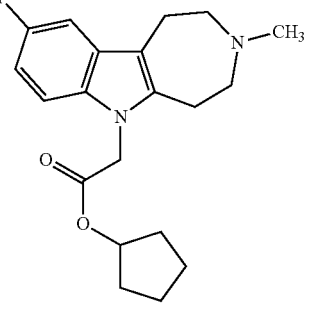 |
| 66 | 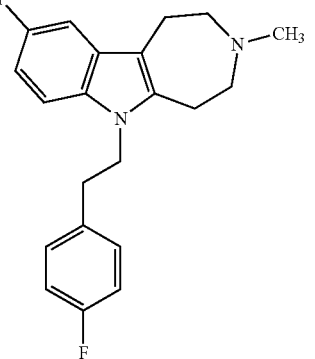 |
| 67 | 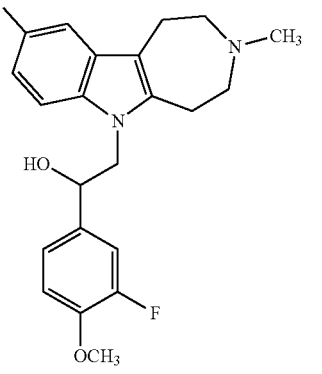 |
| 68 | 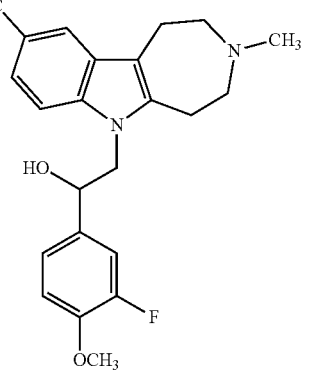 |
| 69 | 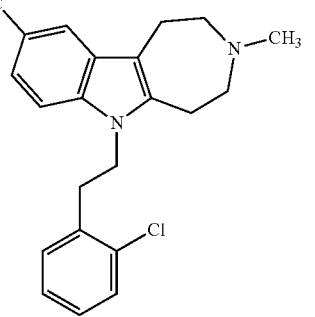 |
| 70 | 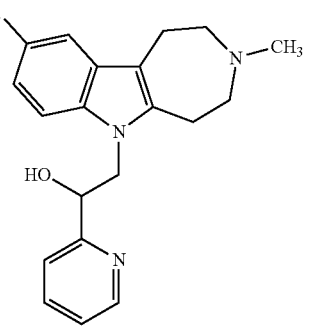 |

TABLE 2-continued
Representative Compounds According to the Invention.
| No. | Structure |
|---|---|
| 71 | 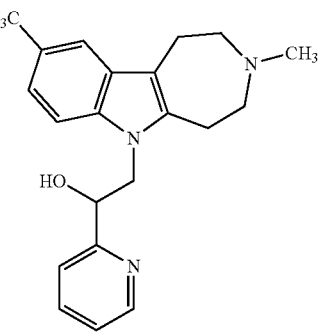 |
| 72 | 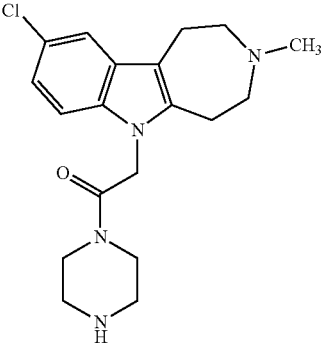 |
| 73 | 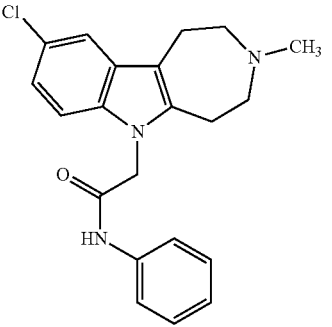 |
| 74 | 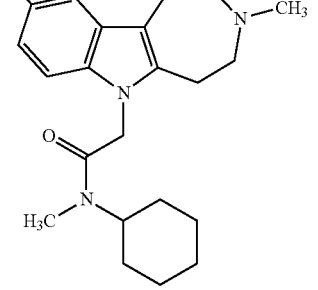 |
| 75 | 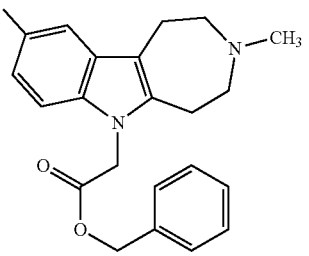 |
| 76 | 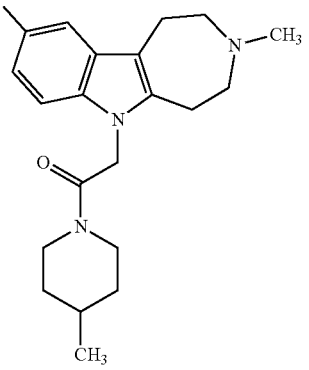 |
| 77 | 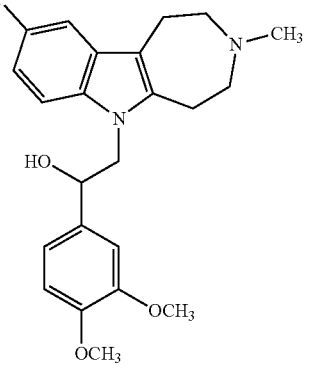 |
| 78 | 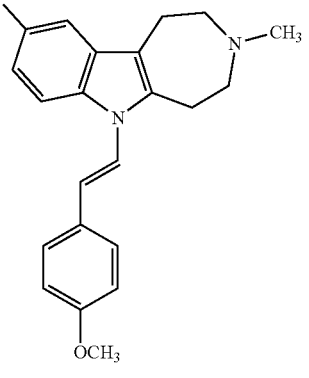 |

TABLE 2-continued
Representative Compounds According to the Invention.
| No. | Structure |
|---|---|
| 79 | 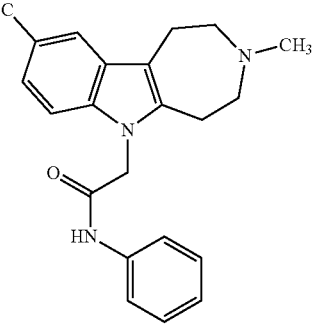 |
| 80 | 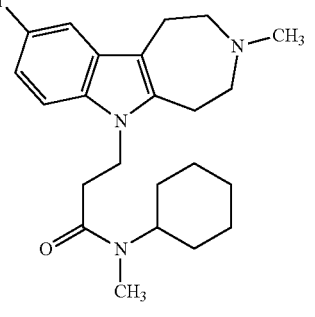 |
| 81 | 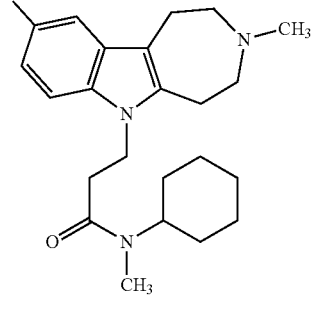 |
| 82 | 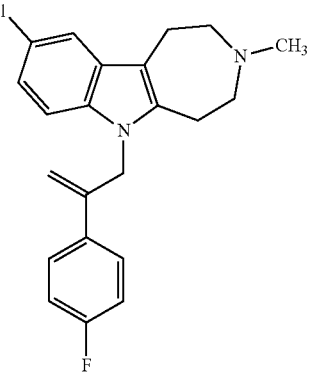 |
| 83 | 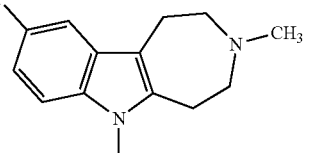 |
| 84 | 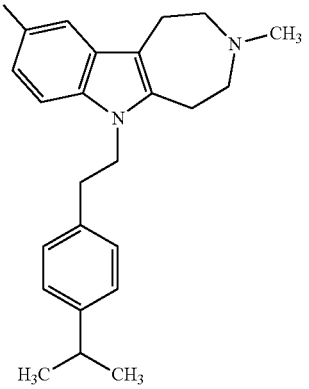 |
| 85 | 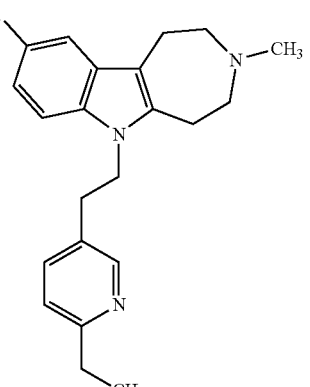 |
| 86 | 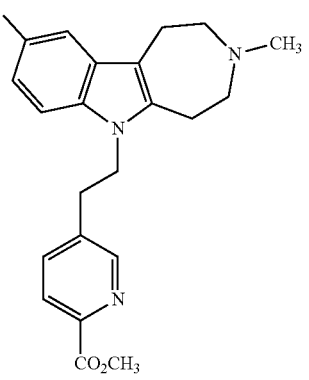 |

TABLE 2-continued

Representative Compounds According to the Invention.

| No. | Structure |
|---|---|
| 87 | (structure) |
| 88 | (structure) |
| 89 | (structure) |
| 90 | (structure) |
| 91 | (structure) |
| 92 | (structure) |
| 93 | (structure) |
| 94 | (structure) |

TABLE 2-continued
Representative Compounds According to the Invention.
| No. | Structure |
|---|---|
| 95 | 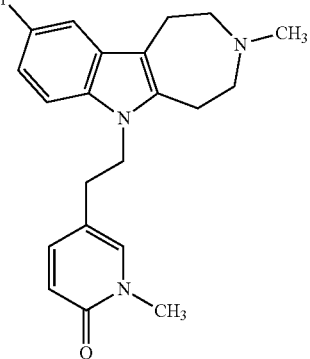 |
| 96 | 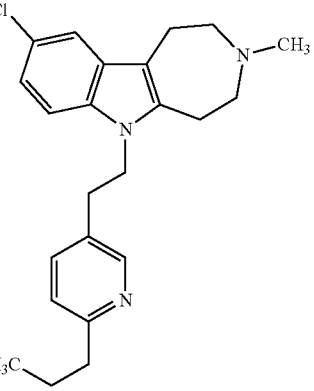 |
| 97 | 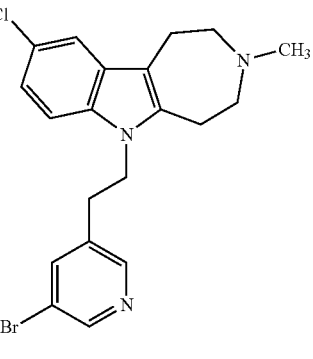 |
| 98 | 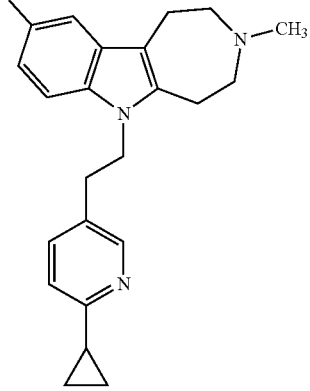 |
| 99 | 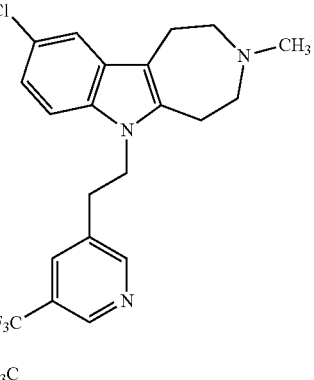 |
| 100 | 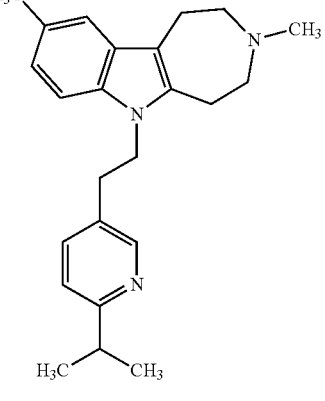 |
| 101 | 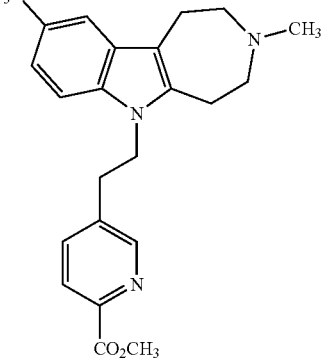 |
| 102 | 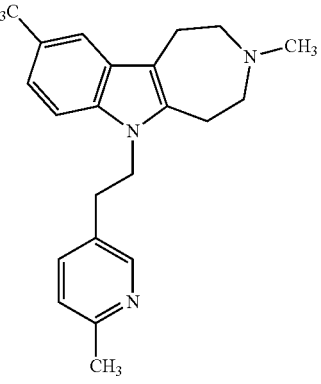 |

TABLE 2-continued

Representative Compounds According to the Invention.

| No. | Structure |
|-----|-----------|
| 103 | (structure) |
| 104 | (structure) |
| 105 | (structure) |
| 106 | (structure) |
| 107 | (structure) |
| 108 | (structure) |
| 109 | (structure) |
| 110 | (structure) |

TABLE 2-continued

Representative Compounds According to the Invention.

| No. | Structure |
|-----|-----------|
| 111 | 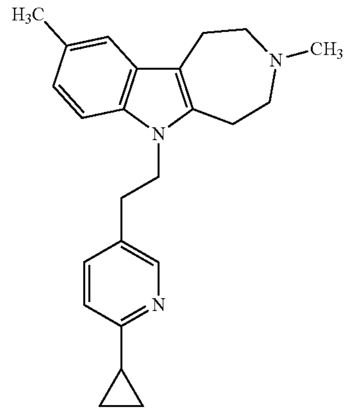 |
| 112 | 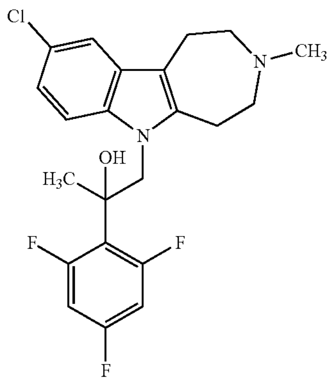 |
| 113 | 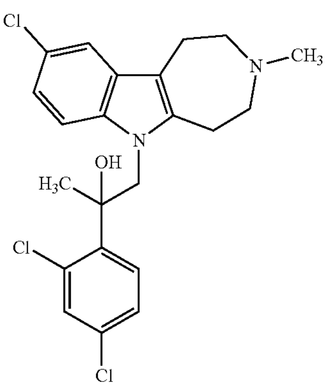 |
| 114 | 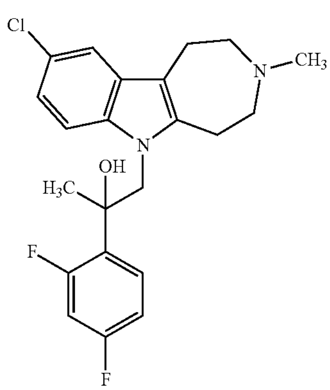 |
| 115 | |
| 116 | |
| 117 | |
| 118 | |

TABLE 2-continued
Representative Compounds According to the Invention.
| No. | Structure |
|---|---|
| 119 | 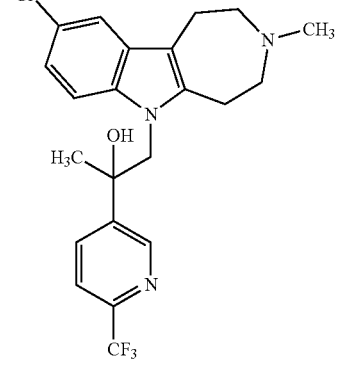 |
| 120 | 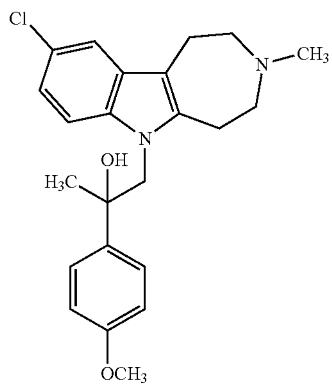 |
| 121 | 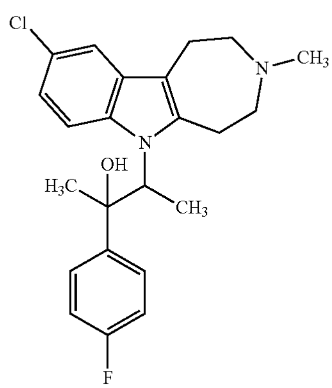 |
| 122 | 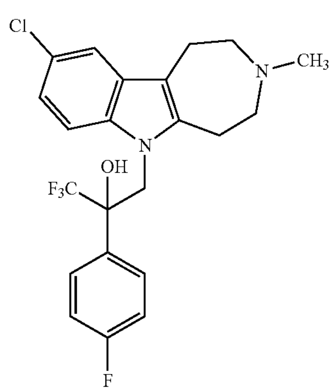 |
| 123 | 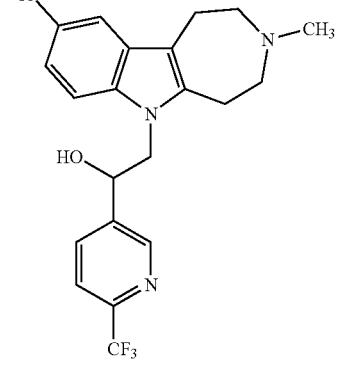 |
| 124 | |
| 125 | |
| 126 | |

TABLE 2-continued

Representative Compounds According to the Invention.

| No. | Structure |
|---|---|
| 127 | (structure) |
| 128 | (structure) |
| 129 | (structure) |
| 130 | (structure) |
| 131 | (structure) |
| 132 | (structure) |
| 133 | (structure) |
| 134 | (structure) |

TABLE 2-continued

Representative Compounds According to the Invention.

| No. | Structure |
|---|---|
| 135 | (structure) |
| 136 | (structure) |
| 137 | (structure) |
| 138 | (structure) |
| 139 | (structure) |
| 140 | (structure) |
| 141 | (structure) |
| 142 | (structure) |

TABLE 2-continued

Representative Compounds According to the Invention.

| No. | Structure |
|---|---|
| 143 | (structure) |
| 144 | (structure) |
| 145 | (structure) |
| 146 | (structure) |
| 147 | (structure) |
| 148 | (structure) |
| 149 | (structure) |
| 150 | (structure) |

TABLE 2-continued

Representative Compounds According to the Invention.

| No. | Structure |
|-----|-----------|
| 151 | 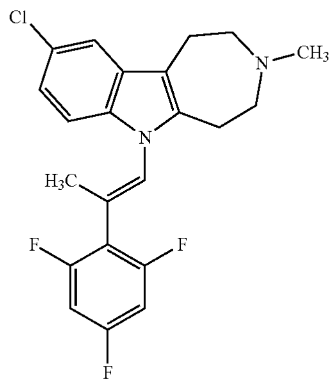 |
| 152 | 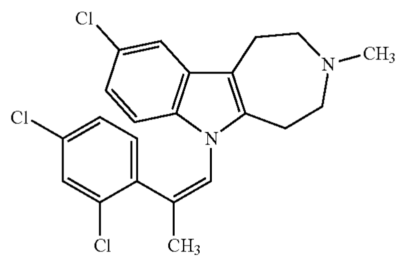 |
| 153 | 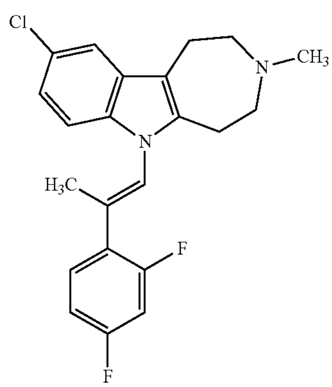 |
| 154 | 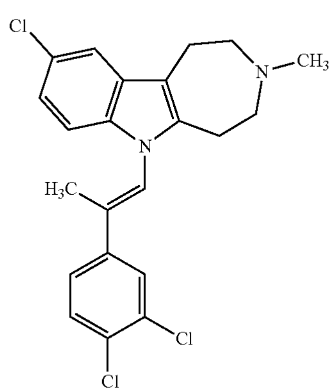 |
| 155 | |
| 156 | |
| 157 | |
| 158 | |

TABLE 2-continued
Representative Compounds According to the Invention.
| No. | Structure |
|---|---|
| 159 | 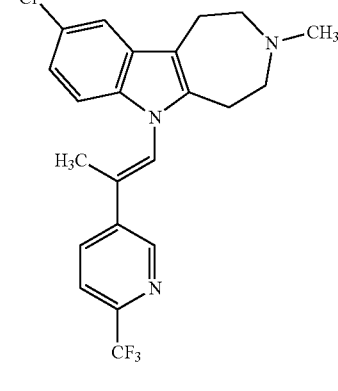 |
| 160 | 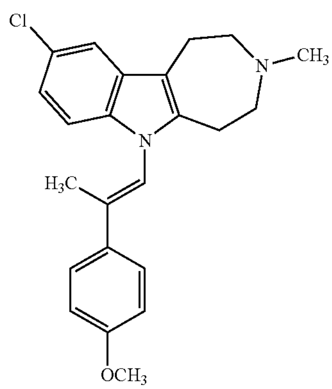 |
| 161 | 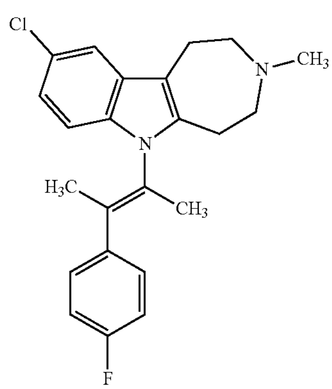 |
| 162 | 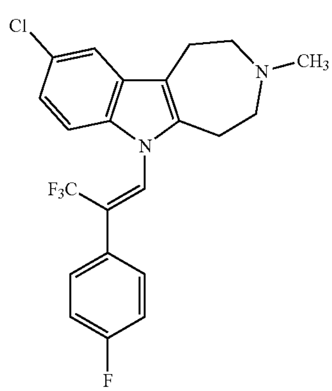 |
TABLE 2-continued
Representative Compounds According to the Invention.
| No. | Structure |
|---|---|
| 163 | 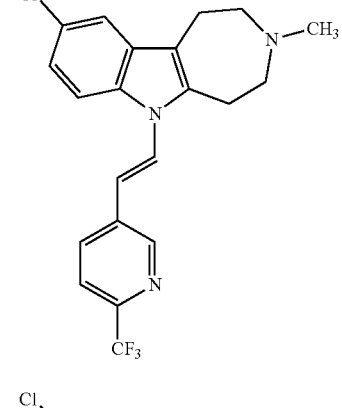 |
| 164 | 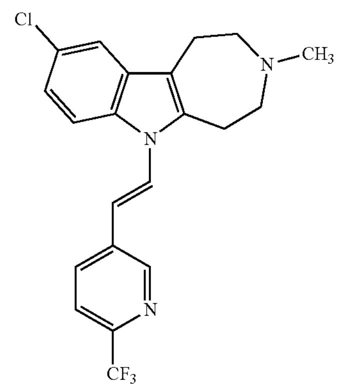 |
| 165 | 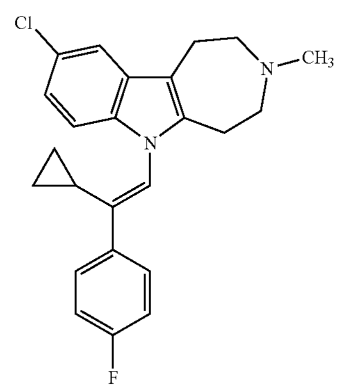 |
| 166 | 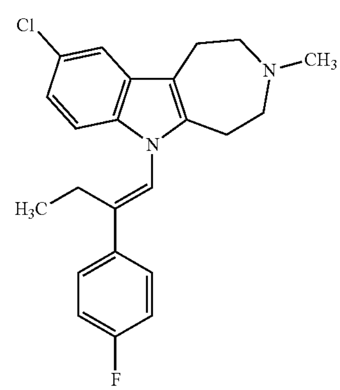 |

TABLE 2-continued
Representative Compounds According to the Invention.
| No. | Structure |
|---|---|
| 167 | 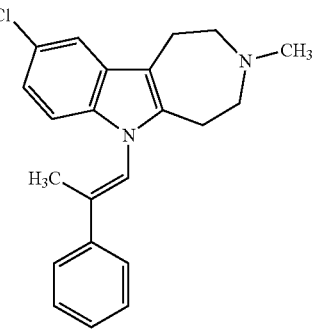 |
| 168 | 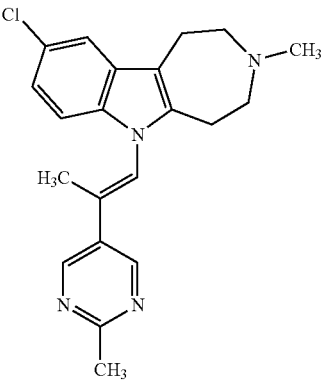 |
| 169 | 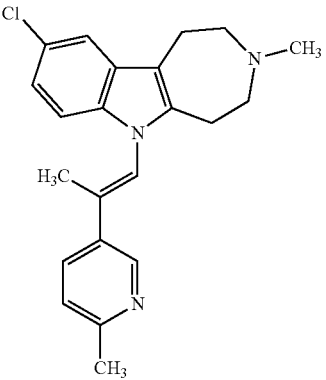 |
| 170 | 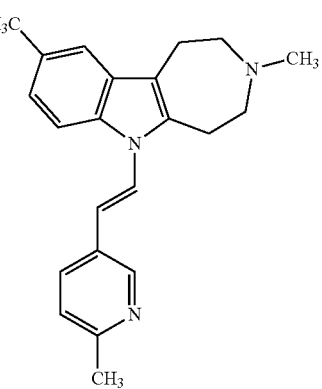 |
TABLE 2-continued
Representative Compounds According to the Invention.
| No. | Structure |
|---|---|
| 171 | 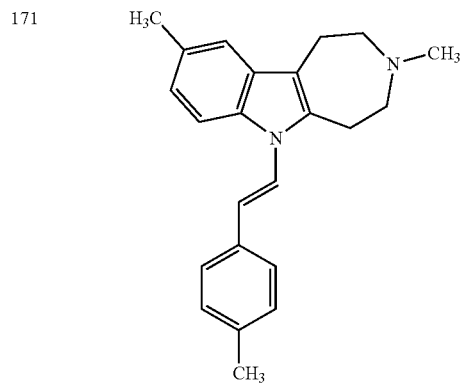 |
| 172 | 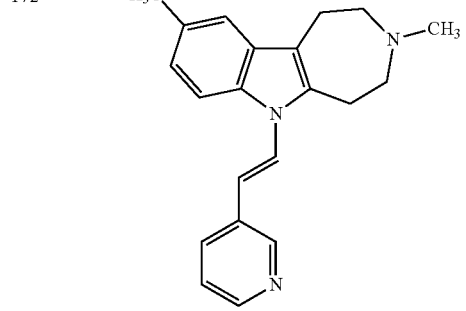 |
| 173 | 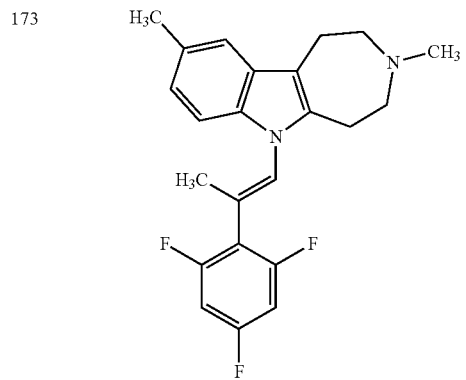 |
| 174 | 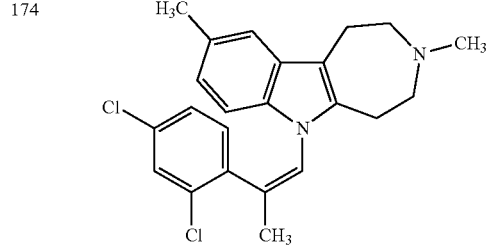 |

TABLE 2-continued

Representative Compounds According to the Invention.

| No. | Structure |
|-----|-----------|
| 175 | (structure) |
| 176 | (structure) |
| 177 | (structure) |
| 178 | (structure) |
| 179 | (structure) |
| 180 | (structure) |
| 181 | (structure) |
| 182 | (structure) |

TABLE 2-continued

Representative Compounds According to the Invention.

| No. | Structure |
|---|---|
| 183 | 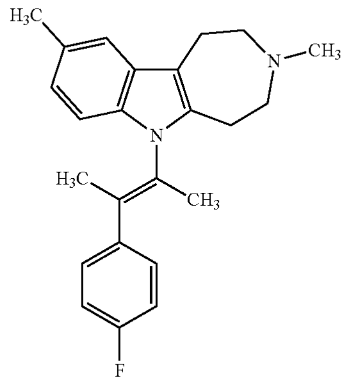 |
| 184 | 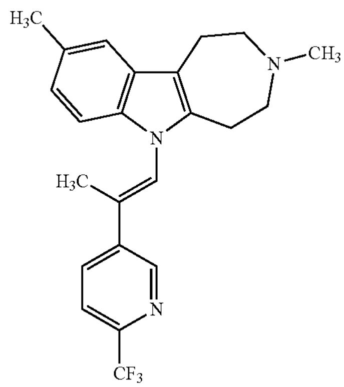 |
| 185 | 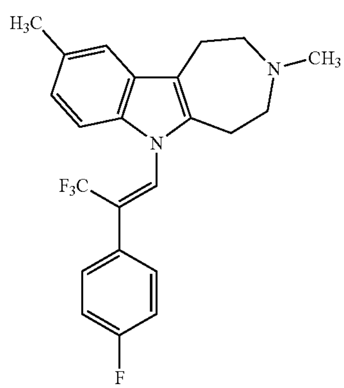 |
| 186 | 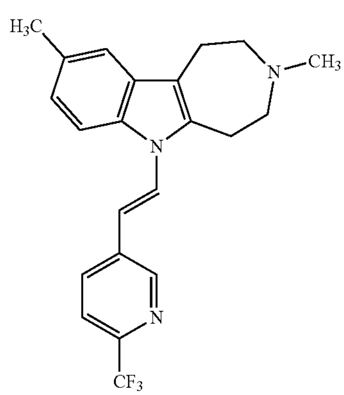 |
| 187 | |
| 188 | |
| 189 | |
| 190 | |

TABLE 2-continued

Representative Compounds According to the Invention.

| No. | Structure |
|---|---|
| 191 | (structure) |
| 192 | (structure) |
| 193 | (structure) |
| 194 | (structure) |
| 195 | (structure) |
| 196 | (structure) |
| 197 | (structure) |
| 198 | (structure) |

TABLE 2-continued

Representative Compounds According to the Invention.

| No. | Structure |
|---|---|
| 199 | 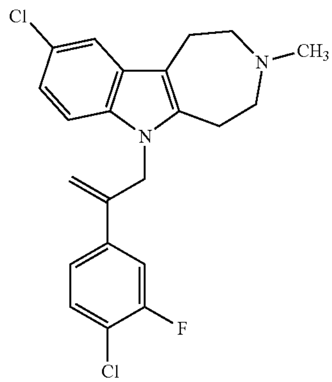 |
| 200 | 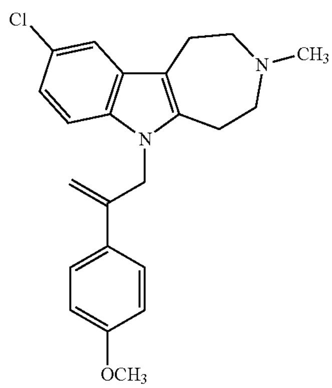 |
| 201 | 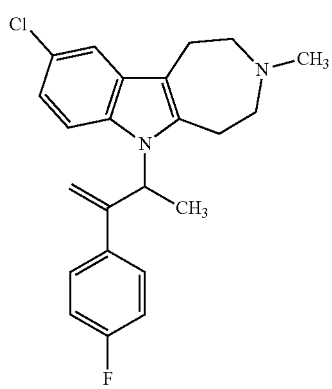 |
| 202 | 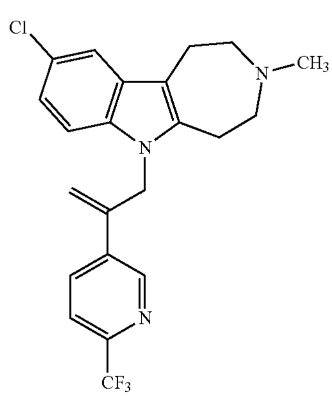 |
| 203 | |
| 204 | |
| 205 | |
| 206 | |

TABLE 2-continued

Representative Compounds According to the Invention.

| No. | Structure |
|---|---|
| 207 | (structure) |
| 208 | (structure) |
| 209 | (structure) |
| 210 | (structure) |
| 211 | (structure) |
| 212 | (structure) |
| 213 | (structure) |
| 214 | (structure) |

TABLE 2-continued
Representative Compounds According to the Invention.
| No. | Structure |
|---|---|
| 215 | 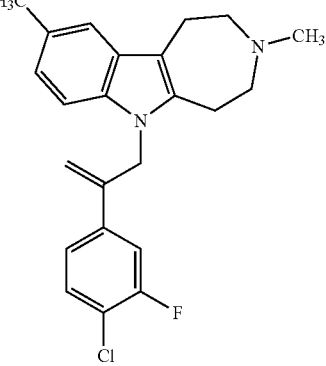 |
| 216 | 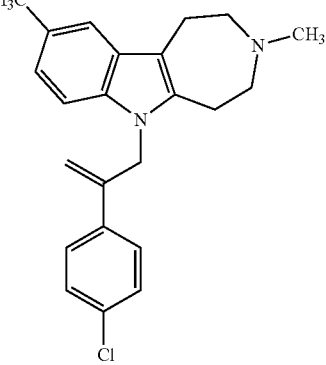 |
| 217 | 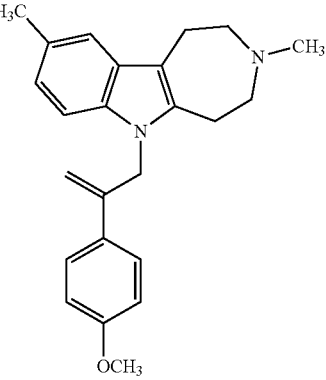 |
| 218 | 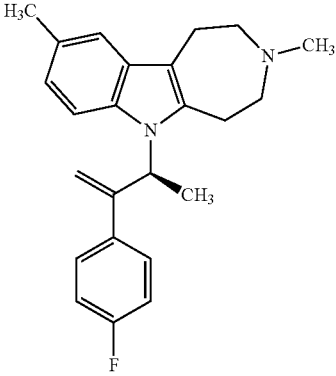 |
| 219 | 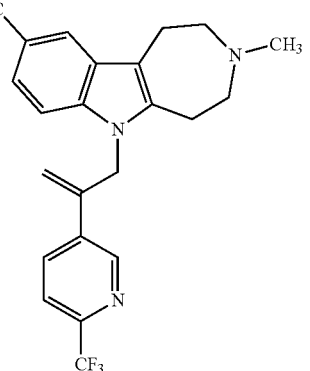 |
| 220 | 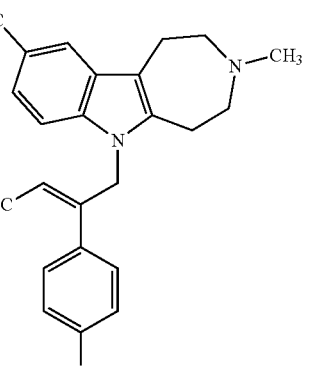 |
| 221 | 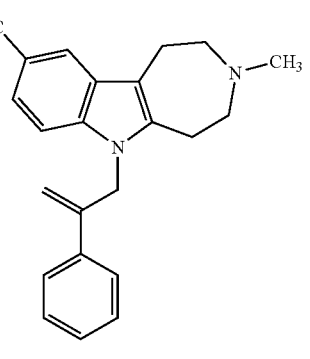 |
| 222 | 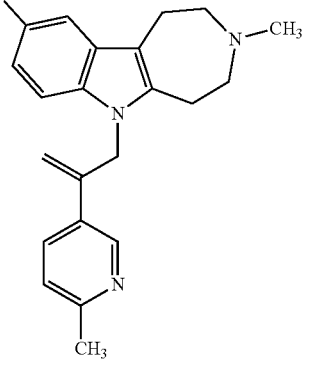 |

TABLE 2-continued

Representative Compounds According to the Invention.

| No. | Structure |
|---|---|
| 223 | 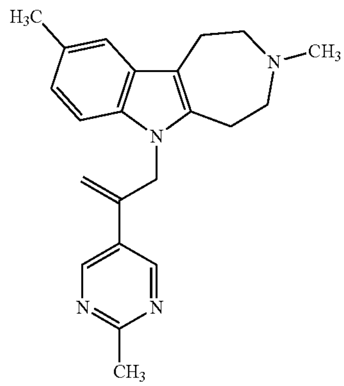 |
| 224 | 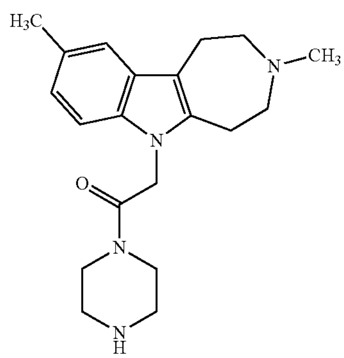 |
| 225 | 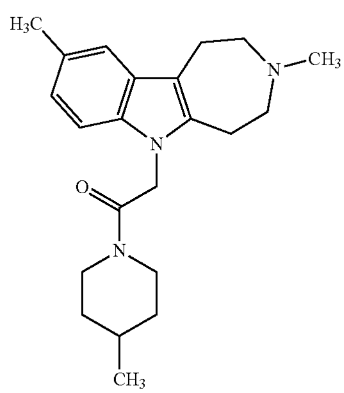 |
| 226 | 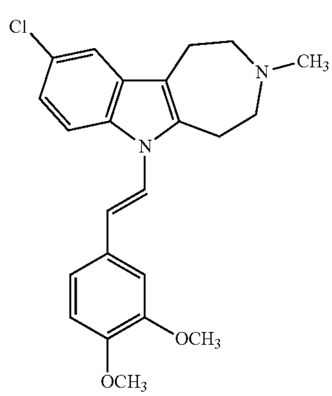 |
| 227 | |
| 228 | |
| 229 | |
| 230 | |

TABLE 2-continued

Representative Compounds According to the Invention.

| No. | Structure |
|---|---|
| 231 | (structure) |
| 232 | (structure) |
| 233 | (structure) |
| 234 | (structure) |
| 235 | (structure) |
| 236 | (structure) |
| 237 | (structure) |
| 238 | (structure) |

TABLE 2-continued

Representative Compounds According to the Invention.

| No. | Structure |
|---|---|
| 239 | 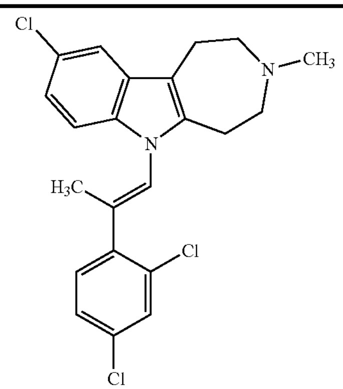 |
| 240 | 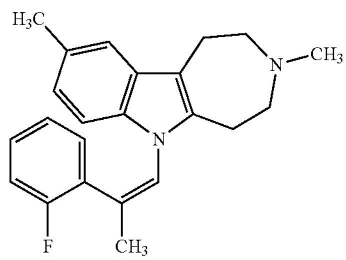 |
| 241 | 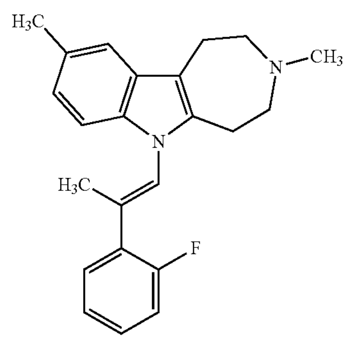 |
| 242 | 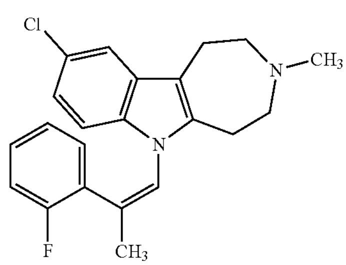 |
| 243 | 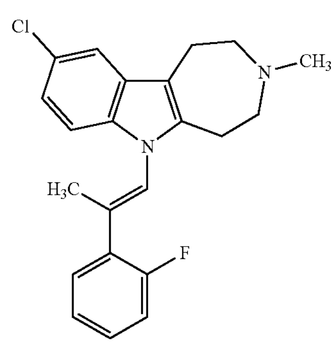 |
| 244 | |
| 245 | |
| 246 | |
| 247 | |

TABLE 2-continued

Representative Compounds According to the Invention.

| No. | Structure |
|---|---|
| 248 | [structure] |
| 249 | [structure] |
| 250 | [structure] |
| 251 | [structure] |
| 252 | [structure] |
| 253 | [structure] |
| 254 | [structure] |
| 255 | [structure] |
| 256 | [structure] |

TABLE 2-continued

Representative Compounds According to the Invention.

| No. | Structure |
|---|---|
| 257 | (structure) |
| 258 | (structure) |
| 259 | (structure) |
| 260 | (structure) |
| 261 | (structure) |
| 262 | (structure) |
| 263 | (structure) |
| 264 | (structure) |

TABLE 2-continued

Representative Compounds According to the Invention.

| No. | Structure |
|---|---|
| 265 | 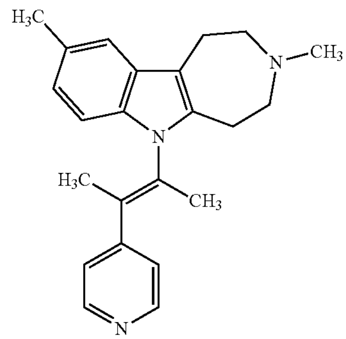 |
| 266 | 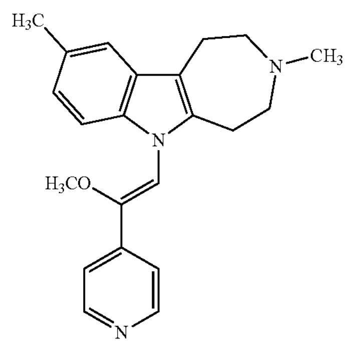 |
| 267 | 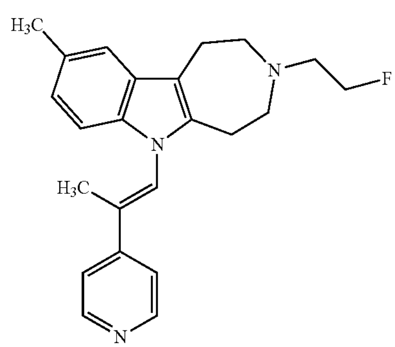 |
| 268 | 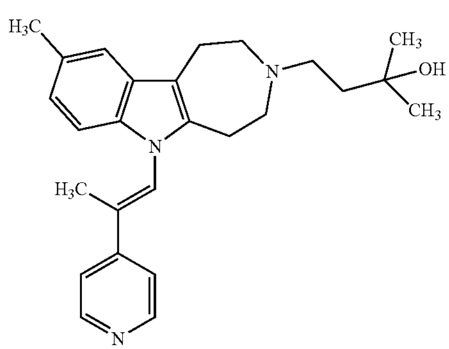 |
| 269 | |
| 270 | |
| 271 | |
| 272 | |

TABLE 2-continued

Representative Compounds According to the Invention.

| No. | Structure |
|---|---|
| 273 | (structure) |
| 274 | (structure) |
| 275 | (structure) |
| 276 | (structure) |
| 277 | (structure) |
| 278 | (structure) |
| 279 | (structure) |
| 280 | (structure) |

TABLE 2-continued

Representative Compounds According to the Invention.

| No. | Structure |
|---|---|
| 281 | (structure) |
| 282 | (structure) |
| 283 | (structure) |
| 284 | (structure) |
| 285 | (structure) |
| 286 | (structure) |

Additional compounds of the invention are provided by formulae (J-1)-(J-11) as detailed below Compounds of the formula (J-1) are provided:

(J-1)

wherein:

$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $Z^1$, $Z^2$, $Z^3$ and $Z^4$ is independently N or $CR^2$;

each $R^2$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

X is H, OH, substituted or unsubstituted $C_1$-$C_8$ alkyl or is taken together with Y to form a moiety of the formula —OCH$_2$CH$_2$O—, or is taken together with Y and the carbon to which they are attached to form a cyclopropyl moiety;

Y is halo, substituted or unsubstituted aryl, substituted or unsubstituted heteroaryl, unsubstituted $C_1$-$C_8$ alkyl, $C_1$-$C_8$ alkyl substituted with a carbonylalkoxy, carboxyl or acylamino moiety, substituted or unsubstituted $C_3$-$C_6$ cycloalkyl, or is taken together with X to form a moiety of the formula —OCH$_2$CH$_2$O—, or is taken together with X and the carbon to which they are attached to form a cyclopropyl moiety; and $R^3$ is acylamino, carbonylalkoxy, acyloxy, aminoacyl or aminocarbonylalkoxy, provided that when $R^3$ is carbonylalkoxy, Y is halo, unsubstituted $C_1$-$C_8$ alkyl, $C_1$-$C_8$ alkyl substituted with a carbonylalkoxy, carboxyl or acylamino moiety, substituted or unsubstituted $C_3$-$C_6$ cycloalkyl, or is taken together with X to form a moiety of the formula —OCH$_2$CH$_2$O—, or is taken together with X and the carbon to which they are attached to form a cyclopropyl moiety;

or a salt or solvate thereof.

In one variation, the salt of formula (J-1) is a pharmaceutically acceptable salt.

In one variation of formula (J-1), $Z^1$, $Z^2$, $Z^3$ and $Z^4$ are each $CR^2$ and the compound is of the formula (J-2):

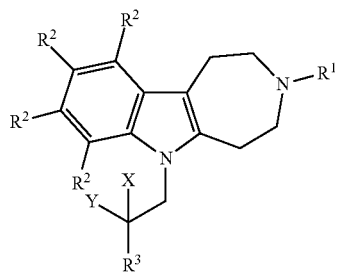

(J-2)

where $R^1$, $R^2$, $R^3$, X and Y are as defined for formula (J-1). In one aspect of formula (J-2), at least one of the $R^2$ moieties is H. In another aspect of formula (J-2), at least two $R^2$ moieties are H. In a further aspect of formula (J-2), at least three $R^2$ moieties are H, such as when (J-2) is of the formula (J-3):

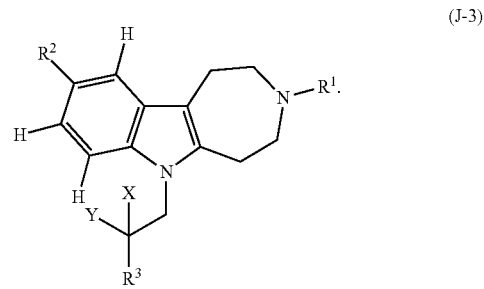

(J-3)

In one variation of formula (J-3), $R^2$ is halo or an unsubstituted $C_1$-$C_8$ alkyl, such as when $R^2$ is chloro or methyl. In one aspect, compounds of the formula (J-3) are provided wherein the compound further has one or more of the following structural features: (i) $R^1$ is a substituted or unsubstituted $C_1$-$C_8$ alkyl; (ii) $R^3$ is an acylamino, carbonylalkoxy or aminoacyl moiety; (iii) X is H, OH, unsubstituted $C_1$-$C_8$ alkyl or is taken together with Y to form a moiety of the formula —OCH$_2$CH$_2$O—, or is taken together with Y and the carbon to which they are attached to form a cyclopropyl moiety, (iv) Y is halo, unsubstituted aryl, unsubstituted $C_1$-$C_8$ alkyl, $C_1$-$C_8$ alkyl substituted with a carbonylalkoxy, carboxyl or acylamino moiety, substituted or unsubstituted $C_3$-$C_6$ cycloalkyl, or is taken together with X to form a moiety of the formula —OCH$_2$CH$_2$O—, or is taken together with X and the carbon to which they are attached to form a cyclopropyl moiety and (v) $R^2$ is halo or an unsubstituted $C_1$-$C_8$ alkyl. In a particular variation, compounds of the formula (J-3) are provided wherein at least two of provisions (i)-(v) apply. In a particular variation, compounds of the formula (J-3) are provided wherein at least three of provisions (i)-(v) apply. In a particular variation of formula (J-3), X and Y are as defined in provisions (iii) and (iv). In a further such variation, X and Y are as defined in provisions (iii) and (iv) and at least one of provisions (i), (ii) and (v) also apply.

Compounds of the formula (J-1) where at least one of $Z^1$, $Z^2$, $Z^3$ and $Z^4$ is N are also embraced. In one aspect, $Z^1$ is N. In another aspect, $Z^2$ is N. In a further aspect, $Z^3$ is N. In yet another aspect, $Z^4$ is N. Where more than one of $Z^1$, $Z^2$, $Z^3$ and $Z^4$ is N, the N atoms may be positioned at any available annular ring position. For example, when $Z^1$ is N, any of $Z^2$, $Z^3$ or $Z^4$ may also be N.

In another variation of formula (J-1), (J-2) or (J-3), $R^1$ is a substituted or unsubstituted $C_1$-$C_8$ alkyl. In a further variation of formula (J-1), (J-2) or (J-3), $R^1$ is an unsubstituted $C_1$-$C_4$ alkyl such as methyl.

In still a further variation of formula (J-1), (J-2) or (J-3), $R^3$ is an acylamino, carbonylalkoxy or aminoacyl moiety. In one aspect of formula (J-1), (J-2) or (J-3), when $R^3$ is an acylamino moiety, $R^3$ is an acyclic acylamino moiety, such as when $R^3$ is an acyclic acylamino moiety of the formula —C(O)NR$_a$R$_b$ where R$_a$ is H or a $C_1$-$C_8$ substituted or unsubstituted alkyl and R$_b$ is H, a $C_1$-$C_8$ substituted or unsubstituted alkyl (e.g., methyl, ethyl, isopropyl or benzyl) or a heterocycle. In another aspect of formula (J-1), (J-2) or (J-3), when $R^3$ is an acylamino moiety, $R^3$ is an acyclic acylamino moiety, such as when $R^3$ is of the formula —C(O)NR$_a$R$_b$ where R$_a$ taken together with R$_b$ and the nitrogen to which they are attached to form a 3-8 membered heterocyclic ring (e.g., —C(O)(1-piperidinyl). In one aspect of formula (J-1), (J-2)

or (J-3), when $R^3$ is a carbonylalkoxy moiety, $R^3$ is of the formula —C(O)O-alkyl (e.g., methyl, ethyl, cyclopentyl) or —C(O)O-substituted alkyl and Y is halo, unsubstituted $C_1$-$C_8$ alkyl, $C_1$-$C_8$ alkyl substituted with a carbonylalkoxy, carboxyl or acylamino moiety, substituted or unsubstituted $C_3$-$C_6$ cycloalkyl, or is taken together with X to form a moiety of the formula —OCH$_2$CH$_2$O—, or is taken together with X and the carbon to which they are attached to form a cyclopropyl moiety. For instance, in one variation of formula (J-1), (J-2) or (J-3), $R^3$ is a carbonylalkoxy moiety of the formula —C(O)OR where R is a $C_1$-$C_8$ substituted or unsubstituted alkyl, where in one variation the substitute on the $C_1$-$C_8$ substituted alkyl is one or more halo groups, such as an alkyl substituted with a perhaloalkyl moiety. Compounds of the formula (J-1), (J-2) or (J-3) are provided where $R^3$ is an aminoacyl moiety of the formula —NR$_a$C(O)R$_b$ where R$_a$ is H and R$_b$ is an unsubstituted or substituted alkyl, an unsubstituted or substituted aryl, an unsubstituted or substituted heteroaryl, or a substituted or unsubstituted heterocyclic moiety. In one aspect of formula (J-1), (J-2) or (J-3), $R^3$ is an aminoacyl moiety of the formula —NR$_a$C(O)R$_b$ where R$_a$ is H and R$_b$ is a $C_1$-$C_8$ unsubstituted or substituted alkyl; in another such aspect, R$_a$ is H and R$_b$ is an unsubstituted $C_1$-$C_4$ alkyl. In another aspect of formula (J-1), (J-2) or (J-3), $R^3$ is an aminoacyl moiety of the formula —NR$_a$C(O)R$_b$ where R$_a$ is H and R$_b$ is an unsubstituted or substituted single ring aryl moiety, an unsubstituted or substituted single ring heteroaryl moiety, or a substituted or unsubstituted single ring heterocyclic moiety, where the heteroaryl or heterocyclic moieties in one variation bear nitrogen heteroatoms (e.g., pyridinyl, piperidinyl).

Compounds of the formula (J-1), (J-2) or (J-3) are also provided where X is H, OH, unsubstituted $C_1$-$C_8$ alkyl or is taken together with Y to form a moiety of the formula —OCH$_2$CH$_2$O—, or is taken together with Y and the carbon to which they are attached to form a cyclopropyl moiety, and Y is halo, unsubstituted aryl, unsubstituted $C_1$-$C_8$ alkyl, $C_1$-$C_8$ alkyl substituted with a carbonylalkoxy, carboxyl or acylamino moiety, substituted or unsubstituted $C_3$-$C_6$ cycloalkyl, or is taken together with X to form a moiety of the formula —OCH$_2$CH$_2$O—, or is taken together with X and the carbon to which they are attached to form a cyclopropyl moiety. In one variation of formula (J-1), (J-2) or (J-3), X is H, OH or an unsubstituted $C_1$-$C_8$ alkyl (e.g., methyl) and Y is halo, an unsubstituted $C_1$-$C_8$ alkyl (e.g., methyl, isopropyl, n-butyl or cyclobutyl) or an unsubstituted single ring aryl moiety (e.g., phenyl). In one variation of formula (J-1), (J-2) or (J-3), X is OH and Y is an unsubstituted aryl. In one aspect, Y is phenyl. In another variation, X is H and Y is a $C_1$-$C_8$ alkyl substituted with a carbonylalkoxy, carboxyl or acylamino moiety. In one aspect, Y is a methylene substituted with a carbonylalkoxy, carboxyl or acylamino moiety. In a particular aspect, Y is a moiety selected from the following structures

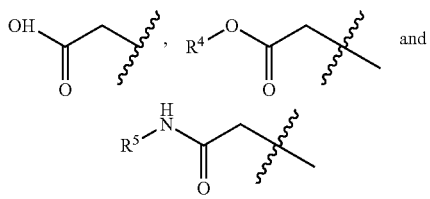

where each $R^4$ and $R^5$ is independently an unsubstituted $C_1$-$C_8$ alkyl. In one variation, Y is a moiety selected from the following structures

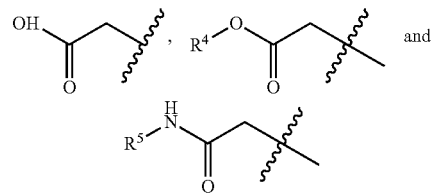

where each $R^4$ and $R^5$ is independently an unsubstituted $C_1$-$C_8$ alkyl and X is H. In another variation, X is an unsubstituted $C_1$-$C_8$ alkyl and Y is halo. In a particular aspect, Y is fluoro.

In a particular variation of formula (J-1), (J-2) or (J-3), $R^1$ is an unsubstituted $C_1$-$C_4$ alkyl; X is H, OH, unsubstituted $C_1$-$C_8$ alkyl or is taken together with Y to form a moiety of the formula —OCH$_2$CH$_2$O—, or is taken together with Y and the carbon to which they are attached to form a cyclopropyl moiety; Y is halo, unsubstituted aryl, unsubstituted $C_1$-$C_8$ alkyl, $C_1$-$C_8$ alkyl substituted with a carbonylalkoxy, carboxyl or acylamino moiety, substituted or unsubstituted $C_3$-$C_6$ cycloalkyl, or is taken together with X to form a moiety of the formula —OCH$_2$CH$_2$O—, or is taken together with X and the carbon to which they are attached to form a cyclopropyl moiety; and $R^3$ is an acylamino, carbonylalkoxy or aminoacyl moiety, provided that when $R^3$ is carbonylalkoxy, Y is halo, unsubstituted $C_1$-$C_8$ alkyl, $C_1$-$C_8$ alkyl substituted with a carbonylalkoxy, carboxyl or acylamino moiety, substituted or unsubstituted $C_3$-$C_6$ cycloalkyl, or is taken together with X to form a moiety of the formula —OCH$_2$CH$_2$O—, or is taken together with X and the carbon to which they are attached to form a cyclopropyl moiety. In another variation of formula (J-1), (J-2) or (J-3), $R^1$ is an unsubstituted $C_1$-$C_4$ alkyl; X is H, OH, unsubstituted $C_1$-$C_8$ alkyl or is taken together with Y to form a moiety of the formula —OCH$_2$CH$_2$O—, or is taken together with Y and the carbon to which they are attached to form a cyclopropyl moiety; Y is halo, unsubstituted aryl, unsubstituted $C_1$-$C_8$ alkyl, $C_1$-$C_8$ alkyl substituted with a carbonylalkoxy, carboxyl or acylamino moiety, substituted or unsubstituted $C_3$-$C_6$ cycloalkyl, or is taken together with X to form a moiety of the formula —OCH$_2$CH$_2$O—, or is taken together with X and the carbon to which they are attached to form a cyclopropyl moiety; and $R^3$ is an acylamino or aminoacyl moiety. It is understood that when $R^3$ is an acylamino, carbonylalkoxy or aminoacyl moiety, $R^3$ may be any such moiety detailed herein, including but not limited to the moieties provided herein above. As such, it is understood that in one aspect, compounds of the formula (J-1), (J-2) or (J-3) are provided wherein $R^1$ is an unsubstituted $C_1$-$C_4$ alkyl; X is H, OH, unsubstituted $C_1$-$C_8$ alkyl or is taken together with Y to form a moiety of the formula —OCH$_2$CH$_2$O—, or is taken together with Y and the carbon to which they are attached to form a cyclopropyl moiety; Y is halo, unsubstituted aryl, unsubstituted $C_1$-$C_8$ alkyl, $C_1$-$C_8$ alkyl substituted with a carbonylalkoxy, carboxyl or acylamino moiety, substituted or unsubstituted $C_3$-$C_6$ cycloalkyl, or is taken together with X to form a moiety of the formula —OCH$_2$CH$_2$O—, or is taken together with X and the carbon to which they are attached to form a cyclopropyl moiety; and $R^3$ is an acyclic or cyclic acylamino as detailed herein or an aminoacyl moiety of the formula —NR$_a$C(O)R$_b$ where R$_a$ is H and R$_b$ is an unsubstituted or substituted alkyl, an unsubstituted or substituted aryl, an unsubstituted or substituted heteroaryl, or a substituted or unsubstituted heterocyclic moiety.

In one variation of formula (J-3), $R^1$ is unsubstituted $C_1$-$C_8$ alkyl or a $C_1$-$C_8$ alkyl substituted with a perhaloalkyl moiety;

and $R^2$ is independently H, halo, unsubstituted $C_1$-$C_8$ alkyl or unsubstituted $C_1$-$C_8$ alkoxy. In one variation of formula (J-3), $R^1$ is unsubstituted $C_1$-$C_8$ alkyl; $R^2$ is unsubstituted $C_1$-$C_8$ alkyl, H or halo, and $R^3$ is acylamino, carbonylalkoxy, acyloxy, aminoacyl or aminocarbonylalkoxy.

In one variation of formula (J-3), X is OH and Y is a substituted or unsubstituted $C_1$-$C_8$ alkyl. In another variation of (J-3), X is OH and the compound is further defined by one or more of the following structural features: (i) Y is a substituted or unsubstituted $C_1$-$C_8$ alkyl (which in one aspect is methyl, butyl or isopropyl); (ii) $R^1$ and $R^2$ are independently an unsubstituted $C_1$-$C_8$ alkyl (in one aspect both $R^1$ and $R^2$ are methyl); (iii) $R^3$ is acylamino, carbonylalkoxy, acyloxy, aminoacyl or aminocarbonylalkoxy. In a particular variation of formula (J-3), X is OH, Y is a substituted or unsubstituted $C_1$-$C_8$ alkyl; $R^1$ and $R^2$ are each methyl and $R^3$ is acylamino, carbonylalkoxy, acyloxy, aminoacyl or aminocarbonylalkoxy.

In one variation of formula (J-3), X is OH and Y is H. In one variation of formula (J-3), X is OH; Y is H; and $R^1$ and $R^2$ are independently an unsubstituted $C_1$-$C_8$ alkyl. In a particular variation of formula (J-3), X is OH; Y is H; $R^1$ and $R^2$ are independently an unsubstituted $C_1$-$C_8$ alkyl; and $R^3$ is acylamino, carbonylalkoxy, acyloxy, aminoacyl or aminocarbonylalkoxy. In one variation of formula (J-3), X is OH; Y and H; $R^1$ and $R^2$ are each methyl; and $R^3$ is acylamino, carbonylalkoxy, acyloxy, aminoacyl or aminocarbonylalkoxy. In a particular variation of formula (J-3), X is OH; Y is H; $R^1$ and $R^2$ are each methyl; and $R^3$ is acylamino, carbonylalkoxy or aminoacyl.

Compounds of the formula (J-4) are detailed herein:

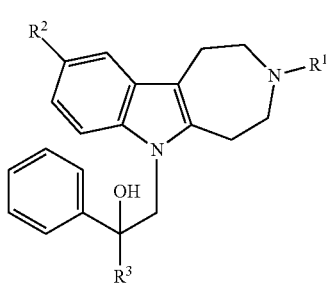

(J-4)

or a salt or solvate thereof, where $R^1$, $R^2$ and $R^3$ are as defined for formula (J-1). In one variation of formula (J-4), $R^1$ and $R^2$ are independently an unsubstituted $C_1$-$C_8$ alkyl. In a particular variation of formula v, $R^1$ and $R^2$ are independently an unsubstituted $C_1$-$C_8$ alkyl and $R^3$ is acylamino, carbonylalkoxy, acyloxy, aminoacyl or aminocarbonylalkoxy. In one variation, $R^1$ and $R^2$ are each methyl and $R^3$ is acylamino, carbonylalkoxy, acyloxy, aminoacyl or aminocarbonylalkoxy. In another variation of formula (J-4), $R^1$ is an unsubstituted $C_1$-$C_8$ alkyl; $R^2$ is halo or an unsubstituted $C_1$-$C_8$ alkyl and $R^3$ is aminoacyl. In one such variation of formula (J-4), $R^1$ is methyl; $R^2$ is halo or a $C_1$-$C_4$ unsubstituted alkyl; and $R^3$ is an aminoacyl of the formula —$NR_aC(O)R_b$ where $R_a$ is H and $R_b$ is an unsubstituted or substituted alkyl, an unsubstituted or substituted aryl, an unsubstituted or substituted heteroaryl, or a substituted or unsubstituted heterocyclic moiety.

Compounds of the formula (J-5) are also detailed herein:

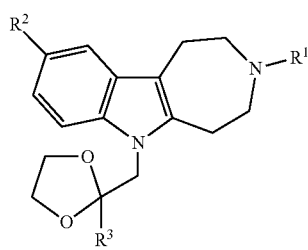

(J-5)

or a salt or solvate thereof, where $R^1$, $R^2$ and $R^3$ are as defined for formula (J-1). In one variation of formula (J-5), $R^1$ is an unsubstituted $C_1$-$C_8$ alkyl (e.g., methyl). In another variation of formula (J-5), $R^2$ is H, an unsubstituted $C_1$-$C_8$ alkyl (e.g., methyl) or halo (e.g., chloro). In one aspect of formula (J-5), $R^1$ is an unsubstituted $C_1$-$C_8$ alkyl and $R^2$ is H, an unsubstituted $C_1$-$C_8$ alkyl or halo. In another variation of formula (J-5), $R_2$ is a halo or an unsubstituted $C_1$-$C_8$ alkyl and $R^1$ is an unsubstituted $C_1$-$C_4$ alkyl. In a particular variation of formula (J-5), $R^1$ is methyl and $R^2$ is H, methyl or chloro. In one variation of formula (J-5), $R^1$ and $R^2$ are independently an unsubstituted $C_1$-$C_8$ alkyl such as methyl. In a further variation of formula (J-5), $R^1$ is an unsubstituted $C_1$-$C_8$ alkyl; $R^2$ is H, an unsubstituted $C_1$-$C_8$ alkyl or halo and $R^3$ is acylamino, carbonylalkoxy, acyloxy, aminoacyl or aminocarbonylalkoxy. In a particular variation, compounds of formula (J-5) are provided where $R^1$ is methyl, $R^2$ is H, methyl or chloro and $R^3$ is acylamino, carbonylalkoxy, acyloxy, aminoacyl or aminocarbonylalkoxy. In a further variation of formula (J-5), $R^1$ is an unsubstituted $C_1$-$C_8$ alkyl; $R^2$ is halo or an unsubstituted $C_1$-$C_8$ alkyl; and $R^3$ is an acylamino of the formula —C(O)$NR_aR_b$ where $R_a$ is H and $R_b$ is an unsubstituted $C_1$-$C_8$ alkyl.

Compounds of the formula (J-6) are also detailed herein:

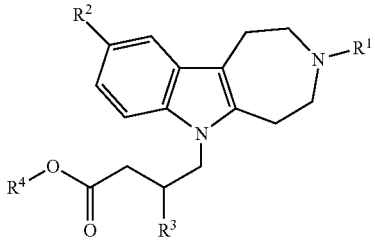

(J-6)

or a salt or solvate thereof, where $R^1$, $R^2$ and $R^3$ are as detailed for formula (J-1) and $R^4$ is an unsubstituted $C_1$-$C_8$ alkyl. In one variation of formula (J-6), $R^1$ is an unsubstituted $C_1$-$C_8$ alkyl. In one variation of formula (J-6), $R^2$ is an unsubstituted $C_1$-$C_8$ alkyl or halo. In one variation of formula (J-6), $R^1$ and $R^2$ are independently an unsubstituted $C_1$-$C_8$ alkyl (e.g., methyl or ethyl). In one variation of formula (J-6), $R^1$ is an unsubstituted $C_1$-$C_8$ alkyl (e.g., methyl or ethyl) and $R^2$ is an unsubstituted $C_1$-$C_8$ alkyl or halo. In a particular variation of formula (J-6), $R^4$ is an unsubstituted $C_1$-$C_4$ alkyl. In a further variation of formula (J-6), $R^4$ is methyl, ethyl, propyl or butyl. In one aspect, $R^4$ is iso-propyl. In another aspect, $R^4$ is tert-butyl. In a particular variation of formula (J-6), $R^1$ is an unsubstituted $C_1$-$C_8$ alkyl; $R^2$ is an unsubstituted $C_1$-$C_8$ alkyl or halo and $R^4$ is an unsubstituted $C_1$-$C_4$ alkyl. In a further variation of formula (J-6), $R^1$ is an unsubstituted $C_1$-$C_8$ alkyl; $R^2$ is an unsubstituted $C_1$-$C_8$ alkyl or halo; $R^4$ is an unsubstituted $C_1$-$C_4$ alkyl and $R^3$ is acylamino, carbonylalkoxy, acyloxy, aminoacyl or aminocarbonylalkoxy. In a particular variation, compounds of formula (J-6) are provided where $R^1$ is methyl or ethyl, $R^2$ is methyl or chloro; $R^4$ is methyl, ethyl, isopropyl or tert-butyl and $R^3$ is acylamino, carbonylalkoxy, acyloxy, aminoacyl or aminocarbonylalkoxy. In a further variation of formula (J-6), $R^1$ is an unsubstituted $C_1$-$C_4$ alkyl; $R^2$ is an unsubstituted $C_1$-$C_4$ alkyl or halo; $R^4$ is an unsubstituted $C_1$-$C_4$ alkyl; and $R^3$ is acylamino or aminoacyl. In yet a further variation of formula (J-6), $R^1$ is an unsubstituted $C_1$-$C_4$ alkyl; $R^2$ is an unsubstituted $C_1$-$C_4$ alkyl or halo; $R^4$ is an unsubstituted $C_1$-$C_4$ alkyl; and $R^3$ is either an acylamino of the formula —C(O)NR$_a$R$_b$ where R$_a$ and R$_b$ are independently an unsubstituted $C_1$-$C_8$ alkyl or R$_a$ and R$_b$ are taken together with the nitrogen to which they are attached to form a heterocyclic moiety or an aminoacyl.

Compounds of the formula (J-7) are also detailed herein:

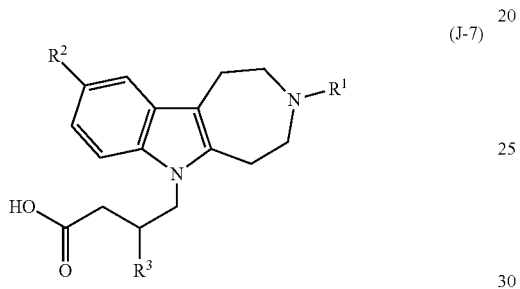

(J-7)

or a salt of solvate thereof, where $R^1$, $R^2$ and $R^3$ are as detailed for formula (J-1). In one variation of formula (J-7), $R^1$ is an unsubstituted $C_1$-$C_8$ alkyl (e.g., methyl). In another variation of formula (J-7), $R^2$ is unsubstituted $C_1$-$C_8$ alkyl (e.g., methyl) or halo (e.g., chloro). In a particular variation of formula (J-7), $R^1$ is an unsubstituted $C_1$-$C_8$ alkyl and $R^2$ is unsubstituted $C_1$-$C_8$ alkyl or halo. In another variation of formula (J-7), $R^1$ and $R^2$ are independently an unsubstituted $C_1$-$C_8$ alkyl (e.g., methyl). In one variation of formula (J-7), $R^1$ is an unsubstituted $C_1$-$C_8$ alkyl, $R^2$ is unsubstituted $C_1$-$C_8$ alkyl or halo and $R^3$ is acylamino, carbonylalkoxy, acyloxy, aminoacyl or aminocarbonylalkoxy. In a particular variation of formula (J-7), $R^1$ and $R^2$ are independently an unsubstituted $C_1$-$C_8$ alkyl and $R^3$ is acylamino, carbonylalkoxy, acyloxy, aminoacyl or aminocarbonylalkoxy. In one variation of formula (J-7), $R^3$ is acylamino.

Compounds of the formula (J-8) are also detailed herein:

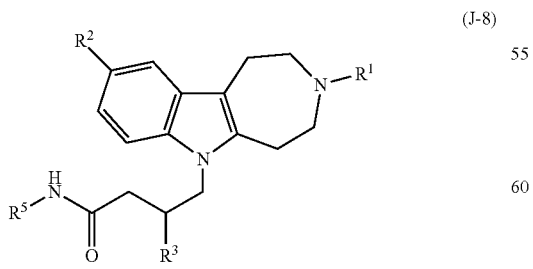

(J-8)

or a salt of solvate thereof, where $R^1$, $R^2$ and $R^3$ are as detailed for formula (J-1) and $R^5$ is an unsubstituted $C_1$-$C_8$ alkyl. In one variation of formula (J-8), $R^1$ is an unsubstituted $C_1$-$C_8$ alkyl (e.g., methyl or ethyl). In another variation of formula (J-8), $R^2$ is unsubstituted $C_1$-$C_8$ alkyl (e.g., methyl) or halo (e.g., chloro). In a particular variation of formula (J-8), $R^1$ is an unsubstituted $C_1$-$C_8$ alkyl and $R^2$ is unsubstituted $C_1$-$C_8$ alkyl or halo. In another variation of formula (J-8), $R^1$ and $R^2$ are independently an unsubstituted $C_1$-$C_8$ alkyl. In a particular variation of formula (J-8), $R^5$ is an unsubstituted $C_1$-$C_4$ alkyl. In a further variation of formula (J-8), $R^5$ is methyl, ethyl, propyl or butyl. In one aspect, $R^5$ is iso-propyl. In another aspect, $R^5$ is tert-butyl. In one variation of formula (J-8), $R^1$ is an unsubstituted $C_1$-$C_8$ alkyl, $R^2$ is unsubstituted $C_1$-$C_8$ alkyl or halo and $R^3$ is acylamino, carbonylalkoxy, acyloxy, aminoacyl or aminocarbonylalkoxy. In a further variation of formula (J-8), $R^1$ is an unsubstituted $C_1$-$C_8$ alkyl, $R^2$ is unsubstituted $C_1$-$C_8$ alkyl or halo and $R^3$ is acylamino, or aminoacyl.

Compounds of the formula (J-9) are also detailed herein:

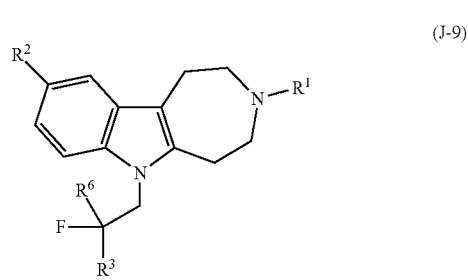

(J-9)

or a salt or solvate thereof, where $R^1$, $R^2$ and $R^3$ are as defined for formula (J-1) and $R^6$ is an unsubstituted $C_1$-$C_8$ alkyl. In one variation of formula (J-9), $R^1$ is an unsubstituted $C_1$-$C_8$ alkyl (e.g., methyl, ethyl or isopropyl). In another variation of formula (J-9), $R^2$ is unsubstituted $C_1$-$C_8$ alkyl (e.g., methyl) or halo (e.g., chloro). In a particular variation of formula (J-9), $R^1$ is an unsubstituted $C_1$-$C_8$ alkyl and $R^2$ is unsubstituted $C_1$-$C_8$ alkyl or halo. In another variation of formula (J-9), $R^1$ and $R^2$ are independently an unsubstituted $C_1$-$C_8$ alkyl. In a particular variation of formula (J-9), $R^6$ is an unsubstituted $C_1$-$C_4$ alkyl. In a further variation of formula (J-9), $R^6$ is methyl, ethyl, propyl or butyl. In one aspect, $R^6$ is iso-propyl. In another aspect, $R^6$ is tert-butyl. In one variation of formula (J-9), $R^1$ is an unsubstituted $C_1$-$C_8$ alkyl, $R^2$ is unsubstituted $C_1$-$C_8$ alkyl or halo and $R^3$ is acylamino, carbonylalkoxy, acyloxy, aminoacyl or aminocarbonylalkoxy.

Compounds of the formula (J-10) are also detailed herein:

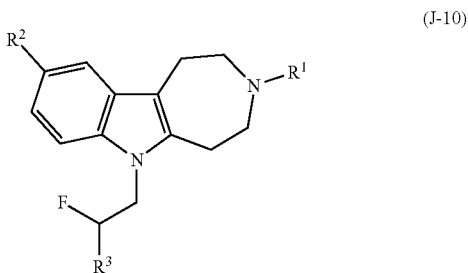

(J-10)

or a salt or solvate thereof, where $R^1$, $R^2$ and $R^3$ are as defined for formula (J-1). In one variation of formula (J-10), $R^1$ and $R^2$ are each an unsubstituted $C_1$-$C_8$ alkyl group. In another variation of formula (J-10), $R^1$ and $R^2$ are each an unsubstituted $C_1$-$C_8$ alkyl group and $R^3$ is acylamino, carbonylalkoxy, acyloxy, aminoacyl or aminocarbonylalkoxy. In another variation of formula (J-10), $R^1$ is an unsubstituted $C_1$-$C_8$ alkyl; $R^2$ is an unsubstituted $C_1$-$C_8$ alkyl or halo and $R^3$ is acylamino or aminoacyl.

Compounds of the formula (J-11) are also detailed herein:

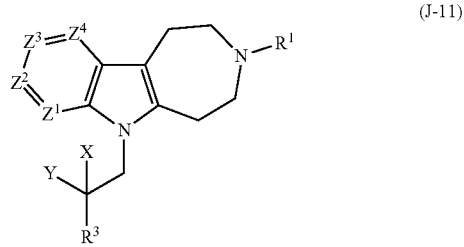

(J-11)

wherein:

each $Z^1$, $Z^2$, $Z^3$ and $Z^4$ is independently N or $CR^2$ each $R^2$ is independently H, halo, unsubstituted $C_1$-$C_8$ alkyl or unsubstituted $C_1$-$C_8$ alkoxy;

$R^1$ is unsubstituted $C_1$-$C_8$ alkyl or a $C_1$-$C_8$ alkyl substituted with a perhaloalkyl moiety;

X is OH, substituted or unsubstituted $C_1$-$C_8$ alkyl or is taken together with Y and the carbon to which they are attached to form a cyclopropyl moiety;

Y is H, substituted or unsubstituted $C_1$-$C_8$ alkyl or is taken together with X and the carbon to which they are attached to form a cyclopropyl moiety; and $R^3$ is acylamino, carbonylalkoxy, acyloxy, aminoacyl or aminocarbonylalkoxy;

or a salt or solvate thereof.

In one variation, the salt of formula (J-11) is a pharmaceutically acceptable salt.

In one variation of formula (J-11), each of $Z^1$, $Z^2$, $Z^3$ and $Z^4$ is $CR^2$. In another variation of formula (J-11), at least one of $Z^1$, $Z^2$, $Z^3$ and $Z^4$ is N, which may positioned at any of $Z^1$, $Z^2$, $Z^3$ and $Z^4$. Where more than one of $Z^1$, $Z^2$, $Z^3$ and $Z^4$ is N, the annular nitrogen atoms may be located at any available positions.

In one variation of formula (J-11), $R^1$ and $R^2$ are independently an unsubstituted $C_1$-$C_8$ alkyl. In a particular variation of formula (J-11), $R^1$ and $R^2$ are independently an unsubstituted $C_1$-$C_8$ alkyl and $R^3$ is acylamino, carbonylalkoxy, acyloxy, aminoacyl or aminocarbonylalkoxy. In one variation, $R^1$ and $R^2$ are each methyl and $R^3$ is acylamino, carbonylalkoxy, acyloxy, aminoacyl or aminocarbonylalkoxy. In a particular variation of formula (J-11), $R^1$ and $R^2$ are each methyl and $R^3$ is acylamino, carbonylalkoxy, acyloxy, aminoacyl or aminocarbonylalkoxy.

Examples of compounds according to the invention are depicted in Table 2A. The compounds depicted may be present as salts even if salts are not depicted and it is understood that the invention embraces all salts and solvates of the compounds depicted here, as well as the non-salt and non-solvate form of the compound, as is well understood by the skilled artisan.

TABLE 2A

Representative Compounds

| Compound | Structure |
|---|---|
| J-1 | 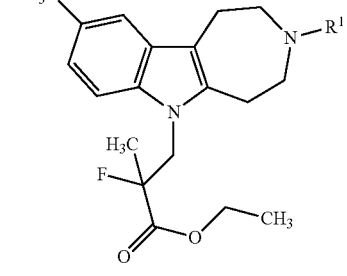 |
| J-2 | 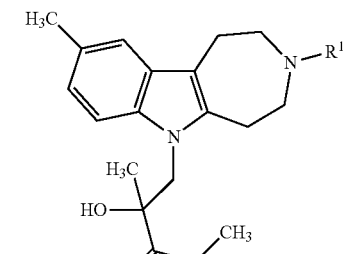 |
| J-3 | 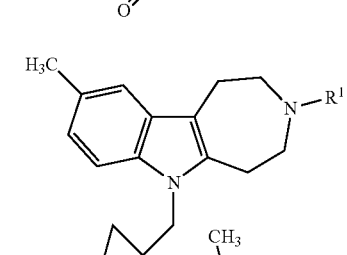 |
| J-4 | 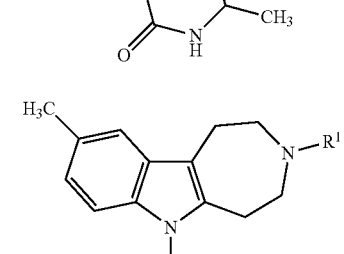 |
| J-5 | 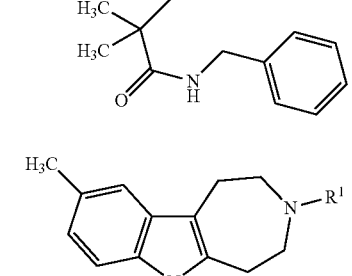 |

TABLE 2A-continued

Representative Compounds

| Compound | Structure |
|---|---|
| J-6 | (structure) |
| J-7 | (structure) |
| J-8 | (structure) |
| J-9 | (structure) |
| J-10 | (structure) |
| J-11 | (structure) |
| J-12 | (structure) |
| J-13 | (structure) |
| J-14 | (structure) |
| J-15 | (structure) |

TABLE 2A-continued

Representative Compounds

| Compound | Structure |
|---|---|
| J-16 | 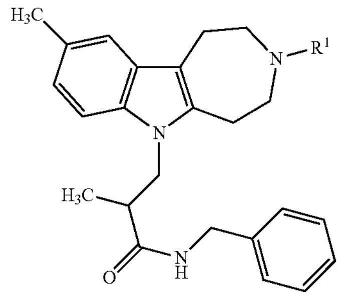 |
| J-17 | 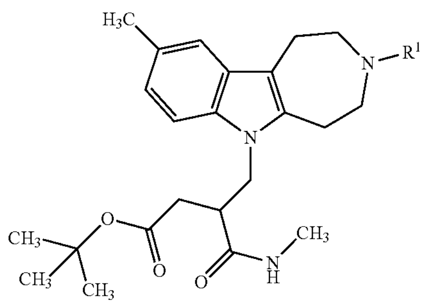 |
| J-18 | 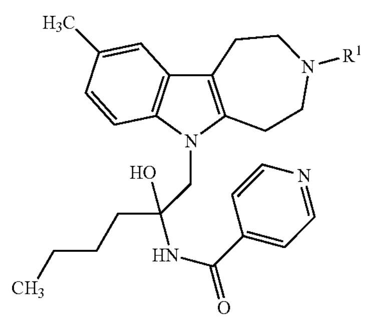 |
| J-19 | 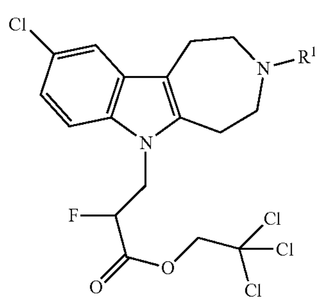 |
| J-20 | 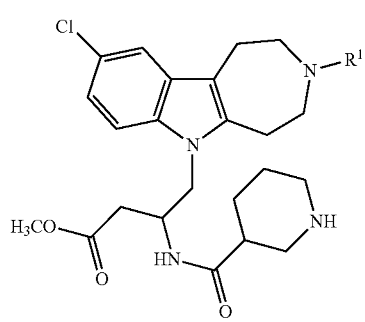 |
| J-21 | |
| J-22 | |
| J-23 | |
| J-24 | |
| J-25 | |

TABLE 2A-continued

Representative Compounds

| Compound | Structure |
|---|---|
| J-26 | 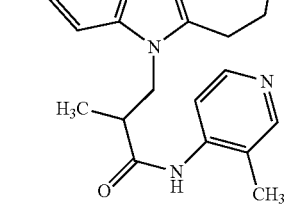 |
| J-27 | 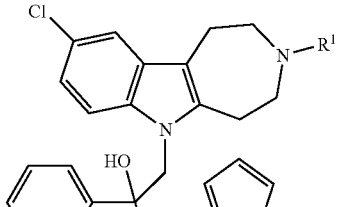 |
| J-28 | 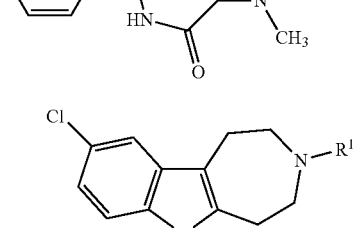 |
| J-29 | 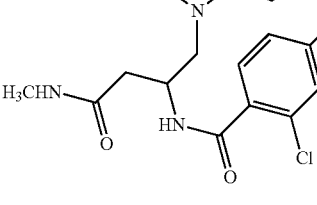 |
| J-30 | 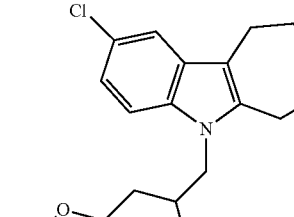 |

Compounds of the formula (K-1) are also detailed herein:

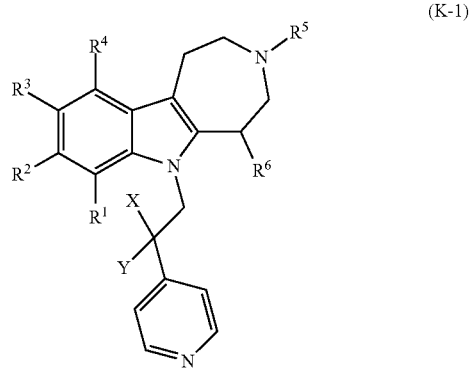

(K-1)

wherein:

$R^1$, $R^2$, $R^3$ and $R^4$ are independently H, halo, $C_1$-$C_8$ unsubstituted alkyl or $C_1$-$C_8$ unsubstituted alkoxy, provided that $R^3$ is other than methyl or chloro when $R^1$, $R^2$ and $R^3$ are each H and X is OH and Y is methyl;

$R^5$ is unsubstituted $C_1$-$C_8$ alkyl or a $C_1$-$C_8$ alkyl substituted with a perhaloalkyl moiety;

$R^6$ is H or an unsubstituted $C_1$-$C_8$ alkyl;

X is OH, $C_1$-$C_8$ alkyl or is taken together with Y to form a cyclopropyl moiety;

Y is H, $C_1$-$C_8$ alkyl or is taken together with X to form a cyclopropyl moiety, or a salt thereof, such as a pharmaceutically acceptable salt thereof, or solvate of the foregoing.

In one variation of formula (K-1), $R^1$ is H, halo or $C_1$-$C_8$ unsubstituted alkoxy; $R^2$ is H; $R^3$ is H, halo, $C_1$-$C_8$ unsubstituted alkyl or $C_1$-$C_8$ unsubstituted alkoxy, provided that $R^3$ is other than methyl or chloro when $R^1$, $R^2$ and $R^3$ are each H and X is OH and Y is methyl; $R^4$ is H or halo; $R^5$ is methyl; $R^6$ is H or methyl; X is OH, $C_1$-$C_8$ alkyl or is taken together with Y to form a cyclopropyl moiety and Y is H, $C_1$-$C_8$ alkyl or is taken together with X to form a cyclopropyl moiety. In another variation of formula (K-1), at least two of $R^1$, $R^2$, $R^3$ and $R^4$ are halo (e.g., when $R^2$ and $R^3$ are chloro). In another variation of formula (K-1), X is OH and Y is H, methyl, ethyl or isopropyl. In a further variation of formula (K-1), $R^1$, $R^2$ and $R^4$ are H. In another variation of formula (K-1), three of $R^1$, $R^2$, $R^3$ and $R^4$ are H and one is methyl, methoxy, isopropyl, chloro or fluoro.

Also provided are compounds of the formula (K-2):

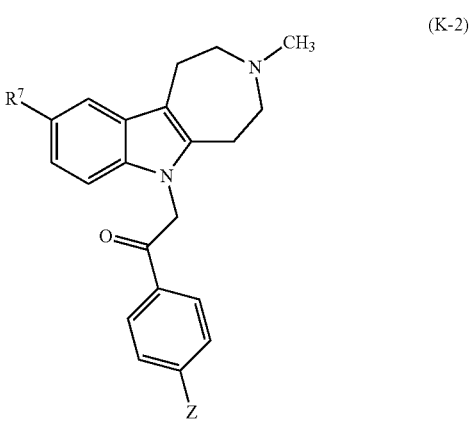

(K-2)

wherein:

R$^7$ is H, hydroxyl, nitro, cyano, halo, C$_1$-C$_8$ perhaloalkyl, substituted or unsubstituted C$_1$-C$_8$ alkyl, substituted or unsubstituted C$_2$-C$_8$ alkenyl, substituted or unsubstituted C$_2$-C$_8$ alkynyl, substituted or unsubstituted aryl, substituted or unsubstituted heteroaryl, C$_1$-C$_8$ perhaloalkoxy, C$_1$-C$_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl; and Z is H, halo or C$_1$-C$_8$ alkyl, or a salt thereof, such as a pharmaceutically acceptable salt thereof, or solvate of the foregoing.

In one variation of formula (K-2), R$^7$ is unsubstituted C$_1$-C$_8$ alkyl or halo. In another variation of formula (K-2), Z is H or halo. In a further variation of formula (K-2), R$^7$ is an unsubstituted C$_1$-C$_8$ alkyl or halo and Z is H or halo. In a particular variation, R$^7$ is methyl or chloro and Z is H, chloro or fluoro.

Compounds of the formula (K-3) are also embraced:

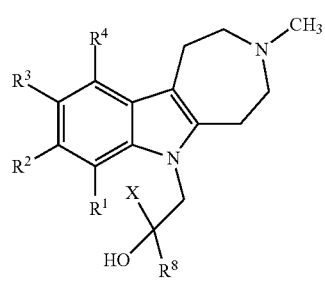

(K-3)

wherein:

R$^1$, R$^2$, R$^3$ and R$^4$ are as defined for formula (K-1);

R$^8$ is a substituted or unsubstituted aryl or a substituted or unsubstituted heteroaryl; and X is a C$_4$-C$_6$ unsubstituted n-alkyl or cycloalkyl or a C$_3$-C$_6$ unsubstituted branched alkyl, or a salt thereof, such as a pharmaceutically acceptable salt thereof, or solvate of the foregoing.

In one variation of formula (K-3), R$^1$, R$^2$ and R$^4$ are each H and R$^3$ is an unsubstituted C$_1$-C$_8$ alkyl (e.g., methyl) or halo (e.g., chloro). In another variation of formula (K-3), X is cyclohexyl, cyclobutyl, n-butyl or iso-propyl. In a particular variation of formula (K-3), R$^1$, R$^2$ and R$^4$ are each H; R$^3$ is an unsubstituted C$_1$-C$_8$ alkyl or halo and X is cyclohexyl, cyclobutyl, n-butyl or iso-propyl. In a further variation of formula (K-3), R$^8$ is a substituted aryl or an unsubstituted heteroaryl. In one aspect, R$^8$ of formula (K-3) is a substituted phenyl or an unsubstituted pyridyl. In a particular aspect, R$^8$ of formula (K-3) is 4-halo-phenyl or 4-pyridyl. In another variation of formula (K-3), R$^1$, R$^2$ and R$^4$ are each H; R$^3$ is an unsubstituted C$_1$-C$_8$ alkyl or halo; X is cyclohexyl, cyclobutyl, n-butyl and R$^8$ is a substituted phenyl. In another variation of formula (K-3), R$^1$, R$^2$ and R$^4$ are each H; R$^3$ is an unsubstituted C$_1$-C$_8$ alkyl or halo; X is isopropyl and R$^8$ is an unsubstituted pyridyl.

Compounds of the formula (K-4) are also provided:

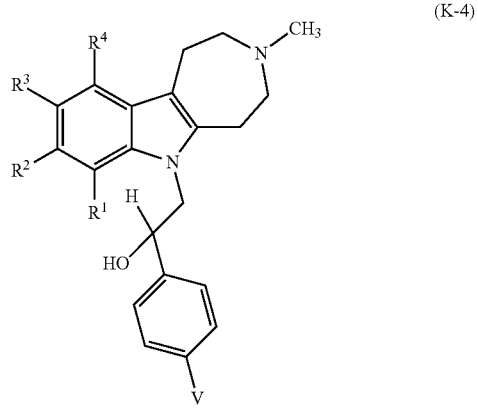

(K-4)

wherein:

R$^1$, R$^2$, R$^3$ and R$^4$ are as defined for formula (K-1); and

V is a halo, or a salt thereof, such as a pharmaceutically acceptable salt thereof, or solvate of the foregoing.

In one variation of formula (K-4), R$^1$, R$^2$ and R$^4$ are H and R$^3$ is unsubstituted C$_1$-C$_8$ alkyl such as methyl. In another variation of formula (K-4), V is fluoro.

Compounds of the formula (K-5) are also detailed herein:

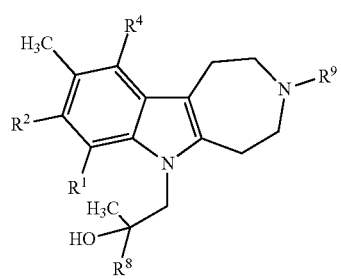

(K-5)

wherein:

R$^1$, R$^2$ and R$^4$ are as defined for formula (K-1); and

R$^8$ is 6-pyrimidyl, 3-methyl-4-pyridyl or a phenyl substituted either: (i) with at least one alkoxy or hydroxyl group or (ii) with at least two halo groups;

R$^9$ is an unsubstituted C$_1$-C$_3$ alkyl;

or a salt thereof, such as a pharmaceutically acceptable salt thereof, or solvate of the foregoing.

In one variation of formula (K-5), R$^1$, R$^2$ and R$^4$ are each H. In another variation of formula (K-5), R$^9$ is methyl. In a further variation of formula (K-5), R$^1$, R$^2$ and R$^4$ are each H and R$^9$ is methyl. In another variation of formula (K-5), R$^8$ is a phenyl substituted with at least one unsubstituted C$_1$-C$_8$ alkoxy group such as methoxy. In one aspect of formula (K-5), R$^1$, R$^2$ and R$^4$ are each H and R$^8$ is a methoxy-substituted phenyl. In another aspect of formula (K-5), R$^9$ is methyl and R$^8$ is a methoxy or hydroxyl-substituted phenyl. In another variation, R$^8$ is a phenyl substituted with at least two halo groups and R$^1$, R$^2$ and R$^4$ are each H.

Also provided are compounds of the formula (K-6):

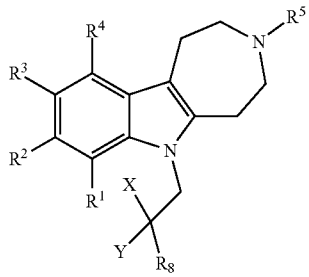

(K-6)

wherein:
R$^1$, R$^2$, R$^3$ and R$^4$ are as defined for formula (K-1);
R$^5$ is

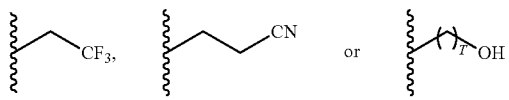

where T is 3 or 4;
X is H or OH;
Y is H or C$_1$-C$_8$ alkyl; and
R$^8$ is a substituted or unsubstituted heteroaryl,
or a salt thereof, such as a pharmaceutically acceptable salt thereof, or solvate of the foregoing.

In one variation of formula (K-6), R$^1$, R$^2$ and R$^4$ are H. In another variation of formula (K-6), R$^3$ is unsubstituted C$_1$-C$_8$ alkyl. In another variation of formula (K-6), R$^1$, R$^2$ and R$^4$ are H and R$^3$ is unsubstituted C$_1$-C$_8$ alkyl. In another variation of formula (K-6), R$^8$ is a substituted or unsubstituted pyridyl. When R$^8$ is an unsubstituted pyridyl, it may be bound to the parent structure at any available position, e.g., 4-pyridyl. When R$^8$ is a substituted pyridyl, in one aspect the pyridyl is substituted with an unsubstituted C$_1$-C$_8$ alkyl such as methyl. When R$^8$ is a substituted pyridyl, it may be bound to the parent structure at any available ring position, e.g., 6-methyl-3-pyridyl. In a particular variation of formula (K-6), R$^1$, R$^2$ and R$^4$ are H; R$^3$ is unsubstituted C$_1$-C$_8$ alkyl and R$^8$ is a substituted or unsubstituted pyridyl. In a further variation of formula (K-6), X and Y are both H. For example, in one aspect a compound is of the formula (K-6) where R$^1$, R$^2$ and R$^4$ are H; R$^3$ is unsubstituted C$_1$-C$_8$ alkyl and R$^8$ is a substituted or unsubstituted pyridyl and X and Y are both H.

Compounds of the formula (K-7) are also detailed herein:

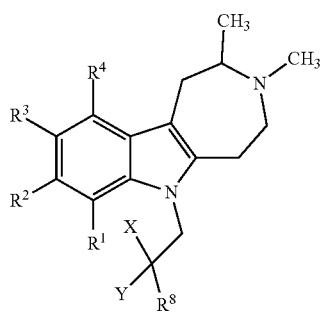

(K-7)

wherein:
R$^1$, R$^2$ and R$^4$ are as defined for formula (K-1);
R$^3$ is methyl or chloro, provided that R$^3$ is methyl when R$^8$ is a substituted heteroaryl;
X is H or OH;
Y is H or C$_1$-C$_8$ alkyl; and
R$^8$ is a substituted or unsubstituted heteroaryl,
or a salt thereof, such as a pharmaceutically acceptable salt thereof, or solvate of the foregoing.

In one aspect of formula (K-7), R$^1$, R$^2$ and R$^4$ are each H. In another aspect of formula (K-7), X is H and Y is an unsubstituted C$_1$-C$_8$ alkyl. In another aspect of formula (K-7), Y and Y are both H. In a particular variation of formula (K-7), R$^1$, R$^2$ and R$^4$ are each H and either (i) X and Y are both H or (ii) X is H and Y is an unsubstituted C$_1$-C$_8$ alkyl such as methyl. In a particular variation, R$^8$ is a substituted or unsubstituted pyridyl. In a specific variation of formula (K-7), R$^8$ is a substituted or unsubstituted pyridyl and either (i) X and Y are both H or (ii) X is H and Y is an unsubstituted C$_1$-C$_8$ alkyl.

Examples of compounds according to the invention are depicted in Table 2B. The compounds depicted may be present as salts even if salts are not depicted and it is understood that the invention embraces all salts and solvates of the compounds depicted here, as well as the non-salt and non-solvate form of the compound, as is well understood by the skilled artisan.

TABEL 2B

Representative Compounds According to the Invention.

| Compound | Structure |
|---|---|
| K-1 | 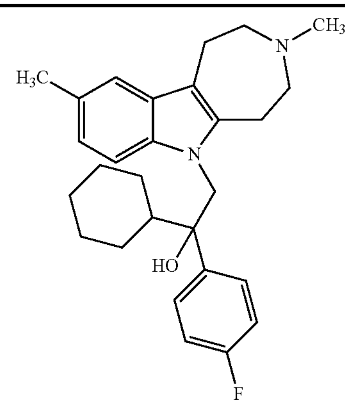 |
| K-2 | 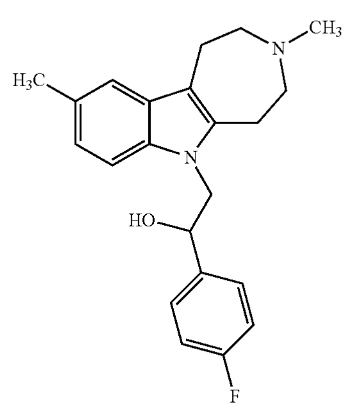 |

TABEL 2B-continued
Representative Compounds According to the Invention.
| Compound | Structure |
|---|---|
| K-3 | 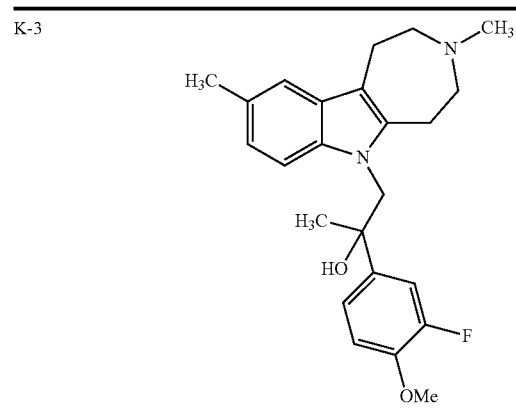 |
| K-4 | 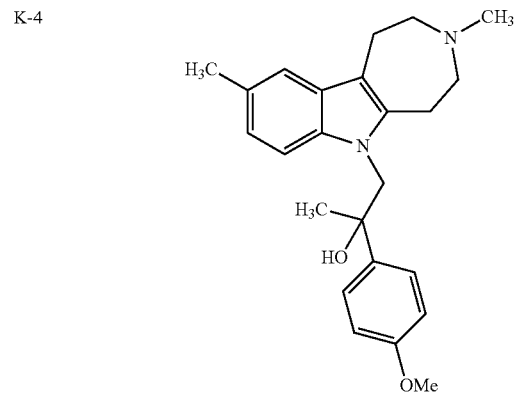 |
| K-5 | 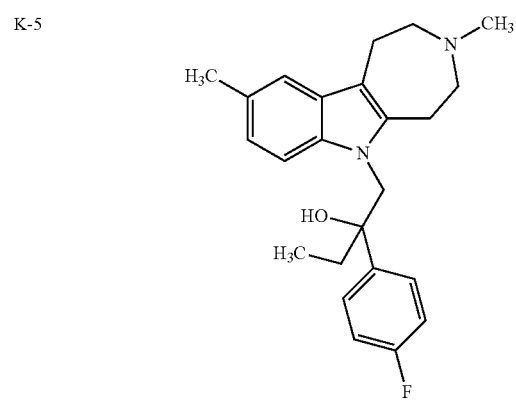 |
| K-6 | 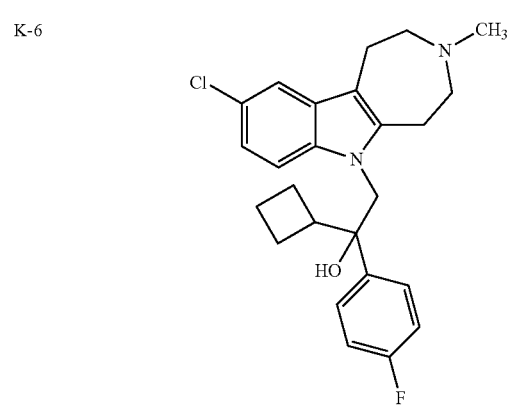 |
| K-7 | 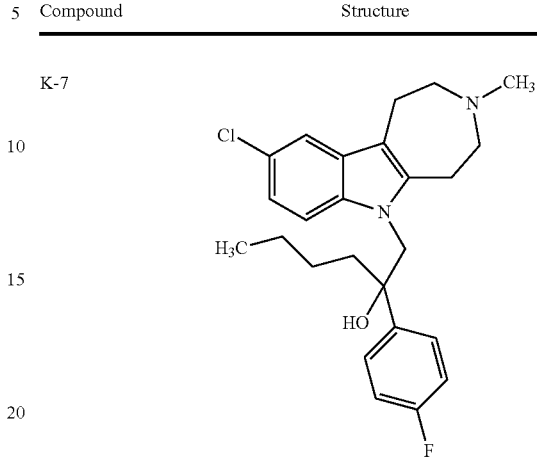 |
| K-8 | 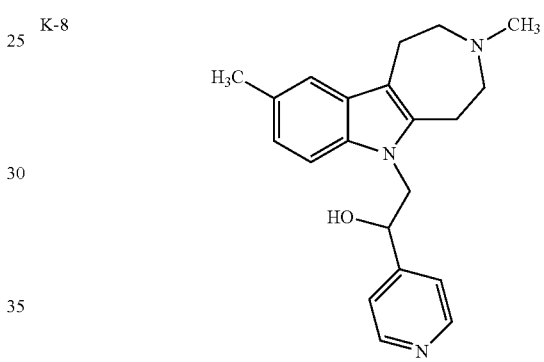 |
| K-9 | 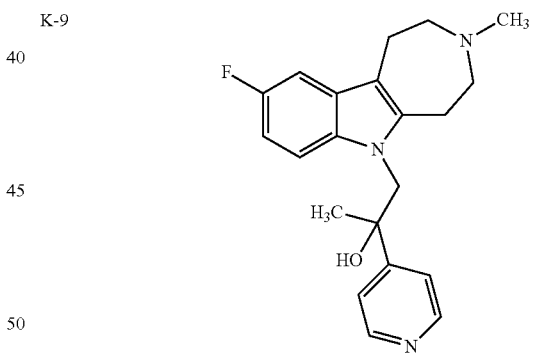 |
| K-10 | 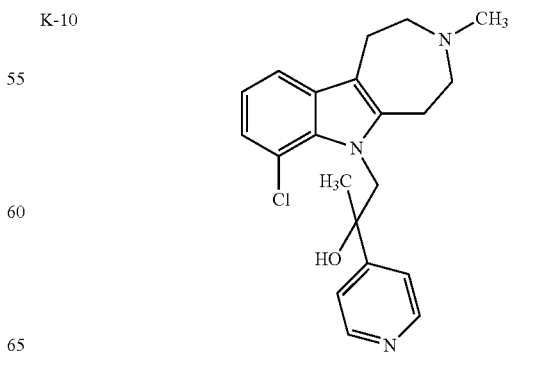 |

TABEL 2B-continued

Representative Compounds According to the Invention.

| Compound | Structure |
|---|---|
| K-11 | 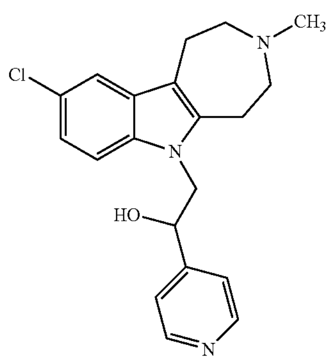 |
| K-12 | 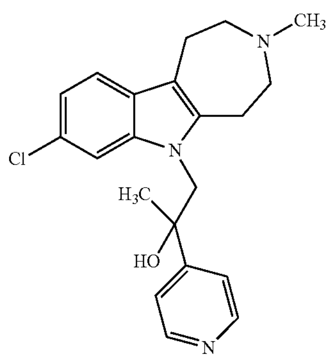 |
| K-13 | 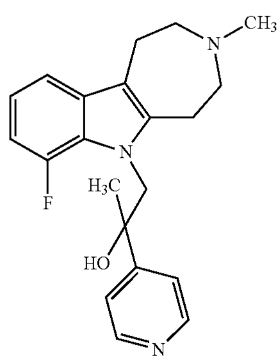 |
| K-14 | 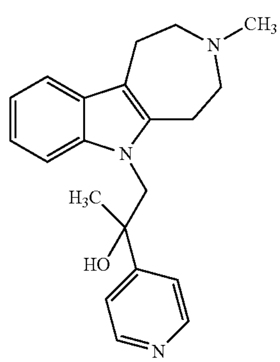 |
| K-15 | |
| K-16 | |
| K-17 | |
| K-18 | |

TABEL 2B-continued

Representative Compounds According to the Invention.

| Compound | Structure |
|---|---|
| K-19 | 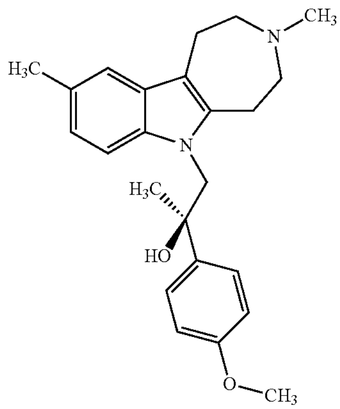 |
| K-20 | 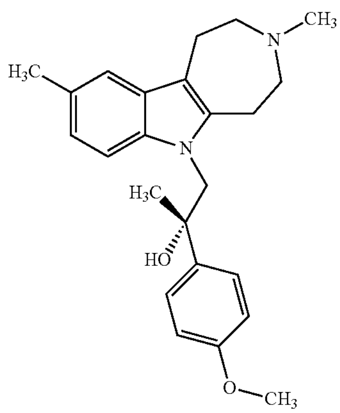 |
| K-21 | 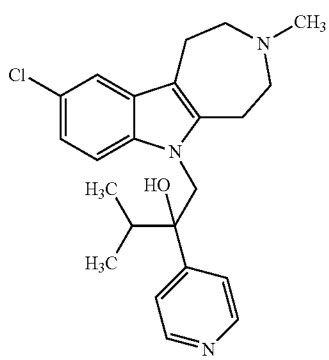 |
| K-22 | 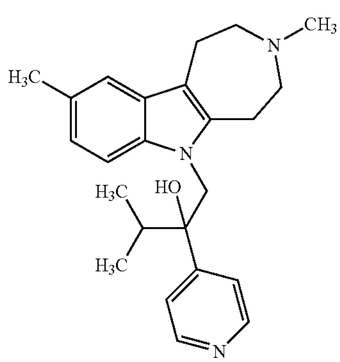 |
| K-23 | 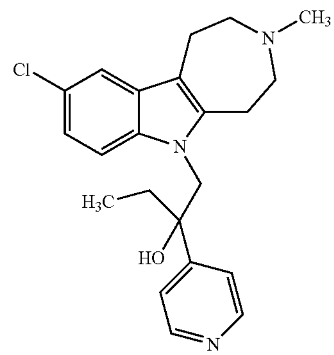 |
| K-24 | 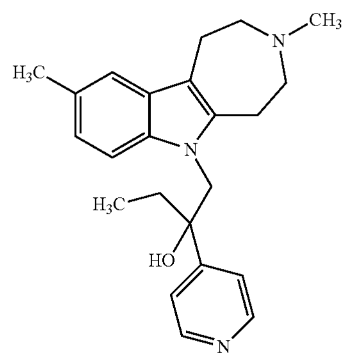 |
| K-25 | 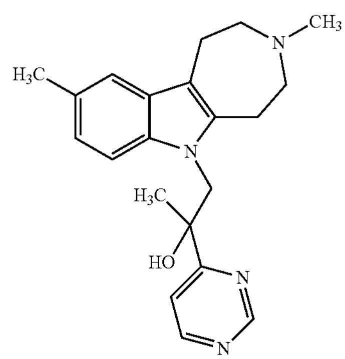 |
| K-26 | 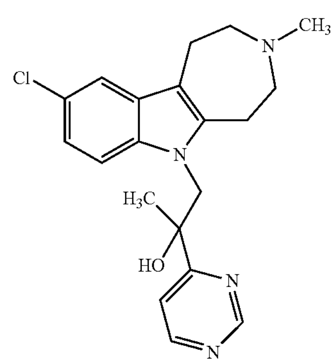 |

TABEL 2B-continued

Representative Compounds According to the Invention.

| Compound | Structure |
|---|---|
| K-27 | (structure) |
| K-28 | (structure) |
| K-29 | (structure) |
| K-30 | (structure) |
| K-31 | (structure) |
| K-32 | (structure) |
| K-33 | (structure) |
| K-34 | (structure) |

TABEL 2B-continued
Representative Compounds According to the Invention.
| Compound | Structure |
|---|---|
| K-35 | 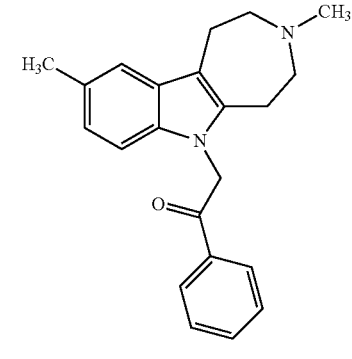 |
| K-36 | 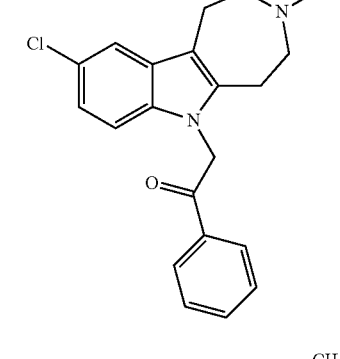 |
| K-37 | 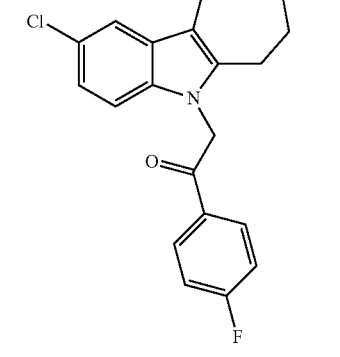 |
| K-38 | 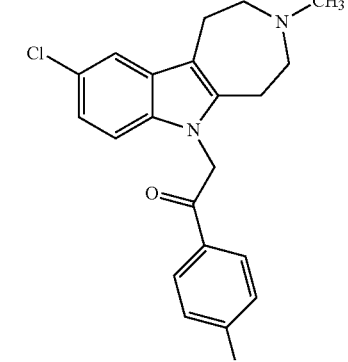 |
| K-39 | 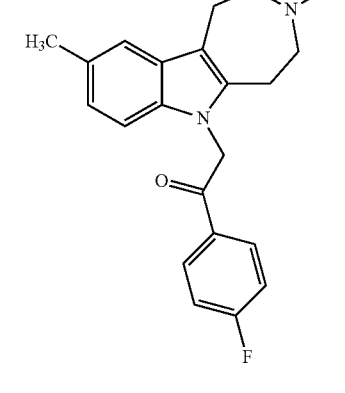 |
| K-40 | 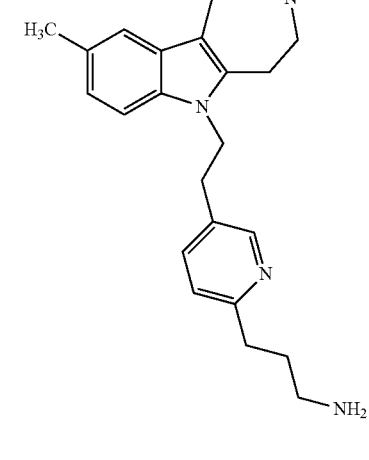 |
| K-41 | 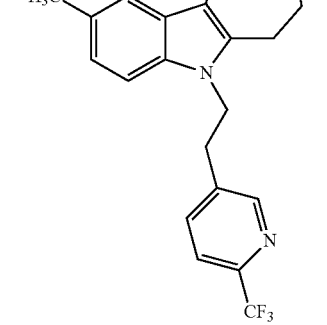 |

TABEL 2B-continued
Representative Compounds According to the Invention.
| Compound | Structure |
|---|---|
| K-42 | 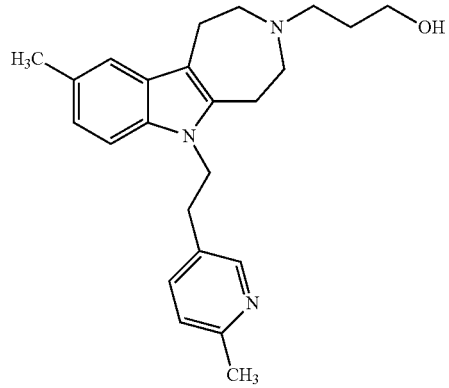 |
| K-43 | 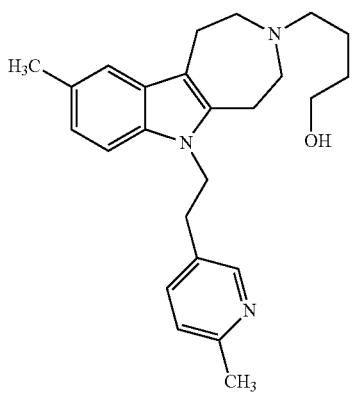 |
| K-44 | 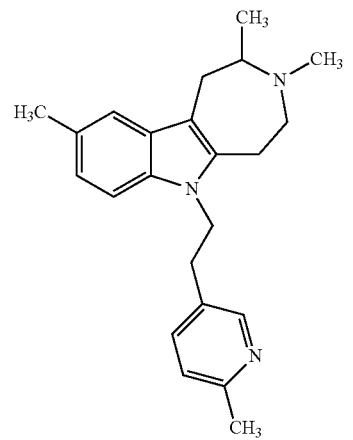 |
| K-45 | 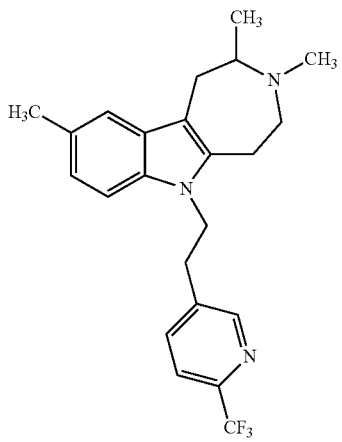 |
| K-46 | 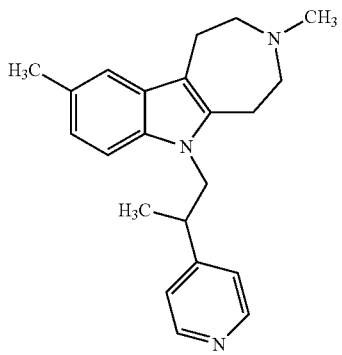 |
| K-47 | 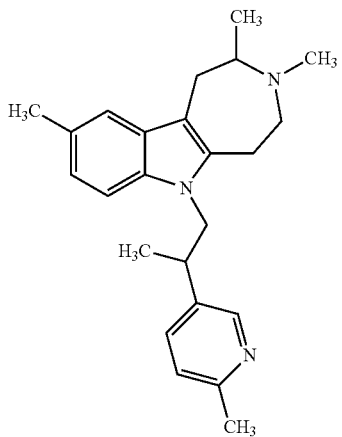 |

TABEL 2B-continued
Representative Compounds According to the Invention.
| Compound | Structure |
|---|---|
| K-48 | 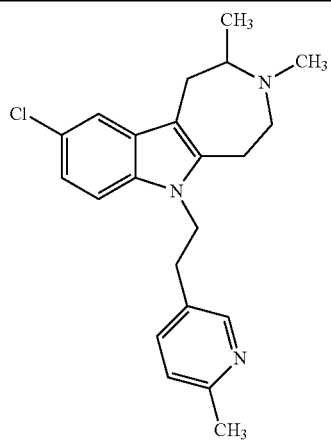 |
| K-49 | 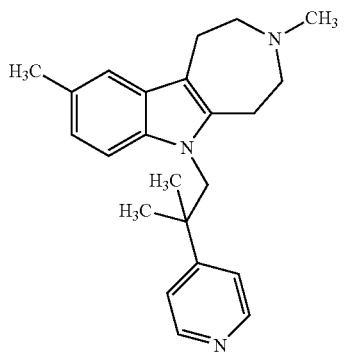 |
| K-50 | 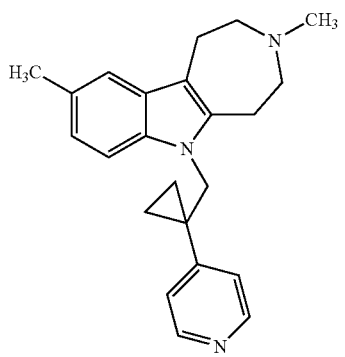 |
| K-51 | 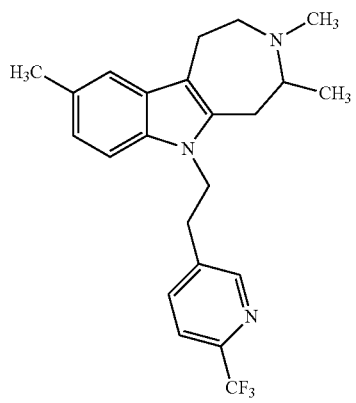 |
TABEL 2B-continued
Representative Compounds According to the Invention.
| Compound | Structure |
|---|---|
| K-52 | 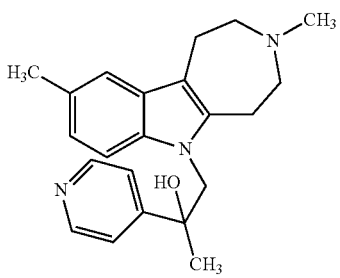 |
| K-53 | 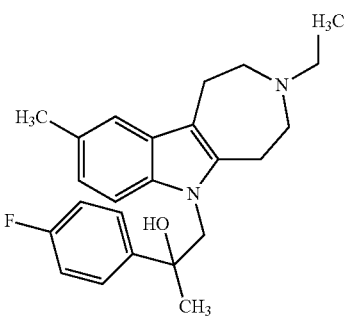 |
| K-54 | 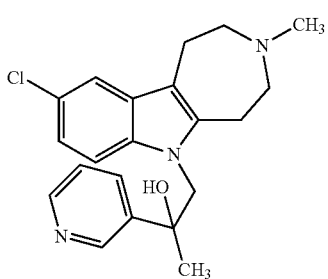 |
| K-55 | 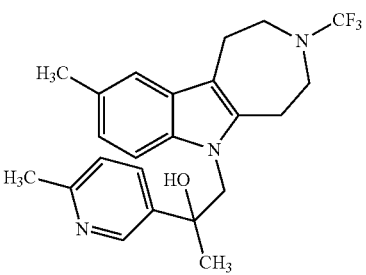 |
| K-56 | 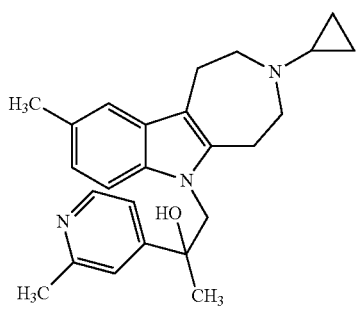 |

TABEL 2B-continued

Representative Compounds According to the Invention.

| Compound | Structure |
|---|---|
| K-57 | 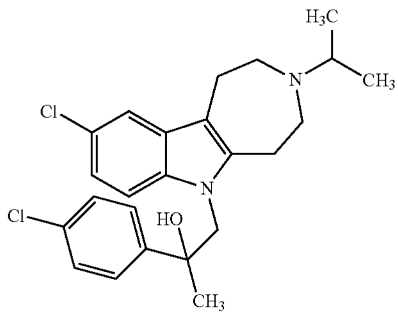 |
| K-58 | 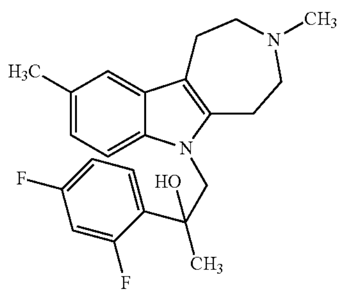 |
| K-59 | 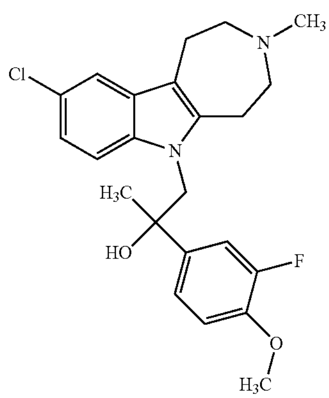 |

Compounds of the formula (L-1) are also provided:

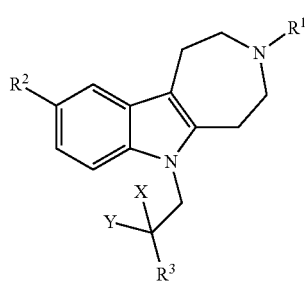

(L-1)

wherein:

R¹ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

R² is H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

X is OH, H, $C_1$-$C_8$ unsubstituted alkyl or is taken together with Y to form a cyclic moiety of the formula —OCH₂CH₂O—;

Y is halo, substituted or unsubstituted aryl, substituted or unsubstituted heteroaryl, $C_1$-$C_8$ alkyl substituted with a carbonylalkoxy, carboxyl or acylamino moiety or is taken together with X to form a cyclic moiety of the formula —OCH₂CH₂O—; and R³ is a substituted or unsubstituted aryl, substituted or unsubstituted heteroaryl, substituted or unsubstituted cycloalkyl, substituted or unsubstituted cycloalkenyl or a substituted or unsubstituted heterocyclyl;

or a salt or solvate thereof.

In one variation of formula (L-1), R¹ is $C_1$-$C_8$ unsubstituted alkyl; R² is $C_1$-$C_8$ unsubstituted alkyl, H or halo and R³ is a substituted or unsubstituted aryl or a substituted or unsubstituted heteroaryl. In a particular variation of formula (L-1), R¹ is methyl, ethyl or isopropyl; R² is methyl, H or chloro and R³ is a substituted or unsubstituted aryl or a substituted or unsubstituted heteroaryl. When R³ is an unsubstituted aryl in one variation it is a phenyl moiety. When R³ is a substituted aryl in one aspect it is a substituted phenyl. When R³ is a substituted phenyl, the phenyl may be substituted with one or more than one substituent. For example, on one variation, R³ is a monosubstituted phenyl where the substituent is a halo group. In another variation, R³ is a disubstituted phenyl substituent with two halo groups which may be the same or different. In a particular variation, R³ is 4-fluorophenyl, 2-fluorophenyl, 4-chlorophenyl, 2-chlorophenyl, 4-methoxyphenyl or 2,4-difluorophenyl. When R³ is an unsubstituted heteroaryl in one variation it is a heteroaryl containing an annular nitrogen atom. In one aspect, when R³ is unsubstituted heteroaryl the heteroaryl contains only nitrogen and carbon annular atoms. In a particular variation, R³ is an unsubstituted heteroaryl selected from pyridyl or pyrimidinyl and wherein such groups may be bound to the parent structure at any available ring position. For example, in one variation, R³ is 4-pyridyl, 3-pyridyl or 6-pyrimidyl. When R³ is a substituted heteroaryl in one aspect it is a substituted pyridyl. When R³ is a substituted pyridyl, the pyridyl may be substituted with one or more than one substituent and the substituted pyridyl may be bound to the parent structure at any available ring position. For example, on one variation, R³ is a monosubstituted pyridyl where the substituent is a $C_1$-$C_8$ unsubstituted alkyl (e.g., methyl). In a particular variation, R³ is 2-methyl-4-pyridyl, 6-methyl-3-pyridyl or 3-methyl-4-pyridyl.

In one variation of formula (L-1), X is OH and Y is an unsubstituted aryl. In one aspect, Y is phenyl. In another variation, X is H and Y is a $C_1$-$C_8$ alkyl substituted with a carbonylalkoxy, carboxyl or acylamino moiety. In one aspect, Y is a methylene substituted with a carbonylalkoxy, carboxyl or acylamino moiety. In a particular aspect, Y is a moiety selected from the following structures

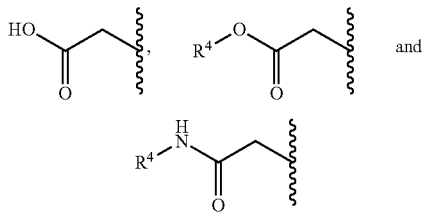

where $R^4$ is a $C_1$-$C_8$ unsubstituted alkyl. In one variation, Y is a moiety selected from the following structures

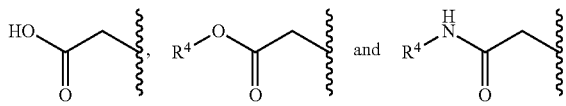

where $R^4$ is a $C_1$-$C_8$ unsubstituted alkyl and X is H. In another variation, X is an unsubstituted $C_1$-$C_8$ alkyl and Y is halo. In a particular aspect, Y is fluoro.

The invention also embraces compounds of the formula (L-2):

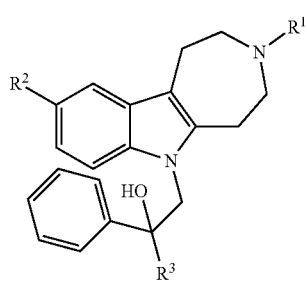

(L-2)

or a salt or solvate thereof, where $R^1$, $R^2$ and $R^3$ are as defined for formula (L-1). In one variation of formula (L-2), $R^1$ and $R^2$ are independently an unsubstituted $C_1$-$C_8$ alkyl. In another variation of formula (L-2), $R^3$ is a substituted aryl, such as a substituted phenyl group, or an unsubstituted heteroaryl, such as pyridyl. In one aspect, $R^3$ is a halo substituted phenyl or pyridyl moiety. When $R^3$ is a halo substituted phenyl, in a particular variation the phenyl is substituted with a fluoro that may be at any position on the phenyl ring. When $R^3$ is a pyridyl group it may be bound to the parent structure at any available ring position. In a particular aspect, $R^3$ is 4-pyridyl. In a particular variation of formula (L-2), $R^1$ and $R^2$ are independently an unsubstituted $C_1$-$C_8$ alkyl and $R^3$ is a substituted aryl or an unsubstituted heteroaryl. In one variation, $R^1$ and $R^2$ are each methyl and $R^3$ is a substituted aryl or unsubstituted heteroaryl. In a particular variation of formula (L-2), $R^1$ and $R^2$ are each methyl and $R^3$ is a fluoro substituted phenyl or pyridyl moiety.

The invention also embraces compounds of the formula (L-3):

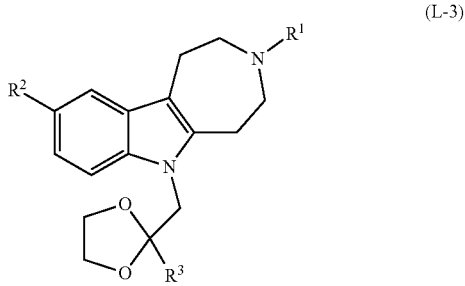

(L-3)

or a salt or solvate thereof, where $R^1$, $R^2$ and $R^3$ are as defined for formula (L-1). In one variation of formula (L-3), $R^1$ is an unsubstituted $C_1$-$C_8$ alkyl (e.g., methyl). In another variation of formula (L-3), $R^2$ is H, an unsubstituted $C_1$-$C_8$ alkyl (e.g., methyl) or halo (e.g., chloro). In one aspect of formula (L-3), $R^1$ is an unsubstituted $C_1$-$C_8$ alkyl and $R^2$ is H, an unsubstituted $C_1$-$C_8$ alkyl or halo. In a particular variation of formula (L-3), $R^1$ is methyl and $R^2$ is H, methyl or chloro. In one variation of formula (L-3), $R^1$ and $R^2$ are independently an unsubstituted $C_1$-$C_8$ alkyl such as methyl. In one variation of formula (L-3), $R^3$ is a substituted or unsubstituted aryl or a substituted or unsubstituted heteroaryl, such as those listed herein for formula (L-1). For example, compounds of the formula (L-3) are intended wherein $R^3$ is an unsubstituted aryl, which in one variation is a phenyl moiety. Compounds of the formula (L-3) are also intended wherein $R^3$ is a substituted aryl, which in one aspect it is a substituted phenyl. When $R^3$ is a substituted phenyl, the phenyl may be substituted with one or more than one substituent. For example, on one variation, $R^3$ is a monosubstituted phenyl where the substituent is a halo group. In another variation, $R^3$ is a disubstituted phenyl substituent with two halo groups which may be the same or different. In a particular variation, $R^3$ is 4-fluorophenyl, 2-fluorophenyl, 4-chlorophenyl, 2-chlorophenyl, 4-methoxyphenyl or 2,4-difluorophenyl. Compounds of formula (L-3) are provided where $R^3$ is an unsubstituted heteroaryl, which in one variation is a heteroaryl containing an annular nitrogen atom. In one aspect, when $R^3$ is unsubstituted heteroaryl the heteroaryl contains only nitrogen and carbon annular atoms. In a particular variation of formula (L-3), $R^3$ is an unsubstituted heteroaryl selected from pyridyl or pyrimidinyl and wherein such groups may be bound to the parent structure at any available ring position. For example, in one variation of formula (L-3), $R^3$ is 4-pyridyl, 3-pyridyl or 6-pyrimidyl. When $R^3$ is a substituted heteroaryl in one aspect it is a substituted pyridyl. When $R^3$ is a substituted pyridyl, the pyridyl may be substituted with one or more than one substituent and the substituted pyridyl may be bound to the parent structure at any available ring position. For example, in one variation of formula (L-3), $R^3$ is a monosubstituted pyridyl where the substituent is a $C_1$-$C_8$ unsubstituted alkyl (e.g., methyl). In a particular variation of formula (L-3), $R^3$ is 2-methyl-4-pyridyl, 6-methyl-3-pyridyl or 3-methyl-4-pyridyl. In another variation of formula (L-3), $R^3$ is a substituted aryl, such as a substituted phenyl group. In one aspect, $R^3$ is a halo substituted phenyl. When $R^3$ is a halo substituted phenyl, in a particular variation the phenyl is substituted with a fluoro or chloro that may be at any position on the phenyl ring. In a further variation of formula (L-3), $R^1$ is an unsubstituted $C_1$-$C_8$ alkyl; $R^2$ is H, an unsubstituted $C_1$-$C_8$ alkyl or halo and $R^3$ is a substituted or unsubstituted phenyl, a substituted or unsubstituted pyridyl or an unsubstituted pyrimidyl. In a particular variation, compounds of formula (L-3) are provided where $R^1$ is methyl, $R^2$ is H, methyl or chloro and $R^3$ is a substituted or unsubstituted phenyl, a substituted or unsubstituted pyridyl or an unsubstituted pyrimidyl.

Compounds of the formula (L-4) are also provided:

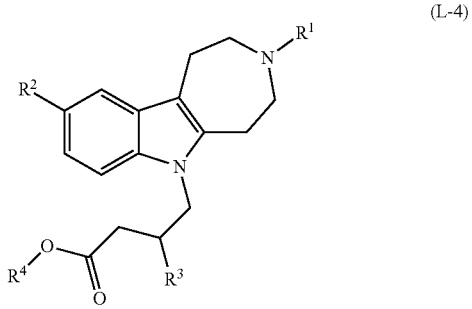

(L-4)

or a salt or solvate thereof, where $R^1$, $R^2$ and $R^3$ are as detailed for formula (L-1) and $R^4$ is an unsubstituted $C_1$-$C_8$ alkyl. In one variation of formula (L-4), $R^1$ is an unsubstituted $C_1$-$C_8$ alkyl. In one variation of formula (L-4), $R_2$ is an unsubstituted $C_1$-$C_8$ alkyl or halo. In one variation of formula (L-4), $R^1$ and $R^2$ are independently an unsubstituted $C_1$-$C_8$ alkyl (e.g., methyl or ethyl). In one variation of formula (L-4), $R^1$ is an unsubstituted $C_1$-$C_8$ alkyl (e.g., methyl or ethyl) and $R^2$ is an unsubstituted $C_1$-$C_8$ alkyl or halo. In a particular variation of formula (L-4), $R^4$ is a $C_1$-$C_4$ unsubstituted alkyl. In a further variation of formula (L-4), $R^4$ is methyl, ethyl, propyl or butyl. In one aspect, $R^4$ is iso-propyl. In another aspect, $R^4$ is tert-butyl. In a particular variation of formula (L-4), $R^1$ is an unsubstituted $C_1$-$C_8$ alkyl; $R^2$ is an unsubstituted $C_1$-$C_8$ alkyl or halo and $R^4$ is a $C_1$-$C_4$ unsubstituted alkyl. In another variation of formula (L-4), $R^3$ is a substituted or unsubstituted aryl or a substituted or unsubstituted heteroaryl, such as those listed herein for formula (L-1). For example, compounds of the formula (L-4) are intended wherein $R^3$ is a substituted aryl, which in one aspect it is a substituted phenyl. When $R^3$ is a substituted phenyl, the phenyl may be substituted with one or more than one substituent. For example, on one variation, $R^3$ is a monosubstituted phenyl where the substituent is a halo group. In another variation, $R^3$ is a dihalosubstituted phenyl wherein the halo moieties may be the same or different. In a particular variation, $R^3$ is 4-fluorophenyl, 4-chlorophenyl, 2,4-difluorophenyl or 4-methoxyphenyl. Compounds of formula (L-4) are also provided where $R^3$ is an unsubstituted heteroaryl, which in one variation is a heteroaryl containing an annular nitrogen atom. In one aspect, when $R^3$ is unsubstituted heteroaryl the heteroaryl contains only nitrogen and carbon annular atoms. In a particular variation of formula (L-4), $R^3$ is an unsubstituted heteroaryl selected from pyridyl or pyrimidinyl and wherein such groups may be bound to the parent structure at any available ring position. For example, in one variation of formula (L-4), $R^3$ is 4-pyridyl, 3-pyridyl or 6-pyrimidyl. When $R^3$ is a substituted heteroaryl in one aspect it is a substituted pyridyl. When $R^3$ is a substituted pyridyl, the pyridyl may be substituted with one or more than one substituent and the substituted pyridyl may be bound to the parent structure at any available ring position. For example, in one variation of formula (L-4), $R^3$ is a monosubstituted pyridyl where the substituent is a $C_1$-$C_8$ unsubstituted alkyl (e.g., methyl). In a particular variation of formula (L-4), $R^3$ is 2-methyl-4-pyridyl, 6-methyl-3-pyridyl or 3-methyl-4-pyridyl. In a further variation of formula (L-4), $R^1$ is an unsubstituted $C_1$-$C_8$ alkyl; $R^2$ is an unsubstituted $C_1$-$C_8$ alkyl or halo; $R^4$ is a $C_1$-$C_4$ unsubstituted alkyl and $R^3$ is a substituted phenyl, a substituted or unsubstituted pyridyl or an unsubstituted pyrimidyl. In a particular variation, compounds of formula (L-4) are provided where $R^1$ is methyl or ethyl, $R^2$ is methyl or chloro; $R^4$ is methyl, ethyl, isopropyl or tert-butyl and $R^3$ is a substituted phenyl, a substituted or unsubstituted pyridyl or an unsubstituted pyrimidyl.

Also provided herein are compounds of the formula (L-5):

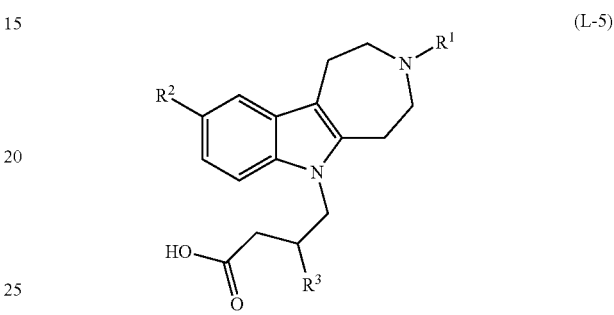

(L-5)

or a salt of solvate thereof, where $R^1$, $R^2$ and $R^3$ are as detailed for formula (L-1). In one variation of formula (L-5), $R^1$ is an unsubstituted $C_1$-$C_8$ alkyl (e.g., methyl). In another variation of formula (L-5), $R^2$ is unsubstituted $C_1$-$C_8$ alkyl (e.g., methyl) or halo (e.g., chloro). In a particular variation of formula (L-5), $R^1$ is an unsubstituted $C_1$-$C_8$ alkyl and $R^2$ is unsubstituted $C_1$-$C_8$ alkyl or halo. In another variation of formula (L-5), $R^1$ and $R^2$ are independently an unsubstituted $C_1$-$C_8$ alkyl (e.g., methyl). In one variation of formula (L-5), $R^3$ is a substituted or unsubstituted aryl or a substituted or unsubstituted heteroaryl, such as those listed herein for formula (L-1). For example, compounds of the formula (L-5) are intended wherein $R^3$ is a substituted aryl, which in one aspect it is a substituted phenyl. When $R^3$ is a substituted phenyl, the phenyl may be substituted with one or more than one substituent. For example, on one variation, $R^3$ is a monosubstituted phenyl where the substituent is a halo group. In another variation, $R^3$ is a disubstituted phenyl substituent with two halo groups which may be the same or different. In a particular variation, $R^3$ is 4-fluorophenyl, 2-fluorophenyl, 4-chlorophenyl, 4-methoxyphenyl or 2,4-difluorophenyl. Compounds of formula (L-5) are also provided where $R^3$ is an unsubstituted heteroaryl, which in one variation is a heteroaryl containing an annular nitrogen atom. In one aspect, when $R^3$ is unsubstituted heteroaryl the heteroaryl contains only nitrogen and carbon annular atoms. In a particular variation of formula (L-5), $R^3$ is an unsubstituted heteroaryl selected from pyridyl or pyrimidinyl and wherein such groups may be bound to the parent structure at any available ring position. For example, in one variation of formula (L-5), $R^3$ is 4-pyridyl, 3-pyridyl or 6-pyrimidyl. When $R^3$ is a substituted heteroaryl in one aspect it is a substituted pyridyl. When $R^3$ is a substituted pyridyl, the pyridyl may be substituted with one or more than one substituent and the substituted pyridyl may be bound to the parent structure at any available ring position. For example, in one variation of formula (L-5), $R^3$ is a monosubstituted pyridyl where the substituent is a $C_1$-$C_8$ unsubstituted alkyl (e.g., methyl). In a particular variation of formula (L-5), $R^3$ is 2-methyl-4-pyridyl, 6-methyl-3-pyridyl or 3-methyl-4-pyridyl. In one variation of formula (L-5), $R^1$ is an unsubstituted $C_1$-$C_8$ alkyl, $R^2$ is unsubstituted $C_1$-$C_8$ alkyl or halo and $R^3$ is a substituted phenyl, a substituted or unsubstituted pyridyl or an unsubstituted pyrimidyl. In a particular variation of formula (L-5), $R^1$ and $R^2$ are independently an unsubstituted $C_1$-$C_8$ alkyl and $R^3$ is a substituted phenyl, a substituted or unsubstituted pyridyl or an unsubstituted pyrimidyl.

Additional compounds detailed herein are of the formula (L-6):

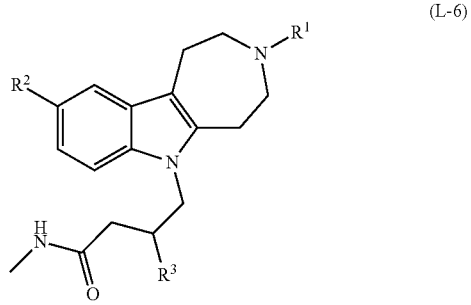

(L-6)

or a salt of solvate thereof, where $R^1$, $R^2$ and $R^3$ are as detailed for formula (L-1). In one variation of formula (L-6), $R^1$ is an unsubstituted $C_1$-$C_8$ alkyl (e.g., methyl or ethyl). In another variation of formula (L-6), $R^2$ is unsubstituted $C_1$-$C_8$ alkyl (e.g., methyl) or halo (e.g., chloro). In a particular variation of formula (L-6), $R^1$ is an unsubstituted $C_1$-$C_8$ alkyl and $R^2$ is unsubstituted $C_1$-$C_8$ alkyl or halo. In another variation of formula (L-6), $R^1$ and $R^2$ are independently an unsubstituted $C_1$-$C_8$ alkyl. In one variation of formula (L-6), $R^3$ is a substituted or unsubstituted aryl or a substituted or unsubstituted heteroaryl, such as those listed herein for formula (L-1). For example, compounds of the formula (L-6) are intended wherein $R^3$ is a substituted aryl, which in one aspect it is a substituted phenyl. When $R^3$ is a substituted phenyl, the phenyl may be substituted with one or more than one substituent. For example, on one variation, $R^3$ is a monosubstituted phenyl where the substituent is a halo group. In another variation, $R^3$ is a disubstituted phenyl substituent with two halo groups which may be the same or different. In a particular variation, $R^3$ is 4-fluorophenyl, 2-fluorophenyl, 4-chlorophenyl, 4-methoxyphenyl or 2,4-difluorophenyl. Compounds of formula (L-6) are also provided where $R^3$ is an unsubstituted heteroaryl, which in one variation is a heteroaryl containing an annular nitrogen atom. In one aspect, when $R^3$ is unsubstituted heteroaryl the heteroaryl contains only nitrogen and carbon annular atoms. In a particular variation of formula (L-6), $R^3$ is an unsubstituted heteroaryl selected from pyridyl or pyrimidinyl and wherein such groups may be bound to the parent structure at any available ring position. For example, in one variation of formula (L-6), $R^3$ is 4-pyridyl, 3-pyridyl or 6-pyridyl. When $R^3$ is a substituted heteroaryl in one aspect it is a substituted pyridyl. When $R^3$ is a substituted pyridyl, the pyridyl may be substituted with one or more than one substituent and the substituted pyridyl may be bound to the parent structure at any available ring position. For example, in one variation of formula (L-6), $R^3$ is a monosubstituted pyridyl where the substituent is a $C_1$-$C_8$ unsubstituted alkyl (e.g., methyl). In a particular variation of formula (L-6), $R^3$ is 2-methyl-4-pyridyl, 6-methyl-3-pyridyl or 3-methyl-4-pyridyl. In one variation of formula (L-6), $R^1$ is an unsubstituted $C_1$-$C_8$ alkyl, $R^2$ is unsubstituted $C_1$-$C_8$ alkyl or halo and $R^3$ is a substituted phenyl, a substituted or pyridyl or an unsubstituted pyrimidyl.

Compounds of the formula (L-7) are also detailed herein:

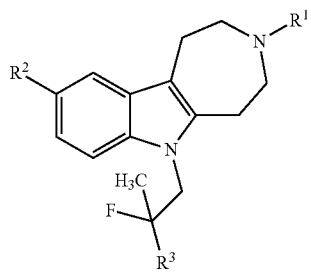

(L-7)

or a salt or solvate thereof, where $R^1$, $R^2$ and $R^3$ are as defined for formula (L-1). In one variation of formula (L-7), $R^1$ is an unsubstituted $C_1$-$C_8$ alkyl (e.g., methyl, ethyl or isopropyl). In another variation of formula (L-7), $R^2$ is unsubstituted $C_1$-$C_8$ alkyl (e.g., methyl) or halo (e.g., chloro). In a particular variation of formula (L-7), $R^1$ is an unsubstituted $C_1$-$C_8$ alkyl and $R^2$ is unsubstituted $C_1$-$C_8$ alkyl or halo. In another variation of formula (L-7), $R^1$ and $R^2$ are independently an unsubstituted $C_1$-$C_8$ alkyl. In one variation of formula (L-7), $R^3$ is a substituted or unsubstituted aryl or a substituted or unsubstituted heteroaryl, such as those listed herein for formula (L-1). For example, compounds of the formula (L-7) are intended wherein $R^3$ is a substituted aryl, which in one aspect it is a substituted phenyl. When $R^3$ is a substituted phenyl, the phenyl may be substituted with one or more than one substituent. For example, on one variation, $R^3$ is a monosubstituted phenyl where the substituent is a halo group. In another variation, $R^3$ is a disubstituted phenyl substituent with two halo groups which may be the same or different. In a particular variation, $R^3$ is 4-fluorophenyl, 4-chlorophenyl, 4-methoxyphenyl or 2,4-difluorophenyl. Compounds of formula (L-7) are also provided where $R^3$ is an unsubstituted heteroaryl, which in one variation is a heteroaryl containing an annular nitrogen atom. In one aspect, when $R^3$ is unsubstituted heteroaryl the heteroaryl contains only nitrogen and carbon annular atoms. In a particular variation of formula (L-7), $R^3$ is an unsubstituted heteroaryl selected from pyridyl or pyrimidinyl and wherein such groups may be bound to the parent structure at any available ring position. For example, in one variation of formula (L-7), $R^3$ is 4-pyridyl, 3-pyridyl or 6-pyridyl. When $R^3$ is a substituted heteroaryl in one aspect it is a substituted pyridyl. When $R^3$ is a substituted pyridyl, the pyridyl may be substituted with one or more than one substituent and the substituted pyridyl may be bound to the parent structure at any available ring position. For example, in one variation of formula (L-7), $R^3$ is a monosubstituted pyridyl where the substituent is a $C_1$-$C_8$ unsubstituted alkyl (e.g., methyl). In a particular variation of formula (L-7), $R^3$ is 6-methyl-3-pyridyl or 3-methyl-4-pyridyl. In one variation of formula (L-7), $R^1$ is an unsubstituted $C_1$-$C_8$ alkyl, $R^2$ is unsubstituted $C_1$-$C_8$ alkyl or halo and $R^3$ is a substituted phenyl, a substituted or pyridyl or an unsubstituted pyrimidyl.

Compounds of the formula (L-8) are also provided:

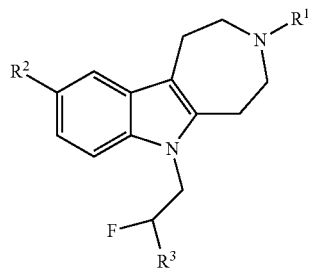
(L-8)

or a salt or solvate thereof, where $R^1$, $R^2$ and $R^3$ are as defined for formula (L-1). In one variation of formula (L-8), $R^1$ and $R^2$ are each a $C_1$-$C_8$ unsubstituted alkyl group. In another variation of formula (L-8), $R^3$ is an unsubstituted heteroaryl such as pyridyl. In a particular variation of formula (L-8), $R^1$ and $R^2$ are each a $C_1$-$C_8$ unsubstituted alkyl group and $R^3$ is an unsubstituted heteroaryl.

Examples of compounds according to the invention are depicted in Table 2C. The compounds depicted may be present as salts even if salts are not depicted and it is understood that the invention embraces all salts and solvates of the compounds depicted here, as well as the non-salt and non-solvate form of the compound, as is well understood by the skilled artisan.

TABLE 2C-continued

Representative Compounds According to the Invention.

| Compound | Structure |
|---|---|
| L-7 | (structure) |
| L-8 | (structure) |
| L-9 | (structure) |
| L-10 | (structure) |
| L-11 | (structure) |
| L-12 | (structure) |
| L-13 | (structure) |
| L-14 | (structure) |

TABLE 2C-continued

Representative Compounds According to the Invention.

| Compound | Structure |
|---|---|
| L-15 | 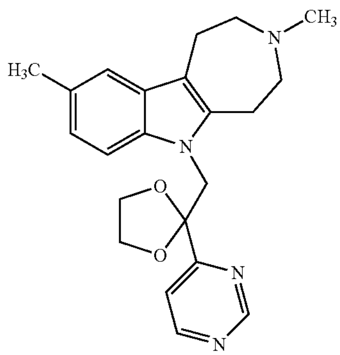 |
| L-16 | 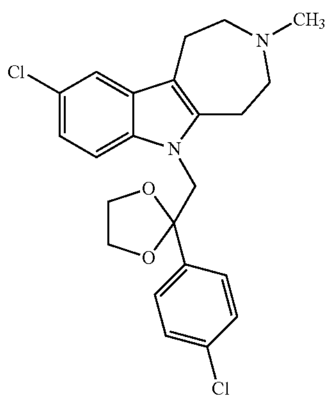 |
| L-17 | 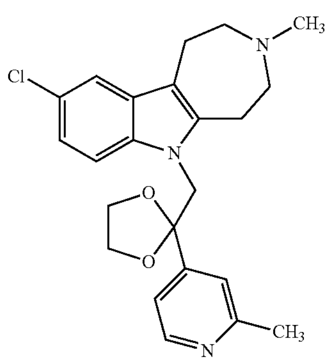 |
| L-18 | 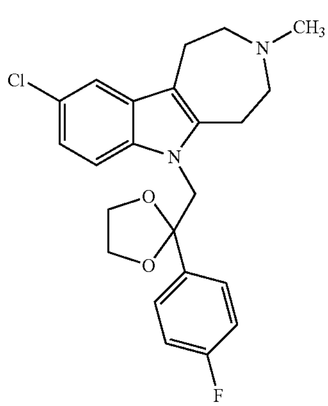 |
| L-19 | |
| L-20 | |
| L-21 | |
| L-22 | |

TABLE 2C-continued
Representative Compounds According to the Invention.
| Compound | Structure |
|---|---|
| L-23 | 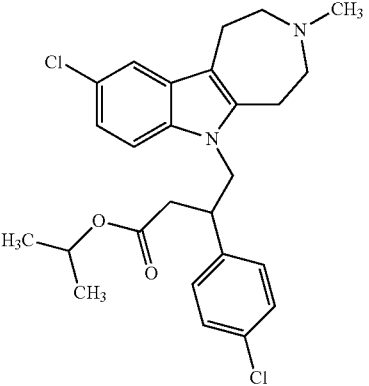 |
| L-24 | 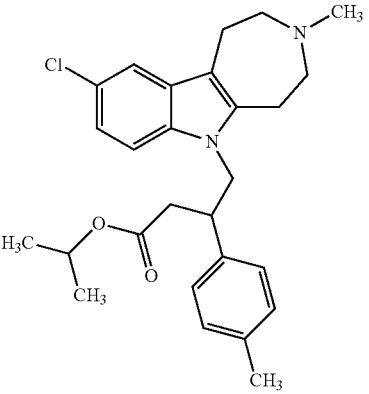 |
| L-25 | 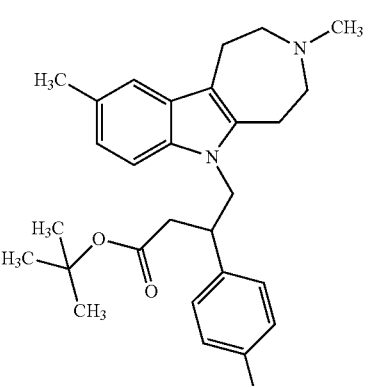 |
| L-26 | 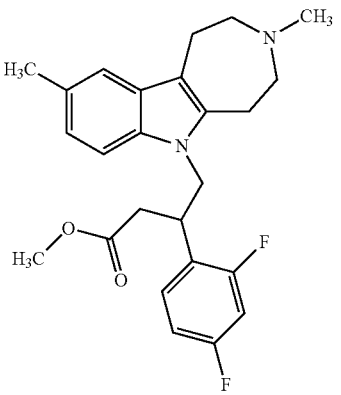 |
| L-27 | 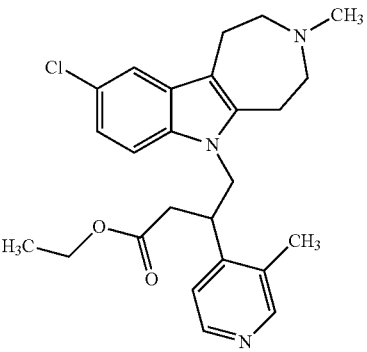 |
| L-28 | 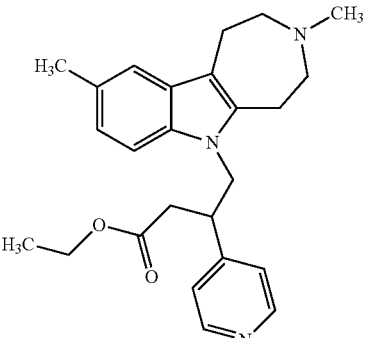 |
| L-29 | 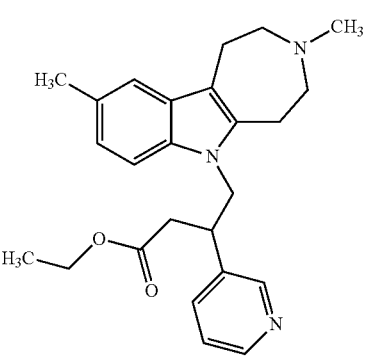 |

TABLE 2C-continued

Representative Compounds According to the Invention.

| Compound | Structure |
|---|---|
| L-30 | (structure) |
| L-31 | (structure) |
| L-32 | (structure) |
| L-33 | (structure) |
| L-34 | (structure) |
| L-35 | (structure) |
| L-36 | (structure) |
| L-37 | (structure) |

TABLE 2C-continued
Representative Compounds According to the Invention.
| Compound | Structure |
|---|---|
| L-38 | 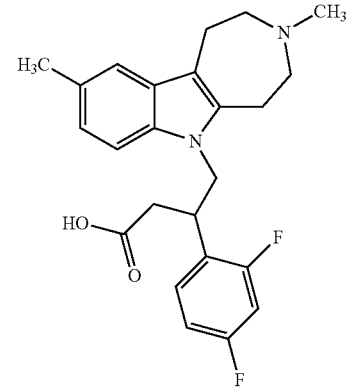 |
| L-39 | 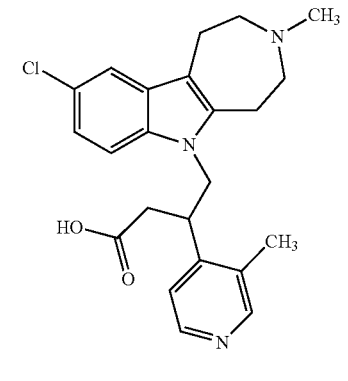 |
| L-40 | 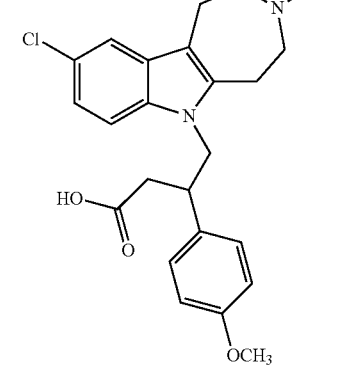 |
| L-41 | 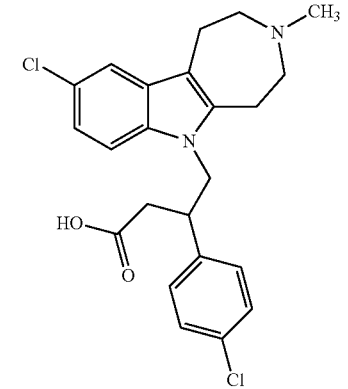 |
| L-42 | 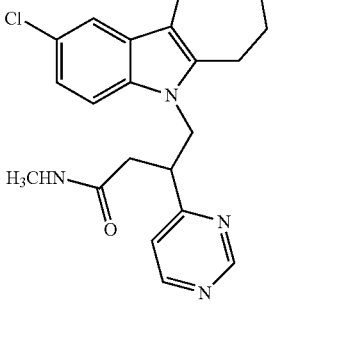 |
| L-43 | 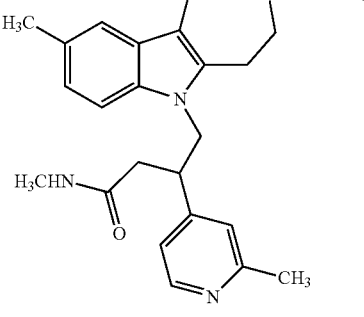 |
| L-44 | 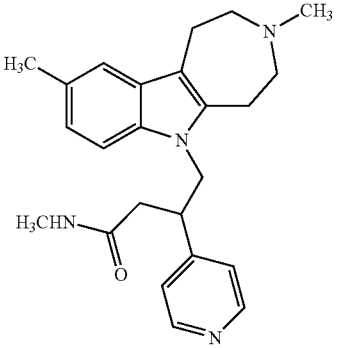 |
| L-45 | 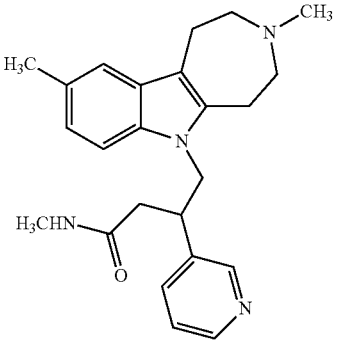 |

TABLE 2C-continued
Representative Compounds According to the Invention.
| Compound | Structure |
|---|---|
| L-46 | 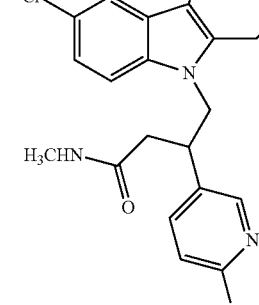 |
| L-47 | 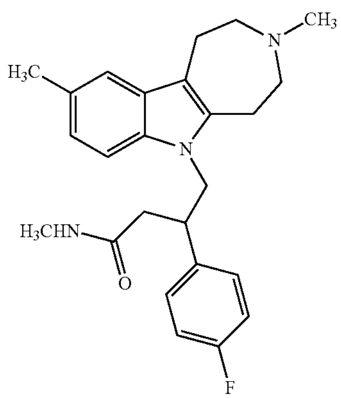 |
| L-48 | 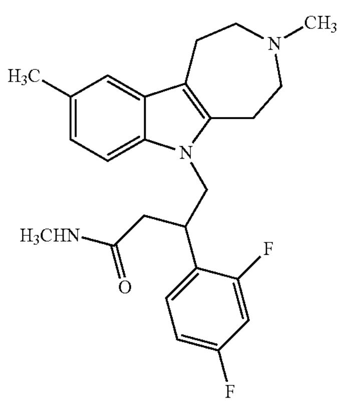 |
| L-49 | 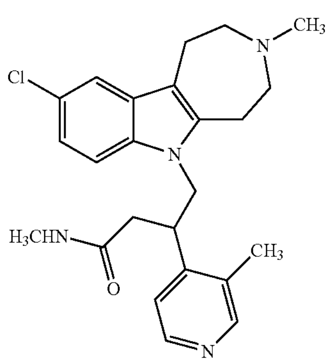 |
| L-50 | 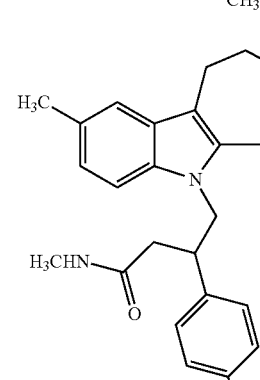 |
| L-51 | 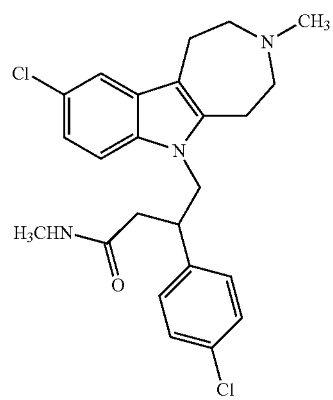 |
| L-52 | 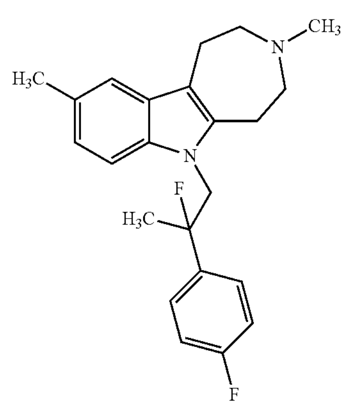 |

TABLE 2C-continued

Representative Compounds According to the Invention.

| Compound | Structure |
|---|---|
| L-53 | 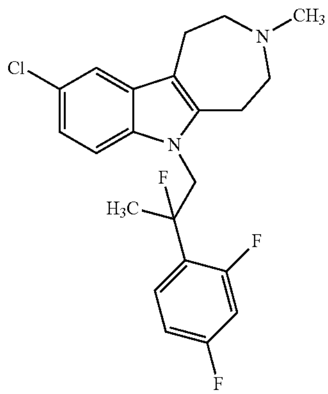 |
| L-54 | 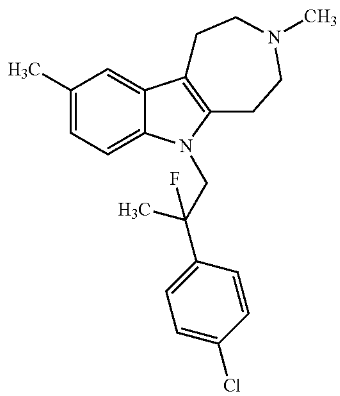 |
| L-55 | 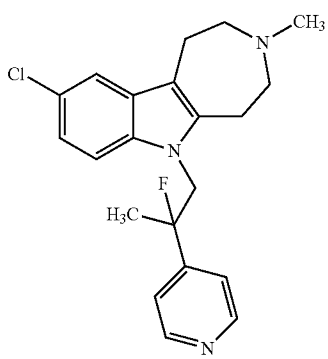 |
| L-56 | 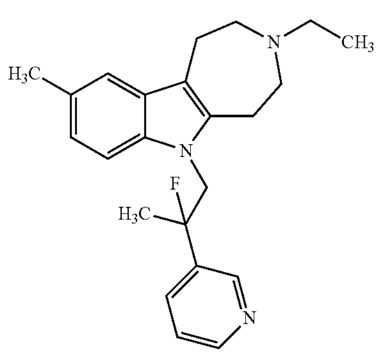 |
| L-57 | |
| L-58 | |
| L-59 | |
| L-60 | |

TABLE 2C-continued

Representative Compounds According to the Invention.

| Compound | Structure |
|---|---|
| L-61 | 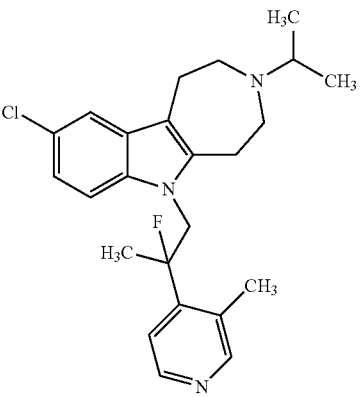 |

Pharmaceutical compositions of any of the compounds detailed herein are embraced by this invention. Thus, the invention includes pharmaceutical compositions comprising a compound of the invention or a pharmaceutically acceptable salt thereof and a pharmaceutically acceptable carrier or excipient. In one aspect, the pharmaceutically acceptable salt is an acid addition salt, such as a salt formed with an inorganic or organic acid. Pharmaceutical compositions according to the invention may take a form suitable for oral, buccal, parenteral, nasal, topical or rectal administration, or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. Unless otherwise stated, "substantially pure" intends a composition that contains no more than 35% impurity, wherein the impurity denotes a compound other than the compound comprising the majority of the composition or a salt thereof. Taking compound 1 as an example, a composition of substantially pure compound 1 intends a composition that contains no more than 35% impurity, wherein the impurity denotes a compound other than compound 1 or a salt thereof. In one variation, a composition of substantially pure compound or a salt thereof is provided wherein the composition contains no more than 25% impurity. In another variation, a composition of substantially pure compound or a salt thereof is provided wherein the composition contains or no more than 20% impurity. In still another variation, a composition of substantially pure compound or a salt thereof is provided wherein the composition contains or no more than 10% impurity. In a further variation, a composition of substantially pure compound or a salt thereof is provided wherein the composition contains or no more than 5% impurity. In another variation, a composition of substantially pure compound or a salt thereof is provided wherein the composition contains or no more than 3% impurity. In still another variation, a composition of substantially pure compound or a salt thereof is provided wherein the composition contains or no more than 1% impurity. In a further variation, a composition of substantially pure compound or a salt thereof is provided wherein the composition contains or no more than 0.5% impurity.

In one variation, compounds of the invention are synthetic compounds prepared for administration to an individual. In another variation, compositions are provided containing compounds of the invention in substantially pure form. In another variation, the invention embraces pharmaceutical compositions comprising a compound of the invention and a pharmaceutically acceptable carrier. In another variation, methods of administering a compound of the invention are provided. The purified forms, pharmaceutical compositions and methods of administering the compounds are suitable for any compound or form thereof detailed herein, such as compound 11.

Strikingly, it has been discovered that compounds included in the invention that contain a substituted vinyl moiety, such as methylvinyl, exhibit a lower binding affinity to $H_1$ as compared to their unsubstituted vinyl counterparts. Thus, it is believed that substituted vinyl moieties, such as methylvinyl, may be responsible for reduced $H_1$ affinity.

Compounds that exhibit affinity for the histamine receptor $H_1$ may induce undesirable side effects, such as metabolic syndrome, diabetes type 2, weight gain, hyperlipidemia, hyperglycemia, hypertension and drowsiness (Kroeze et al., Neuropsychopharmacology (2003) 28, 519-526). The number and extent of undesirable side effects increases with increasing affinity for the $H_1$ receptor. Thus, in one aspect, compounds of the formulae herein display reduced, low or no affinity to histamine receptor $H_1$. Compounds with low affinity to $H_1$ are those compounds which display less than about 80% inhibition of binding of a ligand to $H_1$. Inhibition of binding of a ligand to $H_1$ for all variations detailed herein is determined by a suitable assay known in the art such as the assay described herein. In some variations, compounds of the formulae herein inhibit binding of a ligand to $H_1$ by less than about any of 80%, 75%, 70%, 65%, 60% 55% and 50%. In one variation, compounds of the formulae herein inhibit binding of a ligand to $H_1$ by between about 50% to about 80%. In aspect, compounds of the formulae herein inhibit binding of a ligand to $H_1$ by less than about any of 80%, 75%, 70%, 65%, 60% 55% and 50% at any concentration, such as those detailed herein, e.g., 0.1 µM and 1 µM. In one variation, compounds of the formulae herein inhibit binding of Pyrilamine to $H_1$ as determined in the assay described herein. In a further variation, percent inhibition of binding to $H_1$ is measured by assays detailed herein.

Compounds containing a substituted vinyl moiety, such as methylvinyl moiety, are detailed herein wherein the compounds exhibit reduced $H_1$ affinity as compared to their unsubstituted vinyl counterparts. In one aspect, compounds that contain a substituted vinyl moiety, such as a methylvinyl moiety, exhibit low or no $H_1$ affinity and thus provide compounds with fewer or lesser undesirable side effects than compounds containing an unsubstituted vinyl moiety. In one variation, compounds as detailed herein containing a substituted vinyl moiety, such as methylvinyl, inhibit binding of a ligand to $H_1$ by less than about any of 80%, 75%, 70%, 65%, 60% 55% and 50%. In another variation, compounds as detailed herein containing a substituted vinyl moiety, such as methylvinyl, inhibit binding of a ligand to $H_1$ by less than about any of 50%, 40%, 30%, 20%, 10% and 5%.

General Description of Biological Assays

The binding properties of compounds disclosed herein to a panel of aminergic G protein-coupled receptors including adrenergic receptors, dopamine receptors, serotonin receptors, histamine receptors and an imidazoline receptor may be determined. Binding properties may be assessed by methods known in the art, such as competitive binding assays. In one variation, compounds are assessed by the binding assays detailed herein. Compounds disclosed herein may also be tested in cell-based assays or in in vivo models for further characterization. In one aspect, compounds disclosed herein are of any formula detailed herein and further display one or more of the following characteristics: inhibition of binding of a ligand to an adrenergic receptor (e.g., $\alpha_{1D}$, $\alpha_{2A}$ and $\alpha_{2B}$), inhibition of binding of a ligand to a serotonin receptor (e.g., 5-HT$_{2A}$, 5-HT$_{2C}$, 5-HT$_6$ and 5-HT$_7$), inhibition of binding of a ligand to a dopamine receptor (e.g., $D_{2L}$), and inhibition of binding of a ligand to a histamine receptor (e.g., $H_1$, $H_2$ and $H_3$); agonist/antagonist activity to a serotonin receptor (e.g., 5-HT$_{2A}$, 5-HT$_6$); agonist/antagonist activity to a dopamine receptor (e.g., $D_{2L}$, $D_{2S}$); agonist/antagonist activity to a histamine receptor (e.g., $H_1$); activity in a neurite outgrowth assay; efficacy in a preclinical model of memory dysfunction associated with cholinergic dysfunction/hypofunction; efficacy in a preclinical model of attention impulsivity and executive function, and efficacy in a preclinical model of schizophrenia.

In one variation, inhibition of binding of a ligand to a receptor is measured in the assays described herein. In another variation, inhibition of binding of a ligand is measured in an assay known in the art. In one variation, binding of a ligand to a receptor is inhibited by at least about 80% as determined in a suitable assay known in the art such as the assays described herein. In one variation, binding of a ligand to a receptor is inhibited by greater than about any one of 80%, 85%, 90%, 95%, 100%, or between about 85% and about 95% or between about 90% and about 100% as determined in a suitable assay known in the art such as the assays described herein. In one variation, binding of a ligand to a receptor is inhibited by at least about 80%±20% as determined in an assay known in the art.

In one variation, a compound of the invention inhibits binding of a ligand to at least one receptor and as many as eleven as detailed herein (e.g. $\alpha_{1D}$, $\alpha_{2A}$, $\alpha_{2B}$, 5-HT$_{2A}$, 5-HT$_{2C}$, 5-HT$_6$, 5-HT$_7$, $D_2$, $H_1$, $H_2$, $H_3$). In one variation, a compound of the invention inhibits binding of a ligand to at least one receptor and as many as eleven as detailed herein (e.g. $\alpha_{1D}$, $\alpha_{2A}$, $\alpha_{2B}$, 5-HT$_{2A}$, 5-HT$_{2C}$, 5-T$_6$, 5-HT$_7$, $D_{2L}$, $H_1$, $H_2$, $H_3$). In one variation, a compound of the invention inhibits binding of a ligand to at least one and as many as eleven receptors detailed herein and further displays agonist or antagonist activity to one or more receptors detailed herein (e.g., serotonin receptor 5-HT$_{2A}$, serotonin receptor 5-HT$_6$, dopamine receptor $D_{2L}$, and dopamine receptor $D_{2S}$ and histamine receptor $H_1$) as measured in the assays described herein. In one variation, agonist response of serotonin receptor 5-HT$_{2A}$ is inhibited by compounds of the invention by at least about any one of 50%, 50%, 70%, 80%, 90%, 100%, 110%, 120%, 130%, 140%, 150% as determined in a suitable assay such as the assay described herein.

In one variation, a compound of the invention displays the above described neurotransmitter receptor binding profile i.e. inhibits binding of a ligand to at least one receptor and as many as eleven as detailed herein and further stimulates neurite outgrowth, e.g. as measured by the assays described herein. Certain compounds of the invention showed activity in neurite outgrowth assays using primary neurons in culture. Data is presented indicating that a compound of the invention has activity comparable in magnitude to that of naturally occurring prototypical neurotrophic proteins such as brain derived neurotrophic factor (BDNF) and nerve growth factor (NGF). Notably, neurite outgrowth plays a critical part of new synaptogenesis, which is beneficial for the treatment of neuronal disorders. In one variation, neuronal disorders include ADHD. In one variation, neurite outgrowth is observed with a potency of about 1 µM as measured in a suitable assay known in the art such as the assays described herein. In another variation, neurite outgrowth is observed with a potency of about 500 nM. In a further variation, neurite outgrowth is observed with a potency of about 50 nM. In another variation, neurite outgrowth is observed with a potency of about 5 nM.

In another variation, a compound of the invention inhibits binding of a ligand to at least one receptor and as many as eleven as detailed herein, further displays agonist or antagonist activity to one or more receptors detailed herein and further stimulates neurite outgrowth.

In a further variation, a compound of the invention inhibits binding of a ligand to at least one and as many as eleven receptors as detailed herein and/or display the above described neurotransmitter receptor binding profile and further shows efficacy in a preclinical model of memory dysfunction associated with cholinergic dysfunction/hypofunction, and in preclinical models of attention impulsivity and executive function, i.e. shows pro-cognitive effects in a preclinical model of memory dysfunction. Compounds of the invention have been shown to be effective in a preclinical model of memory dysfunction associated with cholinergic hypofunction. As H1 antagonism may contribute to sedation, weight gain and reduced cognition, low affinity (less than about 80% inhibition of binding of Pyrilamine at 1 µM in the assay described herein) for this receptor may be associated with pro-cognitive effects and a more desirable side effect profile. Furthermore, compounds of the invention with increased potency as a 5-HT$_6$ antagonist may have cognition-enhancing effects as serotonin acting through this receptor may impair memory.

In another variation, a compound of the invention inhibits binding of a ligand to at least one and as many as eleven receptors as detailed herein, further shows efficacy in a preclinical model of memory dysfunction associated with cholinergic dysfunction/hypofunction i.e. shows pro-cognitive effects in a preclinical model of memory dysfunction, in preclinical models of attention impulsivity and executive function, and further displays agonist or antagonist activity to one or more receptors detailed herein.

In a further variation, a compound of the invention inhibits binding of a ligand to at least one and as many as eleven receptors as detailed herein, further shows efficacy in a preclinical model of memory dysfunction associated with cholinergic dysfunction/hypofunction i.e. shows pro-cognitive effects in a preclinical model of memory dysfunction, in preclinical models of attention impulsivity and executive function, and further stimulates neurite outgrowth.

In another variation, a compound of the invention inhibits at least one and as many as eleven receptors as detailed herein, further shows efficacy in a preclinical model of memory dysfunction associated with cholinergic dysfunction/hypofunction i.e. shows pro-cognitive effects in a preclinical model of memory dysfunction, in preclinical models of attention impulsivity and executive function, and further displays agonist or antagonist activity to one or more receptor detailed herein and further stimulates neurite outgrowth.

In a further variation, a compound of the invention inhibits binding of a ligand to at least one and as many as eleven receptors and further possesses anti-psychotic effects as measured in a preclinical model of schizophrenia, i.e., shows efficacy in a preclinical model of schizophrenia.

In another variation, a compound of the invention inhibits binding of a ligand to at least one and as many as eleven receptors, further shows efficacy in a preclinical model of schizophrenia and further displays agonist or antagonist activity to one or more receptors detailed herein.

In a further variation, a compound of the invention inhibits binding of a ligand to at least one and as many as eleven receptors, further shows efficacy in a preclinical model of schizophrenia and further stimulates neurite outgrowth.

In a further variation, a compound of the invention inhibits binding of a ligand to at least one and as many as eleven receptors, further shows efficacy in a preclinical model of memory dysfunction associated with cholinergic dysfunction/hypofunction such as enhancement of memory retention and reduction of memory impairment, in preclinical models of attention impulsivity and executive function, and further shows efficacy in a preclinical model of schizophrenia.

In another variation, a compound of the invention inhibits binding of a ligand to at least one and as many as eleven receptors, further shows efficacy in a preclinical model of schizophrenia, further displays agonist or antagonist activity to one or more receptors detailed herein and further shows efficacy in a preclinical model of memory dysfunction associated with cholinergic dysfunction/hypofunction such as enhancement of memory retention and reduction of memory impairment, and in preclinical models of attention impulsivity and executive function.

In another variation, a compound of the invention inhibits binding of a ligand to at least one and as many as eleven receptors, further shows efficacy in a preclinical model of schizophrenia, further stimulates neurite outgrowth and further shows efficacy in a preclinical model of memory dysfunction associated with cholinergic dysfunction/hypofunction such as enhancement of memory retention and reduction of memory impairment, and in preclinical models of attention impulsivity and executive function.

In a further variation, a compound of the invention inhibits binding to at least one and as many as eleven receptors detailed herein, further displays agonist or antagonist activity to one or more receptors detailed herein, further stimulates neurite outgrowth and further shows efficacy in a preclinical model of schizophrenia.

In another variation, a compound of the invention inhibits binding of a ligand to at least one and as many as eleven receptors, further shows efficacy in a preclinical model of schizophrenia, further displays agonist or antagonist activity to one or more receptors detailed herein, further stimulates neurite outgrowth and further shows efficacy in a preclinical model of memory dysfunction associated with cholinergic dysfunction/hypofunction such as enhancement of memory retention and reduction of memory impairment, and in preclinical models of attention impulsivity and executive function.

In another variation, a compound of the invention stimulates neurite outgrowth. In another variation, a compound of the invention shows efficacy in a preclinical model of schizophrenia and further stimulates neurite outgrowth. In another variation, a compound of the invention stimulates neurite outgrowth and further shows efficacy in a preclinical model of memory dysfunction associated with cholinergic dysfunction/hypofunction such as enhancement of memory retention and reduction of memory impairment, and in preclinical models of attention impulsivity and executive function. In another variation, a compound of the invention shows efficacy in a preclinical model of schizophrenia, further stimulates neurite outgrowth and further shows efficacy in a preclinical model of memory dysfunction associated with cholinergic dysfunction/hypofunction such as enhancement of memory retention and reduction of memory impairment, and in preclinical models of attention impulsivity and executive function.

In one aspect, compounds of the invention inhibit binding of a ligand to adrenergic receptors $\alpha_{1D}$, $\alpha_{2A}$, $\alpha\alpha_{2B}$ and inhibit binding of a ligand to serotonin receptor 5-HT$_6$. In another variation, compounds of the invention inhibit binding of a ligand to adrenergic receptors $\alpha_{1D}$, $\alpha\alpha_{2A}$, $\alpha_{2B}$, to serotonin receptor 5-HT$_6$ and to any one or more of the following receptors: serotonin receptor 5-HT$_7$, 5-HT$_{2A}$ and 5-HT$_{2C}$. In another variation, compounds of the invention inhibit binding of a ligand to adrenergic receptors $\alpha_{1D}$, $\alpha_{2A}$, $\alpha_{2B}$, to serotonin receptor 5-HT$_6$ and to any one or more of the following receptors: serotonin receptor 5-HT$_7$, 5-HT$_{2A}$ and 5-HT$_{2C}$ and further show weak inhibition of binding of a ligand to histamine receptor H$_1$ and/or H$_2$. In one variation, compounds of the invention that also display strong inhibition of binding of a ligand to the serotonin receptor 5-HT$_7$ are particularly desired. In another variation, compounds of the invention inhibit binding of a ligand to adrenergic receptors $\alpha_{1D}$, $\alpha_{2A}$, $\alpha_{2B}$, to serotonin receptor 5-HT$_6$ and further show weak inhibition of binding of a ligand to histamine receptor H$_1$ and/or H$_2$. Weak inhibition of binding of a ligand to the histamine H$_1$ receptor is permitted as agonists of this receptor have been implicated in stimulating memory as well as weight gain. In one variation, binding to histamine receptor H1 is inhibited by less than about 80%. In another variation, binding of a ligand to histamine receptor H1 is inhibited by less than about any of 75%, 70%, 65%, 60%, 55%, or 50% as determined by a suitable assay known in the art such as the assays described herein.

In another variation, compounds of the invention inhibit binding of a ligand to dopamine receptor D$_2$. In another variation, compounds of the invention inhibit binding of a ligand to dopamine receptor D$_2$ and to serotonin receptor 5-HT$_{2A}$. In another variation, compounds of the invention inhibit binding of a ligand to dopamine receptor D$_{2L}$. In another variation, compounds of the invention inhibit binding of a ligand to dopamine receptor D$_{2L}$ and to serotonin receptor 5-HT$_{2A}$.

In another variation, compounds of the invention inhibit binding of a ligand to histamine receptor H$_1$. In certain aspects, compounds of the invention further show one or more of the following properties: strong inhibition of binding of a ligand to the serotonin 5-HT$_7$ receptor, strong inhibition of binding of a ligand to the serotonin 5-HT$_{2A}$ receptor, strong inhibition of binding of a ligand to the serotonin 5-HT$_{2C}$ receptor, weak inhibition of binding of a ligand to the histamine H$_1$ receptor, weak inhibition of binding of ligands to the histamine H$_2$ receptor, and antagonist activity to serotonin receptor 5-HT$_{2A}$.

In one variation, compounds of the invention show any of the receptor binding aspects detailed herein and further display agonist/antagonist activity to one or more of the following receptors: serotonin receptor 5-HT$_{2A}$, serotonin receptor 5-HT$_6$, dopamine receptor D$_{2L}$, dopamine receptor D$_{2S}$ and histamine receptor H$_1$. In one variation, compounds of the invention show any of the receptor binding aspects detailed herein and further stimulate neurite outgrowth. In one variation, compounds of the invention show any of the receptor binding aspects detailed herein and further show efficacy in a preclinical model of memory dysfunction associated with cholinergic dysfunction/hypofunction, such as enhancement of memory retainment and reduction of memory impairment, and in preclinical models of attention impulsivity and executive function. In one variation, compounds of the invention show any of the receptor binding aspects detailed herein and further show efficacy in a preclinical model of schizophrenia. In one variation, compounds of the invention show any of the receptor binding aspects detailed herein and further show efficacy in any one or more of agonist/antagonist assays (e.g., to serotonin receptor 5-HT$_{2A}$, 5-HT$_6$, dopamine receptor D$_{2L}$, dopamine receptor D$_{2S}$ and histamine receptor H$_1$), neurite outgrowth, a preclinical model of memory dysfunction associated with cholinergic dysfunction/hypofunction and a preclinical model of schizophrenia.

In some aspects, compounds of the invention inhibit binding of a ligand to adrenergic receptors $\alpha_{1D}$, $\alpha_{2A}$, $\alpha_{2B}$, serotonin receptor 5-HT$_6$ and dopamine receptor D$_2$ by at least about 80% as determined in a suitable assay known in the art such as the assays described herein. In one variation binding is inhibited by at least about 80% as measured in a suitable assay such as the assays described herein. In some aspects, compounds of the invention inhibit binding of a ligand to adrenergic receptors $\alpha_{1D}$, $\alpha_{2A}$, $\alpha_{2B}$, serotonin receptor 5-HT$_6$ and dopamine receptor D$_{2L}$ by at least about 80% as determined in a suitable assay known in the art such as the assays described herein. In one variation binding is inhibited by at least about 80% as measured in a suitable assay such as the assays described herein. In one variation, binding of a ligand to a receptor is inhibited by greater than about any one of 80%, 85%, 90%, 95%, 100%, or between about 85% and about 95%, or between about 90% and about 100% as determined in a suitable assay known in the art such as the assays described herein.

In some aspects, compounds of the invention display the above described neurotransmitter receptor binding profile and further show antipsychotic effects. It is recognized that compounds of the invention have binding profiles similar to compounds with antipsychotic activity and several compounds of the invention have been shown to be effective in a preclinical model of schizophrenia. In addition, compounds of the invention might possess the cognitive enhancing properties of dimebon and thus add to the beneficial pharmacology profile of these antipsychotic molecules. In one variation, compounds of the invention display the above described neurotransmitter receptor binding profile and further show procognitive effects in a preclinical model of memory dysfunction such as enhancement of memory retention and reduction of memory impairment. In another variation, compounds of the invention display the above described neurotransmitter receptor binding profile and do not show pro-cognitive effects in a preclinical model of memory dysfunction, learning and memory.

In one variation, compounds of the invention demonstrate pro-cognitive effects in a preclinical model of memory dysfunction, learning and memory. In a further variation, compounds of the invention possess anti-psychotic effects in a preclinical model of schizophrenia. In a further variation, compounds of the invention demonstrate pro-cognitive effects in a preclinical model of memory dysfunction, learning and memory and further possess anti-psychotic effects in a preclinical model of schizophrenia.

Overview of the Methods

The compounds described herein may be used to treat, prevent, delay the onset and/or delay the development of cognitive disorders, psychotic disorders, neurotransmitter-mediated disorders and/or neuronal disorders in individuals, such as humans. In one aspect, the compounds described herein may be used to treat, prevent, delay the onset and/or delay the development of a cognitive disorder. In one aspect, cognitive disorders include ADHD. In one variation, cognitive disorder as used herein includes and intends disorders that contain a cognitive component, such as psychotic disorders (e.g., schizophrenia) containing a cognitive component (e.g., CIAS). In another aspect, the compounds described herein may be used to treat, prevent, delay the onset and/or delay the development of a psychotic disorder. In one variation, psychotic disorder as used herein includes and intends disorders that contain a psychotic component, for example cognitive disorders (e.g., Alzheimer's disease) that contain a psychotic component (e.g., psychosis of Alzheimer's Disease or dementia). In one variation, methods of improving at least one cognitive and/or psychotic symptom associated with schizophrenia are provided. In one aspect, methods of improving cognition in an individual who has or is suspected of having CIAS are provided. In a particular aspect, methods of treating schizophrenia are provided wherein the treatment provides for an improvement in one or more negative symptom and/or one or more positive symptom and/or one or more disorganized symptom of schizophrenia. In yet another aspect, the compounds described herein may be used to treat, prevent, delay the onset and/or delay the development of a neurotransmitter-mediated disorders disorder. In one aspect, neurotransmitter-mediated disorders include ADHD. In one embodiment, the neurotransmitter-mediated disorder includes spinal cord injury, diabetic neuropathy, allergic diseases (including food allergies) and diseases involving geroprotective activity such as age-associated hair loss (alopecia), age-associated weight loss and age-associated vision disturbances (cataracts). In another variation, the neurotransmitter-mediated disorder includes spinal cord injury, diabetic neuropathy, fibromyalgia and allergic diseases (including food allergies). In still another embodiment, the neurotransmitter-mediated disorder includes Alzheimer's disease, Parkinson's Disease, autism, ADD, ADHD, Guillain-Barré syndrome, mild cognitive impairment, multiple sclerosis, stroke and traumatic brain injury. In yet another embodiment, the neurotransmitter-mediated disorder includes schizophrenia, anxiety, bipolar disorders, psychosis and depression and ADHD. In one variation, depression as used herein includes and intends treatment-resistant depression, depression related to a psychotic disorder, or depression related to a bipolar disorder. In another aspect, the compounds described herein may be used to treat, prevent, delay the onset and/or delay the development of a neuronal disorder. In one aspect, the compounds described herein may also be used to treat, prevent, delay the onset and/or delay the development of cognitive disorders, psychotic disorders, neurotransmitter-mediated disorders and/or neuronal disorders for which the modulation of an aminergic G protein-coupled receptor is believed to be or is beneficial.

The invention also provides methods of improving cognitive functions and/or reducing psychotic effects comprising administering to an individual in need thereof an amount of a compound of the invention or a pharmaceutically acceptable salt thereof effective to improve cognitive functions and/or reduce psychotic effects. In a particular variation, a method of treating schizophrenia is provided, wherein the treatment provides an improvement in at least one cognitive function, such as an improvement in a cognitive function in an individual who has or is suspected of having CIAS. In a further variation, a method of treating schizophrenia is provided wherein the method reduces psychotic effects associated with schizophrenia. In one embodiment, a method of treating schizophrenia is provided wherein the method improves the negative symptoms of schizophrenia in an individual in need thereof. In one embodiment, a method of treating schizophrenia is provided wherein the method improves the positive symptoms of schizophrenia in an individual in need thereof. In a further variation, a method of treating schizophrenia is provided wherein the method both improves cognitive function and reduces psychotic effects in an individual in need thereof. A method of improving one or more negative, positive and disorganized symptoms of schizophrenia is also provided, where the method entails administering a compound as detailed herein, or a pharmaceutically acceptable salt thereof, to an individual in need of such improvement. In one variation, a method of improving at least one negative symptom of schizophrenia is provided, where the method entails administering a compound as detailed herein, or a pharmaceutically acceptable salt thereof, to an individual in need of such improvement. In another variation, a method of improving at least one negative and at least one positive symptom of schizophrenia is provided, where the method entails administering a compound as detailed herein, or a pharmaceutically acceptable salt thereof, to an individual in need of such improvement. In yet another variation, a method of improving at least one negative and at least one disorganized symptom of schizophrenia is also provided, where the method entails administering a compound as detailed herein, or a pharmaceutically acceptable salt thereof, to an individual in need of such improvement. In still another variation, a method of improving at least one positive and at least one disorganized symptom of schizophrenia is also provided, where the method entails administering a compound as detailed herein, or a pharmaceutically acceptable salt thereof, to an individual in need of such improvement. In still a further variation, a method of improving at least one negative, at least one positive and at least one disorganized symptom of schizophrenia is provided, where the method entails administering a compound as detailed herein, or a pharmaceutically acceptable salt thereof, to an individual in need of such improvement.

The invention also provides methods of stimulating neurite outgrowth and/or promoting neurogenesis and/or enhancing neurotrophic effects in an individual comprising administering to an individual in need thereof an amount of a compound of the invention or a pharmaceutically acceptable salt thereof effective to stimulate neurite outgrowth and/or to promote neurogenesis and/or to enhance neurotrophic effects.

The invention further encompasses methods of modulating an aminergic G protein-coupled receptor comprising administering to an individual in need thereof an amount of a compound of the invention or a pharmaceutically acceptable salt thereof effective to modulate an aminergic G protein-coupled receptor.

It is to be understood that methods described herein also encompass methods of administering compositions comprising the compounds of the invention.

Methods for Treating, Preventing, Delaying the Onset, and/or Delaying the Development Cognitive Disorders, Psychotic Disorders, Neurotransmitter-Mediated Disorders and/or Neuronal Disorders In one aspect, the invention provides methods for treating, preventing, delaying the onset, and/or delaying the development of cognitive disorders, psychotic disorders, neurotransmitter-mediated disorders and/or neuronal disorders for which the modulation of an aminergic G protein-coupled receptor is believed to be or is beneficial, the method comprising administering to an individual in need thereof a compound of the invention. In some variations, modulation of adrenergic receptor $\alpha_{1D}$, $\alpha_{2A}$, $\alpha_{2B}$, serotonin receptor 5-HT$_{2A}$, 5-HT$_6$, 5-HT$_7$, histamine receptor H$_1$ and/or H$_2$ is expected to be or is beneficial for the cognitive disorders, psychotic disorders, neurotransmitter-mediated disorders and/or neuronal disorders. In some variations, modulation of adrenergic receptor $\alpha_{1D}$, $\alpha_{2A}$, $\alpha_{2B}$ and a serotonin receptor 5-HT$_6$ receptor is expected to be or is beneficial for the cognitive disorders, psychotic disorders, neurotransmitter-mediated disorders and/or neuronal disorders. In some variations, modulation of adrenergic receptor $\alpha_{1D}$, $\alpha_{2A}$, $\alpha_{2B}$, and a serotonin receptor 5-HT$_6$ receptor and modulation of one or more of the following receptors serotonin 5-HT$_7$, 5-HT$_{2A}$, 5-HT$_{2C}$ and histamine H$_1$ and H$_2$ is expected to be or is beneficial for the cognitive disorders, psychotic disorders, neurotransmitter-mediated disorders and/or neuronal disorders. In some variations, modulation of a dopamine receptor D$_2$ is expected to be or is beneficial for the cognitive disorders, psychotic disorders, neurotransmitter-mediated disorders and/or neuronal disorders. In some variations, modulation of dopamine receptor D$_{2L}$ is expected to be or is beneficial for the cognitive disorders, psychotic disorders, neurotransmitter-mediated disorders and/or neuronal disorders. In certain variations, modulation of a dopamine D$_2$ receptor and serotonin receptor 5-HT$_{2A}$ is expected to be or is beneficial for the cognitive disorders, psychotic disorders, neurotransmitter-mediated disorders and/or neuronal disorders. In certain variations, modulation of a dopamine D$_{2L}$ receptor and serotonin receptor 5-HT$_{2A}$ is expected to be or is beneficial for the cognitive disorders, psychotic disorders, neurotransmitter-mediated disorders and/or neuronal disorders. In some variations, the cognitive disorders, psychotic disorders, neurotransmitter-mediated disorders and/or neuronal disorders are treated, prevented and/or their onset or development is delayed by administering a compound of the invention.

Methods to Improve Cognitive Functions and/or Reduce Psychotic Effects

The invention provides methods for improving cognitive functions by administering a compound of the invention to an individual in need thereof. In some variations, modulation of one or more of adrenergic receptor $\alpha_{1D}$, $\alpha_{2A}$, $\alpha_{1D}$, serotonin receptor 5-HT$_{2A}$, 5-HT$_6$, 5-HT$_7$, histamine receptor H$_1$ and/or H$_2$ is desirable or expected to be desirable to improve cognitive functions. In some variations modulation of $\alpha_{1D}$, $\alpha_{2A}$, $\alpha_{2B}$ adrenergic receptors and a serotonin 5-HT$_6$ receptor is desirable or expected to be desirable to improve cognitive functions. In some variations, modulation of $\alpha_{1D}$, $\alpha_{2A}$, $\alpha_{2B}$ adrenergic receptors and serotonin receptor 5-HT$_6$ and modulation of one or more of the following receptors: serotonin receptor 5-HT$_7$, 5-HT$_{2A}$, 5-HT$_{2C}$ and histamine receptor H$_1$ and H$_2$, is desirable or expected to be desirable to improve cognitive functions. In another aspect, the invention encompasses methods to reduce psychotic effects by administering a compound of the invention to an individual in need thereof. In some embodiments, modulation of a dopamine D$_2$ receptor is expected to be or is desirable to reduce psychotic effects. In some embodiments, modulation of a dopamine D$_{2L}$ receptor is expected to be or is desirable to reduce psychotic effects. In some embodiments, modulation of a dopamine D$_2$ receptor and a serotonin 5-HT$_{2A}$ receptor is expected to be or is desirable to reduce psychotic effects. In some variations, a compound of the invention is administered to an individual in need thereof. In some embodiments, modulation of a dopamine D$_{2L}$ receptor and a serotonin 5-HT$_{2A}$ receptor is expected to be or is desirable to reduce psychotic effects. In some variations, a compound of the invention is administered to an individual in need thereof.

Methods to Stimulate Neurite Outgrowth, Promote Neurogenesis and/or Enhance Neurotrophic Effects In a further aspect, the invention provides methods of stimulating neurite outgrowth and/or enhancing neurogenesis and/or enhancing neurotrophic effects comprising administering a compound of the invention or pharmaceutically acceptable salt thereof under conditions sufficient to stimulate neurite outgrowth and/or to enhance neurogenesis and/or enhance neurotrophic effects to an individual in need thereof. In some variations, a compound of the invention stimulates neurite outgrowth at a potency of about 1 µM as measured in a suitable assay such as the assays described herein. In some variations, a compound of the invention stimulates neurite outgrowth at a potency of about 500 nM as measured in a suitable assay such as the assays described herein. In some variations, a compound of the invention stimulates neurite outgrowth at a potency of about 50 nM as measured in a suitable assay such as the assays described herein. In some variations, a compound of the invention stimulates neurite outgrowth at a potency of about 5 nM as measured in a suitable assay such as the assays described herein.

Methods to Modulate an Aminergic G Protein-Coupled Receptor

The invention further contemplates methods for modulating the activity of an aminergic G-protein-coupled receptor comprising administering a compound of the invention or pharmaceutically acceptable salt thereof under conditions sufficient to modulate the activity of an aminergic G protein-coupled receptor. In some variations, the aminergic G protein-coupled receptor is a $\alpha_{1D}$, $\alpha_{2A}$, $\alpha_{2B}$ adrenergic receptor and a serotonin 5-HT$_6$ receptor. In some variations, the aminergic G protein-coupled receptor is a $\alpha_{1D}$, $\alpha_{2A}$, $\alpha_{2B}$ adrenergic receptor and a serotonin 5-HT$_6$ and 5-HT$_7$ receptor. In some variations, the aminergic G protein-coupled receptor is a $\alpha_{1D}$, $\alpha_{2A}$, $\alpha_{2B}$ adrenergic receptor, a serotonin 5-HT$_6$ and one or more of the following receptors: serotonin 5-HT$_7$, 5-HT$_{2A}$ and 5-HT$_{2C}$ and histamine H$_1$ and H$_2$ receptor. In some variations, the aminergic G protein-coupled receptor is a dopamine D$_{2L}$ receptor. In some variations, the aminergic G protein-coupled receptor is a dopamine D$_{2L}$ receptor and a serotonin 5-HT$_{2A}$ receptor. In some variations, the aminergic G protein-coupled receptor is a histamine H$_1$ receptor.

Dose-Dependent Therapy (DDT)

Dose dependent therapy refers to the concept that a single molecule may be used for different indications depending on the dose at which it is administered. It has been shown that compounds included in the invention exert pro-cognitive effects (where in one aspect pro-cognitive effects are achieved by reducing one or more symptoms associated with impaired cognition) when administered at low dose, whereas at high dose, these compounds induce both pro-cognitive and anti-psychotic effects (where in one aspect anti-psychotic effects are achieved by reducing one or more symptoms associated with a psychotic disorder). These compounds are further referred to as Dose-Dependent Therapy compounds (DDT compounds). When administered at high dose, DDT compounds in one aspect show fewer and/or lesser side-effects such as, e.g., extrapyramidal syndrome (EPS), as compared to other anti-psychotics, such as anti-psychotics which are not 5-HT$_{2A}$ receptor modulators. It is believed that EPS is caused, at least in part, by high D$_2$ receptor occupancy, the effect of which can be counteracted by compounds displaying a high affinity to the serotonin receptor 5-HT$_{2A}$. EPS can be determined using various scales known in the art such as the Abnormal Involuntary Movement Scale (AIMS), Barnes Akathisia Rating Scale (BARS), Simpson-Angus Rating Scale (SARS), Extrapyramidal Symptoms Rating Scale (ESRS) and the Extrapyramidal Symptoms Rating Scale-Abbreviated (ESRS-A). DDT compounds in one aspect are 5-HT$_{2A}$ modulators, and preferably are antagonists of 5-HT$_{2A}$. In one variation, DDT compounds have low or no affinity for the histamine receptor H$_1$, which is also implicated in undesirable side effects such as metabolic syndrome, diabetes type 2, weight gain, hyperlipidemia, hyperglycemia, hypertension and drowsiness (Kroeze et al., *Neuropsychopharmacology* (2003) 28, 519-526).

DDT Compounds

DDT compounds modulate at least serotonin receptor 5-HT$_{2A}$ and/or serotonin receptor 5-HT$_6$ and modulate dopamine receptor D$_2$, such as D$_{2L}$. In one aspect, DDT compounds inhibit binding of a ligand to at least 5-HT$_{2A}$ and/or 5-HT$_6$ and binding of a ligand to D$_2$. Inhibition of binding for all variations detailed herein is determined in a suitable assay known in the art, such as the assays described herein. In one aspect, DDT compounds act as antagonists of 5-HT$_{2A}$ and/or 5-HT$_6$ and act as antagonists of D$_2$. In another aspect, DDT compounds act as antagonists of 5-HT$_{2A}$ and D$_2$. In another aspect, DDT compounds act as antagonists of 5-HT$_{2A}$, 5-HT$_6$ and D$_2$. In one variation, DDT compounds inhibit binding of a ligand to 5-HT$_{2A}$ and/or 5-HT$_6$ by at least about 50% at a DDT concentration of about 0.1 µM and inhibit binding of a ligand to D$_2$ by at least about 90% at a DDT concentration of about 1 µM. In another variation, DDT compounds inhibit binding of a ligand to 5-HT$_{2A}$ and/or 5-HT$_6$ by greater than about any of 50%, 60%, 70% or 80% at a DDT concentration of at least about 0.1 µM. In a further variation, DDT compounds inhibit binding of a ligand to 5-HT$_{2A}$ and/or 5-HT$_6$ by greater than about any of 50%, 60%, 70% or 80% at a DDT concentration of less than about 0.1 µM (e.g., greater than about 0.01 µM and less than about 0.1 µM). In a further variation, DDT compounds inhibit binding of a ligand to 5-HT$_{2A}$ and/or 5-HT$_6$ by at least about 80% at a DDT concentration of about 0.1 µM. In one variation, DDT compounds inhibit binding of a ligand to D$_2$ by at least about 90% at a DDT concentration of greater than about 1 µM. In another variation, DDT compounds inhibit binding of a ligand to D$_2$ by at least about 90% at a DDT concentration of between about 1 µM to about 3 µM. In one variation, DDT compounds inhibit binding of Ketanserin, LSD and Spiperone to 5-HT$_{2A}$, 5-HT$_6$ and D$_2$, respectively, as determined in the assays described herein. In another variation, binding of a ligand to 5-HT$_{2A}$ and/or 5-HT$_6$ is inhibited by greater than about any of 80%, 85%, 90% or 95%, or by about 100% at a DDT concentration of about 0.1 µM. In a further variation, binding of a ligand to 5-HT$_{2A}$ and/or 5-HT$_6$ is inhibited between about 85% to about 95% or between about 90% to about 100% at a DDT concentration of about 0.1 µM. In another variation, binding of a ligand to D$_2$ is inhibited by greater than about any of 90% and 95%, or by about 100% at a DDT concentration of about 1 µM. In a further variation, binding of a ligand to D$_2$ is inhibited by between about 90% to about 100% at a concentration of about 1 µM. In another variation, inhibition of binding of a ligand to 5-HT$_{2A}$ and/or 5-HT$_6$ is at least 80%±20% at a DDT concentration of about 0.1 µM and binding of a ligand to D$_2$ is inhibited by at least about 90% at a concentration of about 1 µM as determined in assays known in the art. In one aspect, DDT compounds inhibit binding of a ligand to 5-HT$_{2A}$ and D$_2$. In another aspect, DDT compounds inhibit binding of a ligand to 5-HT$_6$ and D$_2$. In yet another aspect, DDT compounds inhibit binding of a ligand to 5-HT$_{2A}$, 5-HT$_6$ and D$_2$. In one variation, percent inhibition of binding to 5-HT$_{2A}$, 5-HT$_6$ and D$_2$ is measured by assays detailed herein.

In one aspect, DDT compounds display low affinity to histamine receptor H$_1$. Compounds with low affinity to H$_1$ are those compounds which display less than about 80% inhibition of binding of a ligand to H$_1$. Inhibition of binding of a ligand to H$_1$ for all variations detailed herein is determined by a suitable assay known in the art such as the assay described herein. In some variations, DDT compounds inhibit binding of a ligand to H$_1$ by less than about any of 80%, 75%, 70%, 65%, 60% 55% or 50%. In one variation, DDT compounds inhibit binding of a ligand to H$_1$ by between about 50% to about 80%. In some variations, DDT compounds inhibit binding by less than about 80% at any DDT concentration, e.g., at about 0.1 µM to about 1 µM. In one variation, DDT compounds inhibit binding of Pyrilamine to H1 as determined in the assay described herein. In a further variation, percent inhibition of binding to $H_1$ is measured by assays detailed herein.

In some aspects, DDT compounds act as 5-$HT_{2A}$ and $D_2$ antagonists. Antagonist activity for all variations is measured in suitable assays known in the art such as the assays described herein. In one variation, 5-$HT_{2A}$ activity is inhibited by at least about 70% at a DDT concentration of about 0.1 µM. In another variation, 5-$HT_{2A}$ activity is inhibited by greater than about any of 70%, 75%, 80%, 85%, 90%, or 95%, or by about 100% at a DDT concentration of about 0.1 µM. In one variation, $D_2$ activity is inhibited by at least about 70% at a DDT concentration of about 1 µM. In another variation, $D_2$ activity is inhibited by greater than about any of 70%, 75%, 80%, 85%, 90%, or 95%, or by about 100% at a DDT concentration of about 1 µM. In one variation, percent inhibition of activity is determined in the assays described herein. In one aspect, DDT compounds inhibit 5-$HT_{2A}$ and $D_2$ activity. In another aspect, DDT compounds inhibit 5-$HT_{2A}$, 5-$HT_6$ and $D_2$ activity.

In one aspect, DDT compounds display any of the activities detailed herein for DDT compounds and further have a structure of the formulae provided herein. In one aspect, DDT compounds contain a substituted vinyl moiety, such as a methylvinyl moiety. Accordingly, in a particular aspect, DDT compounds are of the formula (C), or any variation thereof, including compounds of the formula (C), where at least one of $R^{8d}$ and $R^{8f}$ is other than H, such as when at least one of $R^{8d}$ and $R^{8f}$ is a $C_1$-$C_8$ alkyl, $C_3$-$C_8$ cycloalkyl, or $C_1$-$C_8$ perhaloalkyl. DDT compounds may also be of the formulae (X-1), (X-1a), (X-1b), (X-2), (X-2a), (X-2b), (X-3), (X-4), (X-5), (X-6), (X-7), (X-8), (X-9) or (X-10), or any variation thereof. DDT compounds may also be of the formulae (C-1), (C-1a), (C-1b), (C-2), (C-2a), (C-2b), (C-3a), (C-3b), (C-4a), (C-4b), (C-5a), (C-5b), (C-6a) or (C-6b).

DDT compounds may be present as pharmaceutically acceptable salts, or solvates thereof. Pharmaceutical compositions comprising a DDT compound and a pharmaceutically acceptable carrier are also embraced. These pharmaceutical compositions may take a form suitable for oral, buccal, parenteral, nasal, topical or rectal administration or a form suitable for administration by inhalation.

High Dose

In one aspect, high dose of a DDT compound corresponds to an amount that results in at least 65% of receptor occupancy of dopamine receptor $D_2$, which may be assessed by known methods, such as Positron Emission Tomography (PET) (Pani et al., *European Psychiatry* (2007) 22, 276-275). In some variations, a high dose provides $D_2$ occupancy that is greater than any one of 65%, 70%, 75%, 80%, 85% and 90%. In one variation, a high dose provides $D_2$ occupancy that is at least 65%. In another variation, a high dose provides a $D_2$ occupancy that is from at least 65% to 90%, or from at least 65% to 85%, or from at least 65% to 80%, or from at least 65% to 75%, or from at least 65% to 70%, or from at least 70% to 90%, or from at least 70% to 85%, or from at least 70% to 80%, or from at least 70% to 75%, or from at least 75% to 90%, or from at least 75% to 85%, or from at least 75% to 80%, or from at least 80% to 90%. In one variation, a high dose provides $D_2$ occupancy that is less than 80% and greater than 65%.

In another aspect, high dose of a DDT compound corresponds to a daily dose of at least about 1 mg/kg. In another variation, high dose corresponds to a daily dose of about 1 mg/kg. In another variation, high dose corresponds to a daily dose of at least about 1 mg/kg to at least about 3 mg/kg. In yet another variation, high dose corresponds to a daily dose of at least about 1 mg/kg to about 5 mg/kg. In a further variation, high dose corresponds to a daily dose of greater than 1 mg/kg.

In a further aspect, high dose of a DDT compound corresponds to an amount that induces anti-psychotic effects as determined by the Positive and Negative Syndrome Scale (PANSS). In another variation, anti-psychotic effects are measured by one or more of the following: PANSS, Brief Psychiatric Rating Scale (BPRS), Positive symptom sub-scale of PANSS, Young Mania Rating Scale (Y-MRS), Mania Rating Scale (MRS). In a further variation, anti-psychotic effects are measured by another scale and/or test known in the art.

In another aspect of the invention, high dose of a DDT compound corresponds to at least about 100 times the amount that induces pro-cognitive effects but does not induce anti-psychotic effects. In one variation, pro-cognitive effects are determined by cognition scales known in the art such as the Measurement and Treatment Research to Improve Cognition in Schizophrenia MATRICS. In another variation, pro-cognitive effects are determined by measuring the cognitive components of one or more of the following scales and/or tests: MATRICS, Negative Symptoms Assessment scale (NSA), Scale for the Assessment of Negative Symptoms (SANS), Schedule for the Deficit Syndrome (GDS), Negative symptom sub-scale of PANSS, MATRICS Consensus Cognition Battery (MCCB), CNSVitalSigns, CogState battery, Cognitive Drug Research battery (CDR), Brief Assessment of Cognition in Schizophrenia (BACS), Schizophrenia Cognition Rating Scale (SCoRS), Clinical Global Impression of Cognition in Schizophrenia (CGI-CogS), Repeatable Battery for the Assessment of Neuropsychological Status (RBANS), Test of Adaptive Behavior in Schizophrenia (TABS), Independent Living Skills Inventory (ILS), UCSD Performance-Based Skills Assessment (UPSA), Cognitive Assessment Interview (CAI), Global Assessment of Function from CAI (GAF), Quality of Life Scale (QLS), Maryland Assessment of Social Competence (MASC), Calgary Depression Scale (CDS), and Montgomery-Åsberg Depression Rating Scale (MADRS). In a further variation, pro-cognitive effects are determined by another scale and/or test known in the art.

Low Dose

In one aspect, low dose of a DDT compound corresponds to an amount that results in less than 65% receptor occupancy of dopamine receptor $D_2$. In some variations, a low dose provides $D_2$ occupancy that is less than any one of 65%, 60%, 55% and 50%.

In another aspect, low dose of a DDT compound corresponds to a daily dose of about 0.03 mg/kg. In another variation, low dose corresponds to a daily dose of about 0.03 to about 0.3 mg/kg. In another variation, low dose corresponds to a daily dose of about 0.3 mg/kg. In yet another variation, low dose corresponds to a daily dose of about 0.03 to about 1 mg/kg. In a further variation, low dose corresponds to a daily dose of about 0.01 mg/kg. In yet another variation, low dose corresponds to a daily dose of 0.01 to about 1 mg/kg. In a further variation, low dose corresponds to a daily dose of about 0.5 mg/kg. In yet another variation, low dose corresponds to a daily dose of less than about 0.5 mg/kg. In another variation, low dose corresponds to a daily dose of less than 1 mg/kg.

In a further aspect, low dose of a DDT compound corresponds to an amount that induces pro-cognitive effects as determined by cognition scales such as MATRICS but does not induce anti-psychotic effects. In another variation, pro-cognitive effects are determined by measuring the cognitive components of one or more of the following scales and/or tests: MATRICS, Negative Symptoms Assessment scale (NSA), Scale for the Assessment of Negative Symptoms (SANS), Schedule for the Deficit Syndrome (GDS), Negative symptom sub-scale of PANSS, MATRICS Consensus Cognition Battery (MCCB), CNSVitalSigns, CogState battery, Cognitive Drug Research battery (CDR), Brief Assessment of Cognition in Schizophrenia (BACS), Schizophrenia Cognition Rating Scale (SCoRS), Clinical Global Impression of Cognition in Schizophrenia (CGI-CogS), Repeatable Battery for the Assessment of Neuropsychological Status (RBANS), Test of Adaptive Behavior in Schizophrenia (TABS), Independent Living Skills Inventory (ILS), UCSD Performance-Based Skills Assessment (UPSA), Cognitive Assessment Interview (CAI), Global Assessment of Function from CAI (GAF), Quality of Life Scale (QLS), Maryland Assessment of Social Competence (MASC), Calgary Depression Scale (CDS), and Montgomery-Åsberg Depression Rating Scale (MADRS). In a further variation, pro-cognitive effects are determined by another scale and/or test known in the art.

In another aspect of the invention, low dose of a DDT compound corresponds to at least about $1/100$ the amount that induces anti-psychotic effects. In one variation, anti-psychotic effects are determined by assays such as PANSS. In another variation, anti-psychotic effects are measured by one or more of the following: PANSS, Brief Psychiatric Rating Scale (BPRS), Positive symptom sub-scale of PANSS, Young Mania Rating Scale (Y-MRS), Mania Rating Scale (MRS). In a further variation, anti-psychotic effects are measured by another scale and/or test known in the art.

Unit Dosage Forms

DDT compounds may be provided in various unit dosage forms. In one aspect, single therapy dosages are provided. In one variation, a unit dosage form comprises a low dose as described herein of a DDT compound. In another variation, a unit dosage form comprises a high dose as described herein of a DDT compound.

In another aspect, combination therapy dosage forms are provided. In one variation, combination dosage forms comprise a low dose as described herein of a DDT compound and a second drug suitable for anti-psychotic therapy. In another variation, combination dosage forms comprise a high dose as described herein of a DDT compound and a second drug suitable for anti-psychotic therapy.

Kits

The present invention further provides for kits comprising DDT compounds with instructions for achieving pro-cognitive effects at low dose as detailed herein or pro-cognitive effects and anti-psychotic effects at high dose as detailed herein. In one aspect, kits comprise a low dose of a DDT compound and instructions for achieving only pro-cognitive effects. In some variations, pro-cognitive effects include (i) improvement of CIAS such as improvement of any one or more of memory (e.g., short term memory, working memory, social memory), attention, impulsivity, verbal fluency and executive function and/or (ii) improvement of negative symptoms of schizophrenia such as improvement of any one or more of blunted affect, avolition, anhedonia, alogia, dysphoria, suicidality, hopelessness, depression and low mood. Thus, kits for use to achieve pro-cognitive effects in one aspect comprise a low dose of a DDT compound as described herein. In another variation, kits for use to achieve pro-cognitive effects comprise a unit dosage form containing a low dose of a DDT compound as described herein.

In a further aspect, kits of the present invention comprise a high dose of a DDT compound and instructions for achieving both pro-cognitive and anti-psychotic effects. In some variations, anti-psychotic effects comprise improvement of any one or more of psychotic symptoms such as positive symptoms of schizophrenia (e.g., delusions, hallucinations, disorganized thought and agitation). Kits comprising a high dose of a DDT compound may be used to achieve one or more pro-cognitive effects and one or more anti-psychotic effects. Thus, kits for use to achieve pro-cognitive and anti-psychotic effects in one aspect comprise a high dose of a DDT compound as described herein. In another variation, kits for use to achieve pro-cognitive and anti-psychotic effects comprise a unit dosage form containing a high dose of a DDT compound as detailed herein. In a further variation, kits for use to achieve pro-cognitive and anti-psychotic effects comprise a low dose of a DDT compound and a second drug suitable for anti-psychotic therapy. In yet another variation, kits for use to achieve pro-cognitive and anti-psychotic effects comprise a high dose of a DDT compound and a second drug suitable for anti-psychotic therapy. In one aspect, kits for use to achieve pro-cognitive and anti-psychotic effects comprise DDT compounds in unit dosage forms as detailed herein.

Methods of Treatment

The invention provides methods of treating diseases or conditions in which cognition and/or psychosis are implicated. The present invention provides methods of treating cognitive disorders and/or psychotic disorders by administering a DDT compound at a pharmaceutically effective dose to a subject in need thereof. In one variation, cognitive disorder as used herein includes and intends disorders that contain a cognitive component, such as psychotic disorders (e.g., schizophrenia) containing a cognitive component (e.g., CIAS). In one variation, a cognitive disorder is a disorder which affects executive function. In one variation, psychotic disorder as used herein includes and intends disorders that contain a psychotic component, for example cognitive disorders (e.g., Alzheimer's disease) that contain a psychotic component (e.g., psychosis of Alzheimer's Disease or dementia). In one variation, a psychotic disorder is psychosis associated with dementia.

In one aspect, the present invention encompasses methods of improving cognition by administering a DDT compound at a pharmaceutically effective dose to a subject in need thereof. In one variation, improving cognition comprises reducing one or more symptoms associated with impaired cognition. In a further aspect, the present invention provides methods of (i) improving cognition and (ii) reducing symptoms associated with psychotic disorders in a subject in need thereof. In yet another aspect, the present invention encompasses methods of improving cognition and not reducing symptoms associated with psychotic disorders in a subject in need thereof. In yet a further aspect, the present invention provides methods of improving cognition and not significantly reducing symptoms associated with psychotic disorders in a subject in need thereof. In some variations, a subject in need thereof is an individual who is refractory to other pro-cognitive and/or anti-psychotic therapy.

In one aspect, the invention is directed to methods of improving cognition and/or reducing symptoms associated with impaired cognition by administering a DDT compound at either low or high dose. In one variation improving cognition comprises (i) improvement of CIAS such as improvement of any one or more of memory (e.g., short term memory, working memory, social memory), attention, impulsivity, verbal fluency and executive function and/or (ii) improvement of negative symptoms of schizophrenia such as improvement of any one or more of blunted affect, avolition, anhedonia, alogia, dysphoria, suicidality, hopelessness, depression and low mood.

In a further aspect, the invention provides methods of both (i) improving cognition (e.g., as set forth herein) and/or reducing symptoms associated with impaired cognition and (ii) reducing symptoms associated with psychotic disorders by administering a DDT compound at high dose. In one variation, reducing symptoms associated with psychotic disorders comprises improvement of any one or more of psychotic symptoms such as positive symptoms of schizophrenia (e.g., delusions, hallucinations, disorganized thought and agitation). In one variation, the invention is directed to methods of treating schizophrenia by administering a high dose of a DDT compound. In another variation, the invention provides methods of reducing one or more symptom of positive symptoms of schizophrenia by administering a high dose of a DDT compound. In a further variation, the invention encompasses methods of reducing one or more symptom of positive and/or one or more symptom of negative symptoms of schizophrenia by administering a high dose of a DDT compound. In yet another variation, the invention provides methods of reducing one or more symptom of positive symptoms and/or one or more symptom of CIAS by administering a high dose of a DDT compound. In yet another variation, the invention provides methods of reducing one or more symptom of positive symptoms and/or one or more symptom of negative symptoms and/or one or more of disorganized symptoms of schizophrenia by administering a high dose of a DDT compound.

In another aspect, the invention is directed to methods of improving cognition and/or reducing symptoms associated with impaired cognition and not reducing symptoms associated with psychotic disorders by administering a DDT compound at low dose. In one variation improving cognition comprises (i) improvement of CIAS such as improvement of any one or more of memory (e.g., short term memory, working memory, social memory), attention, impulsivity, verbal fluency and executive function and/or (ii) improvement of negative symptoms of schizophrenia such as improvement of any one or more of blunted affect, avolition, anhedonia, alogia, dysphoria, suicidality, hopelessness, depression and low mood.

In yet another aspect, the invention encompasses methods of improving cognition and/or reducing symptoms associated with impaired cognition without significantly improving symptoms associated with psychotic disorders by administering a DDT compound at low dose.

Methods of Manufacturing a Medicament

In a further aspect of the invention use of DDT compounds and compositions thereof in the manufacture of a medicament is provided. Particularly, the manufacture of a medicament for use in the treatment of diseases or conditions in which cognition and/or psychosis are implicated are described herein. Further, pharmaceutical compositions of DDT compounds are also intended for use in the manufacture of a medicament for use in treatment of diseases or conditions in which cognition and/or psychosis are implicated.

Method of Determining a Dose/Treatment

The present invention further encompasses methods of determining a suitable or optimal dose of a DDT compound to either (i) achieve pro-cognitive effects alone or (ii) achieve both pro-cognitive effects and anti-psychotic effects in an individual in need thereof. In one aspect, a suitable dose is determined by measuring the percentage of $D_2$ occupancy and adjusting an individual's dosage in response thereto. In one variation, dosage is increased to achieve anti-psychotic effects if $D_2$ occupancy is less than 65% as determined by methods known in the art such as PET. In another variation, dosage is increased to achieve anti-psychotic effects if $D_2$ occupancy is less than any one of 65%, 60%, 55%, and 50%. In a further variation, dosage is reduced to achieve pro-cognitive and not anti-psychotic effects if $D_2$ occupancy is at least 65%. In yet another variation, dosage is reduced to achieve pro-cognitive and not anti-psychotic effects if $D_2$ occupancy is at greater than any one of 65%, 70%, 75%, 80% and 90%. In a further variation, dosage is reduced to achieve pro-cognitive and no significant anti-psychotic effects if $D_2$ occupancy is greater than 65%. One indication of at least 65% $D_2$ occupancy or greater than any one of 65%, 70%, 75%, 80% and 90% $D_2$ occupancy is the reduction in the number or severity of one or more symptoms associated with a psychotic disorder.

In another aspect, a suitable dose is determined by assessing pro-cognitive and/or anti-psychotic effects in an individual and adjusting an individual's dosage in response thereto. For example, in one variation, an individual's dosage is increased from a first dosage to a higher, second dosage, in order to achieve anti-psychotic effects at the second dosage level, if it is determined that the first dosage does not induce anti-psychotic effects in the individual, as may be assessed by suitable test and/or scales known in the art. In another variation, dosage is reduced from a first dosage to a lower, second dosage wherein the second dosage still achieves anti-psychotic effects but reduces side effects as compared to the first dosage. Side effects may be determined by suitable tests and/or scales known in the art. In another variation, dosage is decreased from a first dosage to a lower, second dosage, in order to achieve pro-cognitive and not anti-psychotic effects. In another variation, dosage is decreased from a first dosage to a lower, second dosage, in order to achieve pro-cognitive and not anti-psychotic effects and wherein the dosage induces fewer or lesser side effects than the first dosage. Thus, in yet another variation, dosage is reduced to a minimum dosage which still achieves pro-cognitive effects but reduces side-effects as determined by suitable tests and/or scales.

In one aspect, an individual's therapy is monitored as set forth above for a period of time, such as one week, two weeks, three weeks, one month, two months, three months, four months, five months, 6 months or more (such as throughout the course of an individual's therapy), to adjust an individual's dosage level as needed. As such, individualized therapy as detailed herein provides for methods of measuring therapeutic parameters and adjusting dosage in response thereto in order to achieve an optimal dosage amount according to an individual's initial and continued response to therapy.

General Synthetic Methods

The compounds of the invention may be prepared by a number of processes as generally described below and more specifically in the Examples hereinafter. In the following process descriptions, the symbols when used in the formulae depicted are to be understood to represent those groups described above in relation to formula (I), (Ia), (Ib), (Ic) or (C) or any variation thereof unless otherwise indicated.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g. a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

The following abbreviations are used herein: thin layer chromatography (TLC); Hour (h); Minute (min.); Second (sec.); Ethanol (EtOH); dimethylsulfoxide (DMSO); N,N-dimethylformamide (DMF); trifluoroacetic acid (TFA); tetrahydrofuran (THF); Normal (N); aqueous (aq.); methanol (MeOH); dichloromethane (DCM); Retention factor (Rf).

A method of synthesizing an intermediate used in the synthesis of compounds of the invention is shown as General Method 1. Although identifiers such as R are shown in the methods below, it is understood that these moieties apply to the compounds detailed herein even if different identifiers or variations thereof are used elsewhere. It is also understood that modifications to the specific materials shown in the methods below are intended, e.g., where a method using a compound having an aryl group such as phenyl can likewise be can utilized with a compound having a heteroaryl group such as pyridyl to arrive at heteroaryl containing products.

General Method 1.

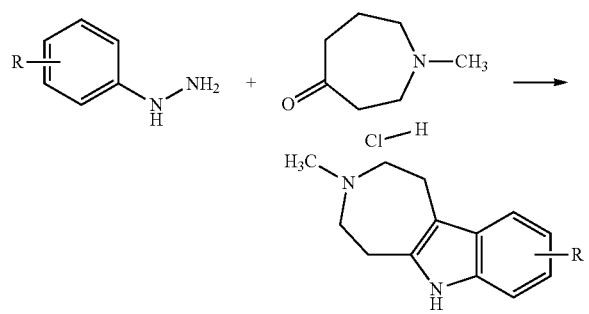

The 1-methylazepan-4-one hydrochloride (1 equiv.) and appropriately substituted arylhydrazine hydrochloride (1 equiv.) are refluxed in a mixture of 7% sulfuric acid in 1,4-dioxane (2-3 mL) overnight under nitrogen. The mixture is poured on to ice and basified with 50% aq NaOH. The resulting precipitate is filtered, washed well with water, and dried in air to provide the substituted 1,2,3,4,5,6-hexahydroazepino[4,5-b]indole derivative.

A method of synthesizing another intermediate used in the synthesis of compounds of the invention is shown as General Method 2.

General Method 2.

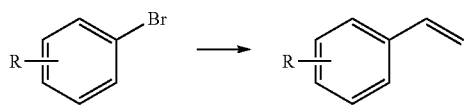

The appropriate aryl bromide (1 equiv.) is dissolved in DMF. Tributylvinyltin (1.1 equiv.) and Pd(PPh$_3$)$_4$ (0.02 equiv.) are added to this solution at RT under nitrogen and the reaction mixture is heated at 100° C. for 1.5 h. The reaction mixture is cooled to RT, diluted with water and extracted with DCM. The organic layer is dried over anhydrous sodium sulfate and concentrated under reduced pressure below 40° C. The crude product is purified through column chromatography in silica gel to provide the desired vinylarene derivative.

A method of synthesizing another intermediate used in the synthesis of compounds of the invention is shown as General Method 3.

General Method 3.

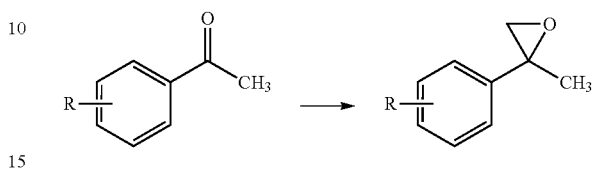

NaH (1 equiv.) is added to DMSO and heated to 65° C. for 1 h. THF is added at the same temperature and the reaction mixture is heated for another 10 min., after which the reaction mixture is cooled to 0° C. Trimethylsulfonium iodide (1 equiv.) is then added and the reaction mixture is stirred for 10 min. The solution of appropriate ketone (1 equiv.) in THF is added dropwise. After completion of addition, the reaction mixture is stirred at RT for 2 h. The reaction mixture is poured into ice water and product extracted in diethyl ether, dried over Na$_2$SO$_4$ and concentrated at 25° C.

A method of synthesizing certain compounds of the invention is shown as General Method 4.

General Method 4.

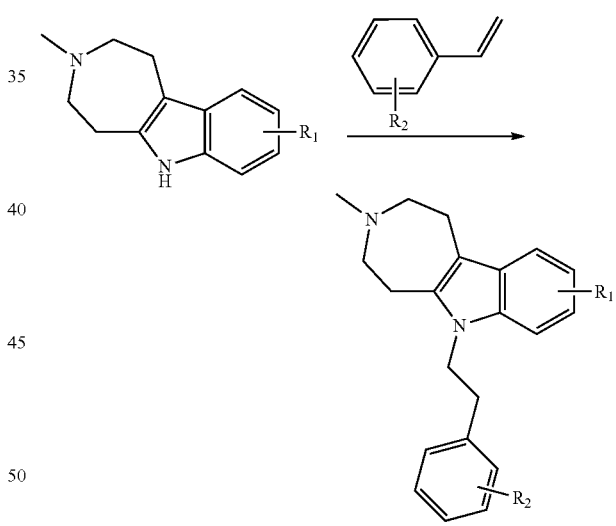

A mixture of appropriately substituted 1,2,3,4,5,6-hexahydroazepino[4,5-b]indole (1 equiv.), 2-trifluoromethyl-5-vinylpyridine (1.1 equiv.) and KOH (3.5 equiv.) in NMP (0.5 mL/mmol) is stirred and heated at 50-100° C. for 3 h. The reaction mixture is cooled to RT and diluted by adding ice and satd. aqueous NaCl. The aqueous mixture is extracted with ethyl acetate and organic layer is washed with brine, dried over anhydrous sodium sulfate and concentrated under vacuum to obtain crude product. The crude product is purified either by flash chromatography on silica gel or by reverse phase HPLC.

A method of synthesizing certain compounds of the invention is shown as General Method 5.

General Method 5.

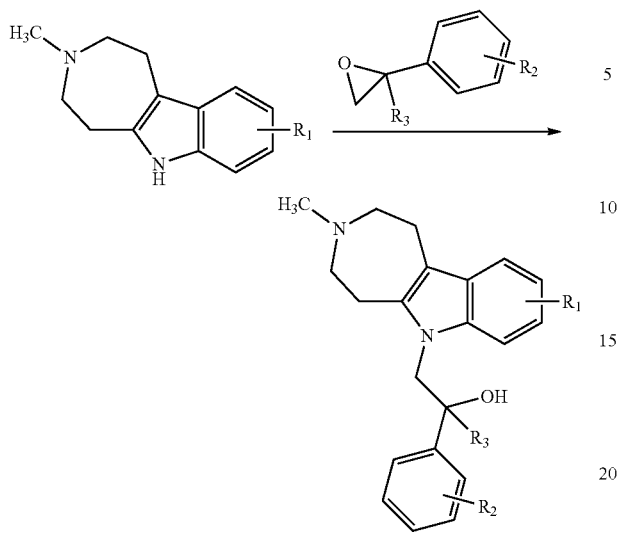

The appropriately substituted 1,2,3,4,5,6-hexahydroazepino[4,5-b]indole (1 equiv.) is dissolved in DMF (2 mL/mmol). To this solution sodium hydride (2.2 equiv.) is added in portions at RT and stirred for 10 min. The appropriate aryl oxirane (2 equiv.) in DMF (0.5 mL/mmol) is added dropwise over 10 min. and stirred overnight at RT. The product is detected by LCMS, and the reaction mixture is quenched with methanol and concentrated to dryness. Water is added to the residue and product is extracted into ethyl acetate (3×50 mL). The organic layer is dried over anhydrous sodium sulfate and evaporated under reduced pressure. The crude product is purified by reverse phase chromatography.

A method of synthesizing certain compounds of the invention is shown as General Method 6.

General Method 6.

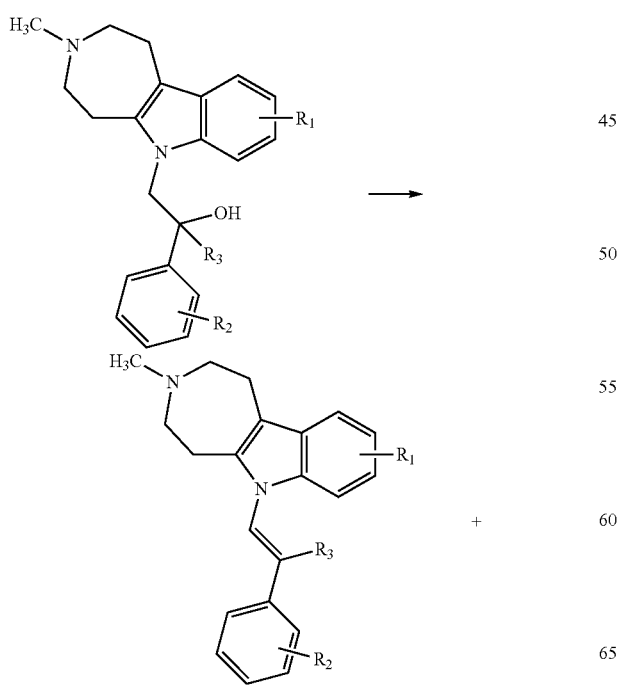

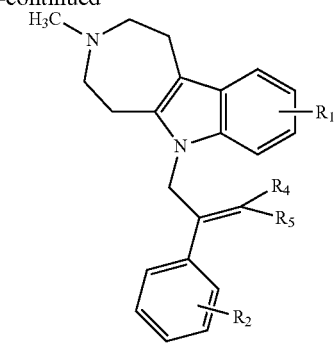

The appropriately substituted 2-(2,3,4,5-tetrahydroazepino[4,5-b]indol-6(1H)-yl)ethanol (1 equiv.) is taken into 25% aqueous $H_2SO_4$ (8 mL/mmol), and stirred at 90° C. for 3 h. The reaction is monitored by TLC and LCMS. The reaction mixture is cooled and basified with aq. KOH solution and extracted with ethyl acetate. The organic layer is dried over anhydrous sodium sulfate and evaporated under reduced pressure. The crude product is purified using reverse phase chromatography.

A method of synthesizing certain compounds of the invention is shown as General Method 7.

General Method 7.

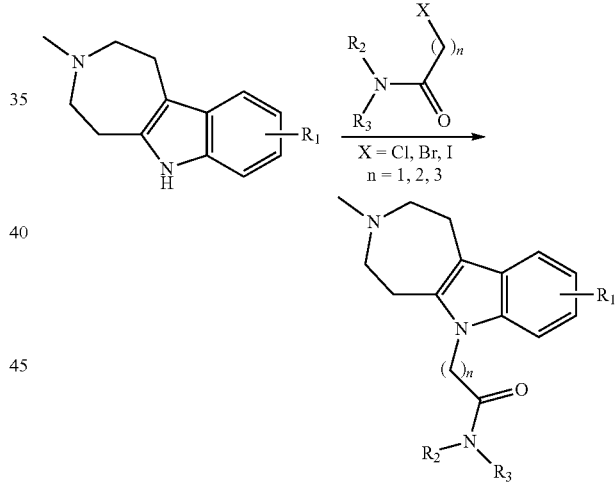

The appropriately substituted 1,2,3,4,5,6-hexahydroazepino[4,5-b]indole (1 equiv.), is taken into DMF. CuI (0.1 equiv.), L-proline (0.2 equiv.) and $K_3PO_4$ (2 equiv.) are added to the solution and the mixture stirred for 10 min. at RT. The 2-haloacetamide derivative (1.2 equiv.) is added dropwise. The reaction mixture is heated at 90° C. for 12 h. After completion of reaction, the reaction mixture is filtered through Celite. DMF is evaporated under reduced pressure and then the residue extracted with ethyl acetate. The organic layer is dried over anhydrous $Na_2SO_4$, and concentrated under reduced pressure to obtain the crude product that is purified by column chromatography.

A method of synthesizing certain compounds of the invention is shown as General Method 8.

General Method 8.

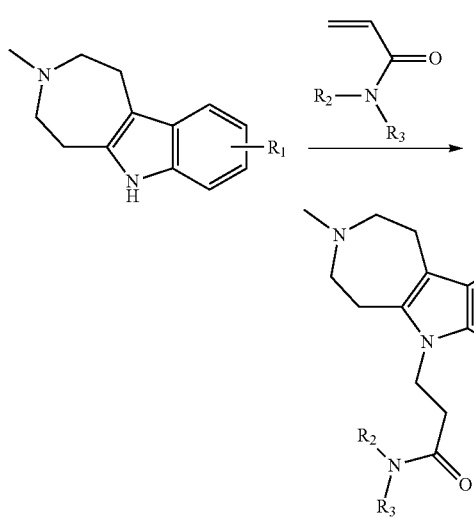

Sodium hydride (1.5 equiv.) is washed with hexane for removal of oil and dried under vacuum. It is then suspended in THF. To this suspension carboline (1 equiv.) in THF is added dropwise at 0° C. Then the reaction mixture is stirred for 0.5 h. A solution of vinyl compound (2 equiv.) in THF is added dropwise into the reaction mixture. The reaction mixture is stirred at RT for 2 h and monitored by TLC. After completion of reaction, the reaction mixture is quenched with ice-water. The crude compound is purified by preparative TLC. The pure compound is stirred in ethanolic HCl to give the corresponding HCl salt.

A method of synthesizing certain compounds of the invention is shown as General Method 9.

General Method 9.

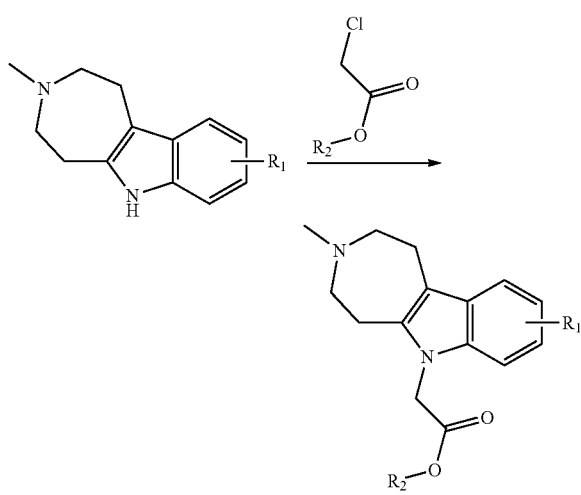

The substituted carboline (1 equiv.) is taken into DMF. CuI (9 mg, 0.046 mmol), L-proline (0.2 equiv.) and $K_3PO_4$ (2 equiv.) are added to the solution and the mixture stirred for 10 min. at RT. The 2-chloroacetate (1.2 equiv.) is added dropwise. The reaction mixture is heated at 90° C. for 12 h. After completion of reaction, the reaction mixture is filtered through Celite. DMF is evaporated under reduced pressure and the residue extracted with ethyl acetate. The organic layer is dried over $Na_2SO_4$, and concentrated under reduced pressure. Then the purified compound is taken in ethanol in HCl to give HCl salt of desired compound.

A method of synthesizing another intermediate used in the synthesis of compounds of the invention is shown as General Method 10.

General Method 10.

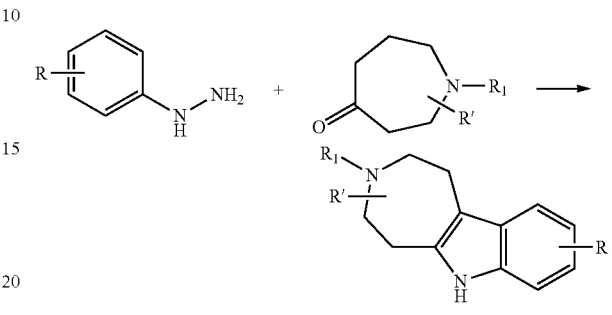

The appropriately substituted azepan-4-one hydrochloride (1 equiv.) and appropriately substituted arylhydrazine hydrochloride (1 equiv.) are refluxed in a mixture of 7% sulfuric acid in 1,4-dioxane overnight under nitrogen. The mixture is poured on to ice and basified with 50% aq NaOH. The resulting precipitate is filtered, washed well with water, and dried in air to provide the substituted 1,2,3,4,5,6-hexahydroazepino [4,5-b]indole derivative.

A method of synthesizing compounds of the invention is shown in General Method 11.

General Method 11.

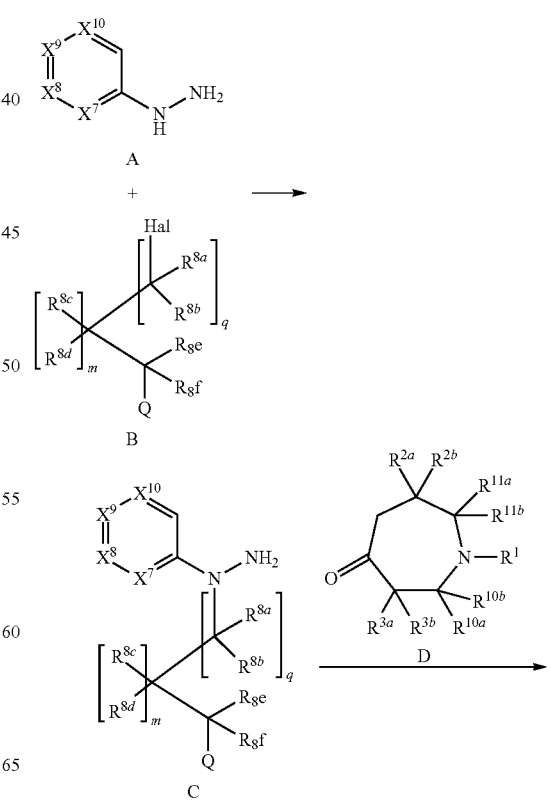

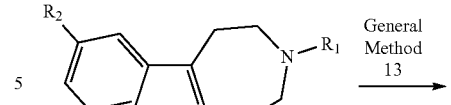

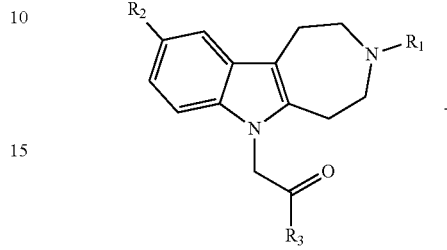

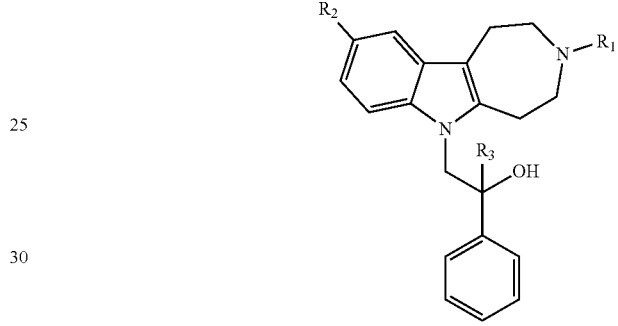

In general, a suitably substituted hydrazine A can be reacted with an appropriately substituted alkyl halide B to generate a substituted hydrazine C, where the internal nitrogen on the hydrazine is substituted, as shown above. The reaction of intermediate D with an appropriately substituted azepan-4-one D should provide structures of the type generally described by structure E.

General Method 12.

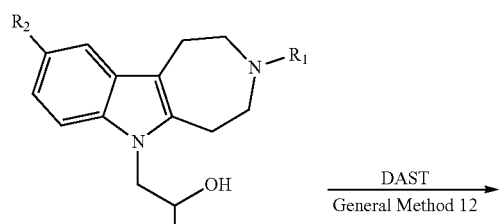

General Method 13

To a solution of appropriate carboline (1 equiv.) in N-methyl-2-pyrrolidone is added KOH (7 equiv.). The reaction mixture is stirred at RT for 20 min. A solution of appropriate 2-bromo-1-(aryl)ethanone (1 equiv.) in N-methyl-2-pyrrolidone is added dropwise and stirring is continued for additional 2-4 h. The reaction is monitored by LCMS and TLC. The reaction mixture is diluted by adding water and extracted with ethyl acetate. The organic layer is washed with water, dried over anhydrous sodium sulfate and concentrated under reduced pressure. The residue is purified by silica gel chromatography to give the keto product.

General Method 14

The keto compound from General Method 13 (1 equiv.) is dissolved in anhydrous THF. Grignard reagent (3 equiv) is added to it dropwise at RT under nitrogen atmosphere and reaction mixture is stirred at RT for 1 h. Water is added to the reaction mixture and the product is extracted with ethyl acetate. The organic layer is washed with water, dried over anhydrous sodium sulfate and concentrated under reduced pressure. The residue is purified by HPLC to give pure alcohol product.

Appropriate alcohol-carboline (1 equiv.) is dissolved in DCM and the solution is cooled to 0° C. Diethylaminosulfur trifluoride (DAST) (1.5 equiv.) is added dropwise and the reaction mixture is stirred at RT for 2 h. The reaction mixture is diluted with saturated aqueous NaHCO$_3$ solution and the organic layer is separated. The organic layer is dried over anhydrous sodium sulfate and evaporated under reduced pressure. The residue is purified by chromatography on neutral alumina to give the fluorinated product.

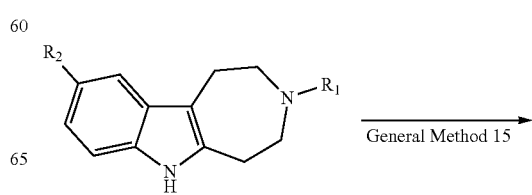

-continued

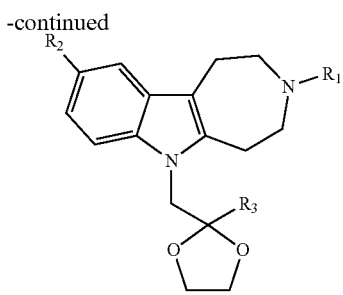

General Method 15

Appropriately substituted carboline (1 equiv.) is dissolved in DMF (2 mL per mmol) and sodium hydride (2 equiv.) is added to it under nitrogen atmosphere. An appropriate 2-(bromomethyl)-1,3-dioxolane (1 equiv.) is added and the reaction mixture is heated at 100° C. overnight. The reaction mixture is diluted by adding water and extracted with ethyl acetate. The organic layer is washed with water, dried over anhydrous sodium sulfate and concentrated under reduced pressure. The residue is purified by silica gel chromatography to give pure dioxolanyl product.

The methods detailed above may be adapted as known by those of skill in the art. Particular examples of each General Method are provided in the Examples below. Additional synthetic methods which may be adapted to arrive at the compounds detailed herein are found in U.S. application Ser. No. 12/259,234 and PCT Application No. PCT/US2008/081390, both filed Oct. 27, 2008.

The following Examples are provided to illustrate but not limit the invention.

All references disclosed herein are incorporated by reference in their entireties.

EXAMPLES

Example 1

Preparation of 9-chloro-1,2,3,4,5,6-hexahydro-3-methylazepino[4,5-b]indole

The title compound was prepared by following general procedure 1. 1-Methylazepan-4-one hydrochloride (164 mg, 1 mmol) and 4-chlorophenylhydrazine hydrochloride (179 mg, 1 mmol) were heated in a mixture of 7% sulfuric acid in 1,4-dioxane (2-3 mL) overnight under nitrogen. Two liquid layers persisted throughout the reaction. The mixture was poured on to ice and basified with 50% aq NaOH. The resulting precipitate was filtered, washed well with water, and dried in air to give 9-chloro-1,2,3,4,5,6-hexahydro-3-methylazepino[4,5-b]indole as a dark brown solid (183 mg 78% yield).

Example 2

Preparation of 1,2,3,4,5,6-hexahydro-3,9-dimethylazepino[4,5-b]indole

The title compound was prepared by following general procedure 1. p-Tolyl hydrazine hydrochloride (15 g, 94.55 mmol) was taken into 7% $H_2SO_4$ in 1,4-dioxane (650 mL), 1-methylazepan-4-one. HCl (15.4 g, 94.55 mmol) was added and stirred at RT for 10 min. The reaction mixture was stirred at 80° C. for 14 h. After completion of the reaction, reaction mass was slowly basified with 50% NaOH solution, extracted with ethyl acetate. The organic layer was dried over anhydrous sodium sulfate and evaporated to dryness and purified by column chromatography (silica gel 100-200 mesh; eluent: 10% methanol-DCM) to afford 3,9-dimethyl-1,2,3,4,5,6-hexahydroazepino[4,5-b]indole (5 g).

Example 3

Preparation of 2-ethyl-5-vinyl-pyridine

The title compound was prepared by following general procedure 2. 2-Ethyl-5-bromopyridine (0.6 g, 0.00322 mol) was dissolved in DMF:THF (3:1 6 mL), and to this solution, tributylvinyltin (1.03 mL, 0.00354 mol) and $Pd(PPh_3)_4$ (0.048 g, 0.000041 mol) were added at RT under nitrogen and the mixture heated at 100° C. for 30 min. After completion of the reaction (TLC), the reaction mixture was cooled to RT and diluted with water (60 mL) and extracted with DCM (3×100 mL). The organic layer was dried over anhydrous sodium sulfate and concentrated under reduced pressure using rotary evaporator below 40° C. The crude was purified through column chromatography (2% ethylacetate:hexane in silica 100-200 mesh, Diameter of column—5.0 cm, Height of silica—approx. 5 inch) to provide 2-ethyl-5-vinylpyridine as a light yellow liquid (0.4 g, 93% yield).

Example 4

Preparation of 2-isopropyl-5-vinyl-pyridine

The title compound was prepared by following general procedure 2. 5-Bromo-2-isopropyl-pyridine (0.75 g, 3.7 mmol) was dissolved in DMF:THF (3:1, 6 mL). Tributylvinyltin (1.2 mL, 4.12 mmol) and $Pd(PPh_3)_4$ (0.070 g, 0.06 mmol) was added to this solution at RT under nitrogen and was heated at 100° C. for 30 min. The reaction mixture was cooled to RT and diluted with water (60 mL) and extracted with DCM (3×100 mL). The organic layer was dried over anhydrous sodium sulfate and concentrated under reduced pressure below 40° C. The crude was purified through column chromatography (90% DCM-Hexane in silica 100-200 mesh, Diameter of column—5.0 cm, Height of silica—approx. 5 inch) to provide 2-isopropyl-5-vinylpyridine as a light yellow liquid (0.5 g, 90% yield).

Example 5

Preparation of 2-trifluoromethyl-5-vinyl-pyridine

The title compound was prepared by following general procedure 2. 5-Bromo-2-trifluoromethylpyridine (2.0 g, 8.8 mmol) was dissolved in DMF:THF (3:1, 12 mL). Tributylvinyltin (3.0 g, 9.68 mmol) and $Pd(PPh_3)_4$ (0.135 g, 0.11 mmol) was added to this solution at RT under nitrogen and was heated at 100° C. for 2 h. After completion of the reaction (TLC), the reaction mixture was cooled to RT and diluted with water (120 mL) and extracted with ethyl acetate (3×100 mL). The organic layer was dried over anhydrous sodium sulfate and concentrated under reduced pressure using rotary evaporator below 40° C. The crude was purified through column chromatography (2% ethylacetate:hexane in silica 100-200 mesh, Diameter of column—5.0 cm, Height of silica—approx. 5 inch) to provide 2-(trifluoromethyl)-5-vinylpyridine as a light yellow oil (0.8 g, 52% yield).

Example 6

Preparation of methyl 5-vinylpyridine-2-carboxylate

The title compound was prepared by following general procedure 2. Methyl 5-bromopyridine-2-carboxylate (4.0 g, 18.5 mmol) was dissolved in 160 mL dioxane. Vinyltributyltin (11.7 g, 37 mmol) was added to this solution at 25° C., followed by addition of dichlorobis(triphenylphosphine)palladium (1.5 g, mmol). The reaction mixture was degassed and purged with nitrogen for 5 min. and then heated at 100° C. for 2 h. The reaction mixture was evaporated under reduced pressure and the residue was purified by $SiO_2$ chromatography (100-200 mesh, eluent: hexane-50% ethyl acetate-hexane gradient). The requisite fractions were concentrated below 40° C. under reduced pressure to obtain 2 g of methyl 5-vinylpyridine-2-carboxylate as a pale yellow oil (solid at −20° C.). TLC $R_f$ 0.3 in 40% Ethyl acetate:Hexane.

Example 7

Preparation of 2-methyl-5-vinyl-pyridine

The title compound was prepared by following general procedure 2. 5-Bromo-2-methyl pyridine (5 g, 29.0 mmol) was dissolved in DMF:THF (3:1, 35 mL): tributylvinyltin (10.2 g, 31.9 mmol) and $Pd(PPh_3)_4$ (0.44 g, 0.432 mmol) was added to this solution at RT under nitrogen and was heated at 100° C. for 2 h. After completion of the reaction (TLC), the reaction mixture was cooled to RT and diluted with water (350 mL) and extracted with ethyl acetate (3×200 mL). The organic layer was dried over anhydrous sodium sulfate and concentrated under reduced pressure using rotary evaporator below 40° C. The crude was purified through column chromatography (6% ethylacetate:hexane in silica 100-200 mesh, Diameter of column—2.5 cm, Height of silica—approx. 5 inch) to provide 2-methyl-5-vinylpyridine as a light yellow oil (1.6 g, 47% yield).

Example 8

Preparation of 3-vinyl pyridine

The title compound was prepared by following general procedure 2. 3-Bromo pyridine (3.0 g, 18.9 mmol) was dissolved in DMF (9 mL), tributylvinyltin (6.62 g, 20.8 mmol) and $Pd(PPh_3)_4$ (0.326 g, 0.282 mol) was added to this solution at RT under nitrogen and heated at 80° C. for 3 h. The reaction mixture was cooled to RT, diluted with water (90 mL) and extracted with DCM (3×150 mL). The organic layer was dried over anhydrous sodium sulfate and concentrated under reduced pressure below 40° C. The crude was purified through column chromatography (5% ethylacetate:hexane in silica 100-200 mesh, Diameter of column—5.0 cm, Height of silica—approx. 5 inch) to provide the desired compound as a light yellow liquid (0.62 g, 30% yield).

Example 9

Preparation of 2-methyl-5-vinyl-pyrimidine

The title compound was prepared by following general procedure 2. 5-Bromo-2-methyl-pyrimidine (1.7 g, 9.87 mmol) was dissolved in DMF:THF (3:1 24 mL). Tributylvinyltin (3.2 mL, 10.8 mmol) and $Pd(PPh_3)_4$ (0.148 g, 0.128 mmol) was added to this solution at RT under nitrogen and was heated at 120° C. for 30 min. The reaction mixture was cooled to RT and diluted with water (60 mL) and extracted with DCM (3×100 mL). The organic layer was dried over anhydrous sodium sulfate and concentrated under reduced pressure using rotary evaporator below 40° C. The crude was purified through column chromatography (20% Ethyl acetate-Hexane in silica 100-200 mesh, Diameter of column—5.0 cm, Height of silica—approx. 5 inch) to provide 2-methyl-5-vinylpyrimidine a as light yellow liquid (1.1 g, 91% yield).

Example 10

Preparation of 5-vinyl-pyrimidine

The title compound was prepared by following general procedure 2. 5-Bromo pyrimidine (0.5 g, 3.2 mmol) was dissolved in DMF (6 mL), to this solution, tributylvinyltin (1.15 g, 3.5 mmol) and $Pd(PPh_3)_4$ (0.06 g, 0.05 mmol) was added at RT under nitrogen and was heated at 100° C. for 1.5 h. The reaction mixture was cooled to RT and diluted with water (60 mL) and extracted with DCM (3×100 mL). The organic layer was dried over anhydrous sodium sulfate and concentrated under reduced pressure using rotary evaporator below 40° C. The crude was purified through column chromatography (4% ethylacetate:hexane in silica 100-200 mesh, Diameter of column—2.5 cm, Height of silica—approx. 5 inch) to provide 5-vinylpyrimidine as a light yellow liquid (0.32 g, 95% yield).

Example 11

Preparation of 2-methyl-5-vinyl-pyrazine

The title compound was prepared by following general procedure 2. 5-Bromo-2-methyl pyrazine (2.0 g, 11 mmol) was dissolved in DMF:THF (3:1, 24 mL). Tributylvinyltin (3.0 g, 12.6 mmol) and $Pd(PPh_3)_4$ (0.172 g, 0.143 mmol) was added to this solution at RT under nitrogen and was heated at 100° C. for 3 h. The reaction mixture was cooled to RT and diluted with water (240 mL) and extracted with ethyl acetate (3×150 mL), the combined organic layer was dried over anhydrous sodium sulfate and concentrated under reduced pressure below 40° C. The crude was purified through column chromatography (2% ethylacetate:hexane in silica 100-200 mesh, Diameter of column—5.0 cm, Height of silica—approx. 5 inch) to provide 2-methyl-5-vinylpyrazine as a light yellow oil (1.0 g, 71% yield).

Example 12

Preparation of 1-methyl-5-vinylpyridin-2(1H)-one

The title compound was prepared by following general procedure 2. To a solution of 5-bromo-1-methylpyridin-2 (1H)-one (2 g, 10.63 mmol) in 20 mL of 1,4-dioxane, dichlorobis(triphenylphosphine)palladium(II) (0.834 g, 1.19 mmol) was added at RT and stirred at the same temperature for 5 min. Tributylvinyltin (3.46 mL, 1.19 mmol) was added slowly at RT and stirred at 100-105° C. for 2 h. The reaction was monitored by TLC and LCMS. After completion of the starting material, the solvent was evaporated and the residue purified by column chromatography using 60% ethyl acetate-hexane to afford 1.2 g of 1-methyl-5-vinylpyridin-2(1H)-one.

Example 13

Preparation of 2-propyl-5-vinyl-pyridine

The title compound was prepared by following general procedure 2. 5-Bromo-2-propyl-pyridine (0.5 g, 2.5 mmol) was dissolved in DMF:THF (3:1, 8 mL). To this solution, tributylvinyltin (1.3 mL, 3.7 mmol) and $Pd(PPh_3)_4$ (0.057 g, 0.05 mmol) was added at RT under nitrogen and was heated at 100° C. for 2 h. The reaction mixture was cooled to RT and diluted with water (80 mL) and extracted with DCM (3×100 mL), the organic layer was dried over anhydrous sodium sulfate and concentrated under reduced pressure using rotary evaporator below 40° C. The crude was purified through column chromatography (3% ethylacetate:hexane in silica 100-200 mesh, Diameter of column—2.5.0 cm, Height of silica—approx. 5 inch) to provide 2-propyl-5-vinylpyridine as a light yellow liquid (0.15 g, 41% yield).

Example 14

Preparation of 5-vinylpicolinic acid

The title compound was prepared by following general procedure 2. To a solution of 5-bromo pyridine-2-carboxylic acid (5 g, 24.75 mmol) in 50 mL of 1,4-dioxan, dichlorobis (triphenylphosphine)palladium(II) (2.08 g, 2.96 mmol) was added at RT and stirred at RT for 5 min. Tributylvinyltin (11.7 g, 36.9 mmol) was added slowly at RT and stirred at 100° C. for 3 h. The reaction mixture was monitored by TLC and LCMS. After completion of the starting material, evaporated the solvent below 40° C. and purified by column chromatography using ethyl acetate to afford the 5-vinylpyridine-2-carboxylic acid (3.5 g, 94.5%).

Example 15

Preparation of 2-methyl-5-(oxiran-2-yl)pyridine

The title compound was prepared by following general procedure 3. DMSO (4 mL) was added to NaH 60% dispersion in oil (0.314 g, 7.8 mmol, 1.3 equiv.) and heated to 65° C. for 1 h. THF (10 mL) was added at the same temperature and heated for another 10 min. After 10 min., the reaction mixture was cooled to 0° C. Trimethylsulfonium iodide (1.2 g, 5.9 mmol, 1 equiv.) was added and stirred for 10 min. and then a solution of 6-methylnicotinaldehyde (0.720 g, 5.9 mmol, 1 equiv.) in THF was added dropwise. After complete addition, the reaction mixture was stirred at RT for 2 h, the product was detected by LCMS. The reaction mixture was poured into ice water and the product was extracted in diethyl ether (4×50 mL), dried over $Na_2SO_4$ and concentrated at 25° C. to get the crude product 2-methyl-5-(oxiran-2-yl)pyridine (1.1 g crude).

Example 16

Preparation of 2-(4-fluorophenyl)-2-methyloxirane

The title compound was prepared by following general procedure 3. To a solution of trimethylsulfonium iodide (3.5 g, 17.15 mmol, 1.2 equiv.) in DMSO (30 mL) was added sodium hydride 50%-55% dispersion in oil (0.97 g, 22.2 mmol, 1.5 equiv.) portionwise over 5 min. and stirred for 1 h at RT. A solution of 1-(4-fluorophenyl)ethanone (2 g, 14.47 mmol, 1 equiv.) in DMSO (10 mL) was added to the reaction mixture dropwise over 20 min. and stirred at RT for 4 h. The progress of the reaction was checked by TLC and the reaction mixture was poured in 100 mL water and extracted with ethyl acetate (3×100 mL). The combined organic extracts were washed with water (2×150 mL), followed by brine. The organic layer was dried over sodium sulfate and evaporated to dryness to yield a brown oil (2.2 g). $^1$H NMR (d6-acetone) was consistent with the structure. Product $R_f$ 0.8 (ethyl acetate:hexane 10:90)

Example 17

Preparation of 2-p-tolyloxirane

The title compound was prepared by following general procedure 3. To a solution of trimethylsulfonium iodide (10.28 g, 50.37 mmol, 1.2 equiv.) in DMSO (70 mL) was added sodium hydride 60% dispersion in oil (2.82 g, 70.5 mmol, 1.7 equiv.) portionwise over 5 min. and stirred for 1 h at RT. A solution of 4-methylbenzaldehyde (5.0 g, 42.0 mmol, 1 equiv.) in DMSO (25 mL) was added to the reaction mixture dropwise over 20 min. It was stirred at RT for 4 h. The reaction mixture was checked by TLC and the reaction mixture was poured in water (150 mL) and extracted with ethyl acetate. The combined organic extract was washed with water and brine and dried over anhydrous sodium sulfate and evaporated to dryness to afford 2-p-tolyloxirane (5.2 g).

Example 18

Preparation of 3-(oxiran-2-yl)pyridine

The title compound was prepared by following general procedure 3. Sodium hydride 50% dispersion in oil (1.64 g, 34.2 mmol, 1.8 equiv.) was taken into DMSO (12 mL) and heated at 65° C. for 1 h. THF (36 mL) was added at the same temperature and heated for 10 min. The reaction mixture was cooled to 0° C. and trimethylsulfonium iodide (3.81 g, 18.6 mmol, 1 equiv.) was added, followed by nicotinaldehyde (2 g, 18.6 mmol, 1 equiv.) and stirred at RT for 1 h. The reaction was monitored by TLC and LCMS. After completion of the reaction, the reaction mixture was poured in ice and extracted with diethyl ether, dried over anhydrous sodium sulfate and evaporated under reduced pressure to afford 3-(oxiran-2-yl) pyridine (1 g).

Example 19

Preparation of 2-(2,4,6-trifluorophenyl)-2-methyloxirane

The title compound was prepared by following general procedure 3. DMSO was added to NaH (1 equiv.) and heated to 65° C. for 1 h. THF was added at the same temperature and heated for another 10 min. After 10 min., the reaction mixture was cooled to 0° C. Trimethylsulfonium iodide (1 equiv.) was added and stirred for 10 min. after which the solution of 1-(2,4,6-trifluorophenyl)ethanone (1 equiv.) in THF was added dropwise. After completion of this addition, the reaction mixture was stirred at RT for 2 h. The product was detected by LCMS and the reaction mixture was poured into ice water, extracted with diethyl ether (4×50 mL), dried over $Na_2SO_4$ and concentrated at 25° C. to obtain the product.

Example 20

Preparation of 2-(2,4-dichlorophenyl)-2-methyloxirane

The title compound was prepared by following general procedure 3. DMSO was added to NaH (1 equiv.) and heated to 65° C. for 1 h. THF was added at the same temperature and heated for another 10 min. After 10 min., the reaction mixture was cooled to 0° C. Trimethylsulfonium iodide (1 equiv.) was added and the reaction mixture was stirred for 10 min. after which the solution of 1-(2,4-dichlorophenyl)ethanone (1 equiv.) in THF was added dropwise. After complete addition, the reaction mixture was stirred at RT for 2 h. The product was detected by LCMS and the reaction mixture was poured into ice water, extracted in diethyl ether (4×50 mL), dried over $Na_2SO_4$ and concentrated at 25° C. to obtain the product.

Example 21

Preparation of
2-(2,4-difluorophenyl)-2-methyloxirane

The title compound was prepared by following general procedure 3. DMSO was added to NaH (1 equiv.) and heated to 65° C. for 1 h. THF was added at the same temperature and heated for another 10 min. After 10 min., the reaction mixture was cooled to 0° C. Trimethylsulfonium iodide (1 equiv.) was added and stirred for 10 min. after which the solution of 1-(2,4-difluorophenyl)ethanone (1 equiv.) in THF was added dropwise. After complete addition, the reaction mixture was stirred at RT for 2 h. The product was detected by LCMS and the reaction mixture was poured into ice water, extracted in diethyl ether (4×50 mL), dried over $Na_2SO_4$ and concentrated at 25° C. to obtain the product.

Example 22

Preparation of
2-(3,4-dichlorophenyl)-2-methyloxirane

The title compound was prepared by following general procedure 3. DMSO was added to NaH (1 equiv.) and heated to 65° C. for 1 h. THF was added at the same temperature and heated for another 10 min. After 10 min., the reaction mixture was cooled to 0° C. Trimethylsulfonium iodide (1 equiv.) was added and stirred for 10 min. after which the solution of 1-(3,4-dichlorophenyl)ethanone (1 equiv.) in THF was added dropwise. After complete addition, the reaction mixture was stirred at RT for 2 h. The product was detected by LCMS and the reaction mixture was poured into ice water, extracted in diethyl ether (4×50 mL), dried over $Na_2SO_4$ and concentrated at 25° C. to obtain the product.

Example 23

Preparation of
2-(3,4-difluorophenyl)-2-methyloxirane

The title compound was prepared by following general procedure 3. DMSO was added to NaH (1 equiv.) and heated to 65° C. for 1 h. THF was added at the same temperature and heated for another 10 min. After 10 min., the reaction mixture was cooled to 0° C. Trimethylsulfonium iodide (1 equiv.) was added and stirred for 10 min. after which the solution of 1-(3,4-difluorophenyl)ethanone (1 equiv.) in THF was added dropwise. After complete addition, the reaction mixture was stirred at RT for 2 h. The product was detected by LCMS and the reaction mixture was poured into ice water, extracted in diethyl ether (4×50 mL), dried over $Na_2SO_4$ and concentrated at 25° C. to obtain the product.

Example 24

Preparation of
2-(3-chloro-4-fluorophenyl)-2-methyloxirane

The title compound was prepared by following general procedure 3. DMSO was added to NaH (1 equiv.) and heated to 65° C. for 1 h. THF was added at the same temperature and heated for another 10 min. After 10 min., the reaction mixture was cooled to 0° C. Trimethylsulfonium iodide (1 equiv.) was added and stirred for 10 min. after which the solution of 1-(3-chloro-4-fluorophenyl)ethanone (1 equiv.) in THF was added dropwise. After complete addition, the reaction mixture was stirred at RT for 2 h. The product was detected by LCMS and the reaction mixture was poured into ice water, extracted in diethyl ether (4×50 mL), dried over $Na_2SO_4$ and concentrated at 25° C. to obtain the product.

Example 25

Preparation of
2-(3-fluoro-4-methoxyphenyl)-2-methyloxirane

The title compound was prepared by following general procedure 3. DMSO was added to NaH (1 equiv.) and heated to 65° C. for 1 h. THF was added at the same temperature and heated for another 10 min. After 10 min., the reaction mixture was cooled to 0° C. Trimethylsulfonium iodide (1 equiv.) was added and stirred for 10 min. after which the solution of 1-(3-fluoro-4-methoxyphenyl)ethanone (1 equiv.) in THF was added dropwise. After complete addition, the reaction mixture was stirred at RT for 2 h. The product was detected by LCMS, the reaction mixture was poured into ice water, extracted in diethyl ether (4×50 mL), dried over $Na_2SO_4$ and concentrated at 25° C. to obtain the product.

Example 26

Preparation of 2-(3-fluoro-4-methoxyphenyl)oxirane

The title compound was prepared by following general procedure 3. DMSO was added to NaH (1 equiv.) and heated to 65° C. for 1 h. THF was added at the same temperature and heated for another 10 min. After 10 min., the reaction mixture was cooled to 0° C. Trimethylsulfonium iodide (1 equiv.) was added and stirred for 10 min. after which the solution of 3-fluoro-4-methoxybenzaldehyde (1 equiv.) in THF was added dropwise. After complete addition, the reaction mixture was stirred at RT for 2 h. The product was detected by LCMS and the reaction mixture was poured into ice water, extracted in diethyl ether (4×50 mL), dried over $Na_2SO_4$ and concentrated at 25° C. to obtain the product.

Example 27

Preparation of
2-(4-chloro-3-fluorophenyl)-2-methyloxirane

The title compound was prepared by following general procedure 3. DMSO was added to NaH (1 equiv.) and heated to 65° C. for 1 h. THF was added at the same temperature and heated for another 10 min. After 10 min., the reaction mixture was cooled to 0° C. Trimethylsulfonium iodide (1 equiv.) was added and stirred for 10 min. after which the solution of 1-(4-chloro-3-fluorophenyl)ethanone (1 equiv.) in THF was added dropwise. After complete addition, the reaction mixture was stirred at RT for 2 h. The product was detected by LCMS and the reaction mixture was poured into ice water, extracted in diethyl ether (4×50 mL), dried over $Na_2SO_4$ and concentrated at 25° C. to obtain the product.

Example 28

Preparation of 2-(4-chlorophenyl)-2-methyloxirane

The title compound was prepared by following general procedure 3. DMSO was added to NaH (1 equiv.) and heated to 65° C. for 1 h. THF was added at the same temperature and heated for another 10 min. After 10 min., the reaction mixture was cooled to 0° C. Trimethylsulfonium iodide (1 equiv.) was added and stirred for 10 min. after which the solution of 1-(4-chlorophenyl)ethanone (1 equiv.) in THF was added dropwise. After complete addition, the reaction mixture was stirred at RT for 2 h. The product was detected by LCMS and the reaction mixture was poured into ice water, extracted in diethyl ether (4×50 mL), dried over Na$_2$SO$_4$ and concentrated at 25° C. to obtain the product.

Example 29

Preparation of 2-(4-fluorophenyl)-2,3-dimethyloxirane

The title compound was prepared by following general procedure 3. DMSO was added to NaH (1 equiv.) and heated to 65° C. for 1 h. THF was added at the same temperature and heated for another 10 min. After 10 min., the reaction mixture was cooled to 0° C. Triethylsulfonium iodide (1 equiv.) was added and stirred for 10 min. after which the solution of 1-(4-fluorophenyl)ethanone (1 equiv.) in THF was added dropwise. After complete addition, the reaction mixture was stirred at RT for 2 h. The product was detected by LCMS and the reaction mixture was poured into ice water, extracted in diethyl ether (4×50 mL), dried over Na$_2$SO$_4$ and concentrated at 25° C. to obtain the product.

Example 30

Preparation of 2-(4-methoxyphenyl)-2-methyloxirane

The title compound was prepared by following general procedure 3. DMSO was added to NaH (1 equiv.) and heated to 65° C. for 1 h. THF was added at the same temperature and heated for another 10 min. After 10 min., the reaction mixture was cooled to 0° C. Trimethylsulfonium iodide (1 equiv.) was added and stirred for 10 min. after which the solution of 1-(4-methoxyphenyl)ethanone (1 equiv.) in THF was added dropwise. After complete addition, the reaction mixture was stirred at RT for 2 h. The product was detected by LCMS and the reaction mixture was poured into ice water, extracted in diethyl ether (4×50 mL), dried over Na$_2$SO$_4$ and concentrated at 25° C. to obtain the product.

Example 31

Preparation of 2-(trifluoromethyl)-2-(4-fluorophenyl)oxirane

The title compound was prepared by following general procedure 3. DMSO was added to NaH (1 equiv.) and heated to 65° C. for 1 h. THF was added at the same temperature and heated for another 10 min. After 10 min., the reaction mixture was cooled to 0° C. Trimethylsulfonium iodide (1 equiv.) was added and stirred for 10 min. after which the solution of 2,2,2-trifluoro-1-(4-fluorophenyl)ethanone (1 equiv.) in THF was added dropwise. After complete addition, the reaction mixture was stirred at RT for 2 h. The product was detected by LCMS and the reaction mixture was poured into ice water, extracted in diethyl ether (4×50 mL), dried over Na$_2$SO$_4$ and concentrated at 25° C. to obtain the product.

Example 32

Preparation of 2-(trifluoromethyl)-5-(2-methyloxiran-2-yl)pyridine

The title compound was prepared by following general procedure 3. DMSO was added to NaH (1 equiv.) and heated to 65° C. for 1 h. THF was added at the same temperature and heated for another 10 min. After 10 min., the reaction mixture was cooled to 0° C. Trimethylsulfonium iodide (1 equiv.) was added and stirred for 10 min. after which the solution of 1-(6-(trifluoromethyl)pyridin-3-yl)ethanone (1 equiv.) in THF was added dropwise. After complete addition, the reaction mixture was stirred at RT for 2 h. The product was detected by LCMS and the reaction mixture was poured into ice water, extracted in diethyl ether (4×50 mL), dried over Na$_2$SO$_4$ and concentrated at 25° C. to obtain the product.

Example 33

Preparation of 2-(trifluoromethyl)-5-(oxiran-2-yl)pyridine

The title compound was prepared by following general procedure 3. DMSO was added to NaH (1 equiv.) and heated to 65° C. for 1 h. THF was added at the same temperature and heated for another 10 min. After 10 min., the reaction mixture was cooled to 0° C. Trimethylsulfonium iodide (1 equiv.) was added and stirred for 10 min. after which the solution of 6-(trifluoromethyl)pyridine-3-carbaldehyde (1 equiv.) in THF was added dropwise. After complete addition, the reaction mixture was stirred at RT for 2 h. The product was detected by LCMS and the reaction mixture was poured into ice water, extracted in diethyl ether (4×50 mL), dried over Na$_2$SO$_4$ and concentrated at 25° C. to obtain the product.

Example 34

Preparation of 2-cyclopropyl-2-(4-fluorophenyl)oxirane

The title compound was prepared by following general procedure 3. DMSO was added to NaH (1 equiv.) and heated to 65° C. for 1 h. THF was added at the same temperature and heated for another 10 min. After 10 min., the reaction mixture was cooled to 0° C. Trimethylsulfonium iodide (1 equiv.) was added and stirred for 10 min. after which the solution of cyclopropyl (4-fluorophenyl)methanone (1 equiv.) in THF was added dropwise. After complete addition, the reaction mixture was stirred at RT for 2 h. The product was detected by LCMS and the reaction mixture was poured into ice water, extracted in diethyl ether (4×50 mL), dried over Na$_2$SO$_4$ and concentrated at 25° C. to obtain the product.

Example 35

Preparation of 2-ethyl-2-(4-fluorophenyl)oxirane

The title compound was prepared by following general procedure 3. DMSO was added to NaH (1 equiv.) and heated to 65° C. for 1 h. THF was added at the same temperature and heated for another 10 min. After 10 min., the reaction mixture was cooled to 0° C. Trimethylsulfonium iodide (1 equiv.) was added and stirred for 10 min. after which the solution of 1-(4-fluorophenyl)propan-1-one (1 equiv.) in THF was added dropwise. After complete addition, the reaction mixture was stirred at RT for 2 h. The product was detected by LCMS and

Example 36

Preparation of 2-methyl-2-phenyloxirane

The title compound was prepared by following general procedure 3. DMSO was added to NaH (1 equiv.) and heated to 65° C. for 1 h. THF was added at the same temperature and heated for another 10 min. After 10 min., the reaction mixture was cooled to 0° C. Trimethylsulfonium iodide (1 equiv.) was added and stirred for 10 min. after which the solution of acetophenone (1 equiv.) in THF was added dropwise. After complete addition, the reaction mixture was stirred at RT for 2 h. The product was detected by LCMS and the reaction mixture was poured into ice water, extracted in diethyl ether (4×50 mL), dried over $Na_2SO_4$ and concentrated at 25° C. to obtain the product.

Example 37

Preparation of 2-methyl-5-(2-methyloxiran-2-yl)pyridine

The title compound was prepared by following general procedure 3. DMSO was added to NaH (1 equiv.) and heated to 65° C. for 1 h. THF was added at the same temperature and heated for another 10 min. After 10 min., the reaction mixture was cooled to 0° C. Trimethylsulfonium iodide (1 equiv.) was added and stirred for 10 min. after which the solution of 1-(6-methylpyridin-3-yl)ethanone (1 equiv.) in THF was added dropwise. After complete addition, the reaction mixture was stirred at RT for 2 h. The product was detected by LCMS and the reaction mixture was poured into ice water, extracted in diethyl ether (4×50 mL), dried over $Na_2SO_4$ and concentrated at 25° C. to obtain the product.

Example 38

Preparation of 2-methyl-5-(2-methyloxiran-2-yl)pyrimidine

The title compound was prepared by following general procedure 3. DMSO was added to NaH (1 equiv.) and heated to 65° C. for 1 h. THF was added at the same temperature and heated for another 10 min. After 10 min., the reaction mixture was cooled to 0° C. Trimethylsulfonium iodide (1 equiv.) was added and stirred for 10 min. after which the solution of 1-(2-methylpyrimidin-5-yl)ethanone (1 equiv.) in THF was added dropwise. After complete addition, the reaction mixture was stirred at RT for 2 h. The product was detected by LCMS and the reaction mixture was poured into ice water, extracted in diethyl ether (4×50 mL), dried over $Na_2SO_4$ and concentrated at 25° C. to obtain the product.

Example 39

Preparation of 9-chloro-6-(2-(6-(trifluoromethyl)pyridin-3-yl)ethyl)-1,2,3,4,5,6-hexahydro-3-methylazepino[4,5-b]indole (Compound No. 1)

The title compound was prepared by following general procedure 4. A mixture of 9-chloro-1,2,3,4,5,6-hexahydro-3-methylazepino[4,5-b]indole (117 mg, 0.5 mmol) 2-trifluoromethyl-5-vinylpyridine (95 mg, 0.55 mmol, 1.1 equiv.) and KOH (crushed, 98 mg, 1.75 mmol, 3.5 equiv.) in NMP (0.3 mL) was stirred and heated at 50° C. for 3 h. The reaction mixture was cooled to RT and diluted by adding ice and satd. aqueous NaCl. The aqueous was extracted with ethyl acetate and organic layer was washed with brine, dried over anhydrous sodium sulfate and concentrated under vacuum to obtain crude product as an orange oil (153 mg). The crude product was purified by flash chromatography on silica gel (6 g, 40-63 micron, 230-400 mesh) eluting with ethyl acetate followed by ethyl acetate: ethanol: aqueous ammonia (90:10:1) to obtain 80 mg (39% yield) of 9-chloro-6-(2-(6-(trifluoromethyl)pyridin-3-yl)ethyl)-1,2,3,4,5,6-hexahydro-3-methylazepino[4,5-b]indole as free base. The free base was converted into its HCl salt by treatment with HCl-ether.

Example 40

Preparation of 9-chloro-3-methyl-6-(2-(5-methylpyridin-3-yl)ethyl)-1,2,3,4,5,6-hexahydroazepino[4,5-b]indole (Compound No. 3)

The title compound was prepared by following general procedure 4. 9-Chloro-3-methyl-1,2,3,4,5,6-hexahydroazepino[4,5-b]indole (100 mg, 0.85 mmol), tetra n-butyl ammonium chloride (11 mg, 0.043 mmol), 3-methyl-5-vinylpyridine (121 mg, 1.02 mmol) were taken into 50% NaOH (6 mL) and the reaction mixture was heated overnight at 90° C. The reaction was monitored by TLC. After completion of reaction, the reaction mixture was extracted with ethyl acetate and water, the organic layer was separated, dried over $Na_2SO_4$, and concentrated under reduced pressure. The crude compound was purified by preparative TLC to obtain 9 mg of 9-chloro-3-methyl-6-(2-(5-methylpyridin-3-yl)ethyl)-1,2,3,4,5,6-hexahydroazepino[4,5-b]indole, isolated as its oxalate salt. 1HNMR (CD3OD, Oxalate salt) δ (ppm): 8.40 (s, 1H), 8.0 (s, 1H), 7.60 (s, 1H), 7.45 (s, 1H), 7.18 (d, 1H), 7.0 (d, 1H), 4.40 (t, 2H), 3.70 (t, 2H), 3.30 (s, 3H), 3.20 (m, 5H), 3.0 (s, 3H), 2.38 (s, 3H).

Example 41

Preparation of 6-(2-(5-chloropyridin-3-yl)ethyl)-1,2,3,4,5,6-hexahydro-3,9-dimethylazepino[4,5-b]indole (Compound No. 4)

The title compound was prepared by following general procedure 4. 3,9-Dimethyl-1,2,3,4,5,6-hexahydroazepino[4,5-b]indole (100 mg, 0.46 mmol), tetra n-butyl ammonium chloride (6 mg, 0.023 mmol), 3-chloro-5-vinylpyridine (77 mg, 0.55 mmol) were taken into 50% NaOH (3 mL). The reaction mixture was heated overnight at 110° C. The reaction mixture was extracted with ethyl acetate and organic layer was dried over $Na_2SO_4$, and concentrated under reduced pressure to obtain 150 mg of 6-(2-(5-chloropyridin-3-yl)ethyl)-3,9-dimethyl-1,2,3,4,5,6-hexahydroazepino[4,5-b]indole as the TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min., injection vol. 5 mL).

Example 42

Preparation of 9-chloro-1,2,3,4,5,6-hexahydro-3-methyl-6-(2-(pyridin-4-yl)ethyl)azepino[4,5-b]indole (Compound No. 5)

The title compound was prepared by following general procedure 4. 9-Chloro-3-methyl-1,2,3,4,5,6-hexahydroazepino[4,5-b]indole (100 mg, 0.42 mmol), tetra n-butyl ammonium chloride (6 mg, 0.025 mmol), 4-vinylpyridine (53 mg, 0.51 mmol) were taken into 50% NaOH (3 mL). The reaction mixture was heated overnight at 110° C. The reaction was monitored by TLC. After completion of reaction, the reaction mixture was extracted with ethyl acetate and water, the organic layer was dried over $Na_2SO_4$, and concentrated under reduced pressure to obtain 40 mg of 9-chloro-3-methyl-6-(2-(pyridin-4-yl)ethyl)-1,2,3,4,5,6-hexahydroazepino[4,5-b]indole as the TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min., injection vol. 5 mL).

Example 43

Preparation of 1,2,3,4,5,6-hexahydro-3,9-dimethyl-6-(2-(pyridin-4-yl)ethyl)azepino[4,5-b]indole (Compound No. 6)

The title compound was prepared by following general procedure 4. 3,9-Dimethyl-1,2,3,4,5,6-hexahydroazepino[4,5-b]indole (100 mg, 0.46 mmol), tetra n-butyl ammonium chloride (6 mg, 0.023 mmol), 4-vinylpyridine (58 mg, 0.55 mmol) were taken into 50% NaOH (3 mL). The reaction mixture was heated overnight at 110° C. The reaction mixture was extracted with ethyl acetate and organic layer was dried over $Na_2SO_4$, and concentrated under reduced pressure to obtain 100 mg of 3,9-dimethyl-6-(2-(pyridin-4-yl)ethyl)-1,2,3,4,5,6-hexahydroazepino[4,5-b]indole as the TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min., injection vol. 5 mL).

Example 44

Preparation of 9-chloro-1,2,3,4,5,6-hexahydro-3-methyl-6-(2-(pyridin-2-yl)ethyl)azepino[4,5-b]indole (Compound No. 8)

The title compound was prepared by following general procedure 4. To a solution of 9-chloro-3-methyl-1,2,3,4,5,6-hexahydroazepino[4,5-b]indole (150 mg, 0.6 mmol) in 50% aq. NaOH solution (7 mL), tetra n-butyl ammonium chloride (9 mg, 0.03 mmol) was added followed by 2-vinylpyridine (74 mg, 0.7 mmol) The reaction mixture was heated at 80° C. for 14 h. After completion of reaction, the reaction mixture was diluted with water, extracted with ethyl acetate; the organic layer was dried over $Na_2SO_4$, and concentrated under reduced pressure. The crude product was purified by reverse phase chromatography to afford 80 mg of 9-chloro-3-methyl-6-(2-(pyridin-2-yl)ethyl)-1,2,3,4,5,6-hexahydroazepino[4,5-b]indole as the TFA salt.

Example 45

Preparation of 1,2,3,4,5,6-hexahydro-3,9-dimethyl-6-(2-(pyridin-2-yl)ethyl)azepino[4,5-b]indole (Compound No. 9)

The title compound was prepared by following general procedure 4. To a solution of 3,9-dimethyl-1,2,3,4,5,6-hexahydroazepino[4,5-b]indole (150 mg, 0.7 mmol) in 50% aq. NaOH solution (7 mL) tetra n-butyl ammonium chloride (9 mg, 0.03 mmol) followed by 2-vinylpyridine (80 mg, 0.77 mmol) was added and the reaction mixture was heated at 80° C. for 14 h. After completion of reaction, the reaction mixture was diluted with water, extracted with ethyl acetate; the organic layer was dried over $Na_2SO_4$, and concentrated under reduced pressure. The crude product was purified by reverse phase chromatography to afford 80 mg of 3,9-dimethyl-6-(2-(pyridin-2-yl)ethyl)-1,2,3,4,5,6-hexahydroazepino[4,5-b]indole as the TFA salt.

Example 46

Preparation of 9-chloro-6-(2-(5-chloropyridin-3-yl)ethyl)-1,2,3,4,5,6-hexahydro-3-methylazepino[4,5-b]indole (Compound No. 10)

The title compound was prepared by following general procedure 4. To a solution of 9-chloro-3-methyl-1,2,3,4,5,6-hexahydroazepino[4,5-b]indole (100 mg, 0.42 mmol) in 50% aq. NaOH solution (5 mL) tetra n-butyl ammonium chloride (9 mg, 0.03 mmol) followed by 3-chloro-5-vinylpyridine (65 mg, 0.47 mmol) was added. The reaction mixture was heated at 60° C. for 8 h. After completion of reaction, the reaction mixture was diluted with water, extracted with ethyl acetate; the organic layer was dried over $Na_2SO_4$, and concentrated under reduced pressure. The crude product was purified by reverse phase chromatography to afford 5 mg of 9-chloro-6-(2-(5-chloropyridin-3-yl)ethyl)-3-methyl-1,2,3,4,5,6-hexahydroazepino[4,5-b]indole as the TFA salt.

Example 47

Preparation of 5-(2-(2,3,4,5-tetrahydro-3,9-dimethylazepino[4,5-b]indol-6(1H)-yl)ethyl)pyridine-2-carboxylic acid (Compound No. 11)

The title compound was prepared by following general procedure 4. To a solution of 3,9-dimethyl-1,2,3,4,5,6-hexahydroazepino[4,5-b]indole (200 mg, 0.93 mmol) in 50% aq. NaOH solution (3 mL) was added, tetra n-butyl ammonium chloride (12 mg, 0.046 mmol) followed by 5-vinylpicolinic acid (153 mg, 1.0 mmol). The reaction mixture was heated at 90° C. for overnight, and the reaction was monitored by TLC. After completion of reaction, the reaction mixture was diluted with water, extracted with ethyl acetate. The organic layer was separated, dried over $Na_2SO_4$, and concentrated under reduced pressure. The crude product was purified by reverse phase chromatography to afford 7 mg of 5-(2-(3,9-dimethyl-2,3,4,5-tetrahydroazepino[4,5-b]indol-6(1H)-yl)ethyl)picolinic acid as the TFA salt.

Example 48

Preparation of 6-(2-(6-(trifluoromethyl)pyridin-3-yl)ethyl)-1,2,3,4,5,6-hexahydro-3,9-dimethylazepino[4,5-b]indole (Compound No. 20)

The title compound was prepared by following general procedure 4. To a solution of 3,9-dimethyl-1,2,3,4,5,6-hexahydroazepino[4,5-b]indole (150 mg, 0.69 mmol) in 50% aq. NaOH solution (3 mL) was added, tetra n-butyl ammonium chloride (9 mg, 0.034 mmol) followed by 2-(trifluoromethyl)-5-vinylpyridine (133 mg, 0.76 mmol). The reaction mixture was heated at 120° C. for 8 h and the reaction was monitored by TLC. After completion of reaction, the reaction mixture was diluted with water, extracted with ethyl acetate. The organic layer was separated, dried over anhydrous $Na_2SO_4$, and concentrated under reduced pressure. The crude product was purified by reverse phase chromatography to afford 15 mg of 3,9-dimethyl-6-(2-(6-(trifluoromethyl)pyridin-3-yl)ethyl)-1,2,3,4,5,6-hexahydroazepino[4,5-b]indole as the TFA salt.

Example 49

Preparation of 5-(2-(9-chloro-2,3,4,5-tetrahydro-3-methylazepino[4,5-b]indol-6(1H)-yl)ethyl)pyridine-2-carboxylic acid (Compound No. 21)

The title compound was prepared by following general procedure 4. To a solution of 9-chloro-3-methyl-1,2,3,4,5,6-hexahydroazepino[4,5-b]indole (200 mg, 0.85 mmol) in 50% aq. NaOH solution (3 mL) was added, tetra n-butyl ammonium chloride (11 mg, 0.042 mmol) followed by 5-vinylpicolinic acid (140 mg, 0.94 mmol). The reaction mixture was heated at 90° C. for overnight and was monitored by TLC. After completion of reaction, the reaction mixture was diluted with water, extracted with ethyl acetate. The organic layer was separated, dried over anhydrous $Na_2SO_4$, and concentrated under reduced pressure. The crude product was purified by reverse phase chromatography to afford 8 mg of 5-(2-(9-chloro-3-methyl-2,3,4,5-tetrahydroazepino[4,5-b]indol-6(1H)-yl)ethyl)picolinic acid as the TFA salt.

Example 50

Preparation of 6-(4-chlorophenethyl)-1,2,3,4,5,6-hexahydro-3,9-dimethylazepino[4,5-b]indole (Compound No. 28)

The title compound was prepared by following general procedure 4. 6-(4-Chlorophenethyl)-3,9-dimethyl-1,2,3,4,5,6-hexahydroazepino[4,5-b]indole 3,9-dimethyl-1,2,3,4,5,6-hexahydroazepino[4,5-b]indole (0.214 g, 1 mmol) along with tetrabutylammonium chloride (0.138 g, 0.0005 mmol) were taken into 50% aq. NaOH solution (5 mL) and stirred for 5 min. at RT, 1-(2-bromoethyl)-4-chlorobenzene (0.219 g, 1 mmol) was added and stirred for 5 min. at RT and then the reaction mixture was heated at 110° C. for overnight. The product detected by LCMS, extracted in ethyl acetate, dried over anhydrous sodium sulfate, concentrated and purified by reverse phase chromatography to get the pure compound 6-(4-chlorophenethyl)-3,9-dimethyl-1,2,3,4,5,6-hexahydroazepino[4,5-b]indole.

Example 51

Preparation of 6-(2-chlorophenethyl)-9-chloro-1,2,3,4,5,6-hexahydro-3-methylazepino[4,5-b]indole (Compound No. 29)

The title compound was prepared by following general procedure 4. 9-Chloro-6-(2-chlorophenethyl)-3-methyl-1,2,3,4,5,6-hexahydroazepino[4,5-b]indole 9-chloro-3-methyl-1,2,3,4,5,6-hexahydroazepino[4,5-b]indole (0.234 g, 1 mmol) along with tetrabutylammonium chloride (0.026 g, 0.094 mmol) were taken into 50% aq. NaOH solution (4 mL) and stirred for 15 min. at RT, 1-(2-bromoethyl)-2-chlorobenzene (0.878 g, 4 mmol) was added and stirred for 10 min. at RT and then the reaction mixture was heated at 100° C. for overnight. Product detected by LCMS. The product was extracted in ethyl acetate, dried over anhydrous sodium sulfate, concentrated and purified by reverse phase chromatography to get pure compound 9-chloro-6-(2-chlorophenethyl)-3-methyl-1,2,3,4,5,6-hexahydro azepino[4,5-b]indole as the TFA salt (70 mg)

Example 52

Preparation of 6-(4-chlorophenethyl)-9-chloro-1,2,3,4,5,6-hexahydro-3-methylazepino[4,5-b]indole (Compound No. 30)

The title compound was prepared by following general procedure 4. 9-Chloro-6-(4-chlorophenethyl)-3-methyl-1,2,3,4,5,6-hexahydroazepino[4,5-b]indole 9-chloro-3-methyl-1,2,3,4,5,6-hexahydroazepino[4,5-b]indole (0.234 g, 1 mmol) along with tetrabutylammonium chloride (0.026 g, 0.094 mmol) were taken into 50% aq. NaOH solution (4 mL) and stirred for 15 m in. at RT, 1-(2-bromoethyl)-4-chlorobenzene (0.878 g, 4 mmol) was added and stirred for 10 min. at RT and the reaction mixture was heated at 100° C. for overnight. The product detected by LCMS, extracted in ethyl acetate, dried over anhydrous sodium sulfate, concentrated and purified by reverse phase chromatography to get pure compound 9-chloro-6-(4-chlorophenethyl)-3-methyl-1,2,3, 4,5,6-hexahydro azepino[4,5-b]indole as the TFA salt (50 mg)

Example 53

Preparation of 9-chloro-3-methyl-6-(4-methylphenethyl)-1,2,3,4,5,6-hexahydroazepino[4,5-b]indole (Compound No. 46)

The title compound was prepared by following general procedure 4. TBACl (138 mg, 0.5 mmol) was taken into 50% NaOH (5 mL), and to it was added 9-chloro-3-methyl-1,2,3,4,5,6-hexahydroazepinol[4,5-b]indole (234 mg, 1.0 mmol), stirred for 5 min. at RT, and added 1-(2-bromoethyl)-4-methylbenzene (199 mg, 1.0 mmol), the reaction was then stirred at 110° C. for 12 h. The completion of reaction was checked by LCMS. Water was added and the mixture extracted by DCM which was dried over sodium sulfate and concentrated under vacuum. The crude so obtained was purified by reverse phase chromatography to get pure product.

Example 54

Preparation of 9-chloro-1,2,3,4,5,6-hexahydro-3-methyl-6-phenethylazepino[4,5-b]indole (Compound No. 56)

The title compound was prepared by following general procedure 4. TBACl (59 mg, 0.213 mmol) was taken into 50% NaOH (5 mL), to it added 9-chloro-3-methyl-1,2,3,4,5,6-hexahydroazepinol[4,5-b]indole (100 mg, 0.426 mmol), stirred for 5 min. at RT and added (2-bromoethyl)benzene (78 mg, 0.426 mmol) the reaction was stirred at 100° C. for 12 h. The completion of reaction was checked by LCMS. Water was added and the mixture extracted with DCM which was dried over sodium sulfate and concentrated under vacuum. The crude so obtained was purified by reverse phase chromatography. The pure compound so obtained was made free base and converted to oxalate salt in THF.

Example 55

Preparation of 6-(2-fluorophenethyl)-9-chloro-1,2,3,4,5,6-hexahydro-3-methylazepino[4,5-b]indole (Compound No. 61)

The title compound was prepared by following general procedure 4. 9-Chloro-3-methyl-1,2,3,4,5,6-hexahydroazepino[4,5-b]indole (234 mg, 1.0 mmol) was taken with copper iodide (19 mg, 0.1 mmol), L-proline (23 mg, 0.2 mmol), potassium phosphate tribasic (426 mg, 2.0 mmol) and then 1-(2-bromoethyl)-2-fluorobenzene (203 mg, 1 mmol) in DMF. The reaction mixture was stirred at 90° C. under argon atmosphere for 12 h and monitored by LCMS. After completion of the reaction, water was added and extracted with ethyl acetate. The ethyl acetate layer was washed with water, dried over sodium sulfate and concentrated under vacuum. The crude product was purified by column chromatography (silica gel 100-200 mesh) (gradient 5% MeOH:DCM). The pure product was converted to its oxalate salt using oxalic acid and THF.

Example 56

Preparation of 1,2,3,4,5,6-hexahydro-3,9-dimethyl-6-phenethylazepino[4,5-b]indole (Compound No. 62)

The title compound was prepared by following general procedure 4. 3,9-Dimethyl-1,2,3,4,5,6-hexahydroazepino[4,5-b]indole (214 mg, 1.0 mmol) was taken with copper iodide (19 mg, 0.1 mmol), L-proline (23 mg, 0.2 mmol), potassium phosphate tribasic (426 mg, 2.0 mmol) and (2-bromoethyl)benzene (185 mg, 1 mmol) and DMF was added, the reaction was stirred at 90° C. under argon atmosphere for 12 h. The reaction was monitored by LCMS. After completion of the reaction, water was added and extracted with ethyl acetate. The organic layer was washed with water, dried over sodium sulfate and concentrated under vacuum. The crude so obtained was purified by column chromatography (silica gel 100-200 mesh) (gradient 5% MeOH:DCM). The pure product was converted to oxalate salt using oxalic acid and THF.

Example 57

Preparation of 6-(2-fluorophenethyl)-1,2,3,4,5,6-hexahydro-3,9-dimethylazepino[4,5-b]indole (Compound No. 63)

The title compound was prepared by following general procedure 4. Tetrabutylammonium chloride (138 mg, 0.0005 mmol) was taken into 50% NaOH (10 mL) 3,9-Dimethyl-1,2,3,4,5,6-hexahydroazepino[4,5-b]indole (214 mg, 1.0 mmol) was added and stirred for 5 min. at RT. 1-(2-Bromoethyl)-2-fluorobenzene (203 mg, 1 mmol) was added, the reaction was stirred at 100° C. for 12 h. The completion of reaction was checked by LCMS. Water was added to the reaction mixture and extracted with DCM which was dried over sodium sulfate and concentrated under vacuum. The crude product was purified by reverse phase chromatography to afford the title compound.

Example 58

Preparation of 6-(2-chlorophenethyl)-1,2,3,4,5,6-hexahydro-3,9-dimethylazepino[4,5-b]indole (Compound No. 69)

The title compound was prepared by following general procedure 4. 3,9-Dimethyl-1,2,3,4,5,6-hexahydroazepino[4,5-b]indole (214 mg, 1.0 mmol) was taken with copper iodide (19 mg, 0.1 mmol), L-praline (23 mg, 0.2 mmol), potassium phosphate tribasic (426 mg, 2.0 mmol), 1-(2-bromoethyl)-2-chlorobenzene (219 mg, 1.0 mmol) and DMF was added, the reaction was stirred at 90° C. under argon atmosphere for 12 h and monitored by LCMS. After completion of the reaction water was added and extracted with ethyl acetate. The organic layer was washed with water, dried over sodium sulfate and concentrated under vacuum. The crude product was purified by reverse phase chromatography to afford 50 mg of the title compound (10.7%).

Example 59

Preparation of N-cyclohexyl-3-(2,3,4,5-tetrahydro-3,9-dimethylazepino[4,5-b]indol-6(1H)-yl)-N-methylpropanamide (Compound No. 81)

The title compound was prepared by following general procedure 8. Sodium hydride (0.027 g, 0.69 mmol) washed with hexane for removal of oil and dried under vacuum. Then the sodium hydride was taken into THF. To this solution 3,9-dimethyl-1,2,3,4,5,6-hexahydroazepino[4,5-b]indole (0.1 g, 0.46 mmol) in THF was added dropwise at 0° C. Then the reaction mixture was stirred for 0.5 h. The solution of N-cyclohexyl-N-methylacrylamide (0.115 g, 0.93 mmol) in THF was added dropwise into the reaction mixture. The reaction mixture was stirred at RT for 2 h and monitored by TLC. After completion of reaction, the reaction mixture was quenched with ice-water. The crude compound was purified by preparative TLC. The pure compound was stirred in ethanolic HCl to give 6 mg HCl salt of N-cyclohexyl-3-(3,9-dimethyl-2,3,4,5-tetrahydroazepino[4,5-b]indol-6(1H)-yl)-N-methylpropanamide.

Example 60

Preparation of 2-(9-chloro-2,3,4,5-tetrahydro-3-methylazepino[4,5-b]indol-6(1H)-yl)-1-(6-methylpyridin-3-yl)ethanol (Compound No. 7)

The title compound was prepared by following general procedure 5. 9-Chloro-3-methyl-1,2,3,4,5,6-hexahydroazepino[4,5-b]indole (234 mg, 1 mmol) was dissolved in DMF (2 mL). To a solution of sodium hydride (50%) (100 mg, 2.2 mmol) was added in portions at RT and stirred at RT for 10 min. A solution of 2-methyl-5-(oxiran-2-yl)pyridine (270 mg, 2 mmol) in DMF (1 mL) was added dropwise for 10 min. and stirred for overnight at RT. The product was detected by LCMS, the reaction mixture was quenched with methanol and concentrated to dryness. Water was added to the residue and product was extracted in ethyl acetate (3×50 mL). The organic layer was dried over anhydrous sodium sulfate and evaporated under reduced pressure. The crude product was purified by reverse phase chromatography to get 2-(9-chloro-3-methyl-2,3,4,5-tetrahydroazepino[4,5-b]indol-6(1H)-yl)-1-(6-methylpyridin-3-yl)ethanol as the TFA salt (195 mg, 40.37%). 1HNMR (DMSO-d6, TFA salt) δ (ppm): 8.40 (s, 1H), 7.90 (s, 1H), 7.60 (s, 1H), 7.40 (m, 2H), 7.0 (m, 1H), 5.80 (m, 1H), 4.90 (m, 1H), 4.30 (m, 1H), 3.60 (m, 4H), 3.20 (m, 4H), 3.0 (m, 4H), 2.80 (s, 3H).

Example 61

Preparation of 1-(9-chloro-2,3,4,5-tetrahydro-3-methylazepino[4,5-b]indol-6(1H)-yl)-2-(4-chlorophenyl)propan-2-ol (Compound No. 12)

The title compound was prepared by following general procedure 5. To a stirred suspension of sodium hydride (61 mg, 0.254 mmol) in 5 mL of DMF, 9-chloro-3-methyl-1,2,3,4,5,6-hexahydroazepino[4,5-b]indole (0.2 g, 0.852 mmol)

was added and stirred at RT for 5 min. 2-(4-Chlorophenyl)-2-methyloxirane (214 mg, 1.27 mmol) was added slowly dropwise and stirred at RT for 14 h. The reaction was monitored by TLC and LCMS. After completion of the reaction, water was added, extracted with ethyl acetate. The organic layer was dried over anhydrous sodium sulfate, evaporated under reduced pressure and purified by reverse phase chromatography to afford 150 mg of (1-(9-chloro-3-methyl-2,3,4,5-tetrahydroazepino[4,5-b]indol-6(1H)-yl)-2-(4-chlorophenyl)propan-2-ol) as the TFA salt.

Example 62

Preparation of 1-(9-chloro-2,3,4,5-tetrahydro-3-methylazepino[4,5-b]indol-6(1H)-yl)-2-(4-fluorophenyl)propan-2-ol (Compound No. 13)

The title compound was prepared by following general procedure 5. To a stirred suspension of sodium hydride (61 mg, 0.254 mmol) in 5 mL of DMF, 9-chloro-3-methyl-1,2,3,4,5,6-hexahydroazepino[4,5-b]indole (0.2 g, 0.852 mmol) was added and stirred at RT for 5 min. 2-(4-Fluorophenyl)-2-methyloxirane (194 mg, 1.27 mmol) was added slowly dropwise and stirred at RT for 14 h. The reaction was monitored by TLC and LCMS. After completion of the reaction, water was added, extracted with ethyl acetate. The organic layer was dried over anhydrous sodium sulfate, evaporated under reduced pressure and purified by reverse phase chromatography to afford 150 mg of (1-(9-chloro-3-methyl-2,3,4,5-tetrahydroazepino[4,5-b]indol-6(1H)-yl)-2-(4-fluorophenyl)propan-2-ol) as the TFA salt. $^1$H NMR (DMSO-d6, TFA salt) δ (ppm): 7.40 (s, 1H), 7.30-7.18 (m, 3H), 7.0-6.80 (m, 3H), 4.40-4.25 (d, 2H), 4.25-4.15 (d, 2H), 3.40-3.20 (d, 2H), 3.20-3.00 (m, 4H), 2.90 (s, 3H), 1.50 (s, 3H).

Example 63

Preparation of 2-(4-fluorophenyl)-1-(2,3,4,5-tetrahydro-3,9-dimethylazepino[4,5-b]indol-6(1H)-yl)propan-2-ol (Compound No. 14)

The title compound was prepared by following general procedure 5. To a stirred suspension of sodium hydride (67 mg, 0.28 mmol) in 5 mL of DMF, 3,9-dimethyl-1,2,3,4,5,6-hexahydroazepino[4,5-b]indole (0.2 g, 0.934 mmol) was added and stirred at RT for 5 min. 2-(4-Fluorophenyl)-2-methyloxirane (212 mg, 1.39 mmol) was added slowly dropwise and stirred at RT for 14 h. The reaction was monitored by TLC and LCMS. After completion of the reaction, water was added, extracted with ethyl acetate. The organic layer was dried over anhydrous sodium sulfate, evaporated under reduced pressure and purified by column chromatography using 10% methanol-DCM. The freebase (30 mg, 0.082 mmol) was dissolved in THF (1.0 mL) and oxalic acid (10 mg, 0.082 mmol) in THF (1.0 mL) was added slowly, the mixture was stirred at RT for 20 min. and the formed solid was filtered, washed with ether and dried to afford the product as oxalate salt (15 mg, brown solid).

Example 64

Preparation of 2-(4-chlorophenyl)-1-(2,3,4,5-tetrahydro-3,9-dimethylazepino[4,5-b]indol-6(1H)-yl)propan-2-ol (Compound No. 15)

The title compound was prepared by following general procedure 5. To a stirred suspension of sodium hydride (67 mg, 0.28 mmol) in 5 mL of DMF, 3,9-dimethyl-1,2,3,4,5,6-hexahydroazepino[4,5-b]indole (0.2 g, 0.934 mmol) was added and stirred at RT for 5 min. 2-(4-Chlorophenyl)-2-methyloxirane (235 mg, 1.4 mmol) was added slowly dropwise and stirred at RT for 14 h. The reaction was monitored by TLC and LCMS. After completion of the reaction, water was added, extracted with ethyl acetate. The organic layer was dried over anhydrous sodium sulfate, evaporated under reduced pressure and purified by column chromatography using 10% methanol-DCM. The freebase (30 mg, 0.078 mmol) was dissolved in THF (1.0 mL) and oxalic acid (9.8 mg, 0.078 mmol) in THF (1.0 mL) was added slowly, the mixture was stirred at RT for 20 min. and the formed solid was filtered, washed with ether and dried to afford product as oxalate salt.

Example 65

Preparation of 2-(9-chloro-2,3,4,5-tetrahydro-3-methylazepino[4,5-b]indol-6(1H)-yl)-1-(4-chlorophenyl)ethanol (Compound No. 16)

The title compound was prepared by following general procedure 5. To a stirred suspension of sodium hydride (153 mg, 6.37 mmol) in 5 mL of DMF, 9-chloro-3-methyl-1,2,3,4,5,6-hexahydroazepino[4,5-b]indole (0.5 g, 2.13 mmol) was added and stirred at RT for 10 min. 2-(4-Chlorophenyl)oxirane (493 mg, 3.19 mmol) in DMF (5 mL) was added slowly dropwise and stirred at RT for 14 h. The reaction was monitored by TLC and LCMS. After completion of the reaction, the reaction mixture quenched with ice water, extracted with ethyl acetate. The organic layer was dried over anhydrous sodium sulfate, evaporated under reduced pressure and purified by reverse phase chromatography to afford 2-(9-chloro-3-methyl-2,3,4,5-tetrahydroazepino[4,5-b]indol-6(1H)-yl)-1-(4-chlorophenyl)ethanol as the TFA salt (110 mg).

Example 66

Preparation of 1-(4-chlorophenyl)-2-(2,3,4,5-tetrahydro-3,9-dimethylazepino[4,5-b]indol-6(1H)-yl)ethanol (Compound No. 17)

The title compound was prepared by following general procedure 5. To a stirred suspension of sodium hydride (167 mg, 6.99 mmol) in DMF (5 mL), 3,9-dimethyl-1,2,3,4,5,6-hexahydroazepino[4,5-b]indole (0.5 g, 2.33 mmol) was added and stirred at RT for 10 min. 2-(4-Chlorophenyl)oxirane (541 mg, 3.504 mmol) in DMF (5 mL) was added slowly dropwise and stirred at RT for 14 h. The reaction was monitored by TLC and LCMS. After completion of the reaction, the reaction mixture quenched with water, extracted with ethyl acetate. The organic layer was washed with brine, dried over anhydrous sodium sulfate, evaporated under reduced pressure and purified by reverse phase chromatography to afford 1-(4-chlorophenyl)-2-(3,9-dimethyl-2,3,4,5-tetrahydroazepino[4,5-b]indol-6(1H)-yl)ethanol as the TFA salt (180 mg).

Example 67

Preparation of 2-(9-chloro-2,3,4,5-tetrahydro-3-methylazepino[4,5-b]indol-6(1H)-yl)-1-(pyridin-3-yl)ethanol (Compound No. 18)

The title compound was prepared by following general procedure 5. To a stirred suspension of sodium hydride (92 mg, 3.83 mmol) in 5 mL of DMF, 9-chloro-3-methyl-1,2,3,4,5,6-hexahydroazepino[4,5-b]indole (0.3 g, 1.27 mmol) was added and stirred at RT for 5 min. 3-(Oxiran-2-yl)pyridine (232 mg, 1.92 mmol) in DMF (5 mL) was added slowly dropwise and stirred at RT for 14 h. The reaction was monitored by TLC and LCMS. After completion of the reaction, the reaction mixture quenched with ice water, extracted with ethyl acetate. The organic layer was washed with brine, dried over anhydrous sodium sulfate, evaporated under reduced pressure and purified by reverse phase chromatography to afford 250 mg of 2-(9-chloro-3-methyl-2,3,4,5-tetrahydroazepino[4,5-b]indol-6(1H)-yl)-1-(pyridin-3-yl)ethanol as the TFA salt.

Example 68

Preparation of 2-(2,3,4,5-tetrahydro-3,9-dimethylazepino[4,5-b]indol-6(1H)-yl)-1-(pyridin-3-yl)ethanol (Compound No. 19)

The title compound was prepared by following general procedure 5. To a stirred suspension of sodium hydride (94 mg, 3.92 mmol) in 5 mL of DMF, 3,9-dimethyl-1,2,3,4,5,6-hexahydroazepino[4,5-b]indole (0.3 g, 1.40 mmol) was added and stirred at RT for 5 min. 3-(Oxiran-2-yl)pyridine (254 mg, 1.54 mmol) in DMF (5 mL) was added slowly dropwise and stirred at RT for 14 h. The reaction was monitored by LCMS. After completion of the reaction, the reaction mixture was diluted with water, extracted with ethyl acetate. The organic layer was dried over anhydrous sodium sulfate, evaporated under reduced pressure and purified by reverse phase chromatography to afford 200 mg of 2-(3,9-dimethyl-2,3,4,5-tetrahydroazepino[4,5-b]indol-6(1H)-yl)-1-(pyridin-3-yl)ethanol as the TFA salt.

Example 69

Preparation of 2-(2,3,4,5-tetrahydro-3,9-dimethylazepino[4,5-b]indol-6(1H)-yl)-1-(6-methylpyridin-3-yl)ethanol (Compound No. 23)

The title compound was prepared by following general procedure 5. 2-(3,9-Dimethyl-2,3,4,5-tetrahydroazepino[4,5-b]indol-6(1H)-yl)-1-(6-methylpyridin-3-yl)ethanol 3,9-Dimethyl-1,2,3,4,5,6-hexahydroazepino[4,5-b]indole (214 mg, 1 mmol) was taken into DMF (2 mL). To a solution of sodium hydride (50%) (100 mg, 2.2 mmol) was in portions at RT and stirred at RT for 10 min. A solution of 2-methyl-5-(oxiran-2-yl)pyridine (270 mg, 2 mmol) in DMF (1 mL) was added dropwise for 10 min. and stirred for overnight at RT. The product was detected by LCMS, the reaction mixture was quenched with methanol and concentrated to dryness. Water was added to the residue and product was extracted in ethyl acetate (3×50 mL). The organic layer was dried over anhydrous sodium sulfate and evaporated under reduced pressure. The crude product was purified by reverse phase chromatography to get pure product 2-(3,9-dimethyl-2,3,4,5-tetrahydroazepino[4,5-b]indol-6(1H)-yl)-1-(6-methylpyridin-3-yl)ethanol as the TFA salt (10 mg).

Example 70

Preparation of 2-(9-chloro-2,3,4,5-tetrahydro-3-methylazepino[4,5-b]indol-6(1H)-yl)-1-phenylethanol (Compound No. 24)

The title compound was prepared by following general procedure 5. (2-(9-Chloro-3-methyl-2,3,4,5-tetrahydroazepino[4,5-b]indol-6(1H)-yl)-1-phenylethanol. To a solution of 9-chloro-3-methyl-1,2,3,4,5,6-hexahydroazepino[4,5-b]indole (300 mg, 1.27 mmol) in 6.0 mL DMF, sodium hydride (92 mg, 3.834 mmol) was added slowly portionwise at RT, followed by the addition of 2-phenyloxirane (230 mg, 1.917 mmol) and stirred at RT for 14 h. The reaction mixture was quenched with water, extracted with ethyl acetate. The organic layer was dried over anhydrous sodium sulfate and evaporated under reduced pressure. The crude product was purified using reverse phase chromatography to obtain 150 mg of product as the TFA salt.

Example 71

Preparation of 2-(2,3,4,5-tetrahydro-3,9-dimethylazepino[4,5-b]indol-6(1H)-yl)-1-phenylethanol (Compound No. 25)

The title compound was prepared by following general procedure 5. (2-(3,9-Dimethyl-2,3,4,5-tetrahydroazepino[4,5-b]indol-6(1H)-yl)-1-phenylethanol). To a solution of 3,9-dimethyl-1,2,3,4,5,6-hexahydroazepino[4,5-b]indole (300 mg, 1.40 mmol) in 10 mL DMF, sodium hydride (100 mg, 4.203 mmol) was added slowly portionwise at RT, followed by the addition of 2-phenyloxirane (252 mg, 2.10 mmol) and stirred at RT for 14 h. LCMS shows the formation of product. The reaction mixture was quenched with water, extracted with ethyl acetate. The organic layer was dried over anhydrous sodium sulfate and evaporated under reduced pressure. The crude product was purified using reverse phase chromatography to obtain 250 mg of product as the TFA salt.

Example 72

Preparation of 2-(9-chloro-2,3,4,5-tetrahydro-3-methylazepino[4,5-b]indol-6(1H)-yl)-1-p-tolylethanol (Compound No. 26)

The title compound was prepared by following general procedure 5. (2-(9-Chloro-3-methyl-2,3,4,5-tetrahydroazepino[4,5-b]indol-6(1H)-yl)-1-p-tolylethanol). To a solution of 9-chloro-3-methyl-1,2,3,4,5,6-hexahydroazepino[4,5-b]indole (300 mg, 1.27 mmol) in 10 mL DMF, sodium hydride (92 mg, 3.834 mmol) was added slowly portionwise at RT, followed by the addition of 2-p-tolyloxirane (256 mg, 1.917 mmol) and stirred at RT for 14 h. The reaction mixture was quenched with water, extracted with ethyl acetate. The organic layer was dried over anhydrous sodium sulfate and evaporated under reduced pressure. The crude product was purified using reverse phase chromatography to obtain 230 mg of product as the TFA salt.

Example 73

Preparation of 2-(2,3,4,5-tetrahydro-3,9-dimethylazepino[4,5-b]indol-6(1H)-yl)-1-p-tolylethanol (Compound No. 27)

The title compound was prepared by following general procedure 5. (2-(3,9-Dimethyl-2,3,4,5-tetrahydroazepino[4,5-b]indol-6(1H)-yl)-1-p-tolylethanol). To a solution of 3,9-dimethyl-1,2,3,4,5,6-hexahydroazepino[4,5-b]indole (300 mg, 1.40 mmol) in 10 mL DMF, sodium hydride (100 mg, 4.203 mmol) was added slowly portionwise at RT, followed by the addition of 2-p-tolyloxirane (281 mg, 2.10 mmol) and stirred at RT for 14 h. LCMS shows the formation of product. The reaction mixture was quenched with water, extracted with ethyl acetate. The organic layer was dried over anhydrous sodium sulfate and evaporated under reduced pressure. The crude product was purified using reverse phase chromatography to obtain 85 mg of (Yield: 17.3.0%) title compound as the TFA salt.

Example 74

Preparation of 2-(9-chloro-2,3,4,5-tetrahydro-3-methylazepino[4,5-b]indol-6(1H)-yl)-1-(2-fluorophenyl)ethanol (Compound No. 40)

The title compound was prepared by following general procedure 5. 9-Chloro-3-methyl-1,2,3,4,5,6-hexahydroazepino[4,5-b]indole (300 mg, 1.27 mmol) was taken into DMF (6 mL). To a solution of sodium hydride (50%) (92 mg, 3.83 mmol) was added in portions at RT and stirred at RT for 10 min. A solution of 2-(2-fluorophenyl)oxirane (264 mg, 1.92 mmol) in DMF (1 mL) was added dropwise for 10 min. and stirred for 14 h at RT. The product was detected by LCMS, the reaction mixture was quenched with ice water, extracted in ethyl acetate. The organic layer was dried over anhydrous sodium sulfate and evaporated under reduced pressure. The crude product was purified by reverse phase chromatography to get pure product 2-(9-chloro-3-methyl-2,3,4,5-tetrahydroazepino[4,5-b]indol-6(1H)-yl)-1-(2-fluorophenyl)ethanol as the TFA salt (240 mg). $^1$H NMR (DMSO-d6, TFA salt) δ (ppm): 7.70-7.50 (m, 2H), 7.40-7.00 (m, 5H), 5.10-5.00 (t, 1H), 4.40-4.20 (m, 4H), 3.40-3.10 (m, 6H), 2.90 (s, 3H).

Example 75

Preparation of 1-(2-fluorophenyl)-2-(2,3,4,5-tetrahydro-3,9-dimethylazepino[4,5-b]indol-6(1H)-yl)ethanol (Compound No. 41)

The title compound was prepared by following general procedure 5. 3,9-Dimethyl-1,2,3,4,5,6-hexahydroazepino[4,5-b]indole (300 mg, 1.40 mmol) was taken into DMF (6 mL). To a solution of sodium hydride (50%) (100 mg, 4.22 mmol) was added in portions at RT and stirred at RT for 10 min. A solution of 2-(2-fluorophenyl)oxirane (290 mg, 2.11 mmol) in DMF (1 mL) was added dropwise for 10 min. and stirred for 14 h at RT. The reaction was monitored by TLC and LCMS. The reaction mixture was quenched with ice water, extracted in ethyl acetate. The organic layer was dried over anhydrous sodium sulfate and evaporated under reduced pressure. The crude product was purified by reverse phase chromatography to get pure product 2-(3,9-dimethyl-2,3,4,5-tetrahydroazepino[4,5-b]indol-6(1H)-yl)-1-(2-fluorophenyl)ethanol as the TFA salt (260 mg). 1HNMR (DMSO-d6, TFA salt) δ (ppm): 7.60 (m, 1H), 7.30 (m, 5H), 6.99 (m, 1H), 5.80 (m, 1H), 5.05 (m, 1H), 4.30 (m, 2H), 3.80 (m, 4H), 3.35 (m, 4H), 3.0 (s, 3H), 2.40 (s, 3H).

Example 76

Preparation of 2-(9-chloro-2,3,4,5-tetrahydro-3-methylazepino[4,5-b]indol-6(1H)-yl)-1-(pyridin-4-yl)ethanol (Compound No. 42)

The title compound was prepared by following general procedure 5. 9-Chloro-3-methyl-1,2,3,4,5,6-hexahydroazepino[4,5-b]indole (300 mg, 1.27 mmol) was taken into DMF (6 mL). To a solution of sodium hydride (50%) (92 mg, 3.83 mmol) was added in portions at RT and stirred at RT for 10 min. A solution of 4-(oxiran-2-yl)pyridine (232 mg, 1.9 mmol) in DMF (1 mL) was added dropwise for 10 min. and stirred for 14 h at RT. The reaction was monitored by TLC and LCMS. The reaction mixture was quenched with ice water, extracted in ethyl acetate. The organic layer was dried over anhydrous sodium sulfate and evaporated under reduced pressure. The crude product was purified by reverse phase chromatography to get pure product 2-(9-chloro-3-methyl-2,3,4,5-tetrahydroazepino[4,5-b]indol-6(1H)-yl)-1-(pyridin-4-yl)ethanol as the TFA salt (230 mg). 1HNMR (DMSO-d6, TFA salt) δ (ppm): 8.65 (m, 2H), 7.80-7.45 (m, 3H), 7.40 (m, 1H), 7.0 (m, 1H), 6.0 (m, 1H), 4.95 (m, 1H), 4.40 (m, 2H), 3.40 (m, 3H), 3.20 (m, 4H), 2.92 (s, 3H).

Example 77

Preparation of 2-(2,3,4,5-tetrahydro-3,9-dimethylazepino[4,5-b]indol-6(1H)-yl)-1-(pyridin-4-yl)ethanol (Compound No. 43)

The title compound was prepared by following general procedure 5. 3,9-Dimethyl-1,2,3,4,5,6-hexahydroazepino[4,5-b]indole (300 mg, 1.40 mmol) was taken into DMF (6 mL). To a solution of sodium hydride (50%) (100 mg, 4.22 mmol) was added in portions at RT and stirred at RT for 10 min. A solution of 4-(oxiran-2-yl)pyridine (254 mg, 2.11 mmol) in DMF (1 mL) was added dropwise for 10 min. and stirred for 14 h at RT. The reaction was monitored by TLC and LCMS. The reaction mixture was quenched with ice water, extracted in ethyl acetate. The organic layer was dried over anhydrous sodium sulfate and evaporated under reduced pressure. The crude product was purified by reverse phase chromatography to get pure product 2-(3,9-dimethyl-2,3,4,5-tetrahydroazepino[4,5-b]indol-6(1H)-yl)-1-(pyridin-4-yl)ethanol as the TFA salt (250 mg).

Example 78

Preparation of 2-(9-chloro-2,3,4,5-tetrahydro-3-methylazepino[4,5-b]indol-6(1H)-yl)-1-(4-methoxyphenyl)ethanol (Compound No. 47)

The title compound was prepared by following general procedure 5. 9-Chloro-3-methyl-1,2,3,4,5,6-hexahydroazepino[4,5-b]indole (300 mg, 1.27 mmol) was taken into DMF (8 mL). To a solution of sodium hydride (50%) (92 mg, 3.83 mmol) was added in portions at RT and stirred at RT for 10 min. A solution of 2-(4-methoxyphenyl)oxirane (287 mg, 1.92 mmol) in DMF (2 mL) was added dropwise for 10 min. and stirred for 14 h at RT. The reaction was monitored by TLC and LCMS. The reaction mixture was quenched with ice water, extracted in ethyl acetate. The organic layer was dried over anhydrous sodium sulfate and evaporated under reduced pressure. The crude product was purified by reverse phase chromatography to get pure product 2-(9-chloro-3-methyl-2,3,4,5-tetrahydroazepino[4,5-b]indol-6(1H)-yl)-1-(4-methoxyphenyl)ethanol as the TFA salt (150 mg).

Example 79

Preparation of 2-(2,3,4,5-tetrahydro-3,9-dimethylazepino[4,5-b]indol-6(1H)-yl)-1-(4-methoxyphenyl)ethanol (Compound No. 48)

The title compound was prepared by following general procedure 5. 3,9-Dimethyl-1,2,3,4,5,6-hexahydroazepino[4,5-b]indole (300 mg, 1.40 mmol) was taken into DMF (8 mL). To a solution of sodium hydride (50%) (100 mg, 4.22 mmol)

was added in portions at RT and stirred at RT for 10 min. A solution of 2-(4-methoxyphenyl)oxirane (315 mg, 2.11 mmol) in DMF (2 mL) was added dropwise for 10 min. and stirred for 14 h at RT. The reaction was monitored by TLC and LC MS. The reaction mixture was quenched with ice water, extracted in ethyl acetate. The organic layer was dried over anhydrous sodium sulfate and evaporated under reduced pressure. The crude product was purified by reverse phase chromatography to get pure product 2-(3,9-dimethyl-2,3,4,5-tetrahydroazepino[4,5-b]indol-6(1H)-yl)-1-(4-methoxyphenyl)ethanol as the TFA salt (210 mg).

Example 80

Preparation of 2-(9-chloro-2,3,4,5-tetrahydro-3-methylazepino[4,5-b]indol-6(1H)-yl)-1-(2-fluoro-4-methoxyphenyl)ethanol (Compound No. 49)

The title compound was prepared by following general procedure 5. 9-Chloro-3-methyl-1,2,3,4,5,6-hexahydroazepino[4,5-b]indole (300 mg, 1.27 mmol) was taken into DMF (8 mL). To a solution of sodium hydride (50%) (92 mg, 3.83 mmol) was added in portions at RT and stirred at RT for 10 min. A solution of 2-(2-fluoro-4-methoxyphenyl)oxirane (322 mg, 1.92 mmol) in DMF (2 mL) was added dropwise for 10 min. and stirred for 14 h at RT. The reaction was monitored by TLC and LCMS. The reaction mixture was quenched with ice water, extracted in ethyl acetate. The organic layer was dried over anhydrous sodium sulfate and evaporated under reduced pressure. The crude product was purified by reverse phase chromatography to get pure product 2-(9-chloro-3-methyl-2,3,4,5-tetrahydroazepino[4,5-b]indol-6(1H)-yl)-1-(2-fluoro-4-methoxy phenyl)ethanol as the TFA salt (230 mg).

Example 81

Preparation of 1-(2-fluoro-4-methoxyphenyl)-2-(2,3,4,5-tetrahydro-3,9-dimethylazepino[4,5-b]indol-6(1H)-yl)ethanol (Compound No. 50)

The title compound was prepared by following general procedure 5. 3,9-Dimethyl-1,2,3,4,5,6-hexahydroazepino[4,5-b]indole (300 mg, 1.40 mmol) was taken into DMF (8 mL). To a solution of sodium hydride (50%) (100 mg, 4.2 mmol) was added in portions at RT and stirred at RT for 10 min. A solution of 2-(2-fluoro-4-methoxyphenyl)oxirane (353 mg, 2.10 mmol) in DMF (2 mL) was added dropwise for 10 min. and stirred for 14 h at RT. The reaction was monitored by TLC and LCMS. The reaction mixture was quenched with ice water, extracted in ethyl acetate. The organic layer was dried over anhydrous sodium sulfate and evaporated under reduced pressure. The crude product was purified by reverse phase chromatography to get pure product 2-(3,9-dimethyl-2,3,4,5-tetrahydroazepino[4,5-b]indol-6(1H)-yl)-1-(2-fluoro-4-methoxyphenyl)ethanol as the TFA salt (300 mg).

Example 82

Preparation of 2-(9-chloro-2,3,4,5-tetrahydro-3-methylazepino[4,5-b]indol-6(1H)-yl)-1-(4-fluorophenyl)ethanol (Compound No. 51)

The title compound was prepared by following general procedure 5. 9-Chloro-3-methyl-1,2,3,4,5,6-hexahydroazepino[4,5-b]indole (300 mg, 1.27 mmol) was taken into DMF (8 mL). To a solution of sodium hydride (50%) (92 mg, 3.83 mmol) was added in portions at RT and stirred at RT for 5 min. A solution of 2-(4-fluorophenyl)oxirane (264 mg, 1.92 mmol) in DMF (2 mL) was added dropwise for 10 min. and stirred for 14 h at RT. The reaction was monitored by TLC and LCMS. The reaction mixture was quenched with ice water, extracted in ethyl acetate. The organic layer was dried over anhydrous sodium sulfate and evaporated under reduced pressure. The crude product was purified by reverse phase chromatography to get pure product 2-(9-chloro-3-methyl-2,3,4,5-tetrahydroazepino[4,5-b]indol-6(1H)-yl)-1-(4-fluorophenyl)ethanol as the TFA salt (90 mg).

Example 83

Preparation of 1-(4-fluorophenyl)-2-(2,3,4,5-tetrahydro-3,9-dimethylazepino[4,5-b]indol-6(1H)-yl)ethanol (Compound No. 52)

The title compound was prepared by following general procedure 5. 3,9-Dimethyl-1,2,3,4,5,6-hexahydroazepino[4,5-b]indole (300 mg, 1.40 mmol) was taken into DMF (8 mL). To a solution of sodium hydride (50%) (100 mg, 4.2 mmol) was added in portions at RT and stirred at RT for 10 min. A solution of 2-(4-fluorophenyl)oxirane (290 mg, 2.10 mmol) in DMF (2 mL) was added dropwise for 10 min. and stirred for 14 h at RT. The reaction was monitored by TLC and LCMS. The reaction mixture was quenched with ice water, extracted in ethyl acetate. The organic layer was dried over anhydrous sodium sulfate and evaporated under reduced pressure. The crude product was purified by reverse phase chromatography to get pure product 2-(3,9-dimethyl-2,3,4,5-tetrahydroazepino[4,5-b]indol-6(1H)-yl)-1-(4-fluorophenyl)ethanol as the TFA salt (150 mg).

Example 84

Preparation of Cyclopentyl-2-(2,3,4,5-tetrahydro-3,9-dimethylazepino[4,5-b]indol-6(1H)-yl)acetate (Compound No. 55)

The title compound was prepared by following general procedure 9. 3,9-Dimethyl-1,2,3,4,5,6-hexahydroazepino[4,5-b]indole (100 mg, 0.46 mmol), was taken into DMF. CuI (9 mg, 0.046 mmol), L-proline (11 mg, 0.093 mmol), $K_3PO_4$ (198 mg, 0.93 mmol) was added to the solution and stirred for 10 min. at RT cyclopentyl 2-chloroacetate (90 mg, 0.56 mmol) was added dropwise. The reaction mixture was heated at 90° C. for 12 h. After completion of reaction, the reaction mixture was filtered through Celite. DMF was evaporated under reduced pressure and then extracted with ethyl acetate. The organic layer was dried over $Na_2SO_4$, and concentrated under reduced pressure. To obtain 20 mg of cyclopentyl 2-(3,9-dimethyl-2,3,4,5-tetrahydroazepino[4,5-b]indol-6(1H)-yl) acetate. Then purified compound was taken into ethanol in HCl to gives HCl salt of desired compound.

Example 85

Preparation of 2-(9-chloro-2,3,4,5-tetrahydro-3-methylazepino[4,5-b]indol-6(1H)-yl)-1-(3,4-difluorophenyl)ethanol (Compound No. 58)

The title compound was prepared by following general procedure 5. 9-Chloro-3-methyl-1,2,3,4,5,6-hexahydroazepino[4,5-b]indole (500 mg, 2.13 mmol) was taken into DMF (8 mL). To a solution of sodium hydride (50%) (153 mg, 6.39 mmol) was added in portions at RT and stirred at RT for 10 min. A solution of 2-(3,4-difluorophenyl)oxirane (498 mg, 3.19 mmol) in DMF (4 mL) was added dropwise for 10 min. and stirred for 14 h at RT. The reaction was monitored by TLC and LCMS. The reaction mixture was quenched with ice water, extracted in ethyl acetate. The organic layer was dried over anhydrous sodium sulfate and evaporated under reduced pressure. The crude product was purified by reverse phase chromatography to get pure product 2-(9-chloro-3-methyl-2,3,4,5-tetrahydroazepino[4,5-b]indol-6(1H)-yl)-1-(3,4-difluorophenyl)ethanol as the TFA salt (180 mg).

Example 86

Preparation of 1-(2,4-difluorophenyl)-2-(2,3,4,5-tetrahydro-3,9-dimethylazepino[4,5-b]indol-6(1H)-yl)ethanol (Compound No. 59)

The title compound was prepared by following general procedure 5. 3,9-Dimethyl-1,2,3,4,5,6-hexahydroazepino[4,5-b]indole (500 mg, 2.33 mmol) was taken into DMF (6 mL). To a solution of sodium hydride (50%) (168 mg, 7.00 mmol) was added in portions at RT and stirred at RT for 10 min. A solution of 2-(2,4-difluorophenyl)oxirane (546 mg, 3.50 mmol) in DMF (4 mL) was added dropwise for 10 min. and stirred for 14 h at RT. The reaction was monitored by LCMS. The reaction mixture was quenched with ice water, extracted in ethyl acetate. The organic layer was washed with brine, dried over anhydrous sodium sulfate and evaporated under reduced pressure. The crude product was purified by reverse phase chromatography to get pure product 2-(3,9-dimethyl-2,3,4,5-tetrahydroazepino[4,5-b]indol-6(1H)-yl)-1-(2-fluorophenyl)ethanol as the TFA salt (60 mg).

Example 87

Preparation of 2-(9-chloro-2,3,4,5-tetrahydro-3-methylazepino[4,5-b]indol-6(1H)-yl)-1-(3-fluoro-4-methoxyphenyl)ethanol (Compound No. 67)

The title compound was prepared by following general procedure 5. 9-Chloro-3-methyl-1,2,3,4,5,6-hexahydroazepino[4,5-b]indole (300 mg, 1.27 mmol) was taken into DMF (6 mL). Sodium hydride (50%) (92 mg, 3.83 mmol) was added in portions at RT and stirred at RT for 10 min. A solution of 2-(3-fluoro-4-methoxyphenyl)oxirane (322 mg, 1.92 mmol) in DMF (4 mL) was added dropwise for 10 min. and stirred for 14 h at RT. The reaction was monitored by TLC and LCMS. The reaction mixture was quenched with ice water, extracted with ethyl acetate. The organic layer was dried over anhydrous sodium sulfate and evaporated under reduced pressure. The crude product was purified by reverse phase chromatography to get pure product 2-(9-chloro-3-methyl-2,3,4,5-tetrahydroazepino[4,5-b]indol-6(1H)-yl)-1-(3-fluoro-4-methoxyphenyl)ethanol as the TFA salt (200 mg).

Example 88

Preparation of 1-(3-fluoro-4-methoxyphenyl)-2-(2,3,4,5-tetrahydro-3,9-dimethylazepino[4,5-b]indol-6(1H)-yl)ethanol (Compound No. 68)

The title compound was prepared by following general procedure 5. 3,9-Dimethyl-1,2,3,4,5,6-hexahydroazepino[4,5-b]indole (300 mg, 1.40 mmol) was taken into DMF (6 mL). To a solution of sodium hydride (50%) (100 mg, 4.20 mmol) was added in portions at RT and stirred at RT for 10 min. A solution of 2-(3-fluoro-4-methoxyphenyl)oxirane (353 mg, 2.10 mmol) in DMF (4 mL) was added dropwise and stirred for 14 h at RT. The reaction was monitored by TLC and LCM S. The reaction mixture was quenched with ice water, extracted with ethyl acetate. The organic layer was washed with brine, dried over anhydrous sodium sulfate and evaporated under reduced pressure. The crude product was purified by reverse phase chromatography to get pure product 2-(3,9-dimethyl-2,3,4,5-tetrahydroazepino[4,5-b]indol-6(1H)-yl)-1-(3-fluoro-4-methoxyphenyl)ethanol as the TFA salt (250 mg).

Example 89

Preparation of Benzyl-2-(9-chloro-2,3,4,5-tetrahydro-3-methylazepino[4,5-b]indol-6(1H)-yl)acetate (Compound No. 75)

The title compound was prepared by following general procedure 9. Preparation of benzyl 2-(9-chloro-3-methyl-2,3,4,5-tetrahydroazepino[4,5-b]indol-6(1H)-yl)acetate. 9-Chloro-3-methyl-1,2,3,4,5,6-hexahydroazepino[4,5-b]indole (100 mg, 0.43 mmol), was taken into DMF. To the above solution CuI (8 mg, 0.043 mmol), L-proline (9 mg, 0.086 mmol), $K_3PO_4$ (183 mg, 0.86 mmol) was added and stirred for 10 min. at RT. Benzyl 2-chloroacetate (95 mg, 0.51 mmol) was added dropwise. The reaction mixture was heated at 90° C. for 12 h. After completion of reaction, the reaction mixture was filtered through Celite. DMF was evaporated under reduced pressure and then extracted with ethyl acetate. The organic layer was dried over $Na_2SO_4$, and concentrated under reduced pressure, to afford 90 mg of benzyl 2-(9-chloro-3-methyl-2,3,4,5-tetrahydroazepino[4,5-b]indol-6(1H)-yl)acetate as the TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min., injection vol. 5 mL).

Example 90

Preparation of 2-(9-chloro-2,3,4,5-tetrahydro-3-methylazepino[4,5-b]indol-6(1H)-yl)-1-(3,4-dimethoxyphenyl)ethanol (Compound No. 77)

The title compound was prepared by following general procedure 5. 9-Chloro-3-methyl-1,2,3,4,5,6-hexahydroazepino[4,5-b]indole (300 mg, 1.27 mmol) was taken into DMF (6 mL). Sodium hydride (50%) (92 mg, 3.83 mmol) was added in portions at RT and stirred at RT for 10 min. A solution of 2-(3,4-dimethoxyphenyl)oxirane (345 mg, 1.92 mmol) in DMF (4 mL) was added dropwise for 10 min. and stirred for 14 h at RT. The reaction was monitored by TLC and LCMS. The reaction mixture was quenched with ice water, extracted with ethyl acetate. The organic layer was dried over anhydrous sodium sulfate and evaporated under reduced pressure. The crude product was purified by reverse phase chromatography to get pure product 2-(9-chloro-3-methyl-2,3,4,5-tetrahydroazepino[4,5-b]indol-6(1H)-yl)-1-(3,4-dimethoxyphenyl)ethanol as the TFA salt (8 mg).

Example 91

Preparation of 9-chloro-6-((E)-2-(4-fluorophenyl)prop-1-enyl)-1,2,3,4,5,6-hexahydro-3-methylazepino[4,5-b]indole (Compound No. 2 and Compound No. 82)

The title compound was prepared by following general procedure 6. 1-(9-Chloro-3-methyl-2,3,4,5-tetrahydroazepino[4,5-b]indol-6(1H)-yl)-2-(4-fluorophenyl)propan-2-ol (100 mg, 0.259 mmol) was taken into 2.0 mL of 25% $H_2SO_4$ in water, and stirred at 90° C. for 3 h. The reaction was monitored by TLC and LCMS. The reaction mixture was cooled and basified with aq. KOH solution and extracted with ethyl acetate. The organic layer was dried over anhydrous sodium sulfate and evaporated under reduced pressure. The crude product was purified using reverse phase chromatography to afford 12 mg of product as the TFA salt along with 9-chloro-6-(2-(4-fluorophenyl)allyl)-3-methyl-1,2,3,4,5,6-hexahydroazepino[4,5-b]indole. Compound No. 82: $^1H$ NMR ($CDCl_3$, freebase) δ (ppm): 7.50-7.30 (m, 3H), 7.20-7.00 (m, 4H), 7.30-7.20 (d, 1H), 5.00-4.90 (t, 2H), 4.40-4.30 (d, 1H), 3.10-2.90 (m, 8H), 2.60 (s, 3H).

Example 92

Preparation of 6-((E)-2-(4-chlorophenyl)prop-1-enyl)-1,2,3,4,5,6-hexahydro-3,9-dimethylazepino[4,5-b]indole (Compound No. 33)

The title compound was prepared by following general procedure 6. 2-(4-Chlorophenyl)-1-(3,9-dimethyl-2,3,4,5-tetrahydroazepino[4,5-b]indol-6(1H)-yl)propan-2-ol (100 mg, 0.261 mmol) was taken into 2.0 mL of 25% $H_2SO_4$ in water, and stirred at 90° C. for 2 h. The reaction was monitored by LCMS. The reaction mixture was cooled and basified with aq. KOH solution and extracted with ethyl acetate. The organic layer was dried over anhydrous sodium sulfate and evaporated under reduced pressure. The crude product was purified using reverse phase chromatography to afford 10 mg of product as the TFA salt along with 6-(2-(4-chlorophenyl)allyl)-3,9-dimethyl-1,2,3,4,5,6-hexahydroazepino[4,5-b]indole.

Example 93

Preparation of 6-((E)-2-(4-fluorophenyl)prop-1-enyl)-1,2,3,4,5,6-hexahydro-3,9-dimethylazepino[4,5-b]indole (Compound No. 34)

The title compound was prepared by following general procedure 6. 1-(3,9-Dimethyl-2,3,4,5-tetrahydroazepino[4,5-b]indol-6(1H)-yl)-2-(4-fluorophenyl)propan-2-ol (100 mg, 0.273 mmol) was taken into 2.0 mL of 25% $H_2SO_4$ in water, and stirred at 90° C. for 2 h. The reaction was monitored by TLC and LCMS. The reaction mixture was cooled and basified with aq. KOH solution and extracted with ethyl acetate. The organic layer was dried over anhydrous sodium sulfate and evaporated under reduced pressure. The crude product was purified using reverse phase chromatography to afford 10 mg of product as the TFA salt along with 6-(2-(4-fluorophenyl)allyl)-3,9-dimethyl-1,2,3,4,5,6-hexahydroazepino[4,5-b]indole.

Example 94

Preparation of 9-chloro-6-((E)-2-(4-chlorophenyl)prop-1-enyl)-1,2,3,4,5,6-hexahydro-3-methylazepino[4,5-b]indole (Compound No. 36 and Compound No. 35)

The title compound was prepared by following general procedure 6. 1-(9-Chloro-3-methyl-2,3,4,5-tetrahydroazepino[4,5-b]indol-6(1H)-yl)-2-(4-chloro phenyl)propan-2-ol (100 mg, 0.248 mmol) was taken into 2.0 mL of 25% $H_2SO_4$ in water and stirred at 90° C. for 2 h. The reaction was monitored by LCMS. The reaction mixture was cooled and basified with aq. KOH solution and extracted with ethyl acetate. The organic layer was dried over anhydrous sodium sulfate and evaporated under reduced pressure. The crude product was purified using reverse phase chromatography to obtain the title compound as the TFA salt along with 9-chloro-6-(2-(4-chlorophenyl)allyl)-3-methyl-1,2,3,4,5,6-hexahydroazepino[4,5-b]indole.

Example 95

Preparation of 6-(4-methoxystyryl)-9-chloro-1,2,3,4,5,6-hexahydro-3-methylazepino[4,5-b]indole (Compound No. 78)

The title compound was prepared by following general procedure 6. To a solution of 2-(9-chloro-3-methyl-2,3,4,5-tetrahydroazepino[4,5-b]indol-6(1H)-yl)-1-(4-methoxyphenyl)ethanol (100 mg, 0.25 mmol) in DCM (2 mL), triethylamine (0.053 mL, 0.38 mmol) was added and stirred for 10 min., methane sulfonyl chloride (0.02 mL, 0.27 mmol) was added slowly at 0° C. and stirred at the same temperature for 1 h and stirred at RT for 2 h. The reaction mixture was diluted with water, extracted with DCM. The organic layer was dried over anhydrous sodium sulfate and evaporated under reduced pressure. The crude product was purified by column chromatography. Pure product was taken into NMP (2.0 mL), KOH powder (72 mg, 1.2 mmol) was added at RT and heated at 80° C. for 24 h. The product was detected by LCMS, the reaction mixture was diluted with water, extracted with ethyl acetate. The organic layer was dried over anhydrous sodium sulfate, concentrated and crude product was purified by reverse phase chromatography to get 6 mg of pure product as the TFA salt.

Example 96

Preparation of N-cyclohexyl-2-(2,3,4,5-tetrahydro-3,9-dimethylazepino[4,5-b]indol-6(1H)-yl)acetamide (Compound No. 22)

The title compound was prepared by following general procedure 7. 3,9-Dimethyl-1,2,3,4,5,6-hexahydroazepino[4,5-b]indole (100 mg, 0.46 mmol), was taken into DMF. CuI (9 mg, 0.045 mmol), L-proline (11 mg, 0.093 mmol), $K_3PO_4$ (198 mg, 0.93 mmol) was added to the solution and stirred for 10 min. at RT. 2-chloro-N-cyclohexylacetamide (98 mg, 0.56 mmol) was added dropwise. The reaction mixture was heated at 90° C. for 12 h. After completion of reaction, the reaction mixture was filtered through Celite. DMF was evaporated under reduced pressure and then extracted with ethyl acetate. The organic layer was dried over anhydrous $Na_2SO_4$, and concentrated under reduced pressure. And purified by column chromatography and then oxalate salt was made by using oxalic acid (35 mg, 0.46 mmol) to obtain 100 mg of N-cyclohexyl-2-(3,9-dimethyl-2,3,4,5-tetrahydroazepino[4,5-b]indol-6(1H)-yl)acetamide as the oxalate salt.

Example 97

Preparation of 2-(9-chloro-2,3,4,5-tetrahydro-3-methylazepino[4,5-b]indol-6(1H)-yl)-N-isopropylacetamide (Compound No. 31)

The title compound was prepared by following general procedure 7. 9-Chloro-3-methyl-1,2,3,4,5,6-hexahydroazepino[4,5-b]indole (100 mg, 0.43 mmol), was taken into DMF. CuI (8 mg, 0.043 mmol), L-proline (9 mg, 0.086 mmol), $K_3PO_4$ (183 mg, 0.86 mmol) was added to the solution and stirred for 10 min. at RT. 2-Chloro-N-isopropylacetamide (65 mg, 0.51 mmol) was added dropwise. The reaction mixture was heated at 90° C. for 12 h. After completion of reaction, the reaction mixture was filtered through Celite. DMF was evaporated under reduced pressure and then the residue was extracted with ethyl acetate. The organic layer was dried over $Na_2SO_4$, and concentrated under reduced pressure to obtain 40 mg of 2-(9-chloro-3-methyl-2,3,4,5-tetrahydroazepino[4,5-b]indol-6(1H)-yl)-N-isopropylacetamide as the TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min., injection vol. 5 mL).

Example 98

Preparation of 2-(2,3,4,5-tetrahydro-3,9-dimethylazepino[4,5-b]indol-6(1H)-yl)-1-(piperidin-1-yl)ethanone (Compound No. 32)

The title compound was prepared by following general procedure 7. 3,9-Dimethyl-1,2,3,4,5,6-hexahydroazepino[4,5-b]indole (100 mg, 0.47 mmol), was taken into DMF. CuI (9 mg, 0.046 mmol), L-proline (11 mg, 0.093 mmol), $K_3PO_4$ (198 mg, 0.93 mmol) were added to the solution and stirred for 10 min. at RT. 2-Chloro-1-(piperidin-1-yl)ethanone (91 mg, 0.56 mmol) was added dropwise. The reaction mixture was heated at 90° C. for 12 h. After completion of reaction, the reaction mixture was filtered through Celite. DMF was evaporated under reduced pressure and then extracted with ethyl acetate. The organic layer was dried over $Na_2SO_4$, and concentrated under reduced pressure to obtain 14 mg of 2-(3,9-dimethyl-2,3,4,5-tetrahydroazepino[4,5-b]indol-6(1H)-yl)-1-(piperidin-1-yl)ethanone as the TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min., injection vol. 5 mL).

Example 99

Preparation of 2-(9-chloro-2,3,4,5-tetrahydro-3-methylazepino[4,5-b]indol-6(1H)-yl)-N-(4-fluorophenyl)acetamide (Compound No. 37)

The title compound was prepared by following general procedure 7. 9-Chloro-3-methyl-1,2,3,4,5,6-hexahydroazepino[4,5-b]indole (100 mg, 0.43 mmol), was taken into DMF. CuI (8 mg, 0.043 mmol), L-proline (9 mg, 0.086 mmol), $K_3PO_4$ (183 mg, 0.86 mmol) were added to the solution and stirred for 10 min. at RT. 2-Chloro-N-(4-fluorophenyl)acetamide (96 mg, 0.53 mmol) was added dropwise. The reaction mixture was heated at 90° C. for 12 h. After completion of reaction, the reaction mixture was filtered through Celite. DMF was evaporated under reduced pressure and then extracted with ethyl acetate. The organic layer was dried over $Na_2SO_4$, and concentrated under reduced pressure, to obtain 20 mg of 2-(9-chloro-3-methyl-2,3,4,5-tetrahydroazepino[4,5-b]indol-6(1H)-yl)-N-(4-fluorophenyl)acetamide as the TFA salt after purification by reverse-phase chromatography (C-18, 5 00 mm×50 mm, Mobile Phase A=0.05% TFA in water, B=0.05% TFA in acetonitrile, Gradient: 10% B to 80% B in 30 min., injection vol. 5 mL).

Example 100

Preparation of 2-(2,3,4,5-tetrahydro-3,9-dimethylazepino[4,5-b]indol-6(1H)-yl)-1-morpholinoethanone (Compound No. 38)

The title compound was prepared by following general procedure 7. 3,9-Dimethyl-1,2,3,4,5,6-hexahydroazepino[4,5-b]indole (100 mg, 0.46 mmol), was taken into DMF. To the above solution CuI (9 mg, 0.046 mmol), L-proline (11 mg, 0.093 mmol), $K_3PO_4$ (198 mg, 0.93 mmol) were added and stirred for 10 min. at RT. 2-Chloro-1-morpholinoethanone (91 mg, 0.56 mmol) was added dropwise. The reaction mixture was heated at 90° C. for 12 h. After completion of reaction, the reaction mixture was filtered through Celite. DMF was evaporated under reduced pressure and then extracted with ethyl acetate. The organic layer was dried over $Na_2SO_4$, and concentrated under reduced pressure. To obtain 4 mg of 2-(3,9-dimethyl-2,3,4,5-tetrahydroazepino[4,5-b]indol-6(1H)-yl)-1-morpholinoethanone as the TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min., injection vol. 5 mL).

Example 101

Preparation of N-(4-fluorophenyl)-2-(2,3,4,5-tetrahydro-3,9-dimethylazepino[4,5-b]indol-6(1H)-yl)acetamide (Compound No. 44)

The title compound was prepared by following general procedure 7. 3,9-Dimethyl-1,2,3,4,5,6-hexahydroazepino[4,5-b]indole (100 mg, 0.46 mmol), was taken into DMF. To the above solution CuI (9 mg, 0.046 mmol), L-proline (11 mg, 0.093 mmol), $K_3PO_4$ (198 mg, 0.93 mmol) were added and stirred for 10 min. at RT. 2-Chloro-N-(4-fluorophenyl)acetamide (105 mg, 0.56 mmol) was added dropwise. The reaction mixture was heated at 90° C. for 12 h. After completion of reaction, the reaction mixture was filtered through Celite. DMF was evaporated under reduced pressure and then extracted with ethyl acetate. The organic layer was dried over $Na_2SO_4$, and concentrated under reduced pressure to obtain 104 mg of 2-(3,9-dimethyl-2,3,4,5-tetrahydroazepino[4,5-b]indol-6(1H)-yl)-N-(4-fluorophenyl)acetamide as the TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min., injection vol. 5 mL).

Example 102

Preparation of 2-(2,3,4,5-tetrahydro-3,9-dimethylazepino[4,5-b]indol-6(1H)-yl)-1-(pyrrolidin-1-yl)ethanone (Compound No. 45)

The title compound was prepared by following general procedure 7. 3,9-Dimethyl-1,2,3,4,5,6-hexahydroazepino[4,5-b]indole (100 mg, 0.46 mmol), was taken into DMF. To the above solution CuI (9 mg, 0.046 mmol), L-proline (11 mg, 0.093 mmol), $K_3PO_4$ (198 mg, 0.93 mmol) were added and stirred for 10 min. at RT. 2-Chloro-1-(pyrrolidin-1-yl)ethanone (82 mg, 0.56 mmol) was added dropwise. The reaction mixture was heated at 90° C. for 12 h. After completion of reaction, the reaction mixture was filtered through Celite. DMF was evaporated under reduced pressure and then extracted with ethyl acetate. The organic layer was dried over $Na_2SO_4$, and concentrated under reduced pressure to obtain 4 mg of 2-(3,9-dimethyl-2,3,4,5-tetrahydroazepino[4,5-b]indol-6(1H)-yl)-1-(pyrrolidin-1-yl)ethanone as the TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min., injection vol. 5 mL).

Example 103

Preparation of 2-(9-chloro-2,3,4,5-tetrahydro-3-methylazepino[4,5-b]indol-6(1H)-yl)-1-(pyrrolidin-1-yl)ethanone (Compound No. 53)

The title compound was prepared by following general procedure 7. 9-Chloro-3-methyl-1,2,3,4,5,6-hexahydroazepino[4,5-b]indole (100 mg, 0.43 mmol), was taken into DMF. CuI (8 mg, 0.043 mmol), L-proline (10 mg, 0.086 mmol), $K_3PO_4$ (183 mg, 0.86 mmol) were added to the solution and stirred for 10 min. at RT. 2-chloro-1-(pyrrolidin-1-yl)ethanone (75 mg, 0.51 mmol) was added dropwise. The reaction mixture was heated at 90° C. for 12 h. After completion of reaction, the reaction mixture was filtered through Celite. DMF was evaporated under reduced pressure and then extracted with ethyl acetate. The organic layer was dried over $Na_2SO_4$, and concentrated under reduced pressure to obtain 15 mg of 2-(9-chloro-3-methyl-2,3,4,5-tetrahydroazepino[4,5-b]indol-6(1H)-yl)-1-(pyrrolidin-1-yl)ethanone as the TFA salt after purification by reverse-phase chromatography (C-18, 5 00 mm×50 mm, Mobile Phase A=0.05% TFA in water, B=0.05% TFA in acetonitrile, Gradient: 10% B to 80% B in 30 min., injection vol. 5 mL).

Example 104

Preparation of 2-(2,3,4,5-tetrahydro-3,9-dimethylazepino[4,5-b]indol-6(1H)-yl)-N-isopropylacetamide (Compound No. 54)

The title compound was prepared by following general procedure 7. 3,9-Dimethyl-1,2,3,4,5,6-hexahydroazepino[4,5-b]indole (100 mg, 0.46 mmol), was taken into DMF. CuI (9 mg, 0.046 mmol), L-proline (11 mg, 0.093 mmol), $K_3PO_4$ (198 mg, 0.93 mmol) were added to the solution and stirred for 10 min. at RT. 2-Chloro-N-isopropylacetamide (76 mg, 0.56 mmol) was added dropwise. The reaction mixture was heated at 90° C. for 12 h. After completion of reaction, the reaction mixture was filtered through Celite. DMF was evaporated under reduced pressure and then extracted with ethyl acetate. The organic layer was dried over $Na_2SO_4$, and concentrated under reduced pressure to obtain 7 mg of 2-(3,9-dimethyl-2,3,4,5-tetrahydroazepino[4,5-b]indol-6(1H)-yl)-N-isopropylacetamide as the TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min., injection vol. 5 mL).

Example 105

Preparation of 2-(9-chloro-2,3,4,5-tetrahydro-3-methylazepino[4,5-b]indol-6(1H)-yl)-1-(piperidin-1-yl)ethanone (Compound No. 57)

The title compound was prepared by following general procedure 7. 9-Chloro-3-methyl-1,2,3,4,5,6-hexahydroazepino[4,5-b]indole (100 mg, 0.43 mmol), was taken into DMF. To the above solution CuI (8 mg, 0.043 mmol), L-proline (9 mg, 0.086 mmol), $K_3PO_4$ (183 mg, 0.86 mmol) were added and stirred for 10 min. at RT. 2-Chloro-1-(piperidin-1-yl)ethanone (83 mg, 0.51 mmol) was added dropwise. The reaction mixture was heated at 90° C. for 12 h. After completion of reaction, the reaction mixture was filtered through Celite. DMF was evaporated under reduced pressure and then extracted with ethyl acetate. The organic layer was dried over $Na_2SO_4$, and concentrated under reduced pressure to obtain 6 mg of 2-(9-chloro-3-methyl-2,3,4,5-tetrahydroazepino[4,5-b]indol-6(1H)-yl)-1-(piperidin-1-yl)ethanone as the TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min., injection vol. 5 mL).

Example 106

Preparation of 2-(9-chloro-2,3,4,5-tetrahydro-3-methylazepino[4,5-b]indol-6(1H)-yl)-1-morpholinoethanone (Compound No. 60)

The title compound was prepared by following general procedure 7. 9-Chloro-3-methyl-1,2,3,4,5,6-hexahydroazepino[4,5-b]indole (100 mg, 0.43 mmol), was taken into DMF. To the above solution CuI (8 mg, 0.043 mmol), L-proline (9 mg, 0.086 mmol), $K_3PO_4$ (183 mg, 0.86 mmol) were added and stirred for 10 min. at RT. 2-Chloro-1-morpholinoethanone (84 mg, 0.51 mmol) was added dropwise. The reaction mixture was heated at 90° C. for 12 h. After completion of reaction, the reaction mixture was filtered through Celite. DMF was evaporated under reduced pressure and then extracted with ethyl acetate. The organic layer was dried over $Na_2SO_4$, and concentrated under reduced pressure to obtain 21 mg of 2-(9-chloro-3-methyl-2,3,4,5-tetrahydroazepino[4,5-b]indol-6(1H)-yl)-1-morpholinoethanone as the TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min., injection vol. 5 mL).

Example 107

Preparation of 2-(9-chloro-2,3,4,5-tetrahydro-3-methylazepino[4,5-b]indol-6(1H)-yl)-1-(piperazin-1-yl)ethanone (Compound No. 72)

The title compound was prepared by following general procedure 7. 9-Chloro-3-methyl-1,2,3,4,5,6-hexahydroazepino[4,5-b]indole (100 mg, 0.43 mmol), was taken into DMF. CuI (8 mg, 0.043 mmol), L-proline (10 mg, 0.086 mmol), $K_3PO_4$ (183 mg, 0.85 mmol) were added to the solution and stirred for 10 min. at RT. 2-Chloro-1-(piperazin-1-yl)ethanone (0.135 mg, 0.51 mmol) was added dropwise. The reaction mixture was heated at 90° C. for 12 h. After completion of reaction, the reaction mixture was filtered through Celite. DMF was evaporated under reduced pressure and then extracted with ethyl acetate. The organic layer was dried over $Na_2SO_4$, and concentrated under reduced pressure. The crude compound was purified by column chromatography to gives 35 mg, and then the compound was stirred in ethanolic HCl to give the HCl salt of 2-(9-chloro-3-methyl-2,3,4,5-tetrahydroazepino[4,5-b]indol-6(1H)-yl)-1-(piperazin-1-yl)ethanone.

Example 108

Preparation of 2-(9-chloro-2,3,4,5-tetrahydro-3-methylazepino[4,5-b]indol-6(1H)-yl)-N-phenylacetamide (Compound No. 73)

The title compound was prepared by following general procedure 7. 9-Chloro-3-methyl-1,2,3,4,5,6-hexahydroazepino[4,5-b]indole (100 mg, 0.43 mmol), was taken into DMF. CuI (8 mg, 0.043 mmol), L-proline (10 mg, 0.086 mmol), $K_3PO_4$ (183 mg, 0.86 mmol) was added to the solution and stirred for 10 min. at RT. 2-Chloro-N-phenylacetamide (87 mg, 0.51 mmol) was added dropwise. The reaction mixture was heated at 90° C. for 12 h. After completion of reaction, the reaction mixture was filtered through Celite. DMF was evaporated under reduced pressure and then extracted with ethyl acetate. The organic layer was dried over $Na_2SO_4$, and concentrated under reduced pressure to obtain 40 mg of 2-(9-chloro-3-methyl-2,3,4,5-tetrahydroazepino[4,5-b]indol-6(1H)-yl)-N-phenylacetamide as the TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min., injection vol. 5 mL).

Example 109

Preparation of 2-(9-chloro-2,3,4,5-tetrahydro-3-methylazepino[4,5-b]indol-6(1H)-yl)-N-cyclohexyl-N-methylacetamide (Compound No. 74)

The title compound was prepared by following general procedure 7. 9-Chloro-3-methyl-1,2,3,4,5,6-hexahydroazepino[4,5-b]indole (100 mg, 0.43 mmol), was taken into DMF. CuI (8 mg, 0.043 mmol), L-proline (10 mg, 0.086 mmol), $K_3PO_4$ (183 mg, 0.86 mmol) were added to the solution and stirred for 10 min. at RT. 2-Chloro-N-cyclohexyl-N-methylacetamide (98 mg, 0.51 mmol) was added dropwise. The reaction mixture was heated at 90° C. for 12 h. After completion of reaction, the reaction mixture was filtered through Celite. DMF was evaporated under reduced pressure and then extracted with ethyl acetate. The organic layer was dried over $Na_2SO_4$, and concentrated under reduced pressure to obtain 56 mg of 2-(9-chloro-3-methyl-2,3,4,5-tetrahydroazepino[4,5-b]indol-6(1H)-yl)-N-cyclohexyl-N-methylacetamide as the TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min., injection vol. 5 mL).

Example 110

Preparation of 2-(9-chloro-2,3,4,5-tetrahydro-3-methylazepino[4,5-b]indol-6(1H)-yl)-1-(4-methylpiperidin-1-yl)ethanone (Compound No. 76)

The title compound was prepared by following general procedure 7. Sodium hydride (34 mg, 0.43 mmol) washed with hexane for removal of oil and dried under vacuum and taken in THF.

To this solution 9-chloro-3-methyl-1,2,3,4,5,6-hexahydroazepino[4,5-b]indole (0.1 g, 0.43 mmol) in THF was added dropwise at 0° C. Then the reaction mixture was stirred for 0.5 h. The solution of 2-chloro-1-(4-methylpiperidin-1-yl)ethanone (89 mg, 0.51 mmol) in THF was added dropwise in reaction mixture. Then the reaction mixture was stirred at RT for 2 h. The reaction monitored by TLC. After completion of the reaction, the reaction mixture was quenched with ice water. THF was evaporated and aqueous layer was extracted with ethyl acetate. The organic layer was dried over anhydrous sodium sulfate. The crude compound was washed with hexane and diethyl ether for removal of color impurities then recrystallized by using methanol to gives 95 mg of desired compound, which was stirred with ethanolic HCl to give the HCl salt of 2-(9-chloro-3-methyl-2,3,4,5-tetrahydroazepino[4,5-b]indol-6(1H)-yl)-1-(4-methylpiperidin-1-yl)ethanone.

Example 111

Preparation of 2-(2,3,4,5-tetrahydro-3,9-dimethylazepino[4,5-b]indol-6(1H)-yl)-N-phenylacetamide (Compound No. 79)

The title compound was prepared by following general procedure 7. 3,9-Dimethyl-1,2,3,4,5,6-hexahydroazepino[4,5-b]indole (100 mg, 0.46 mmol), was taken into DMF. CuI (9 mg, 0.046 mmol), L-proline (11 mg, 0.093 mmol), $K_3PO_4$ (198 mg, 0.93 mmol) was added to the solution and stirred for 10 min. at RT. 2-Chloro-N-phenylacetamide (95 mg, 0.56 mmol) was added dropwise. The reaction mixture was heated at 90° C. for 12 h. After completion of reaction, the reaction mixture was filtered through Celite. DMF was evaporated under reduced pressure and then extracted with ethyl acetate. The organic layer was dried over $Na_2SO_4$, and concentrated under reduced pressure. The crude compound was purified by column chromatography to obtain 2-(3,9-dimethyl-2,3,4,5-tetrahydroazepino[4,5-b]indol-6(1H)-yl)-N-phenylacetamide as the HCl salt using ethanolic HCl (29 mg).

The compounds prepared according to the Examples are further detailed in Table 3.

TABLE 3

| | | | | | |
|---|---|---|---|---|---|
| Synthetic Data | | | | | |
| Compound No. | Salt Type | MW Free Base | FW (Salt Included) | NMR Solvent | NMR_DATA |
| 1 | DiHCL | 407.87 | 480.78 | DMSO | 11.0 (bs, 1H), 8.5 (s, 1H), 7.8 (d, 1H), 7.7 (d, 1H), 7.5 (s, 1H), 7.4 (d, 1H), 7.0 (d, 1H), 4.5 (t, 2H), 3.6 (bs, 2H), 3.3-3.0 (m, 8H), 2.9 (s, 3H), |
| 4 | TFA | 353.90 | 467.91 | CD3OD | 10.13 (bs, 1H), 9.10 (bs, 1H), 8.42 (s, 1H), 8.22 (s, 1H), 7.70 (s, 1H), 7.26 (d, 1H), 7.10 (s, 1H), 6.90 (d, 1H), 4.17-4.22 (m, 2H), 3.10-3.21 (m, 5H), 2.83-3.07 (m, 8H), 2.40 (t, 3H) |
| 5 | TFA | 339.87 | 453.89 | CD3OD | 10.0 (bs, 1H), 8.55 (d, 2H2H), 7.57 (d, 1H), 7.40-7.45 (m, 3H), 7.07 (dd, 1H), 4.50 (t, |

TABLE 3-continued

Synthetic Data

| Compound No. | Salt Type | MW Free Base | FW (Salt Included) | NMR Solvent | NMR_DATA |
|---|---|---|---|---|---|
| | | | | | 2H), 3.50-3.63 (m, 4H), 3.15-3.23 (m, 6H), 2.90 (t, 3H). |
| 6 | TFA | 319.45 | 433.47 | CD3OD | 10.1 (bs, 1H), 8.60 (d, 2H), 7.50 (d, 2H), 7.11-7.20 (m, 2H), 6.90 (d, 1H), 4.42 (t, 2H), 3.10-3.25 (m, 6H), 3.05 (t, 4H), 2.95 (s, 3H), 2.45 (s, 3H). |
| 8 | TFA | 339.87 | 453.89 | DMSO | 8.60-8.56 (d, 1H), 8.20-8.10 (t, 1H), 7.70-7.60 (t, 1H), 7.60-7.50 (d, 1H), 7.40 (s, 1H), 7.20-7.10 (d, 1H), 7.00-6.90 (d, 1H), 4.50-4.40 (t, 2H), 3.60-3.30 (t, 4H), 3.30-3.10 (m, 6H), 2.90 (s, 3H). |
| 9 | TFA | 319.45 | 433.47 | DMSO | 8.60-8.50 (d, 1H), 8.10-8.00 (t, 1H), 7.60-7.50 (t, 1H), 7.50-7.40 (d, 1H), 7.20 (s, 1H), 7.18-7.11 (d, 1H), 6.90-6.80 (d, 1H), 4.50-4.40 (t, 2H), 3.60-3.50 (t, 2H), 3.30-3.10 (m, 8H), 2.90 (s, 3H), 2.30 (s, 3H). |
| 10 | TFA | 374.32 | 488.33 | DMSO | 8.54-8.45 (m, 1H), 8.30-8.25 (s, 1H), 7.75-7.70 (d, 1H), 7.60-7.55 (d, 1H), 7.50-7.45 (d, 1H), 7.05 (d, 1H), 4.5-4.40 (m, 2H), 3.70-3.55 (m, 2H), 3.30-3.10 (m, 6H), 3.05-2.85 (m, 5H). |
| 11 | TFA | 363.46 | 477.48 | DMSO | 2.35-2.40 (s, 3H), 2.65-2.80 (m, 2H), 2.85-2.95 (m, 5H), 3.02-3.20 (m, 6H), 4.35-4.50 (t, 2H), 6.90-6.95 (d, 1H), 7.25-7.35 (m, 2H), 7.65-7.70 (d, 1H), 7.90-7.95 (d, 1H), 8.32-8.35 (s, 1H), 9.75-9.90 (m, 1H). |
| 12 | TFA | 403.36 | 517.37 | DMSO | 7.50-7.20 (m, 6H), 7.00-6.90 (t, 1H), 4.30-4.20 (d, 2H), 4.20-4.10 (d, 2H), 3.60-3.40 (m, 2H), 3.30-3.00 (m, 4H), 2.90 (s, 3H), 1.50-1.40 (d, 3H). |
| 14 | OXALATE | 366.48 | 456.51 | DMSO | 7.50-7.40 (t, 2H), 7.30-7.00 (m, 4H), 6.90-6.80 (d, 1H), 4.30-20 (d, 2H), 4.20-4.10 (d, 2H), 3.20-3.00 (m, 6H), 2.90 (s, 3H), 2.30 (s, 3H), 1.40 (t, 3H). |
| 15 | OXALATE | 382.94 | 472.96 | DMSO | 7.50-7.40 (d, 2H), 7.40-7.20 (m, 3H), 6.90-6.70 (dd, 2H), 4.30-4.20 (d, 2H), 4.20-4.00 (d, 2H), 3.20-3.00 (m, 6H), 2.90 (s, 3H), 2.30 (s, 3H), 1.40 (t, 3H). |
| 16 | TFA | 389.33 | 503.34 | DMSO | 7.50-7.40 (t, 1H), 7.38-7.18 (m, 5H), 7.10-7.00 (d, 1H), 4.80-4.70 (d, 2H), 4.30-4.20 (d, 2H), 3.60-3.50 (m, 4H), 3.20-3.00 (m, 2H), 2.90 (s, 3H).. |
| 17 | TFA | 368.91 | 482.92 | DMSO | 7.40-7.20 (m, 6H), 6.98-6.80 (d, 1H), 4.90-4.70 (dd, 2H), 4.30-4.10 (t, 2H), 3.60-3.40 (m, 2H), 3.30-3.00 (m, 4H), 2.90 (s, 3H), 2.30 (s, 3H). |
| 18 | TFA | 355.87 | 469.88 | DMSO | 8.70-8.50 (dd, 2H), 8.30-8.20 (d, 1H), 7.80-7.70 (m, 1H), 7.50-7.40 (t, 1H), 7.30-7.20 (m, 1H), 7.10-6.90 (t, 1H), 5.10-5.00 (m, 2H), 4.20-4.10 (t, 2H), 3.70-3.58 (m, 2H), 3.40-3.20 (m, 4H), 2.90 (s, 3H). |
| 19 | TFA | 335.45 | 449.47 | DMSO | 8.80-8.60 (dd, 2H), 8.30-8.20 (d, 1H), 7.90-7.70 (m, 1H), 7.10-7.00 (t, 1H), 7.00-6.90 (m, 1H), 6.90-6.80 (t, 1H), 5.10-5.00 (m, 2H), 4.40-4.30 (d, 2H), 3.70-3.50 (m, 2H), 3.40-3.00 (m, 4H), 2.90 (s, 3H), 2.25 (s, 3H). |
| 20 | TFA | 387.45 | 501.46 | DMSO | 10.1-9.9 (m, 1H), 8.45 (s, 1H), 7.95-7.75 (m, 2H), 7.30-7.20 (m, 2H), 6.95-6.85 (d, 1H), 4.50-4.35 (t, 2H), 3.23-3.00 (m, 8H), 2.95-2.85 (m, 6H), 2.35 (s, 3H). |
| 21 | TFA | 383.88 | 497.89 | DMSO | 10.05-9.95 (m, 1H), 8.35 (s, 1H), 7.9-7.85 (d, 1H), 7.75-7.65 (d, 1H), 7.60-7.55 (s, 1H), 7.50-7.40 (d, 1H), 7.10-7.05 (d, 1H), 4.55-4.40 (t, 2H), 3.25-2.80 (m, 13H). |
| 22 | OXALATE | 353.51 | 443.54 | DMSO | −10.9 (s, 1H), 8.62 (d, 1H), 7.19-7.22 (m, 2H), 6.90 (d, 1H), 4.25 (s, 2H), 3.6-4.0 (m, 6H), 3.2-3.4 (m, 6H), 2.4 (s, 3H), 1.5-1.9 (m, 5H), 1.1-1.4 (m, 5H). |
| 23 | TFA | 349.48 | 463.49 | DMSO | 10.8 (s, 1H) 8.97 (s, 1H) 7.90-7.84 (m, 1H) 7.43-7.37 (m, 1H), 7.25-7.15 (m, 1H), 6.70-6.10 (m, 2H), 5.42-5.38 (d, 1H), 4.10-3.70 (m, 6H) 3.20-3.0 (m, 4H) 2.70 (S, 3H) 2.50 (s, 3H) 2.38 (s, 3H). |

TABLE 3-continued

Synthetic Data

| Compound No. | Salt Type | MW Free Base | FW (Salt Included) | NMR Solvent | NMR_DATA |
|---|---|---|---|---|---|
| 24 | TFA | 354.88 | 468.90 | DMSO | 7.80-7.70 (t, 1H), 7.70-7.60 (t, 1H), 7.38-7.30 (m, 5H), 7.20-7.0 (d, 1H), 4.85-4.80 (m, 2H), 4.30-4.20 (d, 4H), 3.0-2.80 (m, 7H). |
| 25 | TFA | 334.47 | 448.48 | DMSO | 7.40-7.25 (m, 6H), 6.95-6.85 (d, 2H), 4.80-4.75 (t, 2H), 4.35-4.25 (m, 4H), 3.0-2.80 (m, 7H), 2.35 (s, 3H). |
| 26 | TFA | 368.91 | 482.92 | DMSO | 7.50-7.40 (m, 2H), 7.20-7.0 (m, 5H), 4.80-4.70 (d, 2H), 4.25-4.20 (t, 4H), 3.25-3.10 (m, 4H), 3.0-2.95 (s, 3H), 2.25 (s, 3H). |
| 27 | TFA | 348.49 | 462.50 | DMSO | 7.40-7.20 (m, 5H), 7.0-6.90 (d, 2H), 4.82-4.70 (d, 2H), 4.30-4.10 (m, 4H), 3.15-2.95 (m, 4H), 2.95-2.90 (t, 3H), 2.40 (s, 3H), 2.30 (s, 3H). |
| 28 | TFA | 352.91 | 466.92 | CD3OD | 1H NMR 7.40-7.10 (m, 3H), 7.10-7.00 (d, 2H), 6.90-6.80 (d, 2H), 4.40-4.30 (t, 2H), 3.20-3.10 (m, 8H), 3.10-3.00 (t, 2H), 3.00 (s, 3H), 2.40 (s, 3H) |
| 29 | TFA | 373.33 | 487.34 | CD3OD | 7.60 (s, 1H), 7.45-7.38 (m, 2H), 7.32-7.05 (m, 4H), 4.42-4.37 (t, 2H), 3.70-3.37 (m, 4H), 3.30-3.0 (m, 6H), 2.90 (s, 3H) |
| 30 | TFA | 373.33 | 487.34 | CD3OD | 7.58 (s, 1H), 7.50-7.45 (d, 1H), 7.35-7.25 (m, 2H), 7.16-7.06 (m, 3H), 4.41-4.36 (t, 2H), 3.72-3.50 (m, 4H), 3.30-3.0 (m, 6H) 2.90 (s, 3H). |
| 31 | TFA | 333.86 | 447.88 | DMSO | −11.23 (s, 1H), 8.53 (d, 1H), 7.52 (s, 1H,), 7.30 (d, 1H), 7.24 (d, 1H), 4.80 (d, 1H), 4.70 (d, 1H), 4.11-4.27 (m, 2H), 3.75-4.0 (m, 5H), 3.10-3.39 (m, 5H), 1.10 (d, 6H). |
| 32 | TFA | 339.48 | 453.50 | CD3OD | 7.23 (s, 1H), 7.19 (d, 1H), 6.94 (d, 1H), 4.60 (s, 2H), 4.18-4.29 (m, 2H), 3.85-3.99 (m, 2H), 3.43-3.60 (m, 7H), 3.23-3.40 (m, 4H), 2.40 (s, 3H), 1.50-1.76 (m, 6H). 10.7 (bs, 1H), 7.20-7.24 (m, 2H), 6.90 (d, 1H), 5.20 (s, 2H), 3.46-3.63 (m, 4H), 3.30-3.40 (m, 2H), 3.09-3.13 (m, 4H), 2.92-3.02 (m, 2H), 2.87 (s, 3H), 2.31 (s, 3H), 1.50-1.62 (m, 4 H), 1.34-1.43 (m, 2H).. |
| 33 | TFA | 364.92 | 478.93 | DMSO | 7.70-7.60 (d, 2H), 7.50-7.40 (d, 2H), 7.30 (s, 2H), 7.10-6.90 (m, 2H), 3.70-3.40 (m, 4H), 2.95 (s, 3H), 2.35 (s, 3H), 1.80-1.70 (m, 4H). |
| 34 | TFA | 348.47 | 462.48 | DMSO | 7.70-7.60 (t, 2H0, 7.35-7.20 (m, 2H), 7.02-6.90 (m, 3H), 3.70-3.50 (m, 4H), 3.30-3.20 (m, 5H), 2.95 (s, 3H), 2.35 (s, 3H), 1.90-1.80 (t, 2H). |
| 35 | TFA | 385.34 | 499.35 | DMSO | 7.60-7.50 (d, 4H), 7.40-7.30 (m, 2H), 7.15-7.00 (m, 1H), 5.30 (s, 1H), 5.10 (s, 1H), 3.70-3.50 (m, 4H), 3.35-3.20 (m, 4H), 2.95 (s, 3H). |
| 36 | TFA | 385.34 | 499.35 | DMSO | 7.75-7.60 (m, 2H), 7.60 (s, 1H), 7.50-7.40 (d, 2H), 7.25-7.20 (m, 2H), 7.00 (s, 1H), 5.30-5.20 (m, 2H), 3.70-3.50 (m, 3H), 3.45-3.35 (m, 2H), 3.10 (s, 3H), 1.95-1.90 (t, 4H). |
| 2 | TFA | 368.89 | 482.90 | DMSO | 7.75-7.60 (m, 2H), 7.65 (s, 1H), 7.35-7.20 (t, 4H), 6.95 (s, 1H), 3.75-3.40 (m, 4H), 3.30-3.20 (m, 5H), 2.95 (s, 2H), 1.95-1.90 (t, 2H). |
| 37 | TFA | 385.87 | 499.89 | DMSO | 11.3 (s, 1H), 10.9 (s, 1H), 7.60-7.63 (m, 2H), 7.56 (s, 1H), 7.35 (d, 1H), 7.24 (t, 2H), 7.06 (d, 1H), 4.53 (s, 2H), 4.0-4.1 (m, 2H), 3.85-3.98 (m, 2H), 3.43 (s, 3H), 3.3-3.39 (m, 2H), 3.19-3.24 (m, 2H). |
| 38 | TFA | 341.46 | 455.47 | CD3OD | 7.22 (s, 1H), 7.19 (d, 1H), 6.9 (d, 1H), 4.6 (s, 2H), 4.2-4.3 (m, 3H), 3.85-4.0 (m, 3H), 3.45-3.7 (m, 7H), 3.4-3.42 (m, 4H), 3.10-3.25 (m, 2H), 2.4 (s, 3H). |
| 43 | TFA | 335.45 | 449.47 | DMSO | DMSO 8.70-8.50 (d, 2H), 8.0-7.90 (m, 1H), 7.70-7.69 (d, 1H), 7.30-7.10 (m, 2H), 6.90-6.70 (m, 1H), 5.10-5.00 (t, 1H), 4.40-4.20 (t, 2H), 3.70-3.60 (m, 4H), 3.30-3.10 (m, 4H), 2.90 (s, 3H), 2.30 (s, 3H). |
| 44 | TFA | 365.45 | 479.47 | DMSO | −10.7-10.9 (m, 2H), 7.52-7.62 (m, 2H), 7.10-7.25 (m, 3H), 6.9 (d, 2H), 4.3-4.41 (m, 3H), 3.75-3.9 (m, 2H), 3.41 (s, 3H), |

TABLE 3-continued

Synthetic Data

| Compound No. | Salt Type | MW Free Base | FW (Salt Included) | NMR Solvent | NMR_DATA |
|---|---|---|---|---|---|
| | | | | | 3.20-3.27 (m, 2H), 3.10-3.19 (m, 2H), 3.0 (s, 1H), 2.30 (s, 3H). |
| 45 | TFA | 325.46 | 439.47 | CD3OD | 7.22 (s, 1H), 7.10 (d, 1H), 7.92 (d, 1H), 4.42-4.6 (m, 5H), 4.2-4.4 (m, 4H), 3.9-4.1 (m, 3H), 3.4-3.6 (m, 4H), 2.28-2.42 (m, 4H), 1.8-2.1 (m, 4H). |
| 46 | TFA | 352.91 | 466.92 | CD3OD | 7.50 (s, 1H), 7.40-7.30 (d, 1H), 7.20-7.10 (d, 1H), 7.00-6.90 (d, 2H), 6.90-6.80 (d, 2H), 4.40-4.30 (t, 2H), 3.00-2.90 (t, 2H), 2.90 (s, 3H), 2.80-2.60 (m, 8H), 2.30 (s, 3H) |
| 47 | TFA | 384.91 | 498.92 | DMSO | 7.60-7.50 (t, 1H), 7.50-7.40 (d, 1H), 7.30-7.20 (m, 2H), 7.10-7.00 (d, 1H), 6.90-6.80 (d, 2H), 4.80-4.70 (t, 1H), 4.30-4.20 (t, 2H), 3.80 (s, 3H), 3.70-3.50 (m, 4H), 3.30-3.10 (m, 4H), 2.90 (s, 3H). |
| 48 | TFA | 364.49 | 478.50 | DMSO | 7.40-7.10 (m, 4H), 7.00-6.80 (m, 3H), 4.80-4.70 (t, 1H), 4.30-4.10 (m, 2H), 3.80 (s, 3H), 3.60-3.40 (m, 4H), 3.20-3.00 (m, 4H), 2.90 (s, 3H), 2.30 (s, 3H). |
| 49 | TFA | 402.90 | 516.91 | DMSO | 7.60-7.50 (t, 1H), 7.50-7.30 (m, 2H), 7.10-7.05 (t, 1H), 6.90-6.70 (m, 2H), 5.10-4.90 (t, 1H), 4.30-4.20 (t, 2H), 3.80 (s, 3H), 3.70-3.60 (m, 4H), 3.30-3.10 (m, 4H), 2.90 (s, 3H). |
| 50 | TFA | 382.48 | 496.49 | DMSO | 7.50-7.40 (m, 1H), 7.30-7.20 (m, 2H), 7.00-6.90 (d, 1H), 6.90-6.70 (m, 2H), 5.10-4.90 (t, 1H), 4.30-4.10 (t, 2H), 3.80 (s, 3H), 3.70-3.60 (m, 4H), 3.30-3.10 (m, 4H), 2.90 (s, 3H), 2.30 (s, 3H). |
| 51 | TFA | 372.87 | 486.89 | DMSO | 7.60-7.50 (t, 1H), 7.50-7.30 (m, 3H), 7.20-7.00 (m, 3H), 4.90-4.70 (t, 1H), 4.30-4.20 (t, 2H), 3.70-3.50 (m, 4H), 3.30-3.10 (m, 4H), 2.80 (s, 3H). |
| 52 | TFA | 352.46 | 466.47 | DMSO | 7.40-7.20 (m, 4H), 7.20-7.10 (m, 2H), 6.90-6.85 (m, 1H), 4.90-4.70 (t, 1H), 4.30-4.10 (m, 2H), 3.30-3.10 (m, 4H), 3.10-3.00 (m, 4H), 2.90 (s, 3H), 2.30 (s, 3H). |
| 53 | TFA | 345.88 | 459.89 | CD3OD | 7.41 (s, 1H), 7.21 (d, 1H), 7.02 (d, 1H), 4.5 (s, 2H), 4.2-4.35 (m, 3H), 3.9-4.01 (m, 3H), 3.4-3.47 (m, 3H), 3.2-3.35 (m, 6H), 2.0-2.1 (m, 2H), 1.9-1.99 (m, 2H). |
| 54 | TFA | 313.45 | 427.46 | CD3OD | 8.4 (bs, 1H), 7.21 (s, 1H), 7.19 (d, 1H), 6.9 (d, 1H), 4.22 (d, 1H), 3.96-4.18 (m, 3H), 3.82-3.92 (m, 2H), 3.5 (s, 3H), 3.22-3.4 (m, 5H), 2.4 (s, 3H), 1.1 (d, 6H). |
| 55 | HCL | 340.47 | 376.92 | CD3OD | 7.21 (s, 1H), 7.19 (d, 1H), 6.9 (d, 1H), 5.27-5.42 (m, 1H), 4.5 (s, 2H), 4.09-4.2 (m, 3H), 3.9-4.0 (m, 2H), 3.5 (s, 3H), 2.4 (s, 3H), 1.9-2.1 (m, 2H), 1.7-1.85 (m, 6H). |
| 56 | OXALATE | 338.88 | 428.91 | CD3OD | 7.50 (s, 1H), 7.40-7.30 (d, 1H), 7.35-7.20 (m, 3H), 7.20-7.10 (d, 1H), 7.00-7.80 (m, 2H), 4.40-4.30 (t, 2H), 3.40-3.30 (t, 2H), 3.30-3.20 (t, 2H), 3.20-3.00 (t, 2H), 2.80 (s, 3H), 2.80-2.70 (m, 4H). |
| 57 | TFA | 359.90 | 473.92 | CD3OD | 7.42 (s, 1H), 7.22 (d, 1H), 7.09 (d, 1H), 4.6 (s, 2H), 4.2-4.3 (m, 3H), 3.9-4.0 (m, 3H), 3.6-3.8 (m, 6H), 3.5 (s, 3H), 3.4 (m, 3H), 1.45-1.9 (m, 6H). 10.7 (bs, 1H), 7.57 (s, 1H), 7.40 (d, 1H), 7.06 (d, 1H), 5.20 (d, 2H), 3.55-3.63 (m, 4H), 3.47-3.54 (m, 4H), 3.30-3.39 (m, 2H), 3.12-3.22 (m, 2H), 2.93-3.02 (m, 2H), 2.88 (s, 3H), 1.50-1.67 (m, 4H), 1.35-1.48 (m, 2H). |
| 58 | TFA | 390.86 | 504.88 | DMSO | 7.62-7.50 (t, 1H), 7.50-7.30 (t, 3H), 7.25-7.00 (m, 2H), 4.85-4.75 (m, 1H), 4.30-4.20 (t, 2H), 3.80-3.60 (m, 4H), 3.25-3.10 (m, 4H), 2.90 (s, 3H). |
| 59 | TFA | 370.45 | 484.46 | DMSO | 7.50-7.30 (m, 5H), 7.00-6.90 (t, 1H), 4.85-4.70 (t, 1H), 4.30-4.15 (m, 2H), 3.35-3.15 (m, 4H), 3.00-2.90 (m, 4H), 2.35 (s, 3H). |

TABLE 3-continued

Synthetic Data

| Compound No. | Salt Type | MW Free Base | FW (Salt Included) | NMR Solvent | NMR_DATA |
|---|---|---|---|---|---|
| 60 | TFA | 361.88 | 475.89 | DMSO | 11.2 (s, 1H), 7.5 (s, 1H), 7.3 (d, 1H), 7.05 (d, 1H), 4.2-4.4 (m, 3H), 3.7-3.9 (m, 4H), 3.5-3.65 (m, 4H), 3.42-3.49 (m, 6H), 3.3-3.4 (m, 6H), 3.12-3.2 (m, 3H). |
| 61 | OXALATE | 356.87 | 446.90 | CD3OD | 7.60-7.50 (m, 3H), 7.30-7.20 (m, 3H), 7.20-7.10 (d, 1H), 4.00-3.80 (m, 6H), 3.80-3.70 (m, 4H), 3.60-3.50 (m, 5H) |
| 62 | OXALATE | 318.47 | 408.49 | CD3OD | 7.40-7.30 (m, 5H), 7.20 (m, 1H), 7.20-7.10 (d, 1H), 7.0-6.80 (d, 1H), 4.0-3.80 (m, 4H), 3.80-3.70 (m, 2H), 3.40 (s, 3H), 3.30-3.20 (m, 6H), 2.40 (s, 3H). |
| 63 | TFA | 336.46 | 450.47 | CD3OD | 7.40-7.20 (m, 3H), 7.20-7.00 (m, 3H), 6.90-6.80 (m, 1H), 4.40-4.20 (m, 6H), 3.20-3.00 (m, 6H), 3.00 (s, 3H), 2.40 (s, 3H). |
| 67 | TFA | 402.90 | 516.92 | DMSO | 7.50 (s, 1H), 7.40-7.30 (t, 1H), 7.10-6.90 (m, 4H), 4.80-4.70 (t, 1H), 4.30-4.20 (t, 2H), 3.80 (s, 3H), 3.60-3.50 (m, 2H), 3.30-3.00 (m, 6H), 2.90 (s, 3H). |
| 68 | TFA | 382.48 | 496.50 | DMSO | 7.30-7.20 (t, 1H), 7.20-6.80 (m, 5H), 4.80-4.70 (t, 1H), 4.30-4.10 (m, 2H), 3.70 (s, 3H), 3.20-3.00 (m, 8H), 2.90 (s, 3H), 2.30 (s, 3H). |
| 69 | TFA | 352.91 | 466.93 | CD3OD | 7.60-7.50 (m, 2H), 7.40-7.30 (m, 2H), 7.30 (s, 1H), 7.20-7.10 (d, 1H), 7.0-6.90 (d, 1H), 4.0-3.80 (m, 4H), 3.70-3.50 (m, 2H), 3.40-3.20 (m, 9H), 2.40 (s, 3H). |
| 72 | DiHCL | 360.89 | 433.80 | DMSO | ~11.3 (s, 1H), 9.5 (bs, 1H), 7.5 (s, 1H), 7.3 (d, 1H), 7.02 (d, 1H), 4.77 (s, 2H), 4.0-4.2 (m, 2H), 3.80-3.95 (m, 2H), 3.65-3.78 (m, 5H), 3.40 (s, 3H), 3.30-3.38 (m, 2H), 3.20-3.26 (m, 4H), 3.12-3.18 (m, 2H). |
| 73 | TFA | 367.88 | 481.90 | DMSO | ~11.22 (s, 1H), 10.58 (s, 1H), 7.60 (d, 2H), 7.53 (s, 1H), 7.27-7.43 (m, 3H), 7.04-7.20 (m, 2H), 4.48-4.50 (m, 2H), 3.82-4.10 (m, 6H), 3.50 (s, 3H), 3.15-3.30 (m, 2H). |
| 74 | TFA | 387.96 | 501.97 | CD3OD | 7.43 (s, 1H), 7.24 (d, 1H), 7.04 (d, 1H), 4.55 (s, 2H), 4.18-4.40 (m, 3H), 3.90-4.20 (m, 2H), 3.50 (s, 3H), 3.32-3.40 (m, 2H), 3.22-3.29 (m, 2H), 2.90 (s, 3H), 1.10-1.90 (m, 10H). |
| 75 | TFA | 382.89 | 496.91 | DMSO | ~11.2 (s, 1H), 7.23-7.52 (m, 6H), 7.05 (d, 2H), 5.30 (s, 2H), 5.16-5.20 (m, 2H), 4.70-4.83 (m, 4H), 3.40 (s, 3H), 3.28-3.36 (m, 2H), 3.18-3.22 (m, 2H). |
| 76 | HCL | 373.93 | 410.38 | DMSO | ~11.02 (bs, 1H), 7.57 (s, 1H), 7.38 (d, 1H), 7.04 (d, 1H), 5.05-5.27 (m, 2H), 4.20-4.27 (m, 1H), 3.93-4.04 (m, 1H), 3.52-3.63 (m, 2H), 3.0-3.26 (m, 4H), 2.90 (s, 3H), 2.50-2.63 (m, 4 H), 1.58-1.78 (m, 3H), 1.03-1.30 (m, 2H), 0.94 (d, 3H). |
| 77 | TFA | 414.94 | 528.94 | DMSO | 7.60 (s, 1H), 7.50-7.40 (t, 1H), 7.10-7.00 (m, 2H), 6.95-6.85 (d, 2H), 5.60-5.50 (m, 2H), 4.80-4.70 (m, 2H), 4.30-4.10 (m, 4H), 3.70 (s, 3H), 3.60 (s, 3H), 3.30-3.10 (m, 2H), 2.95 (s, 3 H). |
| 78 | TFA | 366.89 | 480.89 | CD3OD | 7.60-7.50 (m, 2H), 7.50-7.40 (m, 2H), 7.20-7.18 (d, 1H), 7.10-6.90 (d, 2H), 6.80-6.70 (d, 2H), 4.80-4.79 (d, 2H), 3.80 (s, 3H), 3.80-3.70 (m, 3H), 3.40-3.30 (m, 2H), 3.10 (s, 3H). |
| 79 | HCL | 347.46 | 383.92405 | CD3OD | 10.3 (bs, 1H), 7.62 (d, 2H), 7.35 (t, 2H), 7.21 (s, 1H), 7.16-7.20 (m, 2H), 6.93 (d, 1H), 4.40-4.50 (m, 2H), 4.20-4.30 (m, 3H), 3.90-4.05 (m, 2H), 3.60 (s, 3H), 2.40 (s, 3H). |
| 81 | HCL | 381.57 | 418.03 | DMSO | 10.62 (bs, 1H), 7.23-7.30 (m, 2H), 6.90 (t, 1H), 4.17-4.40 (m, 2H), 3.03-3.34 (m, 7H), 2.86-3.02 (m, 4H), 2.53-2.97 (m, 6H), 2.32 (s, 3H), 1.00-1.78 (m, 10H). |

Example 126

Preparation of N-cyclohexyl-2-(3,9-dimethyl-2,3,4,5-tetrahydroazepino[4,5-b]indol-6(1H)-yl)-N-methylacetamide (Compound No. 232)

Sodium hydride (50%) (46 mg, 1.16 mmol) was dissolved in THF (2 mL) at 0° C. and stirred for 10 min. 3,9-Dimethyl-1,2,3,4,5,6-hexahydroazepino[4,5-b]indole (100 mg, 0.46 mmol) in THF (3 mL) was added dropwise to the reaction mixture at 0° C. and stirred for 10 min. A solution of 2-chloro-N-cyclohexyl-N-methylacetamide (106 mg, 0.56 mmol) was added to the reaction mixture which was stirred at RT for 2 h. The reaction mixture was quenched with ice water, and a white solid was obtained. The solid was filtered, washed with diethyl ether and dried under vacuum to obtain 80 mg of product. The product was treated with ethanolic HCl to afford 74 mg of product as the HCl salt. $^1$H NMR (DMSO-d6, HCl salt) δ (ppm): 7.20 (m, 2H), 6.84 (d, 1H), 5.20-5.04 (m, 2H), 4.10 (m, 1H), 3.80-3.70 (m, 4H), 3.20-3.00 (m, 8H), 2.90 (s, 2H), 2.42 (s, 3H), 1.95-1.80 (m, 2H), 1.70-1.50 (m, 4H), 1.40-1.25 (m, 2H), 1.26-1.20 (m, 2H).

Example 127

Preparation of (E)-6-(2-fluorostyryl)-3,9-dimethyl-1,2,3,4,5,6-hexahydroazepino[4,5-b]indole (Compound No. 233)

A solution of 2-(3,9-dimethyl-2,3,4,5-tetrahydroazepino[4,5-b]indol-6(1H)-yl)-1-(2-fluorophenyl)ethanol (100 mg, 0.28 mmol), triethylamine (0.59 mL, 0.42 mmol) in DCM (6 mL), was stirred for 10 min. at 0° C. Methane sulfonyl chloride (0.026 mL, 0.32 mmol) was added slowly at 0° C. and stirred at RT for 2 h. The reaction mixture was diluted with water and extracted with DCM. The organic layer was dried over anhydrous sodium sulfate and evaporated under reduced pressure to obtain the crude product. The crude product was dissolved in NMP (0.7 mL), KOH powder (160 mg, 2.8 mmol) was added and heated at 90° C. for 14 h. The reaction was monitored by LCMS. Inorganic material was filtered off and the filtrate was purified by reverse phase chromatography to afford 20 mg of TFA salt. $^1$H NMR (CD$_3$OD, TFA salt) δ (ppm): 7.70-7.60 (m, 2H), 7.50-7.40 (d, 1H), 7.40-7.20 (m, 2H), 7.20-7.00 (m, 3H), 6.90-6.80 (d, 1H), 3.80-3.70 (m, 4H), 3.50-3.40 (m, 4H), 3.15 (s, 3H), 2.40 (s, 3H).

Example 128

Preparation of (E)-9-chloro-6-(4-fluorostyryl)-3-methyl-1,2,3,4,5,6-hexahydroazepino[4,5-b]indole (Compound No. 234)

A solution of 2-(9-chloro-3-methyl-2,3,4,5-tetrahydroazepino[4,5-b]indol-6(1H)-yl)-1-(4-fluorophenyl)ethanol (100 mg, 0.268 mmol) and triethylamine (0.055 mL, 0.402 mmol) in DCM (6 mL) was stirred at 0° C. for 10 min. Methane sulfonyl chloride (0.022 mL, 0.295 mmol) was added slowly at 0° C. and the reaction mixture was stirred at RT for 2 h. The reaction mixture was diluted with water, and extracted with DCM. The organic layer was dried over anhydrous sodium sulfate and evaporated under reduced pressure to obtain the crude product. The crude product was dissolved in NMP (1 mL), KOH powder (105 mg, 1.87 mmol) was added at RT and heated at 90° C. for 14 h. the reaction mixture was monitored by LCMS. Inorganic material was filtered off and filtrate was purified by reverse phase chromatography to afford 15 mg of TFA salt. $^1$H NMR (CD$_3$OD, TFA salt) δ (ppm): 7.70-7.50 (m, 4H), 7.20-7.10 (m, 3H), 6.80-6.70 (d, 2H), 3.80-3.70 (m, 2H), 3.50-3.40 (m, 2H), 3.30-3.10 (d, 4H), 3.15 (s, 3H).

Example 129

Preparation of (E)-6-(4-chlorostyryl)-3,9-dimethyl-1,2,3,4,5,6-hexahydroazepino[4,5-b]indole (Compound No. 235)

1-(4-Chlorophenyl)-2-(3,9-dimethyl-2,3,4,5-tetrahydroazepino[4,5-b]indol-6(1H)-yl)ethanol (100 mg, 0.271 mmol) was dissolved in DCM (5 mL) and triethylamine (0.056 mL, 0.406 mmol) was added. The reaction mixture was stirred at 0° C. for 10 min. Methane sulfonyl chloride (0.023 mL, 0.298 mmol) was added slowly at 0° C. and the reaction mixture was stirred at RT for 2 h. The reaction mixture was diluted with water and extracted with DCM. The organic layer was dried over anhydrous sodium sulfate and evaporated under reduced pressure to obtain the crude product. The crude product was dissolved in NMP (0.8 mL), KOH powder (106 mg, 1.88 mmol) was added at RT and the mixture then heated at 90° C. for 14 h. The product was detected by LCMS. Inorganic material was filtered off and the filtrate was purified by reverse phase chromatography to afford 10 mg of TFA salt. $^1$H NMR (CD$_3$OD, TFA salt) δ (ppm): 7.70-7.60 (d, 4H), 7.50-7.40 (t, 3H), 7.30-7.20 (m, 1H), 6.90-6.80 (d, 1H), 3.80-3.70 (m, 2H), 3.50-3.40 (m, 2H), 3.30-3.20 (d, 4H), 3.15 (s, 3H), 2.40 (s, 3H).

Example 130

Preparation of (E)-9-chloro-6-(3,4-difluorostyryl)-3-methyl-1,2,3,4,5,6-hexahydroazepino[4,5-b]indole (Compound No. 236)

2-(9-Chloro-3-methyl-2,3,4,5-tetrahydroazepino[4,5-b]indol-6(1H)-yl)-1-(3,4-difluorophenyl)ethanol (150 mg, 0.384 mmol) was dissolved in DCM (10 mL), triethylamine (0.079 mL, 0.576 mmol) was added and the mixture stirred for 10 min. Methane sulfonyl chloride (0.032 mL, 0.432 mmol) was added slowly at 0° C. and stirred at RT for 2 h. The reaction mixture was diluted with water and extracted with DCM. The organic layer was dried over anhydrous sodium sulfate and evaporated under reduced pressure to obtain the crude product. The crude mixture was dissolved in NMP (1.5 mL), KOH powder (150 mg, 2.68 mmol) was added at RT and the reaction mixture was heated at 90° C. for 14 h. The product was detected by LCMS. Inorganic material was filtered off and the filtrate was purified by reverse phase chromatography to afford 5 mg of TFA salt. $^1$H NMR (CD$_3$OD, TFA salt) δ (ppm): 7.70-7.50 (m, 4H), 7.30-7.10 (m, 3H), 6.90-6.70 (d, 1H), 3.80-3.70 (m, 4H), 3.60-3.40 (m, 4H), 3.15 (s, 3H).

Example 131

Preparation of 6-(2-fluorophenethyl)-3-methyl-1,2,3,4,5,6-hexahydroazepino[4,5-b]indole (Compound No. 237)

2-(9-Chloro-3-methyl-2,3,4,5-tetrahydroazepino[4,5-b]indol-6(1H)-yl)-1-(2-fluorophenyl)ethyl methanesulfonate (530 mg, 0.001177 mol) was dissolved in methanol and 10% Pd—C (62 mg, 0.5885 mmol) was added. A drop of water was added and the reaction mass is stirred at RT for 24 h under hydrogen atmosphere. The reaction mass was filtered through Celite and the filtrate concentrated to obtain the crude compound. The crude was purified by preparative HPLC to obtain 140 mg desired compound. $^1$H NMR (CDCl$_3$, TFA salt) δ (ppm): 7.60 (s, 1H), 7.30-7.20 (m, 2H), 7.20-7.15 (d, 1H), 7.10-7.00 (t, 12H), 7.00-6.90 (t, 1H), 6.90-6.80 (t, 1H), 4.40-4.30 (t, 2H), 3.90-3.85 (t, 2H), 3.60-3.50 (t, 2H), 3.30-3.10 (m, 4H), 3.10 (t, 2H), 2.90 (s, 3H).

Example 132

Preparation of (E)-6-(2-(2,4-dichlorophenyl)prop-1-enyl)-3,9-dimethyl-1,2,3,4,5,6-hexahydroazepino[4,5-b]indole (Compound No. 238)

3,9-Dimethyl-1,2,3,4,5,6-hexahydroazepino[4,5-b]indole (214 mg, 1 mmol), 1-(1-bromoprop-1-en-2-yl)-2,4-dichlorobenzene (318 mg, 1.2 mmol), L-proline (0.2 mmol), CuI (19 mg, 0.1 mmol) and potassium phosphate tribasic (424 mg, 2 mmol) in DMF was stirred at RT and purged with nitrogen. The reaction mixture was heated at 85° C. overnight. An additional 1 eq. of reagents was added and the mixture heated for an additional 24 h. The DMF was evaporated and the residue was poured into water. The precipitate obtained was filtered and purified by silica gel chromatography (100-200-mesh) using 0-5% MeOH:DCM as eluant followed by reverse phase HPLC to separate the isomers. $^1$H NMR (CDCl$_3$, TFA salt) δ (ppm): 7.35 (s, 1H), 7.18 (m, 2H), 7.05 (d, 1H), 6.98 (d, 1H), 6.70 (m, 2H), 3.60 (m, 2H), 3.10 (m, 5H), 2.90 (s, 3H), 2.60 (m, 1H), 2.42 (s, 3H), 2.30 (s, 3H).

Example 133

Preparation of (E)-9-chloro-6-(2-(2,4-dichlorophenyl)prop-1-enyl)-3-methyl-1,2,3,4,5,6-hexahydroazepino[4,5-b]indole (Compound No. 239)

9-Chloro-3-methyl-1,2,3,4,5,6-hexahydroazepino[4,5-b]indole (234 mg, 1 mmol), 1-(1-bromoprop-1-en-2-yl)-2,4-dichlorobenzene (318 mg, 1.2 mmol), L-proline (0.2 mmol), CuI (19 mg, 0.1 mmol) and potassium phosphate tribasic (424 mg, 2 mmol) in DMF was stirred at RT and purged with nitrogen. The reaction mixture was heated at 85° C. overnight. An additional 1 eq. of reagents was added and the mixture heated for an additional 24 h. The DMF was evaporated and the residue was poured into water. The precipitate obtained was filtered and purified by silica gel chromatography (100-200-mesh) using 0-5% MeOH:DCM as eluant followed by reverse phase HPLC to separate the isomers. $^1$HNMR (CDCl$_3$, TFA salt) δ (ppm): 7.50 (d, 2H), 7.32 (m, 2H), 7.20 (s, 2H), 6.50 (s, 1H), 3.95 (m, 2H), 3.60-3.20 (m, 6H), 3.05 (s, 3H), 1.80 (s, 3H).

Example 134

Preparation of (Z)-6-(2-(2-fluorophenyl)prop-1-enyl)-3,9-dimethyl-1,2,3,4,5,6-hexahydroazepino[4,5-b]indole (Compound No. 240)

3,9-Dimethyl-1,2,3,4,5,6-hexahydroazepino[4,5-b]indole (214 mg, 1 mmol), 1-(1-bromoprop-1-en-2-yl)-2-fluorobenzene (260 mg, 1.2 mmol), L-proline (0.2 mmol), CuI (19 mg, 0.1 mmol) and potassium phosphate tribasic (424 mg, 2 mmol) in DMF was stirred at RT and purged with nitrogen. The reaction mixture was heated at 85° C. overnight. An additional 1 eq. of reagents was added and the mixture heated for an additional 24 h. The DMF was evaporated and the residue was poured into water. The precipitate obtained was filtered and purified by silica gel chromatography (100-200-mesh) using 0-5% MeOH:DCM as eluant followed by reverse phase HPLC to separate the isomers. $^1$HNMR (CDCl$_3$, TFA salt) δ (ppm): 7.15 (m, 3H), 7.05 (d, 1H), 6.95 (t, 1H), 6.85 (t, 1H), 6.75 (s, 1H), 6.70 (d, 1H), 3.60 (m, 1H), 3.40 (m, 1H), 3.10 (m, 2H), 2.85 (m, 2H), 2.80 (s, 3H), 2.42 (s, 3H), 2.33 (m, 2H), 2.30 (s, 3H).

Example 135

Preparation of (E)-6-(2-(2-fluorophenyl)prop-1-enyl)-3,9-dimethyl-1,2,3,4,5,6-hexahydroazepino[4,5-b]indole (Compound No. 241)

3,9-Dimethyl-1,2,3,4,5,6-hexahydroazepino[4,5-b]indole (214 mg, 1 mmol), 1-(1-bromoprop-1-en-2-yl)-2-fluorobenzene (260 mg, 1.2 mmol), L-proline (0.2 mmol), CuI (19 mg, 0.1 mmol) and potassium phosphate tribasic (424 mg, 2 mmol) in DMF was stirred at RT and purged with nitrogen. The reaction mixture was heated at 85° C. overnight. An additional 1 eq. of reagents was added and the mixture heated for an additional 24 h. The DMF was evaporated and the residue was poured into water. The precipitate obtained was filtered and purified by silica gel chromatography (100-200-mesh) using 0-5% MeOH:DCM as eluant followed by reverse phase HPLC to separate the isomers. $^1$HNMR (CDCl$_3$, TFA salt) δ (ppm): 7.42 (m, 1H), 7.33 (m, 1H), 7.28 (s, 1H), 7.24 (d, 1H), 7.18 (dd, 1H), 7.11 (d, 1H), 7.09 (d, 1H), 6.72 (s, 1H), 3.82 (m, 2H), 3.40 (m, 1H), 3.30 (m, 5H), 3.0 (s, 3H), 2.45 (s, 3H), 1.90 (s, 3H).

Example 136

Preparation of (Z)-9-chloro-6-(2-(2-fluorophenyl)prop-1-enyl)-3-methyl-1,2,3,4,5,6-hexahydroazepino[4,5-b]indole (Compound No. 242)

9-Chloro-3-methyl-1,2,3,4,5,6-hexahydroazepino[4,5-b]indole (234 mg, 1 mmol), 1-(1-bromoprop-1-en-2-yl)-2-fluorobenzene (260 mg, 1.2 mmol), L-proline (0.2 mmol), CuI (19 mg, 0.1 mmol) and potassium phosphate tribasic (424 mg, 2 mmol) in DMF was stirred at RT and purged with nitrogen. The reaction mixture was heated at 85° C. overnight. An additional 1 eq. of reagents was added and the mixture heated for an additional 24 h. The DMF was evaporated and the residue was poured into water. The precipitate obtained was filtered and purified by silica gel chromatography (100-200-mesh) using 0-5% MeOH:DCM as eluant followed by reverse phase HPLC to separate the isomers. $^1$HNMR (CD$_3$OD, TFA salt) δ (ppm): 7.36 (d, 1H), 7.18 (m, 1H), 7.11 (s, 1H), 6.98 (dd, 1H), 6.92 (m, 3H), 6.86 (s, 1H), 3.60 (m, 2H), 3.10 (m, 3H), 3.0 (s, 3H), 2.90 (m, 3H), 2.30 (s, 3H).

Example 137

Preparation of (E)-9-chloro-6-(2-(2-fluorophenyl)prop-1-enyl)-3-methyl-1,2,3,4,5,6-hexahydroazepino[4,5-b]indole (Compound No. 243)

9-Chloro-3-methyl-1,2,3,4,5,6-hexahydroazepino[4,5-b]indole (234 mg, 1 mmol), 1-(1-bromoprop-1-en-2-yl)-2-fluorobenzene (260 mg, 1.2 mmol), L-proline (0.2 mmol), CuI (19 mg, 0.1 mmol) and potassium phosphate tribasic (424 mg, 2 mmol) in DMF was stirred at RT and purged with nitrogen. The reaction mixture was heated at 85° C. overnight. An additional 1 eq. of reagents was added and the mixture heated for an additional 24 h. The DMF was evaporated and the residue was poured into water. The precipitate obtained was filtered and purified by silica gel chromatography (100-200-mesh) using 0-5% MeOH:DCM as eluant followed by reverse phase HPLC to separate the isomers. $^1$HNMR (CD$_3$OD, TFA salt) δ (ppm): 7.56 (dd, 1H), 7.53 (s, 1H), 7.40 (m, 1H), 7.30 (d, 1H), 7.20 (m, 3H), 6.80 (s, 1H), 3.80 (m, 2H), 3.40 (m, 3H), 3.30 (m, 2H), 3.15 (m, 1H), 3.05 (s, 3H), 1.85 (s, 3H).

Example 138

Preparation of (Z)-9-chloro-6-(2-(2-chlorophenyl) prop-1-enyl)-3-methyl-1,2,3,4,5,6-hexahydroazepino [4,5-b]indole (Compound No. 244)

9-Chloro-3-methyl-1,2,3,4,5,6-hexahydroazepino[4,5-b]indole (234.72 mg, 1 mmol), 1-(1-bromoprop-1-en-2-yl)-2-chlorobenzene (277.82 mg, 1.2 mmol), L-proline (0.2 mmol), CuI (19 mg, 0.1 mmol) and potassium phosphate tribasic (424 mg, 2 mmol) in DMF was stirred at RT and purged with nitrogen. The reaction mixture was heated at 85° C. overnight. An additional 1 eq. of reagents was added and the mixture heated for an additional 24 h. The DMF was evaporated and the residue was poured into water. The precipitate obtained was filtered and purified by silica gel chromatography (100-200-mesh) using 0-5% MeOH:DCM as eluant followed by reverse phase HPLC to separate the isomers. $^1$HNMR (CDCl$_3$, TFA salt) δ (ppm): 7.34 (m, 2H), 7.24 (d, 1H), 7.12 (d, 2H), 6.95 (m, 1H), 6.70 (m, 2H), 3.60 (m, 1H), 3.50 (m, 1H), 3.25 (m, 2H), 3.10 (m, 2H), 3.0 (m, 2H), 2.80 (s, 3H), 2.34 (s, 3H)

Example 139

Preparation of (E)-9-chloro-6-(2-(2-chlorophenyl) prop-1-enyl)-3-methyl-1,2,3,4,5,6-hexahydroazepino [4,5-b]indole (Compound No. 245)

9-Chloro-3-methyl-1,2,3,4,5,6-hexahydroazepino[4,5-b]indole (234.72 mg, 1 mmol), 1-(1-bromoprop-1-en-2-yl)-2-chlorobenzene (277.82 mg, 1.2 mmol), L-proline (0.2 mmol), CuI (19 mg, 0.1 mmol) and potassium phosphate tribasic (424 mg, 2 mmol) in DMF was stirred at RT and purged with nitrogen. The reaction mixture was heated at 85° C. overnight. An additional 1 eq. of reagents was added and the mixture heated for an additional 24 h. The DMF was evaporated and the residue was poured into water. The precipitate obtained was filtered and purified by silica gel chromatography (100-200-mesh) using 0-5% MeOH:DCM as eluant followed by reverse phase HPLC to separate the isomers. $^1$HNMR (CDCl$_3$, TFA salt) δ (ppm): 7.50 (m, 2H), 7.35 (m, 2H), 7.20 (m, 3H), 6.50 (s, 1H), 3.90 (m, 2H), 3.50 (m, 1H), 3.35 (m, 1H), 3.20 (m, 2H), 3.0 (s, 3H), 2.0 (m, 5H).

Example 140

Preparation of (E)-9-chloro-3-methyl-6-(2-(pyridin-3-yl)prop-1-enyl)-1,2,3,4,5,6-hexahydroazepino[4,5-b]indole (Compound No. 246)

9-Chloro-3-methyl-1,2,3,4,5,6-hexahydroazepino[4,5-b]indole (200 mg, 0.85 mmol) was dissolved in DMF (6 mL), CuI (16 mg, 0.085 mmol), L-proline (19 mg, 0.17 mmol), K$_3$PO$_4$ (364 mg, 1.70 mmol) were added and stirred for 10 min. at RT. 3-(1-Bromoprop-1-en-2-yl)pyridine (203 mg, 1.02 mmol) was added dropwise and the reaction mixture was heated at 90° C. for 18 h. DMF was evaporated under reduced pressure and the reaction mixture was poured into water (10 mL). The aqueous mixture was extracted with ethyl acetate. The organic layer was dried over Na$_2$SO$_4$, and concentrated under reduced pressure to obtain the crude compound which was purified by column chromatography to 140 mg of the desired compound. $^1$NMR (CD$_3$OD, TFA salt) δ (ppm): 9.10 (s, 1H), 8.80 (s, 1H), 8.62 (d, 1H), 7.90 (m, 1H), 7.60 (s, 1H), 7.38 (s, 1H), 7.20 (m, 2H), 3.80 (m, 2H), 3.42 (m, 4H), 3.22 (m, 2H), 3.10 (s, 3H), 2.0 (s, 3H).

Example 141

Preparation of (E)-3,9-dimethyl-6-(2-(pyridin-3-yl) prop-1-enyl)-1,2,3,4,5,6-hexahydroazepino[4,5-b] indole (Compound No. 247)

3,9-Dimethyl-1,2,3,4,5,6-hexahydroazepino[4,5-b]indole (200 mg, 0.934 mmol) was dissolved in DMF (6 mL), CuI (17.7 mg, 0.09 mmol), L-proline (21 mg, 0.18 mmol), K$_3$PO$_4$ (397 mg, 1.86 mmol) was added and stirred for 10 min. at RT. 3-(1-Bromoprop-1-en-2-yl)pyridine (222 mg, 1.12 mmol) was added dropwise and the reaction mixture was heated at 90° C. for 18 h. DMF was evaporated under reduced pressure, 10 mL water was added and the mixture extracted with ethyl acetate. The organic layer was dried over Na$_2$SO$_4$, and concentrated under reduced pressure. The crude compound was purified by column chromatography to 180 mg of the desired compound. $^1$HNMR (CD$_3$OD, TFA salt) δ (ppm): 9.10 (s, 1H), 8.80 (s, 1H), 8.70 (d, 1H), 8.0 (t, 1H), 7.36 (s, 2H), 7.08 (m, 2H), 3.80 (m, 2H), 3.40 (m, 4H), 3.20 (m, 2H), 3.05 (s, 3H), 2.42 (s, 3H), 1.05 (s, 3H).

Example 142

Preparation of (E)-9-chloro-3-methyl-6-(2-(pyridin-4-yl)prop-1-enyl)-1,2,3,4,5,6-hexahydroazepino[4,5-b]indole (Compound No. 248)

A mixture of 9-chloro-3-methyl-1,2,3,4,5,6-hexahydroazepino[4,5-b]indole (117 mg, 0.5 mmol) and potassium phosphate tribasic (212 mg, 1 mmol) in DMF was purged with nitrogen and heated at 90° C. 4-(1-Bromoprop-1-en-2-yl)pyridine (107.83 mg, 0.55 mmol), L-proline (11.5 mg, 0.1 mmol), CuI (9.5 mg, 0.05 mmol) in DMF were charged in a separate flask. This mixture was purged with nitrogen and heated at 90° C. for 5 min. Both reaction mixtures were combined and heated at 90° C. overnight. The reaction mixture was poured into water to obtain a precipitate. The precipitate was filtered and purified with silica column chromatography (100-200 mesh) by neutralizing the silica gel with 2-3 drops of aq. NH$_3$ and using 0-2% MeOH:DCM as eluant. Compound was further purified by reverse phase HPLC to obtain the product. $^1$HNMR (CD$_3$OD, TFA salt) δ (ppm): 8.80 (d, 2H), 8.20 (d, 2H), 7.70 (d, 1H), 7.58 (d, 1H), 7.20 (s, 2H), 3.70 (m, 2H), 3.40 (m, 2H), 3.30 (m, 4H), 3.05 (s, 3H), 2.02 (s, 3H).

Example 143

Preparation of (Z)-9-chloro-6-(2-(3-fluorophenyl) prop-1-enyl)-3-methyl-1,2,3,4,5,6-hexahydroazepino [4,5-b]indole (Compound No. 249)

A mixture of 9-chloro-3-methyl-1,2,3,4,5,6-hexahydroazepino[4,5-b]indole (234 mg, 1 mmol), 1-(1-bromoprop-1-en-2-yl)-3-fluorobenzene (258 mg, 1.2 mmol), L-proline (23 mg, 0.2 mmol), CuI (19 mg, 0.1 mmol) and potassium phosphate tribasic (424 mg, 2 mmol) in DMF was stirred at RT and purged with nitrogen. The reaction mixture was heated at 85° C. overnight. An additional 1 eq. of reagents was added and the mixture heated for an additional 24 h. The DMF was evaporated and the residue was poured into water. The precipitate obtained was filtered and purified by silica gel chromatography (100-200-mesh) using 0-5% MeOH:DCM as eluant followed by reverse phase HPLC to separate the isomers. $^1$HNMR (CD$_3$OD, TFA salt) δ (ppm): 7.45 (s, 1H), 7.25 (d, 1H), 7.16 (m, 1H), 7.10 (m, 1H), 6.92 (t, 1H), 6.82 (s, 1H), 6.62 (m, 2H), 3.60 (m, 1H), 3.50 (m, 1H), 3.30-3.0 (m, 4H), 2.90 (s, 3H), 2.70 (m, 2H), 2.35 (s, 3H).

Example 144

Preparation of (E)-9-chloro-6-(2-(3-fluorophenyl) prop-1-enyl)-3-methyl-1,2,3,4,5,6-hexahydroazepino [4,5-b]indole (Compound No. 250)

A mixture of 9-chloro-3-methyl-1,2,3,4,5,6-hexahydroazepino[4,5-b]indole (234 mg, 1 mmol), 1-(1-bromoprop-1-en-2-yl)-3-fluorobenzene (258 mg, 1.2 mmol), L-proline (23 mg, 0.2 mmol), CuI (19 mg, 0.1 mmol) and potassium phosphate tribasic (424 mg, 2 mmol) in DMF was stirred at RT and purged with nitrogen. The reaction mixture was heated at 85° C. overnight. An additional 1 eq. of reagents was added and the mixture heated for an additional 24 h. The DMF was evaporated and the residue was poured into water. The precipitate obtained was filtered and purified by silica gel chromatography (100-200-mesh) using 0-5% MeOH:DCM as eluant followed by reverse phase HPLC to separate the isomers. $^1$HNMR (CD$_3$OD, TFA salt) δ (ppm): 7.58 (s, 1H), 7.42 (m, 3H), 7.15 (m, 3H), 7.05 (s, 1H), 3.80 (m, 2H), 3.40 (m, 2H), 3.30 (m, 4H), 3.05 (s, 3H), 1.90 (s, 3H).

Example 145

Preparation of (Z)-6-(2-(3-fluorophenyl)prop-1-enyl)-3,9-dimethyl-1,2,3,4,5,6-hexahydroazepino[4,5-b]indole (Compound No. 251)

A mixture of 3,9-dimethyl-1,2,3,4,5,6-hexahydroazepino[4,5-b]indole (234 mg, 1 mmol), 1-(1-bromoprop-1-en-2-yl)-3-fluorobenzene (258 mg, 1.2 mmol), L-proline (23 mg, 0.2 mmol), CuI (19 mg, 0.1 mmol) and potassium phosphate tribasic (424 mg, 2 mmol) in DMF was stirred at RT and purged with nitrogen. The reaction mixture was heated at 85° C. overnight. An additional 1 eq. of reagents was added and the mixture heated for an additional 24 h. The DMF was evaporated and the residue was poured into water. The precipitate obtained was filtered and purified by silica gel chromatography (100-200-mesh) using 0-5% MeOH:DCM as eluant followed by reverse phase HPLC to separate the isomers. $^1$HNMR (CD$_3$OD, TFA salt) δ (ppm): 7.30 (s, 1H), 7.16 (m, 2H), 7.0 (d, 1H), 6.92 (t, 1H), 6.85 (s, 1H), 6.70 (d, 1H), 6.62 (d, 1H), 3.60 (m, 1H), 3.40 (m, 1H), 3.25 (m, 1H), 3.10 (m, 1H), 2.95 (m, 2H), 2.90 (s, 3H), 2.70 (m, 2H), 2.42 (s, 3H), 2.30 (s, 3H).

Example 146

Preparation of (E)-6-(2-(3-fluorophenyl)prop-1-enyl)-3,9-dimethyl-1,2,3,4,5,6-hexahydroazepino[4,5-b]indole (Compound No. 252)

A mixture of 3,9-dimethyl-1,2,3,4,5,6-hexahydroazepino[4,5-b]indole (234 mg, 1 mmol), 1-(1-bromoprop-1-en-2-yl)-3-fluorobenzene (258 mg, 1.2 mmol), L-proline (23 mg, 0.2 mmol), CuI (19 mg, 0.1 mmol) and potassium phosphate tribasic (424 mg, 2 mmol) in DMF was stirred at RT and purged with nitrogen. The reaction mixture was heated at 85° C. overnight. An additional 1 eq. of reagents was added and the mixture heated for an additional 24 h. The DMF was evaporated and the residue was poured into water. The precipitate obtained was filtered and purified by silica gel chromatography (100-200-mesh) using 0-5% MeOH:DCM as eluant followed by reverse phase HPLC to separate the isomers. $^1$HNMR (CD$_3$OD, TFA salt) δ (ppm): 7.45 (m, 2H), 7.40 (d, 1H), 7.36 (s, 1H), 7.10 (m, 1H), 7.0 (m, 3H), 3.80 (m, 2H), 3.40 (m, 2H), 3.20 (m, 4H), 3.05 (s, 3H), 2.42 (s, 3H), 1.90 (s, 3H).

Example 147

Preparation of (E)-3,9-dimethyl-6-(2-(pyridin-4-yl) prop-1-enyl)-1,2,3,4,5,6-hexahydroazepino[4,5-b] indole (Compound No. 253)

3,9-Dimethyl-1,2,3,4,5,5a,6,10b-octahydroazepino[4,5-b]indole (107.5 mg, 0.5 mmol), potassium phosphate tribasic (212 mg, 1 mmol) in DMF and the mixture purged with nitrogen. The reaction mass was heated at 85° C. for 5 min. In another flask was added 4-(1-bromoprop-1-en-2-yl)pyridine (107.83 mg, 0.55 mmol), L-proline (11.5 mg, 0.1 mmol), CuI (9.5 mg, 0.05 mmol) in DMF. This mixture was purged with nitrogen and heated at 90° C. for 5 min. The reaction mixtures were combined and heated at 90° C. overnight. The reaction mass was poured into water to obtain a precipitate. The precipitate was filtered and purified with silica column chromatography (100-200 mesh), by neutralizing the silica gel with 2-3 drops of aq. ammonia and using 0-2% MeOH:DCM as eluant. The compound was further purified by reverse phase HPLC to obtain the product. $^1$HNMR (CD$_3$OD, TFA salt) δ (ppm): 8.70 (d, 2H), 8.10 (d, 2H), 7.62 (s, 1H), 7.38 (s, 1H), 7.05 (d, 2H), 3.80 (m, 2H), 3.40 (m, 2H), 3.30 (m, 2H), 3.20 (m, 2H), 3.05 (s, 3H), 2.42 (s, 3H), 2.05 (s, 3H).

Example 148

Preparation of 6-(4-fluorostyryl)-1,2,3,4,5,6-hexahydro-3,9-dimethylazepino[4,5-b]indole (Compound No. 39)

To a solution of 2-(3,9-dimethyl-2,3,4,5-tetrahydroazepino[4,5-b]indol-6(1H)-yl)-1-(4-fluorophenyl)ethanol (150 mg, 0.42 mmol) in DCM (7 mL), triethylamine (0.088 mL, 0.63 mmol) was added and stirred for 10 min, methane sulfonyl chloride (0.036 mL, 0.47 mmol) were added slowly at 0° C. and stirred at RT for 2 h. Reaction was monitored by TLC. The reaction mixture was diluted with DCM and washed with water. The organic layer was dried over anhydrous sodium sulfate and evaporated under reduced pressure. Crude product was dissolved in NMP (0.8 mL), KOH powder (166 mg, 2.97 mmol) was added at RT and heated at 90° C. for 14 h. Reaction was monitored by LCMS. The reaction mixture was diluted with methanol, inorganic material was filtered off and the compound was purified by reverse phase chromatography to afford 10 mg of product as the TFA salt. $^1$H NMR (CD$_3$OD, TFA salt) δ (ppm): 7.70-7.50 (m, 4H), 7.30 (s, 1H), 7.20-7.00 (m, 3H), 6.80-6.70 (d, 1H), 3.90-3.75 (m, 4H), 3.50-3.40 (m, 4H), 3.15 (s, 3H), 2.35 (s, 3H).

Example 149

Preparation of (Z)-9-chloro-6-(2-(2,4-dichlorophenyl)prop-1-enyl)-1,2,3,4,5,6-hexahydro-3-methylazepino[4,5-b]indole (Compound No. 152)

9-Chloro-3-methyl-1,2,3,4,5,6-hexahydroazepino[4,5-b] indole (214 mg, 1 mmol) was dissolved in DMF. Copper (I)

iodide (19 mg, 0.1 mmol), L-proline (23 mg, 0.2 mmol) and K$_3$PO$_4$ (424 mg, 2 mmol) were added and the reaction mixture was stirred for 10 min. at RT. 1-(1-Bromoprop-1-en-2-yl)-2,4-dichlorobenzene (318 mg, 1.2 mmol) was added dropwise and the reaction mixture was purged with nitrogen. The reaction mixture was heated at 85° C. for overnight (prolonged heating in some cases was required). The DMF was evaporated under reduced pressure, the residue was diluted with water and the solid was filtered. The solid material was purified by silica gel chromatography (100-200 mesh) eluting with 0-5% methanol-dichloromethane. The product was further purified by reverse phase HPLC. Yield: 8 mg. $^1$HNMR (CDCl$_3$, TFA salt) δ (ppm): 7.38 (s, 1H), 7.30 (s, 1H), 7.19 (d, 1H), 7.10 (d, 1H), 6.95 (d, 1H), 6.70 (m, 2H), 3.70 (m, 2H), 3.10 (m, 4H), 2.90 (s, 3H), 2.60 (m, 2H), 2.30 (s, 3H).

Example 150

Preparation of (E)-9-chloro-6-(2-(3,4-dichlorophenyl)prop-1-enyl)-1,2,3,4,5,6-hexahydro-3-methylazepino[4,5-b]indole (Compound No. 154)

9-Chloro-3-methyl-1,2,3,4,5,6-hexahydroazepino[4,5-b]indole (74 mg, 0.31 mmol) was dissolved in DMF (5 mL). Copper (I) iodide (6 mg, 0.032 mmol), L-proline (7 mg, 0.063 mmol) and K$_3$PO$_4$ (134 mg, 0.63 mmol) were added and the reaction mixture was stirred for 10 min. at RT. 4-(1-Bromoprop-1-en-2-yl)-1,2-dichlorobenzene (100 mg, 0.378 mmol) was added dropwise and the reaction mixture was purged with nitrogen. The reaction mixture was heated at 80° C. for overnight (prolonged heating in some cases was required). The DMF was evaporated under reduced pressure, the residue was diluted with water and the solid was filtered. The solid material was purified by silica gel chromatography (100-200 mesh). Yield: 74 mg. $^1$HNMR (CD$_3$OD, TFA salt) δ (ppm): 7.82 (d, 1H), 7.62 (d, 2H), 7.57 (s, 1H), 7.18 (d, 2H), 7.10 (d, 1H), 3.78 (m, 2H), 3.40 (m, 4H), 3.20 (m, 2H), 3.06 (s, 3H), 1.90 (s, 3H).

Example 151

Preparation of (E)-9-chloro-6-(2-(3,4-difluorophenyl)prop-1-enyl)-1,2,3,4,5,6-hexahydro-3-methylazepino[4,5-b]indole (Compound No. 155)

9-Chloro-3-methyl-1,2,3,4,5,6-hexahydroazepino[4,5-b]indole (84 mg, 0.359 mmol) was dissolved in DMF (5 mL). Copper (I) iodide (8 mg, 0.035 mmol), L-proline (9 mg, 0.086 mmol) and K$_3$PO$_4$ (183 mg, 0.862 mmol) were added and the reaction mixture was stirred for 10 min. at RT. 4-(1-Bromoprop-1-en-2-yl)-1,2-difluorobenzene (100 mg, 0.431 mmol) was added dropwise and the reaction mixture was purged with nitrogen. The reaction mixture was heated at 80° C. for overnight (prolonged heating in some cases was required). The DMF was evaporated under reduced pressure, the residue was diluted with water and the solid was filtered. The solid material was purified by silica gel chromatography (100-200 mesh). Yield: 55 mg. $^1$HNMR (DMSO-d6, Oxalate salt) δ (ppm): 7.82 (m, 1H), 7.62 (s, 1H), 7.55 (m, 2H), 7.20 (m, 2H), 7.12 (d, 1H), 3.38 (m, 4H), 3.10 (m, 4H), 2.90 (s, 3H), 1.80 (s, 3H).

Example 152

Preparation of (E)-9-chloro-6-(2-(3-fluoro-4-methoxyphenyl)prop-1-enyl)-1,2,3,4,5,6-hexahydro-3-methylazepino[4,5-b]indole (Compound No. 157)

9-Chloro-3-methyl-1,2,3,4,5,6-hexahydroazepino[4,5-b]indole (80 mg, 0.34 mmol) was dissolved in DMF (6 mL). Copper (I) iodide (6 mg, 0.034 mmol), L-proline (8 mg, 0.068 mmol) and K$_3$PO$_4$ (145 mg, 0.68 mmol) were added and the reaction mixture was stirred for 10 min. at RT. 4-(1-Bromoprop-1-en-2-yl)-2-fluoro-1-methoxybenzene (100 mg, 0.34 mmol) was added dropwise and the reaction mixture was purged with nitrogen. The reaction mixture was heated at 80° C. for overnight (prolonged heating in some cases was required). The DMF was evaporated under reduced pressure, the residue was diluted with water and the solid was filtered. The solid material was purified by silica gel chromatography (100-200 mesh). Yield: 46 mg. $^1$HNMR (CD$_3$OD, Oxalate salt) δ (ppm): 7.58 (s, 1H), 7.42 (m, 2H), 7.16 (m, 3H), 6.95 (s, 1H), 3.90 (s, 3H), 3.60 (m, 4H), 3.25 (m, 4H), 3.05 (s, 3H), 1.82 (s, 3H).

Example 153

Preparation of (E)-6-(3-fluoro-4-methoxystyryl)-9-chloro-1,2,3,4,5,6-hexahydro-3-methylazepino[4,5-b]indole (Compound No. 158)

To a solution of 2-(9-chloro-3-methyl-2,3,4,5-tetrahydroazepino[4,5-b]indol-6(1H)-yl)-1-(3-fluoro-4-methoxyphenyl)ethanol (110 mg, 0.273 mmol) in DCM (5 mL), triethylamine (0.056 mL, 0.406 mmol) was added and stirred for 10 min., methane sulfonyl chloride (0.024 mL, 0.03 mmol) was added slowly at 0° C. and stirred at RT for 2 h. Reaction mixture was diluted with water, extracted with dichloromethane. The organic layer was dried over anhydrous sodium sulfate and evaporated under reduced pressure. The crude product was dissolved in NMP (0.8 mL), KOH powder (105 mg, 1.8 mmol) was added at RT and heated at 90° C. for 14 h. Product was detected by LCMS. Inorganic material was filtered off and the compound was purified by reverse phase chromatography to afford 18 mg of TFA salt. $^1$H NMR (DMSO-d6, TFA salt) δ (ppm): 7.80-7.60 (m, 4H), 7.40-7.30 (d, 1H), 7.25-7.15 (t, 2H), 6.80-6.70 (d, 1H), 3.95 (s, 3H), 3.70-3.60 (m, 4H), 3.00-2.90 (m, 4H), 2.45 (s, 3H).

Example 154

Preparation of (E)-9-chloro-1,2,3,4,5,6-hexahydro-6-(2-(4-methoxyphenyl)prop-1-enyl)-3-methylazepino[4,5-b]indole (Compound No. 160)

9-Chloro-3-methyl-1,2,3,4,5,6-hexahydroazepino[4,5-b]indole (43 mg, 0.184 mmol) was dissolved in DMF (4 mL) Copper (I) iodide (4 mg, 0.0184 mmol) L-proline (4.2 mg, 0.037 mmol) and K$_3$PO$_4$ (78 mg, 0.37 mmol) were added and the reaction mixture was stirred for 10 min. at RT. 1-(1-Bromoprop-1-en-2-yl)-4-methoxybenzene (50 mg, 0.22 mmol) was added dropwise and the reaction mixture was purged with nitrogen. The reaction mixture was heated at 80° C. for overnight (prolonged heating in some cases was required). The DMF was evaporated under reduced pressure, the residue was diluted with water and the solid was filtered. The solid material was purified by silica gel chromatography (100-200 mesh). $^1$H NMR (DMSO-d6, Oxalate salt) δ (ppm): 7.60 (m, 3H), 7.10 (m, 2H), 6.98 (m, 3H), 3.80 (s, 3H), 3.60 (m, 4H), 3.10 (m, 4H), 2.82 (s, 3H), 1.80 (s, 3H).

Example 155

Preparation of (Z)-6-(2-(2,4-dichlorophenyl)prop-1-enyl)-1,2,3,4,5,6-hexahydro-3,9-dimethylazepino[4,5-b]indole (Compound No. 174)

3,9-Dimethyl-1,2,3,4,5,6-hexahydroazepino[4,5-b]indole (214 mg, 1 mmol) was dissolved in DMF. Copper (I) iodide (19 mg, 0.1 mmol), L-proline (23 mg, 0.2 mmol) and $K_3PO_4$ (424 mg, 2 mmol) were added and the reaction mixture was stirred for 10 min at RT. 1-(1-Bromoprop-1-en-2-yl)-2,4-dichlorobenzene (318 mg, 1.2 mmol) was added dropwise and the reaction mixture was purged with nitrogen. The reaction mixture was heated at 85° C. for overnight (prolonged heating in some cases was required). The DMF was evaporated under reduced pressure, the residue was diluted with water and the solid was filtered. The solid material was purified by silica gel chromatography (100-200 mesh) eluting with 0-5% methanol-dichloromethane. The product was further purified by reverse phase HPLC. Yield: 30 mg. $^1$HNMR ($CDCl_3$, TFA salt) δ (ppm): 7.50 (s, 1H), 7.38 (s, 2H), 7.28 (d, 1H), 7.18 (d, 1H), 7.05 (d, 1H), 6.56 (s, 1H), 3.90 (m, 2H), 3.40 (m, 1H), 3.22 (m, 5H), 3.0 (s, 3H), 2.42 (s, 3H), 1.82 (s, 3H)

Example 156

Preparation of (E)-6-(2-(3,4-dichlorophenyl)prop-1-enyl)-1,2,3,4,5,6-hexahydro-3,9-dimethylazepino[4,5-b]indole (Compound No. 176)

3,9-Dimethyl-1,2,3,4,5,6-hexahydroazepino[4,5-b]indole (67 mg, 0.31 mmol) was dissolved in DMF (5 mL). Copper (I) iodide (6 mg, 0.032 mmol), L-proline (7 mg, 0.063 mmol) and $K_3PO_4$ (134 mg, 0.63 mmol) were added and the reaction mixture was stirred for 10 min at RT. 4-(1-Bromoprop-1-en-2-yl)-1,2-dichlorobenzene (100 mg, 0.378 mmol) was added dropwise and the reaction mixture was purged with nitrogen. The reaction mixture was heated at 80° C. for overnight (prolonged heating in some cases was required). The DMF was evaporated under reduced pressure, the residue was diluted with water and the solid was filtered. The solid material was purified by silica gel chromatography (100-200 mesh). Yield: 53 mg. $^1$HNMR ($CD_3OD$, TFA salt) δ (ppm): 7.82 (s, 1H), 7.60 (s, 2H), 7.36 (d, 1H), 7.10 (d, 1H), 7.0 (m, 2H), 3.78 (m, 2H), 3.40 (m, 2H), 3.20 (m, 4H), 3.08 (s, 3H), 2.42 (s, 3H), 1.90 (s, 3H).

Example 157

Preparation of (E)-6-(2-(3,4-difluorophenyl)prop-1-enyl)-1,2,3,4,5,6-hexahydro-3,9-dimethylazepino[4,5-b]indole (Compound No. 177)

3,9-Dimethyl-1,2,3,4,5,6-hexahydroazepino[4,5-b]indole (77 mg, 0.36 mmol) was dissolved in DMF (6 mL). Copper (I) iodide (8 mg, 0.036 mmol), L-proline (9 mg, 0.086 mmol) and $K_3PO_4$ (183 mg, 0.86 mmol) were added and the reaction mixture was stirred for 10 min at RT. 4-(1-Bromoprop-1-en-2-yl)-1,2-difluorobenzene (100 mg, 0.43 mmol) was added dropwise and the reaction mixture was purged with nitrogen. The reaction mixture was heated at 80° C. for overnight (prolonged heating in some cases was required). The DMF was evaporated under reduced pressure, the residue was diluted with water and the solid was filtered. The solid material was purified by silica gel chromatography (100-200 mesh). Yield: 52 mg. $^1$HNMR ($CD_3OD$, Oxalate salt) δ (ppm): 7.60 (m, 1H), 7.50 (m, 1H), 7.30 (m, 2H), 7.0 (s, 3H), 3.60 (m, 4H), 3.25 (m, 4H), 3.05 (s, 3H), 2.42 (s, 3H), 1.90 (s, 3H).

Example 158

Preparation of (E)-6-(2-(3-fluoro-4-methoxyphenyl)prop-1-enyl)-1,2,3,4,5,6-hexahydro-3,9-dimethylazepino[4,5-b]indole (Compound No. 179)

3,9-Dimethyl-1,2,3,4,5,6-hexahydroazepino[4,5-b]indole (73 mg, 0.34 mmol) was dissolved in DMF (6 mL). Copper (I) iodide (6 mg, 0.034 mmol), L-proline (8 mg, 0.068 mmol) and $K_3PO_4$ (145 mg, 0.68 mmol) were added and the reaction mixture was stirred for 10 min at RT. 4-(1-Bromoprop-1-en-2-yl)-2-fluoro-1-methoxybenzene (100 mg, 0.34 mmol) was added dropwise and the reaction mixture was purged with nitrogen. The reaction mixture was heated at 80° C. for overnight (prolonged heating in some cases was required). The DMF was evaporated under reduced pressure, the residue was diluted with water and the solid was filtered. The solid material was purified by silica gel chromatography (100-200 mesh). Yield: 70 mg. $^1$HNMR ($CD_3OD$, Oxalate salt) δ (ppm): 7.42 (s, 1H), 7.40 (d, 1H), 7.30 (s, 1H), 7.15 (t, 1H), 7.02 (m, 2H), 6.96 (s, 1H), 3.90 (s, 3H), 3.60 (m, 4H), 3.22 (m, 4H), 3.05 (s, 3H), 2.40 (s, 3H), 1.82 (s, 3H).

Example 159

Preparation of (E)-6-(3-fluoro-4-methoxystyryl)-1,2,3,4,5,6-hexahydro-3,9-dimethylazepino[4,5-b]indole (Compound No. 180)

To a solution of 2-(3,9-dimethyl-2,3,4,5-tetrahydroazepino[4,5-b]indol-6(1H)-yl)-1-(3-fluoro-4-methoxyphenyl)ethanol (160 mg, 0.04 mmol) in DCM (7 mL), triethylamine (0.087 mL, 0.082 mmol) were added and stirred for 10 min., methane sulfonyl chloride (0.022 mL, 0.035 mmol) was added slowly at 0° C. and stirred at RT for 2 h. Reaction mixture was diluted with water, extracted with dichloromethane. The organic layer was dried over anhydrous sodium sulfate and evaporated under reduced pressure. The crude product was dissolved in NMP (0.8 mL), KOH powder (164 mg, 2.93 mmol) was added at RT and heated at 90° C. for 14 h. Product was detected by LCMS. Inorganic material was filtered off and the compound was purified by reverse phase chromatography to afford 38 mg of TFA salt. $^1$H NMR (DMSO-d6, TFA salt) δ (ppm): 7.80-7.60 (m, 3H), 7.50-7.30 (m, 2H), 7.30-7.20 (t, 1H), 7.10-7.00 (d, 1H), 6.80-6.70 (d, 1H), 3.95 (s, 3H), 3.85-3.80 (m, 4H), 3.00-2.80 (m, 2H), 2.95 (s, 3H), 2.45 (s, 2H), 2.38 (s, 3H).

Example 160

Preparation of (E)-1,2,3,4,5,6-hexahydro-6-(2-(4-methoxyphenyl)prop-1-enyl)-3,9-dimethylazepino[4,5-b]indole (Compound No. 182)

3,9-Dimethyl-1,2,3,4,5,6-hexahydroazepino[4,5-b]indole (78 mg, 0.36 mmol) was dissolved in DMF (5 mL) Copper (I) iodide (7 mg, 0.036 mmol) L-proline (8 mg, 0.073 mmol) and $K_3PO_4$ (156 mg, 0.734 mmol) were added and the reaction mixture was stirred for 10 min at RT. 1-(1-Bromoprop-1-en-2-yl)-4-methoxybenzene (100 mg, 0.44 mmol) was added dropwise and the reaction mixture was purged with nitrogen. The reaction mixture was heated at 80° C. for overnight (prolonged heating in some cases was required). The DMF was evaporated under reduced pressure, the residue was diluted with water and the solid was filtered. The solid material was purified by silica gel chromatography (100-200 mesh). $^1$HNMR (DMSO-d6, Oxalate salt) δ (ppm): 7.62 (d, 2H), 7.30 (s, 1H), 7.0 (m, 4H), 6.95 (d, 1H), 3.80 (s, 3H), 3.40 (m, 4H), 3.10 (m, 4H), 2.80 (s, 3H), 2.40 (s, 3H), 1.82 (s, 3H).

Example 161

Preparation of 2-(3,9-dimethyl-2,3,4,5-tetrahydroazepino[4,5-b]indol-6(1H)-yl)-1-(piperazin-1-yl)ethanone (Compound No. 224)

To a solution of sodium hydride (46 mg, 1.16 mmol) in THF (5 ml), 3,9-dimethyl-1,2,3,4,5,6-hexahydroazepino[4, 5-b]indole (0.1 g, 0.46 mmol) was added at 0° C. and stirred at RT for 30 min. tert-Butyl 4-(2-chloroacetyl)piperazine-1-carboxylate (147 mg, 0.55 mmol) was added slowly dropwise at RT and stirred for 2 h at RT. After completion of the reaction (monitored by TLC & LCMS), the reaction was quenched with ice water and extracted with ethyl acetate. The organic layer was washed with brine, dried over anhydrous sodium sulfate and evaporated under reduced pressure. Crude product was purified by column chromatography to afford free base, which was converted to HCl salt using ethanolic HCl (38 mg). The NMR confirmed removal of the Boc group when ethanolic HCl was used. $^1$H NMR (CD$_3$OD, DiHCl salt) δ (ppm): 7.3 (s, 1H), 7.22 (d, 1H), 7.0 (d, 1H), 5.23 (d, 2H), 3.95-4.10 (m, 4H), 3.7-3.9 (m, 4H), 3.36-3.43 (m, 4H), 3.1-3.22 (m, 4H), 3.0 (s, 3H), 2.4 (s, 3H).

Example 162

Preparation of 2-(3,9-dimethyl-2,3,4,5-tetrahydroazepino[4,5-b]indol-6(1H)-yl)-1-(4-methylpiperidin-1-yl)ethanone (Compound No. 225)

To a solution of sodium hydride (46 mg, 1.16 mmol) in THF (5 ml), 3,9-dimethyl-1,2,3,4,5,6-hexahydroazepino[4,5-b]indole (0.1 g, 0.46 mmol) was added at 0° C. and stirred at RT for 30 min. 2-Chloro-1-(4-methylpiperidin-1-yl)ethanone (98 mg, 0.55 mmol) was added slowly dropwise at RT and stirred for 2 h at RT. After completion of the reaction (monitored by TLC & LCMS), the reaction was quenched with ice water and extracted with ethyl acetate. The organic layer was washed with brine, dried over anhydrous sodium sulfate and evaporated under reduced pressure. The crude product was purified by column chromatography to afford free base, which was converted to HCl salt using ethanolic HCl. $^1$H NMR (DMSO-d6, HCl salt) δ (ppm): 11.22 (bs, 1H), 7.20 (m, 2H), 5.0-5.20 (m, 2H), 4.23 (d, 1H), 4.0 (d, 1H), 3.5-3.6 (m, 2H), 3.0-3.23 (m, 4H), 2.8-2.95 (m, 2H), 2.26-2.42 (m, 2H), 1.5-1.8 (m, 3H), 1.09-1.2 (m, 1H), 0.96 (d, 3H).

Example 163

Preparation of (E)-9-chloro-6-(3,4-dimethoxystyryl)-3-methyl-1,2,3,4,5,6-hexahydroazepino[4,5-b]indole (Compound No. 226)

To a solution of 2-(9-chloro-3-methyl-2,3,4,5-tetrahydroazepino[4,5-b]indol-6(1H)-yl)-1-(3,4-dimethoxyphenyl)ethanol (300 mg, 0.722 mmol) in DCM (5 mL), triethylamine (0.15 mL, 1.077 mmol) were added and stirred for 10 min., methane sulfonyl chloride (0.062 mL, 0.795 mmol) was added slowly at 0° C. and stirred at the same temperature for 1 h, then at RT for 2 h. Reaction mixture was diluted with water, extracted with dichloromethane. The organic layer was dried over anhydrous sodium sulfate and evaporated under reduced pressure. The crude product was purified by column chromatography. The pure product was dissolved in NMP (2.0 mL), KOH powder (283 mg, 5.06 mmol) was added at RT and heated at 90° C. for 14 h. Product was detected by LCMS. The reaction mixture was diluted with methanol, filtered and evaporated. Crude product was purified by reverse phase chromatography to get 18 mg of pure product as TFA salt. $^1$H NMR (DMSO-d6, TFA salt) δ (ppm): 7.80-7.60 (m, 2H), 7.35 (s, 1H), 7.30-7.20 (d, 1H), 7.20-7.15 (d, 1H), 7.00-6.90 (d, 1H), 6.80-6.70 (m, 2H), 3.90 (s, 3H), 3.85 (s, 3H), 3.80-3.60 (m, 2H), 2.95 (s, 3H), 2.90-2.80 (m, 2H), 2.60-2.30 (m, 4H).

Example 164

Preparation of 1-(3,4-dimethoxyphenyl)-2-(3,9-dimethyl-2,3,4,5-tetrahydroazepino[4,5-b]indol-6(1H)-yl)ethanol (Compound No. 227)

3,9-Dimethyl-1,2,3,4,5,6-hexahydroazepino[4,5-b]indole (500 mg, 2.33 mmol) was dissolved in DMF (6 ml). A solution of sodium hydride (50%) (168 mg, 7.00 mmol) was added in portions at RT and stirred at RT for 10 min. A solution of 2-(3,4-dimethoxyphenyl)oxirane (630 mg, 3.50 mmol) in DMF (4 ml) was added dropwise for 10 min and stirred for 14 h at RT. Reaction was monitored by LCMS. The reaction mixture was quenched with ice water, extracted with ethyl acetate. The organic layer was washed with brine, dried over anhydrous sodium sulfate and evaporated under reduced pressure. The crude product was purified by column chromatography to get 50 mg of pure product. $^1$H NMR (CDCl$_3$, Oxalate salt) δ (ppm): 7.40-7.30 (m, 2H), 7.10-7.00 (m, 1H), 6.90-6.80 (t, 2H), 6.80-6.60 (t, 1H), 5.00-4.80 (t, 2H), 4.30-4.20 (m, 2H), 3.95 (s, 3H), 3.80 (s, 3H), 3.00-2.90 (m, 4H), 2.80 (s, 3H), 2.75-2.70 (m, 2H), 2.35 (s, 3H).

Example 165

Preparation of (E)-9-chloro-3-methyl-6-styryl-1,2,3,4,5,6-hexahydroazepino[4,5-b]indole (Compound No. 228)

To a solution of 2-(9-chloro-3-methyl-2,3,4,5-tetrahydroazepino[4,5-b]indol-6(1H)-yl)-1-phenylethanol (100 mg, 0.28 mmol) in DCM (6 mL), triethylamine (0.06 mL, 0.42 mmol) was added and stirred for 10 min., methane sulfonyl chloride (0.024 mL, 0.31 mmol) was added slowly at 0° C. and stirred at RT for 2 h. Reaction was monitored by TLC. Reaction mixture was diluted with DCM washed with water. Organic layer was dried over anhydrous sodium sulfate and evaporated under reduced pressure. Crude product was dissolved in NMP (0.7 mL), KOH powder (158 mg, 2.82 mmol) was added at RT and heated at 90° C. for 14 h. Reaction was monitored by LCMS. The reaction mixture was diluted with methanol, inorganic material was filtered off and the compound was purified by reverse phase chromatography to afford 8 mg of TFA salt. $^1$H NMR (CD$_3$OD, TFA salt) δ (ppm): 7.70-7.60 (m, 5H), 7.50-7.40 (t, 2H), 7.30-7.20 (d, 1H), 7.22-7.10 (d, 1H), 6.90-6.80 (d, 1H), 3.85-3.75 (m, 4H), 3.45-3.40 (m, 4H), 3.15 (s, 3H).

Example 166

Preparation of (E)-3,9-dimethyl-6-styryl-1,2,3,4,5,6-hexahydroazepino[4,5-b]indole (Compound No. 229)

To a solution of 2-(3,9-dimethyl-2,3,4,5-tetrahydroazepino[4,5-b]indol-6(1H)-yl)-1-phenylethanol (100 mg, 0.299 mmol) in DCM (2 mL), triethylamine (0.062 mL, 0.44 mmol) was added and stirred for 10 min., methane sulfonyl chloride (0.025 mL, 0.32 mmol) was added slowly at 0° C. and stirred at RT for 2 h. Reaction was monitored by TLC. The reaction mixture was diluted with DCM washed with water. The organic layer was dried over anhydrous sodium sulfate and evaporated under reduced pressure. Crude product was dissolved in NMP (0.7 mL), KOH powder (117 mg, 2.09 mmol) was added at RT and heated at 90° C. for 14 h. Reaction was monitored by LCMS. The reaction mixture was diluted with methanol, inorganic material was filtered off and the compound was purified by reverse phase chromatography to afford 20 mg of TFA salt. $^1$H NMR (CD$_3$OD, TFA salt) δ (ppm): 7.70-7.50 (m, 5H), 7.40-7.20 (m, 3H), 7.15-7.00 (d, 1H), 6.80-6.70 (d, 1H), 3.90-3.80 (t, 2H), 3.60-3.50 (m, 4H), 3.35-3.20 (t, 2H), 3.15 (s, 3H), 2.40 (s, 3H).

Example 167

Preparation of (E)-6-(2-fluoro-4-methoxystyryl)-3,9-dimethyl-1,2,3,4,5,6-hexahydroazepino[4,5-b]indole (Compound No. 230)

To a solution of 2-(3,9-dimethyl-2,3,4,5-tetrahydroazepino[4,5-b]indol-6(1H)-yl)-1-(2-fluoro-4-methoxyphenyl)ethanol (200 mg, 0.52 mmol) in DCM (10 mL), triethylamine (0.11 mL, 0.78 mmol) was added and stirred for 10 min., methane sulfonyl chloride (0.044 mL, 0.56 mmol) was added slowly at 0° C. and stirred at RT for 2 h. Reaction was monitored by TLC. The reaction mixture was diluted with DCM and washed with water. The organic layer was dried over anhydrous sodium sulfate and evaporated under reduced pressure. The crude product was dissolved in NMP (0.8 mL), KOH powder (205 mg, 3.66 mmol) was added at RT and heated at 90° C. for 14 h. Reaction was monitored by LCMS. The reaction mixture was diluted with methanol, inorganic material was filtered off and the compound was purified by reverse phase chromatography to afford 25 mg of TFA salt. $^1$H NMR (CD$_3$OD, TFA salt) δ (ppm): 7.70-7.60 (m, 2H), 7.60-7.50 (m, 1H), 7.40-7.30 (m, 1H), 7.30-7.25 (m, 1H), 7.18-7.10 (d, 1H), 6.90-6.80 (m, 2H), 3.80 (s, 3H), 3.60-3.50 (m, 4H), 3.40-3.30 (m, 4H), 3.15 (s, 3H), 2.41 (s, 3H).

Example 168

Preparation of (E)-3,9-dimethyl-6-(2-(pyrimidin-4-yl)prop-1-enyl)-1,2,3,4,5,6-hexahydroazepino[4,5-b]indole (Compound No. 254)

4-(1-bromoprop-1-en-2-yl)pyrimidine (236 mg, 1.2 mmol) was dissolved in DMF (5 mL) and was added K$_3$PO$_4$ (424 mg, 2 mmol) followed by the addition of Copper (I) iodide (19 mg, 0.1 mmol) and L-proline (23 mg, 0.2 mmol). 1,2,3,4,5,6-hexahydro-3,9-dimethylazepino[4,5-b]indole (214 mg, 1 mmol) was added and purged nitrogen for 2 min. Reaction mass was stirred at 85 degree C. for overnight. Water was added and filtered the solid mass under vacuum. Crude was purified on silica gel (100-200 mesh) using 0-10% methanol: dichloromethane as eluent. Yield: 72 mg. $^1$H NMR (CDCl$_3$, Oxalate salt) δ (ppm): 9.20 (s, 1H), 8.76 (s, 1H), 8.0 (s, 1H), 7.44 (d, 1H), 7.30 (s, 1H), 7.0 (s, 2H), 2.99 (m, 4H), 2.84 (m, 4H), 2.50 (s, 3H), 2.42 (s, 3H), 2.04 (s, 3H).

Example 169

Preparation of 9-chloro-6-(((4-fluorophenyl)ethynyl)-3-methyl-1,2,3,4,5,6-hexahydroazepino[4,5-b]indole (Compound No. 281)

9-Chloro-3-methyl-1,2,3,4,5,6-hexahydroazepino[4,5-b]indole (234 mg, 1 mmol) was dissolved in toluene (4 mL) and the reaction mixture stirred for 10 min. K$_2$CO$_3$ (276 mg, 0.2 mmol), CuSO$_4$.5H$_2$O (249 mg, 0.01 mmol) and 1,10-Phenanthroline (36 mg, 0.2 mmol) were added to the reaction mixture and again stirred for 10 min. 1-(Bromoethynyl)-4-fluorobenzene (220 mg, 1.1 mmol) in toluene (2 mL) was added and reaction mixture was heated at 80-85° C. overnight. Toluene was evaporated under reduced pressure to obtain the crude compound. The crude was purified by silica gel (100-200 mesh) column chromatography using 0-100% Hexane: Ethyl acetate as eluent followed by reverse phase chromatography to obtain the product as TFA salt. $^1$H NMR CD$_3$OD, TFA salt) δ (ppm): 7.60 (m, 2H), 7.30 (m, 2H), 7.18 (m, 2H), 7.08 (m, 1H), 3.60 (m, 4H), 3.46 (m, 2H), 3.20 (m, 2H), 3.05 (s, 3H)

Example 170

Preparation of 9-chloro-6-((4-chlorophenyl)ethynyl)-3-methyl-1,2,3,4,5,6-hexahydroazepino[4,5-b]indole (Compound No. 282)

A mixture of 9-chloro-3-methyl-1,2,3,4,5,6-hexahydroazepino[4,5-b]indole (235 mg, 1 mmol), CuSO$_4$.5H$_2$O (50 mg, 0.2 mmol), 1,10-Phenanthroline (72 mg, 0.4 mmol), K$_3$PO$_4$ (425 mg, 2 mmol) and 1-(bromoethynyl)-4-chlorobenzene (237 mg, 1.1 mmol) in toluene (10 mL) was flushed with nitrogen heated 80° C. for 16 h. The reaction was monitored by LCMS. The reaction mixture was filtered through Celite, washed with DCM. The organic layer was concentrated and purified by column chromatography (silica gel, 60-80% ethyl acetate in hexane) to get 37 mg of product. $^1$H NMR (CDCl$_3$, HCl salt) δ (ppm): 7.50 (s, 1H) 7.49-7.40 (m, 3H), 7.38-7.32 (m, 2H), 7.25-7.20 (d, 1H), 3.22-3.18 (m, 2H), 3.0-2.90 (m, 6H), 2.60 (s, 3H).

Example 171

Preparation of 9-chloro-6-((3-fluoro-4-methoxyphenyl)ethynyl)-3-methyl-1,2,3,4,5,6-hexahydroazepino[4,5-b]indole (Compound No. 283)

9-chloro-3-methyl-1,2,3,4,5,6-hexahydroazepino[4,5-b]indole (100 mg, 0.42 mmol), CuSO$_4$.5H$_2$O (21 mg, 0.085 mmol), 1,10-Phenanthroline (30 mg, 0.17 mmol) and K$_3$PO$_4$ (180 mg, 0.85 mmol) and 4-(bromoethynyl)-2-fluoro-1-methoxybenzene (131 mg, 0.46 mmol) in toluene (5 mL) were charged and flushed with nitrogen. The reaction mixture was heated at 80° C. for 16 h. The reaction was monitored by LCMS. The reaction mixture was filtered through Celite, washed with DCM. The organic layer was concentrated and purified by column chromatography (100-200 mesh size silica gel, 60-80% ethyl acetate in hexane) to get 9-chloro-6-((3-fluoro-4-methoxyphenyl)ethynyl)-3-methyl-1,2,3,4,5,6-hexahydroazepino[4,5-b]indole which was further purified by prep TLC to get 24 mg of product. $^1$HNMR (CDCl$_3$, freebase) δ (ppm): 7.40 (d, 2H), 7.30 (m, 2H), 7.20 (d, 1H), 6.95 (t, 1H), 3.90 (s, 3H), 3.10 (m, 2H), 2.90 (m, 6H), 2.50 (s, 3H).

Example 172

Preparation of 6-((3-fluoro-4-methoxyphenyl)ethynyl)-3,9-dimethyl-1,2,3,4,5,6-hexahydroazepino[4,5-b]indole (Compound No. 284)

3,9-Dimethyl-1,2,3,4,5,6-hexahydroazepino[4,5-b]indole (100 mg, 0.46 mmol), CuSO$_4$.5H$_2$O (23 mg, 0.093 mmol), 1,10-Phenanthroline (33 mg, 0.18 mmol) and K$_3$PO$_4$ (197 mg, 0.93 mmol) and 4-(bromoethynyl)-2-fluoro-1-methoxybenzene (116 mg, 0.51 mmol) in toluene (5 mL) were added and flushed with nitrogen. The reaction mixture was heated at 80° C. for 16 h. The reaction was monitored by LCMS. The reaction mixture was filtered through Celite, washed with DCM. The organic layer was concentrated and purified by column chromatography (100-200 mesh size silica gel, 60-80% ethyl acetate in hexane) to get 6-((3-fluoro-4-methoxyphenyl)ethynyl)-3,9-dimethyl-1,2,3,4,5,6-hexahydroazepino[4,5-b]indole which was repurified by prep TLC to get 8 mg product as brown solid. ¹HNMR (CDCl₃, freebase) δ (ppm): 7.40 (d, 1H), 7.22 (m, 3H), 7.10 (d, 1H), 6.95 (t, 1H), 3.90 (s, 3H), 3.15 (m, 2H), 2.90 (m, 6H), 2.50 (s, 3H), 2.42 (s, 3H).

Example 173

Preparation of 1-(3,9-dimethyl-2,3,4,5-tetrahydroazepino[4,5-b]indol-6(1H)-yl)-2-(4-fluorophenyl)ethanone (Compound No. 285)

3,9-Dimethyl-1,2,3,4,5,6-hexahydroazepino[4,5-b]indole (214 mg, 10 mmol) was dissolved in toluene (3 mL) and stirred for 10 min. $K_2CO_3$ (276 mg, 0.2 mmol), $CuSO_4.5H_2O$ (249 mg, 0.01 mmol) and 1,10-Phenanthraline (36 mg, 0.2 mmol) were added to the reaction mixture and stirred at RT for 10 min. 1-(Bromoethynyl)-4-fluorobenzene (220 mg, 1.1 mmol) in toluene (2 mL) was added and the reaction mixture was heated to 80-85° C. overnight. The toluene was evaporated under reduced pressure to obtain the crude product. The crude product was purified by silica gel (100-200 mesh) column chromatography using 0-5% MeOH in dichloromethane as eluent followed by reverse phase chromatography to obtain the product as TFA salt. ¹HNMR (CD₃OD, TFA salt) δ (ppm): 7.65 (m, 2H), 7.55 (m, 2H), 7.30 (m, 2H), 7.20 (m, 2H), 7.05 (m, 1H), 3.60 (m, 5H), 3.45 (m, 3H), 3.20 (m, 3H), 3.0 (s, 3H).

Example 174

Preparation of (E)-9-chloro-6-(2-fluorostyryl)-3-methyl-1,2,3,4,5,6-hexahydroazepino[4,5-b]indole (Compound No. 83)

To a solution of 2-(9-chloro-3-methyl-2,3,4,5-tetrahydroazepino[4,5-b]indol-6(1H)-yl)-1-(2-fluorophenyl)ethanol (100 mg, 0.26 mmol) in DCM (2.5 mL), triethylamine (0.055 mL, 0.04 mmol) was added and stirred for 10 min, methanesulfonyl chloride (0.022 mL, 0.029 mmol) was added slowly at 0° C. and stirred at RT for 2 h. Reaction mixture was diluted with water, extracted with dichloromethane. Organic layer was dried over anhydrous sodium sulfate and evaporated under reduced pressure. Crude product was taken in NMP (0.7 mL), KOH powder (105 mg, 1.8 mmol) was added at RT and heated at 90° C. for 14 h. The compound was purified by reverse phase chromatography to afford 9 mg of TFA salt. ¹H NMR (CD₃OD, TFA salt) δ (ppm): 7.80-7.70 (m, 2H), 7.60-7.50 (m, 2H), 7.35-7.25 (m, 1H), 7.20-7.10 (m, 3H), 6.90-6.80 (d, 1H), 3.90-3.80 (m, 4H), 3.60-3.50 (m, 4H), 3.15 (s, 3H).

Example 175

Preparation of (E)-9-chloro-6-(2-fluorostyryl)-3-methyl-1,2,3,4,5,6-hexahydroazepino[4,5-b]indole (Compound No. 286)

4-(1-bromoprop-1-en-2-yl)pyrimidine (197 mg, 1 mmol) was dissolved in DMF (5 mL). To this solution was added $K_3PO_4$ (424 mg, 2 mmol) followed by copper (I) iodide (19 mg, 0.1 mmol) and L-proline (23 mg, 0.2 mmol). 9-Chloro-1,2,3,4,5,6-hexahydro-3-methylazepino[4,5-b]indole (234 mg, 1 mmol) was then added and the reaction mixture was purged with nitrogen for 2 min. The reaction mixture was stirred at 85° C. overnight. Water was added and the product was extracted with ethyl acetate. Solvent was removed under reduced pressure and the residue was purified by silica gel chromatography (100-200 mesh) using 0-10% MeOH: DCM as eluent. The compound was further purified through reverse phase chromatography. Yield: 33 mg. ¹H NMR (CD₃OD, Oxalate salt) δ (ppm): 9.18 (s, 1H), 8.81 (d, 1H), 8.0 (s, 1H), 7.80 (d, 1H), 7.60 (s, 1H), 7.18 (m, 2H), 3.60 (m, 4H), 3.30 (m, 4H), 3.10 (s, 3H), 2.0 (s, 3H).

Example B1

Determination of the Ability of Compounds of the Invention to Bind a Histamine Receptor Histamine H1

To evaluate in radioligand binding assays the activity of compounds of the invention, human recombinant histamine H1 receptor expressed in Chinese hamster ovary (CHO) cells (De Backer, M. D. et al., Biochem. Biophys. Res. Comm. 197(3):1601, 1993) in a modified Tris-HCl buffer (50 mM Tris-HCl, pH 7.4, 2 mM $MgCl_2$, 100 mM NaCl, 250 mM Sucrose) was used. Compounds of the invention were incubated with 1.2 nM [³H]Pyrilamine for 180 min. at 25° C. Non-specific binding was estimated in the presence of 1 μM pyrilamine. Receptor proteins were filtered and washed, the filters were then counted to determine [³H]Pyrilamine specifically bound. Compounds were screened at 1 μM or lower, using 1% DMSO as vehicle. Biochemical assay results are presented as the percent inhibition of specific binding in Table 6.

Histamine H2

To evaluate in radioligand binding assays the activity of compounds of the invention, human recombinant histamine H2 receptor expressed in Chinese hamster ovary (CHO) $K_1$ cells (Ruat, M., Proc. Natl. Acad. Sci. USA. 87(5):1658, 1990) in a 50 mM Phosphate buffer, pH 7.4 was used. Compounds of the invention were incubated with 0.1 nM [¹²⁵I] Aminopotentidine for 120 min. at 25° C. Non-specific binding was estimated in the presence of 3 μM Tiotidine. Receptor proteins were filtered and washed, the filters were then counted to determine [¹²⁵I]Aminopotentidine specifically bound. Compounds were screened at 1 μM or lower, using 1% DMSO as vehicle. Biochemical assay results are presented as the percent inhibition of specific binding in Table 6.

Histamine H3

To evaluate in radioligand binding assays the activity of compounds of the invention, human recombinant histamine $H_3$ receptor expressed in Chinese hamster ovary (CHO-K1) cells (Yanai K et al. Jpn J. Pharmacol. 65(2): 107, 1994; Zhu Y et al. Mol. Pharmacol. 59(3): 434, 2001) in a modified Tris-HCl buffer (50 mM Tris-HCl, pH 7.4, 5 mM $MgCl_2$, 0.04% BSA) is used. Compounds of invention are incubated with 3 nM [³H]R(−)-α-Methylhistamine for 90 min. at 25° C. Non-specific binding is estimated in the presence of 1 μM R(−)-α-Methylhistamine. Receptor proteins are filtered and washed, the filters are counted to determine [³H]R(−)-α-Methylhistamine specifically bound. Compounds are screened at 1 μM or lower, using 1% DMSO as vehicle. Compounds of the invention are tested in this biochemical assay and percent inhibition of specific binding is determined.

Example B2

Determination of the Ability of Compounds of the Invention to Bind a Imidazoline $I_2$ Receptor Central Imidazoline $I_2$ To evaluate in radioligand binding assays the activity of compounds of the invention, rat central imidazoline $I_2$ receptor obtained from Wistar Rat cerebral cortex (Brown, C. M. et al., Br. J. Pharmacol. 99:803, 1990) in a modified Tris-HCl buffer (50 mM Tris-HCl buffer, pH 7.4, 0.5 mM EDTA) is used. Compounds of the invention are incubated with 2 nM [³H]Idazoxan for 30 min. at 25° C. Non-specific binding is estimated in the presence of 1 µM Idazoxan. Receptor proteins are filtered and washed, the filters are counted to determine [$^3$H]Idazoxan specifically bound. Compounds are screened at 1 µM or lower, using 1% DMSO as vehicle. Compounds of the invention are tested in this biochemical assay and percent inhibition of specific binding is determined.

TABLE 4

Binding data

| Compound No. | Histamine Binding (1 µM) | |
|---|---|---|
| | H1 | H2 |
| 1 | 96 | 58 |
| 2 | 93 | 105 |
| 3 | 102 | 82 |
| 4 | 100 | 59 |
| 5 | 100 | 62 |
| 6 | 103 | 52 |
| 7 | 101 | 52 |
| 8 | 97 | 68 |
| 9 | 99 | 44 |
| 10 | 101 | 78 |
| 11 | 97 | 7 |
| 12 | 99 | 98 |
| 13 | 98 | 92 |
| 14 | 98 | 83 |
| 15 | 100 | 92 |
| 16 | 103 | 92 |
| 17 | 101 | 84 |
| 18 | 98 | 51 |
| 19 | 99 | 42 |
| 20 | 99 | 37 |
| 21 | 96 | 13 |
| 22 | 12 | 5 |
| 23 | 58 | −3 |
| 24 | 100 | 58 |
| 25 | 91 | 47 |
| 26 | 97 | 84 |
| 27 | 101 | 78 |
| 28 | 103 | 97 |
| 29 | 98 | 105 |
| 30 | 102 | 97 |
| 31 | 14 | −10 |
| 32 | 11 | −5 |
| 33 | 87 | 101 |
| 34 | 95 | 103 |
| 35 | 100 | 104 |
| 36 | 88 | 104 |
| 37 | 13 | 4 |
| 38 | 83 | 26 |
| 39 | 98 | 91 |
| 40 | 101 | 61 |
| 41 | 100 | 52 |
| 42 | 103 | 45 |
| 43 | 100 | 30 |
| 44 | 16 | 1 |
| 45 | 13 | 7 |
| 46 | 108 | 89 |
| 47 | 100 | 70 |
| 48 | 98 | 56 |
| 49 | 94 | 65 |
| 50 | 98 | 65 |
| 51 | 102 | 70 |
| 52 | 96 | 61 |
| 53 | 14 | 3 |
| 54 | 18 | −3 |
| 55 | 15 | −3 |
| 56 | 105 | 74 |
| 57 | 8 | 1 |
| 58 | 98 | 91 |
| 59 | 60 | 37 |
| 60 | 2 | 6 |
| 61 | 97 | 89 |
| 62 | 98 | 79 |
| 63 | 99 | 83 |
| 67 | 100 | 72 |
| 68 | 102 | 69 |
| 69 | 2 | −9 |
| 72 | −12 | 0 |
| 73 | 18 | −5 |
| 74 | 25 | 9 |
| 75 | 20 | −4 |
| 76 | 95 | 19 |
| 77 | 97 | 37 |
| 78 | 100 | 91 |
| 79 | 6 | 0 |
| 82 | 103 | 95 |
| 83 | 97 | 98 |
| 152 | 91 | 86 |
| 154 | 94 | 97 |
| 155 | 93 | 92 |
| 157 | 68 | 93 |
| 158 | 98 | 89 |
| 160 | 87 | 91 |
| 174 | 98 | 99 |
| 176 | 82 | 95 |
| 177 | 93 | 92 |
| 179 | 45 | 88 |
| 180 | 97 | 77 |
| 182 | 62 | 92 |
| 224 | 33 | −4 |
| 225 | 95 | 6 |
| 226 | 99 | 39 |
| 227 | 95 | 19 |
| 228 | 99 | 97 |
| 229 | 100 | 94 |
| 230 | 95 | 89 |
| 232 | 95 | 22 |
| 233 | 98 | 94 |
| 234 | 99 | 92 |
| 235 | 97 | 94 |
| 236 | 99 | 97 |
| 237 | 96 | 81 |
| 238 | 98 | 98 |
| 239 | 91 | 89 |
| 240 | 96 | 87 |
| 241 | 98 | 93 |
| 242 | 100 | 98 |
| 243 | 93 | 84 |
| 244 | 102 | 99 |
| 245 | 96 | 88 |
| 246 | 96 | 48 |
| 247 | 82 | 36 |
| 248 | 88 | 44 |
| 249 | 98 | 97 |
| 250 | 93 | 85 |
| 251 | 96 | 95 |
| 252 | 93 | 87 |
| 253 | 32 | 31 |
| 281 | 56 | 76 |
| 282 | 99 | 87 |
| 283 | 12 | 83 |
| 284 | 11 | 4 |
| 285 | 68 | 74 |

Example B3

Determination of the Ability of Compounds of the Invention to Bind an Adrenergic Receptor Adrenergic $\alpha_{1A}$ To evaluate in radioligand binding assays the activity of compounds of the invention, rat adrenergic $\alpha_{1A}$ receptor obtained from Wistar Rat submaxillary glands (Michel, A. D. et al., Br. J. Pharmacol. 98:883, 1989) in a modified Tris-HCl buffer (50 mM Tris-HCl buffer, pH 7.4, 0.5 mM EDTA) is used. Compounds of the invention are incubated with 0.25 nM [$^3$H]Prozosin for 60 min. at 25° C. Non-specific binding is estimated in the presence of 10 µM phentolamine. Receptor proteins are filtered and washed, the filters are counted to determine [$^3$H]Prozosin specifically bound. Compounds of the invention are screened at 1 µM or lower, using 1% DMSO as vehicle. Compounds of the invention are tested in this biochemical assay and percent inhibition of specific binding is determined.

Adrenergic $\alpha_{1B}$

To evaluate in radioligand binding assays the activity of compounds of the invention, rat adrenergic $\alpha_{1B}$ receptor obtained from Wistar Rat liver (Garcia-S'ainz, J. A. et al., Biochem. Biophys. Res. Commun. 186:760, 1992; Michel A. D. et al., Br. J. Pharmacol. 98:883, 1989) in a modified Tris-HCl buffer (50 mM Tris-HCl buffer, pH 7.4, 0.5 mM EDTA) is used. Compounds of the invention are incubated with 0.25 nM [$^3$H]Prozosin for 60 min. at 25° C. Non-specific binding is estimated in the presence of 10 µM phentolamine. Receptor proteins are filtered and washed, the filters are counted to determine [$^3$H]Prozosin specifically bound. Compounds are screened at 1 µM or lower, using 1% DMSO as vehicle. Compounds of the invention are tested in this biochemical assay and percent inhibition of specific binding is determined.

Adrenergic $\alpha_{1D}$

To evaluate in radioligand binding assays the activity of compounds of the invention, human recombinant adrenergic $\alpha_{1D}$ receptor expressed in human embryonic kidney (HEK-293) cells (Kenny, B. A. et al. Br. J. Pharmacol. 115(6):981, 1995) in a 50 mM Tris-HCl buffer, pH 7.4, was used. Compounds of invention were incubated with 0.6 nM [$^3$H]Prozosin for 60 min. at 25° C. Non-specific binding was estimated in the presence of 10 µM phentolamine. Receptor proteins were filtered and washed, the filters were then counted to determine [$^3$H]Prozosin specifically bound. Compounds were screened at 1 µM or lower, using 1% DMSO as vehicle. Biochemical assay results are presented as the percent inhibition of specific binding in Table 5.

Adrenergic $\alpha_{2A}$

To evaluate in radioligand binding assays the activity of compounds of the invention, human recombinant adrenergic $\alpha_{2A}$ receptor expressed in insect Sf9 cells (Uhlen S et al. J Pharmacol Exp Ther. 271:1558, 1994) in a modified Tris-HCl buffer (50 mM Tris-HCl, pH 7.4, 12.5 mM MgCl$_2$, 2 mM EDTA) was used. Compounds of invention were incubated with 1 nM [$^3$H]MK-912 for 60 min. at 25° C. MK912 is (2S-trans)-1,3,4,5',6,6',7,12b-octahydro-1',3'-dimethyl-spiro[2 h-benzofuro[2,3-a]quinolizine-2,4'(1'H)-pyrimidin]-2'(3'H)-one hydrochloride Non-specific binding was estimated in the presence of 10 µM WB-4101 (2-(2,6-Dimethoxyphenoxyethyl)aminomethyl-1,4-benzodioxane hydrochloride). Receptor proteins were filtered and washed, the filters were then counted to determine [$^3$H]MK-912 specifically bound. Compounds were screened at 1 µM or lower, using 1% DMSO as vehicle. Biochemical assay results are presented as the percent inhibition of specific binding in Table 5.

Adrenergic $\alpha_{2B}$

To evaluate in radioligand binding assays the activity of compounds of the invention, human recombinant adrenergic $\alpha_{2B}$ receptor expressed in Chinese hamster ovary (CHO-K1) cells (Uhlen S et al. Eur J. Pharmacol. 343(1):93, 1998) in a modified Tris-HCl buffer (50 mM Tris-HCl, pH 7.4, 12.5 mM MgCl$_2$, 1 mM EDTA, 0.2% BSA) was used. Compounds of the invention were incubated with 2.5 nM [$^3$H]Rauwolscine for 60 min. at 25° C. Non-specific binding was estimated in the presence of 10 µM Prozosin. Receptor proteins were filtered and washed, the filters were then counted to determine [$^3$H]Rauwolscine specifically bound. Compounds were screened at 1 µM or lower, using 1% DMSO as vehicle. Biochemical assay results are presented as the percent inhibition of specific binding in Table 5.

Adrenergic $\alpha_{2C}$

To evaluate in radioligand binding assays the activity of compounds of the invention, human recombinant adrenergic $\alpha_{2C}$ receptor expressed in insect Sf9 cells (Uhlen S et al. J Pharmacol Exp Ther. 271:1558, 1994) in a modified Tris-HCl buffer (50 mM Tris-HCl, pH 7.4, 12.5 mM MgCl$_2$, 2 mM EDTA) is used. Compounds of the invention are incubated with 1 nM [$^3$H]MK-912 for 60 min. at 25° C. Non-specific binding is estimated in the presence of 10 µM WB-4101. Receptor proteins are filtered and washed, the filters are counted to determine [$^3$H]MK-912 specifically bound. Compounds are screened at 1 µM or lower, using 1% DMSO as vehicle. Compounds of the invention are tested in this biochemical assay and percent inhibition of specific binding is determined.

Example B4

Determination of the Ability of Compounds of the Invention to Bind a Dopamine Receptor Dopamine $D_{2L}$ To evaluate in radioligand binding assays the activity of compounds of the invention, human recombinant dopamine $D_{2L}$ receptor expressed in Chinese hamster ovary (CHO) cells (Grandy, D. K. et al. Proc. Natl. Acad. Sci. USA. 86:9762, 1989; Hayes, G. et al., Mol. Endocrinol. 6:920, 1992) in a modified Tris-HCl buffer (50 mM Tris-HCl, pH 7.4, 1.4 mM Ascorbic Acid, 0.001% BSA, 150 mM NaCl) was used. Compounds of the invention were incubated with 0.16 nM [$^3$H] Spiperone for 120 min. at 25° C. Non-specific binding was estimated in the presence of 10 µM Haloperidol. Receptor proteins were filtered and washed, the filters were then counted to determine [$^3$H]Spiperone specifically bound. Compounds were screened at 1 µM or lower, using 1% DMSO as vehicle. Biochemical assay results are presented as the percent inhibition of specific binding in Table 5.

TABLE 5

Inhibition of ligand binding to aminergic G protein-coupled receptors by compounds of the invention:

| Comp. No. | Adrenergic (1 µM) | | | Dopamine (1 µM) |
| --- | --- | --- | --- | --- |
| | $\alpha_{1D}$ | $\alpha_{2A}$ | $\alpha_{2B}$ | D2L |
| 1 | 90 | 90 | 107 | 23 |
| 2 | 100 | 96 | 111 | 97 |
| 3 | 89 | 91 | 112 | 27 |
| 4 | 76 | 85 | 93 | 2 |
| 5 | 88 | 97 | 100 | 34 |
| 6 | 92 | 93 | 106 | 30 |
| 7 | 69 | 84 | 101 | 15 |
| 8 | 91 | 95 | 103 | 42 |
| 9 | 80 | 88 | 90 | 20 |
| 10 | 89 | 96 | 101 | 35 |
| 11 | 7 | 1 | 3 | −11 |
| 12 | 68 | 101 | 103 | 45 |
| 13 | 76 | 94 | 105 | 38 |
| 14 | 75 | 90 | 100 | 38 |
| 15 | 72 | 93 | 104 | 45 |
| 16 | 85 | 105 | 99 | 37 |
| 17 | 95 | 105 | 99 | 34 |
| 18 | 58 | 92 | 98 | 3 |

TABLE 5-continued

Inhibition of ligand binding to aminergic G protein-coupled receptors by compounds of the invention:

| Comp. No. | Adrenergic (1 μM) | | | Dopamine (1 μM) |
|---|---|---|---|---|
| | $\alpha_{1D}$ | $\alpha_{2A}$ | $\alpha_{2B}$ | D2L |
| 19 | 54 | 69 | 90 | 12 |
| 20 | 91 | 68 | 88 | 13 |
| 21 | 17 | −7 | 6 | 6 |
| 22 | 1 | −14 | −7 | 0 |
| 23 | 17 | 42 | 25 | 4 |
| 24 | 85 | 100 | 99 | 41 |
| 25 | 96 | 100 | 104 | 43 |
| 26 | 94 | 99 | 104 | 65 |
| 27 | 95 | 98 | 100 | 58 |
| 28 | 94 | 96 | 103 | 67 |
| 29 | 71 | 101 | 101 | 67 |
| 30 | 89 | 99 | 100 | 53 |
| 31 | 6 | 31 | 23 | 4 |
| 32 | 4 | 39 | 22 | −1 |
| 33 | 99 | 97 | 103 | 35 |
| 34 | 100 | 94 | 110 | 90 |
| 35 | 96 | 93 | 112 | 50 |
| 36 | 95 | 96 | 101 | 34 |
| 37 | 14 | 68 | 70 | 9 |
| 38 | 38 | 77 | 83 | 21 |
| 39 | 99 | 98 | 105 | 66 |
| 40 | 64 | 96 | 101 | 46 |
| 41 | 75 | 95 | 104 | 34 |
| 42 | 73 | 87 | 107 | 8 |
| 43 | 70 | 78 | 107 | 4 |
| 44 | 10 | 1 | 12 | −8 |
| 45 | 1 | −9 | 9 | −6 |
| 46 | 88 | 100 | 107 | 79 |
| 47 | 97 | 97 | 105 | 45 |
| 48 | 95 | 98 | 103 | 31 |
| 49 | 71 | 96 | 106 | 32 |
| 50 | 84 | 94 | 102 | 34 |
| 51 | 85 | 98 | 103 | 30 |
| 52 | 91 | 97 | 103 | 20 |
| 53 | 13 | 1 | 3 | 2 |
| 54 | −1 | 5 | 1 | 6 |
| 55 | 8 | 12 | 7 | 6 |
| 56 | 83 | 95 | 91 | 62 |
| 57 | −7 | −1 | 87 | 10 |
| 58 | 88 | 95 | 10 | 47 |
| 59 | 73 | 89 | 9 | 20 |
| 60 | −1 | 7 | 53 | −9 |
| 61 | −5 | 23 | 103 | 1 |
| 62 | 12 | 11 | 98 | 7 |
| 63 | 77 | 96 | 73 | 61 |
| 67 | 90 | 102 | 99 | 50 |
| 68 | 93 | 99 | 100 | 40 |
| 69 | −5 | 8 | −4 | −2 |
| 72 | 17 | −6 | 7 | −18 |
| 73 | 1 | 28 | 21 | −14 |
| 74 | 17 | 19 | 27 | −2 |
| 75 | 7 | 7 | 21 | 2 |
| 76 | 37 | 7 | 31 | 0 |
| 77 | 81 | 85 | 113 | 16 |
| 78 | 102 | 83 | 111 | 58 |
| 79 | −6 | 17 | 20 | −7 |
| 82 | 96 | 96 | 91 | 90 |
| 83 | 93 | 99 | 113 | 61 |
| 152 | 47 | 93 | 88 | 3 |
| 154 | | | | 33 |
| 155 | | | | 38 |
| 157 | | | | 24 |
| 158 | 98 | 99 | 109 | 65 |
| 160 | | | | 17 |
| 174 | 89 | 101 | 105 | 34 |
| 176 | | | | 23 |
| 177 | | | | 25 |
| 179 | | | | 23 |
| 180 | 98 | 99 | 103 | 62 |
| 182 | | | | 19 |
| 224 | 19 | 8 | −6 | −2 |
| 225 | 34 | 0 | 13 | 3 |
| 226 | 83 | 93 | 102 | 37 |
| 227 | 73 | 70 | 98 | 5 |
| 228 | 98 | 102 | 110 | 73 |
| 229 | 97 | 100 | 103 | 68 |
| 230 | 97 | 102 | 99 | 48 |
| 232 | 29 | 90 | 39 | 8 |
| 233 | 96 | 97 | 100 | 73 |
| 234 | 97 | 98 | 100 | 71 |
| 235 | 95 | 95 | 98 | 42 |
| 236 | 94 | 89 | 103 | 34 |
| 237 | 70 | 98 | 93 | 50 |
| 238 | 30 | 98 | 103 | 7 |
| 239 | 28 | 93 | 107 | 9 |
| 240 | | | | 57 |
| 241 | | | | 37 |
| 242 | | | | 69 |
| 243 | | | | 32 |
| 244 | | | | 43 |
| 245 | | | | 16 |
| 246 | | | | 14 |
| 247 | | | | 8 |
| 248 | | | | 81 |
| 249 | | | | 35 |
| 250 | | | | 15 |
| 251 | | | | 35 |
| 252 | | | | 19 |
| 253 | | | | 55 |
| 281 | 75 | 92 | 99 | 40 |
| 282 | 67 | 95 | 102 | 1 |
| 283 | | | | 12 |
| 284 | | | | 11 |
| 285 | 89 | 91 | 75 | 21 |

Example B5

Determination of the Ability of Compounds of the Invention to Bind a Serotonin Receptor Serotonin (5-Hydroxytryptamine) 5-$HT_{1A}$ To evaluate in radioligand binding assays the activity of compounds of the invention, human recombinant serotonin (5-Hydroxytryptamine) 5-$HT_{1A}$ receptor expressed in Chinese hamster ovary (CHO-K1) cells (Martin G R and Humphrey P P A. Neuropharmacol. 33:261, 1994; May J A, et al. J Pharmacol Exp Ther. 306(1): 301, 2003) in a modified Tris-HCl buffer (50 mM Tris-HCl, pH 7.4, 0.1% Ascorbic Acid, 0.5 mM EDTA, 10 mM $MgSO_4$) is used. Compounds of invention are incubated with 1.5 nM [$^3$H]8-OH-DPAT for 60 min. at 25° C. Non-specific binding is estimated in the presence of 10 μM Metergoline. Receptor proteins are filtered and washed, the filters are then counted to determine [$^3$H]8-OH-DPAT specifically bound. Compounds are screened at 1 μM or lower, using 1% DMSO as vehicle. Compounds of the invention are tested in this biochemical assay and percent inhibition of specific binding is determined.

Serotonin (5-Hydroxytryptamine) 5-$HT_{1B}$

To evaluate in radioligand binding assays the activity of compounds of the invention, serotonin (5-Hydroxytryptamine) 5-$HT_{1B}$ receptor from Wistar Rat cerebral cortex (Hoyer et al. Eur J. Pharmaco. 118: 1, 1985; Pazos et al. Eur J. Pharmacol. 106: 531, 1985) in a modified Tris-HCl buffer (50 mM Tris-HCl, pH 7.4, 154 mM NaCl, 10 μM Pargyline, 30 μM Isoprenaline) is used. Compounds of invention are incubated with 10 pM [$^{125}$I]Cyanopindolol for 90 min. at 37° C. Non-specific binding is estimated in the presence of 10 µM Serotonin (5-HT). Receptor proteins are filtered and washed, the filters are then counted to determine [$^{125}$I]Cyanopindolol specifically bound. Compounds are screened at 1 µM or lower, using 1% DMSO as vehicle. Compounds of the invention are tested in this biochemical assay and percent inhibition of specific binding is determined.

Serotonin (5-Hydroxytryptamine) 5-HT$_{2A}$

To evaluate in radioligand binding assays the activity of compounds of the invention, human recombinant serotonin (5-Hydroxytryptamine) 5-HT$_{2A}$ receptor expressed in Chinese hamster ovary (CHO-K1) cells (Bonhaus, D. W. et al. Br. J. Pharmacol. 115:622, 1995; Saucier, C. and Albert, P. R., J. Neurochem. 68:1998, 1997) in a 50 mM Tris-HCl buffer, pH 7.4, was used. Compounds of the invention were incubated with 0.5 nM [$^3$H]Ketanserin for 60 min. at 25° C. Non-specific binding was estimated in the presence of 1 µM Mianserin. Receptor proteins were filtered and washed, the filters were then counted to determine [$^3$H]Ketanserin specifically bound. Compounds were screened at 1 µM or lower, using 1% DMSO as vehicle. Biochemical assay results are presented as the percent inhibition of specific binding in Table 6.

Serotonin (5-Hydroxytryptamine) 5-HT$_{2B}$

To evaluate in radioligand binding assays the activity of compounds of the invention, human recombinant serotonin (5-Hydroxytryptamine) 5-HT$_{2B}$ receptor expressed in Chinese hamster ovary (CHO-K1) cells (Bonhaus, D. W. et al., Br. J. Pharmacol. 115:622, 1995) in a modified Tris-HCl buffer (50 mM Tris-HCl, pH 7.4, 4 mM CaCl$_2$, 0.1% Ascorbic Acid) is used. Compounds of invention are incubated with 1.2 nM [$^3$H]Lysergic acid diethylamide (LSD) for 60 min. at 37° C. Non-specific binding is estimated in the presence of 10 µM Serotonin (5-HT). Receptor proteins are filtered and washed, the filters are then counted to determine [$^3$H]LSD specifically bound. Compounds are screened at 1 µM or lower, using 1% DMSO as vehicle. Compounds of the invention are tested in this biochemical assay and percent inhibition of specific binding is determined.

Serotonin (5-Hydroxytryptamine) 5-HT$_{2C}$

To evaluate in radioligand binding assays the activity of compounds of the invention, human recombinant serotonin (5-Hydroxytryptamine) 5-HT$_{2C}$ receptor expressed in Chinese hamster ovary (CHO-K1) cells (Wolf, W. A. and Schutz, J. S., J. Neurochem. 69:1449, 1997) in a modified Tris-HCl buffer (50 mM Tris-HCl, pH 7.4, 0.1% Ascorbic Acid, 10 µM Pargyline) was used. Compounds of the invention were incubated with 1 nM [$^3$H]Mesulergine for 60 min. at 25° C. Non-specific binding was estimated in the presence of 1 µM Mianserin. Receptor proteins were filtered and washed, the filters were then counted to determine [$^3$H]Mesulergine specifically bound. Compounds were screened at 1 µM or lower, using 1% DMSO as vehicle. Biochemical assay results are presented as the percent inhibition of specific binding in Table 6.

Serotonin (5-Hydroxytryptamine) 5-HT$_3$

To evaluate in radioligand binding assays the activity of compounds of the invention, human recombinant serotonin (5-Hydroxytryptamine) 5-HT$_3$ receptor expressed in human embryonic kidney (HEK-293) cells (Miller K et al. Synapse. 11:58, 1992; Boess F G et al. Neuropharmacology. 36:637, 1997) in a modified Tris-HCl buffer (50 mM Tris-HCl, pH 7.4, 1 mM EDTA, 5 mM MgCl$_2$) is used. Compounds of invention are incubated with 0.69 nM [$^3$H]GR-65630 for 60 min. at 25° C. Non-specific binding is estimated in the presence of 10 µM MDL-72222. Receptor proteins are filtered and washed, the filters are then counted to determine [$^3$H]GR-65630 specifically bound. Compounds are screened at 1 µM or lower, using 1% DMSO as vehicle. Compounds of the invention are tested in this biochemical assay and percent inhibition of specific binding is determined.

Serotonin (5-Hydroxytryptamine) 5-HT$_4$

To evaluate in radioligand binding assays the activity of compounds of the invention, serotonin (5-Hydroxytryptamine) 5-HT$_4$ receptor from Duncan Hartley derived Guinea pig striatum (Grossman C J et al. Br J. Pharmacol. 109:618, 1993) in a 50 mM Tris-HCl, pH 7.4, is used. Compounds of invention are incubated with 0.7 nM [$^3$H]GR-113808 for 30 min. at 25° C. Non-specific binding is estimated in the presence of 30 µM Serotonin (5-HT). Receptor proteins are filtered and washed, the filters are then counted to determine [$^3$H]GR-113808 specifically bound. Compounds are screened at 1 µM or lower, using 1% DMSO as vehicle. Compounds of the invention are tested in this biochemical assay and percent inhibition of specific binding is determined.

Serotonin (5-Hydroxytryptamine) 5-HT$_{5A}$

To evaluate in radioligand binding assays the activity of compounds of the invention, human recombinant serotonin (5-Hydroxytryptamine) 5-HT$_{5A}$ receptor expressed in Chinese hamster ovary (CHO-K1) cells (Rees, S. et al., FEBS Lett. 355:242, 1994) in a modified Tris-HCl buffer (50 mM Tris-HCl, pH 7.4, 10 mM MgCl$_2$, 0.5 mM EDTA) is used. Compounds of the invention are incubated with 1.7 nM [$^3$H] Lysergic acid diethylamide (LSD) for 60 min. at 37° C. Non-specific binding is estimated in the presence of 100 µM Serotonin (5-HT). Receptor proteins are filtered and washed, the filters are then counted to determine [$^3$H]LSD specifically bound. Compounds are screened at 1 µM or lower, using 1% DMSO as vehicle. Compounds of the invention are tested in this biochemical assay and percent inhibition of specific binding is determined.

Serotonin (5-Hydroxytryptamine) 5-HT$_6$

To evaluate in radioligand binding assays the activity of compounds of the invention, human recombinant serotonin (5-Hydroxytryptamine) 5-HT6 receptor expressed in human HeLa cells (Monsma, F. J. Jr. et al., Mol. Pharmacol. 43:320, 1993) in a modified Tris-HCl buffer (50 mM Tris-HCl, pH 7.4, 150 mM NaCl, 2 mM Ascorbic Acid, 0.001% BSA) was used. Compounds of the invention were incubated with 1.5 nM [3H]Lysergic acid diethylamide (LSD) for 120 min. at 37° C. Non-specific binding was estimated in the presence of 5 µM Serotonin (5-HT). Receptor proteins were filtered and washed, the filters were then counted to determine [3H]LSD specifically bound. Compounds were screened at 1 µM or lower, using 1% DMSO as vehicle. Biochemical assay results are presented as the percent inhibition of specific binding in Table 6.

Serotonin (5-Hydroxytryptamine) 5-HT$_7$

To evaluate in radioligand binding assays the activity of compounds of the invention, human recombinant serotonin (5-Hydroxytryptamine) 5-HT$_7$ receptor expressed in Chinese hamster ovary (CHO) cells (Roth, B. L. et al., J. Pharmacol. Exp. Ther. 268:1403, 1994; Shen, Y. et al., J. Biol. Chem. 268:18200, 1993) in a modified Tris-HCl buffer (50 mM Tris-HCl, pH 7.4, 10 mM MgCl$_2$, 0.5 mM EDTA) is used. Compounds of invention are incubated with 5.5 nM [$^3$H] Lysergic acid diethylamide (LSD) for 2 hours at 25° C. Non-specific binding is estimated in the presence of 10 µM Serotonin (5-HT). Receptor proteins are filtered and washed, the filters are then counted to determine [$^3$H]LSD specifically bound. Compounds are screened at 1 µM or lower, using 1% DMSO as vehicle.

TABLE 6

Inhibition of ligand binding to aminergic G protein-coupled receptors by compounds of the invention:

| Comp No. | Serotonin (1 μM) | | |
|---|---|---|---|
| | $5\text{-}HT_{2A}$ | $5\text{-}HT_{2C}$ | $5\text{-}HT_6$ |
| 1 | 98 | 79 | 86 |
| 2 | 99 | 88 | 103 |
| 3 | 95 | 94 | 92 |
| 4 | 93 | 89 | 83 |
| 5 | 96 | 90 | 93 |
| 6 | 96 | 92 | 82 |
| 7 | 80 | 64 | 36 |
| 8 | 97 | 95 | 100 |
| 9 | 96 | 93 | 81 |
| 10 | 94 | 92 | 97 |
| 11 | 5 | 34 | 4 |
| 12 | 100 | 92 | 83 |
| 13 | 97 | 89 | 100 |
| 14 | 101 | 95 | 93 |
| 15 | 101 | 100 | 82 |
| 16 | 101 | 92 | 78 |
| 17 | 102 | 93 | 80 |
| 18 | 88 | 64 | 60 |
| 19 | 80 | 52 | 42 |
| 20 | 95 | 77 | 46 |
| 21 | 8 | 29 | 30 |
| 22 | −2 | −4 | −12 |
| 23 | 67 | 37 | 17 |
| 24 | 98 | 95 | 99 |
| 25 | 97 | 94 | 93 |
| 26 | 100 | 93 | 87 |
| 27 | 99 | 91 | 92 |
| 28 | 100 | 94 | 95 |
| 29 | 100 | 101 | 103 |
| 30 | 100 | 98 | 86 |
| 31 | 43 | 56 | 2 |
| 32 | 60 | 48 | 4 |
| 33 | 100 | 86 | 98 |
| 34 | 98 | 97 | 103 |
| 35 | 99 | 91 | 102 |
| 36 | 97 | 83 | 99 |
| 37 | 91 | 85 | 12 |
| 38 | 96 | 98 | 41 |
| 39 | 98 | 97 | 103 |
| 40 | 97 | 97 | 101 |
| 41 | 99 | 99 | 101 |
| 42 | 95 | 101 | 73 |
| 43 | 93 | 91 | 48 |
| 44 | 17 | 41 | 1 |
| 45 | 22 | 16 | 2 |
| 46 | 100 | 98 | 98 |
| 47 | 99 | 98 | 77 |
| 48 | 97 | 98 | 73 |
| 49 | 97 | 98 | 88 |
| 50 | 98 | 95 | 88 |
| 51 | 97 | 98 | 94 |
| 52 | 97 | 96 | 84 |
| 53 | 41 | 32 | −1 |
| 54 | 1 | −2 | −10 |
| 55 | −2 | 32 | 4 |
| 56 | 97 | 95 | 104 |
| 57 | 10 | 65 | −1 |
| 58 | 100 | 16 | 99 |
| 59 | 93 | −3 | 97 |
| 60 | −7 | −5 | 3 |
| 61 | 43 | 89 | 5 |
| 62 | 12 | 101 | −4 |
| 63 | 91 | 5 | 101 |
| 67 | 100 | 93 | 86 |
| 68 | 99 | 95 | 87 |
| 69 | 52 | −1 | −4 |
| 72 | 23 | 53 | 39 |
| 73 | 18 | 11 | 0 |
| 74 | 27 | 1 | −4 |
| 75 | 34 | 13 | −2 |
| 76 | 52 | 78 | 39 |
| 77 | 90 | 72 | 33 |
| 78 | 100 | 98 | 91 |
| 79 | −8 | −18 | −7 |
| 82 | 98 | 98 | 104 |
| 83 | 99 | 100 | 103 |
| 152 | 100 | 94 | 73 |
| 154 | 100 | 99 | 92 |
| 155 | 99 | 98 | 101 |
| 157 | 98 | 101 | 78 |
| 158 | 101 | 99 | 93 |
| 160 | 94 | 103 | 99 |
| 174 | 102 | 101 | 100 |
| 176 | 99 | 99 | 74 |
| 177 | 98 | 99 | 96 |
| 179 | 98 | 100 | 77 |
| 180 | 101 | 100 | 95 |
| 182 | 101 | 102 | 96 |
| 224 | −7 | 11 | −4 |
| 225 | 38 | 44 | 16 |
| 226 | 92 | 82 | 36 |
| 227 | 85 | 66 | 30 |
| 228 | 99 | 97 | 104 |
| 229 | 100 | 98 | 102 |
| 230 | 97 | 96 | 100 |
| 232 | 70 | 93 | 20 |
| 233 | 102 | 100 | 103 |
| 234 | 101 | 98 | 103 |
| 235 | 102 | 98 | 97 |
| 236 | 101 | 100 | 102 |
| 237 | 99 | 100 | 103 |
| 238 | 103 | 100 | 86 |
| 239 | 102 | 97 | 59 |
| 240 | 98 | 97 | 102 |
| 241 | 100 | 97 | 100 |
| 242 | 99 | 94 | 102 |
| 243 | 98 | 102 | 99 |
| 244 | 100 | 101 | 103 |
| 245 | 99 | 99 | 97 |
| 246 | 98 | 99 | 94 |
| 247 | 98 | 99 | 74 |
| 248 | 99 | 101 | 103 |
| 249 | 100 | 98 | 101 |
| 250 | 100 | 99 | 99 |
| 251 | 101 | 99 | 99 |
| 252 | 96 | 87 | 98 |
| 253 | 102 | 101 | 103 |
| 281 | 100 | 98 | 97 |
| 282 | 98 | 103 | 71 |
| 283 | 90 | 100 | 40 |
| 284 | 94 | 100 | 42 |
| 285 | 100 | 99 | 94 |

Example B6

Determination of Serotonin (5-Hydroxytryptamine) $5\text{-}HT_{2A}$ Agonist/Antagonist Activity of Compounds of the Invention To determine for agonist or antagonist activity of compounds of the invention in functional assays, human recombinant serotonin $5\text{-}HT_{2A}$ receptor expressed in human embryonic kidney (HEK-293) cells (Jerman J C, Brough S J, Gager T, Wood M, Coldwell M C, Smart D and Middlemiss D N. Eur J Pharmacol, 414: 23-30, 2001) is used. Cells are suspended in DMEM buffer, and distributed in microplates. A cytoplasmic calcium fluorescent indicator which varies proportionally to the free cytosolic $Ca^{2+}$ ion concentration is mixed with probenecid in HBSS buffer complemented with 20 mM HEPES (pH 7.4), added into each well and equilibrated with the cells for 30 min. at 37° C. followed by 30 min. at 22° C.

To measure agonist effects, compounds of the invention, reference agonist or HBSS buffer (basal control) is added to the cells and changes in fluorescence intensity are measured using a microplate reader. For stimulated control measurements, 5-HT at 100 nM is added in separate assay wells.

The results are expressed as a percent of the control response to 100 nM 5-HT. The standard reference agonist is 5-HT, which is tested in each experiment at several concentrations to generate a concentration-response curve from which its $EC_{50}$ value is calculated.

To measure antagonist effects, the addition of the compounds of the invention, reference antagonist or HBSS buffer is followed by the addition of 3 nM 5-HT or HBSS buffer (basal control) prior the fluorescence measurements. The results are expressed as a percent inhibition of the control response to 3 nM 5-HT. The standard reference antagonist is ketanserin, which is tested in each experiment at several concentrations to generate a concentration-response curve from which its $IC_{50}$ value is calculated. Compounds are screened at 3 µM or lower, using DMSO as vehicle.

Example B7

Determination of Serotonin (5-Hydroxytryptamine) 5-HT6 Agonist/Antagonist Activity of Compounds of the Invention To determine for agonist or antagonist activity of compounds of the invention in functional assays, human recombinant 5-HT$_6$ receptor is transfected in CHO cells (Kohen, R., Metcalf, M. A., Khan, N., Druck, T., Huebner, K., Lachowicz, J. E., Meltzer, H. Y., Sibley, D. R., Roth, B. L. And Hamblin, M. W. Cloning, characterization and chromosomal localization of a human 5-HT6 serotonin receptor, J. Neurochem., 66: 47, 1996) and the activity of compounds of the invention is determined by measuring their effects on cAMP production using the Homogeneous Time Resolved Fluorescence (HTRF) detection method. Cells are suspended in HBSS buffer complemented with HEPES 20 mM (pH 7.4) and 500 µM IBMX, and then distributed in microplates and incubated for 45 min. at 37° C. in the absence (control) or presence of compounds of the invention or the reference agonist or antagonist.

For agonist determinations, stimulated control measurement, separate assay wells contain 10 µM 5-HT. Following incubation, the cells are lysed and the fluorescence acceptor (D2-labeled cAMP) and fluorescence donor (anti-cAMP antibody labeled with europium cryptate) are added. After 60 min. at RT, the fluorescence transfer is measured at lex=337 nm and lem=620 and 665 nm using a microplate reader. The cAMP concentration is determined by dividing the signal measured at 665 nm by that measured at 620 nm (ratio).

The results are expressed as a percent of the control response to 10 µM 5-HT. The standard reference agonist is 5-HT, which is tested in each experiment at several concentrations to generate a concentration-response curve from which its $EC_{50}$ value is calculated.

For antagonist determinations, the reference agonist 5-HT is added at a final concentration of 100 nM. For basal control measurements, separate assay wells do not contain 5-HT. Following 45 min. incubation at 37° C., the cells are lysed and the fluorescence acceptor (D2-labeled cAMP) and fluorescence donor (anti-cAMP antibody labeled with europium cryptate) are added.

After 60 min. at RT, the fluorescence transfer is measured as mentioned above. The results are expressed as a percent inhibition of the control response to 100 nM 5-HT. The standard reference antagonist is methiothepin.

Example B8

Determination of Dopamine D2L Antagonist Activity of Compounds

To determine for agonist or antagonist activity of compounds of the invention in functional assays, human recombinant dopamine $D_{2L}$ receptor stably expressed in Chinese hamster ovary (CHO) cells (Senogles S E et al. J Biol. Chem. 265(8): 4507, 1990) is used. Compounds of invention are pre-incubated with the membranes (0.1 mg/mL) and 10 mM GDP in modified HEPES buffer (20 mM HEPES, pH 7.4, 100 mM NaCl, 10 mM MgCl$_2$, 1 mM DTT, 1 mM EDTA) for 20 min. and Scintillation Proximity Assay (SPA) beads are added for another 60 min. at 30° C. The reaction is initiated by 0.3 nM [$^{35}$S]GTPγS for an additional 15 min. incubation period. Increase of [$^{35}$S]GTPγS binding by 50 percent or more (350%) relative to the 1 mM dopamine response indicates possible dopamine $D_{2L}$ receptor agonist activity. Inhibition of a 10 µM dopamine-induced increase of [$^{35}$S]GTPγS binding response by 50 percent or more (350%) indicates receptor antagonist activity. Compounds are screened at 3 µM or lower, using 0.4% DMSO as vehicle. Assay results are presented as the percent response of specific binding.

Example B9

Determination of Dopamine D2S Antagonist Activity of Compounds of the Invention

To determine for agonist or antagonist activity of compounds of the invention in functional assays, human recombinant dopamine $D_{2S}$ receptor stably expressed in Chinese hamster ovary (CHO) cells (Gilliland S L and Alper R H. Naunyn-Schmiedeberg's Archives of Pharmacology. 361: 498, 2000) is used. Compounds of invention are pre-incubated with the membranes (0.05 mg/mL) and 3 µM GDP in modified HEPES buffer (20 mM HEPES, pH 7.4, 100 mM NaCl, 10 mM MgCl$_2$, 1 mM DTT, 1 mM EDTA) for 20 min. and Scintillation Proximity Assay (SPA) beads are then added for another 60 min. at 30° C. The reaction is initiated by 0.3 nM [$^{35}$S]GTPγS for an additional 30 min. incubation period. Increase of [$^{35}$S]GTPγS binding by 50 percent or more (350%) relative to the 100 µM dopamine response indicates possible dopamine $D_{2S}$ receptor agonist activity. Inhibition of a 3 µM dopamine-induced increase of [$^{35}$S]GTPγS binding response by 50 percent or more (350%) indicates receptor antagonist activity. Compounds are screened at 3 µM or lower, using 0.4% DMSO as vehicle. Assay results are presented as the percent response of specific.

Example B10

Determination for Agonist or Antagonist Activity of Compounds of the Invention in a Histamine H1 Functional Assay To determine for agonist or antagonist activity of compounds of the invention in functional assays, human recombinant Histamine H$_1$ receptor expressed in human embryonic kidney (HEK-293) cells (Miller, T. R., Witte, D. G., Ireland, L. M., Kang, C. H., Roch, J. M., Masters, J. N., Esbenshade, T. A And Hancock, A. A. J. Biomol. Screen., 4: 249-258, 1999) is used. Cells are suspended in DMEM buffer, and then distributed in microplates. A cytoplasmic calcium fluorescent indicator which varies proportionally to the free cytosolic $Ca^{2+}$ ion concentration is mixed with probenecid in HBSS buffer complemented with 20 mM HEPES (pH 7.4) and is then added into each well and equilibrated with the cells for 30 min. at 37° C. and then for another 30 min. at 22° C. To measure agonist effects, compounds of the invention, reference agonist or HBSS buffer (basal control) are added to the cells and changes in fluorescence intensity are measured using a microplate reader. For stimulated control measurements, histamine at 10 µM is added in separate assay wells.

The results are expressed as a percent of the control response to 10 µM histamine. The standard reference agonist is histamine, which is tested in each experiment at several concentrations to generate a concentration-response curve from which its $EC_{50}$ value is calculated.

To measure antagonist effects, the addition of the compounds of the invention, reference antagonist or HBSS buffer is followed by the addition of 300 nM histamine or HBSS buffer (basal control) prior the fluorescence measurements. The results are expressed as percent inhibition of the control response to 300 nM histamine. The standard reference antagonist is ketanserin, which is tested in each experiment at several concentrations to generate a concentration-response curve from which its $IC_{50}$ value is calculated. Compounds are screened at 3 µM or lower, using DMSO as vehicle.

Example B11

Increase of Neurite Outgrowth of Neurons that were Cultured with Compounds of the Invention Neurite Outgrowth in Cortical Neurons Compounds are tested to determine their ability to stimulate neurite outgrowth of cortical neurons. Standard methods are used to isolate cortical neurons. For the isolation of primary rat cortical neurons, the fetal brain from a pregnant rat at 17 days of gestation is prepared in Leibovitz's medium (L15; Gibco). The cortex is dissected out, and the meninges are removed. Trypsin (Gibco) is used to dissociate cortical C with DNAse I. The cells are triturated for 30 min. with a pipette in Dulbecco's Modified Eagle Media ("DMEM"; Gibco) with 10% Fetal Bovine Serum ("FBS") (Gibco) and centrifuged at 350×g for 10 min. at RT. The cells are suspended in Neurobasal medium supplemented with 2% B27 (Gibco) and 0.5 mM L-glutamine (Gibco). The cells are maintained at 30,000 cells per well of poly-L-lysine coated plates at 37° C. in 5% $CO_2$-95% air atmosphere. After adhesion, a vehicle control or compounds of the invention are added at different concentrations to the medium. BDNF (50 ng/mL) is used as a positive control for neurite growth. After treatment, cultures are washed in phosphate-buffered saline ("PBS"; Gibco) and fixed in glutaraldehyde 2.5% in PBS. Cells are fixed after 3 days growth. Several pictures (~80) of cells with neurites are taken per condition with a camera. The length measurements are made by analysis of the pictures using software from Image-Pro Plus (France). The results are expressed as mean (s.e.m.). Statistical analysis of the data is performed using one way analysis of variance (ANOVA).

Neurite Outgrowth in Rat Mixed Cortical Cultures

Cortical mixed cultures are prepared from E18 Wistar rat embryos. The cortices are dissected out and the tissue was cut to small pieces. The cells are separated by 15-min. incubation with DNase and papain. The cells are collected by centrifugation (1500 rpm, 5 min.). The tissue is triturated with a pipette and the cells are plated using the micro-islet protocol (20 000 cells in 25 µl medium) on poly-L-lysine coated 48 wells, in MEM supplemented with 2 mM glutamine, 0.1 µg/mL gentamicin, 10% heat-inactivated fetal bovine serum (FBS-HI) and 10% heat-inactivated horse serum (HS-HI). After the cells has attached to the well, 250 µl medium is added to the wells. Four hours after plating the medium is changed to fresh medium (MEM with supplements and 5% HS-HI) containing test compound at 0.5, 5 and 50 nM concentrations. As positive controls BDNF (50, 100 and/or 150 ng/mL), and/or NGF (50 ng/mL and/or 100 ng/mL) are used. After 2 days in vitro, the cell's conditioned media are collected from plates before fixing the cells. The media samples are centrifuged 13 000 rpm 3 min. to get rid of cell debris. The samples are stored at −20 C for later analysis. Cells are formaldehyde-fixed and processed for immunocytochemistry. BDNF levels in the conditioned media are determined with a BDNF ELISA using the manufacturers (Promega, BDNF Emax® ImmunoAssay System, catalog number: G7610) instructions.

The cultures are fixed with 4% formaldehyde in 0.01 M PBS for 30 min. and washed once with PBS. The fixed cells are first permeabilized and non-specific binding is blocked by a 30-min. incubation with blocking buffer containing 1% bovine serum albumin and 0.3% Triton X-100 in PBS. Rabbit anti-MAP-2 (dilution 1:1000, AB5622, Chemicon, in blocking buffer) is used as a primary antibody. The cells are incubated with the primary antibody for 48 h at +4° C., washed with PBS and incubated with secondary antibody goat anti-rabbit IgG conjugated to Alexa Fluor568 (1:200, A11036, Molecular Probes) for 2 h at RT. The immunopositive cells are visualized by a fluorescence microscope equipped with appropriate filter set, and documented by a high resolution image capturing. The number of cells per field (4 field per well) are counted, and the neurite outgrowth is quantified using Image Pro Plus software.

The number of wells per compound concentration used is 6 (n=6). All data are presented as mean±standard deviation (SD) or standard error of mean (SEM), and differences are considered to be statistically significant at the $p<0.05$ level. Statistical analysis is performed using StatsDirect statistical software. Differences between group means are analyzed by using 1-way-ANOVA followed by Dunnet's test (comparison to the vehicle treated group).

Example B12

Use of an In Vivo Model to Evaluate the Ability of Compounds to Enhance Cognition, Learning and Memory in Scopolamine Treated Rats The two-trial object recognition paradigm developed by Ennaceur and Delacour in the rat is used as a model of episodic/short term memory. Ennaceur, A., and Delacour, J. (1988), *Behav. Brain Res.* 31:47-59. The paradigm is based on spontaneous exploratory activity of rodents and does not involve rule learning or reinforcement. The novel object recognition paradigm is sensitive to the effects of ageing and cholinergic dysfunction. See, e.g., Scali, C., et al., (1994), *Neurosci. Letts.* 170:117-120; and Bartolini, L., et al., (1996), *Biochem. Behav.* 53:277-283.

Male Sprague-Dawley rats between six and seven weeks old, weighing between 220-300 grams are obtained from Centre d'Elevage (Rue Janvier, B.P. 55, Le Genest-Saint-Isle 53940, France). The animals are housed in groups of 2 to 4 in polypropylene cages (with a floor area of 1032 $cm^2$) under standard conditions: at RT (22±2° C.), under a 12 hour light/12 hour dark cycle, with food and water provided ad libitum. Animals are permitted to acclimate to environmental conditions for at least 5 days before the experiment begins, and are numbered on their tails with indelible marker.

The experimental arena is a square wooden box (60 cm×60 cm×40 cm) painted dark blue, with 15 cm×15 cm black squares under a clear plexiglass floor. The arena and objects placed inside the arena are cleaned with water between each trial to eliminate any odor trails left by rats. The arena is placed in a dark room illuminated only by halogen lamps directed towards the ceiling in order to produce a uniformly dim light in the box of approximately 60 lux. The day before testing, animals are allowed to freely explore the experimental arena for three min. in the presence of two objects (habituation). Animals to be tested are placed in the experimental room at least 30 min. before testing.

Novel object recognition test is comprised of two trials separated by an interval of 120 min. or 24 h. When agents that disrupt memory such as the cholinergic antagonist scopolamine are used an inter-trial interval of 120 min. is preferred. Alternatively a 24 h inter-trial interval is used when studying effect of natural forgetting on novel object recognition task. During the first, or acquisition, trial ($T_1$), rats are placed in the arena, where two identical objects have been previously placed. The time required for each animal to complete 15 seconds of object exploration is determined, with a cut-off time of four min. Exploration is considered to be directing the nose at a distance less than 2 centimeters ("cm") from the object and/or touching the object. During the second, or testing, trial ($T_2$), one of the objects presented in the first trial is replaced with an unknown or novel object, while the second, familiar object was left in place. Rats are placed back in the arena for three min., and exploration of both objects is determined. Locomotor activity of rats (number of times rats cross grid lines visible under the clear plexiglass floor) is scored for during $T_1$ and $T_2$. At the conclusion of the experiments, the rats are sacrificed by an overdose of pentobarbital given intraperitoneally.

The following parameters are measured as part of the novel object recognition task: (1) time required to achieve 15 seconds of object exploration during $T_1$; (2) locomotor activity during $T_1$ (number of crossed lines); (3) time spent in active exploration of the familiar object during $T_2$ ($T_{Familiar}$); (4) time spent in active exploration of the novel object during $T_2$ ($T_{Novel}$); and (5) locomotor activity during $T_2$ (number of crossed lines). The difference between time spent in active exploration of the novel object during $T_2$ and time spent in active exploration of the familiar object during $T_2$ ($\delta T_{Novel}$-$T_{Familiar}$) is evaluated. The % of animals in each group with $T_{Novel}$-$T_{Familiar}$ greater than or equal to 5 seconds is also derived; described as % of good learners.

Animals not meeting a minimal level of object exploration are excluded from the study as having naturally low levels of spontaneous exploration. Only rats exploring the objects for at least five seconds ($T_{Novel}$+$T_{Familiar}$>5 seconds) are included in the study.

Animals are randomly assigned to groups of 14. Compounds of the invention and controls are administered to animals the groups as follows: Solutions of compounds are prepared freshly each day at a concentration of 0.25 mg/mL using purified water or saline as vehicle. Donepezil, used as a positive control, and scopolamine are administered simultaneously in a single solution of saline (5 mL/kg) prepared freshly each day. Scopolamine is purchased from Sigma Chemical Co. (Catalog No. S-1875; St. Quentin Fallavier, France) is dissolved in saline to a concentration of 0.06 mg/mL.

Donepezil or its vehicle and scopolamine are administered intraperitoneally 40 min. before the acquisition trial ($T_1$). Compounds or their vehicle are administered by gavage 25 min. before the acquisition trial ($T_1$), i.e., 5 min. after administration of scopolamine. The volume of administration is 5 mL/kg body weight for compounds administered intraperitoneally, and 10 mL/kg for compounds administered orally. Recognition scores and % of good learners for compounds of the invention are determined.

Example B13

Use of an In Vivo Model to Determine the Ability of Compounds to Treat, Prevent and/or Delay the Onset and/or the Development of Schizophrenia in PCP Treated Animals In vivo models of schizophrenia can be used to determine the ability of the compounds described herein to treat and/or prevent and/or delay the onset and/or the development of schizophrenia.

One exemplary model for testing the activity of one or more compounds described herein to treat and/or prevent and/or delay the onset and/or development of schizophrenia employs phencyclidine (PCP), which is administered to the animal (e.g., non-primate (rat) or primate (monkey)), resulting in dysfunctions similar to those seen in schizophrenic humans. See Jentsch et al., 1997, Science 277:953-955 and Piercey et al., 1988, Life Sci. 43(4):375-385). Standard experimental protocols may be employed in this or in other animal models. One protocol involves PCP-induced hyperactivity.

Male mice (various strains, e.g., C57Bl/6J) from appropriate vendor (for example, Jackson Laboratories (Bar Harbor, Me.) are used. Mice are received at 6-weeks of age. Upon receipt, mice are assigned unique identification numbers (tail marked) and are group housed with 4 mice/cage in OPTI mouse ventilated cages. All animals remained housed in groups of four during the remainder of the study. All mice are acclimated to the colony room for at least two weeks prior to testing and are subsequently tested at an average age of 8 weeks. During the period of acclimation, mice are examined on a regular basis, handled, and weighed to assure adequate health and suitability. Animals are maintained on a 12/12 light/dark cycle. The room temperature is maintained between 20 and 23° C. with a relative humidity maintained between 30% and 70%. Food and water are provided ad libitum for the duration of the study. In each test, animals are randomly assigned across treatment groups.

The open filed (OF) test assesses locomotor behavior, i.e. to measure mouse locomotor activity at baseline and in response to pharmacological agents. The open field chambers are Plexiglas square chambers (27.3×27.3×20.3 cm; Med Associates Inc., St Albans, Vt.) surrounded by infrared photobeams (16×16×16) to measure horizontal and vertical activity. The analysis is configured to divide the open field into a center and periphery zone such that the infrared photobeams allow measurement of activity in the center and periphery of the field. Distance traveled is measured from horizontal beam breaks as the mouse moved whereas rearing activity is measured from vertical beam breaks.

Mice (10 to 12 animals per treatment group) are brought to the activity experimental room for at least 1 h acclimation to the experimental room conditions prior to testing. Eight animals are tested in each run. Mice are administered vehicle (e.g., 10% DMSO or 5% PEG200 and 1% Tween 80), compound of the invention, clozapine (positive control, 1 mg/kg ip) and placed in the OF chambers for 30 min. following which they are injected with either water or PCP and placed back in the OF chambers for a 60-min. session. At the end of each OF test session the OF chambers are thoroughly cleaned.

PCP Hyperactivity Mouse Model of Schizophrenia

The test compound at the desired dose is dissolved in appropriate vehicle, e.g., 5% PEG200, 1% Tween 80 and administered orally 30 min. prior to PCP injection. Clozapine (1 mg/kg) is dissolved in 10% DMSO and administered i.p. 30 min. prior to PCP injection. PCP (5 mg/kg) is dissolved in sterile injectable saline solution and administered i.p. Data are analyzed by analysis of variance (ANOVA) followed by post-hoc comparisons with Fisher Tests when appropriate. Baseline activity is measured during the first 30 min. of the test prior to PCP injection. PCP-induced activity is measured during the 60 min. following PCP injection. Statistical outliers that fell above or below 2 standard deviations from the mean are removed from the final analyses. An effect is considered significant if $p<0.05$. Total distances traveled and total rearing following PCP administration are compared between groups treated with compounds and groups treated with vehicle and positive control clozapine.

Example B14

Use of an In Vivo Model to Determine the Ability of Compounds to Treat, Prevent and/or Delay the Onset and/or the Development of Schizophrenia in Amphetamine Treated Animals Male mice (various strains e.g., C57Bl/6J) from appropriate supplier (for example Jackson Laboratories, Bar Harbor, Me.) are used. Mice typically are received at 6-weeks of age. Mice are acclimated to the colony room for at least two weeks prior to testing. During the period of acclimation, mice are examined on a regular basis, handled, and weighed to assure adequate health and suitability and maintained on a 12/12 light/dark cycle. The room temperature is maintained between 20 and 23° C. with a relative humidity maintained between 30% and 70%. Food and water are provided ad libitum for the duration of the study. In each test, animals are randomly assigned between treatment groups.

The open field test (OF) is used to assess motor activity. The open field chambers are plexiglas square chambers (e.g., 27.3×27.3×20.3 cm; Med Associates Inc., St Albans, Vt.) surrounded by infrared photobeam sources (16×16×16). The enclosure is configured to split the open field into a center and periphery zone and the photocell beams are set to measure activity in the center and in the periphery of the OF chambers. Horizontal activity (distance traveled) and vertical activity (rearing) are measured from consecutive beam breaks.

On the day of testing, animals are brought to the experimental room for at least 1 h acclimation prior to start of treatment. Animals are administered with vehicle, haloperidol (positive control, 0.1 mg/kg ip) or test compound and placed in the OF. The time of administration of client compound to each animal is recorded. Baseline activity is recorded for 30 min. following which mice receive amphetamine (4 mg/kg) or water and are placed back in the OF chambers for a 60-min. session. At the end of each open field test session the OF chambers are thoroughly cleaned. Typically ten to twelve mice are tested in each group. Test compound doses typically range from 0.01 mg/kg to 60 mg/kg. Data are analyzed by analysis of variance (ANOVA) followed by post-hoc comparisons with Fisher Tests when appropriate. Baseline activity is measured during the first 30 min of the test prior to amphetamine injection. Amphetamine-induced activity is measured during the 60 min following amphetamine injection. Statistical outliers that fall above or below 2 standard deviations from the mean are removed from the final analyses. An effect is considered significant if $p<0.05$. Total distance traveled and total rearing following amphetamine administration are compared between groups treated with compound and groups treated with vehicle and positive control haloperidol.

Example B15

Use of the In Vivo Conditioned Avoidance Response (CAR) Model to Determine the Ability of Compounds to Treat, Prevent and/or Delay the Onset and/or the Development of Schizophrenia All currently approved antipsychotic agents (typical and atypical) are known to have the ability to selectively suppress conditioned avoidance response (CAR) behavior in the rat. This evidence makes CAR one of the primary tests to assess antipsychotic activity of novel compounds. Rats (various strains, 2 months of age) are trained and tested in a computer-assisted, two-way active avoidance apparatus (shuttle box). This box consists of two compartments of equal size divided by a stainless steel partition containing an opening of 7×7 cm. Each compartment is equipped with an electrified grid floor made of stainless steel rods spaced 1 cm apart. Rats trained to avoid the foot shock are placed each day in the shuttle box for a 4 min. habituation period followed by 30 trials spaced by inter-trial interval varying at random between 20 and 30 sec. Each trial consists of a 10-sec. stimulus light (conditioned stimulus, CS) followed by a 10-sec. foot shock (unconditioned stimulus, US) in presence of the light presented in the compartment where the rat is located. If the animal leaves the compartment prior to the delivery of the foot shock, the response is considered an avoidance response. If the rat does not change compartment during the 10-sec. light period and during the 10-sec. shock+light period, an escape failure is recorded. This test requires animals to be trained 5 d/week. On each training day, rats are submitted to one training session of 30-trials. Treatment with test compound is initiated only when rats reach an avoidance performance of at least 80% on at least two consecutive training sessions. The test compound is administered orally at various doses and various pre-treatment times (depending upon specific pharmacokinetic properties).

Compounds with antipsychotic profile inhibit conditioned avoidance responses with or without increases in escape failures. Statistical analysis is performed using a Friedman two-way ANOVA by ranks followed by the Wilcoxon matched-pairs signed-ranks test to test each dose of the test compound administered versus vehicle control treated rats.

Example B16

An Animal Model of the Negative Symptoms of Schizophrenia: Subchronic PCP-Induced Social Interaction Deficits Phencyclidine (PCP) administered to humans as well to experimental animals induces full-spectrum of schizophrenia symptoms, including negative symptoms and cognitive deficits. A major symptom of schizophrenia is considered to be social isolation/withdrawal as part of the cluster of negative symptoms. Subchronic treatment with PCP in rats leads to the development of clear signs of social withdrawal as measured by deficits in the interaction time with a cage intruder rat. Male Sprague Dawley rats (about 150 g, obtained from different vendors, for example Harlan, Ind.) are used in this study. Upon receipt, rats are group housed in OPTI rat ventilated cages. Rats are housed in groups of 2-3 per cage for the remainder of the study. During the period of acclimation, rats are examined on a regular basis, handled, and weighed to assure adequate health and suitability. Rats are maintained on a 12/12 light/dark cycle with the light on at 7:00 a.m. The room temperature is maintained between 20-23° C. with a relative humidity maintained between 30-70%. Food and water are provided ad libitum for the duration of the study. Animals are randomly assigned across treatment groups and balanced by age.

For five days prior to test, rats are injected twice daily with either PCP (2 mg/kg; s.c) or saline (s.c). On day 6 and following a 30 min pretreatment with vehicle, clozapine (2.5 mg/kg ip dissolved in 5% PEG:5% Tween 80) as positive control and test compound at desired dose dissolved in appropriate vehicle, a pair of rats, unfamiliar to each other, receiving the same treatment are placed in a white plexiglas open field arena (24"×17"×8") and allowed to interact with each other for 6 min. Social interactions ('SI') include: sniffing the other rat; grooming the other rat; climbing over or under or around the other rat; following the other rat; or exploring the ano-genital area of the other rat. Passive contact and aggressive contact are not considered a measure of social interaction. The time the rats spent interacting with each other during the 6 min. test is recorded by a trained observer. The social interaction chambers are thoroughly cleaned between the different rats. Data are analyzed by analysis of variance (ANOVA) followed by post-hoc analysis (e.g., Fischer, Dunnett) when appropriate. An effect is considered significant if $p<0.05$.

Example B17

An Animal Model of Extrapyramidal Syndrome (EPS): Measurement of Catalepsy in the Mouse Bar Test Antipsychotic drugs are known to induce extrapyramidal syndrome (EPS) in animals and in humans. An animal model considered to be predictive of EPS is the mouse bar test, which measures cataleptic responses to pharmacological agents. Male mice (various strains) from appropriate vendor (for example, Jackson Laboratories (Bar Harbor, Me.) are used. Mice are received at 6-weeks of age. Upon receipt, mice are assigned unique identification numbers (tail marked) and are group housed with 4 mice per cage in OPTI mouse ventilated cages. All animals remain housed in groups of four during the remainder of the study. All mice are acclimated to the colony room for at least two weeks prior to testing and are subsequently tested at an average age of 8 weeks. During the period of acclimation, mice are examined on a regular basis, handled, and weighed to assure adequate health and suitability. Animals are maintained on a 12/12 light/dark cycle. The room temperature is maintained between 20-23° C. with a relative humidity maintained between 30-70%. Food and water are provided ad libitum for the duration of the study. In each test, animals are randomly assigned across treatment groups.

In the mouse bar test, the front paws of a mouse are placed on a horizontal bar raised 2" above a Plexiglas platform and time is recorded for up to 30 sec. per trial. The test ends when the animal's front paws return to the platform or after 30 sec. The test is repeated 3 times and the average of 3 trials is recorded as index of catalepsy. In these studies the typical antipsychotic agent haloperidol (2 mg/kg ip dissolved in 10% DMSO) is used as positive control and induces rigidity and catalepsy as measured by time spent holding on the bar. 30 min. prior to the trial, test compound at desired dose and dissolved in appropriate vehicle is administered PO, vehicle and positive control haloperidol (2 mg·kg ip) are administered to separate groups of mice. Catalepsy responses are measure 30 min., 1 h and 3 h following treatments. A trained observer is measuring time spent holding onto the bar during the 30 sec. trial. Data are analyzed by analysis of variance (ANOVA) followed by post-hoc analysis (e.g., Fischer, Dunnett) when appropriate. An effect is considered significant if $p<0.05$.

Example B18

An Animal Model to Test the Anxiolytic Effects of Compounds Using the Elevated Plus Maze (EPM) Test This study may be used to test the anxiolytic properties of compounds detailed herein using the elevated plus maze (EPM) test in C57Bl/6J mice.

Male C57Bl/6J mice from Jackson Laboratories (Bar Harbor, Me.) are used for the open field study. Mice are received at 6-weeks of age. Upon receipt, mice are assigned unique identification numbers (tail marked) and are group housed with 4 mice/cage in OPTI mouse ventilated cages. All animals remain housed in groups of four during the remainder of the study. All mice are acclimated to the colony room for approximately 2 week prior to testing and are subsequently tested at an average age of 8 weeks of age. During the period of acclimation, mice and rats are examined on a regular basis, handled, and weighed to assure adequate health and suitability. Animals are maintained on a 12 h/12 h light/dark cycle. The room temperature is maintained between 20 and 23° C. with a relative humidity maintained between 30% and 70%. Chow and water are provided ad libitum for the duration of the study. In each test, animals are randomly assigned across treatment groups. All animals are euthanized after the completion of the study.

Compounds may be dissolved in 5% PEG200/$H_2O$ and administered orally at a dose volume of 10 mL/kg 30 min prior to test; 2) Diazepam (2.5 mg/kg) is dissolved in 45% hydroxypropyl-β-cyclodextrin and administered orally at a dose volume of 10 mL/kg 30 min prior to test.

The elevated plus maze test assesses anxiety. The maze (Hamilton Kinder) consists of two closed arms (14.5 h×5 w×35 cm length) and two open arms (6 w×351 cm) forming a cross, with a square center platform (6×6 cm). All visible surfaces are made of black acrylic. Each arm of the maze is placed on a support column 56 cm above the floor. Antistatic black vinyl curtains (7' tall) surround the EPM to make a 5'×5" enclosure. Animals are brought to acclimate to the experimental room at least 1 h before the test. Mice are placed in the center of the elevated plus maze facing the closed arm for a 5-min run. All animals are tested once. The time spent, distance traveled and entries in each arm are automatically recorded by a computer. The EPM is thoroughly cleaned after each mouse.

Data are analyzed using analysis of variance (ANOVA) followed by Fisher's LSD post hoc analysis when appropriate. An effect is considered significant if $p<0.05$.

All references throughout, such as publications, patents, patent applications and published patent applications, are incorporated herein by reference in their entireties.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

The invention claimed is:
1. A compound of formula (I):

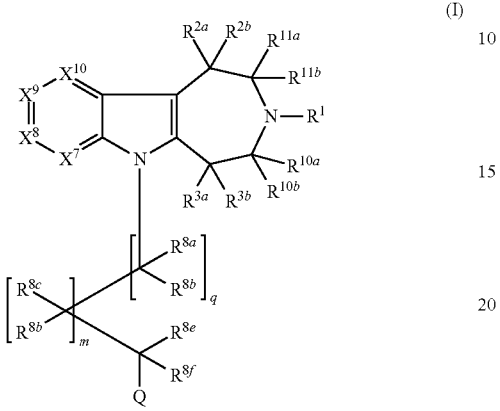

where:
R$^1$ is H, hydroxyl, nitro, cyano, halo, substituted or unsubstituted C$_1$-C$_8$ alkyl, substituted or unsubstituted C$_2$-C$_8$ alkenyl, substituted or unsubstituted C$_2$-C$_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, C$_1$-C$_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy;

each R$^{2a}$, R$^{2b}$, R$^{3a}$ and R$^{3b}$ is independently H, hydroxyl, nitro, cyano, halo, substituted or unsubstituted C$_1$-C$_8$ alkyl, substituted or unsubstituted C$_2$-C$_8$ alkenyl, substituted or unsubstituted C$_2$-C$_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, C$_1$-C$_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal R$^2$ or R$^3$ to form a cycloalkyl moiety or a carbonyl moiety;

each R$^{10a}$, R$^{10b}$, R$^{11a}$ and R$^{11b}$ is independently H, hydroxyl, nitro, cyano, halo, substituted or unsubstituted C$_1$-C$_8$ alkyl, substituted or unsubstituted C$_2$-C$_8$ alkenyl, substituted or unsubstituted C$_2$-C$_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, C$_1$-C$_8$ perhaloalkoxy, alkoxy, aryloxy, carboxyl, thiol, thioalkyl, substituted amino, acylamino, aminoacyl, aminocarbonylamino, aminocarbonyloxy, aminosulfonyl, sulfonylamino, sulfonyl, alkylsulfonylamino, or carbonylalkylenealkoxy, or is taken together with the carbon to which it is attached and a geminal R$^{10}$ or R$^{11}$ to form a cycloalkyl moiety or a carbonyl moiety;

each X$^7$, X$^8$, X$^9$ and X$^{10}$ is independently CR$^4$;

each R$^4$ is independently H, hydroxyl, nitro, cyano, halo, C$_1$-C$_8$ perhaloalkyl, substituted or unsubstituted C$_1$-C$_8$ alkyl, substituted or unsubstituted C$_2$-C$_8$ alkenyl, substituted or unsubstituted C$_2$-C$_8$ alkynyl, substituted or unsubstituted aryl, substituted or unsubstituted heteroaryl, C$_1$-C$_8$ perhaloalkoxy, C$_1$-C$_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each m and q is independently 0 or 1;

each R$^{8a}$, R$^{8b}$, R$^{8c}$, R$^{8d}$, R$^{8e}$ and R$^{8f}$ is independently H, hydroxyl, alkoxy, halo, C$_1$-C$_8$ perhaloalkyl, carboxy, carbonylalkoxy, substituted or unsubstituted aryl, substituted or unsubstituted heteroaryl, substituted or unsubstituted C$_1$-C$_8$ alkyl, substituted or unsubstituted C$_3$-C$_6$ cycloalkyl, substituted or unsubstituted C$_2$-C$_8$ alkenyl, or is taken together with a geminal R$^8$ to form a moiety of the formula —OCH$_2$CH$_2$O—, is taken together with the carbon to which it is attached and a geminal R$^8$ to form a cycloalkyl moiety or a carbonyl moiety, is taken together with a geminal R$^8$ to form a methylene or a substituted methylene, is taken together with a vicinal R$^8$ and the carbon atoms to which they are attached to form a substituted or unsubstituted C$_3$-C$_8$ cycloalkyl, substituted or unsubstituted C$_3$-C$_8$ cycloalkenyl or substituted or unsubstituted heterocyclyl moiety or is taken together with a vicinal R$^8$ to form a bond, provided (i) when an R$^8$ is taken together with a vicinal R$^8$ to form a bond, the geminal R$^8$ is other than hydroxyl, and (ii) at least one of R$^{8a}$, R$^{8b}$, R$^{8c}$, R$^{8d}$, R$^{8e}$ and R$^{8f}$ is hydroxyl; and Q is a substituted or unsubstituted cycloalkyl, substituted or unsubstituted cycloalkenyl, substituted or unsubstituted heterocyclyl, substituted or unsubstituted amino, alkoxy, aminoacyl, acyloxy, carbonylalkoxy, aminocarbonylalkoxy, acylamino, carboxy, cyano or alkynyl;

or a salt or solvate thereof.

2. The compound of claim 1, wherein each R$^4$ is independently H, halo, unsubstituted C$_1$-C$_4$ alkyl, C$_1$-C$_4$ perhaloalkyl or substituted or unsubstituted aryl.

3. The compound of claim 1, wherein R$^1$ is H, substituted or unsubstituted C$_1$-C$_8$ alkyl, acyl, acyloxy, carbonylalkoxy, substituted or unsubstituted heterocyclyl, substituted or unsubstituted aryl, substituted or unsubstituted heteroaryl, or substituted or unsubstituted aralkyl.

4. The compound of claim 1, wherein R$^1$ is methyl, ethyl, cyclopropyl, propylate, trifluoromethyl, isopropyl, tert-butyl, sec-butyl, 2-methylbutyl, propanal, 1-methyl-2-hydroxyethyl, 2-hydroxyethanal, 2-hydroxyethyl, 2-hydroxypropyl, 2-hydroxy-2-methylpropyl, cyclobutyl, cyclopentyl, cyclohexyl, substituted phenyl, piperidin-4-yl, hydroxycyclopent-3-yl, hydroxycyclopent-2-yl, hydroxycycloprop-2-yl, 1-hydroxy-1-methylcycloprop-2-yl, or 1-hydroxy-1,2,2-trimethyl-cycloprop-3-yl.

5. The compound of claim 1, wherein:
each R$^{2a}$ and R$^{2b}$ is independently H, unsubstituted C$_1$-C$_8$ alkyl, or halo, or R$^{2a}$ and R$^{2b}$ are taken together with the carbon to which they are attached to form a carbonyl moiety; and each $R^{3a}$ and $R^{3b}$ is independently H, unsubstituted $C_1$-$C_8$ alkyl, or halo, or $R^{3a}$ and $R^{3b}$ are taken together with the carbon to which they are attached to form a carbonyl moiety.

6. The compound of claim 5, wherein each of $R^{2a}$, $R^{2b}$, $R^{3a}$ and $R^{3b}$ is H.

7. The compound of claim 1, wherein each $R^{10a}$, $R^{10b}$, $R^{11a}$ and $R^{11b}$ is independently H, bromo, methyl, or hydroxyl, or $R^{10a}$ and $R^{10b}$ are taken together with the carbon to which they are attached to form a carbonyl, or $R^{11a}$ and $R^{11b}$ are taken together with the carbon to which they are attached to form a carbonyl.

8. The compound of claim 1, wherein each $R^{8a}$, $R^{8b}$, $R^{8c}$, $R^{8d}$, $R^{8e}$ and $R^{8f}$ is independently H, hydroxyl, or unsubstituted $C_1$-$C_4$alkyl, or is taken together with the carbon to which it is attached and a geminal $R^8$ to form a cycloalkyl moiety.

9. The compound of claim 1, wherein at least one of $R^{8a}$, $R^{8b}$, $R^{8c}$, $R^{8d}$, $R^{8e}$ and $R^{8f}$ is taken together with the carbon to which it is attached and a geminal $R^8$ to form a methylene or a substituted methylene.

10. The compound of claim 1, wherein at least one of $R^{8a}$, $R^{8b}$, $R^{8c}$, $R^{8d}$, $R^{8e}$ and $R^{8f}$ is taken together with a vicinal $R^8$ to form a bond.

11. The compound of claim 1, wherein q is 0 and m is 0 or 1.

12. The compound of claim 1, wherein:
$R^1$ is substituted or unsubstituted $C_1$-$C_8$ alkyl, acyl, acyloxy, carbonylalkoxy, substituted or unsubstituted heterocyclyl, or substituted or unsubstituted aryl;
each $R^{2a}$ and $R^{2b}$ is independently H, methyl, or fluoro, or $R^{2a}$ and $R^{2b}$ are taken together with the carbon to which they are attached to form a carbonyl moiety;
each $R^{3a}$ and $R^{3b}$ is independently H or fluoro;
each $R^{10a}$ and $R^{10b}$ is independently H, fluoro or methyl, or $R^{10a}$ and $R^{10b}$ are taken together with the carbon to which they are attached to form a carbonyl; and
each $R^{11a}$ and $R^{11b}$ is independently H, fluoro or methyl, or $R^{11a}$ and $R^{11b}$ are taken together with the carbon to which they are attached to form a carbonyl.

13. The compound of claim 1, wherein Q is substituted or unsubstituted amino, alkoxy, aminoacyl, acyloxy, carbonylalkoxy, aminocarbonylalkoxy or acylamino.

14. A pharmaceutical composition comprising a compound according to claim 1, or a pharmaceutically acceptable salt thereof, and a pharmaceutically acceptable carrier.

15. A kit comprising a compound according to claim 1, or a pharmaceutically acceptable salt thereof.

16. The compound of claim 1 wherein the compound is selected from the group consisting of compounds J-2, J-13, J-14, J-15, J-18, J-23, J-25, and J-27:

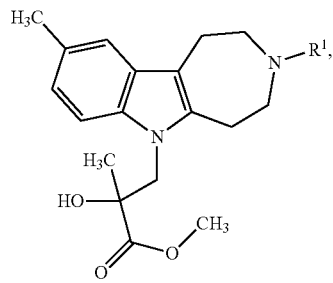
J-2

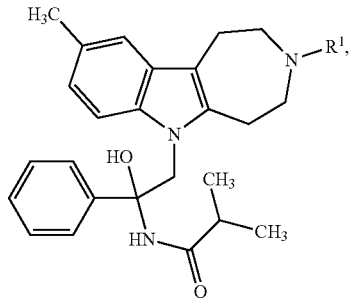
J-13

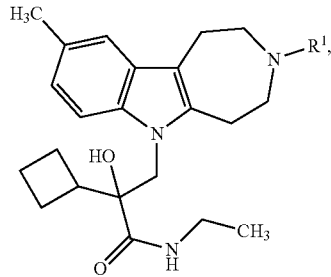
J-14

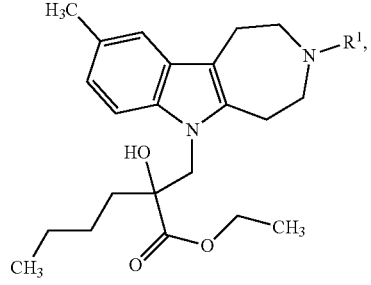
J-15

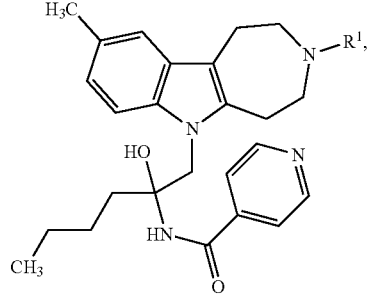
J-18

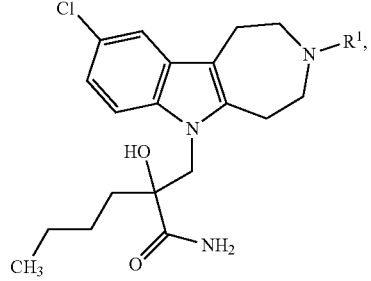
J-23

J-25
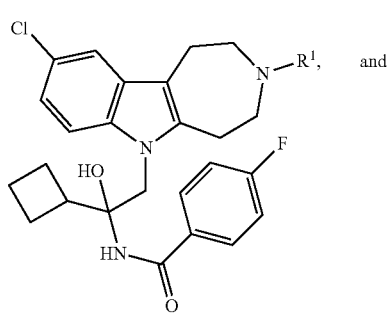
J-27
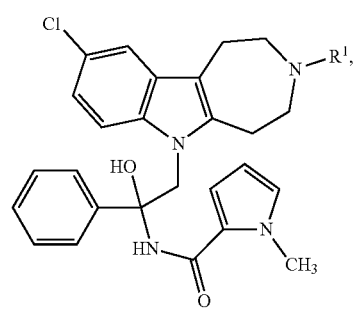
or a salt thereof.
* * * * *